US010053684B2

(12) United States Patent
Nunn, Jr. et al.

(10) Patent No.: US 10,053,684 B2
(45) Date of Patent: *Aug. 21, 2018

(54) XYLOSE ISOMERASE SIGNATURE SEQUENCES

(71) Applicant: BP Corporation North America Inc., Houston, TX (US)

(72) Inventors: David Neal Nunn, Jr., Carlsbad, CA (US); Peter Luginbuhl, San Diego, CA (US); Ling Li, San Diego, CA (US); Adam Martin Burja, San Diego, CA (US); Jon Peter Flash Bartnek, San Diego, CA (US)

(73) Assignee: BP Corporation North America Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/745,202

(22) Filed: Jun. 19, 2015

(65) Prior Publication Data

US 2016/0017310 A1    Jan. 21, 2016

Related U.S. Application Data

(62) Division of application No. 13/948,956, filed on Jul. 23, 2013, now Pat. No. 9,090,889.

(60) Provisional application No. 61/675,241, filed on Jul. 24, 2012.

(51) Int. Cl.

| | |
|---|---|
| *C12N 9/92* | (2006.01) |
| *C12P 7/16* | (2006.01) |
| *C12P 7/56* | (2006.01) |
| *C12P 7/42* | (2006.01) |
| *C12P 7/10* | (2006.01) |
| *C12N 9/90* | (2006.01) |
| *C12P 17/18* | (2006.01) |
| *C12P 35/06* | (2006.01) |
| *C12P 7/06* | (2006.01) |
| *C12P 7/18* | (2006.01) |
| *C12P 7/20* | (2006.01) |
| *C12P 7/40* | (2006.01) |
| *C12P 7/64* | (2006.01) |
| *C12P 13/04* | (2006.01) |
| *C12P 5/02* | (2006.01) |
| *C12P 7/46* | (2006.01) |
| *C12P 7/48* | (2006.01) |
| *C12P 7/54* | (2006.01) |
| *C12P 13/02* | (2006.01) |

(52) U.S. Cl.
CPC .............. *C12N 9/92* (2013.01); *C12N 9/90* (2013.01); *C12P 5/026* (2013.01); *C12P 7/06* (2013.01); *C12P 7/10* (2013.01); *C12P 7/16* (2013.01); *C12P 7/18* (2013.01); *C12P 7/20* (2013.01); *C12P 7/40* (2013.01); *C12P 7/42* (2013.01); *C12P 7/46* (2013.01); *C12P 7/48* (2013.01); *C12P 7/54* (2013.01); *C12P 7/56* (2013.01); *C12P 7/649* (2013.01); *C12P 13/02* (2013.01); *C12P 13/04* (2013.01); *C12P 17/184* (2013.01); *C12P 35/06* (2013.01); *C12Y 503/01005* (2013.01); *C12P 2203/00* (2013.01); *Y02E 50/10* (2013.01); *Y02E 50/13* (2013.01); *Y02E 50/16* (2013.01); *Y02E 50/17* (2013.01); *Y02E 50/343* (2013.01)

(58) Field of Classification Search
None
See application file for complete search history.

(56) References Cited

FOREIGN PATENT DOCUMENTS

| | | |
|---|---|---|
| CN | 102 174 549 | 9/2011 |
| DE | 10 2008 031350 A1 | 1/2010 |
| WO | WO 2003/062430 | 7/2007 |
| WO | WO 2008/000632 A1 | 1/2008 |
| WO | WO 2009/109634 | 11/2009 |
| WO | WO 2010/039692 A2 | 4/2010 |
| WO | WO 2010/074577 | 7/2010 |
| WO | WO 2011/090731 | 7/2011 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Accession AEL74969. Mar. 3, 2011.*
Accession AEL74969, Aug. 10, 2011.
Chica et al., *Curr. Opin. Biotechnol.* (Aug. 16, 2005), 16(4):378-384.
Ethanol Production Related Xylose Isomerase, XP002714606, Nov. 10, 2011, 1 page.
Harhangi, H.R., "Xylose Metabolism in the Anaerobic Fungus *Piromyces* sp. Strain E2 Follows the Bacterial Pathway," Springer, DE (Jun. 13, 2003), 180(2):134-1419557-9560.
Hector et al., "Growth and Fermentation of D-Xylose by *Saacharomyces cerevisiae* Expressing a Novel D-Xylose Isomerase Originating from the Bacterium *Provotella ruminicola* TC2-24", Biotechnology for Biofuels, Ltd. (May 30, 2013).
Kuyper et al., "High-Level Functional Expression of a Fungal Xylose Isomerase," 4:69-78, (Oct. 1, 2013).
"RecName: Full=Xylose Isomerase" XP002714610, Mar. 23, 2010, 1 page.
"RecName: Full=Xylose Isomerase" XP002714611, Oct. 19, 2011, 1 page.
Sen et al., *Appl. Biochem. Biotechnol.* (Dec. 2007), 143(3):212-223.
Brat, Dawid et al.: "*Functional Expression of a Bacterial Xylose Isomerase in Saccharomyces cerevisiae*"; Applied and Environmental Microbiology, American Society for Microbiology, US, vol. 75, No. 8, Apr. 1, 2009, pp. 2304-2311.
European Search Report dated Aug. 24, 2016 regarding EP 13744924.
Jeffries et al.: "*Engineering yeasts for xylose metabolism*"; Current Opinion in Iotechnology, vol. 17, No. 3, Jun. 1, 2006, pp. 320-326.
Madhavan, Anjali et al: "*Xylose isomerase from polycentric fungus Orpinomyces: gene sequencing, cloning,and expression in Saccharomyces cerevisiae for bioconversion of xylose to ethanol*"; Applied Microbiology and Biotechnology, vol. 82, No. 6, Dec. 3, 2008, pp. 1067-1078.

(Continued)

*Primary Examiner* — Christian Fronda
(74) *Attorney, Agent, or Firm* — DLA Piper LLP (US)

(57) ABSTRACT

This disclosure relates to novel xylose isomerases and their uses, particularly in fermentation processes that employ xylose-containing media.

16 Claims, 13 Drawing Sheets

(56) References Cited

OTHER PUBLICATIONS

Van Maris, A. J. A. et al: "*Development of Efficient Xylose Fermentation in Saccharomyces cerevisiae: Xylose Isomerase as a Key Component*"; Advances in Biochemical Engineering, Biotechnology, vol. 108, Jan. 1, 2007, pp. 179-204.

XP002714606: "*Ethanol production related xylose isomerase (XI), SEQ ID 2.*"; Jan. 19, 2012, Database accession No. AZM80432; retrieved from EBI accession No. GSP:AZM80432.

Accession AJ249909: "*Xylose metabolism in the anaerobic fungus Piromyces sp. strain E2 follows the bacterial pathway*"; Apr. 15, 2005, 3 pages.

Accession D3I1K1: "*The Genome Sequence of Prevotella buccae Oral Taxon 560 strain D17*"; Mar. 23, 2010, 2 pages.

\* cited by examiner

XYLOSE ISOMERASE SIGNATURE SEQUENCES

CROSS-REFERENCE TO RELATED APPLICATIONS

This application is a continuation application of U.S. application Ser. No. 13/948,956 filed Jul. 23, 2013, now pending; which claims the benefit under 35 USC § 119(e) to U.S. application Ser. No. 61/675,241 filed Jul. 24, 2012. The disclosure of each of the prior applications is considered part of and is incorporated by reference in the disclosure of this application.

BACKGROUND OF THE INVENTION

The efficient, commercial production of biofuels from plant material, such as sugarcane, requires the fermentation of pentoses, such as xylose. Xylose in plant material typically comes from lignocellulose, which is a matrix composed of cellulose, hemicelluloses, and lignin. Lignocellulose is broken down either by acid hydrolysis or enzymatic reaction, yielding xylose in addition to other monosaccharides, such as glucose. (Maki et al., 2009, Int. J. Biol. Sci. 5:500-516).

Fungi, especially *Saccharomyces cerevisiae*, are commercially relevant microorganisms that ferment sugars into biofuels such as ethanol. However, *S. cerevisiae* does not endogenously metabolize xylose, requiring genetic modifications that allow it to convert xylose into xylulose. Other organisms, whose usefulness in ethanol production is limited, are able to metabolize xylose (Nevigot, 2008, Micobiol. Mol. Biol. Rev. 72:379-412).

Two pathways have been identified for the metabolism of xylose to xylulose in microorganisms: the xylose reductase (XR, EC 1.1.1.307)/xylitol dehydrogenase (XDH, EC 1.1.1.9, 1.1.1.10 and 1.1.1.B19) pathway and the xylose isomerase (XI, EC 5.3.1.5) pathway. Use of the XR/XDH pathway for xylose metabolism creates an imbalance of cofactors (excess NADH and NADP+) limiting the potential output of this pathway for the production of ethanol. The XI pathway, on the otherhand, converts xylose to xylulose in a single step and does not create a cofactor imbalance (Young et al., 2010, Biotechnol. Biofuels 3:24-36).

Because *S. cerevisiae* does not possess a native XI, it has been desirable to search for an XI in another organism to insert into *S. cerevisiae* for the purpose of biofuels production. Several XI genes have been discovered, although little or no enzymatic activity upon expression in *S. cerevisiae* has been a common problem. The XI from *Piromyces* sp. E2 was the first heterologously expressed XI in *S. cerevisiae* whose enzymatic activity could be observed (WO 03/062430).

SUMMARY OF THE INVENTION

Due to the physiology of *S. cerevisiae* and the process of commercial biofuel production, there are other characteristics besides activity that are valuable in a commercially useful XI. During fermentation, the pH of the yeast cell and its environment can become more acidic (Rosa and Sa-Correia, 1991, Appl. Environ. Microbiol. 57:830-835). The ability of the XI to function in an acidic environment is therefore highly desirable. Therefore, there is a still a need in the art for XI enzymes with enhanced activity to convert xylose to xylulose for biofuels production under a broader range of commercially relevant conditions.

The present disclosure relates to novel xylose isomerases. The xylose isomerases have desirable characteristics for xylose fermentation, such as high activity, tolerance to acidic conditions (i.e., pH levels below 7, e.g., pH 6.5 or pH 6), or both.

The present disclosure has multiple aspects. In one aspect, the disclosure is directed to XI polypeptides. The polypeptides of the disclosure typically comprise amino acid sequences having at least 70%, 75%, 80%, 85%, 90%, 93%, 95%, 96%, 98%, 99% or 100% sequence identity to any of the XI polypeptides of Table 1, or the catalytic domain or dimerization domain thereof, or are encoded by nucleic acid sequences comprising nucleotide sequences having at least 70%, 75%, 80%, 85%, 90%, 93%, 95%, 96%, 98%, 99% or 100% sequence identity to any of the nucleic acids of Table 1:

TABLE 1

| SEQ ID NO: | Clone No. | Organism Classification | Type of Sequence | Catalytic Domain | Dimerization Domain |
|---|---|---|---|---|---|
| 1 | 1754MI2_001 | Bacteroidales | DNA | | |
| 2 | 1754MI2_001 | Bacteroidales | Amino Acid | 2-376 | 377-437 |
| 3 | 5586MI6_004 | Bacteroidales | DNA | | |
| 4 | 5586MI6_004 | Bacteroidales | Amino Acid | 2-376 | 377-437 |
| 5 | 5749MI1_003 | Bacteroidales | DNA | | |
| 6 | 5749MI1_003 | Bacteroidales | Amino Acid | 2-381 | 382-442 |
| 7 | 5750MI1_003 | Bacteroidales | DNA | | |
| 8 | 5750MI1_003 | Bacteroidales | Amino Acid | 2-381 | 382-442 |
| 9 | 5750MI2_003 | Bacteroidales | DNA | | |
| 10 | 5750MI2_003 | Bacteroidales | Amino Acid | 2-381 | 382-442 |
| 11 | 5586MI5_004 | Bacteroides | DNA | | |
| 12 | 5586MI5_004 | Bacteroides | Amino Acid | 2-375 | 376-435 |
| 13 | 5586MI202_004 | Bacteroides | DNA | | |
| 14 | 5586MI202_004 | Bacteroides | Amino Acid | 2-377 | 378-438 |
| 15 | 5586MI211_003 | Bacteroides | DNA | | |
| 16 | 5586MI211_003 | Bacteroides | Amino Acid | 2-376 | 377-437 |
| 17 | 5606MI1_005 | Bacteroides | DNA | | |
| 18 | 5606MI1_005 | Bacteroides | Amino Acid | 2-377 | 378-438 |
| 19 | 5606MI2_003 | Bacteroides | DNA | | |
| 20 | 5606MI2_003 | Bacteroides | Amino Acid | 2-378 | 379-439 |
| 21 | 5610MI3_003 | Bacteroides | DNA | | |
| 22 | 5610MI3_003 | Bacteroides | Amino Acid | 2-377 | 378-439 |
| 23 | 5749MI2_004 | Bacteroides | DNA | | |
| 24 | 5749MI2_004 | Bacteroides | Amino Acid | 2-377 | 378-438 |
| 25 | 5750MI3_003 | Bacteroides | DNA | | |
| 26 | 5750MI3_003 | Bacteroides | Amino Acid | 2-377 | 378-438 |
| 27 | 5750MI4_003 | Bacteroides | DNA | | |
| 28 | 5750MI4_003 | Bacteroides | Amino Acid | 2-377 | 378-438 |
| 29 | 5751MI4_002 | Bacteroides | DNA | | |
| 30 | 5751MI4_002 | Bacteroides | Amino Acid | 2-376 | 377-437 |
| 31 | 5751MI5_003 | Bacteroides | DNA | | |
| 32 | 5751MI5_003 | Bacteroides | Amino Acid | 2-377 | 378-438 |
| 33 | 5751MI6_004 | Bacteroides | DNA | | |
| 34 | 5751MI6_004 | Bacteroides | Amino Acid | 2-377 | 378-438 |
| 35 | 5586MI22_003 | Clostridiales | DNA | | |
| 36 | 5586MI22_003 | Clostridiales | Amino Acid | 2-375 | 376-439 |

TABLE 1-continued

| SEQ ID NO: | Clone No. | Organism Classification | Type of Sequence | Catalytic Domain | Dimerization Domain |
|---|---|---|---|---|---|
| 37 | 1753MI4_001 | Firmicutes | DNA | | |
| 38 | 1753MI4_001 | Firmicutes | Amino Acid | 2-374 | 375-440 |
| 39 | 1753MI6_001 | Firmicutes | DNA | | |
| 40 | 1753MI6_001 | Firmicutes | Amino Acid | 2-374 | 375-440 |
| 41 | 1753MI35_004 | Firmicutes | DNA | | |
| 42 | 1753MI35_004 | Firmicutes | Amino Acid | 2-375 | 376-441 |
| 43 | 1754MI9_004 | Firmicutes | DNA | | |
| 44 | 1754MI9_004 | Firmicutes | Amino Acid | 2-375 | 376-440 |
| 45 | 1754MI22_004 | Firmicutes | DNA | | |
| 46 | 1754MI22_004 | Firmicutes | Amino Acid | 2-375 | 376-440 |
| 47 | 727MI1_002 | Firmicutes | DNA | | |
| 48 | 727MI1_002 | Firmicutes | Amino Acid | 2-372 | 373-436 |
| 49 | 727MI9_005 | Firmicutes | DNA | | |
| 50 | 727MI9_005 | Firmicutes | Amino Acid | 2-374 | 375-438 |
| 51 | 727MI27_002 | Firmicutes | DNA | | |
| 52 | 727MI27_002 | Firmicutes | Amino Acid | 2-374 | 375-439 |
| 53 | 1753MI2_006 | Neocallimastigales | DNA | | |
| 54 | 1753MI2_006 | Neocallimastigales | Amino Acid | 2-376 | 377-437 |
| 55 | 5586MI3_005 | Neocallimastigales | DNA | | |
| 56 | 5586MI3_005 | Neocallimastigales | Amino Acid | 2-376 | 377-437 |
| 57 | 5586MI91_002 | Neocallimastigales | DNA | | |
| 58 | 5586MI91_002 | Neocallimastigales | Amino Acid | 2-376 | 377-437 |
| 59 | 5586MI194_003 | Neocallimastigales | DNA | | |
| 60 | 5586MI194_003 | Neocallimastigales | Amino Acid | 2-376 | 377-438 |
| 61 | 5586MI198_003 | Neocallimastigales | DNA | | |
| 62 | 5586MI198_003 | Neocallimastigales | Amino Acid | 2-375 | 376-437 |
| 63 | 5586MI201_003 | Neocallimastigales | DNA | | |
| 64 | 5586MI201_003 | Neocallimastigales | Amino Acid | 2-376 | 377-438 |
| 65 | 5586MI204_002 | Neocallimastigales | DNA | | |
| 66 | 5586MI204_002 | Neocallimastigales | Amino Acid | 2-375 | 376-437 |
| 67 | 5586MI207_002 | Neocallimastigales | DNA | | |
| 68 | 5586MI207_002 | Neocallimastigales | Amino Acid | 2-375 | 376-437 |
| 69 | 5586MI209_003 | Neocallimastigales | DNA | | |
| 70 | 5586MI209_003 | Neocallimastigales | Amino Acid | 2-375 | 376-437 |
| 71 | 5586MI214_002 | Neocallimastigales | DNA | | |
| 72 | 5586MI214_002 | Neocallimastigales | Amino Acid | 2-375 | 376-437 |
| 73 | 5751MI3_001 | Neocallimastigales | DNA | | |
| 74 | 5751MI3_001 | Neocallimastigales | Amino Acid | 2-375 | 376-437 |
| 75 | 5753MI3_002 | Prevotella | DNA | | |
| 76 | 5753MI3_002 | Prevotella | Amino Acid | 2-376 | 377-439 |
| 77 | 1754MI1_001 | Prevotella | DNA | | |
| 78 | 1754MI1_001 | Prevotella | Amino Acid | 2-377 | 378-439 |
| 79 | 1754MI3_007 | Prevotella | DNA | | |
| 80 | 1754MI3_007 | Prevotella | Amino Acid | 2-377 | 378-439 |
| 81 | 1754MI5_009 | Prevotella | DNA | | |
| 82 | 1754MI5_009 | Prevotella | Amino Acid | 2-375 | 376-437 |
| 83 | 5586MI1_003 | Prevotella | DNA | | |
| 84 | 5586MI1_003 | Prevotella | Amino Acid | 2-377 | 378-439 |
| 85 | 5586MI2_006 | Prevotella | DNA | | |
| 86 | 5586MI2_006 | Prevotella | Amino Acid | 2-377 | 378-439 |
| 87 | 5586MI8_003 | Prevotella | DNA | | |
| 88 | 5586MI8_003 | Prevotella | Amino Acid | 2-377 | 378-439 |
| 89 | 5586MI14_003 | Prevotella | DNA | | |
| 90 | 5586MI14_003 | Prevotella | Amino Acid | 2-377 | 378-439 |
| 91 | 5586MI26_003 | Prevotella | DNA | | |
| 92 | 5586MI26_003 | Prevotella | Amino Acid | 2-377 | 378-439 |
| 93 | 5586MI86_001 | Prevotella | DNA | | |
| 94 | 5586MI86_001 | Prevotella | Amino Acid | 2-376 | 377-438 |
| 95 | 5586MI108_002 | Prevotella | DNA | | |
| 96 | 5586MI108_002 | Prevotella | Amino Acid | 2-377 | 378-439 |
| 97 | 5586MI182_004 | Prevotella | DNA | | |
| 98 | 5586MI182_004 | Prevotella | Amino Acid | 2-377 | 378-439 |
| 99 | 5586MI193_004 | Prevotella | DNA | | |
| 100 | 5586MI193_004 | Prevotella | Amino Acid | 2-376 | 377-438 |
| 101 | 5586MI195_003 | Prevotella | DNA | | |
| 102 | 5586MI195_003 | Prevotella | Amino Acid | 2-376 | 377-438 |
| 103 | 5586MI216_003 | Prevotella | DNA | | |
| 104 | 5586MI216_003 | Prevotella | Amino Acid | 2-376 | 377-438 |
| 105 | 5586MI197_003 | Prevotella | DNA | | |
| 106 | 5586MI197_003 | Prevotella | Amino Acid | 2-376 | 377-438 |
| 107 | 5586MI199_003 | Prevotella | DNA | | |
| 108 | 5586MI199_003 | Prevotella | Amino Acid | 2-376 | 377-438 |
| 109 | 5586MI200_003 | Prevotella | DNA | | |
| 110 | 5586MI200_003 | Prevotella | Amino Acid | 2-376 | 377-438 |
| 111 | 5586MI203_003 | Prevotella | DNA | | |
| 112 | 5586MI203_003 | Prevotella | Amino Acid | 2-376 | 377-438 |
| 113 | 5586MI205_004 | Prevotella | DNA | | |
| 114 | 5586MI205_004 | Prevotella | Amino Acid | 2-376 | 377-438 |
| 115 | 5586MI206_004 | Prevotella | DNA | | |
| 116 | 5586MI206_004 | Prevotella | Amino Acid | 2-376 | 377-438 |
| 117 | 5586MI208_003 | Prevotella | DNA | | |
| 118 | 5586MI208_003 | Prevotella | Amino Acid | 2-376 | 377-438 |
| 119 | 5586MI210_002 | Prevotella | DNA | | |
| 120 | 5586MI210_002 | Prevotella | Amino Acid | 2-374 | 375-437 |
| 121 | 5586MI212_002 | Prevotella | DNA | | |
| 122 | 5586MI212_002 | Prevotella | Amino Acid | 2-376 | 377-438 |
| 123 | 5586MI213_003 | Prevotella | DNA | | |
| 124 | 5586MI213_003 | Prevotella | Amino Acid | 2-376 | 377-438 |
| 125 | 5586MI215_003 | Prevotella | DNA | | |
| 126 | 5586MI215_003 | Prevotella | Amino Acid | 2-376 | 377-438 |
| 127 | 5607MI1_003 | Prevotella | DNA | | |
| 128 | 5607MI1_003 | Prevotella | Amino Acid | 2-376 | 377-438 |
| 129 | 5607MI2_003 | Prevotella | DNA | | |
| 130 | 5607MI2_003 | Prevotella | Amino Acid | 2-376 | 377-442 |
| 131 | 5607MI3_003 | Prevotella | DNA | | |
| 132 | 5607MI3_003 | Prevotella | Amino Acid | 2-376 | 377-438 |
| 133 | 5607MI4_005 | Prevotella | DNA | | |
| 134 | 5607MI4_005 | Prevotella | Amino Acid | 2-376 | 377-438 |
| 135 | 5607MI5_002 | Prevotella | DNA | | |
| 136 | 5607MI5_002 | Prevotella | Amino Acid | 2-376 | 377-439 |

TABLE 1-continued

| SEQ ID NO: | Clone No. | Organism Classification | Type of Sequence | Catalytic Domain | Dimerization Domain |
|---|---|---|---|---|---|
| 137 | 5607MI6_002 | Prevotella | DNA | | |
| 138 | 5607MI6_002 | Prevotella | Amino Acid | 2-376 | 377-438 |
| 139 | 5607MI7_002 | Prevotella | DNA | | |
| 140 | 5607MI7_002 | Prevotella | Amino Acid | 2-376 | 377-438 |
| 141 | 5608MI1_004 | Prevotella | DNA | | |
| 142 | 5608MI1_004 | Prevotella | Amino Acid | 2-376 | 377-438 |
| 143 | 5608MI2_002 | Prevotella | DNA | | |
| 144 | 5608MI2_002 | Prevotella | Amino Acid | 2-375 | 376-437 |
| 145 | 5608MI3_004 | Prevotella | DNA | | |
| 146 | 5608MI3_004 | Prevotella | Amino Acid | 2-376 | 377-438 |
| 147 | 5609MI1_005 | Prevotella | DNA | | |
| 148 | 5609MI1_005 | Prevotella | Amino Acid | 2-376 | 377-438 |
| 149 | 5610MI1_003 | Prevotella | DNA | | |
| 150 | 5610MI1_003 | Prevotella | Amino Acid | 2-376 | 377-438 |
| 151 | 5610MI2_004 | Prevotella | DNA | | |
| 152 | 5610MI2_004 | Prevotella | Amino Acid | 2-376 | 377-438 |
| 153 | 5751MI1_003 | Prevotelld | DNA | | |
| 154 | 5751MI1_003 | Prevotella | Amino Acid | 2-376 | 377-438 |
| 155 | 5751MI2_003 | Prevotella | DNA | | |
| 156 | 5751MI2_003 | Prevotella | Amino Acid | 2-376 | 377-438 |
| 157 | 5752MI1_003 | Prevotella | DNA | | |
| 158 | 5752MI1_003 | Prevotella | Amino Acid | 2-376 | 377-438 |
| 159 | 5752MI2_003 | Prevotella | DNA | | |
| 160 | 5752MI2_003 | Prevotella | Amino Acid | 2-376 | 377-438 |
| 161 | 5752MI3_002 | Prevotella | DNA | | |
| 162 | 5752MI3_002 | Prevotella | Amino Acid | 2-376 | 377-438 |
| 163 | 5752MI5_003 | Prevotella | DNA | | |
| 164 | 5752MI5_003 | Prevotella | Amino Acid | 2-376 | 377-438 |
| 165 | 5752MI6_004 | Prevotella | DNA | | |
| 166 | 5752MI6_004 | Prevotella | Amino Acid | 2-376 | 377-438 |
| 167 | 5753MI1_002 | Prevotella | DNA | | |
| 168 | 5753MI1_002 | Prevotella | Amino Acid | 2-376 | 377-438 |
| 169 | 5753MI2_002 | Prevotella | DNA | | |
| 170 | 5753MI2_002 | Prevotella | Amino Acid | 2-376 | 377-438 |
| 171 | 5753MI4_002 | Prevotella | DNA | | |
| 172 | 5753MI4_002 | Prevotella | Amino Acid | 2-376 | 377-438 |
| 173 | 5752MI4_004 | Prevotella | DNA | | |
| 174 | 5752MI4_004 | Prevotella | Amino Acid | 2-376 | 377-438 |
| 175 | 727MI4_006 | Rhizobiales | DNA | | |
| 176 | 727MI4_006 | Rhizobiales | Amino Acid | 2-373 | 374-435 |

In specific embodiments, a polypeptide of the disclosure comprises an amino acid sequence having:

(1) (a) at least 97% or 98% sequence identity to SEQ ID NO:78 or the catalytic domain thereof (amino acids 2-377 of SEQ ID NO:78) and/or (b) at least 80%, 85%, 90%, 93% or 95% sequence identity to SEQ ID NO:78 or the catalytic domain thereof (amino acids 2-377 of SEQ ID NO:78) and further comprises (i) SEQ ID NO:212 or SEQ ID NO:213 and/or (ii) SEQ ID NO:214;

(2) (a) at least 95%, 97% or 98% sequence identity to SEQ ID NO:96 or the catalytic domain thereof (amino acids 2-377 of SEQ ID NO:96) and/or (b) at least 80%, 85%, 90%, 93% or 95% sequence identity to SEQ ID NO:96 or the catalytic domain thereof (amino acids 2-377 of SEQ ID NO:96) and further comprises (i) SEQ ID NO:212 or SEQ ID NO:213 and/or (ii) SEQ ID NO:214;

(3) at least 80%, 85%, 90%, 93%, 95%, 97% or 98% sequence identity to SEQ ID NO:38 or the catalytic domain thereof (amino acids 2-374 of SEQ ID NO:38), and optionally further comprises one, two, three, four or all five of (i) SEQ ID NO:206 or SEQ ID NO:207; (ii) SEQ ID NO:208; (iii) SEQ ID NO:209; (iv) SEQ ID NO:210; and (iv) SEQ ID NO:211;

(4) at least 80%, 85%, 90%, 93%, 95%, 97% or 98% sequence identity to SEQ ID NO:2 or the catalytic domain thereof (amino acids 2-374 of SEQ ID NO:2);

(5) at least 93%, 95%, 97% or 98% sequence identity to SEQ ID NO:58 or the catalytic domain thereof (amino acids 2-376 of SEQ ID NO:58), (6) at least 80%, 85%, 90%, 93%, 95%, 97% or 98% sequence identity to SEQ ID NO:42 or the catalytic domain thereof (amino acids 2-375 of SEQ ID NO:42), and optionally further comprises one, two or all three of (i) SEQ ID NO:206 or SEQ ID NO:207; (ii) SEQ ID NO:210; and (iii) SEQ ID NO:211;

(7) (a) at least 97% or 98% sequence identity to SEQ ID NO:84 or the catalytic domain thereof (amino acids 2-376 of SEQ ID NO:84), and/or (b) at least 80%, 85%, 90%, 93% or 95% sequence identity to SEQ ID NO:84 or the catalytic domain thereof (amino acids 2-376 of SEQ ID NO:84) and further comprises (i) SEQ ID NO:212 or SEQ ID NO:213 and/or (ii) SEQ ID NO:214;

(8) (a) at least 97% or 98% sequence identity to SEQ ID NO:80 or the catalytic domain thereof (amino acids 2-377 of SEQ ID NO:80) and/or (b) at least 80%, 85%, 90%, 93% or 95% sequence identity to SEQ ID NO:80 or the catalytic domain thereof (amino acids 2-377 of SEQ ID NO:80) and further comprises (i) SEQ ID NO:212 or SEQ ID NO:213 and/or (ii) SEQ ID NO:214;

(9) at least 93%, 95%, 97% or 98% sequence identity to SEQ ID NO:54 or the catalytic domain thereof (amino acids 2-376 of SEQ ID NO:54);

(10) at least 80%, 85%, 90%, 93%, 95%, 97% or 98% sequence identity to SEQ ID NO:46 or the catalytic domain thereof (amino acids 2-376 of SEQ ID NO:46), and optionally further comprises SEQ ID NO:206 or SEQ ID NO:207;

(11) at least 90%, 93%, 95%, 97% or 98% sequence identity to SEQ ID NO: 16 or the catalytic domain thereof (amino acids 2-376 of SEQ ID NO: 16);

(12) at least 85%, 90%, 93%, 95%, 97% or 98% sequence identity to SEQ ID NO:82 or the catalytic domain thereof (amino acids 2-375 of SEQ ID NO:82); and/or

(13) at least 90%, 93%, 95%, 97% or 98% sequence identity to SEQ ID NO:32 or the catalytic domain thereof (amino acids 2-377 of SEQ ID NO:32).

The XIs of the disclosure can be characterized in terms of their activity. In some embodiments, a XI of the disclosure has at least 1.3 times the activity of the *Orpinomyces* sp. XI assigned Genbank Accession No. 169733248 ("Op-XI") at pH 7.5, for example using the assay described in any of Examples 5, 7 and 8. In certain specific embodiments, a XI of the disclosure has an activity ranging from 1.25 to 3.0 times, from 1.5 to 3 times, from 1.5 to 2.25 times, or from 0.1.75 to 3 times the activity of Op-XI at pH 7.5.

The XIs of the disclosure can also be characterized in terms of their tolerance to acidic environments (e.g., at a pH of 6.5 or 6). In some embodiments, a XI of the disclosure has at least 1.9 times the activity of the Op-XI at pH 6, for example using the assay described in Example 8. In certain specific embodiments, a XI of the disclosure has an activity ranging from 1.9 to 4.1 times, from 2.4 to 4.1 times, from 2.4 to 3.9 times, or 2.4 to 4.1 times the activity of Op-XI at pH 6.

Tolerance to acidic environments can also be characterized as a ratio of activity at pH 6 to activity at pH 7.5 ("a pH 6 to pH 7.5 activity ratio"), for example as measured using the assay of Example 8. In some embodiments, the pH 6 to pH 7.5 activity ratio is at least 0.5 or at least 0.6. In various embodiments, the pH 6 to pH 7.5 activity ratio is 0.5-0.9 or 0.6-0.9.

In another aspect, the disclosure is directed to a nucleic acid which encodes a XI polypeptide of the disclosure. In various embodiments, the nucleic acid comprises a nucleotide sequence with at least 70%, 75%, 80%, 85%, 90%, 93%, 95%, 96%, 98%, 99% or 100% sequence identity to the nucleotide sequence of any one of SEQ ID NOS:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63; 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, and 175, or the portion of any of the foregoing sequences encoding a XI catalytic domain or dimerization domain.

In other aspects, the disclosure is directed to a vector comprising a XI-encoding nucleotide sequence, for example a vector having an origin of replication and/or a promoter sequence operably linked to the XI-encoding nucleotide sequence. The promoter sequence can be one that is operable in a eukaryotic cell, for example in a fungal cell. In some embodiments, the promoter is operable in yeast (e.g., *S. cerevisiae*) or filamentous fungi.

In yet another aspect, the disclosure is directed to a recombinant cell comprising a nucleic acid that encodes a XI polypeptide. Particularly, the cell is engineered to express any of the XI polypeptides described herein. The recombinant cell may be of any species, and is preferably a eukaryotic cell, for example a yeast cell. Suitable genera of yeast include *Saccharomyces, Kluyveromyces, Candida, Pichia, Schizosaccharomyces, Hansenula, Klockera, Schwanniomyces, Issatchenkia* and *Yarrowia*. In specific embodiments, the recombinant cell is a *S. cerevisiae, S. bulderi, S. barnetti, S. exiguus, S. uvarum, S. diastaticus, K. lactis, I. orientalis, K. marxianus* or *K. fragilis*. Suitable genera of filamentous fungi include *Aspergillus, Penicillium, Rhizopus, Chrysosporium, Myceliophthora, Trichoderma, Humicola, Acremonium* and *Fusarium*. In specific embodiments, the recombinant cell is an *Aspergillus niger, Aspergillus oryzae, Trichoderma reesei, Penicillium chrysogenum, Myceliophthora thermophila*, or *Rhizopus oryzae*.

The recombinant cell may also be mutagenized or engineered to include modifications other than the recombinant expression of XI, particularly those that make the cell more suited to utilize xylose in a fermentation pathway. Exemplary additional modifications create one, two, three, four, five or even more of the following phenotypes: (a) increase in xylose transport into the cell; (b) increase in aerobic growth rate on xylose; (c) increase in xylulose kinase activity; (d) increase in flux through the pentose phosphate pathway into glycolysis, (e) decrease in aldose reductase activity, (f) decrease in sensitivity to catabolite repression, (g) increase in tolerance to biofuels, e.g., ethanol, (h) increase tolerance to intermediate production (e.g., xylitol), (i) increase in temperature tolerance, (j) osmolarity of organic acids, and (k) a reduced production of byproducts.

Increases in activity can be achieved by increased expression levels, for example expression of a hexose or pentose (e.g., xylose) transporter, a xylulose kinase, a glycolytic enzyme, or an ethanologenic enzyme is increased. The increased expression levels are achieved by overexpressing an endogenous protein or by expressing a heterologous protein.

Other modifications to the recombinant cell that are part of the disclosure are modifications that decrease the activity of genes or pathways in the recombinant cell. Preferably, the expression levels of one, two, three or more of the genes for hexose kinase, MIG-1, MIG-2, XR, aldose reductase, and XDH are reduced. Reducing gene activity can be achieved by a targeted deletion or disruption of the gene (and optionally reintroducing the gene under the control of a different promoter that drives lower levels of expression or inducible expression).

In yet other aspects, the disclosure is directed to methods of producing fermentation products, for example one or more of ethanol, butanol, diesel, lactic acid, 3-hydroxypropionic acid, acrylic acid, acetic acid, succinic acid, citric acid, malic acid, fumaric acid, itaconic acid, an amino acid, 1,3-propane-diol, ethylene, glycerol, a β-lactam antibiotic and a cephalosporin. Typically, a cell that recombinantly expresses a XI of the disclosure is cultured in a xylose-containing medium, for example a medium supplemented with a lignocellulosic hydrolysate. The media may also contain glucose, arabinose, or other sugars, particularly those derived from lignocellulose. The media may be of any pH, particularly a pH between 3.0 and 9.0, preferably between 4.0 and 8.0, more preferably between 5.0 and 8.0, even more preferably between 6.0 and 7.5. The culture may occur in any media where the culture is under anaerobic or aerobic conditions, preferably under anaerobic conditions for production of compounds mentioned above and aerobically for biomass/cellular production. Optionally, the methods further comprise recovering the fermentation product produced by the recombinant cell.

DETAILED DESCRIPTION OF THE INVENTION

Xylose Isomerase Polypeptides

Figure 1A:
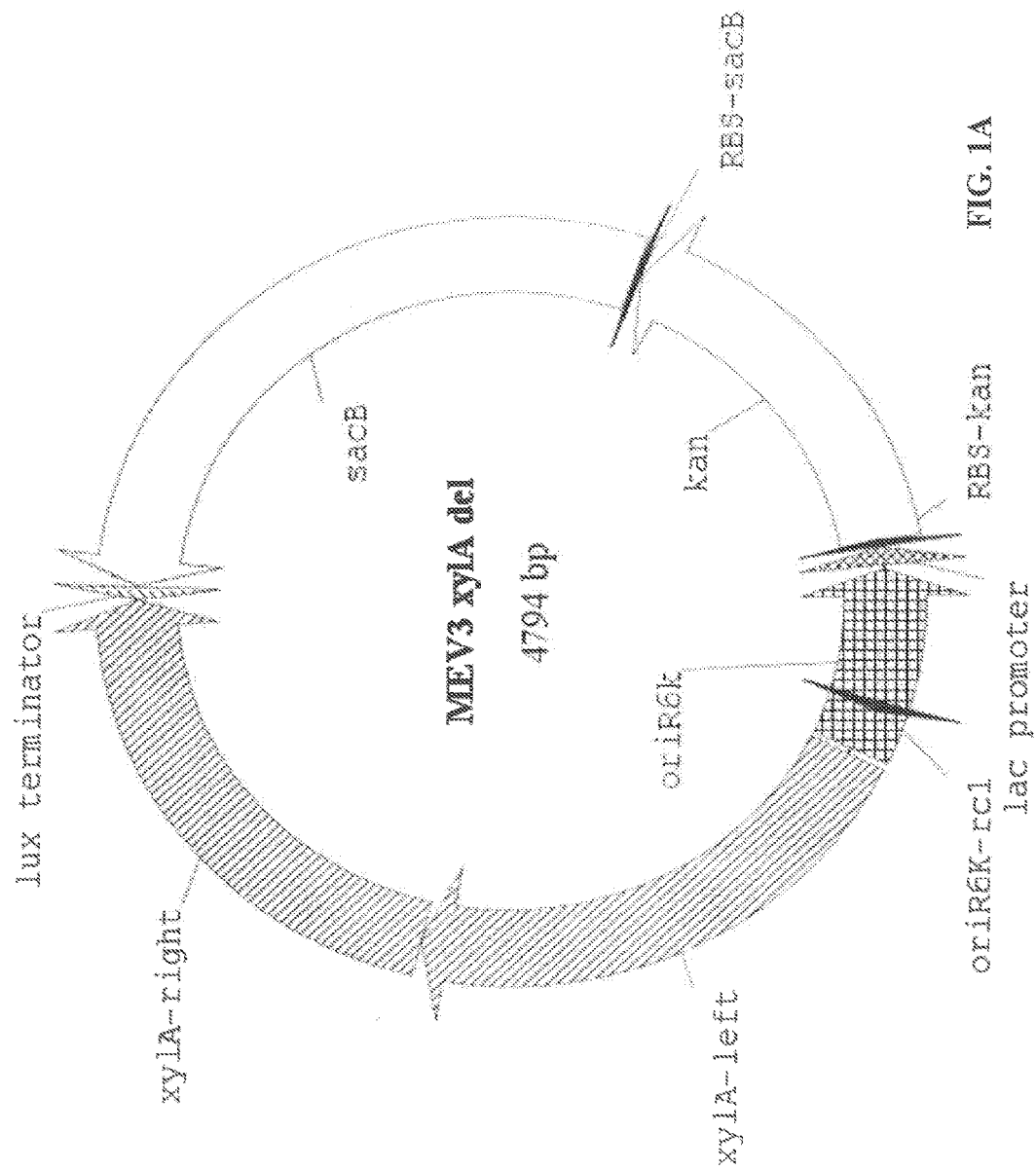
FIGS. 1A-1B are maps for the vector pMEV-ΔxylA (MEV3 xylA del) and PCR-BluntII-TOPO-xylA, respectively, used in the activity-based screen for XIs.

A "xylose isomerase" or "XI" is an enzyme that catalyzes the direct isomerisation of D-xylose into D-xylulose and/or vice versa. This class of enzymes is also known as D-xylose ketoisomerases. A xylose isomerase herein may also be capable of catalyzing the conversion between D-glucose and D-fructose (and accordingly may therefore be referred to as a glucose isomerase).

A "XI polypeptide of the disclosure" or a "XI of the disclosure" is a xylose isomerase having an amino acid sequence that is related to any one of SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, or 176. In some embodiments, the xylose isomerase of the disclosure has an amino acid sequence that is at least about 70%, at least 80%, at least 90%, at least 95%, at least 96%, at least 98%, or at least 99% sequence identity thereto, or to a catalytic or dimerization domain thereof. The xylose isomerase of the disclosure can also have 100% sequence identity to one of the foregoing sequences.

The disclosure provides isolated, synthetic or recombinant XI polypeptides comprising an amino acid sequence having at least about 80%, e.g., at least about 81%, 82%, 83%, 84%, 85%, 86%, 87%, 88%, 89%, 90%, 91%, 92%, 93%, 94%, 95%, 96%, 97%, 98%, 99%, or complete (100%) sequence identity to a polypeptide of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, or 176, over a region of at least about 10, e.g., at least about 15, 20, 25, 30, 35, 40, 45, 50, 55, 60, 65, 70, 75, 80, 85, 90, 95, 100, 125, 150, 175, 200, 225, 250, 275, 300, 325, or 350 residues, or over the full length of the polypeptide, over the length of catalytic domain, or over the length of the dimerization domain.

The XI polypeptides of the disclosure can be encoded by a nucleic acid sequence having at least about 80%, about 85%, about 86%, about 87%, about 88%, about 89%, or about 90% sequence identity to 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, or 175, or by a nucleic acid sequence capable of hybridizing under high stringency conditions to a complement of SEQ ID NO: 1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 1.51, 153, 155, 157, 159, 161, 163, 165, 167, 169, 171, 173, or 175, or to a fragment thereof. Exemplary nucleic acids of the disclosure are described in the following subtitled section "Xylose Isomerase Nucleic Acids".

In specific embodiments, a polypeptide of the disclosure comprises an amino acid sequence having:
(1) (a) at least 97% or 98% sequence identity to SEQ ID NO:78 or the catalytic domain thereof (amino acids 2-377 of SEQ ID NO:78) and/or (b) at least 80%, 85%, 90%, 93% or 95% sequence identity to SEQ ID NO:78 or the catalytic domain thereof (amino acids 2-377 of SEQ ID NO:78) and further comprises (i) SEQ ID NO:212 or SEQ ID NO:213 and/or (ii) SEQ ID NO:214;
(2) (a) at least 95%, 97% or 98% sequence identity to SEQ ID NO:96 or the catalytic domain thereof (amino acids 2-377 of SEQ ID NO:96) and/or (b) at least 80%, 85%, 90%, 93% or 95% sequence identity to SEQ ID NO:96 or the catalytic domain thereof (amino acids 2-377 of SEQ ID NO:96) and further comprises (i) SEQ ID NO:212 or SEQ ID NO:213 and/or (ii) SEQ ID NO:214;
(3) at least 80%, 85%, 90%, 93%, 95%, 97% or 98% sequence identity to SEQ ID NO:38 or the catalytic domain thereof (amino acids 2-374 of SEQ ID NO:38), and optionally further comprises one, two, three, four or all five of (i) SEQ ID NO:206 or SEQ ID NO:207; (ii) SEQ ID NO:208; (iii) SEQ ID NO:209; (iv) SEQ ID NO:210; and (iv) SEQ ID NO:211;

(4) at least 80%, 85%, 90%, 93%, 95%, 97% or 98% sequence identity to SEQ ID NO:2 or the catalytic domain thereof (amino acids 2-374 of SEQ ID NO:2);

(5) at least 93%, 95%, 97% or 98% sequence identity to SEQ ID NO:58 or the catalytic domain thereof (amino acids 2-376 of SEQ ID NO:58), (6) at least 80%, 85%, 90%, 93%, 95%, 97% or 98% sequence identity to SEQ ID NO:42 or the catalytic domain thereof (amino acids 2-375 of SEQ ID NO:42), and optionally further comprises one, two or all three of (i) SEQ ID NO:206 or SEQ ID NO:207; (ii) SEQ ID NO:210; and (iii) SEQ ID NO:211;

(7) (a) at least 97% or 98% sequence identity to SEQ ID NO:84 or the catalytic domain thereof (amino acids 2-376 of SEQ ID NO:84), and/or (b) at least 80%, 85%, 90%, 93% or 95% sequence identity to SEQ ID NO:84 or the catalytic domain thereof (amino acids 2-376 of SEQ ID NO:84) and further comprises (i) SEQ ID NO:212 or SEQ ID NO:213 and/or (ii) SEQ ID NO:214;

(8) (a) at least 97% or 98% sequence identity to SEQ ID NO:80 or the catalytic domain thereof (amino acids 2-377 of SEQ ID NO:80) and/or (b) at least 80%, 85%, 90%, 93% or 95% sequence identity to SEQ ID NO:80 or the catalytic domain thereof (amino acids 2-377 of SEQ ID NO:80) and further comprises (i) SEQ ID NO:212 or SEQ ID NO:213 and/or (ii) SEQ ID NO:214;

(9) at least 93%, 95%, 97% or 98% sequence identity to SEQ ID NO:54 or the catalytic domain thereof (amino acids 2-376 of SEQ ID NO:54);

(10) at least 80%, 85%, 90%, 93%, 95%, 97% or 98% sequence identity to SEQ ID NO:46 or the catalytic domain thereof (amino acids 2-376 of SEQ ID NO:46), and optionally further comprises SEQ ID NO:206 or SEQ ID NO:207;

(11) at least 90%, 93%, 95%, 97% or 98% sequence identity to SEQ ID NO: 16 or the catalytic domain thereof (amino acids 2-376 of SEQ ID NO: 16);

(12) at least 85%, 90%, 93%, 95%, 97% or 98% sequence identity to SEQ ID NO:82 or the catalytic domain thereof (amino acids 2-375 of SEQ ID NO:82); and/or

(13) at least 90%, 93%, 95%, 97% or 98% sequence identity to SEQ ID NO:32 or the catalytic domain thereof (amino acids 2-377 of SEQ ID NO:32).

An example of an algorithm that is suitable for determining sequence similarity is the BLAST algorithm, which is described in Altschul et al., 1990, J. Mol. Biol. 215:403-410. Software for performing BLAST analyses is publicly available through the National Center for Biotechnology Information. This algorithm involves first identifying high scoring sequence pairs (HSPs) by identifying short words of length W in the query sequence that either match or satisfy some positive-valued threshold score T when aligned with a word of the same length in a database sequence. These initial neighborhood word hits act as starting points to find longer HSPs containing them. The word hits are expanded in both directions along each of the two sequences being compared for as far as the cumulative alignment score can be increased. Extension of the word hits is stopped when: the cumulative alignment score falls off by the quantity X from a maximum achieved value; the cumulative score goes to zero or below; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff & Henikoff, 1992, Proc. Nat'l. Acad. Sci. USA 89:10915-10919) alignments (B) of 50, expectation (E) of 10, M'5, N'-4, and a comparison of both strands.

Any of the amino acid sequences described herein can be produced together or in conjunction with at least 1, e.g., at least (or up to) 2, 3, 5, 10, or 20 heterologous amino acids flanking each of the C- and/or N-terminal ends of the specified amino acid sequence, and or deletions of at least 1, e.g., at least (or up to) 2, 3, 5, 10, or 20 amino acids from the C- and/or N-terminal ends of a XI of the disclosure.

The XIs of the disclosure can be characterized in terms of their activity. In some embodiments, a XI of the disclosure has at least 1.3 times the activity of the *Orpinomyces* sp. XI assigned Genbank Accession No. 169733248 ("Op-XI") at pH 7.5, for example using the assay described in any of Examples 5, 7 and 8. In certain specific embodiments, a XI of the disclosure has an activity ranging from 1.25 to 3.0 times, from 1.5 to 3 times, from 1.5 to 2.25 times, or from 1.75 to 3 times the activity of Op-XI at pH 7.5.

The XIs of the disclosure can also be characterized in terms of their tolerance to acidic environments (e.g., at a pH of 6.5 or 6). In some embodiments, a XI of the disclosure has at least 1.9 times the activity of the Op-XI at pH 6, for example using the assay described in Example 8. In certain specific embodiments, a XI of the disclosure has an activity ranging from 1.9 to 4.1 times, from 2.4 to 4.1 times, from 2.4 to 3.9 times, or 2.4 to 4.1 times the activity of Op-XI at pH6.

Tolerance to acidic environments can also be characterized as a ratio of activity at pH 6 to activity at pH 7.5 ("a pH 6 to pH 7.5 activity ratio"), for example as measured using the assay of Example 8. In some embodiments, the pH 6 to pH 7.5 activity ratio is at least 0.5 or at least 0.6. In various embodiments, the pH 6 to pH 7.5 activity ratio is 0.5-0.9 or 0.6-0.9.

The xylose isomerases of the disclosure can have one or more (e.g., up to 2, 3, 5, 10, or 20) conservative amino acid substitutions relative to the polypeptide of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, or 176 or to the portion thereof of discussed above. The conservative substitutions can be chosen from among a group having a similar side chain to the reference amino acid. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Accordingly, exemplary conservative substitutions for each of the naturally occurring amino acids are as follows: ala to ser; arg to lys; asn to gin or his; asp to glu; cys to ser or ala; gin to asn; glu to asp; gly to pro; his to asn or gin; ile to leu or val; leu to ile or val; lys to arg; gin or glu; met to leu or ile; phe to met, leu or tyr; ser to thr; thr to ser; trp to tyr; tyr to trp or phe; and, val to ile or leu.

The present disclosure also provides a fusion protein that includes at least a portion (e.g., a fragment or domain) of a XI polypeptide of the disclosure attached to one or more fusion segments, which are typically heterologous to the XI polypeptide. Suitable fusion segments include, without limitation, segments that can provide other desirable biological activity or facilitate purification of the XI polypeptide (e.g., by affinity chromatography). Fusion segments can be joined to the amino or carboxy terminus of a XI polypeptide. The fusion segments can be susceptible to cleavage.

Xylose Isomerase Nucleic Acids

A "XI nucleic acid of the disclosure" is a nucleic acid encoding a xylose isomerase of the disclosure. In certain embodiments, the xylose isomerase nucleic acid of the disclosure is encoded by a nucleotide sequence of any one of SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, or 175, or a sequence having at least about 70%, at least 80%, at least 90%, at least 95%, at least 96%, at least 98%, or at least 99% sequence identity thereto. The xylose isomerase nucleic acid of the disclosure can also have 100% sequence identity to one of the foregoing sequences.

The present disclosure provides nucleic acids encoding a polypeptide of the disclosure, for example one described in the preceding subtitled section "Xylose Isomerase Polypeptides". The disclosure provides isolated, synthetic or recombinant nucleic acids comprising a nucleic acid sequence having at least about 70%, e.g., at least about 71%, 72%, 73%, 74%, 75%, 76%, 77%, 78%, 79%, 80%, 81%, 82%, 83%, 84%, 85%, 86%, 87%, 88%; 89%, 90%, 91%, 92%, 93%, 94%, 95%, 96%, 97%, 98%, or 99%, or complete (100%) sequence identity to a nucleic acid of SEQ ID NO:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93, 95, 97, 99, 101, 103, 105, 107, 109, 111, 113, 115, 117, 119, 121, 123, 125, 127, 129, 131, 133, 135, 137, 139, 141, 143, 145, 147, 149, 151, 153, 155, 157, 159, 161, 163, 165, 167, 169, 171, 173, or 175, over a region of at least about 0.10, e.g., at least about 15, 20, 25, 30, 35, 40, 45, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, or 2000 nucleotides.

Nucleic acids of the disclosure also include isolated, synthetic or recombinant nucleic acids encoding a XI polypeptide having the sequence of SEQ ID NO:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, or 176, and subsequences thereof (e.g., a conserved domain or a catalytic domain), and variants thereof.

To increase the likelihood that a XI polypeptide is recombinantly expressed, a XI nucleic acid may be adapted to optimize its codon usage to that of the chosen cell. Several methods for codon optimization are known in the art. For expression in yeast, an exemplary method to optimize codon usage of the nucleotide sequences to that of the yeast is a codon pair optimization technology as disclosed in WO2006/077258 and/or WO2008/000632. WO2008/000632 addresses codon-pair optimization. Codon-pair optimization is a method wherein the nucleotide sequences encoding a polypeptide are modified with respect to their codon-usage, in particular the codon-pairs that are used, to obtain improved expression of the nucleotide sequence encoding the polypeptide and/or improved production of the encoded polypeptide. Codon pairs are defined as a set of two subsequent triplets (codons) in a coding sequence.

Host Cells and Recombinant Expression

The disclosure also provides host cells transformed with a XI nucleic acid and recombinant host cells engineered to express XI polypeptides. The XI nucleic acid construct may be extrachromosomal, on a plasmid, which can be a low copy plasmid or a high copy plasmid. The nucleic acid construct may be maintained episomally and thus comprise a sequence for autonomous replication, such as an autosomal replication sequence. Alternatively, a XI nucleic acid may be integrated in one or more copies into the genome of the cell. Integration into the cell's genome may occur at random by non-homologous recombination but preferably, the nucleic acid construct may be integrated into the cell's genome by homologous recombination as is well known in the art. In certain embodiments, the host cell is bacterial or fungal (e.g., a yeast or a filamentous fungus).

Suitable host cells of the bacterial genera include, but are not limited to, cells of *Escherichia*, *Bacillus*, *Lactobacillus*, *Pseudomonas*, and *Streptomyces*. Suitable cells of bacterial species include, but are not limited to, cells of *Escherichia coli*, *Bacillus subtilis*, *Bacillus licheniformis*, *Lactobacillus brevis*, *Pseudomonas aeruginosa*, and *Streptomyces lividans*.

Suitable host cells of the genera of yeast include, but are not limited to, cells of *Saccharomyces*, *Kluyveromyces*, *Candida*, *Pichia*, *Schizosaccharomyces*, *Hansenula*, *Klockera*, *Schwanniomyces*, *Phaffia*, *Issatchenkia* and *Yarrowia*. In specific embodiments, the recombinant cell is a *S. cerevisiae*, *C. albicans*, *S. pombe*, *S. bulderi*, *S. barnetti*, *S. exiguus*, *S. uvarum*, *S. diastaticus*, *H. polymorpha*, *K. lactis*, *I. orientalis*, *K. marxianus*, *K. fragilis*, *P. pastoris*, *P. canadensis*, *K. marxianus* or *P. rhodozyma*. Exemplary yeast strains that are suitable for recombinant XI expression include, but are not limited to, Lallemand LYCC 6391, Lallemand LYCC 6939, Lallemand LYCC 6469, (all from Lallemand, Inc., Montreal, Canada); NRRL YB-1952 (ARS (NRRL) Collection, U.S. Department of Agriculture); and BY4741.

Suitable host cells of filamentous fungi include all filamentous forms of the subdivision Eumycotina. Suitable cells of filamentous fungal genera include, but are not limited to, cells of *Acremonium*, *Aspergillus*, *Aureobasidium*, *Bjerkandera*, *Ceriporiopsis*, *Chrysoporium*, *Coprinus*, *Coriolus*, *Corynascus*, *Chaetomium*, *Cryptococcus*, *Filobasidium*, *Fusarium*, *Gibberella*, *Humicola*, *Hypocrea*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Scytaldium*, *Schizophyllum*, *Sporotrichum*, *Talaromyces*, *Thermoascus*, *Thielavia*, *Tolypocladium*, *Trametes*, and *Trichoderma*. In certain aspects, the recombinant cell is a *Trichoderma* sp. (e.g., *Trichoderma reesei*), *Penicillium* sp., *Humicola* sp. (e.g., *Humicola insolens*); *Aspergillus* sp. (e.g., *Aspergillus niger*), *Chrysosporium* sp., *Fusarium* sp., or *Hypocrea* sp. Suitable cells can also include cells of various anamorph and teleomorph forms of these filamentous fungal genera.

Suitable cells of filamentous fungal species include, but are not limited to, cells of *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium lucknowense*, *Fusarium bactridioides*, *Fusarium cerealis*, *Fusarium crookwellense*, *Fusarium cul-* morum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Neurospora intermedia, Penicillium purpurogenum, Penicillium canescens, Penicillium solitum, Penicillium funiculosum, Phanerochaete chrysosporium, Phlebia radiate, Pleurotus eryngii, Talaromyces flavus, Thielavia terrestris, Trametes villosa, Trametes versicolor, Trichoderma harzianum, Trichoderma koningii, Trichoderma longibrachiatum; Trichoderma reesei, and Trichoderma viride.

Typically, for recombinant expression, the XI nucleic acid will be operably linked to one or more nucleic acid sequences capable of providing for or aiding the transcription and/or translation of the XI sequence, for example a promoter operable in the organism in which the XI is to be expressed. The promoters can be homologous or heterologous, and constitutive or inducible.

Preferably, the XI polypeptide is expressed in the cytosol and therefore lacks a mitochondrial or peroxisomal targeting signal.

Where recombinant expression in a filamentous fungal host is desired, the promoter can be a fungal promoter (including but not limited to a filamentous fungal promoter), a promoter operable in plant cells, a promoter operable in mammalian cells.

As described in U.S. provisional application No. 61/553,901, filed Oct. 31, 2011, the contents of which are hereby incorporated in their entireties, promoters that are constitutively active in mammalian cells (which can derived from a mammalian genome or the genome of a mammalian virus) are capable of eliciting high expression levels in filamentous fungi such as Trichoderma reesei. An exemplary promoter is the cytomegalovirus ("CMV") promoter.

As described in U.S. provisional application No. 61/553,897, filed Oct. 31, 2011, the contents of which are hereby incorporated in their entireties, promoters that are constitutively active in plant cells (which can derived from a plant genome or the genome of a plant virus) are capable of eliciting high expression levels in filamentous fungi such as Trichoderma reesei. Exemplary promoters are the cauliflower mosaic virus ("CaMV") 35S promoter or the Commelina yellow mottle virus ("CoYMV") promoter.

Mammalian, mammalian viral, plant and plant viral promoters can drive particularly high expression when the associated 5' UTR sequence (i.e., the sequence which begins at the transcription start site and ends one nucleotide (nt) before the start codon), normally associated with the mammalian or mammalian viral promoter is replaced by a fungal 5' UTR sequence.

The source of the 5' UTR can vary provided it is operable in the filamentous fungal cell. In various embodiments, the 5' UTR can be derived from a yeast gene or a filamentous fungal gene. The 5' UTR can be from the same species, one other component in the expression cassette (e.g., the promoter or the XI coding sequence), or from a different species. The 5' UTR can be from the same species as the filamentous fungal cell that the expression construct is intended to operate in. In an exemplary embodiment, the 5' UTR comprises a sequence corresponding to a fragment of a 5' UTR from a T. reesei glyceraldehyde-3-phosphate dehydrogenase (gpd). In a specific embodiment, the 5' UTR is not naturally associated with the CMV promoter Examples of other promoters that can be used include, but are not limited to, a cellulase promoter, a xylanase promoter, the 1818 promoter (previously identified as a highly expressed protein by EST mapping Trichoderma). For example, the promoter can suitably be a cellobiohydrolase, endoglucanase, or β-glucosidase promoter. A particularly suitable promoter can be, for example, a T. reesei cellobiohydrolase, endoglucanase, or β-glucosidase promoter. Non-limiting examples of promoters include a cbh1, cbh2, egl1, egl2, egl3, egl4, egl5, pki1, gpd1, xyn1, or xyn2 promoter.

For recombinant expression in yeast, suitable promoters for S. cerevisiae include the MFα1 promoter, galactose inducible promoters such as the GAL1, GAL7 and GAL10 promoters, glycolytic enzyme promoters including the TPI and PGK promoters, the TDH3 promoter, the TEF1 promoter, the TRP1 promoter, the CYCI promoter, the CUP1 promoter, the PHO5 promoter, the ADH1 promoter, and the HSP promoter. Promoters that are active at different stage of growth or production (e.g., idiopliase or trophophase) can also be used (see, e.g., Puig et al., 1996, Biotechnology Letters 18(8):887-892; Puig and Pérez-Ortin, 2000, Systematic and Applied Microbiology 23(2):300-303; Simon et al., 2001, Cell 106:697-708; Wittenberg and Reed, 2005, Oncogene 24:2746-2755). A suitable promoter in the genus Pichia sp. is the AOXI (methanol utilization) promoter.

The engineered host cells can be cultured in conventional nutrient media modified as appropriate for activating promoters, selecting transformants, or amplifying the nucleic acid sequence encoding the XI polypeptide. Culture conditions, such as temperature, pH and the like, are those previously used with the host cell selected for expression, and will be apparent to those skilled in the art. As noted, many references are available for the culture and production of many cells, including cells of bacterial and fungal origin. Cell culture media in general are set forth in Atlas and Parks (eds.), 1993, The Handbook of Microbiological Media, CRC Press, Boca Raton, Fla., which is incorporated herein by reference. For recombinant expression in filamentous fungal cells, the cells are cultured in a standard medium containing physiological salts and nutrients, such as described in Pourquie et al., 1988, Biochemistry and Genetics of Cellulose Degradation, eds. Aubert, et al., Academic Press, pp. 71-86; and Ilmen et al, 1997, Appl. Environ. Microbiol. 63:1298-1306. Culture conditions are also standard, e.g., cultures are incubated at 30° C. in shaker cultures or fermenters until desired levels of XI expression are achieved. Preferred culture conditions for a given filamentous fungus may be found in the scientific literature and/or from the source of the fungi such as the American Type Culture Collection (ATCC). After fungal growth has been established, the cells are exposed to conditions effective to cause or permit the expression of a XI.

In cases where a XI coding sequence is under the control of an inducible promoter, the inducing agent, e.g., a sugar, metal salt or antibiotics, is added to the medium at a concentration effective to induce XI expression.

In addition to recombinant expression of a XI polypeptide, a host cell of the disclosure may further include one or more genetic modifications that increase the cell's ability to utilize xylose as a substrate in a fermentation process. Exemplary additional modifications create one, two, three, four, five or even more of the following phenotypes: (a)

increase in xylose transport into the cell; (b) increase in aerobic growth rate on xylose; (c) increase in xylulose kinase activity; (d) increase influx through the pentose phosphate pathway into glycolysis, (e) modulating in aldose reductase activity, (f) decrease in sensitivity to catabolite repression, (g) increase in tolerance to biofuels, e.g., ethanol, (h) increase tolerance to intermediate production (for example xylitol), (i) increase in temperature tolerance, (j) osmolarity of organic acids, and (k) a reduced production of byproducts.

As illustrated below, a modification that results in one or more of the foregoing phenotypes can be a result of increasing or decreasing expression of an endogenoius protein (e.g., by at least a factor of about 1.1, about 1.2, about 1.5, about 2, about 5, about 10 or about 20) or a result of introducing expression of a heterologous polypeptide. For avoidance of doubt, "decreasing" or "reducing" gene expression encompasses eliminating expression. Decreasing (or reducing) the expression of an endogenous protein can be accomplished by inactivating one or more (or all) endogenous copies of a gene in a cell. A gene can be inactivated by deletion of at least part of the gene or by disruption of the gene. This can be achieved by deleting the some or all of a gene coding sequence or regulatory sequence whose deletion results in a reduction of gene expression in the cell. Examples of modifications that increase xylose utilization or yield of fermentation product are described below.

Increasing Xylose Transport: Xylose transport can be increased directly or indirectly. For example, a recombinant cell may include one or more genetic modifications that result in expression of a xylose transporter. Exemplary transporters include, but are not limited to GXF1, SUT1 and At6g59250 from *Candida intermedia, Pichia stipitis* (now renamed *Scheffersomyces stipitis*; the terms are used interchangeably herein) and *Arabidopsis thaliana*, respectively (Runquist et al., 2010, Biotechnol. Biofuels 3:5), as well as HXT4, HXT5, HXT7, GAL2, AGT1, and GXF2 (see, e.g., Matsushika et al., 2009, Appl. Microbiol. Biotechnol. 84:37-53). Other transporters include PsAraT, SUT2-4 and XUT1-5 from *P. stiptis*; GXS1 from *Candida intermedia*; XylHP and DEHAOD02167 from *Debaryomyces hansenii*; and YALIOC06424 from *Yarrowia lipolytica* (see, e.g., Young et al., 2011, Appl. Environ. Microbiol. 77:3311-3319). Xylose transport can also be increased by (over-) expression of low-affinity hexose transporters, which are capable of non-selectively transporting sugars, including xylose, into the cell once glucose levels are low (e.g., 0.2-1.0 g/l); and includes CgHXT1-CgHXT5 from *Colletotrichum graminicola*. The foregoing modifications can be made singly or in combinations of two, three or more modifications.

Increasing Xylulose Kinase Activity: Xylulose kinase activity can be increased by overexpression of a xylulose kinase, e.g., xylulose kinase (XKS1; *Saccharomyces* genome database ("SGD") accession no. YGR194C) of *S. cerevisiae*, particularly where the recombinant cell is a yeast cell. In one embodiment, a *S. cerevisiae* cell is engineered to include at least 2 additional copies of xylulose kinase under the control of a strong constitutive promoter such as TDH3, TEF1 or PGK1. In another embodiment, overexpression of an endogenous xylulose kinase was engineered. This xylulose kinase having improved kinetic activities through the use of protein engineering techniques known by those skilled in the art.

Increasing Flux Through the Pentose Phosphate Pathway: This can be achieved by increasing expression of one or more genes in the pentose phosphate pathway, for example *S. cerevisiae* transaldolase TAL1 (SGD accession no. YLR354C), transketolase TKL1 (SGD accession no. YPR074C), ribulose 5-phosphate epimerase RPE1 (SGD accession no. YJL121C) and ribose-5-phosphate ketoisomerase RKI1 (SGD accession no. YOR095C) and/or one or more genes to increase glycolytic flux, for example *S. cerevisiae* pyruvate kinase PYK1/CDC19 (SGD accession no. YAL038W), pyruvate decarboxylase PDC1 (SGD accession no. YLR044C), pyruvate decarboxylase PDC5 (SGD accession no. YLR134W), pyruvate decarboxylase PDC6 (SGD accession no. YGR087C), the alcohol dehydrogenases ADH1-5 (SGD accession nos. YOL086C, YMR303C, YMR083W, YGL256W, and YBR145W, respectively), and hexose kinase HXK1-2 (SGD accession nos. YFR053C and YGL253W, respectively). In one embodiment, the yeast cell has one additional copy each of TAL1, TKL1, RPE1 and RKI1 from *S. cerevisiae* under the control of strong constitutive promoters (e.g., PGK1, TDH3, TEF1); and may also include improvements to glycolytic flux (e.g., increased copies of genes such as PYK1, PDC1, PDC5, PDC6, ADH1-5) and glucose-6-phosphate and hexokinase. The foregoing modifications can be made singly or in combinations of two, three or more modifications.

Modulating Aldose Reductase Activity: A recombinant cell can include one or more genetic modifications that increase or reduce (unspecific) aldose reductase (sometimes called aldo-keto reductase) activity. Aldose reductase activity can be reduced by one or more genetic modifications that reduce the expression of or inactivate a gene encoding an aldose reductase, for example *S. cerevisiae* GRE3 (SGD accession no. YHR104W).

In certain embodiments, GRE3 expression is reduced. In one aspect, the recombinant cell is a yeast cell in which the GRE3 gene is deleted. Deletion of GRE3 decreased xylitol yield by 49% and biomass production by 31%, but increased ethanol yield by 19% (Traff-Bjerre et al., 2004, Yeast 21:141-150). In another aspect, the recombinant cell is a yeast cell which has a reduction in expression of GRE3. Reducing GRE3 expression has been shown to result in a two-fold decrease in by-product (i.e., xylitol) formation and an associated improvement in ethanol yield (Traff et al., 2001, Appl. Environ. Microbiol. 67:5668-5674).

In another embodiment, the recombinant cell is a cell (optionally but not necessarily a yeast cell) in which GRE3 is overexpressed. In a study analyzing the effect of GRE3 overexpression in *S. cerevisiae* to investigate the effect on xylose utilization, an increase of about 30% in xylose consumption and about 120% in ethanol production was noted (Traff-Bjerre et al., 2004, Yeast 21:141-150).

Decreasing Xylose Reductase Activity: A recombinant cell may include one or more genetic modifications that reduce xylose reductase activity. Xylose reductase activity can be reduced by one or more genetic modifications that reduce the expression of or inactivate a gene encoding a xylose reductase.

Decreasing Sensitivity to Catabolite Repression: Glucose and other sugars, such as galactose or maltose, are able to cause carbon catabolite repression in Crabtree-positive yeast, such as *S. cerevisiae*. In one study, xylose was found to decrease the derepression of various enzymes of an engineered *S. cerevisiae* strain capable of xylose utilization by at least 10-fold in the presence of ethanol. Xylose also impaired the derepression of galactokinase and invertase (Belinchon & Gancedo, 2003, Arch. Microbiol. 180:293-297). In certain embodiments, in order to reduce catabolite sensitivity, yeast can include one or more genetic modifications that reduce expression of one or more of GRR1

(SGD accession no. YJR090C), the gene assigned SGD accession no. YLR042C, GAT1 (SGD accession no. YKR067W) and/or one or more genetic modifications that decrease expression of one or more of SNF1 (SGD accession no. YDR477W), SNF4 (SGD accession no. YGLI 15W), MIG1 (SGD accession no. YGL035C) and CRE1 (SGD accession no. YJL127C). In further embodiments, yeast can include one or more genetic modifications that result in overexpression of the pentose phosphate pathway enzymes. In yet further embodiments, yeast can include one or more genetic modifications that reduce expression of hexo-/glucokinase. In yet a further embodiment, yeast can include one or more genetic modifications that modulate the activity of one or more GATA factors, for example GAT1, DAL80 (SGD accession no. YKR034W), GZF3 (SGD accession no. YJL110C) and GLN3 (SGD accession no. YER040W). The foregoing modifications can be made singly or in combinations of two, three or more modifications.

Increasing Tolerance to Biofuels (e.g., Ethanol), Pathway Intermediates (e.g., Xvlitol), Organic Acids and Temperature: For efficient bioethanol production from lignocellulosic biomass, it is useful to improve cellular tolerance to toxic compounds released during the pretreatment of biomass. In one study, the gene encoding PHO13 (SGD accession no. YDL236W), a protein with alkaline phosphatase activity, was disrupted. This resulted in improved ethanol production from xylose in the presence of three major inhibitors (i.e., acetic acid, formic acid and furfural). Further, the specific ethanol productivity of the mutant in the presence of 90 mM furfural was four fold higher (Fujitomi et al., 2012, Biores. Tech., 111:161-166). Thus, in one embodiment, yeast has one or more genetic modifications that reduce PHO13 expression. In other embodiments, yeast, bacterial and fungal cells are evolved under selective conditions to identify strains that can withstand higher temperatures, higher levels of intermediates, higher levels of organic acids and/or higher levels of biofuels (e.g., ethanol). In yet other embodiments, yeast are engineered to reduce expression of FPS1 (SGD accession no. YLL043W); overexpress unsaturated lipid and ergosterol biosynthetic pathways; reduce expression of PHO13 and/or SSK2 (SGD accession no. YNR031C); modulate global transcription factor cAMP receptor protein, through increasing or decreasing expression; increase expression of MSN2 (SGD accession no. YMR037C), RCN1 (SGD accession no. YKL159C), RSA3 (SGD accession no. YLR221C), CDC19 and/or ADH1; or increase expression of Rice ASR1. The foregoing modifications can be made singly or in combinations of two, three or more modifications.

Reducing Production of Byproducts:p Glycerol is one of the main byproducts in C6 ethanol production. Reducing glycerol is desirable for increasing xylose utilization by yeast. Production of glycerol can be reduced by deleting the gene encoding the FPS1 channel protein, which mediates glycerol export, and GPD2 (SGD accession no. YOL059W), which encodes glycerol-3-phosphate dehydrogenase; optionally along with overexpression of GLT1 (SGD accession no. YDL171C) and GLN1 (SGD accession no. YPR035W). In one study, FPS1 and GPD2 were knocked-out in one S. cerevisiae strain, and in another were replaced by overexpression of GLT1 and GLN1, which encode glutamate synthase and glutamine synthetase, respectively. When grown under microaerobic conditions, these strains showed ethanol yield improvements of 13.17% and 6.66%, respectively. Conversely, glycerol, acetic acid and pyruvic acid were found to all decrease, with glycerol down 37.4% and 41.7%, respectively (Zhang and Chen, 2008, Chinese J. Chem. Eng. 16:620-625).

Production of glycerol can also be reduced by deleting the NADH-dependent glycerol-3-phosphate dehydrogenase 1 (GPD1; SGD accession no. YDL022W) and/or the NADPH-dependent glutamate dehydrogenase 1 (GDH1; SGD accession no. YOR375C). Sole deletion of GPD1 or GDH1 reduces glycerol production, and double deletion results in a 46.4% reduction of glycerol production as compared to wild-type S. cerevisiae (Kim et al., 2012, Bioproc. Biosys. Eng. 35:49-54). Deleting FPS1 can decrease production of glycerol for osmoregulatory reasons.

Reducing production of acetate can also increase xylose utilization. Deleting ALD6 (SGD accession no. YPL061W) can decrease production of acetate.

ADH2 can also be deleted to reduce or eliminate acetyl-aldehyde formation from ethanol and thereby increase ethanol yield.

The foregoing modifications to reduce byproduct formation can be made singly or in combinations of two, three or more modifications.

In addition to ethanol production, a recombinant XI-expressing cell of the disclosure can be suitable for the production of non-ethanolic fermentation products. Such non-ethanolic fermentation products include in principle any bulk or fine chemical that is producible by a eukaryotic microorganism such as a yeast or a filamentous fungus. Such fermentation products may be, for example, butanol, lactic acid, 3-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic or a cephalosporin. A preferred modified host cell of the diclosure for production of non-ethanolic fermentation products is a host cell that contains a genetic modification that results in decreased alcohol dehydrogenase activity.

Cells expressing the XI polypeptides of the disclosure can be grown under batch, fed-batch or continuous fermentations conditions. Classical batch fermentation is a closed system, wherein the compositions of the medium is set at the beginning of the fermentation and is not subject to artificial alternations during the fermentation. A variation of the batch system is a fed-batch fermentation in which the substrate is added in increments as the fermentation progresses. Fed-batch systems are useful when catabolite repression is likely to inhibit the metabolism of the cells and where it is desirable to have limited amounts of substrate in the medium. Batch and fed-batch fermentations are common and well known in the art. Continuous fermentation is an open system where a defined fermentation medium is added continuously to a bioreactor and an equal amount of conditioned medium is removed simultaneously for processing. Continuous fermentation generally maintains the cultures at a constant high density where cells are primarily in log phase growth. Continuous fermentation systems strive to maintain steady state growth conditions. Methods for modulating nutrients and growth factors for continuous fermentation processes as well as techniques for maximizing the rate of product formation are well known in the art of industrial microbiology.

Fermentation Methods

A further aspect the disclosure relates to fermentation processes in which the recombinant XI-expressing cells are used for the fermentation of carbon source comprising a source of xylose. Thus, in certain embodiments, the disclosure provides a process for producing a fermentation product by (a) fermenting a medium containing a source of xylose with a recombinant XI-expressing cell as defined herein above, under conditions in which the cell ferments xylose to the fermentation product, and optionally, (b) recovery of the fermentation product. In some embodiments, the fermentation product is an alcohol (e.g., ethanol, butanol, etc.), a fatty alcohol (e.g., a C8-C20 fatty alcohol), a fatty acid (e.g., a C8-C20 fatty acid), lactic acid, 3-hydroxypropionic acid, acrylic acid, acetic acid, succinic acid, citric acid, malic acid, fumaric acid, an amino acid, 1,3-propanediol, itaconic acid, ethylene, glycerol, and a β-lactam antibiotic such as Penicillin G or Penicillin V and fermentative derivatives thereof and cephalosporins. The fermentation process may be an aerobic or an anaerobic fermentation process.

In addition to a source of xylose the carbon source in the fermentation medium may also comprise a source of glucose. The source of xylose or glucose may be xylose or glucose as such or may be any carbohydrate oligo- or polymer comprising xylose or glucose units, such as e.g., lignocellulose, xylans, cellulose, starch and the like. Most microorganisms possess carbon catabolite repression that results in sequential consumption of mixed sugars derived from the lignocellulose, reducing the efficacy of the overall process. To increase the efficiency of fermentation, microorganisms that are capable of simultaneous consumption of mixed sugars (e.g., glucose and xylose) have been developed, for example by rendering them less sensitive to glucose repression (see, e.g., Kim et al., 2010, Appl. Microbiol. Biotechnol. 88:1077-85 and Ho et al., 1999, Adv. Biochem. Eng. Biotechnol. 65:163-92). Such cells can be used for recombinant XI expression and in the fermentation methods of the disclosure.

The fermentation process is preferably run at a temperature that is optimal for the recombinant XI-expressing cells. Thus, for most yeasts or fungal host cells, the fermentation process is performed at a temperature which is less than 38° C., unless temperature tolerant mutant strains are used, in which case the temperature may be higher. For most yeast or filamentous fungal host cells, the fermentation process is suitably performed at a temperature which is lower than 35° C., 33° C., 30° C. or 28° C. Optionally, the temperature is higher than 20° C., 22° C., or 25° C.

An exemplary process is a process for the production of ethanol, whereby the process comprises the steps of: (a) fermenting a medium containing a source of xylose with a transformed host cell as defined above, whereby the host cell ferments xylose to ethanol; and optionally, (b) recovery of the ethanol. The fermentation medium can also comprise a source of glucose that is also fermented to ethanol. The source of xylose can be sugars produced from biomass or agricultural wastes. Many processes for the production of monomeric sugars such as glucose generated from lignocellulose are well known, and are suitable for use herein. In brief, the cellulolytic material may be enzymatically, chemically, and/or physically hydrolyzed to a glucose and xylose containing, fraction. Alternatively, the recombinant XI-expressing cells of the disclosure can be further transformed with one or more genes encoding for enzymes effective for hydrolysis of complex substrates such as lignocellulose, and include but are not limited to cellulases, hemicellulases, peroxidases, laccases, chitinases, proteases, and pectinases. The recombinant cells of the disclosure can then be fermented under anaerobic in the presence of glucose and xylose. Where the recombinant cell is a yeast cell, the fermentation techniques and conditions described for example, by Wyman (1994, Biores. Technol. 50:3-16) and Olsson and Hahn-Hagerdal (1996, Enzyme Microb. Technol. 18:312-331) can be used. After completion of the fermentation, the ethanol may be recovered and optionally purified or distilled. Solid residue containing lignin may be discarded or burned as a fuel.

The fermentation process may be run under aerobic and anaerobic conditions. In some embodiments, the process is carried out under microaerobic or oxygen limited conditions. Fermentation can be carried out in a batch, fed-batch, or continuous configuration within (bio)reactors.

EXAMPLE 1

Materials and Methods

Yeast Culture

Unless stated otherwise for a particular example, yeast transformants were grown in SC-ura media with about 2% glucose at 30° C. for about 24 hours. The media contains approx. 20 g agar, approx. 134 g BD Difco™ Yeast Nitrogen Base without amino acids (BD, Franklin Lakes, N.J.), and approx. 2 g SC amino-acid mix containing about 85 mg of the following amino acids unless noted (quantity listed in parentheses): L-Adenine (21.0), L-Alanine, L-Arginine, L-Asparagine, L-Aspartic Acid, L-Cysteine, Glutamine, L-Glutamic Acid, Glycine, L-Histidine, Myo-Inositol, L-Isoleucine, L-Leucine (173.4), L-Lysine, L-Methionine, p-Aminobenzoic Acid (8.6), L-Phenylalanine, L-Proline, L-Serine, L-Threonine, L-Tryptophan, L-Tyrosine, L-Valine).

Xylose Isomerase Activity

XI activity in cell lysates was determined using a method based on that of Kersters-Hilderson et al., 1986, Enzyme Microb. Technol. 9:145-148, in which enzymatic conversion of xylose to xylulose by the XI is coupled with the enzymatic conversion of the product (xylulose) to xylitol via the enzyme sorbitol dehydrogenase (SDH). SDH activity requires the oxidation of NADH to $NAD^+$. The rate of oxidation of NADH is directly proportional to the rate of SDH conversion of D-xylulose to D-xylitol and is measured by the decrease in absorbance at 340 nm. One unit of enzyme activity as measured by this assay is a decrease of 1 μmole of NADH per minute under assay conditions. All reactions, solutions, plates, and spectrophotometer were equilibrated to about 35° C. prior to use. Assays were performed either on fresh lysates immediately after preparation or lysates that had been frozen at −20° C. immediately after preparation. Assays were performed using a BioTek Model: Synergy H1 Hybrid Reader spectrophotometer and 96-well plates (Corning, Model #Costar@#3598). All spectrophotometric readings were performed at 340 nm. A standard curve of NADH was generated with each assay with concentrations ranging from 0 to about 0.6 mM.

The reaction buffer used for experiments at pH 7.5 was about 100 mM Tris-HCl (pH 7.5). The assay mix was prepared as follows: reaction buffer to which was added about 10 mM $MgCl_2$, 0.15 mM NADH and 0.05 mg/ml SDH (Roche, catalog #50-720-3313). For experiments where activity was also measured at pH 6, the buffer was changed to about 100 mM sodium phosphate, pH 6. The assay mix for the entire experiment was then prepared as follows: about 10 mM $MgCl_2$, 1.2 mM NADH and 0.02 mg/ml SDH.

Any sample dilutions were performed using the reaction buffer as diluent. Reactions were set up by aliquotting about 90 μl of assay mix into each well of the plates. About 10 μl of each XI sample was added to the wells. The reactions were started by the addition of about 100 μl substrate solution (about 1 M D-xylose). Reactions were mixed and read immediately using kinetic assay mode for about 10 minutes. Volumetric activity (VA) units are in milli-absorbance (mA) units per minute per ml of lysate added to the reactions (mA/min/ml). Background VA rates of negative control wells (no enzyme added) were subtracted from VA of samples. Determination of fold improvement over positive control (FIOPC) was obtained by dividing the VA of the XI-samples by the VA observed for a control (*Orpinomyces* xylose isomerase, NCBI: 169733248 (Op-XI)) expressed using the same host and expression vector. In some characterizations, the slope of an NADH standard curve was used to convert VA (mA/min) to µmole-NADH/min (or Units). If protein quantitation was performed, specific activities (SA) were calculated where the units for SA are (µmole $NADH^+$/min/mg, or U/mg lysate protein). All activities listed (VA or SA) account for any dilutions, volumes of lysate added, and protein concentrations for the lysates assayed.

EXAMPLE 2

Activity-Based Discovery Screen for Xylose Isomerases

Libraries used for the activity-based discovery ("ABD") screen were in the format of excised phagemids. These libraries were constructed as described in U.S. Pat. No. 6,280,926. Sources for these libraries were environmental rumen samples collected from the foregut of deceased herbivores.

An *Escherichia coli* screening strain was constructed to identify genes from the environmental libraries encoding xylose isomerase activity. Specifically, *E. coli* strain SEL700, a MG1655 derivative that is recA⁻, phage lambda resistant and contains an F' plasmid, was complemented with plasmid pJC859, a derivative of pBR322 containing the *E. coli* recA gene (Kokjohn et al., 1987, J. Bacteriol. 169:1499-1508) to generate a wild-type recA phenotype.

A two-step marker exchange procedure was then used to delete the entire coding sequence of the endogenous xylA xylose isomerase gene. Briefly, pMEV3, a plasmid with apir-dependent replicon (ori6RK) encoding kanamycin-resistance and the sacB levansucrase, was used as a vector for construction of the xylA deletion plasmid. A fragment of DNA containing the flanking regions of the xylA gene (0.7 kb of sequence 5' and 0.9 kb of sequence 3' of xylA) and containing BsaI restriction sites was generated by overlap extension PCR using primers, ligated to pMEV3 digested with BbsI, and transformed into *E. coli* by electroporation. Clones were confirmed by sequencing, resulting in plasmid pMEV3-ΔxylA (FIG. 1A).

Figure 2:
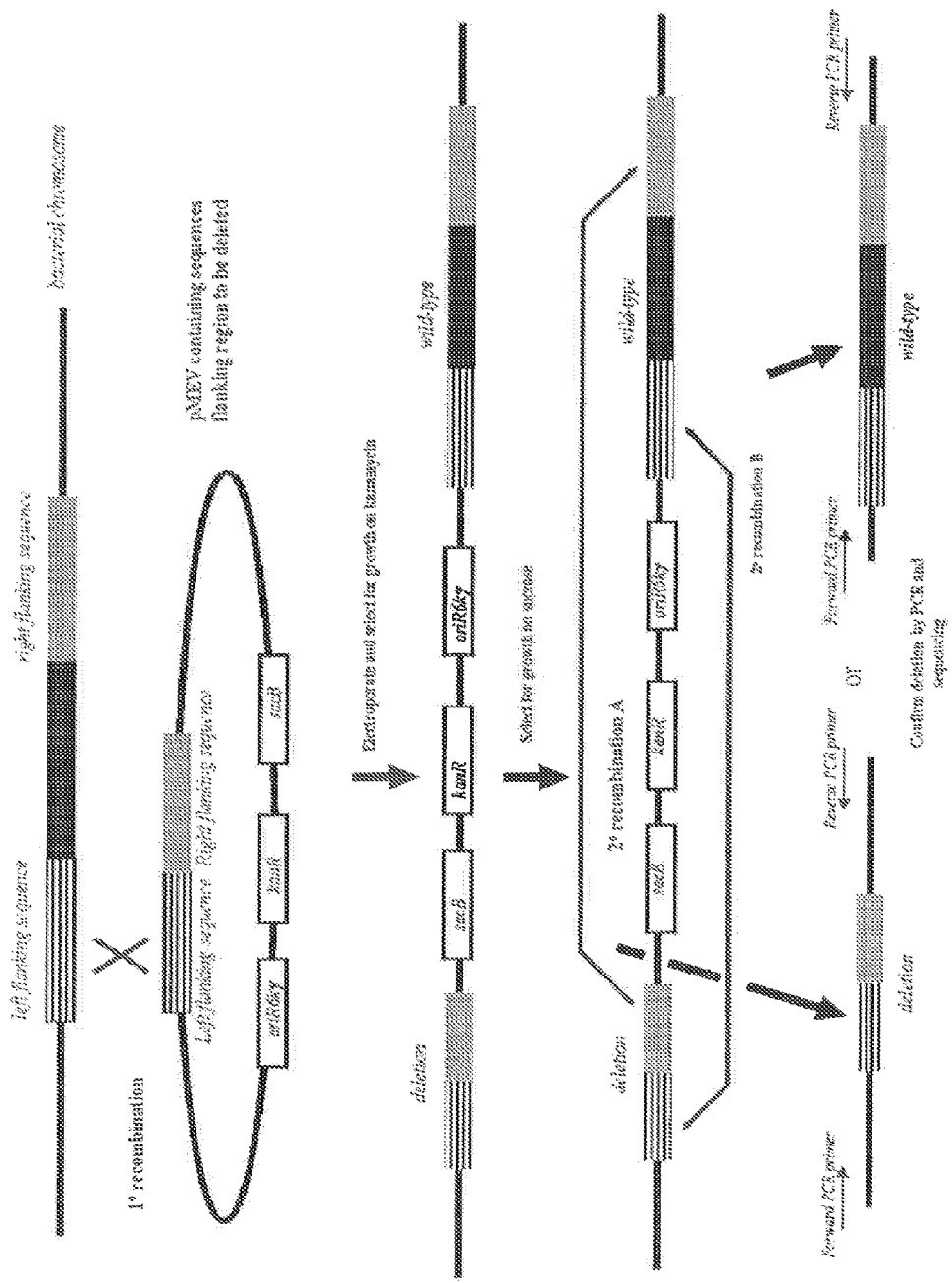
FIG. 2 illustrates the experimental strategy for the two-step marker exchange approach.

The pMEV3-ΔxylA plasmid was then transformed into strain *E. coli* strain SEL700 (MG1655 Δ⁻, Δ(recA-srl)306, srl-301::Tn10-84(Tets), [F'proAB, lacI$^q$, ZΔM15, Tn10 (Tetr)]pJC859). Single-crossover events were selected for by plating on LB agar plates containing kanamycin (final concentration, about 50 µg/ml). After confirmation of integration of pMEV3-ΔxylA on the chromosome, a second crossover event was selected for by growth on LB agar media containing sucrose (FIG. 2). Colonies displaying resistance to kanamycin and the ability to grow on sucrose were screened both by PCR characterization with primers flanking the xylA gene to confirm gene deletion and by growth on a modified MacConkey media (ABD media), comprised of: MacConkey Agar Base (Difco™ #281810) (approximate formula per liter: Pancreatic Digest of Gelatin (17.0 g) Peptones (meat and casein) (3.0 g), Bile Salts No. 3 (1.5 g), Sodium Chloride (5.0 g), Agar (13.5 g), Neutral Red (0.03 g), Crystal Violet (1.0 g, Xylose (30.0 g) and Kanamycin (50 mg). The ABD media contained neutral red, a pH indicator that turns red at a pH<6.8. Colonies of mutants lacking xylA appeared white on this media while colonies with restored xylose metabolism ability appeared red in color due to the fermentation of xylose to xylulose, which lowered the pH of the media surrounding those colonies.

Following the successful deletion of xylA, the resulting strain was cured of pJC859 by the following method: The xylA deletion strain was grown for about 24 hours in LB media containing tetracycline at a final concentration, about 20 µg/ml, at around 37° C. The next day the cells were sub-cultured (1:100 dilution) into LB tetracycline (at the same concentration) media and incubated at about three different temperatures (30, 37, and 42° C.). Cells were passaged the same way as above for about two more days. Dilutions of the resulting cultures were plated on LB plates to isolate single colonies. Colonies were replica plated onto LB agar plates with and without Carbenicillin (at about 100 µg/ml, final concentration). Carbenicillin resistant colonies were deemed to still contain vector pJC859 whereas carbenicillin sensitive colonies were cured of pJC859, restoring the recA genotype of strain SEL700. This strain, SEL700 ΔxylA, was used for the ABD screening.

Figure 1B:
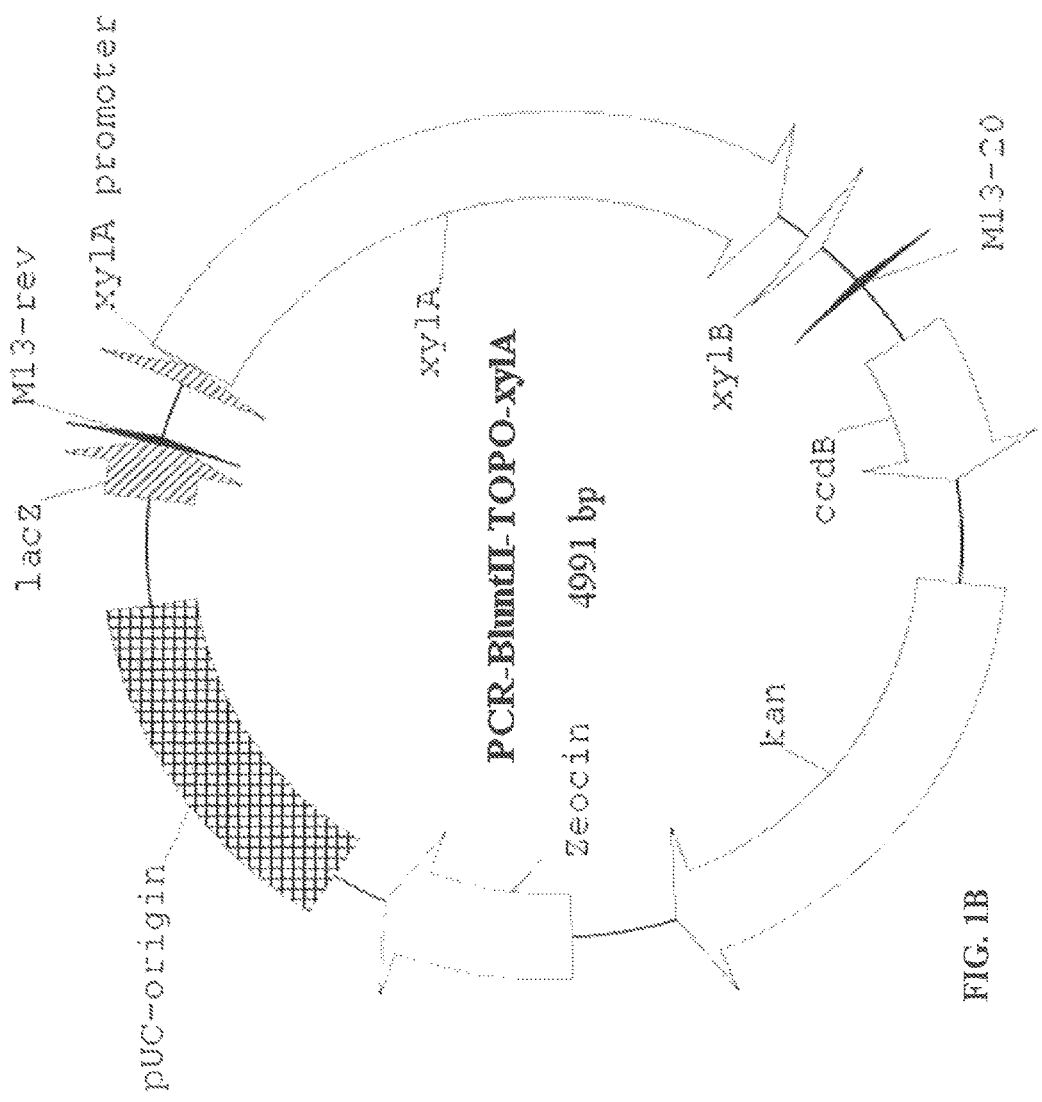

The ABD screening method was verified by creating a positive control strain by PCR amplification of the xylA gene from *E. coli* K12 and cloning into the PCR-BluntII TOPO vector (Invitrogen, Carlsbad, Calif.) using standard procedures. This vector (PCR-BluntII-TOPO-xylA, FIG. 1B) was then transformed into the screening strain (SEL700 ΔxylA). Complementation of the xylose phenotype was verified by growth of transformants on ABD media and appearance of red halos indicating xylose utilization.

The libraries were screened for XI activity by infecting strain SEL700 ΔxylA with the excised phagemid libraries. Infected cells were plated onto ABD media and only colonies with red "halos" (indicating xylose fermentation), were carried forward. Positives were purified to single colonies, and regrown on ABD media to confirm phenotype.

EXAMPLE 3

Sequence-Based Discovery for Xylose Isomerases

Libraries used for sequence-based discovery ("SBD") were in the format of genomic DNA (gDNA) extractions. These libraries were constructed as described in U.S. Pat. No. 6,280,926. Sources for these libraries were samples collected from the guts of deceased herbivores.

XI genes often exist in conserved gene clusters (Dodd et al., 2011, Molecular Microbiol. 79:292-304). In order to obtain full length XI gene sequences from metagenomic samples, primers were designed to both upstream and downstream conserved DNA sequences found in several *Bacteroides* species, typically xylulose kinase and xylose permease, respectively. These flanking DNA sequences were obtained from public databases. Sample genomic DNA was extracted from eleven different animal rumen samples. Left flanking consensus primer has the sequence 5'-GCIGCI-CARGARGGNATYGTVTT-3' (SEQ ID NO:177) (this primer codes for the amino acid motif AAQEGIV(F) (SEQ ID NO:178)). Right flanking consensus primer has the sequence 5'-GCDATYTCNGCRATRTACATSGG-3' (SEQ ID NO:179) (this primer codes for the amino acid motif PMYIAEIA (SEQ ID NO:180)). PCR reactions were carried out using touchdown cycling conditions, and hot start Platinum® Taq DNA polymerase (Invitrogen, Carlsbad, Calif.).

PCR products of expected size were purified and subcloned into pCR4-TOPO vector system (Invitrogen, Carlsbad, Calif.). Positive colonies from the TOPO-based PCR libraries were transformed into TOP10 (Invitrogen, Carlsbad, Calif.) and the transformants grown on LB agar plates with kanamycin (about 25 g/ml final concentration). Resistant colonies were picked and inoculated into 2 columns each of a 96-deep well plate in about 1.2 ml LB kanamycin (25 µg/ml final concentration) media per well. Cultures were grown overnight at about 30° C. The next day plasmids were purified and inserts sequenced. Sequence analysis revealed multiple full length XI genes. Identification of putative ORFs was done by identifying start and stop codons for the longest protein coding region, and subsequent manual curation based on homology to published xylose isomerase DNA sequences.

EXAMPLE 4

XI Sequence Analysis

Plasmids from both ABD and SBD screens were purified and vector inserts were sequenced using an ABI 3730xl DNA Analyzer and ABI BigDye® v3.1 cycle sequencing chemistry. Identification of putative ORFs was done by identifying start and stop codons for the longest protein coding region, and subsequent manual curation based-on homology to published xylose isomerase DNA sequences. The XI ORF identified are set forth in Table 2 below, which indicates the sequences and source organism classification for each XI determined from either the ABD or SBD libraries as well as their assigned sequence identifiers. The putative catalytic domains (based on sequence alignments with other XIs) are underlined.

TABLE 2

| Clone No. | Class of organism | Type of Sequence | SEQ ID NO: | Sequence |
|---|---|---|---|---|
| 1754MI2_001 | Bacteroidales | DNA | 1 | ATGGCAGTTAAAGAATATTTCCCGGAGATAGGCAAGATCGCCTTTGAAGGAAAGGAGTCCAA GAACCCTATGGCATTCCACTACTACAATCCAGAGCAGGTAGTAGCCGGAAAGAAAATGAAAG ATTGGTTCAAGTTCGCTATGGCATGGTGGCACACCCTCTGCGCTGAAGGTGGCGACCAGTTC GGTCCTGGTACCAAGAAATTCCCTTGGAACACAGGTGCAACTGCACTCGAAAGAGCAAAGAA CAAAATGGACGCAGGTTTCGAGATCATGAGCAAGCTCGGTATCGAGTATTTCTGCTTCCACG ATGTTGACCTTATCGACGAGGCTGACACTGTTGAAGAGTACGAGGCTAACATGAAGGCTATC ACAGCTTACGCAAAGGAGAAAATGGCCGCTACTGGCATCAAACTCCTCTGGGGAACAGCCAA TGTATTCGGCAACAAGAGATATATGAACGGCGCTTCTACCAACCCTGACTTCAACGTGGCTG CACGCGCTATGCTCCAGATCAAGAACGCTATCGACGCAACTATCGCTCTCGGTGGTGACTGC TATGTATTCTGGGGCGGCCGTGAGGGTTACATGAGCCTTCTCAACACCGATATGAAGAGAGA GAAAGAGCACATGGCTACCATGCTTACCATGGCACGCGACTATGCTCGTTCTAAGGGCTTCA AGGGTACCTTCCTTATCGAGCCTAAGCCAATGGAGCCGATGAAGCACCAGTACGATGTCGAT ACTGAGACTGTCGTAGGTTTCCTCCGCGCCCATGGTCTTGACAAGGACTTCAAGGTAAACAT CGAGGTTAACCACGCTACTCTCGCAGGCCACACCTTCGAGCACGAGCTCCAGTGCGCCGTTG ACGCAGGCATGCTCGGAAGCATCGACGCCAACCGTGGTGACTACCAGAACGGCTGGGATACC GACCAGTTCCCTATCGACCTCTATGAGCTCGTACAGGCTATGATGGTTATCATCAAGGGCGG CGGTCTCGTCGGCGGTACCAACTTCGACGCCAAGACCCGTCGTAACTCAACAGACCTCGAGG ATATCTTCATCGCTCATGTATCCGGCATGGATGTCATGGCACGCGCTCTCCTCATCGCTGCT GACCTTCTCGAGAAATCTCCTATTCCTGCAATGGTCAAGGAGCGTTACGCTTCCTACGACTC AGGCATGGGCAAGGACTTCGAGAACGGCAAGCTTACTCTCGAGCAGGTTGTCGATTTCGCAA GAAAGAACGGCGAGCCTAAGAGCACCAGCGGAAAGCAGGAGCTCTACGAGTCTATCGTCAAT CTCTACATCTAA |
| 1754MI2_001 | Bacteroidales | Amino Acid | 2 | <u>MAVKEYFPEIGKIAFEGKESKNPMAFHYYNPEQVVAGKKMKDWFKFAMAWWHTLCAEGGDQF GPGTKKFPWNTGATALERAKNKMDAGFEIMSKLGIEYFCFHDVDLIDEADTVEEYEANMKAI TAYAKEKMAATGIKLLWGTANVFGNKRYMNGASTNPDFNVAARAMLQIKNAIDATIALGGDC YVFWGGREGYMSLLNTDMKREKEHMATMLTMARDYARSKGFKGTFLIEPKPMEPMKHQYDVD TETVVGFLRAHGLDKDFKVNIEVNHATLAGHTFEHELQCAVDAGMLGSIDANRGDYQNGWDT DQFPIDLYELVQAMMVIIKGGGLVGGTNFDAKTRRNSTDLEDIFIAHVSGMDVMARALLIAA DLLEKSPIPAMVKERYASYDSGMGKDFENGKLTLEQVVDFARKNGEPKSTSGKQELYESIVN LYI</u> |
| 5586MI6_004 | Bacteroidales | DNA | 3 | ATGGCAAACAAAGAGTACTTCCCGGAGATCGGGAAAATCAAATTCGAAGGCAAGGATTCCAA GAACCCGCTTGCATTCCATTATTACAATCCTGAGCAGGTCGTCTGCGGCAAGCCGATGAAGG ACTGGCTCAAGTTCGCTATGGCATGGTGGCACACCCTCTGCGCAGAGGGTAGCGACCAGTTC GGCGGACCCACCAAGTCATTCCCTTGGAACAAAGCTTCGGATCCCATCGCAAAGGCCAAGCA GAAAGTCGACGCCGGTTTCGAGATCATGCAGAAGCTCGGTATCGGATACTATTGCTTCCACG ATGTAGACCTCATCGACGAGCCCGCCACCATCGAGGAGTATGAGGCCGATCTCAAGGAGATC GTCGCTTACCTCAAGGAGAAGCAGGCCCAGACCGGCATCAAGCTCCTTTGGGGCACCGCCAA CGTCTTCGGTCACAAGCGGTACATGAACGGCGCCTCCACCAACCCTGATTTCGACGTCGCAG CCCGCGCCATGGTCCAGATCAAGAACGCCATGGACGCCACCATCGAGCTCGGCGGCGAGTGC TATGTCTTCTGGGGCGGCCGCGAGGGCTACATGAGCCTCCTCAACACCGACATGAAGCGTGA GAAGCAGCATATGGCCACCATGCTCGGCATGGCCCGCGACTATGCACGCGGCAAGGGCTTCA AGGGCACCTTCCTCATCGAGCCCAAGCCCATGGAGCCGACCAAGCACCAGTATGACGTCGAC ACCGAGACCGTCATCGGTTTCCTCCGTGCCAACGGTCTTGACAAGGACTTCAAGGTCAACAT CGAGGTCAATCACGCCACCCTCGCCGGCCACACCTTCGAGCATGAGCTCCAGTGCGCCGCCG ATGCCGGTCTCCTCGGATCCATCGACGCCAACCGCGGCGACTATCAGAACGGCTGGGATACC GACCAGTTCCCGATCGACCTCTATGAGCTCACCCAGGCCATGATGGTCATCCTCAAGAATGG CGGCCTCGTCGGCGGTACCAACTTCGACGCCAAGACCCGTCGCAACTTCCACCGACCTGGACG ACATCATCATCGCCCACGTCAGCGGTATGGACATCATGGCACGCGCACTCCTCGTCGCTGCC GACGTCCTCACCAAGTCCGAGCTTCCCAAGATGCTCAAGGAGCGTTACGCTTCCTTCGACTC CGGCAAGGGCAAGGAGTTCGAAGAGGGCAAGCTCACTCTCGAGCAGGTCGTAGAGTACGCCA AGACCAAGGGCGAGCCCAAGGCCACCAGCGCAAGCAGGAGCTCTACGAGACCATCGTCAAC ATGTACATCTAA |

TABLE 2-continued

| Clone No. | Class of organism | Type of Sequence | SEQ ID NO: | Sequence |
|---|---|---|---|---|
| 5586MI6_004 | *Bacteroidales* | Amino Acid | 4 | MANKEYFPEIGKIKFEGKDSKNPLAFHYYNPEQVVCGKPMKDWLKFAMAWWHTLCAEGSDQF<br>GGPTKSFPWNKASDPIAKAKQKVDAGFEIMQKLGIGYYCFHDVDLIDEPATIEEYEADLKEI<br>VAYLKEKQAQTGIKLLWGTANVFGHKRYMNGASTNPDFDVAARAMVQIKNAMDATIELGGEC<br>YVFWGGREGYMSLLNTDMKREKQHMATMLGMARDYARGKGFKGTFLIEPKPMEPTKHQYDVD<br>TETVIGFLRANGLDKDFKVNIEVNHATLAGHTFEHELQCAADAGLLGSIDANRGDYQNGWDT<br>DQFPIDLYELTQAMMVILKNGGLVGGTNFDAKTRRNSTDLDDIIIAHVSGMDIMARALLVAA<br>DVLTKSELPKMLKERYASFDSGKGKEFEEGKLTLEQVVEYAKTKGEPKATSGKQELYETIVN<br>MYI |
| 5749MI1_003 | *Bacteroidales* | DNA | 5 | ATGAATTTTTATAAAGGCGAAAAGAATTCTTCCCCGGAATAGGAAAGATTCAGTTTGAAGG<br>ACGCGAGTCAAAGAACCCGATGGCGTTTCATTATTATGACGAAAACAAGGTGGTGATGGGTA<br>AAACACTGAAGGATCATCTTCGTTTTGCAATGGCTTACTGGCATACGCTTTGTGCCGAAGGG<br>GGCGACCAGTTTGGCGGTGGTACGAAAACATTCCCCTGGAATGCTGCTGCCGACCCGATCAG<br>CCGTGCCAATATAAGATGGATGCAGCGTTCGAGTTTATGACAAAATGCAGCATCCCTTATT<br>ACTGTTTCCATGATGTGGACGTGGTGGACGAAGCTCCCACGCTGGCTCAGTTTGAAAAAGAC<br>CTTCATACGATGGTAGGCCATGCCAAAGGGCTTCAGCAGGCAACCGGAAAAAAACTGTTATG<br>GTCTACTGCCAACGTGTTCAGCAACAAAGCTATATGAACGGGGCTGCCACTAATCCTGACT<br>TCTCGGCCGTGGCTTGTGCCGGTACGCAGATCAAGAATGCGATCGATGCCTGTATCGCGCTG<br>GACGGTGAAAACTATGTGTTCTGGGGCGGACGTGAAGGATATATGGGCTTGCTCAATACCGA<br>TATGAAACGCGAAAAGACCATCTGGCCATGATGCTGACGATGGCACGCGACTATGGCCGCA<br>AGAACGGTTTCAAAGGTACTTTCCTGATCGAGCCGAAACCGATGGAACCGACCAAGCATCAA<br>TATGATGTCGACTCGGAAACTGTAATCGGCTTCCTACGTCATTATGGGCCTGGATAAAGACTT<br>CGCCCTGAATATCGAAGTAAATCATGCAACCCTGGCCGGACATACGTTCGAGCACGAATTGC<br>AGGCTGCTGTCGATGCCGGTATGCTGTGCAGTATCGATGCCAACCGTGGTGACTACCAGAAT<br>GGCTGGGATACCGACCAATTCCCGATGGACATCTACGAACTGACTCAGGCTTGGCTGGTCAT<br>TCTGCAAGGTGGTGGTCTGACAACCGGCGGAACGAACTTCGATGCCAAGACCCGCCGCAACT<br>CGACCGACCTGGACGATATCTTCCTGGCTCATATAGGTGGTATGGATGCGTTTGCCCGTGCC<br>CTGATCACGGCTGCTGCCATCCTTGAAAACTCCGATTACACGAAGATGCGTGCCGAACGTTA<br>CACCAGCTTCGATGGTGGCGAAGGCAAAGCGTTTGAAGACGGTAAACTTTCTCTGGAAGACC<br>TGCGTACGATCGCTCTCCGCGACGGAGAACCGAAGATGGTCAGCGGCAAACAGGAATTATAT<br>GAGATGATTCTCAATTTATACATATAA |
| 5749MI1_003 | *Bacteroidales* | Amino Acid | 6 | MNFYKGEKEFFPGIGKIQFEGRESKNPMAFHYYDENKVVMGKTLKDHLRFAMAYWHTLCAEG<br>GDQFGGGTKTFPWNAAADPISRAKYKMDAAFEFMTKCSIPYYCFHDVDVVDEAPTLAQFEKD<br>LHTMVGHAKGLQQATGKKLLWSTANVFSNKRYMNGAATNPDFSAVACAGTQIKNAIDACIAL<br>DGENYVFWGGREGYMGLLNTDMKREKDHLAMMLTMARDYGRKNGFKGTFLIEPKPMEPTKHQ<br>YDVDSETVIGFLRHYGLDKDFALNIEVNHATLAGHTFEHELQAAVDAGMLCSIDANRGDYQN<br>GWDTDQFPMDIYELTQAWLVILQGGGLTTGGTNFDAKTRRNSTDLDDIFLAHIGGMDAFARA<br>LITAAAILENSDYTKMRAERYTSFDGGEGKAFEDGKLSLEDLRTIALRDGEPKMVSGKQELY<br>EMILNLYI |
| 5750MI1_003 | *Bacteroidales* | DNA | 7 | ATGAATTACTTTAAAGGTGAGAAAGAGTTCTTCCCGGGAATCGGGAAAATAGAGTTTGAAGG<br>ACGTGAATCGAAGAATCCGATGGCTTTTCATTACTATGACGAGAACAAGGTTGTCATGGGGA<br>AGACCTTGAAGGACCATCTGCGTTTTGCGATGGCTTATTGGCATACGCTGTGTGCGGAAGGC<br>GCCGACCAGTTCGGCGGCGGGACGAAGGCATTTCCCTGGAATACCGGGGCGGATCGTATTTC<br>CCGTGCCAAGTATAAGATGGATGCTGCTTTTGAGTTTATGACGAAATGTAACATCCCGTACT<br>ATTGTTTCCATGATGTGGATGTGGTGGATGAAGCTCCGACACTGGCCGAATTTGAAAAAGAC<br>TTGCATACGATGGTCGAATATGCCAAGCAGCATCAGGAGGCAACCGGGAAAAAACTGTTGTG<br>GTCTACCGCCAATGTGTTCAGCAATAAACGTTATATGAACGGGGCTGCCACAAATCCGTATT<br>TCCCTGCTGTCGCTTGTGCGGGTACGCAGATCAAGAATGCTATCGACGCTTGTATTGCCCTG<br>GGCGGCGAAAACTATGTGTTCTGGGGCGGTCGTGAAGGGTATATGAGCTTGTTGAACACCAA<br>TATGAAACGCGAAAAGGAACATCTCGCCATGATGTTGACGATGGCTCGCGATTATGCGCGTA<br>AGAACGGCTTCAAAGGTACTTTCCTGGTAGAGCCTAAACCGATGGAACCGACCAAACATCAG<br>TATGATGTGGACACAGAAACTGTTATCGGCTTCCTGCGTCATTACGGCCTTGACAAGGACTT<br>TGCCATCAACATCGAAGTAATCATGCTACATTGGCTGGACATACATTCGAACATGAGCTTC<br>AGGCGGCTGCCGATGCCGGTATGCTGTGCAGCATCGACGCCAACCGCGGCGATTACCAGAAT<br>GGTTGGGACACGGATCAGTTCCCGGTCGACATCTACGAACTGACACAGGCGTGGCTGGTTAT<br>CCTCGAAGCGGGTGGCCTGACTACCGGTGGTACGAACTTCGACGCCAAGACGCGCCGCAACT<br>CGACTGACCTGGACGATATCTTCCTGGCACACATCGGTGGTATGGATTCGTTTGCCCGTGCT<br>TTGATGGCGGCTGCCGATATATTGGAACACTCCGATTACAAAAAGATGCGTGCCGAACGTTA<br>TGCCAGCTTCGATCAAGGCGACGGCAAGAAGTTCGAAGATGGTAAACTCCTTCTCGAGGACC<br>TCCGCACCATCGCTCTTGCCTCCGGCGAACCGAAGCAAATCAGCGGGAAACAGGAATTGTAT<br>GAAATGATTATCAACCAGTACATTTAA |
| 5750MI1_003 | *Bacteroidales* | Amino Acid | 8 | MNYFKGEKEFFPGIGKIEFEGRESKNPMAFHYYDENKVVMGKTLKDHLRFAMAYWHTLCAEG<br>ADQFGGGTKAFPWNTGADRISRAKYKMDAAFEFMTKCNIPYYCFHDVDVVDEAPTLAEFEKD<br>LHTMVEYAKQHQEATGKKLLWSTANVFSNKRYMNGAATNPYFPAVACAGTQIKNAIDACIAL<br>GGENYVFWGGREGYMSLLNTNMKREKEHLAMMLTMARDYARKNGFKGTFLVEPKPMEPTKHQ<br>YDVDTETVIGFLRHYGLDKDFAINIEVNHATLAGHTFEHELQAAADAGMLCSIDANRGDYQN<br>GWDTDQFPVDIYELTQAWLVILEAGGLTTGGTNFDAKTRRNSTDLDDIFLAHIGGMDSFARA<br>LMAAADILEHSDYKKMRAERYASFDQGDGKKFEDGKLLLEDLRTIALASGEPKQISGKQELY<br>EMIINQYI |
| 5750MI2_003 | *Bacteroidales* | DNA | 9 | ATGAATTATTTTAAAGGTGAAAAGAGTTTTTCCCTGGAATCGGGAAAATAGAGTTTGAAGG<br>ACGTGAGTCGAAGAATCCGATGGCTTTTCATTATTATGATGAAAACAAGGTCGTAATGGGCA |

TABLE 2-continued

| Clone No. | Class of organism | Type of Sequence | SEQ ID NO: | Sequence |
|---|---|---|---|---|
| | | | | AGACCTTGAAAGATCACCTCCGCTTTGCAATGGCTTACTGGCATACGTTGTGCGCGGAAGGC<br>GCAGACCAGTTTGGCGGTGGCACAAAATCATTCCCCTGGAATACCGCAGCGGATCGTATTTC<br>CCGCGCTAAATATAAAATGGATGCTGCTTTCGAGTTTATGACCAAGTGCAGTATCCCGTACT<br>ATTGTTTCCATGATGTGGACGTGGTGGACGAAGCTCCGGCACTGGCCGAATTTGAAAAGGAC<br>CTGCATACGATGGTGGGATTCGCCAAACAACACCAGGAAGCAACCGGAAAGAAACTGTTGTG<br>GTCTACAGCCAATGTATTCGGGCATAAACGTTATATGAACGGAGCGGCTACCAATCCTTATT<br>TCCCGGCTGTCGCTTGTGCCGGTACGCAGATCAAGAATGCAATCGACGCCTGTATCGAGCTG<br>GGTGGAGAGAACTATGTATTCTGGGGCGGACGCGAAGGCTACATGAGCCTGCTGAACACCAA<br>TATGAAACGTGAAAAGGATCATTTGGCCATGATGCTGACAATGGCACGCGATTATGCCCGCA<br>AGAATGGTTTCAAGGGTACTTTCCTGGTGGAATCTAAGCCGATGGAACCGACCAAACATCAG<br>TATGACGCAGATACGGAAACCGTGATCGGCTTCCTGCGCCACTATGGCCTCGACAAGGATTT<br>CGCTATCAACATTGAAGTGAACCATGCTACATTGGCCGGCCATACATTCGAACATGAACTTC<br>AGGCTGCTGCCGATGCCGGTATGCTGTGCAGCATCGATGCAAATAGAGGCGACTATCAGAAT<br>GGTTGGGATACGGATCAGTTCCCCGTAGACATTTACGAACTGACACAGGCCTGGCTGGTTAT<br>CCTGGAAGCGGGCGGACTGACAACCGGAGGTACGAACTTCGATGCGAAGACCCGTCGTAACT<br>CGACTGACCTCGACGATATCTTCCTGGCCCATATCGGCGGTATGGATTCGTTTGCACGTGCC<br>TTGATGGCAGCTGCCGATATCCTTGAACATTCTGATTACAAGAAGATGCGTGCCGAACGTTA<br>CGCCAGCTTCGACCAGGGCGACGGCAAGAAGTTCGAAGACGGCAAACTCCTTCTCGAAGACC<br>TGCGCACAATTGCCCTTGCCGGCGACGAACCGAAGCAGATCAGCGGCAAGCAGGAGTTGTAT<br>GAGATGATTATCAATCAGTATATTTAA |
| 5750MI2_003 | Bacteroidales | Amino Acid | 10 | <u>MNYFKGEKEFFPGIGKIEFEGRESKNPMAFHYYDENKVVMGKTLKDHLRFAMAYWHTLCAEG<br>ADQFGGGTKSFPWNTAADRISRAKYKMDAAFEFMTKCSIPYYCFHDVDVVDEAPALAEFEKD<br>LHTMVGFAKQHQEATGKKLLWSTANVFGHKRYMNGAATNPYFPAVACAGTQIKNAIDACIEL<br>GGENYVFWGGREGYMSLLNTNMKREKDHLAMMLTMARDYARKNGFKGTFLVESKPMEPTKHQ<br>YDADTETVIGFLRHYGLDKDFAINIEVNHATLAGHTFEHELQAAADAGMLCSIDANRGDYQN<br>GWDTDQFPVDIYELTQAWLVILEAGGLTTGGTNFDAKTRRNSTDLDDIFLAHIGGMDSFARA<br>LMAAADILEHSDYKKMRAERYASFDQGDGKKFEDGKLLLEDLRTIALAGDEPKQISGKQELY<br>EMIINQYI</u> |
| 5586MI5_004 | Bacteroides | DNA | 11 | ATGAAACAGTATTTCCCGAACATCTCCGCCATCAAGTTTGAGGGCGTCGAGAGCAAGAATCC<br>CCTGGCTTACCGCTACTACGACCGCGACCGCGTCGTCATGGGTAAGAAGATGAGCGAATGGT<br>TTAAGTTCGCTATGTGCTGGTGGCACACCCTCTGCGCCGAGGGCTCCGATCAGTTCGGTCCC<br>GGCACAAAGACCTTCCCCTGGAACGCCGCCGCCGACCCCGTGCAGGCTGCCAAGGACAAGGC<br>CGACGCTGGCTTCGAGATCATGCAGAAATCGGCATCGAGTACTACTGCTTCCACGACGTTG<br>ACCTCGTGGCCGAGGCTCCCGACGTGGAGACCTACGAGAAGAACCTCAAGGAGATCGTGGCT<br>TATCTCAAGCAGAAACAGGCTGAGACGGGCATCAAGCTGCTCTGGGGCACTGCCAACGTCTT<br>CGGACACAAGCGCTACATGAACGGAGCCTCCACGAACCCCGACTTCGATGTCGTGGCACGCG<br>CTATCGTGCAGATCAAGAACGCCATCGATGCTACCATCGAGCTGGGCGGCACCAACTACGTC<br>TTCTGGGGCGGTCGCGAAGGCTACATGAGCCTGCTCAACACCGATATGAAGCGCGAGAAGGA<br>GCACATGGCTACGATGTTGACGATGGCACGCGACTATGCCCGTTCTAAGGGATTCAAGGGCA<br>CGTTCCTCATCGAACCCAAACCCATGGAACCCACGAAGCATCAGTACGATCGGACACCGAG<br>ACGGTCATCGGATTCCTCCGTGCTCATGGTCTCGACAAGGATTTCAAGGTCAACATCGAGGT<br>CAACCACGCCACGCTGGCCGGACACACGTTCGAGCATGAGCTGGCCTGCGCCGTAGACGCCG<br>ATATGCTCGGCAGCATCGATGCCAATCGCGGCGACTATCAGAACGGATGGGACACCGACCAG<br>TTCCCCATCGACCATTACGAACTCACGCAGGCTATGCTGCAGATCATCCGCAACGGAGGTTT<br>CAAGGACGGTGGCACCAATTTTGACGCTAAGACGCGCCGCAACAGCACCGACCTCGAGGATA<br>TCTTCATCGCTCACGTAGCAGCCATGGACGCCATGGCCCACGCCCTGTTGTCGGCTGCCGAT<br>ATCATCGAGAAGTCGCCCATCTGCACGATGGTCAAGGAGCGTTACGCCAGCTTCGATGCCGG<br>CGAAGGCAAGCGCTTCGAAGAAGGCAAGATGACCCTCGAGGAAGCCTACGAGTATGGCAAGA<br>AGGTCGGGGAGCCCAAGCAGACCAGCGGAAAGCAGGAGCTCTACGAAGCCATTGTCAATATG<br>TATTGA |
| 5586MI5_004 | Bacteroides | Amino Acid | 12 | <u>MKQYFPNISAIKFEGVESKNPLAYRYYDRDRVVMGKKMSEWFKFAMCWWHTLCAEGSDQFGP<br>GTKTFPWNAAADPVQAAKDKADAGFEIMQKLGIEYYCFHDVDLVAEAPDVETYEKNLKEIVA<br>YLKQKQAETGIKLLWGTANVFGHKRYMNGASTNPDFDVVARAIVQIKNAIDATIELGGTNYV<br>FWGGREGYMSLLNTDMKREKEHMATMLTMARDYARSKGFKGTFLIEPKPMEPTKHQYDADTE<br>TVIGFLRAHGLDKDFKVNIEVNHATLAGHTFEHELACAVDADMLGSIDANRGDYQNGWDTDQ<br>FPIDHYELTQAMLQIIRNGGFKDGGTNFDAKTRRNSTDLEDIFIAHVAAMDAMAHALLSAAD<br>IIEKSPICTMVKERYASFDAGEGKRFEEGKMTLEEAYEYGKKVGEPKQTSGKQELYEAIVNM<br>Y</u> |
| 5586MI202_004 | Bacteroides | DNA | 13 | ATGGCAACAAAAGAGTATTTTCCCGGAATAGGAAAGATTAAATTCGAAGGTAAAGAGAGTAT<br>GAACCCGATGGCATATCGTTACTACGATGCTGAGAAGGTAATCATGGGTAAGAAGATGAAAG<br>ATTGGTTGAAGTTTGCTATGGCTTGGTGGCACACTCTCTGCGCAGAAGGTGGTGACCAATTC<br>GGTGGCGGAACGAAACAATTCCCTTGGAATGGTGACTCTGACGCTTTGCAAGCAGCTAAAAA<br>TAAATTCGGATGCAGGTTTCGAATTCATGCAGAGAATGGGTATCGAATACTATTGCTTCCACG<br>ATGTAGACCTGATTTCTGAAGGTCAAGCATCGAAGAATACGAAGCTAACCTTGAAAGCTATC<br>GTAGCTTATGCAAAGAAAAACAGGCTGAAACTGGTATCAAGCTGTTGTGGGGTACTGCTAA<br>CGTATTCGGTCATGCACGTTATATGAACGGTGCTGCTACCAATCCTGATTTCGACGTTGTAG<br>CACGCGCTGTCAGATCAAGAACGCTATTGACGCTACTATCGAACTGGGTGGTTCAAAC<br>TATGTATTCTGGGGCGGTCGCGAAGGTTACATGTCTTTGCTGAACACTGACCAGAAACGTGA<br>AAAAGAACACCTTGCAAAGATGTTGACTATCGCTCGTGACTATGCACGTGCTCGTGGCTTCA<br>AAGGTACTTTCCTGATTGAGCCGAAACCGATGGAACCGACAAAACATCAGTATGATGTAGAT<br>ACTGAAACAGTTATCGGCTTCCTGAAAGCTCACGGTTTGGATAAGGATTTCAAAGTAAACAT<br>CGAGGTTAATCACGCAACTTTGGCTGGCCATACTTTCGAACACGAACTGGCTGTAGCTGTTG |

TABLE 2-continued

| Clone No. | Class of organism | Type of Sequence | SEQ ID NO: | Sequence |
|---|---|---|---|---|
| | | | | ACAACGGCATGTTAGGTTCTATCGACGCTAACCGTGGTGACTACCAGAACGGTTGGGATACT<br>GACCAATTCCCTATCGATAACTACGAACTGACTCAAGCTATGATGCAGATCATCCGCAACGG<br>TGGTTTGGGTAATGGCGGTACTAACTTCGACGCTAAGACCCGTCGTAACTCTACCGACCTGG<br>AAGATATCTTCATCGCTCACATTGCAGGTATGGATGCTATGGCACGTGCTCTGGAAAGTGCA<br>GCTAAATTACTGGAAGAATCTCCTTATAAGAAAATGTTGGCTGATCGTTACGCATCATTCGA<br>CGGTGGCAAGGGTAAGGAATTCGAAGAAGGCAAATTGTCTTTGGAAGATGTTGTAGCTTATG<br>CGAAAGCTAACGGCGAACCGAAGCAAACCAGCGGCAAGCAAGAATTGTATGAAGCAATCGTG<br>AATATGTATTGCTAA |
| 5586MI202_004 | Bacteroides | Amino Acid | 14 | MATKEYFPGIGKIKFEGKESMNPMAYRYYDAEKVIMGKKMKDWLKFAMAWWHTLCAEGGDQF<br>GGGTKQFPWNGDSDALQAAKNKLDAGFEFMQKMGIEYYCFHDVDLISEGASIEEYEANLKAI<br>VAYAKEKQAETGIKLLWGTANVFGHARYMNGAATNPDFDVVARAAVQIKNAIDATIELGGSN<br>YVFWGGREGYMSLLNTDQKREKEHLAKMLTIARDYARARGFKGTFLIEPKPMEPTKHQYDVD<br>TETVIGFLKAHGLDKDFKVNIEVNHATLAGHTFEHELAVAVDNGMLGSIDANRGDYQNGWDT<br>DQFPIDNYELTQAMMQIIRNGGLGNGGTNFDAKTRRNSTDLEDIFIAHIAGMDAMARALESA<br>AKLLEESPYKKMLADRYASFDGGKGKEFEEGKLSLEDVVAYAKANGEPKQTSGKQELYEAIV<br>NMYC |
| 5586MI211_003 | Bacteroides | DNA | 15 | ATGGCAAAAGAGTATTTTCCTGGCGTGAAAAAAATCCAGTTCGAGGGTAAGGACAGTAAGAA<br>TCCAATGGCTTACCGTTATTATGATGCAGAGAAGGTCATCATGGGTAAGAAGATGAAGGATT<br>GGTTGAAGTTCGCTATGGCTTGGTGGCACACTTTGTGCGCTGAGGGCGCAGACCAGTTCGGT<br>GGCGGTACTAAGACTTTCCCTTGGAACGAAGGTGCAAACGCTTTGGAAGTTGCTAAGAATAA<br>GGCTGATGCTGGTTTCGAGATTATGGAGAAGCTTGGCATCGAGTACTACTGTTTCCACGATG<br>TAGACCTCGTTGAGGAGGCTGCAACTATCGAGGAGTATGAGGCTAACATGAAGGCTATCGTT<br>GCTTATCTTAAGGAGAAGCAGGCTGCTACTGGCAAGAAGCTTCTTTGGGGTACTGCTAACGT<br>ATTCGGCAACAAGCGCTATATGAACGGTGCTTCTACAAACCCTGACTTCGACGTTGTTGCTC<br>GCGCTTGTGTTCAGATTAAGAACGCTATCGACGCTACTATCGAACTTGGTGGTACAAACTAC<br>GTATTCTGGGGTGGCCGCGAGGGTTATATGAGCCTTCTTAACACAGATATGAAGCGTGAGAA<br>GGAGCACATGGCAACTATGCTTACTAAGGCTCGCGACTACGCTCGTTCAAAGGGCTTTACTG<br>GTACATTCCTTATCGAGCCAAAGCCAATGGAACCATCAAAGCATCAGTATGATGTTGATACT<br>GAGACTGTTTGTGGTTTCTTGAGGGCTCACGGTCTTGACAAGGACTTCAAGGTAAACATCGA<br>GGTTAACCACGCTACTTTGGCTGGTCACACATTCGAGCACGAGTTGGCTGCTGCTGTTGATA<br>ACGGTATGCTTGGCTCTATCGACCGTAACCGCGGTGACTACCAGAACGGTTGGGATACTGAC<br>CAGTTCCCTATCGACAACTACGAGCTGACCCAGGCCATGATGCAGATTATCCGCAACGGTGG<br>TCTTGGCAACGGTGGTACAAACTTCGACGCTAAGACTCGTCGTAACTCAACTGACCTTGAGG<br>ATATCTTCATCGCACACATCGCTGGTATGGATGCAATGGCTCGCGCTCTTGAGAACGCAGCA<br>GACCTTTTGGAGAACTCTCCAATCAAGAAGATGGTTGCTGAGCGTTACGCTTCATTCGACAG<br>CGGCAAGGGTAAGGAGTTCGAGGAAGGCAAGTTGAGCCTTGGGACATCGTTGCTTATGCTA<br>AGCAGAACGGTGAGCCTAAGCAGACAAGCGGTAAGCAGGAGCTTTACGAGGCTATCGTAAAC<br>ATGTACTGCTAA |
| 5586MI211_003 | Bacteroides | Amino Acid | 16 | MAKEYFPGVKKIQFEGKDSKNPMAYRYYDAEKVIMGKKMKDWLKFAMAWWHTLCAEGADQFG<br>GGTKTFPWNEGANALEVAKNKADAGFEIMEKLGIEYYCFHDVDLVEEAATIEEYEANMKAIV<br>AYLKEKQAATGKKLLWGTANVFGNKRYMNGASTNPDFDVVARACVQIKNAIDATIELGGTNY<br>VFWGGREGYMSLLNTDMKREKEHMATMLTKARDYARSKGFTGTFLIEPKPMEPSKHQYDVDT<br>ETVCGFLRAHGLDKDFKVNIEVNHATLAGHTFEHELAAAVDNGMLGSIDANRGDYQNGWDTD<br>QFPIDNFELIQAMMQIIRNGGLGNGGTNFDAKTRRNSTDLEDIFIAHIAGMDAMARALENAA<br>DLLENSPIKKMVAERYASFDSGKGKEFEEGKLSLGDIVAYAKQNGEPKQTSGKQELYEAIVN<br>MYC |
| 5606MI1_005 | Bacteroides | DNA | 17 | ATGGCGACAAAAGAATACTTTCCCGGAATAGGGAAAATCAAGTTTGAGGGTGTGAATAGCTA<br>TAATCCGCTGGCATACAGATATTACGATGCCGAGCGCATAGTCCTTGGCAAGCCGATGAAGG<br>AGTGGCTCAAGTTTGCCATGGCATGGTGGCACACACTCTGCGCAGAGGGTGGCGACCAGTTT<br>GGCGGCGGTACGAAGAATTTTCCCTGGAATGGAGATCCCGATCCGGTACAGGCCGCAAAAAA<br>CAAAGTAGACGCCGGCTTCGAATTCATGACCAAGATGGGAATAGAGTATTTCTGTTTCCACG<br>ACGTGGATCTCGTCAGCGAGGCAGCAACCATCGAGGAGTATGAGGCCAACCTGAAGGAAGTG<br>GTGGGCTACATCAAGGAAAAGCAGGCCGAGACGGGGATCAAAAACCTCTGGGGCACTGCCAA<br>CGTGTTCAGCCACGCGCGCTACATGAACGGAGCCGCCACCAACCCCGACTTCGATGTAGTGG<br>CCCGCGCAGCCGTGCAGATCAAGAATGCTATCGACGCCACGATAGCCTTAGGTGGCACCAAC<br>TACGTGTTCTGGGGTGGCCGTGAAGGTTACATGAGCCTGCTCAACACCGACCAGAAGCGCGA<br>GAAGGAGCATCTGGCAATGATGCTCCGCATGGCCCGCGACTATGCGCGTCAAAAGGCTTCA<br>CCGGCACCTTCCTTATCGAGCCCAAGCCGATGGAGCCCACCAAGCACCAGTATGATGTAGAC<br>ACCGAGACTGTGATAGGCTTCCTCCGTGCCCACGGCCTCGACAAGGACTTCAAGGTCAACAT<br>AGAGGTGAACCACGCCACCCTGGCCGGCCATACCTTCGAGCATGAGCTGGCAGTGGCCGTGG<br>ACAACGGTATGCTCGGCAGCATCGACGCCAACCGCGGTGACTACCAGAACGGCTGGGATACC<br>GACCAGTTCCCCATCGACAACTACGAGCTGACCCAGGCCATGATGCAGATAATACGCAACGG<br>CGGCTTCGGCAACGCGGATGCAACTTCGACGCCAAGACACGCCGCAACTCCACCGACCTGG<br>AGGATATCTTCATAGCCCACATAGCAGGCATGGACGCCATGGCCCGCGCCCTGCTCAGCGCA<br>GCAGAAGTGCTGGAGAAATCGCCCTACAGGAAGATGCTCGCCGAGCGCTACGCACCGTTTGA<br>TGCCGGCAGGGAAAGGCATTTGAAGAGGGCGCAATGTCGCTCACCGACCTTGTGGAGTATG<br>CCAAGGACATGGCGAGCCCACACAGACTTCCGGCAAGCAGGAACTCTATGAGGCAATCGTC<br>AATATGTATTGCTAA |
| 5606MI1_005 | Bacteroides | Amino Acid | 18 | MATKEYFPGIGKIKFEGVNSYNPLAYRYYDAERIVLGKPMKEWLKFAMAWWHTLCAEGGDQF<br>GGGTKNFPWNGDPDPVQAAKNKVDAGFEFMTKMGIEYFCFHDVDLVSEAATIEEYEANLKEV<br>VGYIKEKQAETGIKNLWGTANVFSHARYMNGAATNPDFDVVARAAVQIKNAIDATIALGGTN |

TABLE 2-continued

| Clone No. | Class of organism | Type of Sequence | SEQ ID NO: | Sequence |
|---|---|---|---|---|
| | | | | YVFWGGREGYMSLLNTDQKREKEHLAMMLRMARDYARAKGFTGTFLIEPKPMEPTKHQYDVD<br>TETVIGFLRAHGLDKDFKVNIEVNHATLAGHTFEHELAVAVDNGMLGSIDANRGDYQNGWDT<br>DQFPIDNYELTQAMMQIIRNGGFGNGGCNFDAKTRRNSTDLEDIFIAHIAGMDAMARALLSA<br>AEVLEKSPYRKMLAERYAPFDAGQGKAFEEGAMSLTDLVEYAKEHGEPTQTSGKQELYEAIV<br>NMYC |
| 5606MI2_003 | Bacteroides | DNA | 19 | ATGGCAACAAAGGAATATTTTCCCCATATAGGGAAGATCCAGTTCAAAGGCACGGAATCGTA<br>CGATCCGATGTCGTATCGTTACTATGACGCCGAGCGCGTAGTTCTGGGCAAGCCCATGAAGG<br>AATGGCTGAAATTCGCCATGGCATGGTGGCACACATTGTGCGCCGAGGGCGGCGACCAGTTC<br>GGCGGCGGAACGAAGAAGTTCCCCTGGAACGAGGGCGAGGACGCCATGACCATCGCCAAGCA<br>GAAGGCTGACGCCGGCTTCGAGATCATGCAGAAGCTCGGCATCGAGTATTTCTGCTTCCACG<br>ACATCGACCTGATCGGCGACCTGGGCGACGACATCGAGGACTATGAGAACCGTATGCACGAA<br>ATCACCGCACACCTGAAGGAGAAGATGGCCGCCACGGGCATCAAGAACCTGTGGGGCACTGC<br>CAACGTGTTCGGCCACGCACGCTATATGAACGGCGCCGCCACCAACCCCGACTTCGACGTTG<br>TGGCACGCGCATGTGTGCAGATCAAGAACGCCATCGACGCCACCATCGCTCTAGGCGGTACA<br>AACTATGTATTCTGGGGCGGCCGCGAGGGCTACATGAGCCTGCTGAACACCGACCAGAAGCG<br>CGAGAAAGAGCACTTGGCTACCATGCTGACCATGGCACGCGACTATGCCCGCGCCAATGGCT<br>TCACCGGAACGTTCCTGATCGAGCCCAAACCCATGGAGCCCAGCAAGCATCAGTATGATGTG<br>GATACCGAGACCGTAATCGGCTTCCTGAAGGCCCACAACCTGGACAAGGACTTCAAGGTGAA<br>CATCGAGGTGAACCATGCCACTCTGGCCGGCCACACATTCGAGCATGAGCTGGCAGTAGCCG<br>TGGACAACGGCATGCTGGGCAGCATCGACGCCAACCGCGGCGACTATCAGAACGGCTGGGAC<br>ACCGACCAGTTCCCCATCGACAACTATGAGCTGACCCAGGCCATGATGCAGATAATCCGCAA<br>CGGTGGCCTCGGCAACGGCGGTACCAACTTCGACGCCAAGACACGTCGCAACTCCACCGACC<br>TGGACGACATCTTCATCGCTCACATCGCCGGTATGGACGCTATGGCCCGCGCTCCGCTCAGC<br>GCAGCCGACGTGCTTGAGAAGTCGCCTTACAAGAAGATGCTGGCCGACCGCTACGCTTCATT<br>CGACAGCGGCGAGGGCAAGAAGTTCGAGGAAGGCAAGATGACTCTGGAGGATGTCGTGGCCT<br>ACGCCAAGAAGAATCCCGAACCCGCTCAGACCAGCGGCAAGCAGGAACTCTACGAGGCCATC<br>ATCAACATGTACGCCTGA |
| 5606MI2_003 | Bacteroides | Amino Acid | 20 | MATKEYFPHIGKIQFKGTESYDPMSYRYYDAERVVLGKPMKEWLKFAMAWWHTLCAEGGDQF<br>GGGTKKFPWNEGEDANTIAKQKADAGFEIMQKLGIEYFCFHDIDLIGDLGDDIEDYENRMHE<br>ITAHLKEKMAATGIKNLWGTANVFGHARYMNGAATNPDFDVVARACVQIKNAIDATIALGGT<br>NYVFWGGREGYMSLLNTDQKREKEHLATMLTMARDYARANGFTGTFLIEPKPMEPSKHQYDV<br>DTETVIGFLKAHNLDKDFKVNIEVNHATLAGHTFEHELAVAVDNGMLGSIDANRGDYQNGWD<br>TDQFPIDNYELTQAMMQIIRNGGLGNGGTNFDAKTRRNSTDLDDIFIAHIAGMDAMARAPLS<br>AADVLEKSPYKKMLADRYASFDSGEGKKFEEGKMTLEDVVAYAKKNPEPAQTSGKQELYEAI<br>INMYA |
| 5610MI3_003 | Bacteroides | DNA | 21 | ATGGCAACAAAGAATTTTTCCCGAGATTGGTAAAATCAAGTTTGAGGGCCGCGAAAGCCG<br>CAATCCCCTCGCATTCCGCTACTACGGCCCCGAGAAAGTCGTTCTTGGCAAGAAGATGAAAG<br>ACTGGTTCAAGTTTGCGATGGCTTGGTGGCACACACTGTGCGCCCAGGGCACCGACCAGTTT<br>GGTGGCGACACCAAGCAGTTTCCGTGGAACACTGCCAGTGACCCCATGCAGGCCGCCAAGGA<br>TAAGGTGGATGCCGGATTTGAATTCATGACCAAGATGGGCATTGAGTACTTCTGCTTCCACG<br>ATGTGGATCTCGTCGCCGAGGCCGCCACTGTCGAGGAGTATGAGGCTAACCTCAAGACCATC<br>GTCGCCTACATCAAAGAGAAACAAGCCGAGACCGGCATCAAGAACCTGTGGGGCACAGCCAA<br>CGTATTCGGACACAAACGCTACATGAACGGTGCCGCCACCAACCCCGACTTTGATGTCGTGG<br>CACGCGCCATCGTGCAAATCAAGAACGCCATCGACGCCACCATCGAGTTGGGCGGCACGAGT<br>TACGTCTTTTGGGGCGGCCGCGAGGGCCACATGAGCCTGCTCAACACCGACCAGAAGCGCGA<br>GAAGGAGCACCTTGCACGCATGCTGACCATGGCACGCGACTATGCCCGCGCACGTGGTTTCA<br>ACGGCACCTTCCTCATCGAGCCCAAGCCCATGGAGCCCGACCAAGCACCAATATGATGTGGAC<br>ACCGAGACCGTCATCGGTTTCCTGCGTGCCCATGGTCTGGACAAGGACTTCAAGGTCAACAT<br>CGAGGTGAACCACGCTACACTGGCCGGACACACCTTCGAGCGCGAACTGGCAGTGGCCGTCG<br>ACAACGGTCTACTCGGCTCAATCGACGCCAACCGTGGTGACTATCAGAATGGTTGGGACACC<br>GATCAGTTCCCCATCGACCACTATGAGTTGGTTCAGGGCATGTTGCAGATTATCCGCAATGG<br>TGGTTTCACCGACGGTGGCACCAACTTCGATGCCAAGACCCGCCGCAACTCGACCGACCTCG<br>AGGACATCTTCATCGCCCACATCGCCGCGATGATGCCATGGCTCATGCGCTGGAGAGTGCT<br>GCCTCCATCATCGAGGAGTCGCCCTACTGCCAGATGGTCAAGGATCGCTATGCCTCATTTGA<br>CTCCGGCATCGGCAAGGACTTTGAGGACGGCAAGTTGACACTGGAACAAGCCTACGAGTACG<br>GTAAGCAAGTGGGCGAACCCAAGCAGACCAGTGGCAAGCAAGAACTGTACGAGTCAATCATC<br>AATATGTATTCCATTTAA |
| 5610MI3_003 | Bacteroides | Amino Acid | 22 | MATKEFFPEIGKIKFEGRESRNPLAFRYYGPEKVVLGKKMKDWFKFAMAWWHTLCAQGTDQF<br>GGDTKQFPWNTASDPMQAAKDKVDAGFEFMTKMGIEYFCFHDVDLVAEAATVEEYEANLKTI<br>VAYIKEKQAETGIKNLWGTANVFGHKRYMNGAATNPDFDVVARAIVQIKNAIDATIELGGTS<br>YVFWGGREGHMSLLNTDQKREKEHLARMLTMARDYARARGFNGTFLIEPKPMEPTKHQYDVD<br>TETVIGFLRAHGLDKDFKVNIEVNHATLAGHTFERELAVAVDNGLLGSIDANRGDYQNGWDT<br>DQFPIDHYELVQMLQIIRNGGFTDGGTNFDAKTRRNSTDLEDIFIAHIAAMDAMAHALESA<br>ASIIEESPYCQMVKDRYASFDSGIGKDFEDGKLTLEQAYEYGKQVGEPKQTSGKQELYESII<br>NMYSI |
| 5749MI2_004 | Bacteroides | DNA | 23 | ATGGCAACAAAAGAGTATTTTCCTGGTATAGGAAAGATTAAATTTGAAGGTAAAGAGAGTAA<br>GAATCCGATGGCATTCCGCTATTATGATGCCAATAAAGTAATCATGGGCAAGAAGATGAGCG<br>AGTGGCTGAAGTTTGCCATGGCTTGGTGGCACACATTGTGCGCCAAGGTGGTGACCAGTTT<br>GGTGGTGGAACAAAGACTTTCCCGTGGAACGATTCGGACAACGCCGTAGAAGCAGCCAACCA<br>TAAAGTAGATGCCGGTTTGAATTTATGCAGAAAATGGGCATCGAATACTATTGCTTCCATG<br>ATGTAGACCTCTGCACTGAAGCTGCTACCATTGAAGAATATGAAGCCAATCTGAAGGAAATA |

TABLE 2-continued

| Clone No. | Class of organism | Type of Sequence | SEQ ID NO: | Sequence |
|---|---|---|---|---|
| | | | | GTAGCCTATCCGAAACAGAAACAGGCTGAAACAGGTATCAAACTTCTGTGGGGTACGGCAAA<br>TGTATTTGGTCACAAACGCTATATGAATGGTGCTGCTACCAATCCGGATTTTGATGTAGTGG<br>CTCGTGCTGCTGTACAGATTAAGAATGCGATAGACGCTACAATTGAACTCGGTGGTAGCAAC<br>TACGTGTTCTGGGGCGGCCGTGAAGGTTATATGAGCTTGCTCAATACAGACCAGAAACGTGA<br>GAAAGAGCATTTGGCACAAATGTTGACCATGGCTCGTGACTATGCTCGTGCCAAAGGATTCA<br>AGGGTACCTTCCTGGTTGAACCCAAACCGATGGAACCAACTAAACACCAGTATGATGTAGAT<br>ACGGAAACTGTAATCGGCTTCCTCAAGGCTCATAATTTGGATAAGGATTTCAAGGTAAATAT<br>TGAAGTAAACCATGCTACATTGGCCGGTCATACTTTTGAACACGAATTGGCTGTTGCCGTAG<br>ACAACGATATGCTTGGCTCTATCGATGCCAACCGCGGTGACTATCAGAACGGTTGGGATACT<br>GACCAGTTCCCCATTGACAACTTCGAGCTTATCCAAGCCATGATGCAGATTATTCGCGGTGG<br>TGGCTTCAAAGATGGTGGTACAAACTTCGACGCTAAGACTCGTCGTAACTCTACCGACCTGG<br>AAGATATTTTCATTGCACACATCGCTGGTATGGATGCTATGGCACGTGCTTTGGAAAGTGCA<br>GCCAAGTTGCTTGAGGAATCTCCTTATAAGAAAATGTTGGCTGACCGCTATGCATCGTTCGA<br>TAGTGGCAAAGGTAAGGAGTTTGAAGAAGGCAAGCTGACATTGGAAGACGTTGTAGTTTATG<br>CCAAGCAGAATGGCGAGCCTAAACAGACCAGCGGTAAGCAGGAATTGTATGAGGCAATTGTA<br>AATATGTATGCCTGA |
| 5749MI2_004 | *Bacteroides* | Amino Acid | 24 | <u>MATKEYFPGIGKIKFEGKESKNPMAFRYYDANKVIMGKKMSEWLKFAMAWWHTLCAEGGDQF</u><br><u>GGGTKTFPWNDSDNAVEAANHKVDAGFEFMQKMGIEYYCFHDVDLCTEAATIEEYEANLKEI</u><br><u>VAYPKQKQAETGIKLLWGTANVFGHKRYMNGAATNPDFDVVARAAVQIKNAIDATIELGGSN</u><br><u>YVFWGGREGYMSLLNTDQKREKEHLAQMLTMARDYARAKGFKGTFLVEPKPMEPTKHQYDVD</u><br><u>TETVIGFLKAHNLDKDFKVNIEVNHATLAGHTFEHELAVAVDNDMLGSIDANRGDYQNGWDT</u><br><u>DQFPIDNFELIQAMMQIIRGGGFKDGGTNFDAKTRRNSTDLEDIFIAHIAGMDAMARALESA</u><br><u>AKLLEESPYKKMLADRYASFDSGKGKEFEEGKLTLEDVVVYAKQNGEPKQTSGKQELYEAIV</u><br>NMYA |
| 5750MI3_003 | *Bacteroides* | DNA | 25 | ATGGCAACAAAAGAGTATTTTCCTGGAATAGGAAAGATTAAATTTGAAGGAAAAGAGAGTAA<br>GAACCCGATGGCATTCCGTTGCTACGATGCAGAAAAAGTTATCATGGGTAAGAGAATGAAAG<br>ATTGGTTGAAGTTTGCAATGGCGTGGTGGCATACACTTTGTGCAGAAGGCGGTGACCAATTC<br>GGTGGCGGTACAAAGAGTTTCCCCCGGAACGACTATACTGATAAAATTCAGGCTGCTAAAAA<br>CAAGATGGATGCCGGTTTTGAGTTTATGCAGAAGATGGGGATCGAATACTATTGTTTTCACG<br>ATGTAGACCTCTGCACGGAAGCTGATACCATTGAAGAATACGAAGCTAATTTGAAAGAAATC<br>GTAGTTTACGCAAAGCAAAAGCAGGTAGAAACAGGTATCAAATTATTGTGGGGTACTGCCAA<br>TGTATTCGGTCATGAACGCTATATGAATGGTGCGGCTACCAACCCAGATTTTGATGTTGTAG<br>CCCGTGCTGCTGTTCAGATTAAGAATGCAATTGATGCTACCATTGAACTAGGTGGCTTAAAC<br>TATGTGTTCTGGGGTGGACGCGAAGGTTATATGTCTTTGCTGAACACTGATCAGAAACGTGA<br>GAAAGAACATCTTGCACAAATGCTGACCATTGCCCGTGACTATGCCCGTGCCCGTGGCTTCA<br>AAGGTACATTCTTGGTTGAACCGAAACCGATGGAACCAACCAAACATCAATATGACGTAGAT<br>ACAGAAACAGTTATCGGTTTTTTGAAAGCTCATGCTTTGGATAAAGACTTTAAAGTAAATAT<br>TGAAGTAAATCATGCAACATTAGCCGGTCATACATTTGAACACGAACTGGCAGTGGCTGTCG<br>ACAACGGTATGCTGGGTTCTATTGACGCTAATCGTGGTGATTGTCAAAACGGTTGGGATACA<br>GACCAATTTCCCATTGATAACTATGAACTGACTCAAGCCATGATGCAGATTATTCGTAACGG<br>TGGTTTGGGCAATGGTGGTACGAATTTTGACGCTAAAACTCGCCGTAATTCTACTGATCTTG<br>GAGATATCTTCATTGCTCACATCGCAGGTATGGATGCTATGGCACGTGCATTGGAAAGTGCG<br>GCCAAGTTGTTGGAAGAATCTCCCTATAAGAAGATGCTGGCAGAACGTTATGCATCCTTTGA<br>CAGCGGTAAGGGTAAAGAGTTTGAAGAGGGTAAGTTGACCTTGGAGGATCTTGTTGCTTATG<br>CAAAAGTCAATGGCGAACCGAAACAAATCAGTGGTAAACAAGAATTGTATGAGGCAATTGTG<br>AATATGTATTGCTAA |
| 5750MI3_003 | *Bacteroides* | Amino Acid | 26 | <u>MATKEYFPGIGKIKFEGKESKNPMAFRCYDAEKVIMGKRMKDWLKFAMAWWHTLCAEGGDQF</u><br><u>GGGTKSFPRNDYTDKIQAAKNKMDAGFEFMQKMGIEYYCFHDVDLCTEADTIEEYEANLKEI</u><br><u>VVYAKQKQVETGIKLLWGTANVEGHERYMNGAATNPDFDVVARAAVQIKNAIDATIELGGLN</u><br><u>YVFWGGREGYMSLLNTDQKREKEHLAQMLTIARDYARARGFKGTFLVEPKPMEPTKHQYDVD</u><br><u>TETVIGFLKAHALDKDFKVNIEVNHATLAGHTFEHELAVAVDNGMLGSIDANRGDCQNGWDT</u><br><u>DQFPIDNYELTQAMMQIIRNGGLGNGGTNFDAKTRRNSTDLGDIFIAHIAGMDAMARALESA</u><br><u>AKLLEESPYKKMLAERYASFDSGKGKEFEEGKLTLEDLVAYAKVNGEPKQISGKQELYEAIV</u><br>NMYC |
| 5750MI4_003 | *Bacteroides* | DNA | 27 | ATGGCAACAAAAGAGTATTTCCCGGAATAGGAAAGATTAAATTCGAAGGTAAAGAGAGCAA<br>GAACCCGATGGCATTCCGTTATTACGATGCCGATAAAGTAATCATGGGTAAGAAAATGAGCG<br>AATGGCTGAAGTTCGCCATGGCATGGTGGCACACTCTTTGCGCAGAAGGTGGTGACCAGTTC<br>GGTGGCGGAACAAAGAAATTCCCCTGGAACGGTGAGGCTGACAAGGTTCAGGCTGCCAAGAA<br>CAAAATGGACGCCGGCTTTGAATTCATGCAGAAAATGGGTATCGAATACTACTGCTTCCACG<br>ATGTAGACCTCTGCAAGAAGCCGAGACCATTGAAGAATACGAAGCCAACTTGAAGGAAATC<br>GTAGCGTATGCCAAGCAGAAACAAGCAGAAACCGGCATCAAGCTGTTGTGGGGTACTGCCAA<br>CGTATTCGGCCATGCCCGCTACATGAATGGTGCAGCCACCAACCCCGATTTCGATGTTGTGG<br>CACGTGCAGCCGTCAAATCAAAAGCGCCATCGACGCTACTATCGAGCTGGGAGGTTCGAAC<br>TATGTGTTCTGGGGCGGTCGCGAAGGCTACATGTCATTGCTGAATACAGACCAGAAGCGTGA<br>GAAAGAGCACCTCGCACAGATGTTGACCATCGCCCGCGACTATGCCCGTGCCCGTGGCTTCA<br>AGGTACCTTCCTGATTGAACCGAAACCGATGGAACCTACAAAACACCAGTATGATGTAGAC<br>ACCGAAACCGTTATCGGCTTCTTGAAGGCCCACAATCTGGACAAAGATTTCAAGGTAAACAT<br>CGAAGTGAACCACGCTACTTTGGCGGGCCACACCTTCGAGCACGAACTCGCAGTAGCCGTAG<br>ACAACGGTATGCTCGGCTCCATCGATGCCAACCGTGGTGACTACCAGAACGGCTGGGATACA<br>GACCAGTTCCCCATTGACAACTTCGAACTGACCCAGGCAATGATGCAAATCATCCGTAACGG<br>CGGCTTTGGCAATGGCGGTACAAACTTCGATGCCAAGACCCGTCGTAACTCCACCGACCTGG<br>AAGACATCTTGATTGCCCACATCGCCGGTATGGACGTGATGGCACGTGCACTGGAAAGTGCA |

TABLE 2-continued

| Clone No. | Class of organism | Type of Sequence | SEQ ID NO: | Sequence |
|---|---|---|---|---|
| | | | | GCCAAATTGCTTGAAGAGTCTCCTTACAAGAAGATGCTTGCCGACCGCTATGCTTCCTTCGA<br>CAGTGGTAAAGGCAAGGAATTCGAAGACGGCAAGCTGACACTGGAGGATTTGGCAGCTTACG<br>CAAAAGCCAACGGTGAGCCGAAACAGACCAGCGGCAAGCAGGGATTGTATGAGGCAATCGTA<br>AATATGTACTGCTGA |
| 5750MI4_003 | *Bacteroides* | Amino Acid | 28 | MATKEYFPGIGKIKFEGKESKNPMAFRYYDADKVIMGKKMSEWLKFAMAWWHTLCAEGGDQF<br>GGGTKKFPWNGEADKVQAAKNKMDAGFEFMQKMGIEYYCFHDVDLCEEAETIEEYEANLKEI<br>VAYAKQKQAETGIKLLWGTANVFGHARYMNGAATNPDFDVVARAAVQIKSAIDATIELGGSN<br>YVFWGGREGYMSLLNTDQKREKEHLAQMLTIARDYARARGFKGTFLIEPKPMEPTKHQYDVD<br>TETVIGFLKAHNLDKDFKVNIEVNHATLAGHTFEHELAVAVDNGMLGSIDANRGDYQNGWDT<br>DQFPIDNFELTQAMMQIIRNGGFGNGGTNFDAKTRRNSTDLEDIFIAHIAGMDVMARALESA<br>AKLLEESPYKKMLADRYASFDSGKGKEFEDGKLTLEDLAAYAKANGEPKQTSGKQGLYEAIV<br>NMYC |
| 5751MI4_002 | *Bacteroides* | DNA | 29 | ATGACAAAAGAGTATTTTCCAACCATTGGTAAAATTCAGTTTGAAGGTAAAGAGAGTAAGAA<br>TCCATTAGCATATCGTTATTACGATGCTAACAAAGTAATAATGGGTAAAAAGATGAGCGAAT<br>GGCTCAAGTTTGCAATGGCATGGTGGCACACTTTGTGCTGTGAGGGTAGCGACCAGTTTGGT<br>CCTGGCACCAAGTCATTCCCATGGAACGCATCAACCGACCGTATGCAGGCTGCAAAGATAA<br>GGCTGACGCAGGCTTCGAAATCATGCAAAACTGGGCATCGAATACTACTGTTTCCATGATG<br>TTGACCTCATCGACCCAGCAGACGATATTCCAACATACGAAAAGAATCTCAAGGAAATCGTT<br>GCATACCTCAAGCAAAAACAGGCCGAGACAGGTATCAAATTGCTATGGGGTACAGCTAACGT<br>ATTTGGCCACAAGCGTTATATGAACGGTGCATCTACCAATCCTGACTTTGACGTTGTTGCAC<br>GAGCTATCGTGCAAATCAAGAATGCTATCGATGCAACAATCGAACTGGGCGGCACGAACTAC<br>GTATTCTGGGGTGGTCGCGAAGGTTACATGTCACTGCTCAACACCGACCAAAAGCGCGAGAA<br>AGAGCACATGGCTACCATGTTAGGAATGGCACGTGACTATGCACGTTCTAAAGGCTTTACTG<br>GTACTCTCCTTATCGAGCCAAAGCCTATGGAACCAACTAAGCATCAATACGACGTCGATACA<br>GAAACTGTTATTGGTTTCCTCAAAGCTCACGGATTAGACAAGGACTTCAAGGTAAATATCGA<br>AGTGAACCACGCTACATTGGCTGGCCATACCTTCGAACATGAATTAGCATGTGCTGTTGATG<br>CAGGTATGCTTGGTTCCATCGATGCTAACCGTGGTGATATGCAGAATGGCTGGGATACAGAT<br>CAGTTCCCTATCAACAATTACGAGCTCGTTCAGGCCATGATGCAGATTATCCGCAATGGTGG<br>TTTCGGTAACGGTGGTACAAACTTCGACGCTAAGACACGTCGTAATTCAACCGATTTGGAAG<br>ACATCATCATTGCTCACGTTTCAGCTATGGATGCTATGGCACGTGCTCTTGAATGTGCTGCA<br>GACATTCTTCAAAACTCACCTATTCCACAGATGGTGGCCAACCGTTATGCAAGTTTTGACAA<br>GGGTATAGGTAAAGATTTCGAAGACGGCAAGCTCACCCTCGAGCAAGTATACGAATATGGTA<br>AGACCGTCGGCGAACCAGCTATTACAAGCGGCAAACAGGAGCTCTACGAAGCTATCGTTAAT<br>ATGTATTGCTGA |
| 5751MI4_002 | *Bacteroides* | Amino Acid | 30 | MTKEYFPTIGKIQFEGKESKNPLAYRYYDANKVIMGKKMSEWLKFAMAWWHTLCAEGSDQFG<br>PGTKSFPWNASTDRMQAAKDKADAGFEIMQKLGIEYYCFHDVDLIDPADDIPTYEKNLKEIV<br>AYLKQKQAETGIKLLWGTANVFGHKRYMNGASTNPDFDVVARAIVQIKNAIDATIELGGTNY<br>VFWGGREGYMSLLNTDQKREKEHMATMLGMARDYARSKGFGTLLIEPKPMEPTKHQYDVDT<br>ETVIGFLKAHGLDKDFKVNIEVNHATLAGHTFEHELACAVDAGMLGSIDANRGDMQNGWDTD<br>QFPINNYELVQAMMQIIRNGGFGNGGTNFDAKTRRNSTDLEDIIIAHVSAMDAMARALECAA<br>DILQNSPIPQMVANRYASFDKGIGKDFEDGKLTLEQVYEYGKTVGEPAITSGKQELYEAIVN<br>MYC |
| 5751MI5_003 | *Bacteroides* | DNA | 31 | ATGGCTAACAAAGAATTTTTCCCCGGTATTGGTAAAATCAAATTCGAAGGTAAAGAGAGCAA<br>GAACCCCATGGCATATCGTTACTACGATGCTGAGAAGGTAGTCCTTGGCAAGAATATGAAAG<br>ACTGGTTCAAGTTTGCGATGGCTTGGTGGCACACATTGTGCGCCGAGGGTAGCGACCAGTTT<br>GGTCCCGGCACTAAGTCTTTCCCCTGGAACACCGCAGAGTGCCCCATGCAGGCAGCTAAGGA<br>CAAGGTTGACGCTGGCTTCGAGTTCATGACCAAGATGGGTATTGAATACTTCTGCTTCCACG<br>ATGTAGACCTCGTTGCCGAGGCCGACACTGTTGAGGAGTACGAGGCTCGCATGAAGGAAATC<br>GTTGCTTACATCAAGGAGAAGGTGGCCGAGACTGGCATCAAGAACCTGTGGGGTACAGCTAA<br>CGTATTTGGCAACAAGCGCTACATGAACGGTGCTGCTACTAACCCCGACTTTGACGTTGTGG<br>CTCGCGCTATCGTTCAAATCAAGAACGCTATCGACGCTACTATCGAGCTCGGTGGTACGTCA<br>TACGTATTCTGGGGCGGCCGCGAGGGTTACATGAGCCTCTTGAACACCGACCAGAAGCGTGA<br>GAAAGAGCACCTGGCTACTATGCTCACTATGGCACGCGACTACGCTCGCGCTAAGGGTTTCA<br>AGGGTACATTCCTCATCGAGCCCAAGCCCATGGAGCCCACAAAGCACCAGTACGATGTTGAC<br>ACTGAGACTGTAATCGGCTTCCTTAAGGCACACAACCTTGACAAGGACTTCAAGGTTAACAT<br>TGAGGTTAACCACGCAACTCTCGCTGGTCACACATTTGAGCACGAGCTCGCTTGTGCTGTTG<br>ACGCTGGCATGCTTGGCAGCATCGACGCTAACCGCGGTGACTACCAGAACGGCTGGGATACT<br>GACCAATTCCCCATCGACAACTTCGACCTCACTCAAGCTATGCTCGAGATCATCCGCAACGA<br>TGGTTTCAAGGATGGTGGTACAAACTTCGACGCTAAGACTCGCCGCAACAGCACCGACCTCG<br>AGGATATCTTCATCGCACACATCGCTGGTATGGACGCTATGGCACGTGCTCTCGAGAGCGCT<br>GCTGCAGTACTCGAGGAGTCAGCTCTGCCCCAAATGAAGAAGGACCGCTATGCATCGTTCGA<br>CGCTGGCATGGGTAAGGACTTCGAGGACGGCAAGCTCACCCTGGAGCAAGTTTACGAGTATG<br>GTAAGAAGGTGGGCGAGCCCAAGCAGACTAGCGGCAAGCAAGAGCTGTATGAGGCTATCCTC<br>AACATGTACGTATAA |
| 5751MI5_003 | *Bacteroides* | Amino Acid | 32 | MANKEFFPGIGKIKFEGKESKNPMAYRYYDAEKVVLGKNMKDWFKFAMAWWHTLCAEGSDQF<br>GPGTKSFPWNTAECPMQAAKDKVDAGFEFMTKMGIEYFCFHDVDLVAEADTVEEYEARMKEI<br>VAYIKEKVAETGIKNLWGTANVFGNKRYMNGAATNPDFDVVARAIVQIKNAIDATIELGGTS<br>YVFWGGREGYMSLLNTDQKREKEHLATMLTMARDYARAKGFKGTFLIEPKPMEPTKHQYDVD<br>TETVIGFLKAHNLDKDFKVNIEVNHATLAGHTFEHELACAVDAGMLGSIDANRGDYQNGWDT |

TABLE 2-continued

| Clone No. | Class of organism | Type of Sequence | SEQ ID NO: | Sequence |
|---|---|---|---|---|
| | | | | DQFPIDNFDLTQAMLEIIRNDGFKDGGTNFDAKTRRNSTDLEDIFIAHIAAMDAMARALESA<br>AAVLEESALPQMKKDRYASFDAGMGKDFEDGKLTLEQVYEYGKKVGEPKQTSGKQELYEAIL<br>NMYV |
| 5751MI6_004 | Bacteroides | DNA | 33 | ATGGCTAACAAAGAATTTTTCCCAGGTATTGGTAAAATCAAATTCGAAGGCAAAGAAAGCAA<br>GAACCCCATGGCATATCGTCACTACGATGCCGAGAAGGTAGTCCTTGGTAAGAAGATGAAGG<br>ACTGGTTCAAGTTTGCGATGGCTTGGTGGCACACTCTGTGCGCCGAGGGTAGCGACCAGTTC<br>GGCCCCGTGACCAAGTCTTTCCCCTGGAACCAGGCCGAGTGCCCCATGCAGGCTGCTAAGGA<br>CAAGGTTGACGCCGGCTTCGAGTTCATGACCAAGATGGGTATCGAATACTTCTGTTTCCACG<br>ATGTAGACCTCGTTGCCGAGGCCGACACCGTTGAGGAGTACGAAGCTCGCATGAAGGAAATC<br>GTGGCTTACATCAAGGAGAAGATGGCCGAGACCGGCATCAAGAACCTGTGGGGTACAGCCAA<br>CGTATTCGGCAACAAGCGCTACATGAACGGTGCTGCCACCAACCCCGACTTTGACGTTGTGG<br>CTCGCGCAATCGTTCAGATCAAGAACGCCATCGACGCTACTATCGAGCTCGGCGGTACCTCT<br>TACGTGTTCTGGGGCGGCCGCGAGGGTTACATGACTCTCTTGAACACCGACCAGAAGCGCGA<br>GAAGGAGCACCTGGCTACCATGCTCACCATGGCTCGCGACTATGCTCGCGCTAAGGGCTTCA<br>AGGGTACATTCCTTATCGAGCCCAAGCCCATGGAGCCCACCAAGCACCAGTATGACGTGGAT<br>ACCGAGACCGTTATCGGCTTCCTCAAGGCTCACGGCCTGGACAAGGACTTCAAGGTGAACAT<br>CGAGGTTAACCATGCAACTCTCGCCGGCCACACATTCGAGCACGAACTCGCTTGCGCTGTTG<br>ACGCTGGCATGCTGGGCAGCATCGACGCTAACGCGGCGACTACCAGAACGGCTGGGATACC<br>GACCAGTTCCCCATCGACAACTTCGACCTCACTCAGGCTATGCTCGAGATCATCCGCAACGG<br>TGGTTTCAAGGACGGTGGTACAAACTTCGACGCTAAGACCCGTCGCAACAGCACCGATCTTG<br>AGGACATCTTCATCGCTCACATCGCTGCTATGGACGCAATGGCACGCGCGCTCGAGAGCGCT<br>GCCGCTGTGCTCGAGCAGAGCCCCCTTCCCCAGATGAAGAAAGACCGCTACGCATCGTTCGA<br>TGCCGGCATGGGCAAGGACTTCGAGGACGGCAAGCTCACTCTGGAGCAGGTTTACGAGTATG<br>GTAAGAAGGTAGGCGAGCCCAAGCAGACCAGCGGCAAGCAGGAACTGTACGAGGCTATCCTC<br>AACATGTATGTATAA |
| 5751MI6_004 | Bacteroides | Amino Acid | 34 | MANKEFFPGIGKIKFEGKESKNPMAYRHYDAEKVVLGKKMKDWFKFAMAWWHTLCAEGSDQF<br>GPVTKSFPWNQAECPMQAAKDKVDAGFEFMTKMGIEYFCFHDVDLVAEADTVEEYEARMKEI<br>VAYIKEKMAETGIKNLWGTANVFGNKRYMNGAATNPDFDVVARAIVQIKNAIDATIELGGTS<br>YVFWGGREGYMTLLNTDQKREKEHLATMLTMARDYARAKGFKGTFLIEPKPMEPTKHQYDVD<br>TETVIGFLKAHGLDKDFKVNIEVNHATLAGHTFEHELACAVDAGMLGSIDANRGDYQNGWDT<br>DQFPIDNFDLTQAMLEIIRNGGFKDGGTNFDAKTRRNSTDLEDIFIAHIAAMDAMARALESA<br>AAVLEQSPLPQMKKDRYASFDAGMGKDFEDGKLTLEQVYEYGKKVGEPKQTSGKQELYEAIL<br>NMYV |
| 5586MI22_003 | Clostridiales | DNA | 35 | ATGAAAGAATATTTTCCTATGACAAAAAAAGTTGAATATGAGGGCGCAGCATCTAAAAATCC<br>ATTTGCGTTTAAATACTATGATGCCGAAAGAATTATAGCAGGCAAGCCTATGAAAGAACATC<br>TTAAATTTGCTATGAGTTGGTGGCATACACTTTGTGCGGGCGGTGCAGACCCATTTGGCACA<br>ACAACTATGGACAGAACATACGGCGGACTTACCGACCCAATGGAAATTGCAAAGGCAAAGT<br>AGATGCAGGCTTTGAGTTTATGCAAAAACTCGGTATAGAGTATTTTTGTTTTCACGATGCGG<br>ATATTGCACCGGAAGGAAGCAGTTTTGTTGAAACAAAGAAAAACTTTTGGGAAATAGTAGAT<br>TATATACAGCAAAAGATGAATGAAACAGGCATAAAGTTGCTTTGGGGTACTGCAAACTGCTT<br>TAATGCTCCACGTTATATGCACGGTGCAGGAACATCATGCAATGCGCACAGTTTTGCATATG<br>CAGCCGCACAGATAAAAAATGCAATTGAAGCTACCGTTAAACTGGGTGGAAAAGGCTATGTT<br>TTCTGGGGCGGAAGAGAGGGTTATGAAACACTTCTCAATACGGATATGGCACTTGAACTTGA<br>CAATATGGCAAGACTTATGCATATGGCAGTTGATTATGGCAGAAGCATTGGTTTTGACGGTG<br>ATTTTTATATCGAACCAAAGCCAAAGGAACCAACAAAACATCAATATGACTTTGACTCGGCA<br>ACTGTTTTGGGATTTTTGAGAAAGTACGGTTTAGATAAGGATTTTAAACTTAATATAGAGGC<br>AAATCATGCGACACTTGCAGGTCATACATTTGAACATGAATTGACTGTAGCGCGTATAAACG<br>GTGCATTTGGCAGCATAGATGCAAATAGCGGCGATCCCAATCTTGGCTGGGATACCGACCAA<br>TTCCCAACAGATGTTTATTCGGCAACCCTTTGTATGCTTGAAGTGATAAGAGCAGGCGGCTT<br>TACAAACGGAGGTCTTAATTTTGATGCAAAGGTCAGAAGAGGCTCATTTACGTTTGATGACA<br>TTGTTTATGCATATATCAGCGGTATGGACACTTTTGCGCTGGGTTTTATAAAGGCATATGAA<br>ATAATTGAGGACGGCAGAATAGATGAATTTGTAAAAGAAAGATACGCAAGCTATAATACAGG<br>CATAGGCAAAGATATTATAGATGGAAAGGCAAGCCTTGAAAGTTTGGAAGAATATATTCTTT<br>CAAATGATAATGTTGTAATGCAAAGCGGCAGACAGGAATATCTTGAAACAGTTTTGAATAAT<br>ATTTTGTTTAAAGCATAA |
| 5586MI22_003 | Clostridiales | Amino Acid | 36 | MKEYFPMTKKVEYEGAASKNPFAFKYYDAERIIAGKPMKEHLKFAMSWWHTLCAGGADPFGT<br>TTMDRTYGGLTDPMEIAKAKVDAGFEFMQKLGIEYFCFHDADIAPEGSSFVETKKNFWEIVD<br>YIQQKMNETGIKLLWGTANCFNAPRYMHGAGTSCNAHSFAYAAAQIKNAIEATVKLGGKGYV<br>FWGGREGYETLLNTDMALELDNMARLMHMAVDYGRSIGEDGDFYIEPKPKEPTKHQYDFDSA<br>TVLGELRKYGLDKDFKLNIEANHATLAGHTFEHELTVARINGAFGSIDANSGDPNLGWDTDQ<br>FPTDVYSATLCMLEVIRAGGFTNGGLNFDAKVRRGSFTFDDIVYAYISGMDTFALGFIKAYE<br>IIEDGRIDEFVKERYASYNTGIGKDIIDGKASLESLEEYILSNDNVVMQSGRQEYLETVLNN<br>ILFKA |
| 1753MI4_001 | Firmicutes | DNA | 37 | ATGAAAGAATTTCCCAAATATTCCTGAGATTAAATTCGAAGGAAAAGCAGCAAAAATCC<br>TTTTGCTTTCCATTACTACAACCCAGACCAAATCATCTTAGGCAAACCAATGAAGAACACC<br>TCCCATTCGCTATGGCTTGGTGGCACAATCTTGGTGCAACAGGTGTTGATATGTTTGCACT<br>GGCCCAGCTGATAAGAGTTTCGGTGCTAAAGTTGACAATGGAACACGCTAAGGCCAAAGT<br>CGATGCCGGTTTCGAATTCATGAAGAAACTCGGTATCAGATATTTCTGCTTCCATGATGTTG<br>ACTTAGTTCCAGAATGTGCAGATATCAAAGATACAAACAAGAATTAGATGAAATCAGTGAC<br>TACATCTTAGAAAAGATGAAAGGCACAGATATTAAGTGTTTATGGGGCACCGCAATATGTT<br>CTCTAACCCACGCTTCTGCAATGGTGCGGGTTCCACAAACAGTGCGGATGTCTTCGCTTTCG |

TABLE 2-continued

| Clone No. | Class of organism | Type of Sequence | SEQ ID NO: | Sequence |
|---|---|---|---|---|
| | | | | CCGCTGCTCAAGTTAAGAAAGCCTTAGATATCACCGTTAAATTAGGTGGTAGGGGTTACGTC<br>TTCTGGGGTGGTCGTGAAGGTTACGAAACATTACTCAATACAGACGTTAAATTCGAACAAGA<br>AAACATTGCTCGTTTAATGAAGATGGCTGTTGAATATGGCCGTTCCATCGGTTTCAAAGGCG<br>ATTTCTATATCGAACCAAAACCAAAAGAACCAATGAAACACCAATATGACTTCGACGCCGCT<br>ACAGCTATTGGCTTCTTAAGAGCCCACGGCTTAGACAAAGACTTCAAGTTGAACATCGAAGC<br>TAACCACGCTACATTAGCGGGTCATACATTCCAACACGATTTAAGAATCTCCGCCATTAATG<br>GTATGTTAGGTTCTATCGATGCTAACCAAGGCGATATGCTCTTAGGTTGGGATACAGACGAA<br>TTCCCATTTGATGTCTACAGTGCGACACAATGTATGTACGAAGTCTTAAAGAATGGTGGTCT<br>TACAGGTGGTTTCAACTTTGACTCCAAAACACGTCGTCCATCCTACACAATGGAAGATATGT<br>TCTTAGCCTATATCTTAGGTATGGATACATTCGCTTTAGGTTTAATCAAAGCTGCTCAAATC<br>ATCGAAGATGGCCGTATTGATCAATTCATCGAAAAGAAATATTCTTCCTTCCGTGAAACAGA<br>AATCGGTCAAAGATCTTAAACAACAAGACAAGCTTAAAAGAATTATCCGATTACGCTTGCA<br>AGATGGGTGCTCCAGAACTTCCAGGTAGTGGTCGTCAAGAAATGCTCGAAGCCATCGTTAAC<br>GATGTCTTATTCGGCAAGTAA |
| 1753MI4_001 | Firmicutes | Amino Acid | 38 | MKEIFPNIPEIKFEGKDSKNPFAFHYYNPDQIILGKPMKEHLPFAMWWHNLGATGVDMFGA<br>GPADKSFGAKVGTMEHAKAKVDAGFEFMKKLGIRYFCFHDVDLVPECADIKDTNKELDETSD<br>YILEKMKGTDIKCLWGTANMESNPRECNGAGSTNSADVFAFAAAQVKKALDITVKLGGRGYV<br>FWGGREGYETLLNTDVKFEQENIARLMKMAVEYGRSIGFKGDFYIEPKPKEPMKHQYDFDAA<br>TAIGFLRAHGLDKDFKLNIEANHATLAGHTFQHDLRISAINGMLGSIDANQGDMLLGWDTDE<br>FPFDVYSATQCMYEVLKNGGLTGGFNFDSKTRRPSYTMEDMFLAYILGMDTFALGLIKAAQI<br>IEDGRIDQFIEKKYSSFRETEIGQKILNNKTSLKELSDYACKMGAPELPGSGRQEMLEAIVN<br>DVLFGK |
| 1753MI6_001 | Firmicutes | DNA | 39 | ATGAAAGAAATTTTCCCAAATATTCCTGAGATTAAATTCGAAGGAAAAGACAGCAAAAATCC<br>TTTTGCTTTCCATTACTACAACCCAGACCAAATCATCTTAGGTAAACCAATGAAAGAACACC<br>TCCCATTCGCTATGGCTTGGTGGCACAATCTTGGTGCAACAGGTGTTGATATGTTTGGCGCT<br>GGCCCAGCTGATAAGAGTTTCGGTGCTAAAGTTGGCACAATGGAACACGCTAAGGCCAAAGT<br>CGATGCCGGTTTCGAATTCATGAAGAAACTTGGTATCAGATATTTCTGCTTCCATGATGTTG<br>ACTTAGTTCCAGAATGTGCAGATATCAAAGATACAAACAAAGAATTAGATGAAATCAGTGAC<br>TACATCTTAGAAAAGATGAAAGGCACAGATATCAAGTGTTTATGGGGCACCGCCAATATGTT<br>CTCTAACCCACGTTTCTGCAATGGTGCGGGTTCCACAAACAGTGCGGATGTCTTCGCTTTCG<br>CCGCTGCTCAAGTTAAGAAAGCCTTAGATATCACCGTTAAATTAGGTGGTAGGGGTTACGTC<br>TTCTGGGGTGGTCGTGAAGGTTACGAAACATTACTCAATACAGACGTTAAATTCGAACAAGA<br>AAACATTGCTCGTTTAATGAAGATGGCTGTTGAATATGGCCGTTCCATCGGTTTCAAAGGCG<br>ATTTCTATATCGAACCAAAACCAAAAGAACCAATGAAACACCAATATGACTTCGACGCCGCT<br>ACAGCTATTGGCTTCTTAAGAGCCCACGGCTTAGACAAAGACTTCAAGTTGAACATCGAAGC<br>TAACCACGCTACATTAGCGGGTCATACATTCCAACACGATTTAAGAATCTCCGCCATTAATG<br>GTATGTTAGGTTCTATCGATGCTAACCAAGGCGATATGCTCTTAGGTTGGGATACAGACGAA<br>TTCCCATTTGATGTCTACAGTGCGACACAATGTATGTACGAAGTCTTAAAGAATGGTGGTCT<br>TACAGGTGGTTTCAACTTTGACTCCAAAACACGTCGTCCATCCTACACAATGGAAGATATGT<br>TCTTAGCCTATATCTTAGGTATGGATACATTCGCTTTAGGTTTAATCAAAGCTGCTCAAATC<br>ATCGAAGATGGCCGTATTGATCAATTCATCGAAAAGAAATATTCTTCCTTCCGTGAAACAGA<br>AATCGGTCAAAGATCTTAAACAACAAGACAAGCTTAAAAGAATTATCCGATTACGCTTGCA<br>AGATGGGTGCTCCAGAACTTCCAGGTAGTGGTCGTCAAGAAATGCTCGAAGCCATCGTTAAC<br>GATGTCTTATTCGGCAAGTAA |
| 1753MI6_001 | Firmicutes | Amino Acid | 40 | MKEIFPNIPEIKFEGKDSKNPFAFHYYNPDQIILGKPMKEHLPFAMWWHNLGATGVDMFGA<br>GPADKSFGAKVGTMEHAKAKVDAGFEFMKKLGIRYFCFHDVDLVPECADIKDTNKELDEISD<br>YILEKMKGTDIKCLWGTANMFSNPRFCNGAGSTNSADVFAFAAAQVKKALDITVKLGGRGYV<br>FWGGREGYETLLNTDVKFEQENIARLMKMAVEYGRSIGFKGDFYIEPKPKEPMKHQYDFDAA<br>TAIGFLRAHGLDKDFKLNIEANHATLAGHTFQHDLRISAINGMLGSIDANQGDMLLGWDTDE<br>FPFDVYSATQCMYEVLKNGGLTGGFNFDSKTRRPSYTMEDMFLAYILGMDTFALGLIKAAQI<br>IEDGRIDQFIEKKYSSFRETEIGQKILNNKTSLKELSDYACKMGAPELPGSGRQEMLEAIVN<br>DVLFGK |
| 1753MI35_004 | Firmicutes | DNA | 41 | ATGGAATATTTCCCTTTCGTCAAATCGGTCCAATACAAGGGACCAACCTCAACTGAACCATT<br>CGCTTTCAAGTACTACGATGCCAACCGTGTCGTTCTTGGAAAACCAATGAAAGAATGGATGC<br>CATTCGCTATGGCTTGGTGGCAACCGTCGGCGCTGCCGGTACCGACATGTTCGGCGGCAAC<br>ACCATGGACAAGTCCTGGGGAGTCGATAAAGAAAAGACCCAATGGGCTATGCCAAAGCCAA<br>AGTTGATGCCGGCTTCGAATTCATGCAGAAGATGGGCATCGAATACTACTGCTTCCACGATG<br>TCGACCTCGTCCCAGAGTGCGACGACATCACCGTTATGTACCAGAGACTCGATGAGATCGGT<br>GATTACCTTCTCAAGAAACAGAAGGAAACCGGTATCAAGCTTCTTTGGTCAACCGCCAATGC<br>CTTCGGAACACCGCCGTTTCATGAACGGTGCTGGTTCCAGCAACTCCGCCGAAGTCTATTGCT<br>TCGCCGCCGCCCAGATCAAGAAAGCTCTTGAGCTCTGCGTCAAACTCGGTGGCAAAGGCTAT<br>GTCTTCTGGGGTGGACGTGAAGGCTACGAAACCCTTCTCAACACCGACATGAAGTTCGAACA<br>AGAGAACATCGCCAACCTTATGAAGATGCGCCCGTGACTACGGCCGCAAGATCGGTTTCAAAG<br>GCGACTTCTACATCGAACCAAAACCAAAAGAGCCAACAAAGCATCAGTATGACTTCGACGCC<br>GCTACCGCCATCGGATTCCTCCGTCAGTACGGTCTCGACAAAGACTTCAAGATGAACATCGA<br>AGCCAACCACGCTACCTTAGCTGGCCACACCTTCGAACACGAACTCCGCGTCTCCGCCATGA<br>ACGGCATGCTCGGTTCAATCGACGCCAACGAAGGCGATATGCTCCTCGGATGGGATGTCGAC<br>CGTTTCCCAGCCAACGTCTATAGCGCCACCTTCGCCATGCTCGAAGTCATCAAAGCCGGTGG<br>ACTTACCGGTGGCTTCAACTTCGACGCCAAGACCCGCCGCGCTTCCAACACCTATGAAGATA<br>TGTTCAAGGCTTTCGTCCTTGGTATGGATACCTTCGCTTTAGGTCTTCTCAATGCCGAAGCC<br>ATCATCAAAGACGGCCGCATCGACAAGTTCGTCGAGGATAGATATGCCAGCTTCAAGACCGG<br>CATCGGTGCTAAGGTCCGCGATCACTCCGCTACCCTTGAGGATTTAGCTGCCCACGCCCTTG |

TABLE 2-continued

| Clone No. | Class of organism | Type of Sequence | SEQ ID NO: | Sequence |
|---|---|---|---|---|
| | | | | AGACCAAGGTTTGCCCAGATCCAGGCAGCGGCGACGAGGAAGAACTCCAGGAAATCCTCAAC<br>CAGTTAATGTTCGGTAAGAAATAA |
| 1753MI35_004 | *Firmicutes* | Amino Acid | 42 | <u>MEYFPEVESVQYKGPTSTEPFAFKYYDANRVVLGKPMKEWMPFAMAWWHNLGAAGTDMFGGN<br>TMDKSWGVDKEKDPMGYAKAKVDAGFEFMQKMGIEYYCFHDVDLVPECDDITVMYQRLDEIG<br>DYLLKKQKETGIKLLWSTANAFGHRRFMNGAGSSNSAEVYCFAAAQIKKALELCVKLGGKGY<br>VFWGGREGYETLLNTDMKFEQENIANLMRCARDYGRKIGFKGDFYIEPKPKEPTKHQYDFDA<br>ATAIGFLRQYGLDKDFKMNIEANHATLAGHTFEHELRVSAMNGMLGSIDANEGDMLLGWDVD<br>RFPANVYSATFAMLEVIKAGGLTGGFNFDAKTRRASNTYEDMFKAFVLGMDTFALGLLNAEA<br>II</u>KDGRIDKFVEDRYASFKTGIGAKVRDHSATLEDLAAHALETKVCPDPGSGDEEELQEILN<br>QLMFGKK |
| 1754MI9_004 | *Firmicutes* | DNA | 43 | ATGAGCGAATTTTTTAAGAATATTCCAGAGATTAAATTCGAAGGAAAAGATAGTAAAAATCC<br>ATGGGCATTCAAGTATTACAATCCTGAATTGACCATTATGGGTAAAAAAATGTCTGAACATC<br>TTCCTTTTGCAATGGCCTGGTGGCATAACCTTGGCGCAAATGGAGTTGATATGTTCGGTTCG<br>GGAACCGCCGATAAATCTTTCGGTCAGGCTCCGGGAACTATGGAGCACGCAAAGGCTAAGGT<br>AGATGCAGGTATCGAGTTTATGAAGAAACTCGGAATCAAGTACTACTGCTGGCATGATGTAG<br>ACCTTGTTCCTGAAGATCCAAACGATATCAACGTAACAAACAAGCGCCTTGATGAGATTTCA<br>GATTATATCCTTGAAAAAACAAAGGGAACTGACATCAAGTGTCTCTGGGGAACTGCTAACAT<br>GTTCAGTAATCCCCGCTTTATGAACGGGGCAGGCTCAACAAACTCTGCTGACGTTTACTGCT<br>TTGCAGCTGCCCAGGTTAAAAAGGCTCTTGAGATTACCGTAAAGCTTGGTGGCCGCGGTTAT<br>GTATTCTGGGGTGGACGCGAAGGTTATGAAACTCTTCTTAATACAGATGTAAAGCTTGAACA<br>GGAAAATATTGCAAACCTTATGCACATGGCAGTTGATTATGGCCGTTCAATCGGTTTCAAGG<br>GAGACTTCTACATCGAGCCTAAGCCAAAGGAGCCGATGAGTCATCAGTATGATTTTGATGCC<br>GCAACTGCAATCGGCTTCCTCCGCCAGTATGGCCTCGACAAAGACTTTAAGATGAACATTGA<br>GGCTAACCACGCTTCTCTTGCAAATCATACCTTCCAGCATGAGCTTTATATCAGCCGCATTA<br>ACGGAATGCTTGGTTCTGTAGATGCTAACCAGGGAAATCCAATTCTCGGCTGGGATACAGAT<br>AACTTCCCTTGGAATGTCTACGACGCAACTCTTGCAATGTACGAAGTACTCAAGGCTGGTGG<br>ACTTACAGGTGGCTTCAACTTTGACTCAAAGAACCGCCGCCCATCAAATACATTTGAAGATA<br>TGTTCCACGCTTACATCATGGGAATGGACACTTTTGCTCTTGGTCTTATTAAGGCTGCAGAA<br>ATTATTGAAGACGGAAGAATCGATGGCTTCATTAAGAAAAGTATTCAAGCTACGAAAGTGG<br>AATTGGTAAGAAGATCCGCGACAAGCAGACAACTTTGGAAGAGCTTGCTGCCCGTGCCGCAG<br>AAAATGAAAAGCCATCTGATCCAGGTTCAGGCCGCGAGGAATATCTGGAAGGAGTTGTTAAC<br>AATATCCTCTTTCGCGGATAA |
| 1754MI9_004 | *Firmicutes* | Amino Acid | 44 | <u>MSEFFKNIPEIKFEGKDSKNPWAFKYYNPELTIMGKKMSEHLPFAMAWWHNLGANGVDMFGS<br>GTADKSFGQAPGTMEHAKAKVDAGIEFMKKLGIKYYCWHDVDLVPEDPNDINVTNKRLDEIS<br>DYILEKTKGTDIKCLWGTANMFSNPRFMNGAGSTNSADVYCFAAAQVKKALEITVKLGGRGY<br>VFWGGREGYETLLNTDVKLEQENIANLMHMAVDYGRSIGFKGDFYIEPKPKEPMSHQYDFDA<br>ATAIGFLRQYGLDKDFKMNIEANHASLANHTFQHELYISRINGMLGSVDANQGNPILGWDTD<br>NFPWNVYDATLAMYEVLKAGGLTGGFNFDSKNRRPSNTFEDMFHAYIMGMDTFALGLIKAAE<br>II</u>EDGRIDGFIKEKYSSYESGIGKKIRDKQTTLEELAARAAEMKKPSDPGSGREEYLEGVVN<br>NILFRG |
| 1754MI22_004 | *Firmicutes* | DNA | 45 | ATGAGCGAGTTTTTTAAGAATATTCCTCAAATAAAATACGAAGGAAAAGATAGCAAAAATCC<br>CTGGGCATTCAAGTATTACAATCCTGAATTGACAATCATGGGTAAAAAGATGAGCGAACATC<br>TTCCATTCGCAATGGCATGGTGGCATAACCTTGGCGCAAATGGCGTTGATATGTTTGGTCAG<br>GGAACAGCAGACAAGTCTTTCGGACAGATTCCTGGAACTATGGAGCATGCAAAGGCTAAGGT<br>TGATGCTGGTATAGAGTTTATGAAGAAGCTCGGAATCAAATATTACTGCTGGCACGATGTTG<br>ACCTTGTTCCTGAGGATCCAAACGATATCAACGTAACTAACAAAGTCTGGACGAAATTTCA<br>GATTACATCCTTGAAAAGACAAAAGGAACAGACATTAAGTGTCTCTGGGGAACTGCAAACAT<br>GTTCGGTAACCCTCGCTTTATGAACGGTGCAGGCTCTACAAACTCTGCTGACGTTTACTGTT<br>TTGCTGCCGCTCAGGTAAAAAAGGCTCTTGAGATTACTGTAAAGCTTGGTGGCCGAGGTTAT<br>GTTTTCTGGGGTGGCCGCGAAGGTTACGAAACTCTTCTCAATACAGACGTAAAACTTGAACA<br>GGAAAATATCGCAAACCTTATGCATATGGCTGTTGATTATGGCCGCTCAATCGGTTTCAAGG<br>GAGACTTCTACATCGAGCCTAAGCCAAAGGAGCCAATGAGCCATCAGTATGATTTTGATGCT<br>GCAACAGCAATCGGCTTCCTCCGCCAGTATGGCCTCGACAAAGATTTTAAGATGAACATCGA<br>AGCTAACCATGCCTCACTTGCAAATCACACCTTCCAGCACGAGCTTTGTATCAGCCGCATAA<br>ACGGAATGCTTGGTTCTGTAGATGCAAATCAGGGAAATCCAATTCTTGGCTGGGATACAGAT<br>AACTTCCCATGGAATGTTTACGATGCAACTCTGGCAATGTACGAAGTTCTCAAGGCTGGCGG<br>TCTAACAGGTGGCTTCAACTTTGACTCAAAGAACCGTCGCCCATCAAATACTTTTGAAGATA<br>TGTTCCACGCTTATATCATGGGATGGATACTTTTGCCCTTGGCCTTATTAAGGCTGCAGAA<br>ATTATTGAAGACGGCAGAATTGACGGCTTCATCAAAGAAAGTATTCAAGCTTTCGAAAGTGG<br>AATTGGTAAGAAGATCCGTGACAAGCAGACAAGTTTGGAAGAGCTTGCAGCTCGTGCCGCTG<br>AAATGAAAAGCCATCTGATCCAGGTTCAGGCCGCGAGGAATACCTCGAAGGAGTTGTTAAC<br>AACATCCTCTTTCGCGGATAA |
| 1754MI22_004 | *Firmicutes* | Amino Acid | 46 | <u>MSEFFKNIPQIKYEGKDSKNPWAFKYYNPELTIMGKKMSEHLPFAMAWWHNLGANGVDMFGQ<br>GTADKSFGQIPGTMEHAKAKVDAGIEFMKKLGIKYYCWHDVDLVPEDPNDINVTNKRLDEIS<br>DYILEKTKGTDIKCLWGTANMEGNPRFMNGAGSTNSADVYCFAAAQVKKALEITVKLGGRGY<br>VFWGGREGYETLLNTDVKLEQENIANLMHMAVDYGRSIGFKGDFYIEPKPKEPMSHQYDFDA<br>ATAIGFLRQYGLDKDFKMNIEANHASLANHTFQHELCISRINGMLGSVDANQGNPILGWDTD<br>NFPWNVYDATLAMYEVLKAGGLTGGENFDSKNRRPSNTFEDMFHAYIMGMDTFALGLIKAAE<br>II</u>EDGRIDGFIKEKYSSFESGIGKKIRDKQTSLEELAARAAEMKKPSDPGSGREEYLEGVVN<br>NILFRG |

TABLE 2-continued

| Clone No. | Class of organism | Type of Sequence | SEQ ID NO: | Sequence |
|---|---|---|---|---|
| 727MI1_002 | Firmicutes | DNA | 47 | ATGATATTTGAAAATATTCCCGCAATTCCTTATGAGGGTCCGAAGAGCACAAATCCGCTGGC<br>GTTTAAATTCTATGATCCGGACAAGATCGTTATGGGAAAGCCCATGAAGGAGCATCTGCCCT<br>TTGCAATGGCCTGGTGGCACAACCTTGGCGCGGCCGGAACCGATATGTTCGGGCGCGATACC<br>GCCGACAAATCCTTCGGTGCGGTAAAAGGCACAATGGAGCATGCCAAAGCGAAAGTCGATGC<br>CGGCTTTGAGTTCATGCAGAAGCTGGGGATCCGCTATTTCTGCTTCCATGATGTGGATCTTG<br>TTCCGGAGGCGGATGATATAAAGGAGACCAACCGCCGTCTGGACGAGATCAGCGATTACATC<br>CTTGAAAAGATGAAGGGCACCGATATCAAGTGCCTTTGGGGCACGGCCAATATGTTCTCAAA<br>TCCGCGCTTTATGAACGGCGCAGGCTCCTCCAATTCTGCCGATGTATTCGCTTTTGCGGCAG<br>CACAGGCCAAGAAGGCCTTGGATCTGACCGTCAAACTCGGCGGGCGCGGCTATGTCTTCTGG<br>GGCGGACGTGAGGGCTATGAGACACTTCTCAATACCGACATGAAGTTCGAGCAGGAGAATAT<br>CGCGAAGCTCATGCATATGGCTGTCGATTACGGCCGCAGCATAGGCTTTACCGGTGATTTCT<br>ATATCGAGCCCAAACCGAAAGAGCCGATGAAACACCAGTATGATTTCGATGCAGCCACTGCG<br>ATAGGCTTCCTCCGCCAGTACGGACTCGATAAGGACTTCAAGCTCAACATCGAGGCAAACCA<br>CGCCACACTGGCAGGTCACACTTTCCAGCACGATCTGCGTGTTTCCGCAATAAACGGAATGC<br>TGGGCAGCATTGACGCCAACCAGGGCGATATGCTCCTCGGCTGGGATACCGACGAGTTCCCG<br>TTCAATGTATATGATGCGACCATGTGCATGTATGAGGTGCTCAAGTCAGACGGCTCACCGG<br>CGGCTTTAACTTCGACTCCAAATCACGCCGCCCGAGCTATACGGTCGAGGATATGTTTACAA<br>GCTATATCCTCGGCATGGACACTTTTGCCCTCGGCCTTCTGAAAGCGGCCGAGCTTATCGAA<br>GACGGAAGGCTTGACGCCTTCGTCAAAGAACGCTATTCAAGCTATGAGAGCGGCATCGGCGC<br>AAAGATCCGCAGCGGAGAAACCGATTTGAAGGAATTGGCGAATATGCGGACTCCCTCGGAG<br>CCCCGAACTTCCGGGCAGCGGAAAACAGGAACAGCTCGAGAGCATAGTAAATCAGATACTT<br>TTCGGATAA |
| 727MI1_002 | Firmicutes | Amino Acid | 48 | <u>MIFENIPAIPYEGPKSTNPLAFKFYDPDKIVMGKPMKEHLPFAMAWWHNLGAAGTDMFGRDT<br>ADKSFGAVKGTMEHAKAKVDAGFEFMQKLGIRYFCFHDVDLVPEADDIKETNRRLDEISDYI<br>LEKMKGTDIKCLWGTANMFSNPRFMNGAGSSNSADVFAFAAAQAKKALDLTVKLGGRGYVFW<br>GGREGYETLLNTDMKFEQENIAKLMHMAVDYGRSIGFTGDFYIEPKPKEPMKHQYDFDAATA<br>IGFLRQYGLDKDFKLNIEANHATLAGHTFQHDLRVSAINGMLGSIDANQGDMLLGWDTDEFP<br>FNVYDATMCMYEVLKSDGLTGGFNFDSKSRRPSYTVEDMFTSYILGMDTFALGLLKAAELIE<br>DGRLDAFVKERYSSYESGIGAKIRSGETDLKELAEYADSLGAPELPGSGKQEQLESIVNQIL</u><br>FG |
| 727MI9_005 | Firmicutes | DNA | 49 | ATGAGCGAGTTTTTTGCCAGCATTCCCAAAATTCCCTTTGAAGGCAAGGACAGCGCCAATCC<br>CCTGGCGTTCAAATACTACGACGCCGACAGGATGATACTGGGCAAGCCCATGAAGGAGCACC<br>TTCCCTTCGCCATGGCCTGGTGGCACAACCTGTGCGCCGCGGGCACCGATATGTTTGGCCGG<br>GACACCGCCGACAAGTCCTTCGGCCAGGTCAAGGGCACCATGGAACACGCCAAGGCCAAGGT<br>GGACGCGGGCTTTGAGTTCATGAAGAAGCTGGGCATCCGCTACTTCTGCTTCCACGACGTGG<br>ACATCGTGCCCGAAGCCGACGACATCAAGGAAACCAACCGCCGTCTGGACGAGATCTCCGAC<br>TATATCCTGGAGAAAATGAAAGGCACCGACATCCAGTGCCTGTGGGGCACCGCCAACATGTT<br>CGGCAACCCCCGCTATATGAACGGCGCGGGCAGCTCCAACTCCGCCGACGTATACTGCTTCG<br>CCGCGGCCCAGATCAAAAAGGCCCTGGACATCACCGTGAAGCTGGGCGGCAAGGGCTACGTG<br>TTCTGGGGCGGCCGCGAGGGCTACGAGACCCTGCTGAACACCGATATGAAGTTCGAGCAGGA<br>GAACATCGCCCGCCTGATGCACATGGCCGTGGACTACGGCCGCAGCATCGGCTTCACCGGCG<br>ATTTCTACATCGAGCCCAAGCCCAAGGAGCCCATGAAGCACCAGTACGACTTCGACGCCGCC<br>ACCGCCATAGGCTTTTTGCGCCAGTACGGCCTGGACAAGGATTTCAAGCTGAACATCGAGTC<br>CAACCACGCCACCCTGGCGGGCCATACCTTCCAGCACGACCTGCGCGTTTCCGCCATCAACG<br>GCATGCTGGGCTCCATCGACGCCAACCAGGGCGACTACCTGCTGGGCTGGGATACCGACGAG<br>TTCCCCTACAGCGTATACGAGACCACCATGTGCATGTACGAGGTGCTCAAGGCCGAGGTCT<br>CACCGGCGGCTTCAATTTCGACGCCAAGAACCGCCGTCCCAGCTACACCCCCGAGGATATGT<br>TCCACGCCTACATCCTTGGGATGGACAGCTTCGCCCTGGGCCTGATCAAGGCCGCCGAGCTC<br>ATCGAGGACGGTCGCCTGGACGCCTTCGTCCGGGACCGCTACCAGAGCTGGGAGACCGGCAT<br>CGGCGATAAGATCCGCAAGGGCGAGACCACACTGGCCGAGCTGGCCGAGTACGCCGCCCGGA<br>TGGGCGCGCCCGCGCTGCCCGGCAGCGGCCGCCAGGAATACCTGGAGGGCGTGGTCAACAAT<br>ATCCTGTTCAAATAA |
| 727MI9_005 | Firmicutes | Amino Acid | 50 | <u>MSEFFASIPKIPFEGKDSANPLAFKYYDADRMILGKPMKEHLPFAMAWWHNLCAAGTDMFGR<br>DTADKSFGQVKGTMEHAKAKVDAGFEFMKKLGIRYFCFHDVDIVPEADDIKETNRRLDEISD<br>YILEKMKGTDIQCLWGTANMFGNPRYMNGAGSSNSADVYCFAAAQIKKALDITVKLGGKGYV<br>FWGGREGYETLLNTDMKFEQENIARLMHMAVDYGRSIGFTGDFYIEPKPKEPMKHQYDFDAA<br>TAIGFLRQYGLDKDFKLNIESNHATLAGHTFQHDLRVSAINGMLGSIDANQGDYLLGWDTDE<br>FPYSVYETTMCMYEVLKAGGLTGGFNFDAKNRRPSYTPEDMFHAYILGMDSFALGLIKAAEL<br>IEDGRLDAFVRDRYQSWETGIGDKIRKGETTLAELAEYAARMGAPALPGSGRQEYLEGVVNN</u><br>ILFK |
| 727MI27_002 | Firmicutes | DNA | 51 | ATGAAGACCTATTTCAAAAAAATCCCCGTGATCCCCTACGAGGGACCGAAGTCCCAGAATCC<br>GCTGTCGTTCAAATTCTATGACGCGGACCGCATCGTTCTCGGCAAGCCCATGAAGGAGCATC<br>TGCCCTTCGCCATGGCCTGGTGGCACAATGGGTGCTGCCGGAACGGACATGTTCGGCCGC<br>GATACCGCCGACAAGTCCTTCGGAGCGGAGAAGGGCACCATGGAGCATGCCAAGGCCAAGGT<br>GGACGCTGGCTTCGAGTTTATGAAGAAGGTGGGCATCCGGTATTTCTGCTTCCATGACGTGG<br>ATCTGGTCCCGGAAGCGGACGACATCAAGGAGACCAACCGCCGTCTCGATGAGATCAGCGAC<br>TACATCCTCAAGGAGATGGGCACGGATATCAAGTGCCTCTGGGGCACCGCCAACATGTT<br>CGGCAATCCCCGGTTCATGAACGGCGCGGGCAGCTCCAACAGCGCGGACGTGTTCTGCTTTG<br>CCGCGGCCCAGGTGAAGAAGGCCTTGGACATCACCGTCAAGCTGGCGGCCGGGGCTATGTG<br>TTCTGGGGCGCCGTGAGGGGTATGAGTCCCTGCTGAACACGGACGTGAAGTTTGAGCAGGA<br>GAACATCGCCAAGCTCATGCACCTTGCCGTGGACTACGGCCGCAGCATCGGCTTCACCGGCG<br>ATTTCTACATCGAGCCCAAGCCCAAGGAGCCCATGAAGCACCAGTACGACTTCGATGCCGCC |

TABLE 2-continued

| Clone No. | Class of organism | Type of Sequence | SEQ ID NO: | Sequence |
|---|---|---|---|---|
| | | | | ACCGCCATCGGCTTCCTCAGGCAGTACGGCCTCGATAAGGACTTCAAGATGAACATTGAAGC<br>CAACCACGCGACCCTGGCCGGCCACACCTTCCAGCACGACCTCAGGATCAGCGCCATCAACG<br>GGATGCTGGGCTCCATCGACGCCAACCAGGGCGACCTCCTGCTGGGATGGGACACCGACGAA<br>TTCCCCTTCAACGTCTATGAGGCCACCATGTGCATGTACGAGGTCCTCAAGGCCGGCGGCCT<br>CACCGGCGGCTTCAACTTCGACTCAAAGAACCGCCGTCCCTCCTACACCATGGAGGATATGT<br>TCCACGCCTACATCCTGGGCATGGACACCTTCGCCCTGGGTCTTCTCAAGGCCGCGGAGCTC<br>ATCGAGGACGGTCGGATCGACAAATTCGTGGAGGAGCGCTACGCCAGCTACAAGACCGGCAT<br>CGGCGCCAAGATCCGTTCCGGCGAGACCACGCTTCAGGAGCTGGCCGCCTATGCCGACAAGT<br>TGGGCGCGCCTGCCCTTCCCGGCAGCGGCCGTCAGGAGTACCTGGAGAGCATCGTCAACCAG<br>GTGCTCTTCGGGATGTGA |
| 727MI27_002 | Firmicutes | Amino Acid | 52 | MKTYFKKIPVIPYEGPKSQNPLSFKFYDADRIVLGKPMKEHLPFAMWWHNLGAAGTDMFGR<br>DTADKSFGAEKGTMEHAKAKVDAGFEFMKKVGIRYFCFHDVDLVPEADDIKETNRRLDEISD<br>YILKKMKGTDIKCLWGTANMFGNPRFMNGAGSSNSADVFCFAAAQVKKALDITVKLGGRGYV<br>FWGGREGYESLLNTDVKFEQENIAKLMHLAVDYGRSIGFTGDFYIEPKPKEPMKHQYDFDAA<br>TAIGFLRQYGLDKDFKMNIEANHATLAGHTFQHDLRISAINGMLGSIDANQGDLLLGWDTDE<br>FPFNVYEATMCMYEVLKAGGLTGGFNFDSKNRRPSYTMEDMFHAYILGMDTFALGLLKAAEL<br>IEDGRIDKFVEERYASYKTGIGAKIRSGETTLQELAAYADKLGAPALPGSGRQEYLESIVNQ<br>VLFGM |
| 1753MI2_006 | Neocallimastigales | DNA | 53 | ATGGCTAAAGAGTATTTTCCAGAGATTGGCAAAATCAAGTTTGAAGGCAAGGACAGCAAAAA<br>CCCAATGGCTTTCCACTACTATGACCCCGAGAAGGTGATCATGGGCAAGCCTATGAAAGACT<br>GGCTCCGCTTCGCTATGGCATGGTGGCACACCCTCTGCGCAGAAGGTGGCGACCAGTTCGGT<br>GGCGGCACTAAGAAGTTCCCTTGGAACAACGGCGCTGACGCTGTAGAAATCGCAAAACAGAA<br>GGCTGACGCAGGTTTCGAAATCATGCAGAAGCTCGGCATCCCATATTTCTGCTTCCACGACG<br>TGGACCTCGTGTCTGAGGGCGCATCTGTAGAAGAGTATGAGGCTAACCTCAAGGCTATCACA<br>GACTACCTCGCTGTGAAGATGAAGGAAACAGGCATCAAGCTCCTGTGGTCTACTGCCAACGT<br>ATTCGGCAACGGCCGCTACATGAACGGTGCTTCTACCAACCCTGACTTCGACGTCGTTGCTC<br>GCGCTATCGTGCAGATTAAGAACGCTATCGACGCTGGTATCAAGCTCGGCGCTGAGAACTAC<br>GTGTTCTGGGGCGGACGCGAAGGCTACATGAGCCTCCTCAACACCGACCAGAAGCGTGAGAA<br>GGAGCACATGGCCACTATGCTCACTATGGCTCGCGACTACGCTCGCGCTAAGGGCTTCAAGG<br>GCACATTCCTCATCGAGCCTAAGCCAATGGAGCCTTCTAAGCACCAGTATGACGTTGACACT<br>GAGACTGTCATCGGCTTCCTCAAGGCACACAACCTCGACAAGGACTTCAAGGTGAACATCGA<br>GGTGAACCACGCAACTCTCGCTGGCCACACCTTCGAGCACGAGCTCGCAGTGGCAGTGGACA<br>ACAACATGCTCGGCTCTATCGACGCTAACCGTGGTGACTACCAGAATGGCTGGGATACTGAC<br>CAGTTCCCAATCGACCAGTACGAACTCGTTCAGGCTTGGATGGAAATCATCCGTGGCGGCGG<br>TCTCGGCACTGGCGGCACGAACTTCGACGCTAAGACTCGTCGTAACTCTACCGACCTCGAAG<br>ACATCTTCATCGCACACATCGCAGGCATGGACGCTATGGCACGCGCACTCGAATCGGCTGCT<br>AAGCTCCTCGAAGAGTCTCCATACAAGGCAATGAAGGCAGCTCGCTACGCTTCATTCGACAA<br>CGGTATCGGTAAGGACTTCGAAGATGGCAAGCTCACTCTCGAGCAGGCTTACGAATACGGTA<br>AGAAGGTTGGTGAGCCTAAGCAGACTTCTGGCAAGCAGGAGCTCTACGAAGCCATCGTTGCA<br>ATGTACGCTTAA |
| 1753MI2_006 | Neocallimastigales | Amino Acid | 54 | MAKEYFPEIGKIKFEGKDSKNPMAFHYYDPEKVIMGKPMKDWLRFAMAWWHTLCAEGGDQFG<br>GGTKKFPWNNGADAVEIAKQKADAGFEIMQKLGIPYFCFHDVDLVSEGASVEEYEANLKATT<br>DYLAVKMKETGIKLLWSTANVFGNGRYMNGASTNPDFDVVARAIVQIKNAIDAGIKLGAENY<br>VFWGGREGYMSLLNTDQKREKEHMATMLTMARDYARAKGFKGTFLIEPKPMEPSKHQYDVDT<br>ETVIGFLKAHNLDKDFKVNIEVNHATLAGHTFEHELAVAVDNNMLGSIDANRGDYQNGWDTD<br>QFPIDQYELVQAWMEIIRGGGLGTGGTNFDAKTRRNSTDLEDIFIAHIAGMDAMARALESAA<br>KLLEESPYKAMKAARYASFDNGIGKDFEDGKLTLEQAYEYGKKVGEPKQTSGKQELYEAIVA<br>MYA |
| 5586MI3_005 | Neocallimastigales | DNA | 55 | ATGGCTAAAGAATTTTTCCCAGAGATTGGTAAAATCAAGTTCGAAGGCAAGGATTCAAAGAA<br>TCCAATGGCTTTCCATTACTATGATGCAGAGAAGGTAATCATGGGCAAACCCATGAAGGACT<br>GGCTCCGTTTCGCTATGGCATGGTGGCACACACTCTGTGCAGAGGGCGGCGACCAGTTCGGT<br>GGCGGTACGAAGAAGTTCCCTTGGAACGAGGGTGCTAATGCTGTCGAGATTGCTAAGCAGAA<br>GGCTGACGCTGGTTTCGAAATCATGCAGAAGCTTGGCATTCCTTACTTCTGCTTCCACGATG<br>TTGACCTCGTTTCTGAAGGCGCATCTGTTGAGGAGTATGAGGCCAACCTCAAGGCTATCACT<br>GACTATCTCGCGGTTGAAGATGAAGGAGACTGGCATTAAGCTCCTGTGGTCTACTGCCAACGT<br>GTTCGGCAATGGCCGTTACATGAATGGTGCTTCCACCAACCCTGACTTCGACGTTGTTGCTC<br>GCGCCATCGTTCAGATTAAGAACGCTATCGATGCAGGTATCAAGCTCGGTGCTGAGAACTAT<br>GTGTTCTGGGGCGGTCGTGAAGGTTACATGAGCCTCCTGAACACAGACCAGAAGCGTGAGAA<br>GGAGCACATGGCTACTATGCTCACTATGGCTCGCGACTACGCTCGCGCAAGGGCTTCAAGG<br>GTACTTTCCTCATCGAGCCTAAGCCAATGGAGCCATCTAAGCACCAGTACGACGTTGACACA<br>GAGACTGTTATCGGCTTCCTGAAGGCACACAACCTTGACAAGGACTTCAAGGTGAACATCGA<br>GGTGAACCACGCAACACTCGCTGGTCACACCTTCGAGCACGAGCTCGCTGTGGCTGTCGACA<br>ACAATATGCTTGGTTCTATCGATGCTAACCGCGGTGACTACCAGAATGGTTGGGATACGGAC<br>CAGTTCCCAATCGACCAGTACGAGCTCGTTCAGGCTTGGATGGAGATCATCCGTGGTGGCGG<br>TCTCGGCACAGGTGGTACAAACTTCGACGCTAAGACTCGTCGTAACTCTACCGACCTCGAGG<br>ACATTTTCATTGCTCACATCGCTGGATGGACGCTATGGCTCGCGCTCTTGAGTCAGCAGCT<br>AAGCTCCTTGAGGAGTCTCCATACAAGGAAGATGAAGGCTGCCCGTTATGCTTCTTTCGACAG<br>CGGCATGGGTAAGGACTTTGAGAACGGCAAGCTCACACTCGAACAGGTTTATGAGTATGGTA<br>AGAAGGTAGGTGAGCCCAAGCAGACTTCTGGCAAGCAGGAGCTCTTCGAGGCAATCGTGGCC<br>ATGTACGCATAA |

TABLE 2-continued

| Clone No. | Class of organism | Type of Sequence | SEQ ID NO: | Sequence |
|---|---|---|---|---|
| 5586MI3_005 | Neocallimastigales | Amino Acid | 56 | MAKEFFPEIGKIKFEGKDSKNPMAFHYYDAEKVIMGKPMKDWLRFAMAWWHTLCAEGGDQFG GGTKKFPWNEGANAVEIAKQKADAGFEIMQKLGIPYFCFHDVDLVSEGASVEEYEANLKAIT DYLAVKMKETGIKLLWSTANVFGNGRYMNGASTNPDFDVVARAIVQIKNAIDAGIKLGAENY VFWGGREGYMSLLNTDQKREKEHMATMLTMARDYARSKGFKGTFLIEPKPMEPSKHQYDVDT ETVIGFLKAHNLKDFKVNIEVNHATLAGHTFEHELAVAVDNNMLGSIDANRGDYQNGWDTD QFPIDQYELVQAWMEIIRGGGLGTGGTNFDAKTRRNSTDLEDIFIAHIAGMDAMARALESAA KLLEESPYKKMKAARYASFDSGMGKDFENGKLTLEQVYEYGKKVGEPKQTSGKQELFEAIVA MYA |
| 5586MI91_002 | Neocallimastigales | DNA | 57 | ATGGCTAAAGAGTATTTTCCAGAGATTGGTAAAATCAAGTTTGAAGGCAAGGATTCCAAGAA TCCAATGGCATTCCACTATTATGATGCAGAGAAAGTGATTATGGGTAAGCCTATGAAGGAGT GGCTCCGCTTTGCAATGGCATGGTGGCACACACTCTGTGCAGAGGGTGGCGACCAGTTTGGT GGTGGCACTAAGAAATTCCCATGGAACGAGGGCACTGACGCTGTGACGATTGCTAAGCAGAA GGCTGATGCAGGTTTCGAAATCATGCAGAAACTCGGTTTCCCATATTTTTGCTTCCACGACA TTGACCTCGTTTCCGAAGGCAACAGCATTGAAGAGTATGAGGCTAACCTCCAGGCAATCACT GATTATCTGAAAGTGAAGATGGAAGAGACAGGCATCAAACTCTTTGTGGTCAACTGCCAACGT ATTCGGCAATGGTCGCTACATGAATGGTGCTTCCACAAACCCAGACTTTGACGTGGTGGCTC GTGCCATCGTTCAGATTAAGAACGCAATTGACGCTGGTATCAAACTCGGTGCTGAGAACTAT GTATTCTGGGGCGGTCGCGAAGGCTACATGAGCCTTCTGAACACTGACCAGAAGCGTGAGAA GGAGCACATGGCAACCATGCTCACTATGGCTCGCGACTACGCTCGCAGCAAGGGTTTCAAGG GCACTTTCCTCATTGAGCCAAAGCCAATGGAGCCATCTAAGCACCAGTATGACGTTGACACG GAGACTGTCATCGGCTTCCTCAAGGCACACAACCTCGACAAGGATTTCAAGGTGAACATCGA AGTGAACCACGCTACACTTGCAGGTCATACTTTCGAGCACGAACTTGCTGTGGCTGTTGACA ATGGCATGCTCGGTTCTATCGACGCTAACCGTGGTGACTATCAGAACGGTTGGGACACTGAC CAGTTCCCAATCGACCAGTACGAACTCGTTCAGGCTTGGATGGAAATCATCCGTGGTGGTGG TCTCGGCACAGGTGGTACTAACTTCGATGCTAAGACTCGTCGTAACTCAACTGACCTCGAGG ACATCTTCATCGCACACATCTCTGGTATGGATGCAATGGCACGTGCTCTCGAATCGGCGGCT AAACTTCTTGAGGAGTCTCCATACTGCGCTATGAAGAAGGCTCGTTACGCTTCCTTCGACAG CGGCATCGGTAAGGACTTCGAGGACGGCAAACTCACGCTCGAGCAGGCTTACGAGTACGGCA AGAAAGTCGGCGAACCCAAGCAGACTTCTGGCAAGCAGGAACTCTACGAGGCAATCGTTGCC ATGTACGCATAA |
| 5586MI91_002 | Neocallimastigales | Amino Acid | 58 | MAKEYFPEIGKIKFEGKDSKNEMAFHYYDAEKVIMGKPMKEWLRFAMAWWHTLCAEGGDQFG GGTKKFPWNEGTDAVTIAKQKADAGFEIMQKLGFPYFCFHDIDLVSEGNSIEEYEANLQAIT DYLKVKMEETGIKLLWSTANVFGNGRYMNGASTNPDFDVVARAIVQIKNAIDAGIKLGAENY VFWGGREGYMSLLNTDQKREKEHMATMLTMARDYARSKGFKGTFLIEPKPMEPSKHQYDVDT ETVIGFLKAHNLKDFKVNIEVNHATLAGHTFEHELAVAVDNGMLGSIDANRGDYQNGWDTD QFPIDQYELVQAWMEIIRGGGLGTGGTNFDAKTRRNSTDLEDIFIAHISGMDAMARALESAA KLLEESPYCAMKKARYASFDSGIGKDFEDGKLTLEQAYEYGKKVGEPKQTSGKQELYEAIVA MYA |
| 5586MI194_003 | Neocallimastigales | DNA | 59 | ATGGCAAAAGAGTATTTCCCTACGATCGGTAAGATCGTTTATGAAGGACCGGAGTCCAAGAA CCCTATGGCATTTCATTACTATGACGCAGAGCGCGTAGTAGCTGGTAAAAAAATGAAGGATT GGATGCGTTTCGCTATGGCATGGTGGCACACCCTCTGTGCAGAAGGTGCAGACCAGTTCGGT GGAGGCACCAAACACTTCCCGTGGAGTGAAGGTCCCGATGCCGTAACCATCGCCAAGCAGAA AGCAGACGCAGGTTTTGAGATCATGCAGAAACTCGGCTTCCCGTATTTCTGTTTCCATGACG TGGATCTGGTCAGCGAAGGCAGCAGCGTAGAAGAGTACGAGGCGAACCTCGCAGCCATCACC GATTATCTCAAGCAGAAATGGACGAGTCGGGTATCAAACTCCTTTGGTCCACTGCTAACGT ATTCGGTCACGCCCGTTACATGAACGGTGCCAGCACCAATCCTGACTTTGATGTCGTTGCCC GTGCCGATTGTGCAGATCAAGAATGCTATCGACGCAGGTATCAAACTCGGCGCAGAGAACTAC GTCTTCTGGGGCGGTCGTGAAGGTTATATGAGCCTGCTCAATACCGACCAGAAACGCGAGAA AGAGCATACGGCAATGATGCTGCGTATGGCGCGTGACTATGCCCGCAGCAAAGGTTTCAAAG GTACCTTCCTCATCGAACCCAAACCCATGGAGCCGTCCAAGCACCAGTATGACGTAGATACC GAGACGGTGATAGGTTTCCTCAAAGCACACGGTTTGGAGAAAGACTTTAAGGTAAACATCGA AGTGAACCACGCTACCCTCGCCGGTCACACTTTCGAGCACGAACTGGCAGTAGCCGTAGATA ACGGCATGCTCGGTTCGATCGATGCCAACCGCGGTGACTATCAGAACGGATGGGATACCGAC CAGTTCCCCATCGATAACTTCGAACTGACCCAAGCATGGATGCAGATCGTACGTAACGGTGG TCTCGGCACAGGCGGAACGAACTTCGACTCCAAGACCCGTCGTAACTCCACCGATCTCGAGG ATATCTTCATCGCTCACATCAGTGGATGGACGCTTGTGCCCGTGCCCTATTGAATGCCGTA GAGATCATGGAGAAATCACCGATCCCTGCTATGCTCAAAGAGCGTTACGCTTCCTTCGATAG CGGTCTGGGTAAGATTTCGAGGACGGCAAACTGACCCTTGAGCAAGTCTATGAGTACGGTA AGAAAGTAGGCGAACCCAAACAAACCAGCGGCAAACAAGAACTCTATGAGGCTATCGTTGCC CTCTACGCTAAATAA |
| 5586MI194_003 | Neocallimastigales | Amino Acid | 60 | MAKEYFPTIGKIVYEGPESKNPMAFHYYDAERVVAGKKMKDWMRFAMAWWHTLCAEGADQFG GGTKHFPWSEGPDAVTIAKQKADAGFEIMQKLGFPYFCFHDVDLVSEGSSVEEYEANLAAIT DYLKQKMDESGIKLLWSTANVFGHARYMNGASTNPDFDVVARAIVQIKNAIDAGIKLGAENY VFWGGREGYMSLLNTDQKREKEHTAMMLRMARDYARSKGFKGTFLIEPKPMEPSKHQYDVDT ETVIGFLKAHGLEKDFKVNIEVNHATLAGHTFEHELAVAVDNGMLGSIDANRGDYQNGWDTD QFPIDNFELTQAWMQIVRNGGLGTGGTNFDSKTRRNSTDLEDIFIAHISGMDACARALLNAV EIMEKSPIPAMLKERYASFDSGLGKDFEDGKLTLEQVYEYGKKVGEPKQTSGKQELYEAIVA LYAK |
| 5586MI198_003 | Neocallimastigales | DNA | 61 | ATGAAAGAGTATTTCCCTGAGATCGGTAAGATCCAATTTGAAGGCCCGGAGTCCAAGAACCC GATGGCATTTCACTACTATGACGCAGAGCGCGTCGTAGCCGGTAAAACAATGAAAGAGTGGA |

TABLE 2-continued

| Clone No. | Class of organism | Type of Sequence | SEQ ID NO: | Sequence |
|---|---|---|---|---|
| | | | | TGCGTTTCGCTATGGCTTGGTGGCACACCCTCTGTGCGGAAGGCGGCGACCAGTTCGGAGGC<br>GGAACGAAGAAGTTCCCCTGGAACGAAGGCGCTAACGCTTTGGAGATCGCCAAGCACAAAGC<br>CGATGCGGGATTTGAGATCATGCAGAAACTCGGCATCCCTTATTTCTGTTTCCATGACGTGG<br>ATCTCATCGCCGAGGGCGGTTCGGTAGAAGAGTACGAAGCCAACCTCGCTGCCATCACCGAT<br>TACCTCAAACAGAAAATGGACGAGACTGGCATCAAACTGCTGTGGTCCACGGCGAACGTCTT<br>CAGCAACCCCGTTATATGAACGGCGCCAGCACGAACCCCGATTTCGATGTAGTAGCGCGTG<br>CCATCGTCCAGATCAAGAACGCTATCGACGCCGGTATCAAACTCGGAGCAGAGAACTATGTC<br>TTCTGGGGTGGTCGCGAGGGCTATATGAGCCTCCTCAACACTGACCAGCGCCGAGAGAAGA<br>GCATATGGCTACCATGCTCCGTATGGCGCGTGACTACGCGCGTGCCAAAGGATTCAAGGGCA<br>CCTTCCTCATCGAACCCAAACCATGTGAGCCGTCCAAACATCAGTATGATGTCGATACCGAG<br>ACCGTCATCGGTTTCCTCAAAGCGCATGGACTCGACAAGGATTTCAAAGTCAATATCGAGGT<br>CAACCACGCCACCCTCGCAGGCCACACGTTCGAACACGAACTGGCTTGCGCTGTAGATGCCG<br>GCATGCTCGGTTCGATTGACGCCAACCGCGGTGACGCCCAGAACGGATGGGACACCGACCAG<br>TTCCCTATTGATAACTTCGAACTCACACAGGCTTTCATGCAGATCGTCCGAACGGCGGTTT<br>CGGAACAGGCGGTACGAACTTCGACGCCAAGACACGCCGTAACTCCACCGACTTGGAGGACA<br>TCTTCATCGCCCATATCAGCGGCATGGACGCTTGCGCACGTGCGTTACTCAATGCTGTCGAA<br>ATCCTCGAGAAGAGCCCGATTCCGGCGATGCTCAAAGAGCGTTATGCTTCCTTTGACGGCGG<br>CATCGGAAAGGACTTCGAGGAGGGAAAACTGACTTTCGAGCAGGTCTATGAGTACGGCAAGA<br>AAGTCGGCGAACCCAAACAGACCAGCGGCAAACAGGAGCTCTACGAAACCATCGTCGCCCTC<br>TATGCCAAATAG |
| 5586MI198_003 | Neocallimastigales | Amino Acid | 62 | <u>MKEYFPEIGKIQFEGPESKNPMAFHYYDAERVVAGKTMKEWMRFAMAWWHTLCAEGGDQFGG<br>GTKKFPWNEGANALEIAKHKADAGFEIMQKLGIPYFCFHDVDLIAEGGSVEEYEANLAAITD<br>YLKQKMDETGIKLLWSTANVFSNPRYMNGASTNPDFDVVARAIVQIKNAIDAGIKLGAENYV<br>FWGGREGYMSLLNTDQRREKEHMATMLRMARDYARAKGFKGTFLIEPKPCEPSKHQYDVDTE<br>TVIGFLKAHGLDKDFKVNIEVNHATLAGHTFEHELACAVDAGMLGSIDANRGDAQNGWDTDQ<br>FPIDNFELTQAFMQIVRNGGEGTGGTNEDAKTRRNSTDLEDIFIAHISGMDACARALLNAVE<br>ILEKSPIPAMLKERYASFDGGIGKDFEEGKLTFEQVYEYGKKVGEPKQTSGKQELYETIVAL<br>YAK</u> |
| 5586MI201_003 | Neocallimastigales | DNA | 63 | ATGGCAAAAGAGTATTTCCCTACGATCGGTAAGATCGTTTATGAAGGACCGGAATCCAAGAA<br>CCCTATGGCATTTCATTACTATGACGCAGAGCGCGTAGTAGCTGGTAAAAAAATGAAAGATT<br>GGATGCGTTTCGCTATGGCATGGTGGCACACCCTCTGTGCAGAAGGTGCAGACCAGTTCGGT<br>GGAGGCACCAAACACTTCCCGTGGAATGAAGGTCCCGATGCCGTAACCATCGCCAAGCAGAA<br>AGCAGACGCAGGTTTTGAGATCATGCAGAAACTCGGCTTCCCGTATTTCTGTTTCCATGACG<br>TGGATCTGGTCGGCGAAGGCAGCAGCGTAGAAGAGTACGAGGCGAACCTCGCAGCCATCACC<br>GATTATCTCAAGCAGAAAATGGACGAGTCGGGTATCAAACTCCTTTGGTCCACTGCTAACGT<br>ATTCGGTCACGCCCGTTACATGAACGGTGCCAGCACCAATCCTGACTTTGATGTCGTTGCCC<br>GTGCGATTGTGCAGATCAAGAATGCTATCGACGCAGGTATCAAACTCGGCGCAGAGAACTAC<br>GTCTTCTGGGGCGGTCGTGAAGGTTATATGAGCCTGCTCAACACCGACCAGAAACGCGAGAA<br>AGAGCATACGGCAATGATGCTGCGTATGGCGCGTGACTATGCCCGCAGCAAAGGTTTCAAAG<br>GTACCTTCCTCATCGAACCCAAACCCATGGAGCCGTCCAAGCACCAGTATGACGTAGATACC<br>GAGACGGTGATAGGTTTCCTCAAAGCACACGGTTTGGAGAAAGACTTTAAGGTAAACATCGA<br>AGTGAACCACGCTACCCTCGCCGGTCACACTTTCGAGCACGAACTGGCAGTAGCCGTAGATA<br>ACGGCATGCTCGGTTCGATCGATGCCAACCGCGGTGACTATCAGAACGGATGGGATACCGAC<br>CAGTTCCCCATCGATAACTTCGAACTGACCCAAGCATGGATGCAGATCGTACGTAACGGTGG<br>TCTCGGCACAGGCGGAACGAACTTCGACTCCAAGACCCGTCGTAACTCCACCGATCTCGAGG<br>ATATCTTCATCGCTCACATCAGTGGTATGGACGCTTGTGCCCGTGCCCTATTGAATGCCGTA<br>GAGATCATGGAGAAATCACCGATCCCTGCTATGCTCAAAGAGCGTTACGCTTCCTTCGATAG<br>CGGTCTGGGTAAAGATTTCGAGGACGGCAAACTGACCCTTGAGCAAGTCTATGAGTACGGTA<br>AGAAAGTAGGCGAACCCAAACAAACCAGCGGCAAACAAGAACTCTATGAGGCTATCGTTGCC<br>CTCTACGCTAAATAA |
| 5586MI201_003 | Neocallimastigales | Amino Acid | 64 | <u>MAKEYFPTIGKIVYEGPESKNPMAFHYYDAERVVAGKKMKDWMRFAMAWWHTLCAEGADQFG<br>GGTKHFPWNEGPDAVTIAKQKADAGFEIMQKLGFPYFCFHDVDLVGEGSSVEEYEANLAAIT<br>DYLKQKMDESGIKLLWSTANVFGHARYMNGASTNPDFDVVARAIVQIKNAIDAGIKLGAENY<br>VFWGGREGYMSLLNTDQKREKEHTAMMLRMARDYARSKGFKGTFLIEPKPMEPSKHQYDVDT<br>ETVIGFLKAHGLEKDFKVNIEVNHATLAGHTFEHELAVAVDNGMLGSIDANRGDYQNGWDTD<br>QFPIDNFELTQAWMQIVRNGGLGTGGTNFDSKTRRNSTDLEDIFIAHISGMDACARALLNAV<br>EIMEKSPIPAMLKERYASFDSGLGKDFEDGKLTLEQVYEYGKKVGEPKQTSGKQELYEAIVA<br>LYAK</u> |
| 5586MI204_002 | Neocallimastigales | DNA | 65 | ATGAAAGAGTATTTCCCTGAGGTCGGTAAGATCCAATTTGAAGGCCCGGAGTCTAAGAACCC<br>GATGGCATTTCACTACTATGACGCAGAGCGCGTCGTAGCCGGTAAAACAATGAAAGAGTGGA<br>TGCGTTTCGCTATGGCTTGGTGGCACACCCTCTGTGCAGAAGGCGGCGACCAGTTCGGAGGC<br>GGAACGAAGCATTTCCCGTGGAATGAAGGCGCTAACGCTTTGGAGATCGCCAAACACAAAGC<br>CGATGCGGGATTCGAGATCATGCAGAAACTCGGCATCCCCTATTTCTGTTTCCATGACGTGG<br>ATCTCATCGCCGAGGGCGGTTCGGTAGAAGAGTACGAAACCAACCTCGCTGCTATCACCGAC<br>TACCTCAAGCAGAAAATGGACGAGACCGGCATCAAACTGCTGTGGTCCACGGCGAACGTGTT<br>CAGCAACCCCGTTATATGAACGGCGCGAGCACGAACCCCGATTTCGATGTAGTAGCGCGTG<br>CCATCGTGCAGATCAAGAATGCCATCGACGCCGGCATCAAACTGGGCGCAGAGAACTATGTC<br>TTCTGGGGCGGTCGCGAGGGCTACATGAGCCTGCTCAACACCGACCAGCGCCGCGAGAAAGA<br>GCATATGGCTACTATGCTCCGTATGGCGCGTGACTACGCGCGTGCCAAAGGATTCAAGGGCA<br>CCTTTCTCATCGAACCCAAACCGTGTGAGCCGTCCAAACATCAGTATGATGTCGATACCGAG<br>ACCGTCATCGGTTTCCTCAAAGCGCATGGACTCGACAAGGATTTCAAGGTTAATATCGAGGT<br>CAACCACGCCACCCTCGCAGGCCACACGTTCGAACACGAACTGGCTTGCGCTGTAGATGCCG |

TABLE 2-continued

| Clone No. | Class of organism | Type of Sequence | SEQ ID NO: | Sequence |
|---|---|---|---|---|
| | | | | GCATGCTCGGTTCGATTGACGCCAACCGCGGTGACGCCCAGAACGGATGGGACACCGACCAG<br>TTCCCTATTGATAACTTCGAACTCACACAGGCTTTCATGCAGATCGTCCGCAACGGCGGTTT<br>CGGAACAGGCGGTACGAACTTCGACGCCAAGACACGCCGTAACTCCACCGACTTGGAGGACA<br>TCTTCATCGCCCATATCAGCGGCATGGACGCTTGCGCACGTGCGTTGCTCAACGCCATCGAA<br>ATCCTCGAGAAGAGCCCGATCCCGGCTATGCTCAAAGACCGTTATGCCTCCTTTGATGGCGG<br>CATCGGAAAGGACTTTGAGGAGGGCAAACTGACTTTCGAGCAGGTCTATGAGTACGGCAAGA<br>AGGTCGGAGAACCCAAACAGACCAGCGGCAAACAGGAGCTCTACGAAACCATCGTCGCCCTC<br>TATGCCAAATAG |
| 5586MI204_002 | Neocallimastigales | Amino Acid | 66 | MKEYFPEVGKIQFEGPESKNPMAFHYYDAERVVAGKTMKEWMRFAMAWWHTLCAEGGDQFGG<br>GTKHFPWNEGANALEIAKHKADAGFEIMQKLGIPYFCFHDVDLIAEGGSVEEYETNLAAITD<br>YLKQKMDETGIKLLWSTANVFSNPRYMNGASTNPDFDVVARAIVQIKNAIDAGIKLGAENYV<br>FWGGREGYMSLLNTDQRREKEHMATMLRMARDYARAKGFKGTFLIEPKPCEPSKHQYDVDTE<br>TVIGFLKAHGLDKDFKVNIEVNHATLAGHTFEHELACAVDAGMLGSIDANRGDAQNGWDTDQ<br>FPIDNFELTQAFMQIVRNGGFGTGGTNFDAKTRRNSTDLEDIFIAHISGMDACARALLNAIE<br>ILEKSPIPAMLKDRYASFDGGIGKDFEEGKLTFEQVYEYGKKVGEPKQTSGKQELYETIVAL<br>YAK |
| 5586MI207_002 | Neocallimastigales | DNA | 67 | ATGAAAGAGTATTTCCCTGAGATCGGTAAGATGCAATTTGAAGGCCCGGAGTCCAAGAACCC<br>GATGGCGTTTCACTACTATGACGCTGAGCGCGTCGTAGCCGGTAAAACAATGAAAGAGTGGA<br>TGCGTTTCGCTATGGCTTGGTGGCACACCCTCTGTGCGGAAGGCGGCGACCAGTTCGGAGGA<br>GGAACGAAGAAATTCCCCTGGAACGAAGGGGCAAACGCTTTGGAGATCGCCAAGCACAAAGC<br>CGATGCGGGATTCGAGATCATGCAGAAACTCGGCATCCCTTATTTCTGTTTCCATGACGTGG<br>ATCTCATCGCCGAGGGCGAATCGGTAGAAGAGTACGAAGCCAACCTCGCTGCCATCACCGAT<br>TACCTCAAACAGAAAATGGACGAGACCGGCATCAAACTGCTGTGGTCCACGGCGAACGTGTT<br>CAGCAACCCCCGTTATATGAACGGCGCCAGCACGAACCCCGATTTCGATGTAGTGGCACGCG<br>CTATCGTACAAATCAAGAACGCTATCGACGCCGGTATCAAACTCGGAGCAGAGAACTATGTC<br>TTCTGGGGCGGTCGCGAGGGCTATATGTCGCTCCTCAACACCGACCAGCGCCGAGAGAAAGA<br>GCATATGGCTACTATGCTCCGTATGGCGCGTGACTACGCGCGTTCCAAAGGATTCAAGGGCA<br>CCTTCCTCATCGAACCCAAACCGTGTGAGCCGTCCAAACATCAGTACGATGTGGACACAGAG<br>ACCGTCATCGGTTTCCTTAAAGCGCATGGACTCGACAAGGATTTCAAAGTCAATATCGAGGT<br>CAACCACGCCACCCTCGCAGGCCACACGTTCGAACACGAACTGGCTTGCGCTGTAGATGCCG<br>GCATGCTCGGTTCGATTGACGCCAACCGCGGTGACGCCCAGAACGGATGGGACACCGACCAA<br>TTCCCTATTGATAACTTCGAACTCACTCAGGCTTTCATGCAGATCGTCCGCAACGGCGGTTT<br>CGGAACAGGCGGTACGAACTTCGACGCCAAGACACGCCGTAACTCCACCGACTTGGAGGACA<br>TCTTCATCGCCCATATCAGCGGCATGGACGCTTGCGCTCGTGCGTTGCTCAATGCTGTCGAA<br>ATCCTCGAGAAGAGCCCGATCCCGGCTATGCTCAAAGAGCGTTATGCTTCCTTTGACGGCGG<br>CATCGGAAAGGACTTTGAGGAGGGCAAACTGACTTTCGAGCAGGTCTATGAGTACGGCAAGA<br>AGGTCGGAGAACCCAAACAGACCAGCGGCAAACAGGAGCTCTACGAAACCATCGTCGCCCTC<br>TATGCCAAATGA |
| 5586MI207_002 | Neocallimastigales | Amino Acid | 68 | MKEYFPEIGKIQFEGPESKNPMAFHYYDAERVVAGKTMKEWMRFAMAWWHTLCAEGGDQFGG<br>GTKKFPWNEGANALEIAKHKADAGFEIMQKLGIPYFCFHDVDLIAEGESVEEYEANLAAITD<br>YLKQKMDETGIKLLWSTANVFSNPRYMNGASTNPDFDVVARAIVQIKNAIDAGIKLGAENYV<br>FWGGREGYMSLLNTDQRREKEHMATMLRMARDYARSKGFKGTFLIEPKPCEPSKHQYDVDTE<br>TVIGFLKAHGLDKDFKVNIEVNHATLAGHTFEHELACAVDAGMLGSIDANRGDAQNGWDTDQ<br>FPIDNFELTQAFMQIVRNGGFGTGGTNFDAKTRRNSTDLEDIFIAHISGMDACARALLNAVE<br>ILEKSPIPAMLKERYASFDGGIGKDFEEGKLTFEQVYEYGKKVGEPKQTSGKQELYETIVAL<br>YAK |
| 5586MI209_003 | Neocallimastigales | DNA | 69 | ATGAAAGAGTATTTCCCTGAGATCGGTAAGATCCAATTTGAAGGCCCGGAGTCCAAGAACCC<br>GATGGCGTTTCACTACTATGACGCAGAGCGCGTAGTAGCCGGTAAAACAATGAAAGAATGGA<br>TGCGTTTCGCCATGGCATGGTGGCACACCCTCTGTGCAGAAGGCGGCGACCAGTTCGGAGGA<br>GGAACGAAGCATTTCCCGTGGAATGAAGGCGCTAACGCTTTGGAGATCGCCAAACACAAAGC<br>CGATGCGGGATTCGAGATCATGCAGAAACTCGGCATCCCCTATTTCTGTTTCCATGACGTGG<br>ATCTCATCGCCGAGGGCGATTCGGTGGAGGAGTACGAAGCTAACCCCGCTGCCATCACCGAT<br>TACCTCAAACAGAAAATGGACGAGACCGGCATCAAACTGCTGTGGTCCACGGCGAACGTCTT<br>CAGCAACCCCCGTTACATGAACGGTGCGAGCACGAACCCGGATTTCGATGTAGTGGCACGCG<br>CTATCGTACAAATCAAGAACGCTATCGACGCCGGTATCAAACTCGGAGCAGAGAACTATGTC<br>TTCTGGGGCGGTCGCGAGGGCTATATGTCGCTCCTCAACACCGACCAGCGTCGCGAGAAAGA<br>GCATATGGCTACTATGCTCCGTATGGCGCGTGACTACGCGCGTGCCAAAGGATTCAAGGGCA<br>CCTTCCTCATCGAACCCAAACCATGTGAGCCGTCCAAACATCAGTACGATGTGGACACAGAG<br>ACTGTCATCGGTTTCCTCAAAGCGCATGGACTCGACAAGGATTTCAAAGTCAACATCGAGGT<br>CAACCACGCCACCCTCGCAGGTCACACGTTCGAACACGAACTGGCTTGCGCTGTAGATGCCG<br>GCATGCTCGGTTCGATTGACGCCAACCGCGGTGACGCCCAGAACGGATGGGACACTGACCAG<br>TTCCCTATTGATAACTTCGAACTCACACAGGCTTTCATGCAGATCGTCCGCAACGGCGGTTT<br>CGGAACAGGCGGTACGAACTTCGACGCCAAGACACGCCGTAACTCCACCGACTTGGAGGACA<br>TCTTCATCGCCCATATCAGCGGCATGGACGCTTGTGTCCGTGCGTTGCTCAACGCCATCGAA<br>ATCCTCGAGAAGAGCCCGATCCCGGCTATGCTCAAAGAGCGTTACGCTTCCTTTGACGGCGG<br>CATCGGAAAGGACTTTGAGGATGGTAAACTGACTTTCGAGCAGGTCTATGAGTACGGCAAGA<br>AGGTCGGAGAACCCAAACAGACCAGCGGCAAACAGGAGCTCTACGAAACCATCGTCGCCCTC<br>TATGCCAAGTAA |
| 5586MI209_003 | Neocallimastigales | Amino Acid | 70 | MKEYFPEIGKIQFEGPESKNPMAFHYYDAERVVAGKTMKEWMRFAMAWWHTLCAEGGDQFGG<br>GTKHFPWNEGANALEIAKHKADAGFEIMQKLGIPYFCFHDVDLIAEGDSVEEYEANPAAITD<br>YLKQKMDETGIKLLWSTANVFSNPRYMNGASTNPDFDVVARAIVQIKNAIDAGIKLGAENYV |

TABLE 2-continued

| Clone No. | Class of organism | Type of Sequence | SEQ ID NO: | Sequence |
|---|---|---|---|---|
| | | | | FWGGREGYMSLLNTDQRREKEHMATMLRMARDYARAKGFKGTFLIEPKPCEPSKHQYDVDTE TVIGFLKAHGLDKDFKVNIEVNHATLAGHTFEHELACAVDAGMLGSIDANRGDAQNGWDTDQ FPIDNFELTQAFMQIVRNGGFGTGGTNFDAKTRRNSTDLEDIFIAHISGMDACVRALLNAIE ILEKSPIPAMLKERYASFDGGIGKDFEDGKLTFEQVYEYGKKVGEPKQTSGKQELYETIVAL YAK |
| 5586MI214_002 | Neocallimastigales | DNA | 71 | ATGAAAGAGTATTTCCCTGAGATCGGAAAGATCCAATTCGAAGGCCCGGAGTCCAAGAATCC TATGGCATTTCACTACTATGACGCAGAGCGTGTAGTAGCCGGTAAAACAATGAAAGAGTGGA TGCGTTTCGCTTTGGCATGGTGGCACACGCTCTGCGCAGAAGGCGGCGACCAGTTCGGAGGC GGCACGAAGCATTTCCCTTGGAATGAAGGTGCAAACGCTTTGGAGATCGCCAAGCACAAAGC CGATGCAGGCTTCGAGATCATGCAGAAACTCGGCATCCCCTATTTCTGTTTCCATGACGTGG ATCTGATCGCCGAGGGCGGTTCGGTAGAAGAGTATGAAGCTAATTTAACGGCTATCACCGAT TACCTCAAACAGAAAATGGACGAGACCGGCATCAAACTGCTGTGGTCCACTGCGAACGTGTT CGGTAACGCACGTTATATGAACGGCGCGAGCACGAACCCCGATTTCGATGTAGTGGCACGCG CTATCGTGCAGATCAAGAACGCTATCGACGCCGGCATCAAACTGGGCGCAGAGAACTACGTC TTCCTGGGGCGGTCGCGAGGGATATATGTCGCTCCTGAACACCGACCAGAAGCGTGAGAAGA GCATATGGCTACCATGCTCCGTATGGCGCGTGACTACGCGCGTTCCAAAGGATTCAAAGGTA CGTTCCTCATCGAGCCCAAACCGTGTGAGCCGTCCAAACATCAGTACGACGTGGACACTGAG ACCGTCATCGGTTTCCTCAAAGCCCATGGTCTCGGCAAGGATTTCAAAGTGAACATCGAGGT GAATCACGCCACCCTCGCAGGGCACACGTTCGAACACGAACTGGCTTGCGCCGTAGATGCCG GCATGCTCGGTTCGATCGACGCCAACCGCGGTGACGCACAAAACGGATGGGACACCGACCAG TTCCCTATTGATAATTTCGAACTCACCCAGGCATTCATGCAGATCGTCCGCAACGGCGGTTT CGGAACAGGCGGTACGAACTTCGACGCCAAGACACGCCGTAATTCCACCGACTTGGAGGACA TCTTCATCGCCCATATCAGCGGCATGGACGCTTGTGCCCGTGCGTTGCTCAATGCTGTCGAA ATCCTTGAAAAGAGCCCGATCCCGGCGATGCTCAAAGAGCGTTACGCCTCCTTTGACAGCGG TATGGGTAAGGACTTTGAGGAGGGCAAGCTGACCTTCGAGCAGGTCTATGAGTACGGCAAAC AGGTCGGCGAACCCAAACAGACCAGCGGCAAGCAGGAGCTCTACGAAACCATCGTCGCCCTC TATGCCAAATAG |
| 5586MI214_002 | Neocallimastigales | Amino Acid | 72 | MKEYFPEIGKIQFEGPESKNPMAFHYYDAERVVAGKTMKEWMRFALAWWHTLCAEGGDQFGG GTKHFPWNEGANALEIAKHKADAGFEIMQKLGIPYFCFHDVDLIAEGGSVEEYEANLTAITD YLKQKMDETGIKLLWSTANVFGNARYMNGASTNPDFDVVARAIVQIKNAIDAGIKLGAENYV FWGGREGYMSLLNTDQRREKEHMATMLRMARDYARSKGFKGTFLIEPKPCEPSKHQYDVDTE TVIGFLKAHGLGKDFKVNIEVNHATLAGHTFEHELACAVDAGMLGSIDANRGDAQNGWDTDQ FPIDNFELTQAFMQIVRNGGFGTGGTNFDAKTRRNSTDLEDIFIAHISGMDACARALLNAVE ILEKSPIPAMLKERYASFDSGMGKDFEEGKLTFEQVYEYGKQVGEPKQTSGKQELYETIVAL YAK |
| 5751MI3_001 | Neocallimastigales | DNA | 73 | ATGAAAGAGTATTTTCCACAAATCGGCAAGATCCCATTTGAGGGACCAGAGTCAAAGAACCC AATGGCATTCCACTACTATGACGCAGAGCGCGTAGTTGCCGGTAAGACAATGAAGGAATGGA TGCGTTTCGCTATGGCCTGGTGGCACACTCTCTGTGCTGAGGGTAGCGATCAGTTCGGCCCT GGTACAAAGAAGTTCCCTTGGAACGAGGGCGAGACAGCCCTTGAGCGCGCTAAGCACAAGGC AGATGCTGGCTTCGAGGTTATGCAGAAGCTCGGCATCCCATATTTCTGCTTCCACGATGTAG ACCTTATCGACGAGGGTGCTAACGTGGCTGAGTATGAGGCAAACCTCGCTGCTATCACTGAC TACCTGAAGGAGAAGATGGAGGAGACTGGCGTAAAGCTCCTCTGGTCTACAGCCAACGTGTT CGGTAACGCTCGCTATATGAACGGTGCTTCTACAAATCCTGACTTCGACGTTGTGGCTCGTG CCATCGTACAGATTAAGAACGCTATCGACGCTGGTATCAAGCTTGGTGCTGAGAACTACGTG TTCCTGGGGCGGCCGCGAGGGCTACATGAGCCTTCTGAACACTGACCAGAAGCGCGAGAAGGA GCACATGGCAACTATGCTCGGCATGGCTCGCGACTATGCCCGCGCTAAGGGATTCACCGGTA CCTTCCTCATTGAGCCCAAAGCCAATGGAGCCAACAAAGCATCAGTATGATGTTGACACAGAG ACCGTTATCGGTTTCCTCAAGGCTCACGGTCTGGACAAGGACTTCAAGGTGAACATCGAGGT GAACCACGCTACTCTCGCCGGTCACACCTTCGAGCACGAGCTCGCTTGCGCTGTTGACGCTG GTATGCTCGGTTCTATCGACGCTAACCGCGGTGACGCTCAGAACGGATGGGATACCGACCAG TTCCCCAATCGACAACTTCGAGCTGACACAGGCTTGGATGCAGATTGTTCGCAATGGCGGTCT TGGCACAGGTGGTACCAACTTCGACGCAAAGACCCGTCGTAACTCTACCGACCTCGAGGACA TCTTCATCGCTCACATCTCCGGTATGGACGCTTGTGCACGCGCTCTCCTCAACGCAGTAGAG ATACTCGAGAACTCTCCAATCCCAACAATGCTGAAGGACCGCTATGCAAGCTTCGACTCAGG TATGGGTAAGGACTTCGAGGACGGCAAGCTCACACTTGAGCAGGTTTATGAGTATGGTAAGA AGGTCGACGAGCCAAAGCAGACCTCTGGTAAGCAGGAACTCTATGAGACCATCGTTGCTCTC TATGCAAAATAA |
| 5751MI3_001 | Neocallimastigales | Amino Acid | 74 | MKEYFPQIGKIPFEGPESKNPMAFHYYDAERVVAGKTMKEWMRFAMAWWHTLCAEGSDQFGP GTKKFPWNEGETALERAKHKADAGFEVMQKLGIPYFCFHDVDLIDEGANVAEYEANLAAITD YLKEKMEETGVKLLWSTANVFGNARYMNGASTNPDFDVVARAIVQIKNAIDAGIKLGAENYV FWGGREGYMSLLNTDQRREKEHMATMLGMARDYARAKGFTGTFLIEPKPMEPTKHQYDVDTE TVIGFLKAHGLDKDFKVNIEVNHATLAGHTFEHELACAVDAGMLGSIDANRGDAQNGWDTDQ FPIDNFELTQAWMQIVRNGGLGTGGTNFDAKTRRNSTDLEDIFIAHISGMDACARALLNAVE ILENSPIPTMLKDRYASFDSGMGKDFEDGKLTLEQVYEYGKKVDEPKQTSGKQELYETIVAL YAK |
| 5753MI3_002 | Prevotella | DNA | 75 | ATGCCTAAAGAATACTTCCCCTCCATCGGCAAAATCCCTTTTGAAGGAGGCGACAGCAAAAA TCCCCTCGCTTTCCATTATTATGACGCCGGACGCGTGGTTATGGGCAAGCCCATGAAGGAAT GGCTTAAATTCGCCATGGCCTGGTGGCACACGCTGGGCCAGGCCTCCGGAGACCCCTTCGGC GGCCAGACCCGCAGCTACGAATGGGACAAGGGCGAATGCCCCTACTGCCGCGCCAAAGCCAA GGCCGACGCCGGTTTTGAAATCATGCAAAAGCTGGGTATCGAATACTTCTGCTTCCACGATG TGGACCTTATCGAGGATTGCGATGACATTGCCGAATACGAAGCCCGCATGAAGGACATCACG |

TABLE 2-continued

| Clone No. | Class of organism | Type of Sequence | SEQ ID NO: | Sequence |
|---|---|---|---|---|
| | | | | GACTACCTGCTGGAAAAGATGAAGGAGACCGGCATCAAGAACCTCTGGGGCACCGCCAATGT<br>CTTCGGCCACAAGCGCTACATGAACGGCGCCGGCACCAATCCGCAGTTCGATGTGGTGGCCC<br>GTGCCGCCGTCCAGATCAAGAACGCCCTGGACGCCACCATCAAGCTGGGCGGCTCCAACTAT<br>GTGTTCTGGGGCGGCCGCGAAGGCTATTACACCCTCCTCAACACCCAGATGCAGCGGGGAAAA<br>AGACCACCTGGCCAAGTTGCTGACGGCCGCCCGCGACTATGCCCGCGCCAAGGGCTTCAAGG<br>GCACCTTCCTCATTGAGCCCAAACCCATGGAACCCACCAAGCACCAGTACGACGTGGATACG<br>GAGACGGTCATCGGCTTCCTCCGTGCCAACGGCCTGGACAAGGACTTCAAGGTGAACATCGA<br>GGTGAACCACGCCACCCTGGCCGGCCACACCTTCGAGCATGAGCTCACCGTGGCCCGCGAGA<br>ACGGTTTCCTGGGCTCCATCGGTGCCAACCGCGGCGACGCCCAGAACGGCTGGGACACGGAC<br>CAGTTCCCTGTGGACCCGTACGATCTTACCCAGGCCATGATGCAGGTGCTGCTGAACGGCGG<br>CTTCGGCAACGGCGGCACCAACTTCGACGCCAAACTCCGCCGCTCCTCCACCGACCCTGAGG<br>ACATCTTCATCGCCCATATTTCCGCCATGGATGCCATGGCCCACGCTTTGCTTAACGCAGCT<br>GCCGTGCTGGAAGAGAGCCCCCTGTGCCAGATGGTCAAGGAGCGTTATGCCAGCTTCGACGG<br>CGGCCTCGGCAAACAGTTCGAGGAAGGCAAGGCTACCCTGGAAGACCTGTACGAATACGCCA<br>AGGTCCAGGGTGAACCCGTTGTCGCCTCCGGCAAGCAGGAGCTTTACGAGACTCTCCTGAAC<br>CTGTATGCCGTCAAGTAA |
| 5753MI3_002 | Prevotella | Amino Acid | 76 | <u>MAKEYFPSIGKIPFEGGDSKNPLAFHYYDAGRVVMGKPMKEWLKFAMAWWHTLGQASGDPFG<br>GQTRSYEWDKGECPYCRAKAKADAGFEIMQKLGIEYFCFHDVDLIEDCDDIAEYEARMKDIT<br>DYLLEKMKETGIKNLWGTANVFGHKRYMNGAGTNPQFDVVARAAVQIKNALDATIKLGGSNY<br>VFWGGREGYYTLLNTQMQREKDHLAKLLTAARDYARAKGFKGTFLIEPKPMEPTKHQYDVDT<br>ETVIGFLRANGLDKDFKVNIEVNHATLAGHTFEHELTVARENGFLGSIGANRGDAQNGWDTD<br>QFPVDPYDLTQAMMQVLLNGGFGNGGTNFDAKLRRSSTDPEDIFIAHISAMDAMAHALLNAA<br>AVLEESPLCQMVKERYASFDGGLGKQFEEGKATLEDLYEYAKVQGEPVVASGKQELYETLLN<br>LYAVK</u> |
| 1754MI1_001 | Prevotella | DNA | 77 | ATGGCAAAAGAGTATTTTCCGTTTACCGGTAAGATTCCTTTCGAAGGAAAGGACAGTAAGAA<br>TGTAATGGCTTTCCACTACTACGAGCCTGAGAAGGTCGTGATGGGAAAGAAGATGAAGGACT<br>GGCTGAAGTTCGCTATGGCTTGGTGGCATACACTGGGTGCGCTTCTGCTGACCAGTTTGGT<br>GGTCAGACTCGTTCATACGAGTGGGACAAGGCTGGTGACGCTGTTCAGCGCGCTAAGGATAA<br>GATGGACGCTGGCTTCGAGATCATGGACAAGCTGGGCATCGAGTACTTCTGCTTCCACGATG<br>TTGACCTCGTTGAAGAGGGTGACACCATCGAGGAGTATGAGGCTCGCATGAAGGCCATCACC<br>GACTACGCTCAGGAGAAGATGAAGCAGTTCCCCAACATCAAGCTGCTCTGGGGTACCGCAAA<br>CGTATTCGGTAACAAGCGCTATGCTAACGGTGCTTCTACCAACCCCGACTTCGACGTAGTGG<br>CTCGCGCCATCGTTCAGATCAAGAACGCTATTGATGCTACCATCAAGCTGGGTGGTACCAAC<br>TATGTGTTCTGGGGTGGTCGTGAGGGCTATATGAGTCTGCTGAACACCGACCAGAAGCGTGA<br>GAAGGAGCACATGGCTACTATGCTGACCATGGCTCGCGACTATGCTCGCGCCAAGGGATTCA<br>AGGGTACATTCCTCATTGAGCCGAAGCCCATGGAGCCCAGCAAGCACCAGTATGATGTGGAT<br>ACAGAGACCGTTATCGGCTTCCTGAAGGCACACAACCTGGACAAGGACTTCAAGGTGAACAT<br>CGAGGTGAACCACGCTACACTCGCTGGTCATACCTTCGAGCACGAGCTGGCTTGCGCTGTTG<br>ACGCTGGTATGCTTGGTTCTATCGACGCTAACCGTGGTGATGCTCAGAACGGTTGGGATACC<br>GACCAGTTCCCCATCGACAACTACGAGCTGACACAGGCTATGCTCGAGATCATCCGCAATGG<br>TGGTCTGGGCAATGGTGGTACCAACTTCGATGCTAAGATCCGTCGTAACAGCACCGACCTCG<br>AGGATCTCTTCATCGCTCACATCAGTGGTATGGATGCTATGGCACGCGCTCTGATGAACGCT<br>GCTGACATCCTTGAGAACTCTGAGCTGCCCGCAATGAAGAAGGCTCGCTACGCAAGCTTCGA<br>CCAGGGTGTTGGTAAGGACTTCGAAGATGGCAAGCTGACCCTTGAGCAGGTTTACGAGTATG<br>GTAAGAAGGTGGGTGAGCCCAAGCAGACTTCTGGTAAGCAGGAGAAGTACGAGACCATCGTT<br>GCTCTCTATGCAAAATAA |
| 1754MI1_001 | Prevotella | Amino Acid | 78 | <u>MAKEYFPFTGKIPFEGKDSKNVMAFHYYEPEKVVMGKKMKDWLKFAMAWWHTLGGASADQFG<br>GQTRSYEWDKAGDAVQRAKDKMDAGFEIMDKLGIEYFCFHDVDLVEEGDTIEEYEARMKAIT<br>DYAQEKMKQFPNIKLLWGTANVFGNKRYANGASTNPDFDVVARAIVQIKNAIDATIKLGGTN<br>YVFWGGREGYMSLLNTDQKREKEHMATMLTMARDYARAKGFKGTFLIEPKPMEPSKHQYDVD<br>TETVIGFLKAHNLDKDFKVNIEVNHATLAGHTFEHELACAVDAGMLGSIDANRGDAQNGWDT<br>DQFPIDNYELTQAMLEIIRNGGLGNGGTNFDAKIRRNSTDLEDLFIAHISGMDAMARALMNA<br>ADILENSELPAMKKARYASFDQGVGKDFEDGKLTLEQVYEYGKKVGEPKQTSGKQEKYETIV<br>ALYAK</u> |
| 1754MI3_007 | Prevotella | DNA | 79 | ATGGCAAAAGAGTATTTTCCGTTTACCGGTAAGATTCCTTTCGAAGGAAAAGAGAGCAAGAA<br>CGTAATGGCTTTCCATTACTATGAGCCTGAAAGGTGGTCATGGGCAAGAAAATGAAGGATT<br>GGCTGAAATTCGCCATGGCTTGGTGGCACACCCTCGGTGGAGCCAGCGCCGACCAGTTCGGT<br>GGACAGACCCGCAGCTATGAGTGGGACAAGGCCGAGGATGCCGTACAGCGTGCTAAGGACAA<br>GATGGACGCCGGCTTCGAGATCATGGACAAACTGGGCATCGAGTATTCTGCTTCCACGATG<br>TCGACCTCGTCGACGAGGGTGCTACCGTTGAGGAGTATGAGGCTCGCATGAAAGCCATCACC<br>GACTATGCCCAGGTCAAGATGAAGGAATATCCCAACATCAAACTGCTCTGGGGCACCGCCAA<br>CGTGTTCGGCAACAAGCGTTATGCCAACGGCGCTTCCACCAACCCCGACTTCGACGTGGTGG<br>CACGCGCTATCGTTCAGATCAAGAATGCCATCGACGCTACCATCAAGCTCGGCGGTCAGAAC<br>TACGTGTTCTGGGGCGGACGCGAGGGCTACATGAGCCTGCTCAATACCGATCAGAAACGTGA<br>GAAGGAACACATGGCCACCATGCTCACCATGGCGCGCGACTATGCTCGCAGCAAGGGATTCA<br>AGGGCACCTTCCTCATCGAACCCAAACCCATGGAGCCTTCCAAGCACCAGTATGATGTCGAC<br>ACCGAGACGGTCATCGGCTTCCTCCGCGCCCACAACCTCGACAAGGACTTCAAGGTGAACAT<br>CGAGGTCAACCACGCCACGCTCGCCGGCCACACCTTCGAGCACGAACTGGCTTGCGCCGTCG<br>ACGCCGGCATGCTCGGCAGCATCGACGCCAACCGCGGCGACGCACAGAACGGCTGGGATACC<br>GACCAGTTCCCCATCGACAACTACGAACTGACACAGGCCATGCTGGAGATCATCCGCAATGG<br>CGGCCTCGGCAATGGTGGTACCAACTTCGACGCCAAGATCCGTCGTAACAGCACCGACCTCG<br>AAGATCTCTTCATCGCTCACATCAGCGGTATGGATGCCATGGCTCGCGCGCTGCTCAACGCC |

TABLE 2-continued

| Clone No. | Class of organism | Type of Sequence | SEQ ID NO: | Sequence |
|---|---|---|---|---|
| | | | | GCCGCCATCCTCGAGGAGAGCGAACTGCCCGCCATGAAGAAGGCCCGCTACGCTTCCTTCGA<br>CGAAGGTATCGGCAAGGACTTCGAAGACGGCAAACTCACCCTCGAGCAGGTTTACGAGTACG<br>GCAAGAAGGTAGGCGAGCCCAAGCAGACCTCCGGCAAGCAAGAGAAGTACGAGACCATCGTG<br>GCTCTCTACAGCAAATAA |
| 1754MI3_007 | Prevotella | Amino Acid | 80 | MAKEYFPFTGKIPFEGKESKNVMAFHYYEPEKVVMGKKMKDWLKFAMAWWHTLGGASADQFG<br>GQTRSYEWDKAEDAVQRAKDKMDAGFEIMDKLGIEYFCFHDVDLVDEGATVEEYEARMKAIT<br>DYAQVKMKEYPNIKLLWGTANVFGNKRYANGASTNPDFDVVARAIVQIKNAIDATIKLGGQN<br>YVFWGGREGYMSLLNTDQKREKEHMATMLTMARDYARSKGFKGTFLIEPKPMEPSKHQYDVD<br>TETVIGFLRAHNLDKDFKVNIEVNHATLAGHTFEHELACAVDAGMLGSIDANRGDAQNGWDT<br>DQFPIDNYELTQAMLEIIRNGGLGNGGTNFDAKIRRNSTDLEDLFIAHISGMDAMARALLNA<br>AAILEESELPAMKKARYASFDEGIGKDFEDGKLTLEQVYEYGKKVGEPKQTSGKQEKYETIV<br>ALYSK |
| 1754MI5_009 | Prevotella | DNA | 81 | ATGAAAGAGTATTTCCCGCAAATTGGAAAGATTCCCTTCGAGGGACCAGAGAGCAAGAGTCC<br>ATTGGCGTTCCATTATTATGAGCCGGATCGCATGGTGCTCGGAAAGAGGATGGAGGATTGGC<br>TGAAATTCGCCATGGCATGGTGGCACACCCTTGGCCAGGGCAGCGGCGACCAGTTCGGCGGA<br>CAGACACGTGAGTACGAGTGGGATAAGGCTGGAGATCCGATACAAAGGGCAAAGGATAAGAT<br>GGACGCCGGATTCGAGATCATGGAGAAATTGGGTATCAAGTACTTCTGCTTCCATGATGTGG<br>ATCTCGTCGAGGAAGCTCCCACCATCGCCGAATATGAGGAGCGTATGAGGATCATCACCGAC<br>TATGCGCTCGAGAAGATGAAAGCCACTGGCATCAAACTCCTTTGGGGTACAGCCAATGTTTT<br>CGGACATAAGAGATATATGAATGGGGCCGCCACCAACCCGGAGTTCGGTGTTGTCGCCAGGG<br>CTGCTGTCCAGATCAAGAACGCGATCGACGCCACCATCAAGCTGGGAGGAACAAACTATGTG<br>TTCTGGGGTGGCCGCGAGGGCTACATGAGCCTGCTCAACACCCAGATGCAGAGGGAGAAGGA<br>CCATCTCGCCAATGCTCAAGGCTGCTCGTGACTATGCTCGCGCCAAGGGATTCAAGGGCA<br>CATTCCTCATCGAGCCGAAGCCGATGGAACCTACTAAGCATCAGTACGATGTCGACACTGAG<br>ACCGTGATCGGCTTCCTCCGCGCAAACGGTCTTGACAAGGATTTCAAGGTCAACATCGAGGT<br>CAATCACGCCACTCTTGCGGGTCACACTTTCGAGCATGAGCTCGCCGTGGCTGTCGACAATG<br>GTCTCCTTGGCTCAATCGATGCGAACAGGGGAGATTATCAGAACGGTTGGGACACCGACCAG<br>TTCCCTGTTGATCTCTTTGATTTGACCCAGGCCATGCTCCAGATCATCCGTAACGGAGGCCT<br>CGGTAATGGTGGATCCAACTTCGACGCCAAGCTTCGCCGTAACTCCACTGATCCTGAGGATA<br>TATTCATTGCCCATATTTGCGGTATGGACGCTATGGCCAGGGCTCTCTTGCCGCCGCCGCG<br>ATCGTGGAGGAGTCTCCTATCCCGGCTATGGTCAAAGAGCGTTACGCATCCTTCGACGAAGG<br>TGAGGGCAAGAGATTCGAGGATGGTAAGATGAGTCTGGAGGAACTTGTTGATTACGCGAAGA<br>CTCACGGAGAGCCCGCCCAGAAGAGTGGCAAACAGGAGCTCTACGAAACCCTTGTCAACATG<br>TACATCAAATAA |
| 1754MI5_009 | Prevotella | Amino Acid | 82 | MKEYFPQIGKIPFEGPESKSPLAFHYYEPDRMVLGKRMEDWLKFAMAWWHTLGQASGDQFGG<br>QTREYEWDKAGDPIQRAKDKMDAGFEIMEKLGIKYFCFHDVDLVEEAPTIAEYEERMRIITD<br>YALEKMKATGIKLLWGTANVFGHKRYMNGAATNPEFGVVARAVQIKNAIDATIKLGGTNYV<br>FWGGREGYMSLLNTDMQREKDHLANMLKAARDYARAKGFKGTFLIEPKPMEPTKHQYDVDTE<br>TVIGFLRANGLDKDFKVNIEVNHATLAGHTFEHELAVAVDNGLLGSIDANRGDYQNGWDTDQ<br>FPVDLFDLTQAMLQIIRNGGLGNGGSNFDAKLRRNSTDPEDIFIAHICGMDAMARALLAAAA<br>IVEESPIPAMVKERYASFDEGEGKRFEDGKMSLEELVDYAKTHGEPAQKSGKQELYETLVNM<br>YIK |
| 5586MI1_003 | Prevotella | DNA | 83 | ATGGCAAAAGAGTATTTTCCGTTTACCGGTAAGATTCCTTTCGAGGGAAAGGACAGTAAGAA<br>TGTAATGGCGTTCCACTACTACGAGCCCGAGCGCGTGGTAATGGGCAAGAAGATGAAGGAGT<br>GGCTGAAGTTTGCCATGGCCTGGTGGCACACGCTGGGTGGAGCCAGTGCCGACCAGTTTGGC<br>GGACAGACCCGCAGCTACGAGTGGGACAAGGCTGAAGACGCCGTGCAGCGTGCCAAGGACAA<br>GATGGATGCCGGCTTCGAGATCATGGACAAGCTGGGCATCGAGTATTTCTGCTTCCATGATG<br>TCGATCTCGTTGACGAGGGTGCCACTGTCGAGGAGTATGAGGCTCGCATGCAGGCCATCACC<br>GACTATGCGCAGGAGAAGATGAAGCAGTATCCTGCCATCAAGCTGCTGTGGGGTACGGCCAA<br>TGTCTTTGGCAACAAGCGTTATGCCAACGGTGCCTCTACCAATCCCGACTTCGATGTGGTGA<br>CCCGCGCCATCGTGCAGATTAAGAATGCCATTGATGCCACCATCAAGCTGGGCGGCAGCAAC<br>TATGTGTTCTGGGGCGGTCGCGAGGGCTACATGTCGCTGCTCAACACCGACCAGAAGCGTGA<br>GAAGGAACACATGGCCCGGATGCTGACCATGGCCCGCGACTATGCCCGCTCGAAGGGCTTCA<br>AGGGCAACTTCCTGATTGAGCCCAAGCCCATGGAGCCGTCGAAGCATCAGTACGACGTGGAC<br>ACCGAGACGGTTATCGGATTCCTCCGCGCACATGGCCTTGACAAGGACTTCAAGGTGAACAT<br>CGAGGTGAACCATGCCACGCTTGGCCGGTCATACCTTCGAGCACGAACTGGCTTGCGCCGTAG<br>ATGCCGGCATGCTGGGCAGCATTGATGCCAACCGCGGCGACGCACAGAACGGATGGGACACC<br>GACCAGTTCCCCATCGACAACTATGAGTTGACACAGGCCATGATGGAGATTATCCGCAATGG<br>CGGTCTGGGTCTTGGCGGTACCAATTTCGATGCCAAGATTCGCCGTAACTCCACCGACCTGG<br>AAGACCTCTTCATCGCCCACATCAGTGGCATGGACGCCATGGCTCGTGCGCTCCTTAATGCT<br>GCCGACATTCTGGAGAACAGCGAACTGCCCCGCCATGAAGAAAGCGCGCTACGCCTCGTTCGA<br>CAGTGGCATGGGCAAGGACTTCGAGGACGGCAAACTGACCCTTGAGCAGGTTTACGAATACG<br>GCAAAAAGTCGGCGAACCTAAGCAGACCTCCGGCAAGCAGGAGAAGTACGAGACCATCGTG<br>GCTCTCTATGCCAAGTAA |
| 5586MI1_003 | Prevotella | Amino Acid | 84 | MAKEYFPFTGKIPFEGKDSKNVMAFHYYEPERVVMGKKMKEWLKFAMAWWHTLGGASADQFG<br>GQTRSYEWDKAEDAVQRAKDKMDAGFEIMDKLGIEYFCFHDVDLVDEGATVEEYEARMQAIT<br>DYAQEKMKQYPAIKLLWGTANVFGNKRYANGASTNPDFDVVARAIVQIKNAIDATIKLGGSN<br>YVFWGGREGYMSLLNTDQKREKEHMARMLTMARDYARSKGFKGNFLIEPKPMEPSKHQYDVD<br>TETVIGFLRAHGLDKDEKVNIEVNHATLAGHTFEHELACAVDAGMLGSIDANRGDAQNGWDT<br>DQFPIDNYELTQAMMEIIRNGGLGLGGTNFDAKIRRNSTDLEDLFIAHISGMDAMARALLNA |

TABLE 2-continued

| Clone No. | Class of organism | Type of Sequence | SEQ ID NO: | Sequence |
|---|---|---|---|---|
| | | | | ADILENSELPAMKKARYASFDSGMGKDFEDGKLTLEQVYEYGKKVGEPKQTSGKQEKYETIV<br>ALYAK |
| 5586MI2_006 | Prevotella | DNA | 85 | ATGGCAAAAGAGTATTTTCCGTTTACAGGTAAAATTCCTTTCGAAGGAAAGGACAGTAAGAA<br>CGTAATGGCTTTCCACTACTACGAGCCCGAAAAGGTCGTGATGGGAAAGAAAATGAAAGACT<br>GGCTGAAGTTCGCCATGGCCTGGTGGCACACACTGGGTGGCGCCAGCGCCGACCAGTTTGGC<br>GGCCAGACACGCAGCTATGAGTGGGACAAGGCTGCCGATGCCGTGCAGCGCGCAAAGGACAA<br>GATGGACGCCGGCTTCGAAATCATGGACAAGCTGGGCATCGAGTATTTCTGCTTCCACGACG<br>TGGACCTCGTTGAGGAGGGAGCCACCATCGAGGAGTATGAGGCCCGCATGAAGGCTATCACC<br>GACTATGCCCAGGAGAAGATGAAACAGTATCCCAGCATCAAGCTGCTCTGGGGCACCGCCAA<br>TGTGTTTGGCAACAAGCGCTACGCCAACGGCGCCAGCACCAACCCCGACTTCGACGTCGTGG<br>CCCGTGCCATCGTGCAGATCAAGAACGCCATCGATGCCACCATCAAGCTGGGCGGCACCAAC<br>TACGTGTTCTGGGGCGGACGCGAGGGCTACATGAGCCTGCTCAACACCGACCAGAAGCGCGA<br>GAAGGAGCACATGGCCACCATGCTCACCATGGCCCGCGACTACGCCCGCGCAAAGGGATTCA<br>AGGGCACCTTCCTCATCGAGCCCAAGCCCATGGAGCCGTCGAAGCACCAGTACGACGTGGAC<br>ACCGAGACCGTCATCGGTTTCCTGAAGGCCCACGGTCTGGACAAGGACTTCAAGGTGAACAT<br>CGAGGTGAACCACGCCACGCTGGCCGGCCACACCTTCGAGCATGAGCTGGCCTGCGCCGTCG<br>ACGCCGGTATGCTGGGCAGCATCGATGCCAACCGCGGCGACGCCCAGAACGGCTGGGACACC<br>GACCAGTTCCCCATCGACAACTTCGAGCTCACCCAGGCCATGATGGAAATTATCCGCAACGG<br>CGGCCTCGGCAACGGCGGCACCAACTTCGACGCTAAGATCCGCCGAACTCCACCGACCTCG<br>AGGACCTCTTCATCGCCCACATCAGCGGCATGGACGCCATGGCCCGCGCACTGATGAACGCT<br>GCCGACATTATGGAGAACAGCGAGCTGCCCGCCATGAAGAAGGCACGCTACGCCAGCTTCGA<br>CGCCGGCATCGGCAAGGACTTTGAGGATGGCAAGCTCTCGCTGGAGCAGGTCTACGAGTATG<br>GCAAGAAGGTGGAAGAGCCCAAGCAGACCAGCGGCAAGCAGGAGAAGTACGAGACCATCGTC<br>GCCCTCTATGCCAAGTAA |
| 5586MI2_006 | Prevotella | Amino Acid | 86 | <u>MAKEYFPFTGKIPFEGKDSKNVMAFHYYEPEKVVMGKKMKDWLKFAMAWWHTLGGASADQFG</u><br><u>GQTRSYEWDKAADAVQRAKDKMDAGFEIMDKLGIEYFCFHDVDLVEEGATIEEYEARMKAIT</u><br><u>DYAQEKMKQYPSIKLLWGTANVFGNKRYANGASTNPDFDVVARAIVQIKNAIDATIKLGGTN</u><br><u>YVFWGGREGYMSLLNTDQKREKEHMATMLTMARDYARAKGFKGTFLIEPKPMEPSKHQYDVD</u><br><u>TETVIGFLKAHGLDKDFKVNIEVNHATLAGHTFEHELACAVDAGMLGSIDANRGDAQNGWDT</u><br><u>DQFPIDNFELTQAMMEIIRNGGLGNGGTNFDAKIRRNSTDLEDLFIAHISGMDAMARALMNA</u><br><u>ADIMENSELPAMKKARYASFDAGIGKDFEDGKLSLEQVYEYGKKVEEPKQTSGKQEKYETIV</u><br>ALYAK |
| 5586MI8_003 | Prevotella | DNA | 87 | ATGGCAAAAGAGTATTTCGCCTTTACAGGCAAGATTCCTTTCGAGGGAAAAGACAGTAAGAA<br>CGTGATGGCTTTCCACTACTACGAGCCGGAGCGTGTGGTGATGGGCAAGAAGATGAAGGAGT<br>GGCTGAAGTTCGCCATGGCCTGGTGGCACACACTGGGTGGCGCATCGAGCCGACCAGTTCGGA<br>GGCCAGACACGCAGCTACGAGTGGGACAAGGCCGCCGACGCCGTGCAGCGCGCCAAGGACAA<br>GATGGACGCCGGCTTCGAGATTATGGACAAGCTGGGCATCGAGTACTTCTGCTTCCACGATG<br>TAGACCTCGTTGAGGAGGGTGAGACCATAGCCGAGTACGAGCGCCGCATGAAGGAAATCACC<br>GACTACGCACAGGAGAAGATGAAGCAGTTCCCCAACATCAAGCTGCTCTGGGGACACAGCCAA<br>CGTGTTCGGCAACAAGCGCTACGCCAACGGCGCATCGACCAACCCCGACTTCGACGTTGTGG<br>CACGCGCCATCGTGCAGATCAAGAACGCCATCGACGCCACCATCAAGCTCGGCGGCTCCAAC<br>TATGTGTTCTGGGGCGGACGCGAGGGCTATATGAGCCTGCTCAACACCGACCAGAAGCGCGA<br>GAAGGAGCACATGGCCACCATGCTCACCATGGCCCGCGACTATGCACGCGCCAAGGGATTCA<br>AGGGCACATTCCTCATCGAGCCGAAGCCCATGGAGCCCTCGAAGCACCAGTACGACGTAGAC<br>ACAGAGACCGTCATCGGCTTCCTCCGTGCACACGGGCTGGACAAGGACTTCAAGGTGAACAT<br>CGAGGTAAACCACGCCACACTGGCCGGCCACACCTTCGAGCACGAGCTGGCTTGCGCCGTCG<br>ACGCTGGCATGCTGGGCAGCATCGACGCCAACCGTGGCGACGCCACAGAACGGATGGGACACC<br>GACCAGTTCCCCATCGACAACTTCGAGCTCACACAGGCCATGATGGAAATCATCCGCAATGG<br>CGGACTGGGCAATGGCGGCACCAACTTCGACGCCAAGATCCGTCGTAACAGCACCGACCTCG<br>AAGACCTCTTCATCGCCCACATCAGCGGCATGGACGCCATGGCACGCGCACTGCTCAACGCT<br>GCCGACATCCTGGAGCACAGCGAGCTGCCCAAGATGAAGAAGGAGCGCTACGCCAGCTTCGA<br>CGCAGGCATCGGCAAGGACTTCGAAGACGGCAAGCTCACACTCGAGCAGGTCTACGAGTACG<br>GCAAGAAGGTCGAAGAGCCCCGTCAGACCAGCGGCAAGCAGGAGAAGTACGAGACCATCGTC<br>GCCCTCTATGCCAAGTAA |
| 5586MI8_003 | Prevotella | Amino Acid | 88 | <u>MAKEYFAFTGKIPFEGKDSKNVMAFHYYEPERVVMGKKMKEWLKFAMAWWHTLGGASADQFG</u><br><u>GQTRSYEWDKAADAVQRAKDKMDAGFEIMDKLGIEYFCFHDVDLVEEGETIAEYERRMKEIT</u><br><u>DYAQEKMKQFPNIKLLWGTANVFGNKRYANGASTNPDFDVVARAIVQIKNAIDATIKLGGSN</u><br><u>YVFWGGREGYMSLLNTDQKREKEHMATMLTMARDYARAKGFKGTFLIEPKPMEPSKHQYDVD</u><br><u>TETVIGFLRAHGLDKDFKVNIEVNHATLAGHTFEHELACAVDAGMLGSIDANRGDAQNGWDT</u><br><u>DQFPIDNFELTQAMMEIIRNGGLGNGGTNFDAKIRRNSTDLEDLFIAHISGMDAMARALLNA</u><br><u>ADILEHSELPKMKKERYASFDAGIGKDFEDGKLTLEQVYEYGKKVEEPRQTSGKQEKYETIV</u><br>ALYAK |
| 5586MI14_003 | Prevotella | DNA | 89 | ATGGCAAAAGAGTATTTTCCGTTTACTGGTAAGATTCCTTTCGAGGGAAAGGATAGTAAGAA<br>TGTAATGGCTTTCCACTATTACGAGCCCGAGAAAGTCGTGATGGGAAAGAAGATGAAGGACT<br>GGCTGAAGTTCGCAATGGCTTGGTGGCATACACTGGGTGGTGCATCTGCAGACCAGTTCGGT<br>GGAGAGACCCGCAGCTACGAGTGGGACAAGGCCTGCTGATCCCGTTCAGCGCGCCAAGGACAA<br>GATGGACGCCGGCTTTGAGATTATGGATAAGCTGGGCATCGAGTACTTCTGTTTCCACGATA<br>TAGACCTCGTTCAGGAGGCAGATACCATTCAGAATATGAGGAGCGCATGAAGGCAATTACC<br>GACTATGCTCGGAGAAGATGAAGCAGTTCCCCAACATCAAGTTGCTCTGGGGTACCGCTAA<br>CGTATTTAGCAACAAGCGCTATATGAACGGTGCTTCTACCAATCCCGACTTCGACGTGGTGG<br>CCCGTGCCATCGTTCAGATCAAGAACGCTATTGATGCAACCATCAAACTCGGTGGTACCAAC TABLE 2-continued

| Clone No. | Class of organism | Type of Sequence | SEQ ID NO: | Sequence |
|---|---|---|---|---|
| | | | | TATGTATTCTGGGGTGGTCGTGAGGGTTACATGAGCCTATTGAATACCGACCAGAAGCGTGA<br>AAAGGAGCACATGGCAATGATGCTCGGTATGGCTCGCGACTATGCCCGCAGCAAGGGATTCA<br>AGGGTACGTTCCTCATCGAGCCGAAGCCGATGGAGCCCTCTAAGCATCAGTATGATGTCGAT<br>ACGGAGACTGTGATTGGTTTCCTGAAGGCACACGGTCTGGACAAGGACTTCAAGGTGAACAT<br>CGAGGTGAACCACGCTACACTGGCTGGTCATACCTTCGAGCATGAGCTGGCTTGCGCTGTTG<br>ACGCAGGTATGCTGGGCTCTATCGACGCTAACCGCGGTGATGCCCAGAACGGCTGGGATACC<br>GACCAGTTCCCCATCGACAACTACGAGCTGACACAGGCTATGATGGAAATCATCCGCAACGG<br>TGGTCTGGGCAATGGTGGATACCAACTTCGACGCTAAGATCCGCCGTAACTCTACCGACCTCG<br>AGGATCTGTTCATCGCTCATATCAGTGGTATGGATGCTATGGCCCGTGCTTTGTTGAATGCT<br>GCCGACATTCTGGAGAACTCTGAACTGCCCGCTATGAAGAAGGCCCGCTACGCCAGCTTCGA<br>CAACGGTATCGGTAAGGACTTCGAGGATGGCAAGCTGACCTTCGAGCAGGTTTACGAATATG<br>GTAAGAAAGTTGAAGAGCCGAAGCAGACCTCTGGCAAGCAGGAGAAATACGAGACCATCGTT<br>GCTCTGTATGCTAAATAA |
| 5586MI14_003 | Prevotella | Amino Acid | 90 | MAKEYFPFTGKIPFEGKDSKNVMAFHYYEPEKVVMGKKMKDWLKFAMAWWHTLGGASADQFG<br>GETRSYEWSKAADPVQRAKDKMDAGFEIMDKLGIEYFCFHDIDLVQEADTIAEYEERMKAIT<br>DYALEKMKQFPNIKLLWGTANVFSNKRYMNGASTNPDFDVVARAIVQIKNAIDATIKLGGTN<br>YVFWGGREGYMSLLNTDQKREKEHMAMMLGMARDYARSKGFKGTFLIEPKPMEPSKHQYDVD<br>TETVIGFLKAHGLDKDFKVNIEVNHATLAGHTFEHELACAVDAGMLGSIDANRGDAQNGWDT<br>DQFPIDNYELTQAMMEIIRNGGLGNGGTNFDAKIRRNSTDLEDLFIAHISGMDAMARALLNA<br>ADILENSELPAMKKARYASFDNGIGKDFEDGKLTFEQVYEYGKKVEEPKQTSGKQEKYETIV<br>ALYAK |
| 5586MI26_003 | Prevotella | DNA | 91 | ATGGCAAAAGAGTATTTTCCGTTTACCGGTAAAATTCCTTTCGAGGGAAAGGACAGTAAGAA<br>TGTAATGGCTTTCCACTACTACGAGCCTGAGCGCGTAGTGATGGGAAAGAAGATGAAGGATT<br>GGTTGCGATTTGCAATGGCTTGGTGGCACACACTGGGTGGCGCTTCTGCCGACCAGTTTGGT<br>GGTCAGACCCGCAGTTACGAATGGGACAAGGCTGCTGATGCTGTTCAGCGTGCTAAGGACAA<br>GATGGATGCCGGCTTCGAGATTATGGATAAGCTGGGAATCGAGTTCTTCTGCTGGCACGATA<br>TCGACCTCGTTGAAGAGGGTGAAGCCATTGAAGAGTATGAGCGCCGCATGAAGGCTATCACC<br>GACTATGCTCTTGAGAAGATGCAGCAGTATCCCAACATCAAGAACCTCTGGGGAACAGCCAA<br>TGTGTTTGGCAACAAGCGTTATGCCAACGGTGCCAGCACAAACCCAGACTTTGACGTCGTTG<br>CTCGTGCTATCGTACAGATTAAGAATGCTATCGACGCTACTATCAAGTTGGGTGGTCAGAAT<br>TATGTGTTCTGGGGTGGCCGTGAGGGCTACATGAGCCTGCTCAATACTGACCAGAAGCGTGA<br>GAAGGAGCACATGGCTACAATGCTGACCATGGCACGCGACTATGCCCGCAGCAAGGGATTCA<br>AGGGTAACTTCCTCATTGAGCCCAAGCCCATGGAGCCGTCAAAGCACCAGTATGATGTTGAC<br>ACCGAGACCGTATGCGGTTTCCTGCGTGCCCACAACCTTGACAAGGATTTCAAGGTAAATAT<br>CGAGGTTAACCATGCTACTCTGGCTGGTCATACTTTCGAGCACGAACTGGCATGCGCTGTTG<br>ACGCTGGTATGCTTGGTTCTATCGATGCTAACCGTGGTGATGCCCAGAATGGCTGGGATACC<br>GACCAGTTCCCCATCAACAACTATGAACTCACTCAGGCTATGCTTGAGATCATCCGTAATGG<br>TGGTCTGGGTCTTGGCGGCACAAACTTCGATGCCAAGATTCGTCGTAACTCAACAGATCTTG<br>AGGATCTCTTCATCGCTCACATCAGTGGTATGGATGCCATGGCCCGTGCTCTGCTGAATGCT<br>GCTGCTATTCTGGAGGAGAGCGAGCTGCCTAAGATGAAGAAGGAGCGTTATGCTTCTTTCGA<br>TGCCGGTATCGGTAAGGACTTCGAGGATGGCAAGCTTACCCTTGAGCAGGCTTACGAGTATG<br>GTAAGAAGGTTGAGGAGCCCAAGCAGACTTCAGGCAAGCAGGAGAAGTACGAGACCATCGTT<br>GCTCTGTATGCAAAATAA |
| 5586MI26_003 | Prevotella | Amino Acid | 92 | MAKEYFPFTGKIPFEGKDSKNVMAFHYYEPERVVMGKKMKDWLRFAMAWWHTLGGASADQFG<br>GQTRSYEWDKAADAVQRAKDKMDAGFEIMDKLGIEFFCWHDIDLVEEGETIEEYERRMKAIT<br>DYALEKMQQYPNIKNLWGTANVFGNKRYANGASTNPDFDVVARAIVQIKNAIDATIKLGGQN<br>YVFWGGREGYMSLLNTDQKREKEHMATMLTMARDYARSKGEMNFLIEPKPMEPSKHQYDVD<br>TETVCGFLRAHNLDKDFKVNIEVNHATLAGHTFEHELACAVDAGMLGSIDANRGDAQNGWDT<br>DQFPINNYELTQAMLEIIRNGGLGLGGTNFDAKIRRNSTDLEDLFIAHISGMDAMARALLNA<br>AAILEESELPKMKKERYASFDAGIGKDFEDGKLTLEQAYEYGKKVEEPKQTSGKQEKYETIV<br>ALYAK |
| 5586MI86_001 | Prevotella | DNA | 93 | ATGAAACAGTATTTTCCCCAGATTGGAAAGATACCCTTCGAGGGTGTAGAGAGCAAGAATGT<br>GATGGCTTTCCACTATTATGAGCCAGAAAGAGTAGTCATGGGCAAGCCTATGAAAGAATGGC<br>TGCGCTTCGCTATGGCGTGGTGGCACACGCTGGGGCAGGCGAGCGGCGACCCCTTCGGCGGA<br>CAGACCCGCAGCTACGAGTGGGACCGTGCGGCCGACGCGCTACAGCGCGCCAAGGACAAGAT<br>GGATGCGGGCTTCGAGCTGATGGAGAAGCTTGGCATTGAGTACTTCTGCTTCCACGACGTGG<br>ACCTCGTAGAAGAGGGCGCCACGGTGGAGGAATACGAGCGGCGGATGGCTGCCATCACCGAC<br>TACGCGGTAGAGAAGATGCGCGAGCATCCCGAGATACACTGCCTGTGGGGCACGGCCAATGT<br>CTTCGGCCACAAGCGCTACATGAACGGAGCCGCCACCAACCCCGACTTCGACGTGGTGGCGC<br>GTGCGGTGGTGCAGATAAAGAACAGCATCGACGCCACGATCAAGCTGGGCGGCGAGAACTAT<br>GTGTTCTGGGGCGGACGCGAGGGATATATGAGCCTGCTCAACACCGACCAGCGCCGCGAGAA<br>GGAGCACCTGGCCATGATGCTTGCGAAGGCCCGCGACTATGGCCGCGCCCACGGCTTCAAGG<br>GCACCTTCCTGATAGAGCCCAAGCCGATGGAGCCCATGAAGCACCAGTACGACGTGGACACC<br>GAGACGGTGATAGGTTTCCTGCGTGCCCACGGACTGGACAAGGACTTCAAGGTGAACATCGA<br>GGTGAACCACGCCACGTTGGCGGGCCACACGTTCGAGCACGAGCTGGCCTGTGCCGTCGATG<br>CCGGCATGCTGGGCAGCATCGACGCCAACCGTGGCGACGCGCAGAACGGATGGGATACGGAC<br>CAGTTCCCCATAGACTGCTACGAGCTCACGCAGGCGTGGATGGAGATCATTCGTGGCGGCGG<br>CTTCACCACCGGCGGCACCAACTTCGACGCTAAGCTGCGCCGCAACTCGACCGACCCCGAGG<br>ATATCTTCATAGCTCACATCAGCGGCATGGATGCTATGGCCCGCGCCCTGCTCTGCGCCGCC<br>GACATCTTGGAGCACAGCGAGCTGCCGGAGATGAAGCGGAAGCGCTATGCCTCGTTCGACAG<br>CGGCATGGGCAAGGAGTTCGAAGAGGGCAATCTCAGCTTCGAGCAAATCTATGCCTACGGCA |

TABLE 2-continued

| Clone No. | Class of organism | Type of Sequence | SEQ ID NO: | Sequence |
|---|---|---|---|---|
| | | | | AGCAGGCGGGCGAACCGGCCACGACCAGCGGCAAGCAGGAGAAATACGAAGCCATTGTTTCA<br>CTTTATACCCGATGA |
| 5586MI86_001 | Prevotella | Amino Acid | 94 | MKQYFPQIGKIPFEGVESKNVMAFHYYEPERVVMGKPMKEWLRFAMAWWHTLGQASGDPFGG<br>QTRSYEWDRAADALQRAKDKMDAGFELMEKLGIEYFCFHDVDLVEEGATVEEYERRMAAITD<br>YAVEKMREHPEIHCLWGTANVFGHKRYMNGAATNPDFDVVARAVVQIKNSIDATIKLGGENY<br>VFWGGREGYMSLLNTDQRREKEHLAMMLAKARDYGRAHGFKGTFLIEPKPMEPMKHQYDVDT<br>ETVIGFLRAHGLDKDFKVNIEVNHATLAGHTFEHELACAVDAGMLGSIDANRGDAQNGWDTD<br>QFPIDCYELTQAWMEIIRGGGFTTGGTNFDAKLRRNSTDPEDIFIAHISGMDAMARALLCAA<br>DILEHSELPEMKRKRYASFDSGMGKEFEEGNLSFEQIYAYGKQAGEPATTSGKQEKYEAIVS<br>LYTR |
| 5586MI108_002 | Prevotella | DNA | 95 | ATGGCAAAAGAGTATTTTCCGTTTATCGGTAAGGTTCCTTTCGAAGGAACAGAGAGCAAGAA<br>CGTGATGGCATTCCACTACTATGAGCCCGAAAAGGTGGTCATGGGTAAGAAAATGAAGGACT<br>GGCTGAAGTTCGCTATGGCTTGGTGGCACACACTGGGTGGTGCCAGCGCCGACCAGTTTGGT<br>GGTCAGACTCGCAGCTACGAGTGGGACAAGGCTGCTGATGCCGTTCAGCGCGCCAAGGACAA<br>GATGGATGCTGGCTTCGAGATCATGGATAAGCTCGGCATTGAGTACTTCTGCTTCCATGACG<br>TAGACCTCGTTGAGGAGGGTGAAACCGTCGCTGAGTATGAGGCTCGCATGAAGGTCATCACC<br>GACTATGCCCTGGAGAAGATGCAGCAGTTCCCCAACATCAAACTGCTCTGGGGTACTGCTAA<br>CGTGTTCGGCCACAAGCGCTATGCCAACGGTGCCAGCACCAATCCCGACTTCGACGTCGTGG<br>CCCGTGCTATCGTTCAGATCAAGAATGCCATCGATGCTACCATTAAGCTCGGCGGTACGAAC<br>TATGTGTTCTGGGGTGGTCGTGAGGGCTACATGAGCCTTCTCAACACCGACCAGAAGCGCGA<br>GAAGGAGCACATGGCAACGATGCTGACCATGGCTCGCGACTATGCCCGCGCCAAGGGATTCA<br>AGGGCACGTTCCTCATCGAGCCGAAGCCCATGGAGCCCTCGAAGCATCAGTACGACGTCGAC<br>ACCGAGACCGTCATCGGCTTCCTCCGTGCCCACGGTCTGGATAAGGACTTCAAGGTGAACAT<br>CGAGGTGAACCACGCCACGCTGGCCGGTCATACCTTCGAGCACGAACTGGCTTGCGCCGTTG<br>ATGCCGGCATGCTCGGCTCTATCGATGCCAACGCGGCGACGCTCAGAACGGCTGGGACACC<br>GACCAGTTCCCCATCGACAACTACGAGCTCACTCAGGCCATGATGGAAATCATCCGTAATGG<br>CGGTCTGGGCAACGGCCTGATGCCAAGATCCGTCGTAACGACCGACCTCG<br>AGGACCTCTTCATCGCTCACATCAGCGGCATGGATGCCATGGCACGCGCTCTGATGAACGCT<br>GCTGCCATCCTCGAAGAGAGCGAGCTGCCCGCCATGAAGAAGGCCCGCTATGCTTCGTTCGA<br>CGAGGGTATCGGCAAGGACTTCGAGGACGGCAAGTTGTCACTTGAGCAGGTCTACGAATATG<br>GTAAGAAGGTTGAGGAGCCCAAGCAGACCTCGGGCAAGCAGGAGAAGTACGAGACCATCGTG<br>GCCCTCTATGCCAAGTAA |
| 5586MI108_002 | Prevotella | Amino Acid | 96 | MAKEYFPFIGKVPFEGTESKNVMAFHYYEPEKVVMGKKMKDWLKFAMAWWHTLGGASADQFG<br>GQTRSYEWDKAADAVQRAKDKMDAGFEIMDKLGIEYFCFHDVDLVEEGETVAEYEARMKVIT<br>DYALEKMQQFPNIKLLWGTANVFGHKRYANGASTNPDFDVVARAIVQIKNAIDATIKLGGTN<br>YVFWGGREGYMSLLNTDQKREKEHMATMLTMARDYARAKGFKGTFLIEPKPMEPSKHQYDVD<br>TETVIGFLRAHGLDKDFKVNIEVNHATLAGHTFEHELACAVDAGMLGSIDANRGDAQNGWDT<br>DQFPIDNYELTQAMMEIIRNGGLGNGGTNFDAKIRRNSTDLEDLFIAHISGMDAMARALMNA<br>AAILEESELPAMKKARYASFDEGIGKDFEDGKLSLEQVYEYGKKVEEPKQTSGKQEKYETIV<br>ALYAK |
| 5586MI182_004 | Prevotella | DNA | 97 | ATGGCAAAAGAGTATTTTCCGTTTGTTGGTAAGATTCCTTTCGAGGGAAAGGATAGTAAGAA<br>TGTAATGGCTTTCCACTATTACGAACCAGAGAAGGTCGTGATGGGAAAGAAGATGAAGGACT<br>GGCTGAAGTTCGCCATGGCATGGTGGCACACACTGGGACAGGCCAGTGCCGACCCGTTTGGA<br>GGTCAGACCCGCAGCTACGAGTGGGACAAGGCTGACGATGCTGTGCAGCGCGCAAGGACAA<br>GATGGATGCCGGATTTGAGATCATGGACAAGCTGGGCATCGAGTACTTCTGCTTCCACGATG<br>TAGACCTCGTTGAGGAGGGAGCAACTGTTGAGGAGTACGAGGCTCGCATGAAGGCCATCACC<br>GACTATGCATTGGAGAAGATGAAAGAGTATCCCAACATCAAGAACCTCTGGGGTACAGCCAA<br>TGTATTCAGCAACAAGCGCTATATGAACGGTGCCAGCACCAACCCCGACTTCGACGTTGTTG<br>CACGTGCCATCGTACAGATAAAGAACGCCATTGACGCTACCATCAAGCTCGGCGGTCAGAAC<br>TACGTGTTCTGGGGCGGACGTGAGGGATACATGAGCCTGCTCAACACCGACCAGAAGCGCGA<br>GAAGGAGCACATGGCAACCATGCTGACCATGGCTCGCGACTACGTCGCAAGAACGGTTTCA<br>AGGGCACATTCCTCATCGAGCCTAAGCCCATGGAACCCTCAAAGCACCAGTACGACGTAGAC<br>ACAGAGACCGTATGCGGTTTCCTCCGCGCCCATGGTCTTGACAAGGATTTCAAGGTGAACAT<br>TGAGGTGAACCACGCTACCCTCGCCGGCCACACCTTTGAGCATGAACTGGCTTGCGCCGTCG<br>ACAACGGCATGCTCGGCAGCATCGATGCCAACGCGGCGACGTTCAGAACGGCTGGGACACC<br>GACCAGTTCCCCATCGACAACTACGAGCTGACTCAGGCCATGCTCGAAATCATCCGCAACGG<br>TGGTCTGGGCAACGGCGGTACCAACTTCGACGCCAAGATCCGTCGTAACTCTACCGACCTCG<br>AGGATCTGTTCATCGCCCACATCAGCGGTATGGACGCCATGGCACGTGCACTGCTCAATGCA<br>GCAGCCATACTGAAGGAGGCGAGCTGCCTGCCATGAAGAAGGAGCGTTACGCCAGCTTCGA<br>CAGCGGCATCGGCAAGGACTTCGAGGACGGCAAGCTCACACTTGAGCAGGCCTATGAGTATG<br>GTAAGAAGGTTGAGGAGCCAAAGCAGACCTCTGGCAAGCAGGAGAAGTATGAGACTATAGTA<br>GCCCTCTACGCTAAGTAG |
| 5586MI182_004 | Prevotella | Amino Acid | 98 | MAKEYFPFVGKIPFEGKDSKNVMAFHYYEPEKVVMGKKMKDWLKFAMAWWHTLGQASADPFG<br>GQTRSYEWDKADDAVQRAKDKMDAGFEIMDKLGIEYFCFHDVDLVEEGATVEEYEARMKAIT<br>DYALEKMKEYPNIKNLWGTANVFSNKRYMNGASTNPDFDVVARAIVQIKNAIDATIKLGGQN<br>YVFWGGREGYMSLLNTDQKREKEHMATMLTMARDYARKNGFKGTFLIEPKPMEPSKHQYDVD<br>TETVCGFLRAHGLDKDFKVNIEVNHATLAGHTFEHELACAVDNGMLGSIDANRGDVQNGWDT<br>DQFPIDNYELTQAMLEIIRNGGLGNGGTNFDAKIRRNSTDLEDLFIAHISGMDAMARALLNA<br>AAILEESELPAMKKERYASFDSGIGKDFEDGKLTLEQAYEYGKKVEEPKQTSGKQEKYETIV<br>ALYAK |

TABLE 2-continued

| Clone No. | Class of organism | Type of Sequence | SEQ ID NO: | Sequence |
|---|---|---|---|---|
| 5586MI193_004 | *Prevotella* | DNA | 99 | ATGACTAAAGAGTATTTCCCTACCATTGGCAAGATTCCCTTTGAGGGACCTGAAAGCAAGAA<br>CCCGCTTGCATTCCATTACTATGAGCCCGACCGCCTGGTCATGGGCAAGAAGATGAAAGACT<br>GGCTGCGTTTCGCCATGGCCTGGTGGCACACCCTGGGCCAGGCCTCCGGCGACCAGTTCGGC<br>GGCCAGACCCGCCACTATGCCTGGGATGATCCGGATTGCCCGTATGCACGTGCCAAAGCCAA<br>GGCCGACGCCGGTTTCGAAATCATGCAGAAACTGGGCATTGAATTCTTCTGCTTCCACGACA<br>TCGACCTGGTCGAGGATGCCGATGAAATCGCCGAGTACGAGGCCCGGATGAAGGACATCACC<br>GACTATCTGCTCGTCAAGATGAAAGAGACCGGCATCAAGAACCTTTGGGGAACGGCCAACGT<br>ATTTGGCCACAAGCGCTACATGAACGGCGCCGCCACCAACCCCGATTTCGACGTGCTGGCCC<br>GTGCCGCCGTCCAGATCAAGAACGCCATCGACGCCACCATCAAGTTGGGCGGTCAGAACTAT<br>GTGTTCTGGGGCGGCCGTGAAGGCTACCAGACCCTGCTCAATACCCAGATGCAGCGCGAGAA<br>GGAACACATGGGCCGTATGTTGGCACTGGCCCGCGACTATGGCCGTGCACACGGTTTCAAGG<br>GCACGTTCCTCATCGAGCCCAAACCGATGGAGCCGACCAAGCACCAGTACGATCAGGATACG<br>GAAACCGTCATCGGCTTCCTGCGCCGCCATGGCCTCGACAAGGACTTCAAGGTCAACATCGA<br>GGTGAACCATGCTACCCTGGCGGGCCACACCTTCGAGCACGAGCTGGCTTGCGCCGTCGACC<br>ACGGCATGCTGGGCAGCATCGACGCCAACCGGGTGATGCCCAGAACGGCTGGGACACCGAC<br>CAGTTCCCGATCGATAACTATGAGCTGACGCTGGCCATGCTCCAGATCATCCGCAACGGCGG<br>CCTGGCACCCGGCGGCTCGAACTTCGATGCGAAGCTGCGTCGCAACTCCACCGATCCGGAAG<br>ATATCTTCATCGCGCACATCAGCGCCATGGATGCCATGGCCCGCGCCCTGGTCAATGCTGTC<br>GCCATTCTCGAGGAATCGCCCATCCCGGCCATGGTCAGGGAACGTTACGCCTCGTTCGACAG<br>CGGAAAGGGCAGGGAATATGAGGAAGGCAGGCTGTCTCTCGAAGACATCGTGGCCTATGCCA<br>AAGCCCACGGCGAACCGAAACAGATTTCCGGCAAGCAGGAACTCTACGAAACCATCGTGGCT<br>CTCTATTGCAAGTAG |
| 5586MI193_004 | *Prevotella* | Amino Acid | 100 | <u>MTKEYFPTIGKIPFEGPESKNPLAFHYYEPDRLVMGKKMKDWLRFAMAWWHTLGQASGDQFG</u><br><u>GQTRHYAWDDPDCPYARAKAKADAGFEIMQKLGIEFFCFHDIDLVEDADEIAEYEARMKDIT</u><br><u>DYLLVKMKETGIKNLWGTANVFGHKRYMNGAATNPDFDVLARAAVQIKNAIDATIKLGGQNY</u><br><u>VFWGGREGYQTLLNTQMREKEHMGRMLALARDYGRAHGFKGTFLIEPKPMEPTKHQYDQDT</u><br><u>ETVIGFLRRHGLDKDFKVNIEVNHATLAGHTFEHELACAVDHGMLGSIDANRGDAQNGWDTD</u><br><u>QFPIDNYELTLAMLQIIRNGGLAPGGSNFDAKLRRNSTDPEDIFIAHISAMDAMARALVNAV</u><br><u>AILEESPIPAMVRERYASFDSGKGREYEEGRLSLEDIVAYAKAHGEPKQISGKQELYETIVA</u><br>LYCK |
| 5586MI195_003 | *Prevotella* | DNA | 101 | ATGGCAAAAGAGTATTTCCCGCAGATCGGAAAGATCGGCTTTGAGGGTCCTGCAAGCAAGAA<br>CCCGCTGGCATTCCATTATTATGACGCCGAGCGCGTGGTGATGGGTAAACCCATGAAAGACT<br>GGTTTAAATTCGCCCTCGCGTGGTGGCACAGCCTCGGCCAGGCCTCCGGCGACCCGTTCGGC<br>GGCCAGACCCGCTCCTACGAGTGGGACAAGGGCGAATGCCCCTACTGCCGCGCCCGCGCCAA<br>GGCGGACGCCGGCTTCGAGATCATGCAAAAGCTCGGCATCGGCTATTTCTGCTTCCACGACG<br>TCGACCTCATCGAAGACACGGACGCATCGCCGAATATGAGGGCCGCCTCAAGGACATCACG<br>GACTACCTGCTGGAAAGGATGCAGGAAACCGGCATCAAGAACCTCTGGGGCACGGCCAATGT<br>CTTCGGTCACAAGCGCTACATGAACGGCGCCGGCACCAATCCGCAGTTCGACATCGTCGCCC<br>GCGCTGCCGTCCAGATCAAGAACGCCCTCGACGCCACCATCAAGCTCGGTGGCTCGAACTAC<br>GTCTTCTGGGGCGGCCGCGAAGGTTATTACACGCTGCTCAACACCCAGATGCAGCGCGAGAA<br>AGACCACCTCGCCAAGCTCCTCACCGCCGCCCGCGACTATGCCCGCGCCAAGGGCTTCCAGG<br>GCACCTTCCTGATCGAGCCCAAGCCGATGGAGCCGACCAAGCACCAGTACGATGTCGACACG<br>GAGACTGTAATCGGATTCCTCCGCGCCAACGGACTGGACAAGGACTTCAAGGTCAACATCGA<br>GGTCAACCACGCCACCCTCGCCGGCCATACCTTCGAGCATGAGCTGACCGTCGCCCGCGAGA<br>ACGGATTCCTCGGCAGCATCGACGCCAACCGCGGTGACGCCCAGAACGGCTGGGACACCGAC<br>CAGTTCCCCGTGGACGCCTACGACCTCACCCAGGCCATGATGCAGGTGCTCCTGAACGGCGG<br>TTTCGGCAACGGCGGCACCAATTTCGACGCCAAGCTCCGTCGCAGCTCCACCGATCCCGAGG<br>ACATCTTCATCGCCCACATCAGCGCGATGGACGCCATGGCCCACGCCCTGCTGAACGCCGCG<br>GCCATTCTCGAGGAGAGCCCGCTGCCCGCGATGGTCAAGGAGCGTTACGCCTCCTTCGACAG<br>CGGTCTCGGCAAGCAGTTCGAGGAGGGAAAGGCCACGCTGGAGGACCTCTACGACTACGCCA<br>AGGCCCATGGCGAGCCCGTCGCCGCCTCCGGCAAGCAGGAACTGTGTGAAACTTACCTGAAT<br>CTGTATGCAAAGTAA |
| 5586MI195_003 | *Prevotella* | Amino Acid | 102 | <u>MAKEYFPQIGKIGFEGPASKNPLAFHYYDAERVVMGKPMKDWFKFALAWWHSLGQASGDPFG</u><br><u>GQTRSYEWDKGECPYCRARAKADAGFEIMQKLGIGYFCFHDVDLIEDTDDIAEYEARLKDIT</u><br><u>DYLLERMQETGIKNLWGTANVFGHKRYMNGAGTNPQFDIVARAAVQIKNALDATIKLGGSNY</u><br><u>VFWGGREGYYTLLNTQMQREKDHLAKLLTAARDYARAKGFQGTFLIEPKPMEPTKHQYDVDT</u><br><u>ETVIGFLRANGLDKDFKVNIEVNHATLAGHTFEHELTVARENGFLGSIDANRGDAQNGWDTD</u><br><u>QFPVDAYDLTQAMMQVLLNGGEGNGGTNEDAKLRRSSTDPEDIFIAHISAMDAMAHLLNAA</u><br><u>AILEESPLPAMVKERYASFDSGLGKQFEEGKATLEDLYDYAKAHGEPVAASGKQELCETYLN</u><br>LYAK |
| 5586MI196_003 | *Prevotella* | DNA | 103 | ATGACAAAAGAGTATTTCCCTACCATCGGCAAGATCCCCTTTGAGGGACCCGAGAGCAAAAA<br>CCCCCTCGCTTTTCATTACTATGAGCCCGACCGCCTGGTCATGGGCAAGAAGATGAAAGACT<br>GGCTGCGTTTCGCCATGGCCTGGTGGCACACCCTGGGCCAGGCCTCCGGCGACCAGTTTGGC<br>GGCCAGACCCGCCACTATGCCTGGGATGATCCGGATTGCCCGTATGCACGTGCCAAAGCCAA<br>GGCCGACGCCGGTTTCGAAATCATGCAGAAACTGGGCATTGAATTCTTCTGCTTCCACGACA<br>TCGACCTGATCGAGGATACCGATGACATCGTCGAGTATGAGGCCCGGATGAAGGACATCACC<br>GACTATCTGCTGGTCAAGATGAAAGAGACCGGCATCAAGAATCTCTGGGGAACGGCCAACGT<br>ATTCGGGCACAAGCGCTATATGAACGGCGCTGCCACCAACCCCGATTTCGACGTGCTGGCCC<br>GTGCCGCCGTCCAGATCAAGAACGCCATCGACGCCACCATCAAGTGGGCGGCCAGAATTAT<br>GTGTTCTGGGGCGGCGTGAAGGCTACCAGAGCCTGCTCAATACCCAGATGCAGCGCGAAAA<br>GGAACACATGGGCCGTATGTTGGCACTAGCCCGCGACTATGGCCGTGCACACGGTTTCAAGG<br>GCACGTTCCTCATCGAGCCCAAACCGATGGAGCCGACCAAGCACCAGTACGATCAGGATACG |

TABLE 2-continued

| Clone No. | Class of organism | Type of Sequence | SEQ ID NO: | Sequence |
|---|---|---|---|---|
| | | | | GAGACCGTCATCGGTTTTCTGCGCCGCCATGGCCTCGACAAGGACTTCAAGGTCAACATCGA<br>GGTGAACCATGCTACCCTGGCGGGCCACACCTTCGAGCACGAGCTGGCCTGCGCCGTCGACC<br>ACGGCATGCTGGGCAGTATTGACGCCAACCGCGGTGACGCCCAGAACGGCTGGGACACCGAC<br>CAGTTCCCGATCGATAACTATGAGCTGACGCTGGCCATGCTCCAGATCATCCGCAACGGCGG<br>CCTGGCACCCGGCGGCTCGAACTTCGATGCGAAGCTGCGTCGCAACTCCACCGATCCGGAAG<br>ATATCTTCATCGCGCACATCAGCGCCATGGATGCCATGGCCCGCGCCCTGGTCAACGCTGTC<br>GCCATTCTTGAGGAATCGCCCATTCCGGACATGGTCAAGGAGCGCTACGCTTCGTTCGACAG<br>CGGAAAAGGCAGGGAGTACGAAGAGGGGAAACTTTCCTTCGAGGACCTCGTGGCCTATGCCA<br>AAGCCCACGGCGAACCGAAACAGATTTCCGGCAAGCAGGAACTCTACGAAACCATCGTGGCT<br>CTCTATTGCAAGTAG |
| 5586MI196_003 | Prevotella | Amino Acid | 104 | <u>MTKEYFPTIGKIPFEGPESKNPLAFHYYEPDRLVMGKKMKDWLRFAMAWWHTLGQASGDQFG<br>GQTRHYAWDDPDCPYARAKAKADAGFEIMQKLGIEFFCFHDIDLIEDTDDIVEYEARMKDIT<br>DYLLVKMKETGIKNLWGTANVFGHKRYMNGAATNPDFDVLARAAVQIKNAIDATIKLGGQNY<br>VFWGGREGYQSLLNTQMREKEHMGRMLALARDYGRAHGFKGTFLIEPKPMEPTKHQYDQDT<br>ETVIGFLRRHGLDKDFKVNIEVNHATLAGHTFEHELACAVDHGMLGSIDANRGDAQNGWDTD<br>QFPIDNYELTLAMLQIIRNGGLAPGGSNFDAKLRRNSTDPEDIFIAHISAMDAMARALVNAV<br>AILEESPIPDMVKERYASFDSGKGREYEEGKLSFEDLVAYAKAHGEPKQISGKQELYETIVA<br>LYCK</u> |
| 5586MI197_003 | Prevotella | DNA | 105 | ATGACAAAAGAGTATTTCCCTACCATCGGCAAGATCCCCTTTGAGGGACCCGAGAGCAAAA<br>CCCCCTCGCTTTTCATTACTATGAGCCCGACCGCCTGGTCATGGGCAAGAAGATGAAAGACT<br>GGCTGCGTTTCGCCATGGCCTGGTGGCACACCCTGGGCCAGGCCTCCGGCGACCAGTTTGGC<br>GGCCAGACCCGCCACTATGCCTGGGATGATCCGGATTGCCCGTATGCACGTGCCAAAGCCAA<br>GGCCGACGCCGGTTTCGAAATCATGCAGAAACTGGGCATTGAATTCTTCTGCTTCCACGACA<br>TCGACCTGATCGAGGATACCGATGACATCGTCGAGTATGAGGCCCGGATGAAGGACATCACC<br>GACTATCTGCTGGTCAAGATGAAAGAGACCGGCATCAAGAATCTCTGGGGAACGGCCAACGT<br>ATTCGGGCACAAGCGCTATATGAACGGCGCTGCCACCAACCCCGATTTCGACGTGCTGGCCC<br>GTGCCGCCGTCCAGATCAAGAACGCCATCGACGCCACCATCAAGCTGGGCGGCCAGAATTAT<br>GTGTTCTGGGGCGGGCGTGAAGGCTACCAGAGCCTGCTCAATACCCAGATGCAGCGCGAAAA<br>GGAACACATGGGCCGTATGTTGGCACTAGCCCGCGACTATGGCCGTGCACACGGTTTCAAGG<br>GCACGCTCCTCATCGAGCCCAAACCGATGGAGCCGACCAAGCACCAGTACGATCAGGATACG<br>GAGACCGTCATCGGTTTTCTGCGCCGCCATGGCCTCGACAAGGACTTCAAGGTCAACATCGA<br>GGTGAACCATGCTACCCTGGCGGGCCACACCTTCGAGCACGAGCTGGCCTGCGCCGTCGACC<br>ACGGCATGCTGGGCAGTATTGACGCCAACCGCGGTGACGCCCAGGACGGCTGGGACACCGAC<br>CAGTTCCCGATCGATAACTATGAGCTGACGCTGGCCATGCTCCAGATCATCCGCAACGGCGG<br>CCTGGCACCCGGCGGCTCGAACTTCGATGCGAAGCTGCGTCGCAACTCCACCGATCCGGAAG<br>ATATCTTCATCGCGCACATCAGCGCCATGGATGCCATGGCCCGCGCCCTGGTCAACGCTGTC<br>GCCATTCTTGAGGAATCGCCCATTCCGGACATGGTCAAGGAGCGCTACGCTTCGTTCGACAG<br>CGGAAAAGGCAGGGAGTACGAAGAGGGGAAACTTTCCTTCGAGGACCTCGTGGCCTATGCCA<br>AAGCCCACGGCGAACCGAAACAGATTTCCGGCAAGCAGGAACTCTACGAAACCATCGTGGCT<br>CTCTATTGCAAGTAG |
| 5586MI197_003 | Prevotella | Amino Acid | 106 | <u>MTKEYFPTIGKIPFEGPESKNPLAFHYYEPDRLVMGKKMKDWLRFAMAWWHTLGQASGDQFG<br>GQTRHYAWDDPDCPYARAKAKADAGFEIMQKLGIEFFCFHDIDLIEDTDDIVEYEARMKDIT<br>DYLLVKMKETGIKNLWGTANVFGHKRYMNGAATNPDFDVLARAAAQIKNAIDATIKLGGQNY<br>VFWGGREGYQSLLNTQMREKEHMGRMLALARDYGRAHGFKGTLLIEPKPMEPTKHQYDQDT<br>ETVIGFLRRHGLDKDFKVNIEVNHATLAGHTFEHELACAVDHGMLGSIDANRGDAQDGWDTD<br>QFPIDNYELTLAMLQIIRNGGLAPGGSNFDAKLRRNSTDPEDIFIAHISAMDAMARALVNAV<br>AILEESPIPDMVKERYASFDSGKGREYEEGKLSFEDLVAYAKAHGEPKQISGKQELYETIVA<br>LYCK</u> |
| 5586MI199_003 | Prevotella | DNA | 107 | ATGACAAAAGAGTATTTCCCTACCATCGGCAAGATCCCCTTTGAGGGACCCGAGAGCAAAA<br>CCCCCTCGCTTTTCATTACTATGAGCCCGACCGCCTGGTCATGGGCAAGAAGATGAAAGACT<br>GGCTGCGTTTCGCCATGGCCTGGTGGCACACCCTGGGCCAGGCCTCCGGCGACCAGTTTGGC<br>GGCCAGACCCGCCACTATGCCTGGGATGATCCGGATTGCCCGTATGCACGTGCCAAAGCCAA<br>GGCCGACGCCGGTTTCGAAATCATGCAGAAACTGGGCATTGAATTCTTCTGCTTCCACGACA<br>TCGACCTGATCGAGGATACCGATGACATCGTCGAGTATGAGGCCCGGATGAAGGACATCACC<br>GACTATCTGCTGGTCAAGATGAAAGAGACCGGCATCAAGAATCTCTGGGGAACGGCCAACGT<br>ATTCGGGCACAAGCGCTATATGAACGGCGCTGCCACCAACCCCGATTTCGACGTGCTGGCCC<br>GTGCCGCCGTCCAGATCAAGAACGCCATCGACGCCACCATCAAGCTGGGCGGCCAGAATTAT<br>GTGTTCTGGGGCGGGCGTGAAGGCTACCAGAGCCTGCTCAATACCCAGATGCAGCGCGAAAA<br>GGAACACATGGGCCGTATGTTGGCACTAGCCCGCGACTATGGCCGTGCACACGGTTTCAAGG<br>GCACGTTCCTCATCGAGCCCAAACCGATGGAGCCGACCAAGCACCAGTACGATCAGGATACG<br>GAGACCGTCATCGGTTTTCTGCGCCGCCATGGCCTCGACAAGGACTTCAAGGTCAACATCGA<br>GGTGAACCATGCTACCCTGGCGGGCCACACCTTCGAGCACGAGCTGGCCTGCGCCGTCGACC<br>ACGGCATGCTGGGCAGTATTGACGCCAACCGCGGTGACGCCCAGAACGGCTGGGACACCGAC<br>CAGTTCCCGATCGATAACTATGAGCTGACGCTGGCCATGCTCCAGATCATCCGCAACGGCGG<br>CCTGGCACCCGGCGGCTCGAACTTCGATGCGAAGCTGCGTCGCAACTCCACCGATCCGGAAG<br>ATGTCTTCATCGCGCACATCAGCGCCATGGATGCCATGGCCCGCGCCCTGGTCAACGCTGTC<br>GCCATTCTTGAGGAATCGCCCATTCCGGACATGGTCAAGGAGCGCTACGCTTCGTTCGACAG<br>CGGAAAAGGCAGGGAGTACGAAGAGGGGAAACTTTCCTTCGAGGACCTCGTGGCCTATGCCA<br>AAGCCCACGGCGAACCGAAACAGATTTCCGGCAAGCAGGAACTCTACGAAACCATCGTGGCT<br>CTCTATTGCAAGTAG |

TABLE 2-continued

| Clone No. | Class of organism | Type of Sequence | SEQ ID NO: | Sequence |
|---|---|---|---|---|
| 5586MI199_003 | Prevotella | Amino Acid | 108 | MTKEYFPTIGKIPFEGPESKNPLAFHYYEPDRLVMGKKMKDWLRFAMAWWHTLGQASGDQFG<br>GQTRHYAWDDPDCPYARAKAKADAGFEIMQKLGIEFFCFHDIDLIEDTDDIVEYEARMKDIT<br>DYLLVKMKETGIKNLWGTANVFGHKRYMNGAATNPDFDVLARAAVQIKNAIDATIKLGGQNY<br>VFWGGREGYQSLLNTQMQREKEHMGRMLALARDYGRAHGFKGTFLIEPKPMEPTKHQYDQDT<br>ETVIGFLRRHGLDKDFKVNIEVNHATLAGHTFEHELACAVDHGMLGSIDANRGDAQNGWDTD<br>QFPIDNYELTLAMLQIIRNGGLAPGGSNFDAKLRRNSTDPEDVFIAHISAMDAMARALVNAV<br>AILEESPIPDMVKERYASFDSGKGREYEEGKLSFEDLVAYAKAHGEPKQISGKQELYETIVA<br>LYCK |
| 5586MI200_003 | Prevotella | DNA | 109 | ATGGCAAAAGAGTATTTCCCGACAATCGGAAAGATCCCCTTCGAGGGCGTTGAGAGCAAGAA<br>TCCCCTTGCTTTCCATTATTATGACGCCGAGCGCGTGGTCATGGGCAAGCCCATGAAGGACT<br>GGTTCAAGTTCGCGATGGCCTGGTGGCACACCCTGGGCCAGGCTTCCGCGGACCCGTTCGGC<br>GGCCAGACCCGCTCCTACGAGTGGGACAAGGGCGAGTGCCCCTACTGCCGCGCCCGCGCCAA<br>GGCTGACGCCGGCTTCGAGATCATGCAGAAGCTCGGAATCGGCTACTATTGCTTCCACGACA<br>TCGACCTGGTGGAGGACACCGAGGACATCGCCGAATACGAGGCCCGCATGAAGGACATCACC<br>GACTACCTCGTCGAGAAGCAGAAGGAGACCGGCATCAAGAACCTCTGGGGCACCGCGAACGT<br>GTTCGGCAACAAGCGCTACATGAACGGCGCCGCCACGAACCCGCAGTTCGACATCGTCGCCC<br>GCGCGGCCCTGCAGATCAAGAACGCGATGATGCCACCATCAAGCTCGGCGGCACCGGCTAC<br>GTGTTCTGGGGCGGCCGGGAAGGCTACTACACCCTGCTGAACACCCAGATGCAGCGCGAGAA<br>GGACCACCTCGCCAAGATGCTCACCGCCGCCCGCGACTACGCCCGCGCCAACGGCTTCAAGG<br>GCACCTTCCTCATCGAGCCCAAGCCGATGGAGCCCACCAAGCACCAATACGACGTGGACACG<br>GAGACCGTGATCGGCTTCCTCCGCGCCAATGGCCTGGACAAGGACTTCAAGGTGAACATCGA<br>GGTGAACCACGCCACCCTCGCCGGCCACACCTTCGAGCACGAGCTCACCGTGGCCGTTGACA<br>ACGGCTTCCTCGGCAGCATCGACAACCGCGGCGACGCCCAGAACGGCTGGGATACCGAC<br>CAGTTCCCGGTGGATCCGTACGATCTCACCCAGGCGATGATCCAGATCATCCGCAACGGCGG<br>CTTCAAGGACGGCGGCACCAACTTCGACGCCAGGCTCCGCCGCTCTTCCACCGACCCGGAGG<br>ACATCTTCATCGCCCACATCAGCGCGATGGACGCCATGGCCCACGCCCTGCTGAACGCCGCC<br>GCCGTCATCGAGGAGAGCCCGCTCTGCGAGATGGTCGCCAAGCGTTACGCTTCCTTCGACAG<br>CGGCCTCGGCAAAAAGTTCGAGGAAGGCAAGGCCACCCTCGAGGAACTCTACGAGTATGCCA<br>AGGCGAACGGTGAGGTCAAGGCCGAATCCGGCAAGCAGGAGCTCTACGAGACCCTTCTGAAC<br>CTCTACGCGAAATAG |
| 5586MI200_003 | Prevotella | Amino Acid | 110 | MAKEYFPTIGKIPFEGVESKNPLAFHYYDAERVVMGKPMKDWFKFAMAWWHTLGQASADPFG<br>GQTRSYEWDKGECPYCRARAKADAGFEIMQKLGIGYYCFHDIDLVEDTEDIAEYEARMKDIT<br>DYLVEKQKETGIKNLWGTANVFGNKRYMNGAATNPQFDIVARAALQIKNAIDATIKLGGTGY<br>VFWGGREGYYTLLNTQMREKDHLAKMLTAARDYARANGFKGTFLIEPKPMEPTKHQYDVDT<br>ETVIGFLRANGLDKDFKVNIEVNHATLAGHTFEHELTVAVDNGFLGSIDANRGDAQNGWDTD<br>QFPVDPYDLTQAMIQIIRNGGFKDGGTNFDARLRRSSTDPEDIFIAHISAMDAMAHALLNAA<br>AVIEESPLCEMVAKRYASFDSGLGKKFEEGKATLEELYEYAKANGEVKAESGKQELYETLLN<br>LYAK |
| 5586MI203_003 | Prevotella | DNA | 111 | ATGGCACAAGCGTATTTTCCTACCATCGGGAAAATCCCCTTCGAGGGACCCGAAAGCAAGAA<br>TCCCCTGGCATTCCATTATTATGAGCCCGACCGCTGGTCCTGGGCAAGAAGATGAAGGACT<br>GGCTGCGTTTCGCCATGGCCTGGTGGCACACGCTGGGCCAGGCTTCCGGCGACCAGTTCGGC<br>GGCCAGACCCGCCACTACGCCTGGGACGAGCCCGCCACGCCCCTGGAACGGGCCAAGGCCAA<br>GGCGGATGCCGGTTTCGAGATCATGCAGAAACTGGGCATCGAATTCTTCTGCTTCCACGATG<br>TGGACCTCATCGAAGAGGGCGCCACGATCGAGGAATACGAGCAGCGGATGCAGCAGATCACG<br>GATTATCTGCTGGTCAAGATGAAAGAGACCGGCATCCGCAACCTCTGGGGTACGGCCAACGT<br>GTTCGGCACGAGCGCTACATGAACGGCGCGGCCACGAACCCCGATTTCGATGTCGTGGCCC<br>GCGCGGCCGTGCAGATCAAGACGGCCATCGACGCCACCATCAAGTTGGGCGGCGAGAACTAT<br>GTGTTCTGGGGCGGCCGGGAAGGCTATATGAGCCTGCTCAATACGCAGATGCACCGCGAGAA<br>GCTGCATCTGGGCAAGATGCTCGCCGCGGCCCGCGACTACGGACGCGCCCACGGCTTCAAGG<br>GGACCTTCCTCATCGAACCCAAGCCGATGGAACCCACCAAGCATCAGTATGACCAGGATACG<br>GAGACGGTCATCGGTTTCCTGCGCCGCTACGGCCTGGACGAAGACTTCAAGGTGAACATCGA<br>GGTCAACCACGCTACGCTGGCCGGCCATACCTTCGAACACGAACTGGCCACGGCGGTCGATG<br>CCGGCCTGCTGGGCAGCATCGACGCCAACCGCGGCGACGCCCAGAACGGCTGGGATACCGAC<br>CAGTTCCCGATCGACAACTACGAACTGACCCTGGCGATGCTGCAGGTCATCCGCAACGGCGG<br>TCTGGCCCCGGGCGGCTCGAATTTCGATGCCAAGCTCCGCCGGAACTCCACCGATCCGGAGG<br>ACATCTTCATTGCCCACATCAGCGCGATGGATGCGATGGCGCGGGCCCTGCTCAATGCGGCC<br>GCCCTCTGCGAGACGTCCCCGATTCCGGCGATGGTCAAGGCGCGTTACGCTTCGTCGACAG<br>CGGCGCCGGCAAGGATTTCGAAGAGGGAAGGATGACGCTGGAAGACCTCGTGGCCTATGCCA<br>GGACCCACGGCGAGCCGAAGCGGACCTCGGGCAAGCAGGAACTCTATGAGACCCTCGTGGCG<br>CTTTATTGCAAATAG |
| 5586MI203_003 | Prevotella | Amino Acid | 112 | MAQAYFPTIGKIPFEGPESKNPLAFHYYEPDRLVLGKKMKDWLRFAMAWWHTLGQASGDQFG<br>GQTRHYAWDEPATPLERAKAKADAGFEIMQKLGIEFFCFHDVDLIEEGATIEEYEQRMQQIT<br>DYLLVKMKETGIRNLWGTANVFGHERYMNGAATNPDFDVVARAAVQIKTAIDATIKLGGENY<br>VFWGGREGYMSLLNTQMHREKLHLGKMLAAARDYGRAHGFKGTFLIEPKPMEPTKHQYDQDT<br>ETVIGFLRRYGLDEDFKVNIEVNHATLAGHTFEHELATAVDAGLLGSIDANAGDAQNGWDTD<br>QFPIDNYELTLAMLQVIRKGGLAPGGSNFDAKLRRNSTDPEDIFIAHISAMDAMARALLNAA<br>ALCETSPIPAMVKARYASFDSGAGKDFEEGRMTLEDLVAYARTHGEPKRTSGKQELYETLVA<br>LYCK |
| 5586MI205_004 | Prevotella | DNA | 113 | ATGACCAACGAGTATTTCCCGGAATCGGTGTGATTCCGTTTGAAGGACAGGAAAGCAAGAA<br>TCCCCTGGCTTTCCATTATTATGACGCCAACCGCGTAGTGATGGGCAAACCCATGAAGGAAT |

TABLE 2-continued

| Clone No. | Class of organism | Type of Sequence | SEQ ID NO: | Sequence |
|---|---|---|---|---|
| | | | | GGTTCAAATTTGCCATGGCCTGGTGGCATACGCTGGGGCAGGCATCGGCCGATCCCTTCGGC<br>GGACAGACCCGCTCCTACGCATGGGACAAGGGCGAGTGCCCTTACTGCCGTGCCCGCCAGAA<br>GGCCGACGCCGGCTTTGAACTGATGCAGAAGCTGGGAATCGGCTATTTCTGCTTCCACGATG<br>TGAATATCATCGAGGACTGCGAGGACATTGCCGAGTATGAGGCCCGTATGAAGGACATCACG<br>GACTATCTGCTGGTGAAGATGAAGGAAACGGGCATCAAGAATCTGTGGGGCACGGCCAACGT<br>CTTCGGCCACAAGCGCTATATGAACGGCGCCGCCACCAACCCGCAATTCGACGTGGTAGCCC<br>GCGCTGCGGTCCAGATCAAGAACGCCCTGGACGCCACCATCAAGCTGGGCGGCAGCAATTAT<br>GTGTTCTGGGGCGGCCGGGAAGGCTACTACACCCTTTTGAACACGCAGATGCAGCGGGAGAA<br>GGACCACCTGGCCCAGATGCTCAAGGCGGCCCGCGACTATGCCCGCGGCAAGGGATTCAAGG<br>GCACGTTCCTCATTGAGCCCAAGCCCATGGAGCCCACCAAGCACCAGTACGACGTAGATACG<br>GAGACCGTGATTGGTTTCCTGCGCGCCAACGGGCTGGACAAGGACTTCAAGGTGAATATCGA<br>AGTGAACCACGCCACCCTGGCCGGCCATACCTTCGAGCACGAGCTCACCGTGGCCCGCGAAA<br>ACGGCTTCCTGGGCAGCATCGACGCCAACCGCGGAGACGCCCAGAACGGCTGGGATACAGAC<br>CAGTTCCCCGTGGACGCCTTTGACCTCACCCAGGCCATGATGCAGGTCCTGCTCAACGGCGG<br>ATTCGGCAACGGCGGCACCAACTTCGACGCCAAACTGCGCCGTTCCTCCACGGATCCCGAGG<br>ACATCTTCATCGCCCACATCAGCGCCATGGACGCCATGGCCCACGCCCTCCTGAACGCCGCC<br>GCCATCCTGGAAGAGAGCCCCATGCCGGGCATGGTGAAGGAGCGCTACGCCTTCCTTCGACAA<br>TGGCCTTGGCAAGAAGTTCGAGGAAGGAAAGGCCACGCTGGAAGAGCTGTACGACTATGCCA<br>AGAAGAACGGCGAGCCTGTGGCCGCTTCCGGAAAGCAGGAACTGTACGAAACGCTGCTGAAC<br>CTGTACGCCAAGTAA |
| 5586MI205_004 Prevotella | | Amino Acid | 114 | MTNEYFPGIGVIPFEGQESKNPLAFHYYDANRVVMGKPMKEWFKFAMAWWHTLGQASADPFG<br>GQTRSYAWDKGECPYCRARQKADAGFELMQKLGIGYFCFHDVNIIEDCEDIAEYEARMKDIT<br>DYLLVKMKETGIKNLWGTANVFGHKRYMNGAATNPQFDVVARAAVQIKNALDATIKLGGSNY<br>VFWGGREGYYTLLNTQMQREKDHLAQMLKAARDYARGKGFELIEPKPMEPTKHQYDVDT<br>ETVIGFLRANGLDKDEKVNIEVNHATLAGHTFEHELTVARENGFLGSIDANRGDAQNGWDTD<br>QFPVDAFDLTQAMMQVLLNGGFGNGGTNFDAKLRRSSTDPEDIFIAHISAMDAMAHALLNAA<br>AILEESPMPGMVKERYASFDNGLGKKFEEGKATLEELYDYAKKNGEPVAASGKQELYETLLN<br>LYAK |
| 5586MI206_004 Prevotella | | DNA | 115 | ATGGCAAAAGAGTATTTCCCGACTATCGGCAAGATTCCCTTCGAGGGCGTCGAATCCAAGAA<br>CCCGATGGCATTCCACTATTATGACGCGAAACGCGTCGTGATGGGCAAGCCCATGAAGGACT<br>GGCTCAAGTTCGCGATGCCTGGTGGCACACCCTGGGACAGGCTTCCGGCGACCCGTTCGGC<br>GGCCAGACCCGTTCCTACGAGTGGGACAAGGGCGAGTGCCCCTACTGCCGCGCCAAGGCCAA<br>GGCCGACGCCGGTTTCGAGATCATGCAGAAACTGGGCATCGAGTACTACTGCTTCCATGACA<br>TCGACCTGGTGGAGGACACCGAGGACATCGCCGAGTACGAGGCCCGCATGAAGGACATCACC<br>GACTACCTCGTCGAGAAGCAGAAGGAGACCGGTATCAAGAACCTCTGGGGCACGGCCAACGT<br>GTTCGGCAACAAGCGCTACATGAACGGCGCCGCCACGAACCCGCAGTTCGACGTCGTCGCCC<br>GCGCCGCCGTCCAGATCAAGAACGCCATCGACGCCACCATCAAACTCGGCGGCACCTCTTAC<br>GTGTTCTGGGGCGGCCGTGAAGGCTACTACACCCTCCTGAACACCCAGATGCAGCGCGAGAA<br>GGACCACCTCGCCAAGATGCTCACCGCCGCCCGCGACTACGCCCGCGCCCACGGCTTCAAGG<br>GCACCTTCCTCATCGAGCCCAAGCCCATGGAGCCCACCAAGCACCAGTACGACGTGGACACG<br>GAGACCGTGATCGGCTTCCTCCGCGCCAACGGCCTGGACAAGGACTTCAAGGTCAATATCGA<br>AGTGAACCACGCCACCCTCGCCGGCCACACCTTCGAGCATGAGCTCACCGTGGCCGTCGATA<br>ACGGCTTCCTCGGCTCCATCGACGCCAACCGTGGCGACGCCCAGAACGGCTGGGATACCGAC<br>CAGTTCCCCGGTGGATCCGTATGACGACCTCACCCAGGCCATGATGCAGATCATCCGCAACGG<br>CTTCAAGGACGGCGGCACCAACTTCGACGCCAAACTCCGCCGCTCCTCCACCGACCCGGAGG<br>ACATCTTCATCGCCCACATCAGCGCGATGGACGCCATGGCCCACGCGCTCCTGAACGCCGCC<br>GCCGTCATCGAGGAGAGCCCGCTCTGCAAGATGGTCGAGGAGCGCTACGCTTCCTTCGACAG<br>CGGTCTCGGCAAGCAGTTCGAGGAAGGCAAGGCCACCCTTGAGGACCTCTACGAGTATGCCA<br>AGAAGAACGGCGAGCCCGTCGTCGCTTCCGGCAAGCAGGAGCTCTACGAGACCCTTCTGAAC<br>CTCTACGCGAAGTAG |
| 5586MI206_004 Prevotella | | Amino Acid | 116 | MAKEYFPTIGKIPFEGVESKNPMAFHYYDAKRVVMGKPMKDWLKFAMAWWHTLGQASGDPFG<br>GQTRSYEWDKGECPYCRAKAKADAGFEIMQKLGIEYYCFHDIDLVEDTEDIAEYEARMKDIT<br>DYLVEKQKETGIKNLWGTANVFGNKRYMNGAATNPQFDVVARAAVQIKNAIDATIKLGGTSY<br>VFWGGREGYYTLLNTQMQREKDHLAKMLTAARDYARAHGEKGTFLIEPKPMEPTKHQYDVDT<br>ETVIGFLRANGLDKDFKVNIEVNHATLAGHTFEHELTVAVDNGFLGSIDANRGDAQNGWDTD<br>QFPVDPYDLTQAMMQIIRNGGFKDGGTNFDAKLRRSSTDPEDIFIAHISAMDAMAHALLNAA<br>AVIEESPLCKMVEERYASFDSGLGKQFEEGKATLEDLYEYAKKNGEPVVASGKQELYETLLN<br>LYAK |
| 5586MI208_003 Prevotella | | DNA | 117 | ATGTCAACTGAGTATTTCCCTACAATCGGCAAGATTCCCTTCGAGGGACCCGAGAGCAAGAA<br>CCCCATGGCCTTCCACTACTATGAACCCGAAAAGTTGGTGATGGGCAAGAAGATGAAGGACT<br>GGCTGCGTTTCGCAATGGCCTGGTGGCACACCCTTGGAGCCGCATCCGGCGACCAGTTCGGC<br>GGACAGACCCGCAGTTACGCCTGGGACAAGGGCGACTGCCCTTACAGCCGCGCCCGCGCCAA<br>GGTCGACGCCGGCTTCGAGATCATGCAGAAGCTCGGCATAGAGTTCTTCTGCTTCCATGACA<br>TCGACCTGGTCGAGGATACCGACGACATCGCCGAGTATGAAGCCCGGATGAAAGACATCACG<br>GACTATCTGCTGAAAGATGGAGGCTACCGGCATCAAGAACCTCTGGGGCACGGCCAATGT<br>CTTCGGTCACAAGCGTTATATGAACGGTGCAGCCACAAACCCCGATTTCGCAGTGGTCGCAA<br>GGGCGGCCGTGCAGATCAAGAACGCCATCGACGCCACCATCAAGCTGGGCGGCAGCAACTAT<br>GTGTTCTGGGGTGGACGCGAGGGTTATATGAGCCTGCTCAACACCCAGATGCAGAGGGAGAA<br>GGAACACCTTGCCAAGATGCTCACCGCCGCACGTGACTATGCACGCGCCAAAGGTTTCAAGG<br>GCACGTTCCTCATCGAACCCAAGCCGATGGAACCCACCAAGCACCAGTATGACCAGGATACC<br>GAGACCGTTATCGGATTCCTCCGCAGCCACGGCCTGGACAAGGACTTCAAGGTCAACATCGA<br>GGTGAACCACGCCACCCTGGCGGGCCATACCTTCGAGCACGAACTGGCCACCGCCGTCGACA |

TABLE 2-continued

| Clone No. | Class of organism | Type of Sequence | SEQ ID NO: | Sequence |
|---|---|---|---|---|
| | | | | ACGGCATGCTCGGCAGCATCGACGCCAACCGCGGAGACGCCCAGAACGGCTGGGACACCGAC<br>CAGTTCCCGATCGACAACTTCGAGCTCACGCTTGCCATGATGCAGATAATCCGCAACGGCGG<br>CCTGGCACCGGGCGGTTCGAACTTCGACGCAAAGCTGCGCCGCAATTCCACCGATCCCGAGG<br>ACATCTTCATCGCCCACATCAGCGCGATGGACGCCATGGCCCGCGCCCTCGTCAACGCCGCC<br>GCCATCCTCGGCGAGTCGCCCGTTCCGGCTATGGTCAAGGACCGCTATGCTTCGTTCGACTG<br>CGGCAAGGGCAAGGACTTCGAAGACGGCAAACTGACTCTCGAAGACATCGTCGCCTACGCCA<br>GGGAGAATGGCGAGCCGAAACAGATTTCCGGCAAGCAGGAACTCTACGAAACTATCGTCGCT<br>CTTTACTGCAAGTAA |
| 5586MI208_003 | Prevotella | Amino Acid | 118 | MSTEYFPTIGKIPFEGPESKNPMAFHYYEPEKLVMGKKMKDWLRFAMAWWHTLGAASGDQFG<br>GQTRSYAWDKGDCPYSRARAKVDAGFEIMQKLGIEFFCFHDIDLVEDTDDIAEYEARMKDIT<br>DYLLEKMEATGIKNLWGTANVFGHKRYMNGAATNPDFAVVARAAVQIKNAIDATIKLGGENY<br>VFWGGREGYMSLLNTQMQREKEHLAKMLTAARDYARAKGFKGTFLIEPKPMEPTKHQYDQDT<br>ETVIGFLRSHGLDKDFKVNIEVNHATLAGHTFEHELATAVDNGMLGSIDANRGDAQNGWDTD<br>QFPIDNFELTLAMMQIIRNGGLAPGGSNFDAKLRRNSTDPEDIFIAHISAMDAMARALVNAA<br>AILGESPVPAMVKDRYASFDCGKGKDFEDGKLTLEDIVAYARENGEPKQISGKQELYETIVA<br>LYCK |
| 5586MI210_002 | Prevotella | DNA | 119 | ATGTCATATTTTCCTACTATCGGTAACATCCCCTTTGAGGGTGTAGAGAGCAAGAATCCCCT<br>TGCCTTCCATTATTATGACGCTTCCCGCGTAGTTATGGGCAAGCCCATGAAGGAGTGGCTCA<br>AGTTTGCCATGGCCTGGTGGCACACGCTGGGTCAGGCATCGGCCGACCCTTTCGGCGGACAA<br>ACCCGCAGCTATGCCTGGGACAAAGGCGAGTGCCCCTACTGCCGTGCCCGTGCCAAGGCCGA<br>CGCCGGCTTCGAGCTCATGCAGAAACTGGGCATCGAGTATTTCTGCTCCCACGACATTGACC<br>TCATCGAGGACTGCGACGACATTGCAGAGTACGAGGCCCGTCTGAAGGACATTACGGACTAC<br>CTCCTGGAGAAGATGAAGAAGACCGGTATCAAGAACCTGTGGGGTACGGCCAATGTGTTCGG<br>TAACAAGCGTTACATGAACGGTGCTGCTACCAACCCTCAGTTTGACGTTGTGGCCCGCGCTG<br>CCGTCCAGATCAAGAACGCCATTGACGCTACCATCAAGCTGGGCGGTTCCAACTATGTGTTC<br>TGGGGTGGCCGTGAGGGTTACTACACGCTTCTGAACACCCAGATGCAGCGTGAGAAGAATCA<br>CCTGGCTGCCATGCTCAAGGCTGCCCGCGACTATGCCCGCGCCAACGGTTTCAAGGGCACCT<br>TCCTCATTGAGCCCAAGCCCATGGAGCCCACCAAGCACCAGTACGACGTAGACACGGAGACC<br>GTGATTGGATTCCTCCGCGCAACGGTCTGGAGAAGGACTTCAAGGTGAACATTGAGGTGAA<br>CCACGCTACTCTTGCCGGTCACACCTTCGAGCACGAGCTCACCGTGGCCCGTGAGAACGGCT<br>TCCTGGGTTCCATTGACGCCAACCGCGGAGATGCCCAGAACGGCTGGGACACCGACCAGTTC<br>CCGGTAGATGCCTTTGACCTCACCCAGGCCATGATGCAGATTCTCCTCAACGGAGGCTCCGG<br>CAATGGCGGTACCAACTTTGACGCCAAGCTGCGCCGTTCCTCCACCGACCCCGAGGACATCT<br>TCATCGCGCACATCAGCGCCATGGATGCCATGGCTCACGCCCTGCTCAATGCAGCTGCCGTG<br>CTGGAGGAGAGCCCGCTTTGCAAGATGGTCAAGGAGCGTTACGCTTCCTTCGACAGCGGTCT<br>TGGCAAGCAGTTCGAGGAAGGAAAGGCTACGCTGGAAGATCTGTATGCCTATGCCGTCAAGA<br>ACGGTGAGCCCGTGGTGGCTTCCGGCAAGCAGGAACTGTACGAAACCTTCCTGAACCTCTAT<br>GCAAAATGGTAA |
| 5586MI210_002 | Prevotella | Amino Acid | 120 | MSYFPTIGNIPFEGVESKNPLAFHYYDASRVVMGKPMKEWLKFAMAWWHTLGQASADPFGGQ<br>TRSYAWDKGECPYCRARAKADAGFELMQKLGIEYFCSHDIDLIEDCDDIAEYEARLKDITDY<br>LLEKMKKTGIKNLWGTANVFGNKRYMNGAATNPQFDVVARAAVQIKNAIDATIKLGGSNYVF<br>WGGREGYYTLLNTQMQREKNHLAAMLKAARDYARANGFKGTFLIEPKPMEPTKHQYDVDTET<br>VIGFLRANGLEKDFKVNIEVNHATLAGHTFEHELTVARENGFLGSIDANRGDAQNGWDTDQF<br>PVDAFDLTQAMMQILLNGGSGNGGTNFDAKLRRSSTDPEDIFIAHISAMDAMAHALLNAAAV<br>LEESPLCKMVKERYASFDSGLGKQFEEGKATLEDLYAYAVKNGEPVVASGKQELYETFLNLY<br>AKW |
| 5586MI212_002 | Prevotella | DNA | 121 | ATGTCAACTGAGTATTTCCCTACAATCGGCAAGATTCCCTTCGAGGGACCCGAGAGCAAGAA<br>CCCCATGGCCTTCCACTACTATGAACCCGAAAGTTGGTGATGGGCAAGAAGATGAAGGACT<br>GGCTGCGTTTCGCAATGGCCTGGTGGCACACCCTTGGAGCCGCATCCGGCGACCAGTTCGGC<br>GGACAGACCCGCAGTTACGCCTGGGACAAGGGCGACTGCCCTTACAGCCGCGCGCCGCGCCAA<br>GGTCGACGCCGGCTTCGAGATCATGCAGAAGCTCGGCATAGAGTTCTTCTGCTTCCATGACA<br>TCGACCTGGTCGAGGATACCGACGACATCGCCGAGTATGAAGCCCGGATGAAAGACATCACG<br>GACTATCTGCTGGAAAAGATGGAGGTTACCGGCATCAAGAACCTCTGGGGCACGGCCAATGT<br>CTTCGGTCACAAGCGTTATATGAACGATGCAGCCACAAACCCCGATTTCGCAGTGGTCGCAA<br>GGGCGGCCGTGCAGATCAAGAACGCCATCGACGCCACCATCAAGCTGGGTGGTGAGAACTAT<br>GTGTTCTGGGGTGGACGCGAGGGTTATGAGCCTGCTCAACACCCAGATGCAGAGGGAGAA<br>GGAACACCTTGCCAAGATGCTCACCGCCGCACGTGACTATGCACGCGCCAAAGGTTTCAAGG<br>GCACGTTCCTCATCGAACCCGAGCCGATGGAACCCACCAAGCACCAGTATGACCAGGATACC<br>GAGACCGTTATCGGATTCCTCCGCAGCCACGGCCTGGACAAGGACTTCAAGGTCAACATCGA<br>GGTGAACCACGCCACCCTGGCGGGCCATACCTTCGAGCACGAACTGGCCACCGCCGTCGACA<br>ACGGCATGCTCGGCAGCATCGACGCCAACCGCGGAGACGCCCAGAACGGCTGGGACACCGAC<br>CAGTTCCCGATCGACAACTTCGAGCTCACGCTTGCCATGATGCAGATAATCCGCAACGGCGG<br>CCTGGCACCGGGCGGTTCGAACTTCGACGCAAAGCTGCGCCGCAATTCCACCGATCCCGAGG<br>ACATCATCATCGCCCACATCAGCGCGATGGACGCCATGGCCCGCGCCCTCGTCAACGCCGCC<br>GCCATCCTCGGCGAGTCGCCCGTTCCGGCTATGGTCAAGGACCGCTATGCTTCGTTCGACTG<br>CGGCAAGGGCAAGGACTTCGAAGACGGCAAACTGACTCTCGAAGACATCGTCGCCTACGCCA<br>GGGAGAATGGCGAGCCGAAACAGATTTCCGGCAAGCAGGAACTCTACGAAACTATCGTCGCT<br>CTTTACTGCAAGTAA |
| 5586MI212_002 | Prevotella | Amino Acid | 122 | MSTEYFPTIGKIPFEGPESKNPMAFHYYEPEKLVMGKKMKDWLRFAMAWWHTLGAASGDQFG<br>GQTRSYAWDKGDCPYSRARAKVDAGFEIMQKLGIEFFCFHDIDLVEDTDDIAEYEARMKDIT<br>DYLLEKMEVTGIKNLWGTANVFGHKRYMNDAATNPDFAVVARAAVQIKNAIDATIKLGGENY |

TABLE 2-continued

| Clone No. | Class of organism | Type of Sequence | SEQ ID NO: | Sequence |
|---|---|---|---|---|
| | | | | VFWGGREGYMSLLNTQMQREKEHLAKMLTAARDYARAKGFKGTFLIEPEPMEPTKHQYDQDT<br>ETVIGFLRSHGLDKDFKVNIEVNHATLAGHTFEHELATAVDNGMLGSIDANRGDAQNGWDTD<br>QFPIDNFELTLAMMQIIRNGGLAPGGSNFDAKLRRNSTDPEDIIIAHISAMDAMARALVNAA<br>AILGESPVPAMVKDRYASFDCGKGKDFEDGKLTLEDIVAYARENGEPKQISGKQELYETIVA<br>LYCK |
| 5586MI213_003 | Prevotella | DNA | 123 | ATGACCAACGAGTATTTTCCCGGAATCGGTGTGATTCCGTTTGAAGGACAGGAAAGCAAGAA<br>TCCCCTGGCTTTTCCATTATTATGACGCCAACCGCGTAGTGATGGGCAAACCCATGAAGGAAT<br>GGTTCAAATTTGCCATGGCCTGGTGGCATACGCTGGGGCAGGCATCGGCCGATCCCTTCGGC<br>GGACAGACCCGCTCCTACGCATGGGACAAGGGCGAGTGCCCCTTACTGCCGTGCCCGCCAGAA<br>GGCCGACGCCGGCTTTGAACTGATGCAGAAGCTGGGAATCGGCTATTTCTGCTTCCACGATG<br>TGGATATCATCGAGGACTGCGAGGACATTGCCGAGTATGAGGCCCGTATGAAGGACATCACG<br>GACTATCTGCTGGTGAAGATGAAGGAAACGGGCATCAAGAATCTGTGGGGCACGGCCAACGT<br>CTTCGGCCACAAGCGCTATATGAACGGCGCCGCCACCAACCCGCAATTCGACGTGGTAGCCC<br>GCGCTGCCGTCCAGATCAAGAACGCCCTGGACGCCACCATCAAGCTGGGCGGCAGCAATTAT<br>GTGTTCTGGGGCGGCCGGGAAGGCTACTACACCCTTTTGAACACGCAGATGCAGCGGGAGAA<br>GGACCACCTGGCCCAGATGCTCAAGGCCGCCCGCGACTATGCCCGCGGCAAGGGATTCAAGG<br>GCACGTTCCTCATTGAGCCCAAGCCCATGGAGCCCACCAAGCACCAGTACGACGTAGATACG<br>GAGACCGTGATTGGTTTCCTGCGCGCCAACGGGCTGGACAAGGACTTCAAGGTGAATATCGA<br>AGTGAACCACGCCACCCTGGCCGGCCATACCTTCGAGCACGAGCTCACCGTGGCCCGCGAAA<br>ACGGCTTCCTGGGCAGCATCGACGCCAACCGCGGAGACGCCCAGAACGGCTGGGATACAGAC<br>CAGTTCCCCGTGGACGCCTTTGACCTCACCCAGGCCATGATGCAGGTCCTGCTCAACGGCGG<br>ATTCGGCAACGGCGGCACCAACTTCGACGCCAAACTGCGCCGTTCCTCCACGGATCCCGAGG<br>ACATCTTCATCGCCCACATCAGCGCCATGGACGCCATGGCCCACGCCCTCCTGAACGCCGCC<br>GCCATCCTGGAAGAGAGCCCCATGCCGGGCATGGTGAAGGAGCGCTACGCTTCCTTCGACAA<br>TGGCCTTGGCAAGAAGTTCGAGGAAGGAAAGGCCACGCTGGAAGAGCTGTACGACTATGCCA<br>AGAAGAACGGCGAGCCTGTGGCCGCTTCCGGAAAGCAGGAACTGTACGAAACGCTGCTGAAC<br>CTGTACGCCAAGTAA |
| 5586MI213_003 | Prevotella | Amino Acid | 124 | MTNEYFPGIGVIPFEGQESKNPLAFHYYDANRVVMGKPMKEWFKFAMAWWHTLGQASADPFG<br>GQTRSYAWDKGECPYCRARQKADAGFELMQKLGIGYFCFHDVDIIEDCEDIAEYEARMKDIT<br>DYLLVKMKETGIKNLWGTANVFGHKRYMNGAATNPQEDVVARAAVQIKNALDATIKLGGSNY<br>VFWGGREGYYTLLNTQMQREKDHLAQMLKAARDYARGKGFKGTFLIEPKPMEPTKHQYDVDT<br>ETVIGELRANGLDKDEKVNIEVNHATLAGHTFEHELTVARENGFLGSIDANRGDAQNGWDTD<br>QFPVDAFDLTQAMMQVLLNGGFGNGGTNFDAKLRRSSTDPEDIFIAHISAMDAMAHALLNAA<br>AILEESPMPGMVKERYASFDNGLGKKFEEGKATLEELYDYAKKNGEPVAASGKQELYETLLN<br>LYAK |
| 5586MI215_003 | Prevotella | DNA | 125 | ATGGCAAAAGAGTATTTCCCGCAGATCGGAAAGATCGGCTTTGAGGGTCTTGAGAGCAAGAA<br>CCCGATGGCATTCCATTATTATGACGCCGAGCGTGTCGTGCTCGGAAAGAAGATGAAGGACT<br>GGCTGAAGTTCGCGATGGCCTGGTGGCATACGCTCGGACAGGCTTCCGGCGACCCATTCGGC<br>GGCCAGACTCGCAGCTATGAGTGGGACAAGGGCGAGTGCCCCTACTGCCGTGCCCGCGCCAA<br>GGCCGACGCCGGCTTCGAGCTCATGCAGAAGCTCGGCATCGAGTACTTCTGCTTCCACGACA<br>TCGACCTCATCGAGGACTGCGACGACATCGACGAGTACGAGGCCCGGATGAAGGACATCACC<br>GACTACCTGCTGGAGAAGATGAAGGAGACCGGAATCAAGAATCTCTGGGGAACGGCCAACGT<br>CTTCGGTCACAAGCGCTACATGAACGGCGCCGCTACCAATCCGCAGTTTGAAATCGTCGCCC<br>GCGCTGCCGTCCAGATCAAGAACGCGCTCGACGCCACCATCAAGCTCGGCGGCTCCAACTAC<br>GTCTTCTGGGGCGGCCGCGAGGGCTATTACACGCTGCTGAATACCCAGATGCAGCGCGAGAA<br>GGACCATCTCGCCAGGCTCCTTACCGCCGCCCGCGACTATGCGCGCGCCAAGGGGTTCAAGG<br>GGACCTTCCCCATCGAGCCGAAGCCGATGGAGCCGACCAAGCACCAGTATGACGTCGACACG<br>GAGACCGTCATCGGTTTCCTCCGCCAGAATGGCCTCGACAAGGACTTCAAGGTCAATATCGA<br>GGTGAACCACGCCACCCTCGCCGGCCATACCTTCGAGCACGAGCTGACCGCGCCCGGGAGA<br>ACGGCTTCCTCGGCAGCATCGACGCCAACCGCGGCGACGCCCAGAACGGCTGGGACACCGAC<br>CAGTTCCCCGTGGACGCCTTCGATCTCACGCGGGCCATGATGCAGATCCTGCTCAATGGCGG<br>TTTCGGCAACGGCGGCACCAACTTCGACGCCAAGCTGCGCCGCAGCTCCACCGATCCCGAGG<br>ACATCTTCATCGCCCACATCAGCGCGATGGACGCCATGGCCCACGCCCTGCTGAATGCGGCC<br>GCCATCCTCGAGGAAAGCCCGCTGCCGGCCCTGGTCAAGCAGCGCTATGCGTCCTTCGACAG<br>CGGGTCTCGGCAAGCAGTTCGAGGAGGGTAAGGCCACGCTCGAGGACCTGTACGCATACGCGA<br>AGGAGCACGGCGAGCCCGTCGCGGCCTCCGGCAAGCAGGAGCTCTGCGAGACCTATCTCAAC<br>CTCTACGCGAAATAA |
| 5586MI215_003 | Prevotella | Amino Acid | 126 | MAKEYFPQIGKIGFEGLESKNPMAFHYYDAERVVLGKKMKDWLKFAMANWHTLGQASGDPFG<br>GQTRSYENDKGECPYCRARAKADAGFELMQKLGIEYFCFHDIDLIEDCDDIDEYEARMKDIT<br>DYLLEKMKETGIKNLWGTANVFGHKRYMNGAATNPQFEIVARAAVQIKNALDATIKLGGSNY<br>VFWGGREGYYTLLNTQMQREKDHLARLLTAARDYARAKGFKGTFPIEPKPMEPTKHQYDVDT<br>ETVIGFLRQNGLDKDEKVNIEVNHATLAGHTFEHELTAARENGFLGSIDANRGDAQNGWDTD<br>QFPVDAFDLTRAMMQILLNGGFGNGGTNFDAKLRRSSTDPEDIFIAHISAMDAMAHALLNAA<br>AILEESPLPALVKQRYASFDSGLGKQFEEGKATLEDLYAYAKEHGEPVAASGKQELCETYLN<br>LYAK |
| 5607MI1_003 | Prevotella | DNA | 127 | ATGAGTAAAGAGTATTTTCCTGGGATTGGCAAAATCCCGTATGAGGGAGCCGAGAGCAAGAA<br>TGTGATGGCATTCCACTATTATGATCCGAACGCGTGGTCATGGGCAAGAAAATGAAAGACT<br>GGTTCAAGTTCGCTATTGCCTGGTGGCATACCCTGGGGCAGGCCAGTGCTGACCAGTTTGGC<br>GGACAGACCCGTTTCTATGAATGGGACAAAGCCGAGGACCCCTTGCAGCGTGCCAAGGACAA<br>GATGGATGCCGGTTTTGAAATCATGCAGAAGCTGGGCATCGAGTATTTCTGTTTCCATGATG<br>TGGACCCTCATCGAGGAGGCCGATACCATCGAGGAATATGAAGCCCGCATGCAGGCGATTACC |

TABLE 2-continued

| Clone No. | Class of organism | Type of Sequence | SEQ ID NO: | Sequence |
|---|---|---|---|---|
| | | | | GACTACGCGCTGGAGAAGATGAAGGCAACGGGTATCAAGTTGCTGTGGGGCACTGCCAACGT<br>GTTCGGCCACAAGCGTTACATGAACGGCGCCGCCACCAATCCCGACTTCAATGTCGTGGCAC<br>GTGCAGCCGTGCAGATCAAGAACGCCCTCGATGCTACCATCAAGTTGGGCGGAACGAGCTAC<br>GTCTTCTGGGGCGGTCGTGAAGGCTATCAGAGCCTGCTCAACACCCAGATGCAGCGTGGAGAA<br>GAACCACCTGGCCAAGATGCTCACGGCAGCCCGTGACTATGCCCGTGCTAAGGGCTTCAAGG<br>GCACCTTCCTGATTGAGCCCAAGCCGATGGAACCCACCAAGCACCAGTATGACCAGGACACC<br>GAGACCGTTATCGGCTTCTTGCGTGCCAATGGCTTGACAAGGACTTTAAGGTCAACATTGA<br>GGTCAACCATGCCACGCTGGCTGGCCACACCTTTGCACATGAGTTGGCAGTGGCTGTGGATA<br>ACGGTATGCTGGGCAGCATCGATGCTAACCGTGGTGACCACCAGAACGGCTGGGATACAGAC<br>CAGTTCCCCATCAACAGTTATGAACTCACCAATGCTATGCTGCAGATCATGCACGGCGGCGG<br>TTTCAAGGACGGCGGTACCAACTTTGACGCCAAGCTGCGCCGCAACAGTACCGACCCCGAGG<br>ACATCTTTACCGCTCACATCAGTGGTATGGACGCTCTGGCCCGTGCCCTGTTGAGTGCTGCC<br>GATATCCTTGAGAAGAGCGAGTTGCCTGAAATGCTCAAGGAACGCTATGCCAGCTTTGACGC<br>GGGTGAAGGCAAGCGCTTTGAGGATGGCCAGATGACTCTTGAGGAACTGGTTGCCTATGCCA<br>AGTCCCATGGCGAGCCTGCTACCATCAGTGGCAAGCAGGAAAAATATGAAGCCATCGTGGCT<br>TTGCACGTCAAGTAA |
| 5607MI1_003 | Prevotella | Amino Acid | 128 | MSKEYFPGIGKIPYEGAESKNVMAFHYYDPERVVMGKKMKDWFKFAIAWWHTLGQASADQFG<br>GQTREYEWDKAEDPLQRAKDKMDAGFEIMQKLGIEYFCFHDVDLIEEADTIEEYEARMQAIT<br>DYALEKMKATGIKLLWGTANVFGHKRYMNGAATNPDFNVVARAAVQIKNALDATIKLGGTSY<br>VFWGGREGYQSLLNTQMREKNHLAKMLTAARDYARAKGFKGTFLIEPKPMEPTKHQYDQDT<br>ETVIGFLRANGLDKDEKVNIEVNHATLAGHTFAHELAVAVDNGMLGSIDANRGDHQNGWDTD<br>QFPINSYELTNAMLQIMHGGGFKDGGTNFDAKLRRNSTDPEDIFTAHISGMDALARALLSAA<br>DILEKSELPEMLKERYASFDAGEGKRFEDGQMTLEELVAYAKSHGEPATISGKQEKYEAIVA<br>LHVK |
| 5607MI2_003 | Prevotella | DNA | 129 | ATGAGTAAAGAGTATTATCCTGAGATTGGCAAAATCCCGTTTGAGGGTCCCGAGAGCAAGAA<br>TGTGATGGCGTTCCATTACTATGAACCCGAACGCGTCGTCATGGGTAAGAAGATGAAAGACT<br>GGCTCAAGTTTGCCATGTGCTGGTGGCACAGCCTGGGTCAGGCCAGTGCCGACCAGTTCGGC<br>GGACAGACACGTTTCTACGAGTGGGACAAGGCCGATACCCCCCTGCAGCGTGCCAAGGACAA<br>AATGGATGCCGGATTTGAAATCATGCAGAAGTTGGGCATCGAGTACTTCTGCTTCCACGATG<br>TGGACCTCATCGAGGAGGCCGATACCATCGAGGAATACGAGGCCCGCATGAAGGCCATTACC<br>GACTATGCGCTGGAGAAGATGCAGGCCACCGGCATCAAGTTGCTGTGGGGCACTGCCAATGT<br>GTTCGGCCACAAGCGCTACATGAACGGCGCCGCCACCAATCCCGATTTCAATGTCGTGGCAC<br>GTGCCGCCGTCCAAATCAAGAATGCCATCGATGCCACCATCAAGCTGGGCGGCACGAGTTAC<br>GTCTTCTGGGGTGGTCGTGAGGGCTATCAGAGTCTGCTCAACACGCAGATGCAGCGCGAGAA<br>GGACCATCTGGCCCGCATGCTGGCGGCAGCCCGCGACTATGGCCGTGCCCATGGCTTCAAGG<br>GCACTTTCCTGATCGAGCCCAAACCCATGGAGCCCACCAAGCACCAGTATGATGTGGACACC<br>GAGACCGTGCTCGGCTTCCTGCGTGCCCACGGCTGGACAAGGACTTCAAGGTTAACATCGA<br>GGTCAATCATGCTACGCTGGCGGGACACACTTTCAGCCACGAACTGGCTGTGGCCGTGGACA<br>ACGGTATGCTGGGCAGCATCGACGCCAACCGCGGCGATTATCAGAATGGCTGGGACACCGAC<br>CAGTTCCCCATCGACAGCTTCGAGCTCACCCAGGCCATGCTGCAGATCATGCGCGGCGGCGG<br>CTTCAAGGACGGAGGTACCAACTTCGATGCCAAGCTGCGTCGCAACAGTACCGACCCTGAGG<br>ACATCTTCATCGCCCACATCAGCGGTATGGATGCCATGGCACGCGGCCTGTTGAGCGCTGCC<br>GCTATCCTCGAGGATGGCGAGTTGCCCGCGATGCTCAAGGCACGTTATGCCAGCTTTGACCA<br>GGGCGAGGGTAAGCGCTTTGAGGACGGCGAGATGACGCTCGAGCAGCTGGTGGATTATGCAA<br>AGGATTATGCCAAATCGCACGGCGAGCCTGATGTCATCAGCGGCAAGCAGGAGAAGTTTGAA<br>ACCATCGTGGCCCTTTACGCCAAGTAA |
| 5607MI2_003 | Prevotella | Amino Acid | 130 | MSKEYYPEIGKIPFEGPESKNVMAFHYYEPERVVMGKKMKDWLKFAMCWWHSLGQASADQFG<br>GQTRFYEWDKADTPLQRAKDKMDAGFEIMQKLGIEYFCFHDVDLIEEADTIEEYEARMKAIT<br>DYALEKMQATGIKLLWGTANVFGHKRYMNGAATNPDFNVVARAAVQIKNAIDATIKLGGTSY<br>VFWGGREGYQSLLNTQMREKDHLARMLAAARDYGRAHGFKGTFLIEPKPMEPTKHQYDVDT<br>ETVLGFLRAHGLDKDFKVNIEVNHATLAGHTFSHELAVAVDNGMLGSIDANRGDYQNGWDTD<br>QFPIDSFELTQAMLQIMRGGGFKDGGTNFDAKLRRNSTDPEDIFAHISGMDAMARGLLSAA<br>AILEDGELPAMLKARYASFDQGEGKRFEDGEMTLEQLVDYAKDYAKSHGEPDVISGKQEKFE<br>TIVALYAK |
| 5607MI3_003 | Prevotella | DNA | 131 | ATGACCAACGAGTATTTTCCCGGAATCGGTGTGATTCCGTTTGAAGGACAGGAAAGCAAGAA<br>TCCCCTGGCTTTCCATTATTATGACGCCAACCGCGTAGTGATGGGCAAACCCATGAAGGAAT<br>GGTTCAAATTTGCCATGGCCTGGTGGCATACGCTGGGCAGGCATCGGCCGATCCCTTCGGC<br>GGACAGACCCGCTCCTACGCATGGGACAAGGGCGAGTGCCCTTACTGCCGTGCCCGCCAGAA<br>GGCCGACGCCGGCTTTGAACTGATGCAGAAGCTGGGAATCGGCTATTTCTGCTTCCACGATG<br>TGGATATCATCGAGGACTGCGAGGACATTGCCGAGTATGAGGCCCGTATGAAGGACATCACG<br>GACTATCTGCTGGTGAAGATGAAGGAAACGGGCATCAAGAATCTGTGGGGCACGGCCAACGT<br>CTTCGGCCACAAGCGCTATATGAACGGCGCCGCCACCAACCCGCAATTCGACGTGGTAGCCC<br>GCGCTGCCGTCCAGATCAAGAACGCCCTGGACGCCACCATCAAGCTGGGCGGCAGCAATTAT<br>GTGTTCTGGGGCGGCCGGGAAGGCTACTACACCCTTTTGAACACGCAGATGCAGCGGGAGAA<br>GGACCACCTGGCCCAGATGCTCAAGGCGGCCCGCGACTATGCCCGCGGCAAGGGATTCAAGG<br>GCACGTTCCTCATTGAGCCCAAGCCCATGGAGCCCACCAAGCACCAGTACGACGTAGATACG<br>GAGACCGTGATTGGTTCCTGCGCGCCAACGGGCCGGACAAGGACTTCAAGGTGAATATCGA<br>AGTGAACCACGCCACCCTGGCCGGCCATACCTTCGAGCACGAGCTCACCGTGGCCCGCGAAA<br>ACGGCTTCCTGGGCAGCATCGACGCCAACCGCGGAGACGCCCAGAACGGCTGGGATACAGAC<br>CAGTTCCCCGTGGACGCCTTTGACCTCACCCAGGCCATGATGCAGGTCCTGCTCAACGGCGG<br>ATTCGGCAACGGCGGCACCAACTTCGACGCCAAACTGCGCCGTTCCTCCACGGATCCCGAGG<br>ACATCTTCATCGCCCACATCAGCGCCATGGACGCCATGGCCCACGCCCTCCTGAACGCCGCC |

TABLE 2-continued

| Clone No. | Class of organism | Type of Sequence | SEQ ID NO: | Sequence |
|---|---|---|---|---|
| | | | | GCCATCCTGGAAGAGAGCCCCATGCCGGGCATGGTGAAGGAGCGCTACGCTTCCTTCGACAA<br>TGGCCTTGGCAAGAAGTTCGAGGAAGGAAAGGCCACGCTGGAAGAGCTGTACGACTATGCCA<br>AGAAGAACGGCGAGCCTGTGGCCGCTTCCGGAAAGCAGGAACTGTACGAAACGCTGCTGAAC<br>CTGTACGCCAAGTAA |
| 5607MI3_003 | *Prevotella* | Amino Acid | 132 | MTNEYFPGIGVIPFEGQESKNPLAFHYYDANRVVMGKPMKEWFKFAMAWWHTLGQASADPFG<br>GQTRSYAWDKGECPYCRARQKADAGFELMQKLGIGYFCFHDVDIIEDCEDIAEYEARMKDIT<br>DYLLVKMKETGIKNLWGTANVEGHKRYMNGAATNPQEDVVARAAVQIKNALDATIKLGGSNY<br>VFWGGREGYYTLLNTQMQREKDHLAQMLKAARDYARGKGFKGTFLIEPKPMEPTKHQYDVDT<br>ETVIGFLRANGPDKDFKVNIEVNHATLAGHTFEHELTVARENGFLGSIDANRGDAQNGWDTD<br>QFPVDAFDLTQAMMQVLLNGGFGNGGTNFDAKLRRSSTDPEDIFIAHISAMDAMAHALLNAA<br>AILEESPMPGMVKERYASFDNGLGKKFEEGKATLEELYDYAKKNGEPVAASGKQELYETLLN<br>LYAK |
| 5607MI4_005 | *Prevotella* | DNA | 133 | ATGACTAAAGAGTATTTCCCTTCCGTCGGCAAGATTGCCTTTGAAGGACCCGAAAGCAAGAA<br>CCCTATGGCCTTCCATTATTATGACGCCAATCGCGTGGTAATGGGAAAGCCGATGAAGAAT<br>GGCTTAAATTTGCCATGGCCTGGTGGCACACCCTGGGCCAGGCCTCTGCAGACCCCTTCGGC<br>GGTCAGACCCGCTCCTACGAGTGGGACAAGGGCGAGTGCCCCTACTGCCGCGCCAAGGCCAA<br>GGCCGATGCCGGCTTTGAACTGATGCAGAAACTGGGCATCGAGTATTTCTGCTTCCACGATA<br>TAGACCTGGTGGAAGACTGCGATGATATCGCCGAATACGAGGCCCGCATGAAGGACATCACG<br>GACTATCTCCTGGAAGAGATGAAGGAAACCGGCATCAAGAACCTCTGGGGAACCGCCAACGT<br>GTTCGGCCACAAGCGCTATATGAACGGCGCCGCCACCAACCCTCAGTTCGACATCGTGGCCC<br>GTGCCGCTGTCCAGATCAAGAACGCCCTGGATGCCACCATCAAGCTGGGCGGCTCCAACTAT<br>GTGTTCTGGGGCGGCCGTGAGGGCTACTATACCCTCCTGAACACCCAGATGCAGAGAGAGAA<br>GGACCACCTGGCCAAGATGCTCACCGCCCGCCGCGACTATGCCCGTGCCAAGGGCTTCAAGG<br>GCACCTTCCTCATCGAACCCAAGCCGATGGAGCCCACCAAGCACCAGTACGACGTAGATACG<br>GAGACCGTGATCGGCTTCCTCCGCGCCAACGGCCTGGACAAGGACTTCAAGGTGAATATTGA<br>GGTGAACCACGCCACCCTGGCCGGCCACACCTTCGAGCACGAGCTCACCGTGGCCCGCGAGA<br>ACGGCTTCCTGGGCAGCATCGACGCCAACCGCGGAGACGCCCAGAACGGCTGGGATACGGAC<br>CAGTTCCCGGTGGATGCCTTCGACCTCACCCAGGCTATGATGCAGATCCTTCTGAACGGAGG<br>CTTCGGCAACGGCGGTACCAACTTCGACGCCAAACTGCGCCGCTCCTCCACGGACCCCGAGG<br>ACATCTTCATCGCCCACATCAGCGCTATGGATGCCATGGCCCACGCCCTGCTGAATGCAGCC<br>GCCATCCTGGAGGAAAGCCCGCTTCCGAAGATGCTGAAAGAGCGTTATGCCAGCTTTGACGG<br>CGGTCTGGGCAAGAAGTTCGAAGAAGGCAAGGCCTCTCTGGAAGAACTCTACGAGTATGCCA<br>AGAGCAACGGAGAGCCCGTGGCCGCTTCCGGCAAGCAGGAGCTCTGCGAAACGTACCTGAAC<br>CTCTACGCTAAGTAA |
| 5607MI4_005 | *Prevotella* | Amino Acid | 134 | MTKEYFPSVGKIAFEGPESKNPMAFHYYDANRVVMGKPMKEWLKFAMAWWHTLGQASADPFG<br>GQTRSYEWDKGECPYCRAKAKADAGFELMQKLGIEYFCFHDIDLVEDCDDIAEYEARMKDIT<br>DYLLEKMKETGIKNLWGTANVFGHKRYMNGAATNPQFDIVARAAVQIKNALDATIKLGGSNY<br>VFWGGREGYYTLLNTQMQREKDHLAKMLTAARDYARAKGFKGTFLIEPKPMEPTKHQYDVDT<br>ETVIGFLRANGLDKDFKVNIEVNHATLAGHTFEHELTVARENGFLGSIDANRGDAQNGWDTD<br>QFPVDAFDLTQAMMQILLNGGFGNGGTNFDAKLRRSSTDPEDIFIAHISAMDAMAHALLNAA<br>AILEESPLPKMLKERYASFDGGLGKKFEEGKASLEELYEYAKSNGEPVAASGKQELCETYLN<br>LYAK |
| 5607MI5_002 | *Prevotella* | DNA | 135 | ATGGCTAAAGAATACTTCCCCTCCATCGGCAAAATCCCTTTTGAAGGAGCCGACAGCAAAA<br>TCCCCTCGCTTTCCATTATTATGACGCCGGACGCGTGGTTATGGGCAAGCCCATGAAGGAAT<br>GGCTTAAATTCGCCATGGCCTGGTGGCACACGCTGGGCCAGGCCTCCGGAGACCCCTTCGGC<br>GGCCAGACCCGCAGCTACGAGTGGGACAAGGGCGAATGCCCCTACTGCCGCGCCAAGGCCAA<br>GGCCGACGCCGGTTTTGAAATCATGCAAAAGCTGGGCATCGAATACTTCTGCTTCCACGATG<br>TGGACCTTATCGAGGATTGCGATGACATTGCCGAATACGAAGCCCGCATGAAGGACATCACG<br>GACTACCTGCTGGAAAAGATGAAGGAGACCGGCATCAAGAACCTCTGGGGCACCGCCAATGT<br>CTTCGGCCACAAGCGCTACATGAACGGCGCCGGCACCAATCCGCAGTTCGATGTGGTGGCCC<br>GTGCCGCCGTCCAGATCAAGAACGCCCTGGACGCCACCATCAAGCTGGGCGGCTCCAACTAT<br>GTGTTCTGGGGCGGCCGCGAAGGCTATTACACCCTCCTCAACACACAGATGCAGCGGGAAAA<br>AGACCACCTGGCCAAGTTGCTGACGGCCGCCCGCGACTATGCCCGCGCCAAGGGCTTCAAGG<br>GCACCTTCCTCATTGAGCCCAAACCCATGGAACCCACCAAGCACCAGTACGACGTGGATACG<br>GAGACGGTCATCGGCTTCCTCCGTGCCAACGGCCTGGACAAGGACTTCAAGGTGAACATCGA<br>GGTGAACCACGCCACCCTGGCCGGCCACACCTTCGAGCATGAGCTCACCGTGGCCCGCGAGA<br>ACGGTTTCCTGGGCTCCATCGATGCCAACCGCGGCGACGCCCAGAACGGCTGGGACACGGAC<br>CAGTTCCCTGTGGACCCGTACGATCTTACCCAGGCCATGATGCAGGTGCTGCTGAACGGCGG<br>CTTCGGCAACGGCGGCACCAACTTCGACGCCAAACTCCGCCGCTCCTCCACCGACCCCGAGG<br>ACATCTTCATCGCCCATATTTCCGCCATGGATGCCATGGCCCACGCCCTTGCTTAACGCAGCT<br>GCCGTGCTGGAAGAGAGCCCCCTGTGCCAGATGGTCAAGGAGCGTTATGCCAGCTTCGACGA<br>TGGCCTCGGCAAACAGTTCGAGGAAGGCAAGGCTACCCTGGAAGACCTGTACGAATACGCCA<br>AGGCCCAGGGTGAACCCGTTGTCGCCTCCGGCAAGCAGGAGCTTTACGAGACTCTCCTGAAC<br>CTGTATGCCGTCAAGTAA |
| 5607MI5_002 | *Prevotella* | Amino Acid | 136 | MAKEYFPSIGKIPFEGADSKNPLAFHYYDAGRVVMGKPMKEWLKFAMAWWHTLGQASGDPFG<br>GQTRSYEWDKGECPYCRAKAKADAGFEIMQKLGIEYFCFHDVDLIEDCDDIAEYEARMKDIT<br>DYLLEKMKETGIKNLWGTANVFGHKRYMNGAGTNPQFDVVARAAVQIKNALDATIKLGGSNY<br>VFWGGREGYYTLLNTQMQREKDHLAKLLTAARDYARAKGFKGTFLIEPKPMEPTKHQYDVDT<br>ETVIGFLRANGLDKDFKVNIEVNHATLAGHTFEHELTVARENGFLGSIDANRGDAQNGWDTD<br>QFPVDPYDLTQAMMQVLLNGGFGNGGTNFDAKLRRSSTDPEDIFIAHISAMDAMAHALLNAA |

TABLE 2-continued

| Clone No. | Class of organism | Type of Sequence | SEQ ID NO: | Sequence |
|---|---|---|---|---|
| | | | | AVLEESPLCQMVKERYASFDDGLGKQFEEGKATLEDLYEYAKAQGEPVVASGKQELYETLLN LYAVK |
| 5607MI6_002 | Prevotella | DNA | 137 | ATGACCAAAGAATATTTCCCTACCGTCGGGAAGATCCCCTTCGAGGGCCCCGAAAGCAAGAA CCCTATGGCCGTTCCATTACTATGACCCCAACCGTCTGGTGATGGGCAAGAAGATGAAAGACT GGCTGCGTTTCGCCATGGCCTGGTGGCACACCCTCGGCCAGGCGTCGGGCGACCAGTTCGGC GGCCAGACCCGCAGTTATGCGTGGGACGAGGGAGAATGCCCGTACGAGCGCGCCCGTGCCAA GGCTGACGCCGGCTTCGAGATCATGCAGAAACTCGGTATCGAGTTCTTCTGCTTCCACGACA TCGACCTGATCGAGGATACCGACGACATCGCCGAGTATGAGGCCCGCCTGAAAGACATCACG GACTATCTGCTCGAGAAGATGAAAGCCACTGGCATCAAAAATCTCTGGGGAACGGCCAACGT GTTCGGCCACAAGCGTTGCATGAACGGCGCCGCCACCAACCCGGACTTCGCCGTGCTGGCCC GCGCTGCCGTCCAGATCAAGAACGCCATCGACGCCACCATCAAGCTGGGCGGCGAGAACTAT GTGTTCTGGGGTGGCCGCGAAGGCTACACGAGCCTGCTCAACACCCAGATGCAGCGTGAGAA AGAGCACCTGGGCGCCTGCTGTCCCTGGCCCGCGACTATGGCCGCGCCCACGGCTTCAAGG GTACCTTCCTGATCGAGCCCAAGCCGATGGGACCGACGAAACACCAGTACGACCAGGATACG GAAACTGTCATCGGTTTCCTGCGCCGCCACGGTCTAGACAAGGACTTCAAGGTCAATATCGA GGTGAACCATGCCACGCTGGCGGGCCACACCTTCGAACACGAACTGGCCTGCGCCGTGGATC ACGGTATGCTGGGCAGCATCGACGCCAACCGCGGTGACGCACAGAACGGCTGGGATACCGAC CAGTTCCCGATCGACAACTTCGAGCTGACCCTTTCCATGCTCCAGATCATCCGCAACGGTGG CCTGGCACCCGGCGGCTCGAATTTCGATGCCAAGCTGCGCCGCAACTCCACCGATCCCGAAG ACATTTTCATCGCGCACATCAGCGCCGATGGACGCCATGGCCCGCGCATTGGTCAATGCGGC GCCATCCTGGAGGAGAGCGCTATTCCGAAGATGGTCAAGGAGCGTTACGCTTCGTTCGACAG CGGCAAAGGCAAGGAATACGAGGAAGGCAAGCTGACGCTCGAAGACATCGTGGCCTATGCCA AGGCGAACGGAGAACCGAAGCAGATTTCCGGCAAACAGGAACTCTACGAGACGCTTGTCGCA CTCTATAGCAAATAA |
| 5607MI6_002 | Prevotella | Amino Acid | 138 | MTKEYFPTVGKIPFEGPESKNPMAFHYYDPNRLVMGKKMKDWLRFAMAWWHTLGQASGDQFG GQTRSYAWDEGECPYERARAKADAGFEIMQKLGIEFFCFHDIDLIEDTDDIAEYEARLKDIT DYLLEKMKATGIKNLWGTANVFGHKRCMNGAATNPDFAVLARAAVQIKNAIDATIKLGGENY VFWGGREGYTSLLNTQMQREKEHLGRLLSLARDYGRAHGFKGTFLIEPKPMGPTKHQYDQDT ETVIGFLRRHGLDKDFKVNIEVNHATLAGHTFEHELACAVDHGMLGSIDANRGDAQNGWDTD QFPIDNFELTLSMLQIIRNGGLAPGGSNFDAKLRRNSTDPEDIFIAHISAMDAMARALVNAA AILEESAIPKMVKERYASFDSGKGKEYEEGKLTLEDIVAYAKANGEPKQISGKQELYETLVA LYSK |
| 5607MI7_002 | Prevotella | DNA | 139 | ATGACCAAAGGGTATTTCCCTACCATCGGCAGGATTCCCTTCGAGGGAACTGAAAGCAAGAA TCCCCTCGCATTCCATTACTATGAGCCCGACCGGTCGTACTGGGCAAGAAAATGAAAGACT GGCTGCGTTTCGCCGATGGCCTGGTGGCACACCCTGGGCCAGGCGTCCGGCGACCAGTTCGGC GGCCAGACCCGCAGCTATGCCTGGGACAAGGCCGAGTGCCCCTATGAGCGCGCCAAGGCCAA AGCCGACGCCGGCTTCGAGATCATGCAGAAACTCGGCATCGAGTTCTTCTGTTTCCACGACA TTGACCTCGTTGAGGATACCGACGACATCGCCGAGTATGAGGCCCGGATGAAGGACATTACC GACTATCTCCTGGTCAAGATGAAGGAGACCGGAATCAAGAACCTCTGGGGTACGGCCAATGT CTTCGGCCACAAGCGCTATATGAACGGCGCCGCCACCAATCCCGACTTCGACGTGGTGGCCC GCGCCGCCGTCCAGATCAAGAACGCCCTCGATGCCACCATCAAGCTGGGCGGTGAAAACTAT GTGTTCTGGGGCGGCCGCGAAGGCTATATGAGCCTGCTCAACACGCAGATGCAGCGTGAGAA GGAGCACCTGGGCCGGATGCTGGTCGCCGCCCGCGACTACGCCCGCGCCCACGGCTTCAAGG GTACCTTCCTCATCGAGCCCAAACCGATGGAACCGACCAAGCACCAGTACGACCAGGATACG GAAACCGTGATCGGCTTCCTTCGCCGCCACGGCCTGGACAAGGATTTCAAGGTGAACATCGA AGTGAACCACGCCACGCTGGCCGGCCACACCTTCGAGCACGAACTGGCCACCGCCGTCGACT GCCGGCTGCTGGGCAGCATCGACGCCAATCGCGGCGACGCTCAGAACGGCTGGGATACCGAC CAGTTCCCGATCGACAACTTCGAACTCACGCTGGCCATGCTGCAGATTATCCGCAACGGCGG TCTGGCACCCGGCGGCTCGAACTTCGACGCCAAACTGCGCCGTAACTCCACCGATCCCGGAAG ATATCTTCATCGCCCACATCAGTGCGATGGACGCGATGGCCCGTGCGCTGGTCAACGCCGCC GCAATCTGGGAAGAGTCTCCCATCCCGCAGATGAAGAAAGAACGCTACGCGTCGTTCGACAG CGGCAAGGGCAAGGAATTCGAAGAGGGCAAGCTCTGCCTCGAAGACCTCGTGGCCTATGCCA AGGCGAACGGAGAACCGAAACAGATCTCCGGCAGGCAGGAACTATATGAGACCATCGTCGCC CTTTATTGCAAATAG |
| 5607MI7_002 | Prevotella | Amino Acid | 140 | MTKGYFPTIGRIPFEGTESKNPLAFHYYEPDRLVLGKKMKDWLRFAMAWWHTLGQASGDQFG GQTRSYAWDKAECPYERAKAKADAGFEIMQKLGIEFFCFHDIDLVEDTDDIAEYEARMKDIT DYLLVKMKETGIKNLWGTANVFGHKRYMNGAATNPDFDVVARAAVQIKNALDATIKLGGENY VFWGGREGYMSLLNTQMQREKEHLGRMLVAARDYARAHGFKGTFLIEPKPMEPTKHQYDQDT ETVIGFLRRHGLDKDFKVNIEVNHATLAGHTFERELATAVDCGLLGSIDANRGDAQNGWDTD QFPIDNFELTLAMLQIIRNGGLAPGGSNFDAKLRRNSTDPEDIFIAHISAMDAMARALVNAA AIWEESPIPQMKKERYASFDSGKGKEFEEGKLCLEDLVAYAKANGEPKQISGRQELYETIVA LYCK |
| 5608MI1_004 | Prevotella | DNA | 141 | ATGACCAACGAGTATTTCCCCGGAATCGGTGTGATTCCGTTTGAAGGACAGGAAAGCAAGAA TCCCATGGCTTTCCATTATTATGACGCCAACCGCGTAGTGATGGGCAAACCCATGAAGGAAT GGTTCAAATTTGCCATGGCCTGGTGGCATACGCTGGGGCAGGCATCGGCCGATCCCTTCGGC GGACAGACCCGCTCCTACGCATGGGACAAGGGCGAGTGCCCTTACTGCCGATGCCCGCCAGAA GGCCGACGCCGGCTTTGAACTGATGCAGAAGCTGGGTATCGGCTATTTCTGCTTCCACGATG TGGATATCATCGAGGACTGCGAAGACATTGCCGAGTATGAGGCCCGTATGAAGGACATCACG GACTATCTGCTGGTGAAGATGAAGGAAACGGGCATCAAGAACCTGTGGGGCACGGCCAACGT CTTCGGCCACAAGCGCTATATGAACGGCGCTGCCACCAACCCGCAGTTCGACTGGTGGCCC GCGCTGCCGTCCAGATCAAGAACGCCCTGGACGCCACCATCAAGCTGGGCGGCAGCAATTAC |

TABLE 2-continued

| Clone No. | Class of organism | Type of Sequence | SEQ ID NO: | Sequence |
|---|---|---|---|---|
| | | | | GTGTTCTGGGGCGGCCGCGAAGGCTATTATACCCTTTGGAACACGCAGATGCGGCGGGAGAA<br>GGACCACCTGGCCCAGATGCTCAAGGCAGCCCGTGACTATGCCCGCGGCAAGGGATTCAAGG<br>GCACGTTCCTCATTGAGCCCAAGCCCATGGAGCCCACCAAGCACCAGTACGACGTAGATACG<br>GAGACCGTGATTGGCTTCCTGCGCGCGAACGGACTGGACAAGGACTTCAAGGTGAATATCGA<br>AGTGAACCACGCCACCCTGGCCGGCCACACCTTCGAGCACGAACTCACCGTGGCCGCGAAA<br>ACGGCTTCCTGGGCAGCATCGACGCCAACCGCGGAGACGCCCAGAACGGTTGGGATACAGAC<br>CAGTTCCCCATAGATGCCTTTGACCTCACCCAGGCCATGATGCAGGTCCTGCTCAACGGCGG<br>ATTCGGCAACGGCGGCACCAACTTCGACGCCAAACTGCGCCGTTCCTCCACGGATCCCGAGG<br>ACATCTTCATCGCCCACATCGGCGCCATGGACGCCATGGCCCACGCCCTCCTGAACGCCGCC<br>GCCATCCTGGAAGAGAGCCCCATGCCGGGCATGGTGAAGGAGCGCTACGCTTCCTTCGACAA<br>TGGCCTTGGCAAGAAGTTCGAGGAAGGAAAGGCCACGCTGGAAGAGCTGTACGACTATGCCA<br>AGAAGAACGGCGAGCCTGTGGCCGCTTCCGGCAAGCAGGAACTGTACGAAACGCTGCTGAAC<br>CTGTACGCCAAGTAA |
| 5608MI1_004 | *Prevotella* | Amino Acid | 142 | <u>MTNEYFPGIGVIPFEGQESKNPMAFHYYDANRVVMGKPMKEWFKFAMAWWHTLGQASADPFG<br>GQTRSYAWDKGECPYCRARQKADAGFELMQKLGIGYFCFHDVDIIEDCEDIAEYEARMKDIT<br>DYLLVKMKETGIKNLWGTANVFGHKRYMNGAATNPQFDVVARAAVQIKNALDATIKLGGSNY<br>VFWGGREGYYTLWNTQMRREKDHLAQMLKAARDYARGKGFKGTFLIEPKPMEPTKHQYDVDT<br>ETVIGFLRANGLDKDFKVNIEVNHATLAGHTFEHELTVARENGFLGSIDANRGDAQNGWDTD<br>QFPIDAFDLTQAMMQVLLNGGFGNGGTNFDAKLRRSSTDPEDIFIAHIGAMDAMAHALLNAA<br>AILEESPMPGMVKERYASFDNGLGKKFEEGKATLEELYDYAKKNGEPVAASGKQELYETLLN<br>LYAK</u> |
| 5608MI2_002 | *Prevotella* | DNA | 143 | ATGAAAGAATACTTCCCTACCATCGGAAAAATCCCTTTCGAGGGCCCTCAGAGCAAGAATCC<br>GCTCGCATTCCATTACTATGACGCCAACCGCGTTGTCGCCGGCAAACCCATGAAGGACTGGC<br>TCAAGTTCGCCATGGCTTGGTGGCACACCCTGGGCGCAGCATCGGCAGACCCCTTCGGCGG<br>CAGACCCGCAGCTACGAGTGGGACAAAGCCGAGTGCCCTTACTGCCGTGCCCGTGAAAAGGC<br>CGACGCCGGCTTCGAGATCATGCAGAAACTTGGAATCGAGTACTTCTGCTTCCATGACATCG<br>ACCTTGTGGAAGACTGCGAGGACATTGCCGAGTACGAGGCCCGCATGAAGGACATCACGGAC<br>TACCTCCTGGAGAAGATGAAGGCCACCGGCATCAAGAACCTGTGGGGCACCGCCAACGTCTT<br>TGGCAACAAGCGCTACATGAACGGCGCAGCCACCAACCCTCAGTTCGACATCGTTGCCCGTG<br>CAGCTGTCCAGATCAAGAACGCCATCGACGCAACAATCAAGCTGGGCGGTACCGGTTACGTA<br>TTCTGGGGCGGCCGCGAGGGCTACTACACCCTCCTGAACACCCAGATGCAGCGCGAGAAGGA<br>CCACCTTGCCAAGATGCTCACCGCAGCCCGCGACTACGCCCGCGCCAAGGGATTCAAGGGCA<br>CATTCCTCATCGAGCCCAAGCCCATGGAGCCCACCAAGCACCAGTACGATGTTGACACGGAA<br>ACCGTCATCGGCTTCCTCCGCGCCAACGGCCTGGACAAGGACTTCAAGGTGAACATCGAGGT<br>GAACCACGCCACCCTGGCCGGCCACACCTTCGAGCACGAGCTCACCGTGGCCGTGGACAACG<br>GCTTCCTGGGCAGCATCGACGCAAACCGCGGCGACGCCCAGAACGGCTGGGACACTGACCAG<br>TTCCCTGTGGATCCTTACGACCTCACCCAGGCAATGATGCAGATTATCCGCAACGGCGGCTT<br>CAAGGACGGCGGCACCAACTTCGACGCCAAACTCCGCCGCAGCTCCACGGACCCCGAGGACA<br>TCTTCATCGCCCACATCAGCGCAATGGATGCAATGGCACACGCCCTCATCAACGCTGCTGCA<br>GTGCTTGAGGAAAGCCCTCTGTGCGAGATGGTTGCAAAGCGCTACGCCAGCTTTGACAGCGG<br>TCTTGGCAAGAAGTTCGAGGAAGGCAAAGCCACTCTCGAGGAGATCTACGAGTATGCCAAGA<br>AGGCCCCGGCACCCGTCGCCGCCTCCGGCAAGCAGGAGCTCTACGAGACACTGCTCAATCTG<br>TACGCTAAATAA |
| 5608MI2_002 | *Prevotella* | Amino Acid | 144 | <u>MKEYFPTIGKIPFEGPQSKNPLAFHYYDANRVVAGKPMKDWLKFAMAWWHTLGAASADPFGG<br>QTRSYEWDKAECPYCRAREKADAGFEIMQKLGIEYFCFHDIDLVEDCEDIAEYEARMKDITD<br>YLLEKMKATGIKNLWGTANVFGNKRYMNGAATNPQFDIVARAAVQIKNAIDATIKLGGTGYV<br>FWGGREGYYTLLNTQMREKDHLAKMLTAARDYARAKGFKGTFLIEPKPMEPTKHQYDVDTE<br>TVIGFLRANGLDKDFKVNIEVNHATLAGHTFEHELTVAVDNGFLGSIDANRGDAQNGWDTDQ<br>FPVDPYDLTQAMMQIIRNGGFKDGGTNFDAKLRRSSTDPEDIFIAHISAMDAMAHALINAAA<br>VLEESPLCEMVAKRYASFDSGLGKKFEEGKATLEEIYEYAKKAPAPVAASGKQELYETLLNL<br>YAK</u> |
| 5608MI3_004 | *Prevotella* | DNA | 145 | ATGACCAAAGAGTATTTCCCTACAATCGGAAAGATTCCCTTCGAAGGCCCGGAGAGCAAGAA<br>TCCGCTGGCATTCCATTACTATGAACCCGACAGAATCATCCTCGGCAGGAAGATGAAGGACT<br>GGCTGCGCTTCGCCGTGGCCTGGTGGCACACCCTCGGCCAGGCGTCCGGCGACCAGTTCGGA<br>GGCCAGACCCGCAACTATGCGTGGGACGAGCCCGAATGCCCGGTAGAGCGCGCGAAAGCCAA<br>GGCCGACGCCGGCTTCGAGCTGATGCAGAAGCTGGGCATCGAGTATTTCTGCTTCCACGACG<br>TAGACCTCATAGAGGAGGCCGCAACCATCGAAGAATATGAGGAGCGCATGGGCATCATAACC<br>GACTACCTGCTCGGGAAGATGAAGGAGACAGGTATCAAGAACCTCTGGGGCACCGCCAACGT<br>GTTCGGCCACAAGCGTTACATGAACGGAGCCGCCACCAACCCCGACTTCGACGTGGTGGCCC<br>GTGCGGCCGTGCAGATCAAGAACGCCATCGACGCCACCATCAAGCTGGGCGGCAGCGAGAAT<br>TACGTATTCTGGGGCGGACGCGAGGGCTATGCAAGCCTGCTCAACACTCAGATGCAGCGCGAGAA<br>AGACCACCTGGGACGCATGCTGGCTGCAGCCCGCGACTATGGCCGCGCCCACGGATTCAAGG<br>GCACTTTCCTCATCGAGCCCAAACCCATGGAGCCTACCAAGCACCAGTACGACCAGGATACC<br>GAGACCGTTATCGCCTTCCTGCGCAGGAACGGCCTCGACAAGGATTTCAAGGTAAACATCGA<br>GGTGAACCACGCCACCCTGGCGGGCCACACCTTCGAGCACGAACTGGCGGTGGCAGTGGACA<br>ACGGCCTGCTTGGCAGCATCGACGCCAACCGCGGCGACGCGCAGAACGGATGGGACACCGAC<br>CAGTTCCCCATCGACAACTTCGAGCTCACCCAGGCCATGCTGCAGATAATCCGCAACGGCGG<br>ACTGGGAACCGGCGGATCGAACTTCGACGCCAAGCTGCGCCGCAATTCCACCGACCCTGAGG<br>ATATCTTCATCGCCCACATCAGTGCGATGGACGCCATGGCACGCGCGCTGGCAAACGCCGCC<br>GCAATCATCGAAGAGAGCCCCATCCCCGCAATGCTGAAGGAGCGCTACGCATCGTTCGACAG<br>CGGCAAGGGCAAGGAGTTCGAGGACGGCAAACTGAGCCCTCGAAGAACTGGTAGCCTACGCCA |

TABLE 2-continued

| Clone No. | Class of organism | Type of Sequence | SEQ ID NO: | Sequence |
|---|---|---|---|---|
| | | | | AGGCGAACGGCGAGCCGAAGCAGATTTCCGGCAAGCAGGAACTCTACGAAACCATAGTGGCC<br>CTCTATTGCAAGTAA |
| 5608MI3_004 | Prevotella | Amino Acid | 146 | MTKEYFPTIGKIPFEGPESKNPLAFHYYEPDRIILGRKMKDWLRFAVAWWHTLGQASGDQFG<br>GQTRNYAWDEPECPVERAKAKADAGFELMQKLGIEYFCFHDVDLIEEAATIEEYEERMGIIT<br>DYLLGKMKETGIKNLWGTANVFGHKRYMNGAATNPDFDVVARAAVQIKNAIDATIKLGGENY<br>VFWGGREGYASLLNTQMQREKDHLGRMLAAARDYGRAHGFKGTFLIEPKPMEPTKHQYDQDT<br>ETVIAFLRRNGLDKDFKVNIEVNHATLAGHTFEHELAVAVDNGLLGSIDANRGDAQNGWDTD<br>QFPIDNFELTQAMLQIIRNGGLGTGGSNFDAKLRRNSTDPEDIFIAHISAMDAMARALANAA<br>AIIEESPIPAMLKERYASFDSGKGKEFEDGKLSLEELVAYAKANGEPKQISGKQELYETIVA<br>LYCK |
| 5609MI1_005 | Prevotella | DNA | 147 | ATGGCACAAGAATACTTCCCTACCATTGGGAAAATCCCCTTCGAGGGCACTGAGAGCAAGA<br>ATCCCCTTGCTTTCCATTACTATGAGCCGGAGCGCATTGTCTGCGGCAAACCCATGAAAGAAT<br>GGCTCAAGTTTGCCATGGCCTGGTGGCACACGCTGGGGCAGGCATCGGCCGATCCCTTCGGC<br>GGCCAAACCCGCAGCTATGCCTGGGATAAGGGCGAATGCCCCTACTGCCGTGCCCGCGCCAA<br>GGCGGACGCCGGCTTCGAGATTATGCAAAAGCTGGGCATCGAGTACTTCTGCTTCCACGATA<br>TCGACCTGGTAGAAGACTGTGACGATATTGCGGAATACGAAGCCCGCATGAAGGACATCACG<br>GACTACCTCCTGGAGAAGATGAAGGAAACCGGTATCAAGAACCTCTGGGGCACCGCCAATGT<br>GTTTGGTCACAAGCGCTACATGAACGGCGCCGCCACCAACCCGCAGTTTGACGTAGTGGCCC<br>GTGCCGCTGTTCAGATTAAGAACGCCATTGACGCCACCATCAAGTTGGGCGGTGCCAATTAC<br>GTGTTCTGGGGCGGCCGCGAGGGCTATTACAGCCTCCTGAACACCCAGATGCAGCGGGAGAA<br>GGACCACCTGGCCAAGCTGCTCACGGCAGCCCGCGACTATGCCCGCGCCAACGGCTTCAAGG<br>GAACCTTCCTGATTGAGCCCAAGCCCATGGAGCCCACCAAGCACCAGTACGACGTGGATACG<br>GAGACGGTCATTGGCTTCCTCCGCGCCAACGGCCTGGACAAGGACTTCAAGGTGAATATCGA<br>GGTGAACCACGCCACGTTGGCCGGCCACACCTTTGAGCACGAGCTCACCGTGGCCCGCGAGA<br>ACGGCTTCCTGGGCAGCATCGACGCCAACCGCGGCGATGCCCAGAACGGCTGGGATACGGAC<br>CAGTTCCCGGTAGACGCTTATGAGCTCACCCAGGCCATGATGCAGGTGCTCCTGAACGGAGG<br>CTTCGGCAACGGCGGCACCAACTTCGACGCCAAGCTGCGCCGCTCCTCCACGGACCCGGAGG<br>ACATCTTCATCGCCCATATCAGTGCGATGGATGCCATGGCCCACGCCCTGCTCAACGCCGCC<br>GCCGTGCTGGAGGAAAGCCCCCTGTGCCAGATGGTGAAGGAGCGCTACGCCAGCTTTGACAG<br>CGGTCCGGGCAAGCAGTTCGAGGAAGGAAAGGCCACCCTGGAGGACCTGTACAACTACGCCA<br>AGCCACCGGTGAACCCGTGGTTGCCTCCGGCAAGCAGGAACTTTACGAGACCCTCCTGAAC<br>CTCTATGCAAAGTAG |
| 5609MI1_005 | Prevotella | Amino Acid | 148 | MAQEYFPTIGKIPFEGTESKNPLAFHYYEPERIVCGKPMKEWLKFAMAWWHTLGQASADPFG<br>GQTRSYAWDKGECPYCRARAKADAGFEIMQKLGIEYFCFHDIDLVEDCDDIAEYEARMKDIT<br>DYLLEKMKETGIKNLWGTANVFGHKRYMNGAATNPQFDVVARAAVQIKNAIDATIKLGGANY<br>VFWGGREGYYSLLNTQMQREKDHLAKLLTAARDYARANGFKGTFLIEPKPMEPTKHQYDVDT<br>ETVIGFLRANGLDKDFKVNIEVNHATLAGHTFEHELTVARENGFLGSIDANRGDAQNGWDTD<br>QFPVDAYELTQAMMQVLLNGGFGNGGTNFDAKLRRSSTDPEDIFIAHISAMDAMAHALLNAA<br>AVLEESPLCQMVKERYASFDSGPGKQFEEGKATLEDLYNYAKATGEPVVASGKQELYETLLN<br>LYAK |
| 5610MI1_003 | Prevotella | DNA | 149 | ATGGCACAAGAATACTTCCCTACCATTGGGAAAATCCCCTTCGAGGGCACTGAGAGCAAGA<br>ATCCCCTTGCTTTCCATTACTATGAGCCGGAGCGCATTGTCTGCGGCAAACCCATGAAAGAAT<br>GGCTCAAGTTTGCCATGGCCTGGTGGCACACGCTGGGGCAGGCATCGGCCGATCCCTTCGGC<br>GGCCAAACCCGCAGCTATGCCTGGGATAAGGGCGAATGCCCCTACTGCCGTGCCCGTGCCAA<br>GGCGGACGCCGGTTTTGAGATTATGCAAAAGCTGGGCATCGAGTACTTCTGCTTCCACGATA<br>TCGACCTGGTAGAAGACTGTGACGATATTGCGGAATACGAAGCCCGCATGAAGGACATCACG<br>GACTACCTCCTGGAGAAGATGAAGGAAACCGGCATCAAGAACCTCTGGGGCACCGCCAATGT<br>GTTTGGTCACAAGCGCTACATGAACGGCGCCGGCACCAATCCGCAGTTTGACGTGGTGGCCC<br>GTGCTGCCGTGCAAATCAAGAACGCCATTGACGCCACCATCAAGTTGGGCGGTGCCAATTAC<br>GTGTTCTGGGGCGGCCGCGAGGGCTATTACAGCCTCCTGAACACCCAGATGCAGCGGGAGAA<br>GGACCACCTGGCCAAGCTGCTCACGGCAGCCCGCGACTATGCCCGCGCCAACGGCTTCAAGG<br>GAACCTTCCTGATTGAGCCCAAGCCCATGGAGCCCACCAAGCACCAGTACGACGTGGATACG<br>GAGACGGTCATTGGCTTCCTCCGCGCCAACGGCCTGGACAAGGACTTCAAGGTGAATATCGA<br>GGTGAACCACGCCACGCTGGCCGGCCACACCTTTGAGCACGAGCTCACCGTGGCCCGCGAGA<br>ACGGCTTCCTGGGCAGCATCGACGCCAACCGCGGCGATGCCCAGAACGGCTGGGATACGGAC<br>CAGTTCCCGGTAGACGCTTATGAGCTCACCCAGGCCATGATGCAGGTGCTCCTGAACGGAGG<br>CTTCGGCAACGGCGGCACCAACTTCGACGCCAAGCTGCGCCGCTCCTCCACGGACCTGGAGG<br>ACATCTTCATCGCCCATATCAGTGCGATGGATGCCATGGCCCACGCCCTGCTCAACGCCGCC<br>GCCGTGCTGGAGGAAAGCCCCCTGTGCCAGATGGTGAAGGAGCGCTACGCCAGCTTTGACAG<br>CGGTCCGGGCAAGCAGTTCGAGGAAGGAAAGGCCACCCTGGAGGACCTGTACAACTACGCCA<br>AGCCAACGGTGAACCCGTGGTTGCCTCCGGCAAGCAGGAACTTTACGAGACCCTCCTGAAC<br>CTCTATGCAAAGTAG |
| 5610MI1_003 | Prevotella | Amino Acid | 150 | MAQEYFPTIGKIPFEGTESKNPLAFHYYEPERIVCGKPMKEWLKFAMAWWHTLGQASADPFG<br>GQTRSYAWDKGECPYCRARAKADAGFEIMQKLGIEYFCFHDIDLVEDCDDIAEYEARMKDIT<br>DYLLEKMKETGIKNLWGTANVFGHKRYMNGAGTNPQFDVVARAAVQIKNAIDATIKLGGANY<br>VFWGGREGYYSLLNTQMQREKDHLAKLLTAARDYARANGFKGTFLIEPKPMEPTKHQYDVDT<br>ETVIGFLRANGLDKDFKVNIEVNHATLAGHTFEHELTVARENGFLGSIDANRGDAQNGWDTD<br>QFPVDAYELTQAMMQVLLNGGFGNGGTNFDAKLRRSSTDLEDIFIAHISAMDAMAHALLNAA<br>AVLEESPLCQMVKERYASFDSGPGKQFEEGKATLEDLYNYAKANGEPVVASGKQELYETLLN<br>LYAK |

TABLE 2-continued

| Clone No. | Class of organism | Type of Sequence | SEQ ID NO: | Sequence |
|---|---|---|---|---|
| 5610MI2_004 | Prevotella | DNA | 151 | ATGGCAAAAGAATATTTCCCTACCATCGGCAAGATTCCTTTTGAAGGAACCGACAGCAAGAG<br>TCCCCTCGCCTTCCATTACTATGACGCCCAGCGCGTTGTGATGGGCAAACCCATGAAGGAAT<br>GGCTCAAGTTCGCCATGGCCTGGTGGCACACCCTGGGCCAGGCATCGGCCGACCCCTTCGGC<br>GGTCAGACCCGCCACTATGCCTGGGATGAAGGCGAATGCCCCTACTGCCGCGCCAAAGCCAA<br>GGCCGACGCCGGCTTCGAGATCATGCAGAAACTGGGCATCGAGTACTTCTGCTTCCACGATG<br>TGGACCTGGTGGAAGACTGCGACGACATCGCCGAGTACGAAGCCCGCATGAAGGACATCACG<br>GACTACCTGCTGGAGAAGATGAAGGAAACCGGCATCAAGAACCTCTGGGGCACGGCCAATGT<br>GTTCGGCCACAAGCGTTACATGAACGGCGCCGGGACCAACCCGCAGTTTGACATTGTGGCCC<br>GCGCTGCCGTCCAGATCAAAAACGCCCTGGACGCCACCATCAAGCTGGGCGGTTCCAACTAC<br>GTGTTCTGGGGCAGCCGCGAAGGCTACTACACCCTCCTGAACACCCAGATGCAGCGGGAGAA<br>AGACCACCTGGCCAAGCTCCTGACCGCCGCCCGCGACTACGCCCGCGCCAAAGGCTTCAAGG<br>GAACCTTCCTCATCGAGCCCAAACCCATGGAGCCCACCAAGCACCAGTACGACGTGGACACC<br>GAGACCGTAATCGGCTTCCTGCGTGCCAACGGCCTGGACAAGGACTTCAAGGTGAACATCGA<br>GGTGAACCACGCCACCCTGGCTGGCCACACCTTCGAGCACGAACTCACCGTCGCCCGTGAAA<br>ACGGCTTCCTCGGATCGATCGACGCCAACCGCGGCGACGCCCAGAACGGCTGGGACACCGAC<br>CAGTTCCCCGTAGACGCCTATGACCTCACCCAGGCCATGATGCAGGTGCTGCTGAACGGCGG<br>TTTCGGCAATGGCGGTACCAACTTCGACGCCAAGCTCCGCCGCTCCTCCACGGATCCGGAAG<br>ACATCTTCATCGCCCACATCAGCGCCATGGACGCCATGGCCCACGCCCTGCTGAACGCCGCC<br>GCCGTGCTGGAAGAAAGCCCGCTTCCCGCCATGGCGAAGAGCGCTACGCCTCCTTTGACAG<br>CGGACTTGGCAAGAAGTTCGAAGAGGGAAAGGCCACCCTCGAAGAGCTGTACGACTATGCCA<br>AGGCTAACGACGCCCCTGTCGCCGCCTCCGGCAAGCAGGAACTTTACGAAACCTTCTTGAAC<br>CTCTATGCAAAATAG |
| 5610MI2_004 | Prevotella | Amino Acid | 152 | <u>MAKEYFPTIGKIPFEGTDSKSPLAFHYYDAQRVVMGKPMKEWLKFAMAWWHTLGQASADPFG</u><br><u>GQTRHYAWDEGECPYCRAKAKADAGFEIMQKLGIEYFCFHDVDLVEDCDDIAEYEARMKDIT</u><br><u>DYLLEKMKETGIKNLWGTANVFGHKRYMNGAGTNPQFDIVARAAVQIKNALDATIKLGGSNY</u><br><u>VFWGSREGYYTLLNTQMREKDHLAKLLTAARDYARAKGFKGTFLIEPKPMEPTKHQYDVDT</u><br><u>ETVIGFLRANGLDKDFKVNIEVNHATLAGHTFEHELTVARENGFLGSIDANRGDAQNGWDTD</u><br><u>QFPVDAYDLTQAMMQVLLNGGFGNGGTNFDAKLRRSSTDPEDIFIAHISAMDAMAHALLNAA</u><br><u>AVLEESPLPAMAKERYASFDSGLGKKFEEGKATLEELYDYAKANDAPVAASGKQELYETFLN</u><br><u>LYAK</u> |
| 5751MI1_003 | Prevotella | DNA | 153 | ATGGCAAAACAGTATTTTCCGCAAATCGGAAAGATTAAATTCGAAGGAACAGAGAGCAAGAA<br>TCCGCTTGCGTTCCATTATTATGACGCAAACAGGGTAGTCCTCGGAAAGGCAATGGAGGAGT<br>GGCTCAAGTTCGCAATGGCTTGGTGGCATACTCTCGGACAGGCTTCCGGAGACCAGTTCGGC<br>GGCCAGACCCGCAGCTACGAGTGGGATCTTGCAGCCACCCCCGAGCAGCGCGCAAAGGACAA<br>GCTCGACGCCGGCTTCGAAATAATGGAGAAACTTGGAATCAAGTATTTCTGTTTCCACGATG<br>TTGACCTTATCGAAGACAGCGACGATATTGCAGACATATGAGGCTCGTCTCAAGGACCTTACA<br>GACTACGCTGCAGAGCAGATGAAGCTCCACGACATCAAGCTCCTCTGGGGTACAGCGAATGT<br>ATTCGGCAACAAGCGCTACATGAACGGTGCGGCTACAAACCCTGATTTCGATGTAGTTGCCC<br>GCGCAGCCGTTCAGATTAAGAACGCTATCGACGCGACCATCAAGCTCGGTGGTACCAGCTAT<br>GTATTCTGGGGCGGTCGTGAGGGATATCAGAGCCTGCTCAACACTCAGATGCAGCGTGAGAA<br>GGACCACCTCGCAACCATGCTTACAATCGCTCGCGACTATGCTCGCAGCAAGGGCTTTACCG<br>GAACCTTCCTTATCGAGCCTAAGCCGATGGAGCCTACAAAACACCAGTACGACGTAGATACA<br>GAGACTGTTGTCGGCTTCCTCAAGGCACACGGCCTGGACAAGGACTTCAAGGTAAATATCGA<br>GGTTAACCACGCAACTCTCGCAGGCCACACCTTCGAGCACGAACTCACCGTTGCTGTGGATA<br>ACGGAATGCTCGGTTCTATCGACGCTAACCGCGGTGATGCACAGAACGGCTGGGATACAGAC<br>CAGTTCCCTGTAAGCGCTGAGGAGCTTACCCTCGCTATGATGCAGATTATCCGTAATGGTGG<br>CCTTGGCAACGGAGGATCCAACTTCGACGCAAAGCTTCGCCGCAACTCTACCGATCCTGAAG<br>ACATCTTCATCGCACACATCTGCGGTATGGATGCAATGGCACACGCTCTCCTCAATGCAGCT<br>GCAATTATCGAGGAGTCTCCTATCCCTACAATGGTTAAGGAGCGTTACGCTTCCTTCGACAG<br>CGGTATGGGTAAGGACTTCGAGGATGGAAAGCTTACCCTCGAGGATCTCTACAGCTACGGCG<br>TGAAGAACGGAGAGCCAAAGCAGACCAGCGCAAAGCAGGAGCTCTATGAGACTCTCATGAAT<br>ATCTATTGCAAGTAA |
| 5751MI1_003 | Prevotella | Amino Acid | 154 | <u>MAKQYFPQIGKIKFEGTESKNPLAFHYYDANRVVLGKAMEEWLKFAMAWWHTLGQASDQFG</u><br><u>GQTRSYEWDLAATPEQRAKDKLDAGFEIMEKLGIKYFCFHDVDLIEDSDDIATYEARLKDLT</u><br><u>DYAAEQMKLHDIKLLWGTANVFGNKRYMNGAATNPDFDVVARAAVQIKNAIDATIKLGGTSY</u><br><u>VFWGGREGYQSLLNTQMREKDHLATMLTIARDYARSKGFTGTFLIEPKPMEPTKHQYDVDT</u><br><u>ETVVGFLKAHGLDKDFKVNIEVNHATLAGHTFEHELTVAVDNGMLGSIDANRGDAQNGWDTD</u><br><u>QFPVSAEELTLAMMQIIRNGGLGNGGSNFDAKLRRNSTDPEDIFIAHICGMDAMAHALLNAA</u><br><u>AIIEESPIPTMVKERYASFDSGMGKDFEDGKLTLEDLYSYGVKNGEPKQTSAKQELYETLMN</u><br><u>IYCK</u> |
| 5751MI2_003 | Prevotella | DNA | 155 | ATGGCAAAAGATTTTTTCCACAAGTAGGCAAGATTCCATTTGAGGGTCCTGAAAGTACTAA<br>CGTACTCGCATTCCACTACTATGATCCAGAACGCGAAGTTCTTGGTAAGAAAATGAAAGATT<br>GGCTGAAGTATGCTATGGCTTGGTGGCACACACTCGGTCAGGCAAGTGGCGACCAATTCGGT<br>GGTCAAACTCGTTCGTATGAATGGGATGAAGCCGACGATGTTCTTCAACGCGCAAAGGATAA<br>AATGGATGCTGGTTTGAATTGATGACCAAACTTGGCATTGAATACTACTGCTTCCATGATG<br>TCGACCTTATTGAAGAAGGTGCAACAATTGAAGAATATGAAGCTCGTATGCAAGCTATCACC<br>GACTACGCATTAGAAAAACAAAAAGAAACCGGCATTAAGCTCCTTTGGGGTACTGCTAATGT<br>GTTTGGTCATAAGCGTTATATGAATGGTGCGGCAACAAACCCTGACTTTGATGTAGTGGCTC<br>GCGCTGCTGTACAAATCAAGAACGCTATCGATGCAACTATCAAGCTTGGTGGTCAAAACTAT<br>GTATTCTGGGGTGGCCGCGAAGGTTATATGAGTTTGCTCAACACTCAAATGCAACGCGAAAA<br>AGACCACTTGGCAAAGATGCTTACCGCAGCTCGCGACTATGCTCGTGCTAAGGGCTTCAAGG<br>GTACATTCCTCGTTGAACCTAAGCCTATGGAACCAACTAAGCATCAATATGATACCGATACA |

TABLE 2-continued

| Clone No. | Class of organism | Type of Sequence | SEQ ID NO: | Sequence |
|---|---|---|---|---|
| | | | | GAAACTGTGATTGGTTTCCTCCGTGCAAATGGTCTTGAAAAAGACTTCAAGGTGAACATTGA<br>AGTGAACCATGCTACTCTCGCTCAGCACACTTTCGAACACGAACTCGCTGTGGCTGTCGACA<br>ATGGCATGCTCGGTTCTATCGACGCTAACCGTGGCGATGCTCAAAATGGCTGGGATACCGAC<br>CAATTCCCAATCGACAACTACGAACTCACCCTCGCTATGCTCCAAATCATTCGCAATGGTGG<br>TCTTGGCAATGGCGGTAGCAACCTCGACGCTAAGATTCGTCGTAATAGCACCGACCTTGAAG<br>ACCTCTTTATCGCTCACATCAGTGGATGGATGCTATGGCTCGTGCACTTCTCAATGCTGCT<br>GCAATCGTTGAAAAGAGCGAAATTCCTGCTATGTTGAAGCAGCGTTATGCAAGCTCTGATGC<br>AGGTATGGGTAAGGACTTCGAAGAAGGAAAACTCACTCTCGAACAACTCGTAGACTATGCTA<br>AGGCTAACGGCGAACCTGCTACAGTAAGCGGCAAGCAAGAAAAGTATGAAACTCTCGTTGCT<br>CTCTACGCTAAGTAA |
| 5751MI2_003 | Prevotella | Amino Acid | 156 | <u>MAKEFFPQVGKIPFEGPESTNVLAFHYYDPEREVLGKKMKDWLKYAMAWWHTLGQASGDQFG<br>GQTRSYEWDEADDVLQRAKDKMDAGFELMTKLGIEYYCFHDVDLIEEGATIEEYEARMQAIT<br>DYALEKQKETGIKLLWGTANVFGHKRYMNGAATNPDFDVVARAAVQIKNAIDATIKLGGQNY<br>VFWGGREGYMSLLNTQMREKDHLAKMLTAARDYARAKGFKGTFLVEPKPMEPTKHQYDTDT<br>ETVIGFLRANGLEKDFKVNIEVNHATLAQHTFEHELAVAVDNGMLGSIDANRGDAQNGWDTD<br>QFPIDNYELTLAMLQIIRNGGLGNGGSNLDAKIRRNSTDLEDLFIAHISGMDAMARALLNAA<br>AIVEKSEIPAMLKQRYASSDAGMGKDFEEGKLTLEQLVDYAKANGEPATVSGKQEKYETLVA<br>LYAK</u> |
| 5752MI1_003 | Prevotella | DNA | 157 | ATGACTAAAGAGTATTTCCCGGGAATCGGAAAGATTCCGTTTGAAGGAACCAAGAGCAAGAA<br>CCCCCTGGCCTTCCATTATTATAACGCCTCCCAGGTAGCGATGGGCAAGCCCATGAAGGACT<br>GGCTCAAGTATGCCATGGCCTGGTGGCACACCCTGGGCCAGGCCTCTGCAGACCCCTTTGGC<br>GGCCAGACCCGCTCCTACGAATGGGACAAGGGCGAGTGCCCTTATTGCCGCGCCAAGCAGAA<br>GGCCGATGCCGGCTTTGAGCTCATGCAGAAGCTGGGCATCGAGTACTACTGCTTCCACGACG<br>TGGACATCATCGAGGACTGCGAGGACATTGCCGAGTACGAGGCCCGCATGAAGGACATCACG<br>GACTACCTGCTGGAGAAGCAGAAAGAGACCGGCATCAAGAACCTCTGGGGCACCGCCAACGT<br>GTTTGGCCACAAGCGCTACATGAACGGCGCCGCCACCAACCCTCAGTTTGACATTGTGGCCC<br>GTGCCGCCGTCCAGATCAAGAACGCCCTGGATGCCACCATCAAGCTGGGTGGTACCAACTAC<br>GTGTTCTGGGGTGGCCGCGAAGGCTACTACACGCTGCTCAACACCCAGATGCAGCGGGAGAA<br>GAACCACTGGCCAAGATGCTCACCGCCGCCCGCGACTACGCCCGCGCCAAGGGCTTCAAGG<br>GCACCTTCCTCATTGAGCCCAAACCCATGGAGCCCACCAAGCACCAGTACGACGTGGACACC<br>GAGACCGTGATTGGTTTCATCCGCGCCAACGGCCTGGACAAGGACTTCAAGGTAAACATTGA<br>GGTAAACCACGCCACCCTGGCCGGCCACACCTTTGAGCACGAGCTCACCGTGGCCCGCGAGA<br>ACGGCTTCCTGGGCTCCATCGACGCCAACCGCGGAGATGCCCAGAACGGCTGGGATACGGAC<br>CAGTTCCCCATCGACGCCCTGGATCTCACCCAGGCTATGATGCAGGTCATCCTCAACGGTGG<br>CTTCGGCAATGGCGGCACCAACTTTGACGCCAAGCTCCGCCGCTCCTCCACCGATCCCGAGG<br>ACATCTTCATCGCCCACATCAGCGCCATGGATGCCATGGCAGCCCCTCCTGAACGCAGCC<br>GCCATCCTGGAAGAGAGCCCCCTGCCCGCCATGGTCAAGGAGCGTTACGCTTCCTTCGACAG<br>CGGTCTGGGCAAGAAGTTCGAAGAAGGCAAGGCCTCCCTGGAAGAACTTTACGAATATGCCA<br>AGAAGAATGGAGAGCCCGTGGCCGCTTCCGGCAAACAGGAGCTCTGCGAAACTTACTTGAAC<br>CTCTATGCAAAGTAG |
| 5752MI1_003 | Prevotella | Amino Acid | 158 | <u>MTKEYFPGIGKIPFEGTKSKNPLAFHYYNASQVAMGKPMKDWLKYAMAWWHTLGQASADPFG<br>GQTRSYEWDKGECPYCRAKQKADAGFELMQKLGIEYYCFHDVDIIEDCEDIAEYEARMKDIT<br>DYLLEKQKETGIKNLWGTANVFGHKRYMNGAATNPQFDIVARAAVQIKNALDATIKLGGTNY<br>VFWGGREGYYTLLNTQMREKNHLAKMLTAARDYARAKGFKGTFLIEPKPMEPTKHQYDVDT<br>ETVIGFIRANGLDKDFKVNIEVNHATLAGHTFEHELTVARENGFLGSIDANRGDAQNGWDTD<br>QFPIDALDLTQAMMQVILNGGFGNGGTNFDAKLRRSSTDPEDIFIAHISAMDAMAHALLNAA<br>AILEESPLPAMVKERYASFDSGLGKKFEEGKASLEELYEYAKKNGEPVAASGKQELCETYLN<br>LYAK</u> |
| 5752MI2_003 | Prevotella | DNA | 159 | ATGACTAAAGAGTATTTCCCGGGAATCGGAAAGATTCCGTTTGAAGGAACCAAGAGCAAGAA<br>CCCCCTGGCCTTCCATTATTATAACGCCTCCCAGGTAGTGATGGGCAAGCCCATGAAGGACT<br>GGCTCAAGTATGCCATGGCCTGGTGGCACACCCTGGGCCAGGCCTCTGCAGACCCCTTTGGC<br>GGCCAGACCCGCTCCTACGAATGGGACAAGGGCGAGTGCCCGTACTGCCGCGCCAAGCAGAA<br>GGCCGATGCCGGCTTTGAGCTCATGCAGAAGCTGGGCATCGAGTACTACTGCTTCCACGACG<br>TGGACATCATCGAGGACTGCGAGGACATTGCCGAGTACGAGGCCCGCATGAAGGACATCACG<br>GACTACCTGCTGGAGAAGCAGAAAGAGACCGGCATCAAGAACCTCTGGGGCACCGCCAACGT<br>GTTTGGCCACAAGCGCTACATGAACGGCGCCGCCACCAACCCTCAGTTTGACATTGTGGCCC<br>GTGCCGCCGTCCAGATCAAGAACGCCCTGGATGCCACCATCAAACTGGGTGGTACCAACTAC<br>GTGTTCTGGGGTGGCCGCGAAGGCTACTACACGCTGCTCAACACCCAGATGCAGCGGGAGAA<br>GAACCACTGGCCAAGATGCTCACCGCCGCCCGCGACTACGCCCGCGCCAAGGGCTTCAAGG<br>GCACCTTCCTCATTGAGCCCAAACCCATGGAGCCCACCAAGCACCAGTACGACGTGGACACC<br>GAGACCGTGATTGGTTTCATCCGCGCCAACGGCCTGGACAAGGACTTCAAGGTAAACATTGA<br>GGTAAACCACGCCACCCTGGCCGGCCACACCTTTGAGCACGAGCTCACCGTGGCCCGCGAGA<br>ACGGCTTCCTGGGCTCCATCGACGCCAACCGCGGAGATGCCCAGAACGGCTGGGATACGGAC<br>CAGTTCCCCATCGACGCCCTGGATCTCACCCAGGCTATGATGCAGGTCATCCTCAACGGTGG<br>CTTCGGCAATGGCGGCACCAACTTTGACGCCAAGCTCCGCCGCTCCTCCACCGATCCCGAGG<br>ACATCTTCATCGCCCACATCAGCGCCATGGATGCCATGGCACACGCCCTCCTGAACGCAGCC<br>GCCATCCTGGAAGAGAGCCCCCTGCCCGCCATGGTCAAGGAGCGTTACGCTTCCTTCGACAG<br>CGGTCTGGGCAAGAAGTTCGAAGAAGGCAAGGCCTCCCTGGAAGAACTTTACGAATATGCCA<br>AGAAGAATGGAGAGCCCGTGGCCGCTTCCGGCAAACAGGAGCTCTGCGAAACTTACTTGAAC<br>CTCTATGCAAAGTAG |

TABLE 2-continued

| Clone No. | Class of organism | Type of Sequence | SEQ ID NO: | Sequence |
|---|---|---|---|---|
| 5752MI2_003 | Prevotella | Amino Acid | 160 | MTKEYFPGIGKIPFEGTKSKNPLAFHYYNASQVVMGKPMKDWLKYAMAWWHTLGQASADPFG<br>GQTRSYEWDKGECPYCRAKQKADAGFELMQKLGIEYYCFHDVDIIEDCEDIAEYEARMKDIT<br>DYLLEKQKETGIKNLWGTANVFGHKRYMNGAATNPQFDIVARAAVQIKNALDATIKLGGTNY<br>VFWGGREGYYTLLNTQMREKNHLAKMLTAARDYARAKGFKGTFLIEPKPMEPTKHQYDVDT<br>ETVIGFIRANGLDKDFKVNIEVNHATLAGHTFEHELTVARENGFLGSIDANRGDAQNGWDTD<br>QFPIDALDLTQAMMQVILNGGFGNGGTNFDAKLRRSSTDPEDIFIAHISAMDAMAHALLNAA<br>AILEESPLPAMVKERYASFDSGLGKKFEEGKASLEELYEYAKKNGEPVAASGKQELCETYLN<br>LYAK |
| 5752MI3_002 | Prevotella | DNA | 161 | ATGGCAAAAGAGTATTTCCCGACTATCGGCAAGATTCCCTTCGAGGGCGTCGAATCCAAGAA<br>CCCGATGGCATTCCACTACTATGACGCGAACCGCGTCGTGATGGGCAAGCCCATGAAGGACT<br>GGCTCAAGTTCGCGATGGCCTGGTGGCACACCCTGGGACAGGCTTCCGGCGACCCGTTCGGC<br>GGCCAGACCCGTTCCTACGAGTGGGACAAGGGCGAGTGCCCCTACTGCCGCGCCAAGGCCAA<br>GGCCGACGCCGGCTTCGAGATCATGCAGAAGCTCGGTATCGAGTACTACTGCTTCCATGACA<br>TCGACCTCGTGGAGGACACCGAGGACATCGCCGAGTACGAGGCCCGCATGAAGGACATCACC<br>GACTACCTCGTCGAGAAGCAGAAGGAAACCGGCATCAAGAACCTCTGGGGCACGGCCAACGT<br>GTTCGGCAACAAGCGCTACATGAACGGCGCCGCCACGAACCCGCAGTTCGACGTCGTCGCCC<br>GCGCCGCCGTCCAGATCAAGAACGCCATCGACGCCACCATCAAGCTCGGCGGTACCGGTTAC<br>GTGTTCTGGGGCGGCCGTGAAGGCTACTACACCCTCCTGAACACCCAGATGCAGCGCGAGAA<br>GGACCACCTCGCCAAGATGCTCACCGCCGCCCGCGACTACGCCCGCGCCCACGGCTTCCAGG<br>GCACCTTCCTCATCGAGCCCAAGCCCATGGAGCCCACCAAGCACCAGTACGACGTGGACACG<br>GAGACCGTGATCGGCTTCCTGCGCGCCAACGGTCTGGACAAGGACTTCAAGGTCAATATCGA<br>GGTGAACCACGCCACCCTCGCCGGCCACACCTTCGAGCACGAGCTCACCGTGGCTGTCGATA<br>ACGGCTTCCTCGGCTCCATCGACGCCAACCGCGGCGACGCCCAGAACGGCTGGGACACCGAC<br>CAGTTCCCCGTGGACCCGTACGACCTCACCCAGGCCATGATGCAGATCATCCGCAACGGCGG<br>TTTCAAGGACGGCGGCACCAACCTCGACGCCAAGCTCCGCCGCTCTTCCACCGACCCGGAGG<br>ACATCTTCATCGCCCACATCAGCGCGATGGACGCCATGGCCCACGCCCTGCTGAACGCCGCC<br>GCCGTCATCGAGGAGAGCCCGCTCTGCAAGATGGTCGAGGAGCGCTACGCTTCCTTCGACAG<br>CGGCCTCGGCAAGCAGTTCGAGGAAGGCAAGGCCACCCTCGAGGACCTCTACGAGTATGCCA<br>AGAAGAATGGCGAGCCCGTCGTCGCCTCCGGCAAGCAGGAGCTCTACGAGACGCTGCTGAAC<br>CTTTACGCGAAGTAG |
| 5752MI3_002 | Prevotella | Amino Acid | 162 | MAKEYFPTIGKIPFEGVESKNPMAFHYYDANRVVMGKPMKDWLKFAMAWWHTLGQASGDPFG<br>GQTRSYEWDKGECPYCRAKAKADAGFEIMQKLGIEYYCFHDIDLVEDTEDIAEYEARMKDIT<br>DYLVEKQKETGIKNLWGTANVFGNKRYMNGAATNPQEDVVARAAVQIKNAIDATIKLGGTGY<br>VFWGGREGYYTLLNTQMQREKDHLAKMLTAARDYARAHGFQGTFLIEPKPMEPTKHQYDVDT<br>ETVIGFLRANGLDKDFKVNIEVNHATLAGHTFEHELTVAVDNGFLGSIDANRGDAQNGWDTD<br>QFPVDPYDLTQAMMQIIRNGGFKDGGTNFDAKLRRSSTDPEDIFIAHISAMDAMAHALLNAA<br>AVIEESPLCKMVEERYASFDSGLGKQFEEGKATLEDLYEYAKKNGEPVVASGKQELYETLLN<br>LYAK |
| 5752MI5_003 | Prevotella | DNA | 163 | ATGGCAAAAGAGTATTTCCCGACAATCGGTAAGATCCCCTTCGAGGGACCCGAGTCCAAGAA<br>CCCGATGGCATTCCACTACTATGACGCGGAGCGCGTGGTGATGGGCAAGAAGATGAAGGACT<br>GGTTCAAGTTCGCGATGGCCTGGTGGCACACCCTGGGCCAGGCTTCCGCCGACCCGTTCGGC<br>GGCCAGACCCGCTCCTACGAGTGGGACAAGGGCGAAGGCCCCTGCTCCCGCGCCCGCGCCAA<br>GGCTGACGCCGGTTTCGAGATCATGCAGAAACTGGGCATCGGCTACTACTGCTTCCACGACA<br>TCGACCTGGTGGAGGACACCGAGGACATCGCCGAGTATGAAGCCCGCATGAAGGACATCACC<br>GACTACCTCGTGGAGAAGCAGAAGGAGACCGGCATCAAGAACCTCTGGGGCACGGCCAACGT<br>ATTCGGCAACAAGCCCTACATGAACGGCGCCGCCACGAACCCGCAGTTCGACATCGCCGCCC<br>GCGCGGCCCTGCAGACCAAGAACGCCATCGATGCCACCATCAAGCTGGGCGGCACCGGTTAC<br>GTGTTCTGGGGCGGCCGTGAAGGCTACTACACCCTCCTGAACACCCAGATGCAGCGCGAGAA<br>GGACCACCTTGCCAAGATGCTCACCGCGGCTCGCGACTATGCCCGCGCCCACGGCTTCAAGG<br>GCACCTTCTTCATCGAGCCGAAACCGATGGAGCCCACCAAGCACCAGTACGACGTGGACACG<br>GAGACCGTGATCGGCTTCCTCCGCGCCAACGGCCTGGACAAGGACTTCAAGGTGAACATCGA<br>AGTGAACCACGCCACCCTCGCCGGCCACACCTTCGAGCACGGGCTCACCGTGGCCGTTGACA<br>ACGGCTTCCTCGGCAGCATCGACGCCAACCGCGGAGACGCCCAGAACGGCTGGGATACCGAC<br>CAGTTCCCCGGTGGATCCGTACGACCTCACCCAGGCGATGATCCAGATCATCCGCAATGGCGG<br>CTTCAAGGACGGCGGTACCAACTTCGACGCCAAGCTCCGCCGCTCTTCCACCGACCCGGAGG<br>ACATCTTCATCGCCCACATCAGCGCGATGGACGCCATGGCCCACGCCCTGCTGAACGCCGCC<br>GCCGTGCTCGAGGAGAGCCCGCTCTGCGAGATGGTTGCAAAGCGTTACGCTTCCTTCGACAG<br>CGGTCTCGGCAAGAAGTTCGAGGAAGGCAACGCCACCCTCGAGGAACTCTACGAGTACGCCA<br>AGGCGAAGGGCGAGGTCGTTGCCGAATCCGGCAAGCAGGAACTCTACGAGACCCTGCTGAAC<br>CTCTACGCGAAGTAG |
| 5752MI5_003 | Prevotella | Amino Acid | 164 | MAKEYFPTIGKIPFEGPESKNPMAFHYYDAERVVMGKKMKDWFKFAMAWWHTLGQASADPFG<br>GQTRSYEWDKGEGPCSRARAKADAGFEIMQKLGIGYYCFHDIDLVEDTEDIAEYEARMKDIT<br>DYLVEKQKETGIKNLWGTANVFGNKPYMNGAATNPQFDIAARAALQTKNAIDATIKLGGTGY<br>VFWGGREGYYTLLNTQMREKDHLAKMLTAARDYARAHGFKGTFFIEPKPMEPTKHQYDVDT<br>ETVIGFLRANGLDKDFKVNIEVNHATLAGHTFEHGLTVAVDNGFLGSIDANRGDAQNGWDTD<br>QFPVDPYDLTQAMIQIIRNGGFKDGGTNFDAKLRRSSTDPEDIFIAHISAMDAMAHALLNAA<br>AVLEESPLCEMVAKRYASFDSGLGKKFEEGNATLEELYEYAKAKGEVVAESGKQELYETLLN<br>LYAK |

TABLE 2-continued

| Clone No. | Class of organism | Type of Sequence | SEQ ID NO: | Sequence |
|---|---|---|---|---|
| 5752MI6_004 | Prevotella | DNA | 165 | ATGGCAAAAGAGTATTTCCCGACAATCGGAAAGATCCCCTTCGAGGGCGCTGAGAGCAAGAA<br>TCCCCTTGCTTTCCACTATTATGACGCCGAGCGTGTGGTCATGGGCAAGCCCATGAAGGACT<br>GGTTCAAGTTCGCGATGGCCTGGTGGCACACCCTGGGCCAGGCTTCCGCCGACCCGTTCGGC<br>GGCCAGACCCGCTCCTACGAGTGGGACAAGGGCGAGTGCCCCTACTGCCGCGCCCGCCAGAA<br>GGCTGACGCCGGTTTCGAGATCATGCAGAAGCTCGGCATCGGCTACTACTGCTTCCACGACA<br>TCGACCTGGTCGAGGACACCGAGGACATCGCCGAGTACGAGGCCCGCATGAAGGACATCACC<br>GACTACCTCGTCGAGAAGCAGAAGGAGACCGGCATCAAGAACCTCTGGGGCACGGCCAACGT<br>GTTCGGCAACAAGCGCTACATGAACGGCGCCGCCACGAACCCGCAGTTCGACATCGTCGCCC<br>ACGCGGCCCTGCAGATCAAGAACGCGATCGGCGCCACCATCAAGCTCGGCGGCACCGGTTAC<br>GTGTTCTGGGGCGGCCGTGAAGGTTACTACACCCTCCTGAACACCCAGATGCAGCGCGAGAA<br>GGACCACCTCGCCAAGATGCTCACCGCCGCCCGCGACTACGCCCGCGCCAACGGCTTCAAGG<br>GCACCTTCCTCATCGAGCCGAAGCCGATGGAGCCCACCAAGCACCAGTATGACGTGGACACG<br>GAGACCGTGATCGGCTTCCTCCGCGCCAACGGCCTGGACAAGGACTTCAAGGTGAACATCGA<br>GGTGAACCACGCCACCCTCGCCGGCCACACCTTCGAGCACGAGCTCACCGTGGCCGGTCGACA<br>ACGGCTTCCTCGGCAGCATCGACGCCAACCGCGGTGACGCCCAGAACGGCTGGGATACCGAC<br>CAGTTCCCGGTTGGATCCGTACGATCTCACCCAGGCGATGATCCAGATCATCCGCAACGGCGG<br>CTTCAAGGATGGCGGCACCAACTTCGACGCCAAGCTCCGCCGCTCTTCCACCGACCCGGAGG<br>ACATCTTCATCGCCCACATCAGCGCGATGGACGCCATGGCCCACGCCCTGCTGAACGCCGCC<br>GCCGTCATCGAGGAGAGCCCGCTCTGCGAGATGGTCGCCAAGCGCTACGCTTCCTTCGACAG<br>CGGTCTCGGCAAGAAGTTCGAGGAAGGCAACGCCACCCTCGAGGAACTCTACGAGTACGCCA<br>AGGCGAACGGTGAGGTCAAGGCCGAATCCGGCAAGCAGGAGCTCTACGAGACCCTTCTGAAC<br>CTCTACGCGAAATAG |
| 5752MI6_004 | Prevotella | Amino Acid | 166 | <u>MAKEYFPTIGKIPFEGAESKNPLAFHYYDAERVVMGKPMKDWFKFAMAWWHTLGQASADPFG</u><br><u>GQTRSYEWDKGECPYCRARQKADAGFEIMQKLGIGYYCFHDIDLVEDTEDIAEYEARMKDIT</u><br><u>DYLVEKQKETGIKNLWGTANVFGNKRYMNGAATNPQFDIVAHAALQIKNAIGATIKLGGTGY</u><br><u>VFWGGREGYYTLLNTQMREKDHLAKMLTAARDYARANGFKGTFLIEPKPMEPTKHQYDVDT</u><br><u>ETVIGFLRANGLDKDFKVNIEVNHATLAGHTFEHELTVAVDNGFLGSIDANRGDAQNGWDTD</u><br><u>QFPVDPYDLTQAMIQIIRNGGFKDGGTNFDAKLRRSSTDPEDIFIAHISAMDAMAHALLNAA</u><br><u>AVIEESPLCEMVAKRYASFDSGLGKKFEEGNATLEELYEYAKANGEVKAESGKQELYETLLN</u><br><u>LYAK</u> |
| 5753MI1_002 | Prevotella | DNA | 167 | ATGGCAAAAGAGTATTTCCCCACTATCGGGAAGATTCCTTTCGAAGGAGTCGAGAGCAAGAA<br>CCCCCTTGCATTCCATTATTATGACGCAAACCGCATGGTCATGGGCAAGCCCATGAAGGACT<br>GGTTCAAGTTCGCCATGGCATGGTGGCACACCCTGGGACAGGCCTCCGCAGACCCGTTCGGC<br>GGCCAGACCCGCTCCTACGAATGGGACAAGGGCGAATGCCCCTACTGCCGCGCCAGGGCAAA<br>GGCCGATGCCGGCTTCGAGATCATGCAGAAACTGGGTATCGAGTATTTCTGCTTCCATGACA<br>TCGACCTGGTAGAGGACTGCGACGACATCGCCGAGTACGAGGCCCGCATGAAGGACATCACG<br>GACTATCTCCTGGAGAAGATGAAGGAAACCGGCATCAAGAACCTCTGGGGCACCGCCAACGT<br>GTTCGGCAACAAGCGTTACATGAACGGCGCCGGCACCAATCCGCAGTTCGACGTAGTGGCCC<br>GCGCTGCCGTCCAGATCAAGAACGCCATCGACGCCACCATCAAGCTCGGCGGTTCCAACTAT<br>GTGTTCTGGGGCGGCCGTGAAGGATACTACACCCTGCTGAACACCCAGATGCAGCGCGAGAA<br>GGACCACCTCGGCAAACTGCTCACCGCCGCCCGCGACTATGCCCGCAAGAACGGCTTCAAGG<br>GCACCTTCCTCATCGAGCCCAAGCCGATGGAGCCCACCAAGCACCAGTACGACGTAGACACG<br>GAGACCGTGATCGGCTTCCTCCGCGCCAACGGCCTGGAGAAAGACTTCAAGGTGAACATCGA<br>GGTGAACCACGCCACCCTGGCCGGCCATACCTTCGAGCATGAACTCACCGTGGCCGTGGACA<br>ACGGCTTCCTGGGATCCATCGACGCCAACCGCGGCGACGCCCAGAACGGCTGGGATACGGAC<br>CAGTTCCCGGTAGACCCGTACGACCTCACCCAGGCCATGATGCAGATCATCCGCAACGGCGG<br>CCTCGGCAACGGCGGTACCAACTTCGACGCCAAACTGCGCCGTTCCTCCACCGATCCTGAGG<br>ACATCTTCATCGCCCACATCAGCGCCATGGACGCCATGGCCCACGCCCTGCTCAACGCAGCC<br>GCCGTGCTGGAAGAAGTCCGCTCTGTGAGATGGTCAAGGAGCGCTACGCTTCCTTCGACAG<br>CGGTCTCGGCAAGAAGTTCGAAGAGGGCAAGGCTACCCTGGAAGAAATCTACGAGTATGCCA<br>AGAAGAGCGGCGAACCCGTGGTCGCTTCCGGCAAGCAGGAGCTCTACGAAACCCTGCTGAAC<br>CTCTACGCCAAGTAG |
| 5753MI1_002 | Prevotella | Amino Acid | 168 | <u>MAKEYFPTIGKIPFEGVESKNPLAFHYYDANRMVMGKPMKDWFKFAMAWWHTLGQASADPFG</u><br><u>GQTRSYEWDKGECPYCRARAKADAGFEIMQKLGIEYFCFHDIDLVEDCDDIAEYEARMKDIT</u><br><u>DYLLEKMKETGIKNLWGTANVFGNKRYMNGAGTNPQEDVVARAAVQIKNAIDATIKLGGSNY</u><br><u>VFWGGREGYYTLLNTQMREKDHLGKLLTAARDYARKNGFKGTFLIEPKPMEPTKHQYDVDT</u><br><u>ETVIGFLRANGLEKDFKVNIEVNHATLAGHTFEHELTVAVDNGFLGSIDANRGDAQNGWDTD</u><br><u>QFPVDPYDLTQAMMQIIRNGGLGNGGTNFDAKLRRSSTDPEDIFIAHISAMDAMAHALLNAA</u><br><u>AVLEESPLCEMVKERYASFDSGLGKKFEEGKATLEEIYEYAKKSGEPVVASGKQELYETLLN</u><br><u>LYAK</u> |
| 5753MI2_002 | Prevotella | DNA | 169 | ATGGCTAAAGAATACTTCCCCTCCATCGGCAAAATCCCTTTTGAAGGAGGCGACAGCAAAAA<br>TCCCCTCGCTTTCCATTATTATGACGCCGGACGCGTGGTTATGGGCAAGCCCATGAAGGAAT<br>GGCTTAAAATTCGCCATGGCCTGGTGGCACACGCTGGGCCAGGCTCCGGAGACCCCTTCGGC<br>GGCCAGACCCGCAGCTACAATGGGACAAGGGCGAATGCCCCTACTGCCGCGCCAAAGCCAA<br>GGCCGACGCCGGTTTTGAAATCATGCAAAAGCTGGGTATCGAATACTTCTGCTTCCACGATG<br>TGGACCTTATCGAGGATTGCGATGACATTGCCGAATACGAAGCCCGCATGAAAGACATCACG<br>GACTACCTGCTGGAAAAGATGAAGGAGACCGGCATCAAGAACCTCTGGGGCACCGCCAATGT<br>CTTCGGCAACAAGCGCTACATGAACGGCGCCGCCACGAACCCGCAGTTCGACGTGGTCGCCC<br>GCGCCGCCGTCCAGATCAAGAACGCGATTGACGCCACCATCAAGCTCGGCGGTACCAGTTAT<br>GTATTCTGGGGCGGCCGCGAGGGCTACTACACCCTCCTGAACACCCAGATGCAGCGTGAGAA<br>AGACCACCTGGCCAAGATGCTCACCGCAGCCCGCGACTACGCCCGCGCCAAGGGCTTCAAGG |

TABLE 2-continued

| Clone No. | Class of organism | Type of Sequence | SEQ ID NO: | Sequence |
|---|---|---|---|---|
| | | | | GCACCTTCCTCATCGAGCCCAAGCCGATGGAGCCCACCAAGCACCAGTACGACGTTGACACG<br>GAGACCGTGATCGGCTCCCTGCGCGCCAACGGCCTGGACAAGGACTTCAAGGTGAACATCGA<br>GGTGAACCACGCCACCCTGGCCGGCCACACCTTCGAGCACGAACTCACCGTGGCTGTTGACA<br>ACGGCTTCCTGGGCTCCATCGACGCCAACCGCGGCGACGCCCAGAACGGCTGGGATACGGAC<br>CAGTTCCCGGTAGACCCGTACGACCTCACCCAGGCCATGATGCAGATTATCCGCAACGGCGG<br>CTTCAAGGACGGCGGCACCAACTTCGATGCCAAACTGCGCCGCTCTTCCACCGATCCGGAAG<br>ACATCTTCATCGCCCACATCAGCGCTATGGATGCCATGGCACACGCCCTGCTCAACGCCGCC<br>GCCGTGCTGGAAGAGAGCCCGCTGTGCAACATGGTCAAGGAGCGTTACGCCGGCTTCGACAG<br>CGGCCTTGGCAAGAAGTTCGAGGAAGGGAAGGCAACGCTGGAGGAAATCTATGACTATGCCA<br>AGAAGAGCGGCGAACCCGTCGTGGCTTCCGGCAAGCAGGAACTCTACGAAACCATCCTGAAC<br>CTCTATGCCAAGTAG |
| 5753MI2_002 | Prevotella | Amino Acid | 170 | MAKEYFPSIGKIPPFEGGDSKNPLAFHYYDAGRVVMGKPMKEWLKFAMAWWHTLGQASGDPFG<br>GQTRSYEWDKGECPYCRAKAKADAGFEIMQKLGIEYFCFHDVDLIEDCDDIAEYEARMKDIT<br>DYLLEKMKETGIKNLWGTANVFGHKRYMNGAATNPQFDVVARAAVQIKNAIDATIKLGGTSY<br>VFWGGREGYYTLLNTQMREKDHLAKMLTAARDYARAKGFKGTFLIEPKPMEPTKHQYDVDT<br>ETVIGSLRANGLDKDFKVNIEVNHATLAGHTFEHELTVAVDNGFLGSIDANRGDAQNGWDTD<br>QFPVDPYDLTQAMMQIIRNGGFKDGGTNFDAKLRRSSTDPEDIFIAHISAMDAMAHALLNAA<br>AVLEESPLCNMVKERYAGFDSGLGKKFEEGKATLEEIYDYAKKSGEPVVASGKQELYETILN<br>LYAK |
| 5753MI4_002 | Prevotella | DNA | 171 | ATGTCAAAAGAGTATTTCCCTACAATCGGCAGGGTCCCCTTCGAGGGACCTGAGAGCAAGAA<br>TCCGCTGGCGTTCCACTATTACGAGCCGGACCGGCTCGTCCTGGGCAGGAAAATGAAGGACT<br>GGCTGCGCTTCGCAATGGCCTGGTGGCATACGCTCGGGCAGGCTTCCGGCGACCAGTTCGGC<br>GGACAGACCTGCACATACGCTGGGATGAAGGCGAGTGTCCCGTCTGCCGGGCAAAGGCCAA<br>GGCTGACGCCGGCTTTGAACTGATGCAGAAACTGGGCATCGGGTATTTCTGCTTCCACGACG<br>TGGACCTGGTCGAGGAGGCCGACACCATTGAAGAATACGAGGAGCGGATGCGGATCATCACC<br>GACTACCTGCTCGAGAAGATGGAAGAGACCGGCATCCGCAATCTCTGGGGAACCGCCAATGT<br>CTTCGGACACAAGCGCTATATGAACGGCGCCGCCACCAATCCCGACTTCGACGTCGTGGCCC<br>GTGCCGCGGTCCAGATCAAGAATGCCATCGATGCCACCATCAAACTGGGTGGTGAGAACTAT<br>GTGTTCTGGGGTGGCCGCGAGGGCTATACGAGCCTGCTCAACACGCAGATGCACCGGGAAAA<br>ACACCACCTCGGAAATATGCTCAGGGCAGCCCGCGACTATGGCCGTGCCCACGGTTTCAAGG<br>GAACGTTCCTGATCGAGCCCAAGCCGATGGAGCCGACCAAGCATCAGTACGACCAGGATACG<br>GAGACGGGTCATCGGTTTCCTGCGCTGTCACGGCCTGGACAAGGATTTCAAGGTGAACATCGA<br>GGTGAACCACGCCACGCTCGCCGGACACACCTTCGAGCACGAACTGGCCACTGCGGTCGATG<br>CCGGCCTGCTGGGCAGCATCGATGCCAACCGCGGCGACGCCCAGAACGGCTGGGATACCGAC<br>CAGTTCCCCGATCGACAACTACGAACTCACGCTGGCGATGCTGCAGATCATCCGCAATGGCGG<br>ACTGCACCCGGCGGATCGAACTTCGATGCCAAGTTGCGCCGCAATTCACCGATCCGGAAG<br>ACATCTTCATCGCCCACATCAGCGCGATGGACGCGATGGCCCGTGCCCTGCTCAATGCGGCG<br>GCCATCTGGACCGAATCGCCGATTCAGGATATGGTCAGGGACCGCTATGCTTCCTTCGACAG<br>CGGAAAGGGCAGGGAGTTCGAGGAAGGCAGACTCAGTCTGGAAGACCTCGTGGCCTATGCGA<br>AGGAGCACGGTGAGCCGCGCCAGATCTCCGGCAGGCAGGAACTTTATGAAACCATCGTAGCG<br>CTTTACTGCAGGTAA |
| 5753MI4_002 | Prevotella | Amino Acid | 172 | MSKEYFPTIGRVPFEGPESKNPLAFHYYEPDRLVLGRKMKDWLRFAMAWWHTLGQASGDQFG<br>GQTCTYAWDEGECPVCRAKAKADAGFELMQKLGIGYFCFHDVDLVEEADTIEEYEERMRIIT<br>DYLLEKMEETGIRNLWGTANVFGHKRYMNGAATNPDFDVVARAAVQIKNAIDATIKLGGENY<br>VFWGGREGYTSLLNTQMHREKHHLGNMLRAARDYGRAHGFKGTFLIEPKPMEPTKHQYDQDT<br>ETVIGFLRCHGLDKDFKVNIEVNHATLAGHTFEHELATAVDAGLLGSIDANRGDAQNGWDTD<br>QFPIDNYELTLAMLQIIRNGGLAPGSNFDAKLRRNSTDPEDIFIAHISAMDAMARALLNAA<br>AIWTESPIQDMVRDRYASFDSGKGREFEEGRLSLEDLVAYAKEHGEPRQISGRQELYETIVA<br>LYCR |
| 5752MI4_004 | Prevotella | DNA | 173 | ATGACTAAAGAGTATTTCCCGGGAATCGGAACGATTCCGTTTGAAGGAACCAAGAGCAAGAA<br>CCCCCTGGCCTTCCATTATTATAACGCCTCCCAGGTAGTGATGGGCAAGCCCATGAAGGACT<br>GGCTCAAGTATGCCATGGCCTGGTGGCACACCCTGGGCCAGGCCTCTGCAGACCCCTTTGGC<br>GGCCAGACCCGCTCCTACGAATGGGACAAGGGCGAGTGCCCGTACTGCCGCGCCAAGCAGAA<br>GGCCGATGCCGGCTTTGAGCTCATGCAGAAGCTGGGCATCGAGTACTACTGCTTCCACGACG<br>TGGACATCATCGAGGACTGCAGGACATTGCCGAGTACGAGGCCCGCATGAAGGACATCACG<br>GACTACCTGCTGGAGAAGCAGAAAGAGACCGGCATCAAGAACCTCTGGGGCACCGCCAACGT<br>GTTTGGCCACAAGCGCTACATGAACGGCGCCGCCACCAACCCTCAGTTTGACATTGTGGCCC<br>GTGCCGCCGTCCAGATCAAGAACGCCCTGGATGCCGCCATCAAACTGGGTGGTACCAACTAC<br>GTGTTCTGGGGTGGCCGCGAAGGCTACTACACGCTGCTCAACACCCAGATGCAGCGGGAGAA<br>GAACCACCTGGCCAAGATGCTCACCGCCGCCCGCGACTACGCCGCCAAGGGCTTCAAGG<br>GCACCTTCCTCATTGAGCCCAAACCCATGGAGCCCACCAAGCACCAGTACGACGTGGACACC<br>GAGACCGTGATTGGTTTCATCCGCGCCAACGGCCTGGACAAGGACTTCAAGGTAAACATTGA<br>GGTAAACCACGCCACCCTGGCCGGCCACACCTTTGAGCACGAGCTCACCGTGGCCCGCGAGA<br>ACGGCTTCCTGGGCTCCATCGACGCCAACCGCGGAGATGCCCAGAACGGCTGGGATACGGAC<br>CAGTTCCCCATCGACGCCCTGGATCTCACCCAGGCTATGATGCAGGTCATCCTCAACGGTGG<br>CTTCGGCAATGGCGGCACCAACTTTGACGCCAAGCTCCGCCGCTCCTCCACCGATCCCGAGG<br>ACATCTTCATCGCCCACATCAGCGCGCCATGGATGCCATGGCACACGCCCTCTGAACGCAGCC<br>GCCATCCTGGAAGAGAGCCCCCTGCCCGCCATGGTCAAGGAGCGTTACGCTTCCTTCGACAG<br>CGGTCTGGGCAAGAAGTTCGAAGAAGGCAAGGCCTCCCTGGAAGAACTTTACGAATATGCCA<br>AGAAGAATGGAGAGCCCGTGGCCGCTTCCGGCAAACAGGAGCTCTGCGAAACTTACTTGAAC<br>CTCTATGCAAAGTAG |

TABLE 2-continued

| Clone No. | Class of organism | Type of Sequence | SEQ ID NO: | Sequence |
|---|---|---|---|---|
| 5752MI4_004 | Prevotella | Amino Acid | 174 | MTKEYFPGIGTIPFEGTKSKNPLAFHYYNASQVVMGKPMKDWLKYAMAWWHTLGQASADPFG GQTRSYEWDKGECPYCRAKQKADAGFELMQKLGIEYYCFHDVDIIEDCEDIAEYEARMKDIT DYLLEKQKETGIKNLWGTANVFGHKRYMNGAATNPQFDIVARAAVQIKNALDAAIKLGGTNY VFWGGREGYYTLLNTQMQREKNHLAKMLTAARDYARAKGFKGTFLIEPKPMEPTKHQYDVDT ETVIGFIRANGLDKDFKVNIEVNHATLAGHTFEHELTVARENGFLGSIDANRGDAQNGWDTD QFPIDALDLTQAMMQVILNGGFGNGGTNFDAKLRRSSTDPEDIFIAHISAMDAMAHALLNAA AILEESPLPAMVKERYASFDSGLGKKFEEGKASLEELYEYAKKNGEPVAASGKQELCETYLN LYAK |
| 727MI4_006 | Rhizobiales | DNA | 175 | GTGACTGATTTCTTCAAGGGCATCGCGCCCGTCAAGTTTGAGGGGCCGCAGAGCTCCAATCC GCTGGCCTATCGCCACTATAACAAGGACGAAATCGTCCTCGGCAAGCGGATGGAAGACCATA TCCGTCCCGGCGTTGCCTATTGGCACACCTTCGCCTATGAGGGCGGCGATCCGTTTGGCGGC CGCACCTTCGATCGCCCCTGGTTCGACAAGGGTATGGACGGCGCCGCCTCAAGGCCGACGT GGCCTTCGAACTGTTCGACCTGCTCGACGTTCCTTTCTTCTGTTTCCACGATGCTGATATCG CTCCCGAAGGCGCAACGCTGGCCGAGAGCAACCGCAATGTGCGCGAGATTGGCGAGATCTTC GCTCGCAAGATGGAAACCAGCCGCACCAAGCTGCTCTGGGGTACGGCAAACCTGTTCTCCAA TCGCCGCTACATGGCCGGCGCCGCCACCAACCCGGACCCGGAAATCTTCGCCTATGCCGCTG GGCAGGTGAAGAACGTGCTGGAACTGACCCACGAACTGGGCGGCGCCAACTATGTGCTGTGG GGCGGTCGCGAGGGTTATGAAACCCTGCTCAACACCAAGATCGGCCAGGAAATGGACCAGAT GGGCCGTTTTCTGTCGATGGTCGTCGAGCATGCCGAAAAGATCGGCTTCAAGGGCCAGATCC TGATCGAGCCCAAGCCGCAGGAGCCGAGCAAGCACCAGTATGACTTCGACGTTGCAACCGTT TACGGCTTCCTCAAGAAGTATGGTCTCGAAACCAAGGTGAAGTGCAATATCGAGGTCGGCCA TGCCTTCCTCGCCAATCACTCCTTCGAGCATGAACTGGCTTTGGCCGCATCGCTGGGCATTC TCGGCTCGGTCGACGCCAATCGCAACGATCTACAGTCCGGCTGGGATACCGACCAGTTCCCC AATAATGTCCCCGAAACCGCACTCGCCTTCTATCAGATTCTCAAGGCGGGCGGACTGGGCAA TGGCGGCTGGAACTTCGACGCCCGCGTGCGCCGCCAGTCACTTGATCCGGCCGACCTGCTGC ACGGCCATATCGGCGGCCTCGACGTGCTGGCGCGCGGCCTCAAGGCCGCCGCGGCGCTGATC GAGGACGGCACCTATGACAAGGTCGTCGACGCCCGCTATGCCGGCTGGAACCAGGGCCTGGG CAAGGATATCCTTGGTGGCAAGCTGAACCTTGCCGACCTGGCTGCCAAGGTCGACGCCGAAA ACCTCAACCCGCAGCCTAGGTCCGGCCAGCAGGAATATCTCGAAAACCTGATCAACCGGTTC GTTTAG |
| 727MI4_006 | Rhizobiales | Amino Acid | 176 | MTDFFKGIAPVKFEGPQSSNPLAYRHYNKDEIVLGKRMEDHIRPGVAYWHTFAYEGGDPFGG RTFDRPWFDKGMDGARLKADVAFELFDLLDVPFFCFHDADIAPEGATLAESNRNVREIGEIF ARKMETSRTKLLWGTANLFSNRRYMAGAATNPDPEIFAYAAGQVKNVLELTHELGGANYVLW GGREGYETLLNTKIGQEMDQMGRELSMVVEHAEKIGFKGQILIEPKPQEPSKHQYDFDVATV YGFLKKYGLETKVKCNIEVGHAFLANHSFEHELALAASLGILGSVDANRNDLQSGWDTDQFP NNVPETALAFYQILKAGGLGNGGWNFDARVRRQSLDPADLLHGHIGGLDVLARGLKAAAALI EDGTYDKVVDARYAGWNQGLGKDILGGKLNLADLAAKVDAENLNPQPRSGQQEYLENLINRF V |

EXAMPLE 5

Quantification of XI Enzyme Activity

Figure 3:
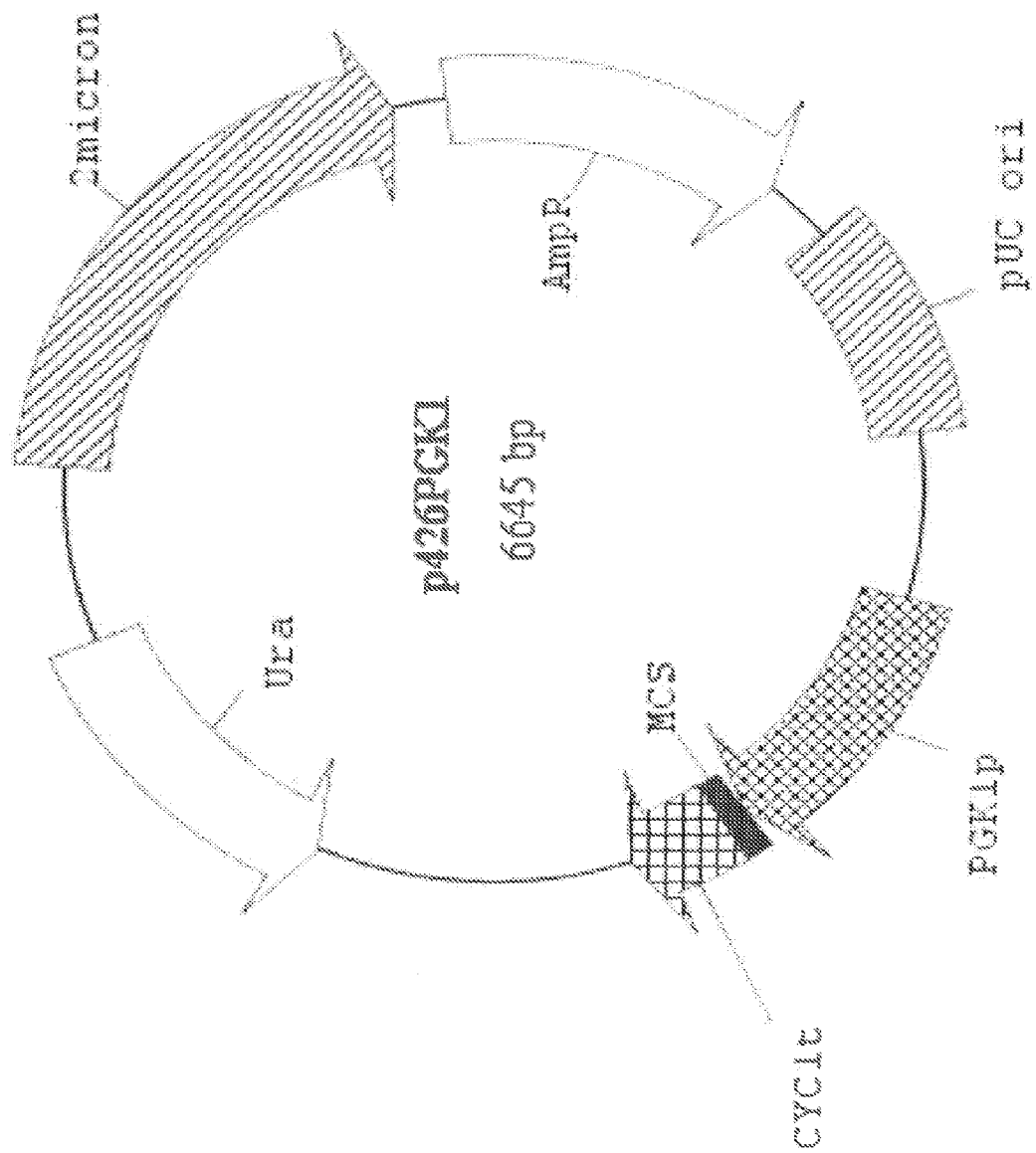
FIG. 3 is a map of the vector p426PGK1 for expressing XI in yeast strain, *Saccharomyces cerevisiae* CEN.PK2-1Ca (ATCC: MYA1108).

The clones identified in the ABD and SBD screens (see Table 2) were subcloned into vector p426PGK1 (FIG. 3), a modified version of p426GPD (ATCC accession number 87361) in which the GPD promoter was replaced with the PGK1 promoter from *Saccharomyces cerevisiae* (ATCC accession number 204501) gDNA. The clones were then transformed into yeast strain MYA11008.

Cells were grown as described in the materials and methods. Cell pellets were resuspended in about 300 µl of lysis buffer: approximate concentrations (50 mM NaH$_2$PO$_4$ (pH 8.0), 300 mM NaCl, 10 mM imidazole (Sigma, #15513), to which was added about 2 µl/ml beta-mercaptoethanol (BME)), and protease inhibitor cocktail tablet (Roche, 11836170001) (1 tablet for about 10 ml cell extract). The cell suspension was added to a 2 ml screw-cap microcentrifuge tube that had been pre-aliquotted with about 0.5 ml of acid washed glass beads (425-600 µm). Cells were lysed using a FastPrep-24 (MP Biomedicals, Solon, Ohio) at amplitude setting of about 6 for about 3 repetitions of about 1 minute. Cells were chilled on ice for about 5 minutes between repetitions. Samples were centrifuged at about 10,000×g for about 10 minutes at 4° C. Recovered supernatants were used in the XI enzyme activity assay. XI enzyme activity was performed as described in the materials and methods. Results are shown in Table 3.

TABLE 3

XI activity at pH 7.5

| SEQ ID NO: | Volumetric Activity | FIOPC |
|---|---|---|
| 2 | −60.73 | 2.58 |
| 4 | −21.84 | 0.93 |
| 6 | 0.86 | −0.05 |
| 8 | −2.14 | 0.12 |
| 10 | −2.38 | 0.13 |
| 12 | −12.82 | 0.54 |
| 14 | −26.97 | 1.45 |
| 16 | −76.50 | 4.12 |
| 18 | −15.32 | 0.83 |
| 20 | −5.33 | 0.29 |
| 22 | 0.48 | −0.03 |
| 24 | 0.36 | −0.02 |
| 26 | 0.81 | −0.04 |
| 28 | −6.65 | 0.36 |
| 30 | −9.10 | 0.49 |
| 32 | −38.10 | 2.05 |
| 34 | −21.76 | 1.17 |
| 36 | −13.82 | 0.59 |
| 38 | −17.58 | 0.75 |
| 40 | −12.34 | 0.52 |
| 42 | −74.88 | 3.18 |
| 44 | −37.10 | 1.57 |

TABLE 3-continued

XI activity at pH 7.5

| SEQ ID NO: | Volumetric Activity | FIOPC |
|---|---|---|
| 46 | −35.57 | 1.51 |
| 48 | −24.69 | 1.05 |
| 50 | −32.23 | 1.37 |
| 52 | −26.72 | 1.13 |
| 54 | −90.79 | 3.85 |
| 56 | −39.89 | 1.69 |
| 58 | −74.26 | 3.15 |
| 60 | −11.91 | 0.64 |
| 62 | −15.43 | 0.83 |
| 64 | −12.98 | 0.70 |
| 66 | −27.45 | 1.48 |
| 68 | −29.43 | 1.59 |
| 70 | −4.54 | 0.24 |
| 72 | −8.93 | 0.48 |
| 74 | −0.20 | 0.01 |
| 76 | −0.33 | 0.02 |
| 78 | −50.55 | 2.15 |
| 80 | −57.13 | 2.42 |
| 82 | −58.09 | 2.47 |
| 84 | −46.42 | 1.97 |
| 86 | −35.95 | 1.53 |
| 88 | −2.16 | 0.09 |
| 90 | −32.77 | 1.39 |
| 92 | −30.82 | 1.31 |
| 94 | −8.16 | 0.35 |
| 96 | −46.18 | 1.96 |
| 98 | −30.05 | 1.28 |
| 100 | −8.40 | 0.45 |
| 102 | −8.34 | 0.45 |
| 104 | −3.80 | 0.20 |
| 106 | −4.81 | 0.26 |
| 108 | −12.06 | 0.65 |
| 110 | −6.10 | 0.33 |
| 112 | −7.71 | 0.42 |
| 114 | −4.17 | 0.22 |
| 116 | −7.07 | 0.38 |
| 118 | −13.50 | 0.73 |
| 120 | −1.15 | 0.06 |
| 122 | 0.03 | 0.00 |
| 124 | −4.41 | 0.24 |
| 126 | −0.85 | 0.05 |
| 128 | −14.60 | 0.79 |
| 130 | −17.26 | 0.93 |
| 132 | −0.75 | 0.04 |
| 134 | −11.55 | 0.62 |
| 136 | −7.20 | 0.39 |
| 138 | 0.16 | −0.01 |
| 140 | −3.63 | 0.20 |
| 142 | −3.63 | 0.20 |
| 144 | −1.20 | 0.06 |
| 146 | −16.77 | 0.90 |
| 148 | −2.00 | 0.11 |
| 150 | −1.40 | 0.08 |
| 152 | −3.63 | 0.20 |
| 154 | −7.09 | 0.38 |
| 156 | −0.96 | 0.05 |
| 158 | −2.79 | 0.15 |
| 160 | −3.23 | 0.17 |
| 162 | −10.17 | 0.55 |
| 164 | −0.51 | 0.03 |
| 166 | −3.43 | 0.19 |
| 168 | −5.65 | 0.30 |
| 170 | −2.35 | 0.13 |
| 172 | −1.20 | 0.06 |
| 174 | −2.29 | 0.12 |
| 176 | −1.92 | 0.08 |
| Op-XI (ABD) | −23.56 | NA |
| Op-XI (SBD) | −18.55 | NA |
| Vo-ctrl | −1.74 | NA |

EXAMPLE 6

Growth of Yeast Containing XI Clones on Xylose

Figure 4:
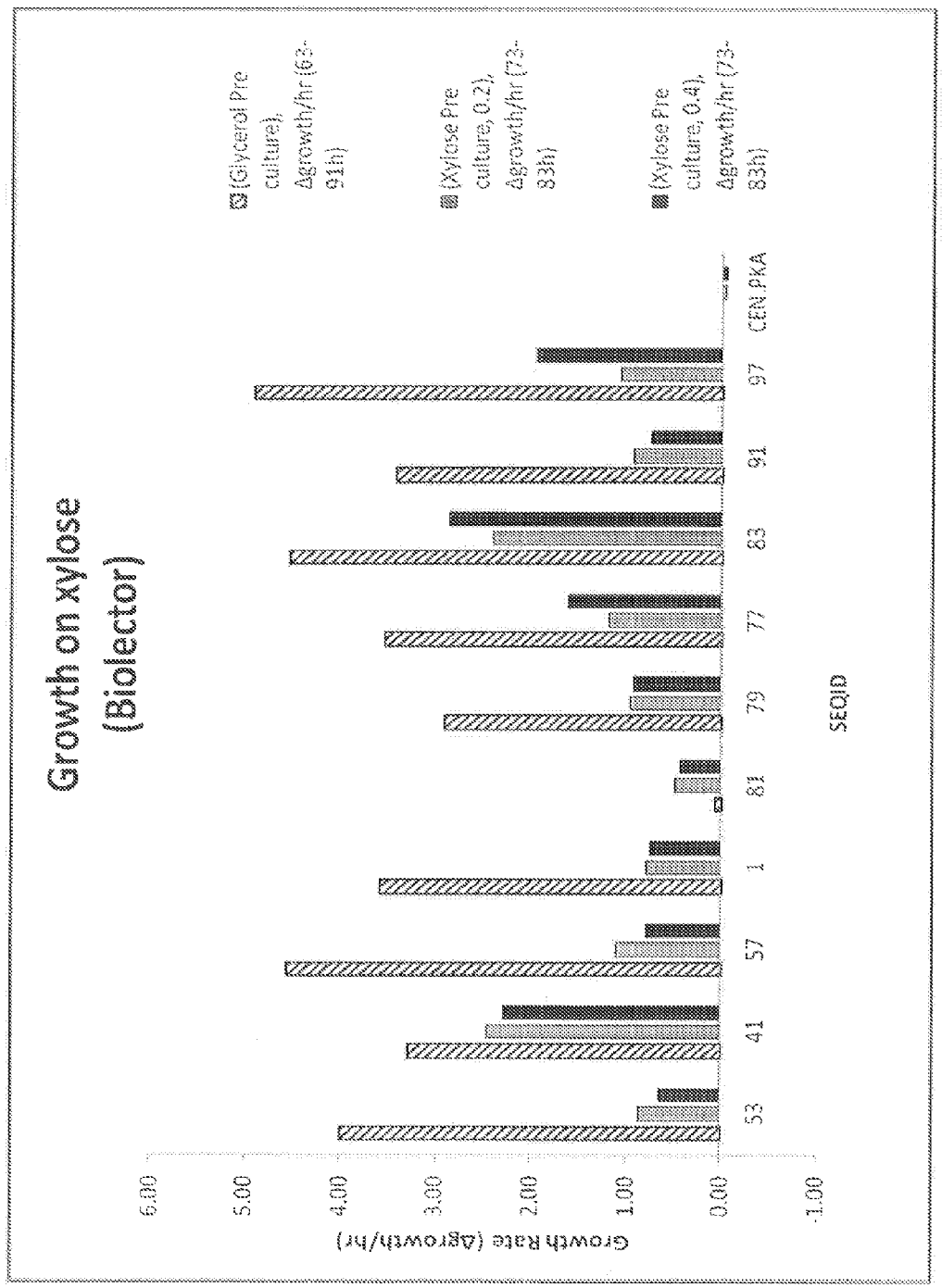
FIG. 4 shows the growth rates on xylose containing media of selected clones expressed in yeast strain, *Saccharomyces cerevisiae* CEN.PK2-1Ca (ATCC: MYA1108).

A subset of the XI genes from Example 5 were expressed in *Saccharomyces cerevisiae* CEN.PK2-1Ca (ATCC: MYA1108) and assayed for ability to confer the ability to grow on xylose. This assay was carried out as follows: colonies were isolated on SC-ura+2% glucose agar plates and inoculated into about 3 ml "pre-cultures" of both SC-ura 2% glycerol and SC-ura 2% xylose media, incubated at about 30° C., about 220 rpm, overnight. Cells were harvested by centrifugation (about 100×g, 5 minutes), supernatant discarded and washed twice and resuspended in about 1 ml of SC-ura 2% xylose. Cells were inoculated into Biolector plates, containing SC-ura, 2% xylose, and inoculums were normalized to two different starting optical densities of about OD600 0.2 and 0.4. Plates were covered using gas permeable seals and incubated in a BioLector microfermentation device (m2p-labs, Model G-BL100) at about 30° C. for about 4 days at 800 rpm and 90% humidity. Growth readings from the Biolector were acquired for 60-100 hours according to manufacturer's recommendations. Results are shown in FIG. 4.

EXAMPLE 7

Ethanol Production Under Anaerobic Conditions

A subset of the XI expressing yeast clones in strain *Saccharomyces cerevisiae* CEN.PK2-1Ca (ATCC: MYA1108) were assayed for ability to ferment xylose to ethanol (EtOH). In brief, single colonies were inoculated into about 25 ml of SC-ura medium supplemented with about 0.1% glucose and about 3% xylose. Cultures were incubated under microaerobic conditions at about 30° C. and about 200 rpm. Samples were harvested at about 0, 24, 48, 72 h, and ethanol concentration determined via HPLC standard assays. Ethanol productivity was calculated, and listed in units of grams of EtOH-per liter per hour, and FIOPC was generated comparing productivity of the control Op-XI. Results are shown in Table 4.

TABLE 4

Anaerobic EtOH Production.

| | Time (h) | | | | EtOH | |
| SEQ ID NO: | 0 | 24 | 48 | 72 | (g/L/h) | FIOPC |
|---|---|---|---|---|---|---|
| 6 | 0.28 | 0 | 0 | 0 | −0.004 | −0.5 |
| 8 | 0 | 0 | 0 | 0 | 0.000 | 0.0 |
| 10 | 0 | 0 | 0 | 0 | 0.000 | 0.0 |
| 14 | 0.37 | 0.28 | 0.71 | 1.24 | 0.013 | 1.7 |
| 16 | 0.33 | 0.275 | 0.72 | 1.06 | 0.011 | 1.4 |
| 18 | 0.29 | 0.135 | 0.31 | 0.595 | 0.005 | 0.6 |
| 20 | 0.33 | 0 | 0 | 0 | −0.004 | −0.5 |
| 22 | 0.32 | 0 | 0 | 0 | −0.004 | −0.5 |
| 24 | 0.28 | 0 | 0 | 0 | −0.004 | −0.5 |
| 26 | 0.26 | 0 | 0 | 0 | −0.003 | −0.4 |
| 28 | 0.23 | 0.385 | 1.015 | 1.54 | 0.019 | 2.5 |
| 30 | 0.27 | 0 | 0 | 0.07 | −0.003 | −0.3 |
| 32 | 0 | 0.165 | 0.48 | 0.815 | 0.012 | 1.5 |
| 34 | 0 | 0.125 | 0.33 | 0.615 | 0.009 | 1.1 |
| 36 | 0 | 0 | 0 | 0 | 0.000 | 0.0 |
| 46 | 0 | 0.285 | 0.905 | 1.625 | 0.023 | 3.0 |
| 60 | 0.45 | 0.35 | 0.87 | 1.39 | 0.014 | 1.8 |
| 62 | 0 | 0 | 0 | 0.065 | 0.001 | 0.1 |
| 64 | 0.38 | 0.275 | 0.735 | 1.18 | 0.012 | 1.6 |
| 66 | 0 | 0 | 0.12 | 0.22 | 0.003 | 0.4 |

TABLE 4-continued

Anaerobic EtOH Production.

| SEQ ID NO: | Time (h) | | | | EtOH | |
| --- | --- | --- | --- | --- | --- | --- |
| | 0 | 24 | 48 | 72 | (g/L/h) | FIOPC |
| 68 | 0 | 0.05 | 0.275 | 0.5 | 0.007 | 0.9 |
| 70 | 0 | 0 | 0 | 0 | 0.000 | 0.0 |
| 72 | 0.119 | 0 | 0.054 | 0.1685 | 0.001 | 0.1 |
| 74 | 0.21 | 0.11 | 0.275 | 0.57 | 0.005 | 0.7 |
| 76 | 0.28 | 0 | 0 | 0 | −0.004 | −0.5 |
| 90 | 0 | 0.24 | 0.69 | 1.09 | 0.016 | 2.0 |
| 100 | 0.104 | 0.642 | 0.141 | 0.366 | 0.001 | 0.2 |
| 102 | 0.185 | 0 | 0 | 0.054 | −0.002 | −0.2 |
| 104 | 0.235 | 0.536 | 0 | 0 | −0.005 | −0.7 |
| 106 | 0.188 | 0.4835 | 0 | 0 | −0.004 | −0.6 |
| 108 | 0.19 | 0.5855 | 0.1455 | 0.313 | 0.000 | 0.0 |
| 110 | 0.3 | 0 | 0 | 0.05 | −0.003 | −0.4 |
| 112 | 0.19 | 0.5535 | 0.106 | 0.1135 | −0.003 | −0.4 |
| 114 | 0.174 | 0 | 0 | 0 | −0.002 | −0.3 |
| 116 | 0.15 | 0 | 0.0515 | 0.211 | 0.001 | 0.1 |
| 118 | 0.177 | 0.7075 | 0.5065 | 0.941 | 0.009 | 1.1 |
| 120 | 0.153 | 0 | 0 | 0 | −0.002 | −0.2 |
| 122 | 0.169 | 0.553 | 0 | 0.074 | −0.003 | −0.5 |
| 124 | 0.125 | 0 | 0 | 0 | −0.002 | −0.2 |
| 126 | 0.32 | 0 | 0 | 0 | −0.004 | −0.5 |
| 128 | 0 | 0 | 0 | 0 | 0.000 | 0.0 |
| 130 | 0 | 0 | 0 | 0 | 0.000 | 0.0 |
| 132 | 0.121 | 0 | 0 | 0 | −0.002 | −0.2 |
| 134 | 0.118 | 0 | 0 | 0.1105 | 0.000 | 0.0 |
| 136 | 0.108 | 0 | 0 | 0 | −0.001 | −0.2 |
| 138 | 0.172 | 0.513 | 0 | 0 | −0.004 | −0.6 |
| 140 | 0.17 | 0.542 | 0 | 0.3135 | 0.000 | −0.1 |
| 142 | 0.102 | 0 | 0 | 0 | −0.001 | −0.2 |
| 144 | 0.28 | 0 | 0 | 0 | −0.004 | −0.5 |
| 146 | 0.103 | 0.635 | 0.263 | 0.563 | 0.004 | 0.5 |
| 150 | 0.27 | 0 | 0 | 0 | −0.003 | −0.4 |
| 149 | 0.27 | 0 | 0 | 0 | −0.003 | −0.4 |
| 152 | 0.17 | 0 | 0 | 0 | −0.002 | −0.3 |
| 154 | 0.23 | 0 | 0 | 0 | −0.003 | −0.4 |
| 156 | 0.23 | 0 | 0. | 0 | −0.003 | −0.4 |
| 158 | 0.4 | 0 | 0.105 | 0.23 | −0.002 | −0.2 |
| 160 | 0.38 | 0 | 0 | 0 | −0.005 | −0.6 |
| 162 | 0.36 | 0.055 | 0.23 | 0.41 | 0.001 | 0.2 |
| 164 | 0.32 | 0 | 0 | 0 | −0.004 | −0.5 |
| 166 | 0.31 | 0 | 0 | 0 | −0.004 | −0.5 |
| 168 | 0.32 | 0 | 0.295 | 0.6 | 0.005 | 0.6 |
| 170 | 0.164 | 0.4995 | 0 | 0 | −0.004 | −0.5 |
| 172 | 0.27 | 0 | 0 | 0 | −0.003 | −0.4 |
| 174 | 0.3 | 0 | 0.17 | 0.345 | 0.001 | 0.2 |
| OP-XI (pos) | 0.2385 | 0.5875 | 0.6965 | 0.81508 | 0.008 | NA |
| Host-(neg) | 0.23625 | 0.088125 | 0 | 0 | −0.003 | NA |

EXAMPLE 8

Impact of PH on XI Activity

Extracts from strain *Saccharomyces cerevisiae* CEN.PK2-1Ca (ATCC: MYA1108, expressing XI gene candidates in vector p426PGK1, were prepared as described in the Materials and Methods and assayed for XI activity at pH 7.5 and pH 6.0. Percent activity listed was calculated by dividing the VA at pH 6 by the VA at pH 7.5 and multiplying by 100. Results are listed in Table 5.

TABLE 5

XI activity at pH 6 and pH 7.5

| SEQ ID NO: | Organism Classification | VA, pH 6 (U/ml) | VA, pH 7.5 (U/ml) | Percent activity (pH 6) |
| --- | --- | --- | --- | --- |
| 2 | Bacteroidales | 1.92 | 2.59 | 74% |
| 14 | Bacteroides | 0.32 | 0.98 | 32% |
| 16 | Bacteroides | 1.16 | 2.40 | 48% |
| 32 | Bacteroides | 1.17 | 2.21 | 53% |
| 38 | Firmicutes | 2.46 | 2.77 | 89% |
| 42 | Firmicutes | 1.71 | 2.18 | 79% |
| 44 | Firmicutes | 0.19 | 0.25 | 76% |
| 46 | Firmicutes | 1.49 | 1.95 | 76% |
| 50 | Firmicutes | 0.81 | 0.95 | 86% |
| 52 | Firmicutes | 0.02 | 0.08 | 26% |
| 54 | Neocallimastigales | 1.46 | 2.90 | 51% |
| 58 | Neocallimastigales | 1.89 | 3.05 | 62% |
| 68 | Neocallimastigales | 1.50 | 1.97 | 76% |
| 72 | Neocallimastigales | 0.57 | 1.04 | 55% |
| 78 | Prevotella | 2.40 | 3.61 | 67% |
| 80 | Prevotella | 1.52 | 2.29 | 66% |
| 82 | Prevotella | 1.48 | 1.65 | 89% |
| 84 | Prevotella | 1.79 | 2.96 | 61% |
| 96 | Prevotella | 2.13 | 3.56 | 60% |
| 116 | Prevotella | 0.06 | 0.13 | 47% |
| Host-neg | | 0.04 | 0.02 | NA |
| Op-XI | | 0.61 | 1.25 | 49% |

EXAMPLE 9

$K_M$ for Selected XI Clones

The $K_m$ and $V_{max}$ at pH 6 were determined for a subset of the XI clones, expressed on p426PGK1 vector in *Saccharomyces cerevisiae* CEN.PK2-1Ca (ATCC: MYA1108), using the XI activity assay described in the Materials and Methods and varying the concentrations of xylose from about 40-600 mM. Results shown are calculated using the Hanes Plot, which rearranges the Michaelis-Menten equation ($v=V_{max}[S]/(K_m+[S])$) as: ($[S]/v=K_m/V_{max}+[S]/V_{max}$), where plotting $[S]/v$ against $[S]$, resulting in a straight line and where the y intercept$=K_m/V_{max}$, the slope$=1/V_{max}$, and the x intercept$=-K_m$. Results are listed in Table 6.

TABLE 6

$K_m$ determination for 3 XIs

| SEQ ID NO: | $K_m$ | $V_{max}$ |
| --- | --- | --- |
| 78 | 35.2 | 27.6 |
| 96 | 33.7 | 28.0 |
| 38 | 28.8 | 28.6 |

EXAMPLE 10

Figure 5A:
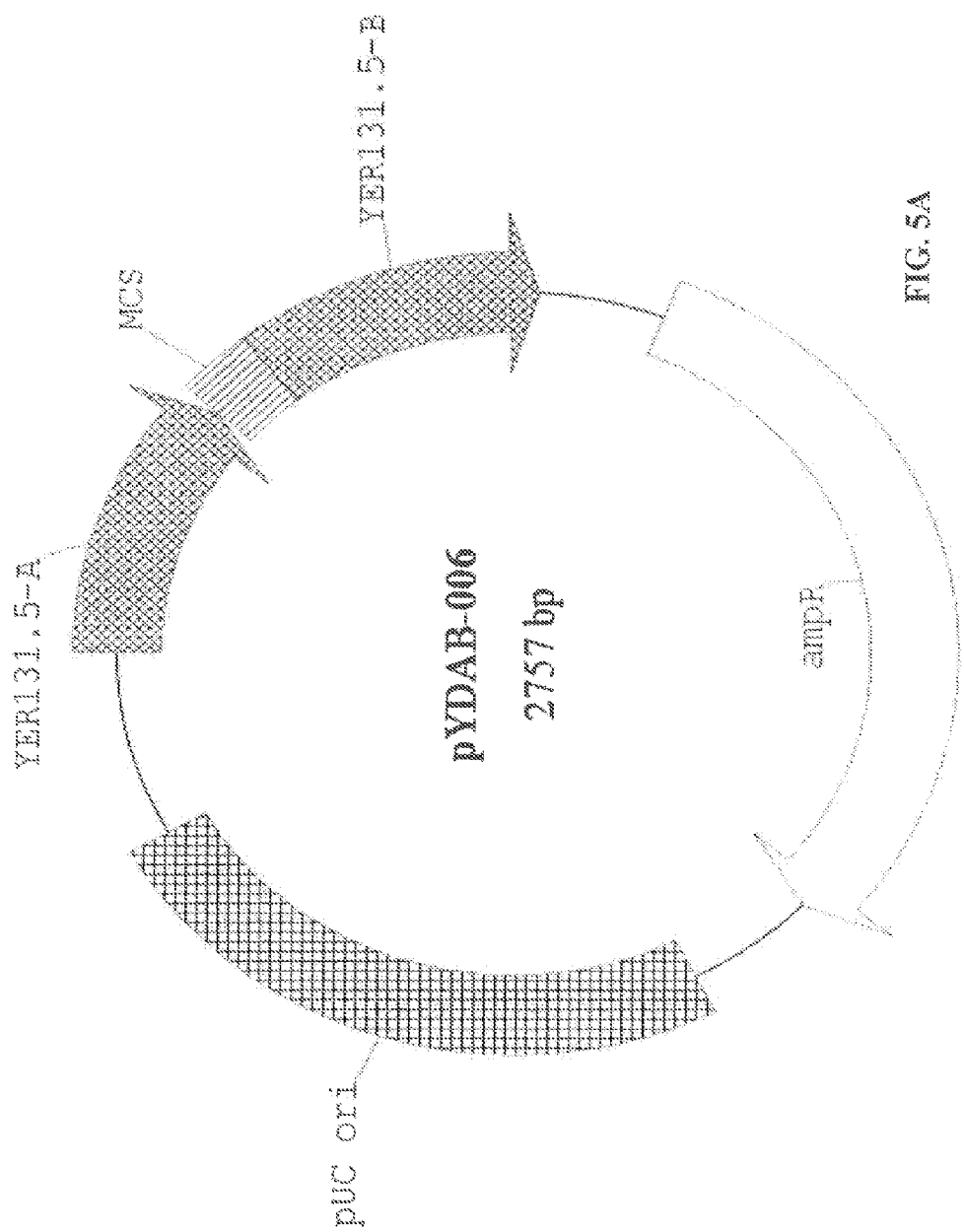
FIGS. 5A-5D are maps for the vectors pYDAB-006, pYDURA01, pYDPt-005 and pYDAB-0006, respectively, all used in creating strains of industrial *S. cerevisiae* strain yBPA130 with a single genomic copy of select XI clones.

Quantification of XI Activity Expressed from Single Genomic Integration Locus A vector named pYDAB006 (FIG. 5A) for integration into locus YER131.5 (between YER131W and YER132C) in the *S. cerevisiae* genome was constructed using conventional cloning methods. The vector backbone with a PacI site at each end was derived from pBluescript II SK (+) (Agilent Technologies, Inc. Santa Clara, Calif.) by standard PCR techniques, which contained only the pUC origin of replication and bla gene encoding ampicillin resistance protein as a selectable marker. Two 300-base pair segments named YER131.5-A and YER 131.5-B were amplified from yeast genomic DNA by standard PCR techniques and connected with a multiple cloning site (MCS 1: 5'-GGCGCGCCTCTA-GAAAGCTTACGCGTGAGCTCCCTGCAGGGATATCG-GTACCG CGGCCGC-3' (SEQ ID NO:181)) using the overlapping PCR technique. The PCR primers used in the overlapping PCR are shown in Table 7 below:

TABLE 7

Primers Used in pYDAB006 Construction

| Primer | SEQ ID NO: | Sequence (PacI site is underlined) |
|---|---|---|
| 131.5AF | 182 | caccattaattaaAGCTTTGTAAATATGATGAGAGAATAATATAAATCAAACG |
| 131.5AR | 183 | GGCGCGCCTCTAGAAAGCTTAATCGACAAGAACACTTCTATTTATATAGGTATGAAA |
| 131.5BF | 184 | GCAGGGATATCGGTACCCACCAGCGGCCGCTGAAGAAGGTTTATTTCGTTTCGCTGT |
| 131.5BR | 185 | caccattaattaaCCCAGGTGAGACTGGATGCTCCATA |
| ABMCSF | 186 | GCCTCTAGAAAGCTTACGCGTGAGCTCCCTGCAGGGATATCGGTACCCACCAGCGGCCGC |
| ABMCSR | 187 | CGCTGGTGGGTACCGATATCCCTGCAGGGAGCTCACGCGTAAGCTTTCTAGAGGCGCGCC |

The overlapping PCR product was then ligated with the vector backbone resulting in plasmid pYDAB006.

Figure 5B:
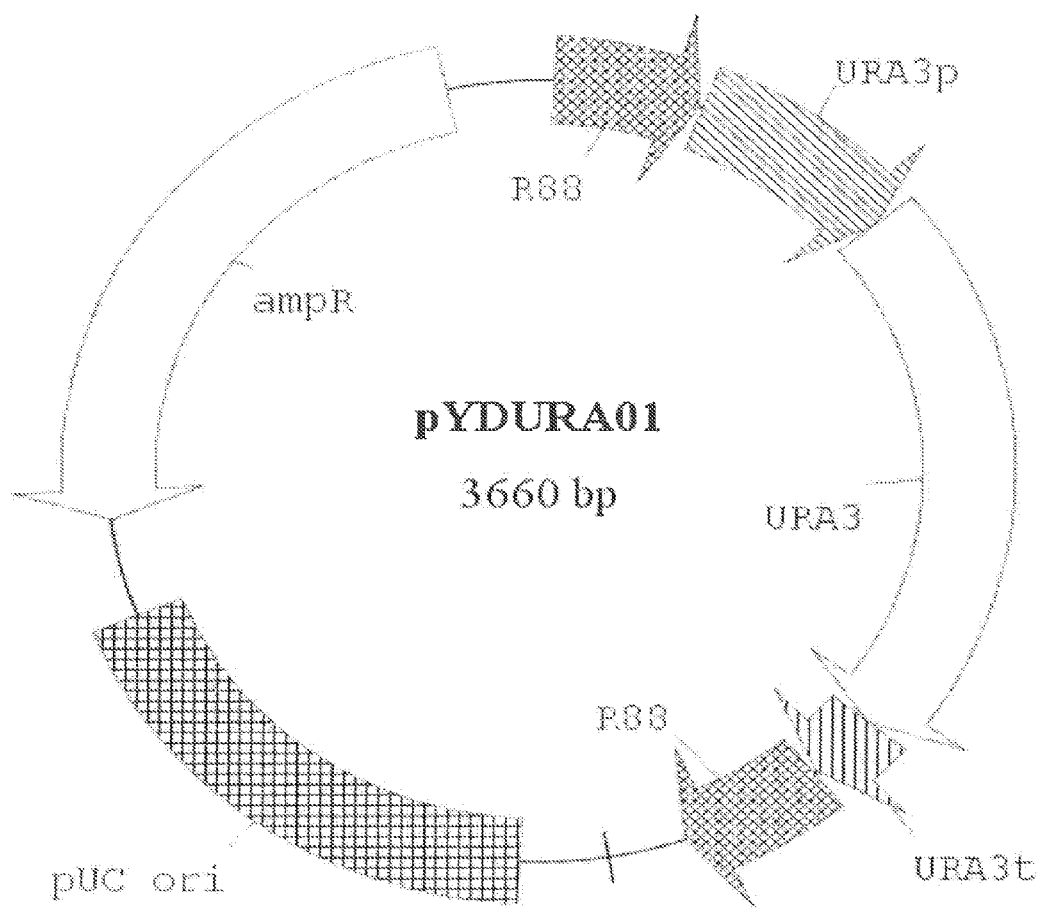

A vector named pYDURA01 (FIG. 5B) for generating yeast selectable and recyclable marker was constructed using similar method as pYDAB006. The URA3 expression cassette was amplified from yeast genomic DNA by standard PCR techniques. The 200 base pair fingerprint sequence (named R88:

```
                                    (SEQ ID NO: 188))
TGCGTGTGCCGCGAGTCCACGTCTACTCGCGAACCGAGTGCAGGCGGGTC

TTCGGCCAGGACGGCCGTGCGTGACCCCGGCCGCCAGACGAAACGGACC
```

-continued
```
GCGCTCGCCAGACGCTACCCAGCCCGTTCATGCCGGCCGCGAGCCGACC

TGTCTCGGTCGCTTCGACGCACGCGCGGTCCTTTCGGGTACTCGCCTAA

GAC
``` at both sides of URA3 cassette was amplified by standard PCR techniques from the genomic DNA of yBPA317, which was a diploid strain having genotypes MATa/MATalpha; URA3/ura3; YDL074.5::P(TDH3)-CBT1-T(CYC1)-R88 YLR388.5::P(TDH3)-StBGL-T(CYC1)-R88/YLR388.5::P(TDH3)-StBGL-T(CYC1)-R88. The primers used in the amplification are described in Table 8 below:

TABLE 8

Primers Used in pYDURA01 Construction

| Primer | SEQ ID NO: | Sequence (KpnI and NotI sites are underlined) |
|---|---|---|
| NotI-KpnI-R88-F | 189 | caatagcggccgcggtaccTGCGTGTGCCGCGAGTCCAC |
| R88-BamHI-R | 190 | TGTTAGGATCCGTCTTAGGCGAGTACCCGAAAGG |
| BamHI-ura-F | 191 | caataggatccAGGCATATTTATGGTGAAGAATAAGT |
| ura-Xho-R | 192 | TGTTACTCGAGAAATCATTACGACCGAGATTCCCG |
| XhoI-R88-F | 193 | caatactcgagTGCGTGTGCCGCGAGTCCAC |
| R88-NotI-R | 194 | TGTTAGCGGCCGCGTCTTAGGCGAGTACCCGAAAGG |

Figure 5C:
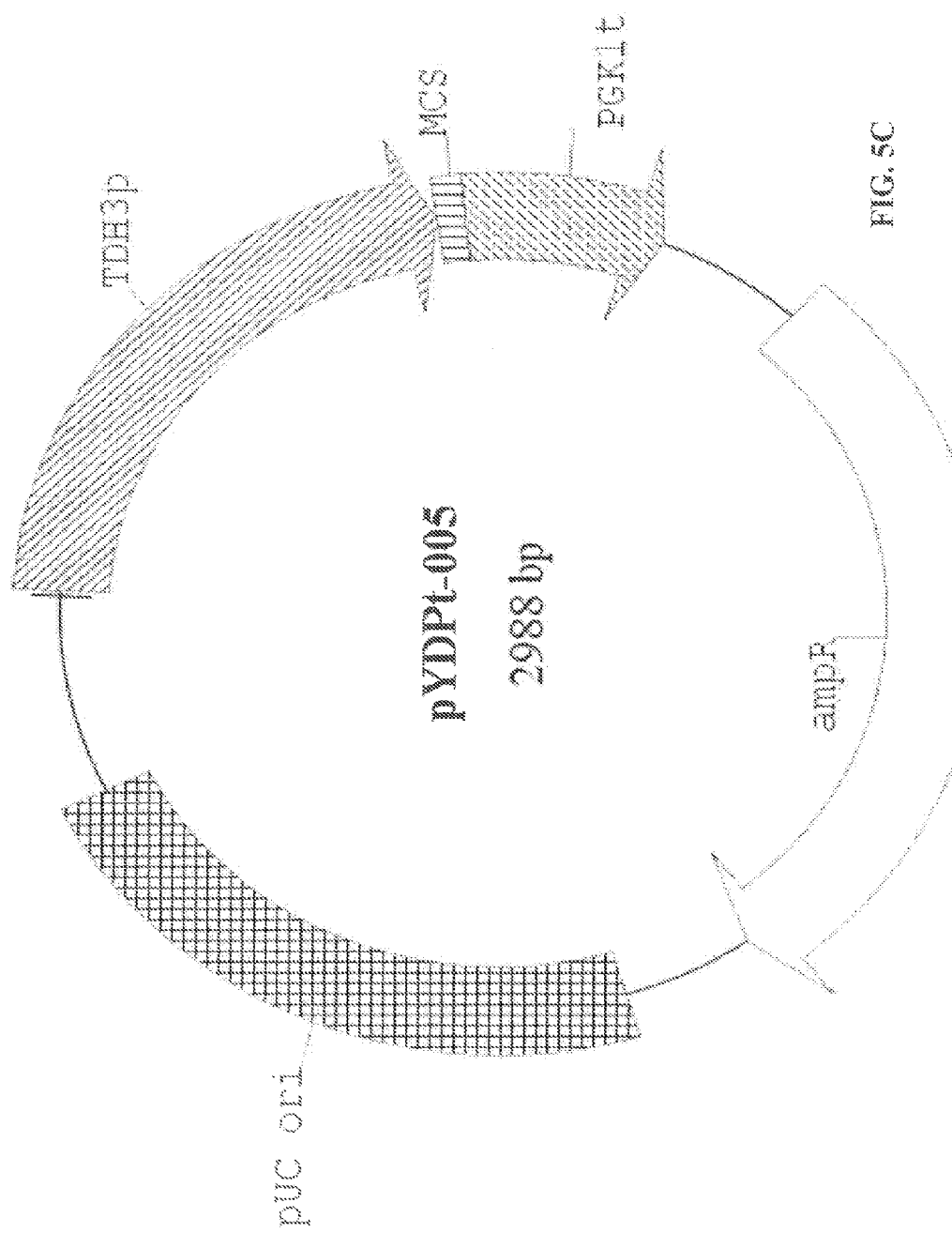

An expression cassette was generated for the XI genes by cloning into a vector named pYDPt005 (FIG. 5C). pYDPt005 was generated using similar method as pYDAB006. It contained a TDH3 promoter and a PGK1 terminator flanking a multiple cloning site (MCS 2: 5'-ACT<u>AGT</u>GGATCCCT<u>CGAG</u>GTCGAC<u>GTTTAAAC</u>-3' (SEQ ID NO:195), where single underline is SpeI site, double underline is XhoI site, and jagged underline is PmeI site). The promoter and the terminator were amplified from *S. cerevisiae* genomic DNA; an AscI site was added to the 5' end of the TDH3 promoter while a Kpn1 site was added to the 3' end of the PGK1 terminator during amplification. Primers used in the amplification are described in Table 9.

TABLE 9

Primers Used in pYDPt005 Construction

| Primer | SEQ ID NO: | Sequence (AscI and KpnI sites are underlined) |
|---|---|---|
| TDH-F | 196 | CACCA<u>GGCGCGCC</u>TCTAGAAAGCTTACGCGTAGTTTATCATTATCAATACTGCCATTTCAAAGA |
| overlap-TDH-R | 197 | AACGTCGACCTCGAGGGATCCACTAGTTCGAAACTAAGTTCTTGGTGTTTTAAAACT |
| overlap-PGK-F | 198 | GTGGATCCCTCGAGGTCGACGTTTAAACATTGAATTGAATTGAAATCGATAGATCAAT |
| PGK-R | 199 | CACCAGCGGCCGC<u>GGTACC</u>GATATCCCTGCAGGGAGCTCGAAATATCGAATGGGAAAAAAAAACTGGAT |

Figure 5D:
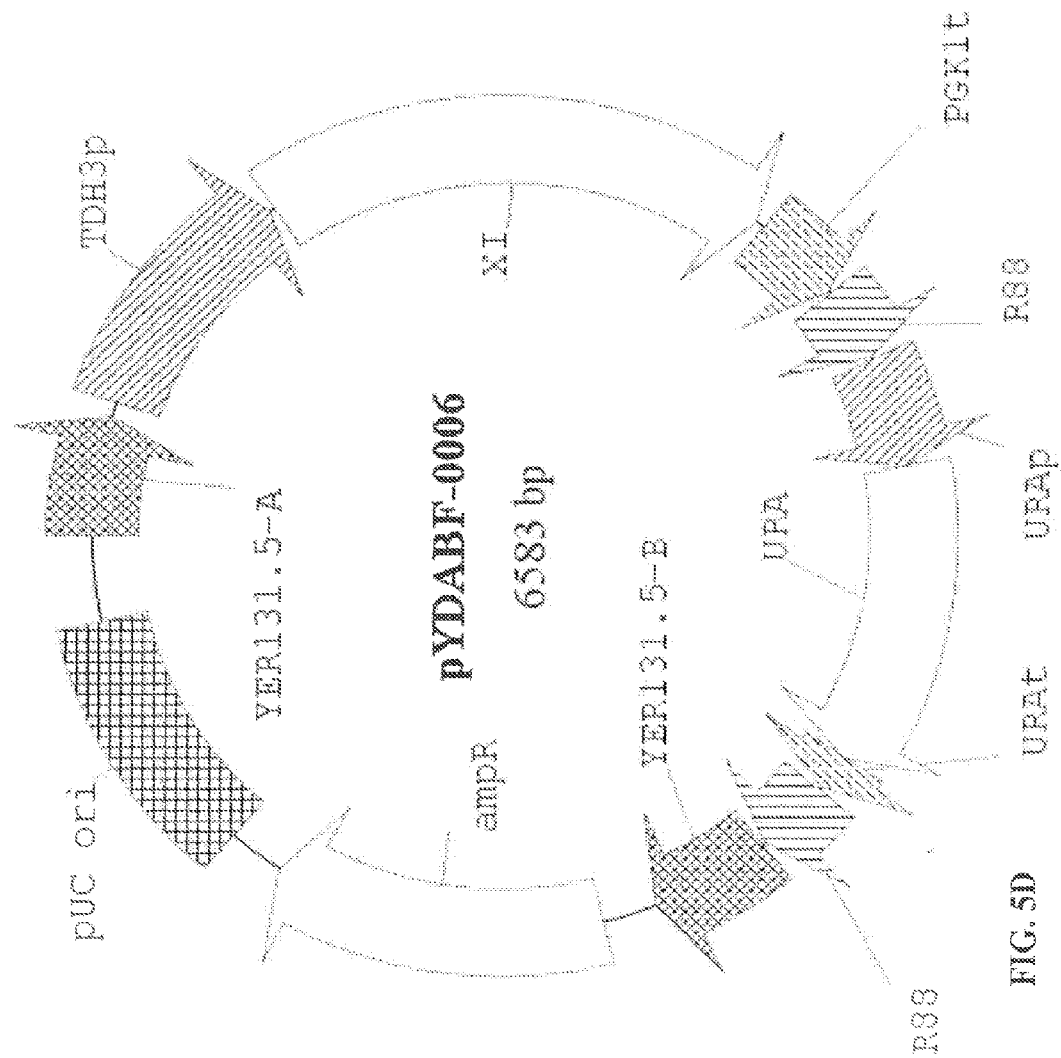

An *Orpinomyces* sp. XI gene (NCBI:169733248) was cloned in this vector between the SpeI and XhoI sites. The *Orpinomyces* sp. XI expression cassette and R88-Ura-R88 fragment were then cloned into vector pYDAB006 using AscI, KpnI and NotI sites; the resulting plasmid was named pYDABF006 (FIG. 5D). Subsequently, the *Orpinomyces* sp. XI gene in pYDABF0006 was replaced with a subset of the XI genes of Table 2 by digestion of pYDABF0006 with SpeI and PmeI and ligation to a DNA fragment encoding the appropriate XI sequence which had been amplified from p426PGK1-XI constructs. A SpeI site followed by a Kozak-like sequence (6 consecutive adenines) was added immediately in front of the start codon of the XI genes while a Pme1 site was added to the 3' end of the XI genes during amplification.

XI gene integration cassettes were extracted by PacI digestion and used to transform yeast strain yBPA130 using standard techniques. Transformants were selected for growth on SC-Ura (Synthetic Complete, Ura dropout) agar plates. Integration position and existence of XI cassette in transformants was confirmed by PCR using the primers shown in Table 10.

TABLE 10

Primers Used in Integration Verification

| Primer | SEQ ID NO: | Sequence |
|---|---|---|
| 5' of integration | 200 | ACAGGGATAACAAAGTTTCTCCAGC |
| 3' of integration | 201 | CATACCAAGTCATGCGTTACCAGAG |
| 5' of R88-ura-R88 | 202 | TTTCCCATTCGATATTTCGAGCTCC |
| 3' of integration | 203 | CATACCAAGTCATGCGTTACCAGAG |

Confirmed clones were then grown about 18 hours in liquid YPD to allow looping out of the URA3 marker and were selected for growth on SC+5-FOA agar plate. The absence of the URA3 marker was confirmed by PCR.

Strains containing the confirmed XI expression cassettes were inoculated into about 3 ml of modified YP Media (YP+0.1% Glucose+3.0% Xylose) and incubated overnight at about 30° C. and about 220 rpm. These overnight cultures were subcultured into about 25 ml of the same media to about $OD_{600}$=0.2. Samples were incubated overnight at about 30° C. and about 220 rpm. Cultures were harvested when $OD_{600}$ was between about 3 and 4. Pellets were collected by centrifugation for about 5 minutes at about 4000 rpm. The supernatant was discarded and pellets washed with about 25 ml of distilled-deionized water and centrifuged again using the same conditions. Supernatant was discarded and the pellet frozen at about −20° C. until lysis and characterization.

Cell pellets were thawed and about 200 mg of each pellet sample was weighed out into 2 ml microcentrifuge tubes. About 50 µl of Complete®, EDTA-free Protease Inhibitor cocktail (Roche Part#11873 580 001) at 5 times the concentration stated in the manufacturer's protocol was added to each sample. To this was added about 0.5 ml of Y-PER Plus® Dialyzable Yeast Protein Extraction Reagent (Thermo Scientific Part#78999) (YP+) to each sample. Samples were incubated at about 25° C. for about 4 hours on-rotating mixer. Sample supernatants were collected after centrifugation at about 10,000×g for about 10 minutes for characterization.

Total protein concentrations of the XI sample extracts prepared above were carried out using Bio-Rad Protein Assay Dye Reagent Concentrate (Bio-Rad, cat#500-0006, Hercules Calif.) which is a modified version of the Bradford method (Bradford).

Yeast physiological pH ranges are known to range from about pH 6 to about pH 7.5 (Pena, Ramirez et al., 1995, J. Bacteriology 4:1017-1022). Ranking of XI activity at yeast physiological pH was accomplished using the assay conditions at pH 7.5 and modified for pH 6.0 as described in the materials and methods. The specific activities of 20 XIs when expressed from a single copy integrated into the yeast YER131.5 locus were evaluated. The results are listed in Table 11.

TABLE 11

SA of XI Expressed in an Industrial *S. cerevisiae*

| SEQ ID NO: | Organism Classification | SA, pH6 (U/mg) | SA, pH 7.5 (U/mg) |
|---|---|---|---|
| 2 | *Bacteroidales* | 0.86 | 1.08 |
| 14 | *Bacteroides* | 0.33 | 1.07 |
| 16 | *Bacteroides* | 0.57 | 1.05 |
| 32 | *Bacteroides* | 0.53 | 1.00 |
| 38 | *Firmicutes* | 1.00 | 0.94 |
| 42 | *Firmicutes* | 0.79 | 0.82 |
| 44 | *Firmicutes* | 0.08 | 0.10 |
| 46 | *Firmicutes* | 0.62 | 0.69 |
| 50 | *Firmicutes* | 0.35 | 0.41 |
| 52 | *Firmicutes* | 0.01 | 0.03 |
| 54 | *Neocallimastigales* | 0.64 | 1.17 |
| 58 | *Neocallimastigales* | 0.79 | 1.10 |
| 68 | *Neocallimastigales* | 0.01 | 0.02 |
| 72 | *Neocallimastigales* | 0.22 | 0.40 |
| 78 | *Prevotella* | 1.10 | 1.45 |
| 80 | *Prevotella* | 0.74 | 1.11 |
| 82 | *Prevotella* | 0.54 | 0.60 |
| 84 | *Prevotella* | 0.76 | 1.06 |
| 96 | *Prevotella* | 1.10 | 1.62 |
| 116 | *Prevotella* | 0.03 | 0.06 |
| Host neg ctrl | | 0.00 | 0.02 |

EXAMPLE 11

Identification of Sequence Motifs in Acid Tolerant XIs

The proposed mechanism of xylose isomerases can be summarized as follows: (i) binding of xylose to xylose isomerase, so that O3 and O4 are coordinated by metal ion I; (ii) enzyme-catalyzed ring opening (the identity of the ring-opening group remains a subject for further investigation; ring opening may be the rate limiting step in the overall isomerization process); (iii) chain extension (sugar binds in a linear extended form) in which O2 and O4 now coordinate metal ion I; (iv) O2 becomes deprotonated causing a shift of metal ion II from position 1 to an adjacent position 2 in which it coordinates O1 and O2 of the sugar together with metal ion I; (v) isomerization via an anionic transition state arises by a hydride shift promoted by electrophilic catalysis provided by both metal ions; (vi) collapse of transition state by return of metal ion II to position 1; (vii) chain contraction to a pseudo-cyclic position with ligands to metal ion I changing from O2/O4 back to O3/O4; (viii) enzyme-catalyzed ring closure; (ix) dissociation of xylulose from xylose isomerase (Lavie et al., 1994, Biochemistry 33(18), 5469-5480).

Many XIs identified contained one or both of two signature sequences characteristic of XIs, [LI]EPKP.{2}P (SEQ ID NO:204) and [FL]HD[^K]D[LIV].[PD].[GDE](SEQ ID NO:205). Additional sequence motifs present in the top performing Firmicutes and *Prevotella* XIs were identified. The motifs are located near the active site including residues in direct contact with the D-xylose and/or the metal ions. The motifs are shown in Table 12 below:

TABLE 12

XI Sequence Motifs

| XI Source | Motif | Sequence | SEQ ID NO: |
|---|---|---|---|
| Firmicutes | 1A | P[FY][AST][MLVI][AS][WYFL]W[HT]N[LFMG]GA | 206 |
| Firmicutes | 1B | P[FY][AS].{2}[WYFL]W[HT][^TV].GA | 207 |
| Firmicutes | 2 | [GSN][IVA]R[YFHG][FYLIV]C[FW]HD.D | 208 |
| Firmicutes | 3 | T[ASTC][NK][^L]F.[NDH][PRKAG][RVA][FY]C | 209 |
| Firmicutes | 4 | [WFY]D[TQVI]D.[FY][PF][^T].{2, 4}[YFH]S[ATL]T | 210 |
| Firmicutes | 5 | GF[NH]FD[SA]KTR | 211 |
| Prevotella | 1A | FG.QT[RK].{2}E[WYF][DNG].{2, 3}[DNEGT][AT] | 212 |
| Prevotella | 1B | FG.QT[RK].{2}E[WYF][DNG].{3}[^C][AP] | 213 |
| Prevotella | 2 | [FW]HD.D[LVI].[DE]EG[^P][TSD][IV][EA]E | 214 |

EXAMPLE 12

In Vivo Evaluation of Xylose Isomerase

Haploid *S. cerevisiae* strain yBPA130 (MATa::ura3) and yBPA136 (MATalpha::ura3) were genetically modified to enhance C5 xylose utilization during fermentation. The modification includes the following: the native glucose repressible alcohol dehydrogenase II gene ADH2 was disrupted by inserting an expression cassette of the endogenous transaldolase gene TAL1 (SEQ ID NO:215) and xylulokinase gene XKS1 (SEQ ID NO:216). PHO13 encoding the native alkaline phosphatase specific for p-nitrophenyl phosphate gene was disrupted by inserting the native transketolase-1 gene TKL1 (SEQ ID NO:217). Native aldose reductase gene GRE3 was disrupted by inserting native D-ribulose-5-phosphate 3-epimerase gene RPE1 (SEQ ID NO:218) and Ribose-5-phosphate ketol-isomerase gene RKI1 (SEQ ID NO:219). Also one expression cassette of native galactose permease gene GAL2 (SEQ ID NO:220) was integrated into the *S. cerevisiae* strain, resulting in haploid strains pBPB007 (MATa::ura3) and pBPB008 (MATalpha::ura3). The genotype of pBPB007 and pBPB008 is adh2::TAL1-XKS1, pho13::TKL1-XKS1, gre3::RPE1-RKI1 and YLR388.5::GAL2. The sequences are shown in Table 13, below:

TABLE 13

| Sequence Name | Type of sequence | SEQ ID NO: | Sequence |
|---|---|---|---|
| TAL1 (*S. cerevisiae*) | DNA | 215 | ATGTCTGAACCAGCTCAAAAGAAACAAAAGGTTGCTAACAACTCT<br>CTAGAACAATTGAAAGCCTCCGGCACTGTCGTTGTTGCCGACACT<br>GGTGATTTCGGCTCTATTGCCAAGTTTCAACCTCAAGACTCCACA<br>ACTAACCCATCATTGATCTTGGCTGCTGCCAAGCAACCAACTTAC<br>GCCAAGTTGATCGATGTTGCCGTGGAATACGGTAAGAAGCATGGT<br>AAGACCACCGAAGAACAAGTCGAAAATGCTGTGGACAGATTGTTA<br>GTCGAATTCGGTAAGGAGATCTTAAAGATTGTTCCAGGCAGAGTC<br>TCCACCGAAGTTGATGCTAGATTGTCTTTTGACACTCAAGCTACC<br>ATTGAAAAGGCTAGACATATCATTAAATTGTTTGAACAAGAAGGT<br>GTCTCCAAGGAAAGAGTCCTTATTAAAATTGCTTCCACTTGGGAA<br>GGTATTCAAGCTGCCAAAGAATTGGAAGAAAAGGACGGTATCCAC<br>TGTAATTTGACTCTATTATTCTCCTTCGTTCAAGCAGTTGCCTGT<br>GCCGAGGCCCAAGTTACTTTGATTTCCCCATTTGTTGGTAGAATT<br>CTAGACTGGTACAAATCCAGCACTGGTAAAGATTACAAGGGTGAA<br>GCCGACCCAGGTGTTATTTCCGTCAAGAAAATCTACAACTACTAC<br>AAGAAGTACGGTTACAAGACTATTGTTATGGGTGCTTCTTTCAGA<br>AGCACTGACGAAATCAAAAACTTGGCTGGTGTTGACTATCTAACA<br>ATTTCTCCAGCTTTATTGGACAAGTTGATGAACAGTACTGAACCT<br>TTCCCAAGAGTTTTGGACCCTGTCTCCGCTAAGAAGGAAGCCGGC<br>GACAAGATTTCTTACATCAGCGACGAATCTAAATTCAGATTCGAC<br>TTGAATGAAGACGCTATGGCCACTGAAAAATTGTCCGAAGGTATC<br>AGAAAATTCTCTGCCGATATTGTTACTCTATTCGACTTGATTGAA<br>AAGAAAGTTACCGCTTAA |
| XKS1 (*S. cerevisiae*) | DNA | 216 | ATGTTGTGTTCAGTAATTCAGAGACAGACAAGAGAGGTTTCCAAC<br>ACAATGTCTTTAGACTCATACTATCTTGGGTTTGATCTTTCGACC<br>CAACAACTGAAATGTCTCGCCATTAACCAGGACCTAAAAATTGTC<br>CATTCAGAAACAGTGGAATTTGAAAAGGATCTTCCGCATTATCAC<br>ACAAAGAAGGGTGTCTATATACACGGCGACACTATCGAATGTCCC<br>GTAGCCATGTGGTTAGAGGCTCTAGATCTGGTTCTCTCGAAATAT<br>CGCGAGGCTAAATTTCCATTGAACAAAGTTATGGCCGTCTCAGGG<br>TCCTGCCAGCAGCACGGGTCTGTCTACTGGTCCTCCCAAGCCGAA<br>TCTCTGTTAGAGCAATTGAATAAGAAACCGGAAAAAGATTTATTG<br>CACTACGTGAGCTCTGTAGCATTTGCAAGGCAAACCGCCCCCAAT<br>TGGCAAGACCACAGTACTGCAAAGCAATGTCAAGAGTTTGAAGAG<br>TGCATAGGTGGGCCTGAAAAAATGGCTCAATTAACAGGGTCCAGA<br>GCCCATTTTAGATTTACTGGTCCTCAAATTCTGAAAATTGCACAA<br>TTAGAACCAGAAGCTTACGAAAAAACAAAGACCATTTCTTTAGTG<br>TCTAATTTTTTGACTTCTATCTTAGTGGGCCATCTTGTTGAATTA<br>GAGGAGGCAGATGCCTGTGGTATGAACCTTTATGATATACGTGAA<br>AGAAAATTCAGTGATGAGCTACTACATCTAATTGATAGTTCTTCT<br>AAGGATAAAACTATCAGACAAAAATTAATGAGAGCACCCATGAAA<br>AATTTGATAGCGGGTACCATCTGTAAATATTTTATTGAGAAGTAC<br>GGTTTCAATACAAACTGCAAGGTCTCTCCCATGACTGGGGATAAT<br>TTAGCCACTATATGTTCTTTACCCCTGCGGAAGAATGACGTTCTC<br>GTTTCCCTAGGAACAAGTACTACAGTTCTTCTGGTCACCGATAAG<br>TATCACCCCTCTCCGAACTATCATCTTTTC<br>ATTCATCCAACTCTGCCAAACCATTATATGGGTATGATTTGTTAT<br>TGTAATGGTTCTTTGGCAAGGGAGAGGATAAGAGACGAGTTAAAC<br>AAAGAACGGGAAATAATTATGAGAAGACTAACGATTGGACTCTT<br>TTTAATCAAGCTGTGCTAGATGACTCAGAAAGTAGTGAAAATGAA<br>TTAGGTGTATATTTTCCTCTGGGGGAGATCGTTCCTAGCGTAAAA<br>GCCATAAACAAAAGGGTTATCTTCAATCCAAAAACGGGTATGATT<br>GAAAGAGAGGTGGCCAAGTTCAAAGACAAGAGGCACGATGCCAAA<br>AATATTGTAGAATCACAGGCTTTAAGTTGCAGGGTAAGAATATCT<br>CCCCTGCTTTCGGATTCAAACGCAAGCTCACAACAGAGACTGAAC<br>GAAGATACAATCGTGAAGTTTGATTACGATGAATCTCCGCTGCGG<br>GACTACCTAAATAAAAGGCCAGAAAGGACTTTTTTTGTAGGTGGG<br>GCTTCTAAAAACGATGCTATTGTGAAGAAGTTTGCTCAAGTCATT<br>GGTGCTACAAAGGGTAATTTTAGGCTAGAAACACCAAACTCATGT |

TABLE 13-continued

| Sequence Name | Type of sequence | SEQ ID NO: | Sequence |
|---|---|---|---|
| | | | GCCCTTGGTGGTTGTTATAAGGCCATGTGGTCATTGTTATATGAC<br>TCTAATAAAATTGCAGTTCCTTTTGATAAATTTCTGAATGACAAT<br>TTTCCATGGCATGTAATGGAAAGCATATCCGATGTGGATAATGAA<br>AATTGGGATCGCTATAATTCCAAGATTGTCCCCTTAAGCGAACTG<br>GAAAAGACTCTCATCTAA |
| TKL1 (S. cerevisiae) | DNA | 217 | ATGACTCAATTCACTGACATTGATAAGCTAGCCGTCTCCACCATA<br>AGAATTTTGGCTGTGGACACCGTATCCAAGGCCAACTCAGGTCAC<br>CCAGGTGCTCCATTGGGTATGGCACCAGCTGCACACGTTCTATGG<br>AGTCAAATGCGCATGAACCCAACCAACCCAGACTGGATCAACAGA<br>GATAGATTTGTCTTGTCTAACGGTCACGCGGTCGCTTTGTTGTAT<br>TCTATGCTACATTTGACTGGTTACGATCTGTCTATTGAAGACTTG<br>AAACAGTTCAGACAGTTGGGTTCCAGAACACCAGGTCATCCTGAA<br>TTTGAGTTGCCAGGTGTTGAAGTTACTACCGGTCCATTAGGTCAA<br>GGTATCTCCAACGCTGTTGGTATGGCCATGGCTCAAGCTAACCTG<br>GCTGCCACTTACAACAAGCCGGGCTTTACCTTGTCTGACAACTAC<br>ACCTATGTTTTCTTGGGTGACGGTTGTTTGCAAGAAGGTATTTCT<br>TCAGAAGCTTCCTCCTTGGCTGGTCATTTGAAATTGGGTAACTTG<br>ATTGCCATCTACGATGACAACAAGATCACTATCGATGGTGCTACC<br>AGTATCTCATTCGATGAAGATGTTGCTAAGAGATACGAAGCCTAC<br>GGTTGGGAAGTTTTGTACGTAGAAAATGGTAACGAAGATCTAGCC<br>GGTATTGCCAAGGCTATTGCTCAAGCTAAGTTATCCAAGGACAAA<br>CCAACTTTGATCAAAATGACCACAACCATTGGTTACGGTTCCTTG<br>CATGCCGGCTCTCACTCTGTGCACGGTGCCCCATTGAAAGCAGAT<br>GATGTTAAACAACTAAAGAGCAAATTCGGTTTCAACCCAGACAAG<br>TCCTTTGTTGTTCCACAAGAAGTTTACGACCACTACCAAAAGACA<br>ATTTTAAAGCCAGGTGTCGAAGCCAACAACAAGTGGAACAAGTTG<br>TTCAGCGAATACCAAAAGAAATTCCCAGAATTAGGTGCTGAATTG<br>GCTAGAAGATTGAGCGGCCAACTACCCGCA<br>AATTGGGAATCTAAGTTGCCAACTTACACCGCCAAGGACTCTGCC<br>GTGGCCACTAGAAAATTATCAGAAACTGTTCTTGAGGATGTTTAC<br>AATCAATTGCCAGAGTTGATTGGTGGTTCTGCCGATTTAACACCT<br>TCTAACTTGACCAGATGGAAGGAAGCCCTTGACTTCCAACCTCCT<br>TCTTCCGGTTCAGGTAACTACTCTGGTAGATACATTAGGTACGGT<br>ATTAGAGAACACGCTATGGGTGCCATAATGAACGGTATTTCAGCT<br>TTCGGTGCCAACTACAAACCATACGGTGGTACTTTCTTGAACTTC<br>GTTTCTTATGCTGCTGGTGCCGTTAGATTGTCCGCTTTGTCTGGC<br>CACCCAGTTATTTGGGTTGCTACACATGACTCTATCGGTGTCGGT<br>GAAGATGGTCCAACACATCAACCTATTGAAACTTTAGCACACTTC<br>AGATCCCTACCAAACATTCAAGTTTGGAGACCAGCTGATGGTAAC<br>GAAGTTTCTGCCGCCTACAAGAACTCTTTAGAATCCAAGCATACT<br>CCAAGTATCATTGCTTTGTCCAGACAAAACTTGCCACAATTGGAA<br>GGTAGCTCTATTGAAAGCGCTTCTAAGGGTGTTACGTACTACAA<br>GATGTTGCTAACCCAGATATTATTTTAGTGGCTACTGGTTCCGAA<br>GTGTCTTTGAGTGTTGAAGCTGCTAAGACTTTGGCCGCAAAGAAC<br>ATCAAGGCTCGTGTTGTTTCTCTACCAGATTTCTTCACTTTTGAC<br>AAACAACCCCTAGAATACAGACTATCAGTCTTACCAGACAACGTT<br>CCAATCATGTCTGTTGAAGTTTTGGCTACCACATGTTGGGGCAAA<br>TACGCTCATCAATCCTTCGGTATTGACAGATTTGTGCCTCCGGT<br>AAGGCACCAGAAGTCTTCAAGTTCTTCGGTTTCACCCCAGAAGGT<br>GTTGCTGAAAGAGCTCAAAAGACCATTGCATTCTATAAGGGTGAC<br>AAGCTAATTTCTCCTTTGAAAAAGCTTTCTAA |
| RPE1 (S. cerevisiae) | DNA | 218 | ATGGTCAAACCAATTATAGCTCCCAGTATCCTTGCTTCTGACTTC<br>GCCAACTTGGGTTGCGAATGTCATAAGGTCATCAACGCCGGCGCA<br>GATTGGTTACATATCGATGTCATGGACGGCCATTTTGTTCCAAAC<br>ATTACTCTGGGCCAACCAATTGTTACCTCCCTACGTCGTTCTGTG<br>CCACGCCCTGGCGATGCTAGCAACACAGAAAAGAAGCCCACTGCG<br>TTCTTCGATTGTCACATGATGGTTGAAAATCCTGAAAAATGGGTC<br>GACGATTTTGCTAAATGTGGTGCTGACCAATTTACGTTCCACTAC<br>GAGGCCACACAAGACCCTTTGCATTTAGTTAAGTTGATTAAGTCT<br>AAGGGCATCAAAGCTGCATGCGCCATCAAACCTGGTACTTCTGTT<br>GACGTTTTATTTGAACTAGCTCCTCATTTGGATATGGCTCTTGTT<br>ATGACTGTGGAACCTGGGTTTGGAGGCCAAAAATTCATGGAAGAC<br>ATGATGCCAAAAGTGGAAACTTTGAGAGCCAAGTTCCCCCATTTG<br>AATATCCAAGTCGATGGTGGTTTGGGCAAGGAGACCATCCCGAAA<br>GCCGCCAAAGCCGGTGCCAACGTTATTGTCGCTGGTACCAGTGTT<br>TTCACTGCAGCTGACCCGCACGATGTTATCTCCTTCATGAAAGAA<br>GAAGTCTCGAAGGAATTGCGTTCTAGAGATTTGCTAGATTAG |
| RKI1 (S. cerevisiae) | DNA | 219 | ATGGCTGCCGGTGTCCCAAAAATTGATGCGTTAGAATCTTTGGGC<br>AATCCTTTGGAGGATGCCAAGAGAGCTGCAGCATACAGGACAGTT<br>GATGAAAATTTAAAATTTGATGATCACAAAATTATTGGAATTGGT<br>AGTGGTAGCACAGTGGTTTATGTTGCCGAAAGAATTGGACAATAT<br>TTGCATGACCCTAAATTTTATGAAGTAGCGTCTAAATTCATTTGC<br>ATTCCAACAGGATTCCAATCAAGAAACTTGATTTTGGATAACAAG<br>TTGCAATTAGGCTCCATTGAACAGTATCCTCGCATTGATATAGCG |

TABLE 13-continued

| Sequence Name | Type of sequence | SEQ ID NO: | Sequence |
|---|---|---|---|
| | | | TTTGACGGTGCTGATGAAGTGGATGAGAATTTACAATTAATTAAA<br>GGTGGTGGTGCTTGTCTATTTCAAGAAAAATTGGTTAGTACTAGT<br>GCTAAAACCTTCATTGTCGTTGCTGATTCAAGAAAAAAGTCACCA<br>AAACATTTAGGTAAGAACTGGAGGCAAGGTGTTCCCATTGAAATT<br>GTACCTTCCTCATACGTGAGGGTCAAGAATGATCTATTAGAACAA<br>TTGCATGCTGAAAAAGTTGACATCAGACAAGGAGGTTCTGCTAAA<br>GCAGGTCCTGTTGTAACTGACAATAATAACTTCATTATCGATGCG<br>GATTTCGGTGAAATTTCCGATCCAAGAAAATTGCATAGAGAAATC<br>AAACTGTTAGTGGGCGTGGTGGAAACAGGTTTATTCATCGACAAC<br>GCTTCAAAAGCCTACTTCGGTAATTCTGACGGTAGTGTTGAAGTT<br>ACCGAAAAGTGA |
| GAL2 (S. cerevisiae) | DNA | 220 | ATGGCAGTTGAGGAGAACAATATGCCTGTTGTTTCACAGCAACCC<br>CAAGCTGGTGAAGACGTGATCTCTTCACTCAGTAAAGATTCCCAT<br>TTAAGCGCACAATCTCAAAAGTATTCTAATGATGAATTGAAAGCC<br>GGTGAGTCAGGGTCTGAAGGCTCCCAAAGTGTTCCTATAGAGATA<br>CCCAAGAAGCCCATGTCTGAATATGTTACCGTTTCCTTGCTTTGT<br>TTGTGTGTTGCCTTCGGCGGCTTCATGTTTGGCTGGGATACCGGT<br>ACTATTTCTGGGTTTGTTGTCCAAACAGACTTTTTGAGAAGGTTT<br>GGTATGAAACATAAGGATGGTACCCACTATTTGTCAAACGTCAGA<br>ACAGGTTTAATCGTCGCCATTTTCAATATTGGCTGTGCCTTTGGT<br>GGTATTATACTTTCCAAAGGTGGAGATATGTATGGCCGTAAAAAG<br>GGTCTTTCGATTGTCGTCTCGGTTTATATAGTTGGTATTATCATT<br>CAAATTGCCTCTATCAACAAGTGGTACCAATATTTCATTGGTAGA<br>ATCATATCTGGTTTGGGTGTCGGCGGCATCGCCGTCTTATGTCCT<br>ATGTTGATCTCTGAAATTGCTCCAAAGCACTTGAGAGGCACACTA<br>GTTTCTTGTTATCAGCTGATGATTACTGCAGGTATCTTTTTGGGC<br>TACTGTACTAATTACGGTACAAAGAGCTATTCGAACTCAGTTCAA<br>TGGAGAGTTCCATTAGGGCTATGTTTCGCTTGGTCATTATTTATG<br>ATTGGCGCTTTGACGTTAGTTCCTGAATCCCCACGTTATTTATGT<br>GAGGTGAATAAGGTAGAAGACGCCAAGCGTTCCATTGCTAAGTCT<br>AACAAGGTGTCACCAGAGGATCCTGCCGTCCAGGCAGAGTTAGAT<br>CTGATCATGGCCGGTATAGAAGCTGAAAAACTGGCTGGCAATGCG<br>TCCTGGGGGGAATTATTTTCCACCAAGACCAAAGTATTTCAACGT<br>TTGTTGATGGGTGTGTTTGTTCAAATGTTC<br>CAACAATTAACCGGTAACAATTATTTTTTCTACTACGGTACCGTT<br>ATTTTCAAGTCAGTTGGCCTGGATGATTCCTTTGAAACATCCATT<br>GTCATTGGTGTAGTCAACTTTGCCTCCACTTTCTTTAGTTTGTGG<br>ACTGTCGAAAACTTGGGACATCGTAAATGTTTACTTTTGGGCGCT<br>GCCACTATGATGGCTTGTATGGTCATCTACGCCTCTGTTGGTGTT<br>ACTAGATTATATCCTCACGGTAAAAGCCAGCCATCTTCTAAAGGT<br>GCCGGTAACTGTATGATTGTCTTTACCTGTTTTTATATTTCTGT<br>TATGCCACAACCTGGGCGCCAGTTGCCTGGGTCATCACAGCAGAA<br>TCATTCCCACTGAGAGTCAAGTCGAAATGTATGGCGTTGGCCTCT<br>GCTTCCAATTGGGTATGGGGGTTCTTGATTGCATTTTTCACCCCA<br>TTCATCACATCTGCCATTAACTTCTACTACGGTTATGTCTTCATG<br>GGCTGTTTGGTTGCCATGTTTTTTTATGTCTTTTTCTTTGTTCCA<br>GAAACTAAAGGCCTATCGTTAGAAGAAATTCAAGAATTATGGGAA<br>GAAGGTGTTTTACCTTGGAAATCTGAAGGCTGGATTCCTTCATCC<br>AGAAGAGGTAATAATTACGATTTAGAGGATTTACAACATGACGAC<br>AAACCGTGGTACAAGGCCATGCTAGAATAA |

Figure 6:
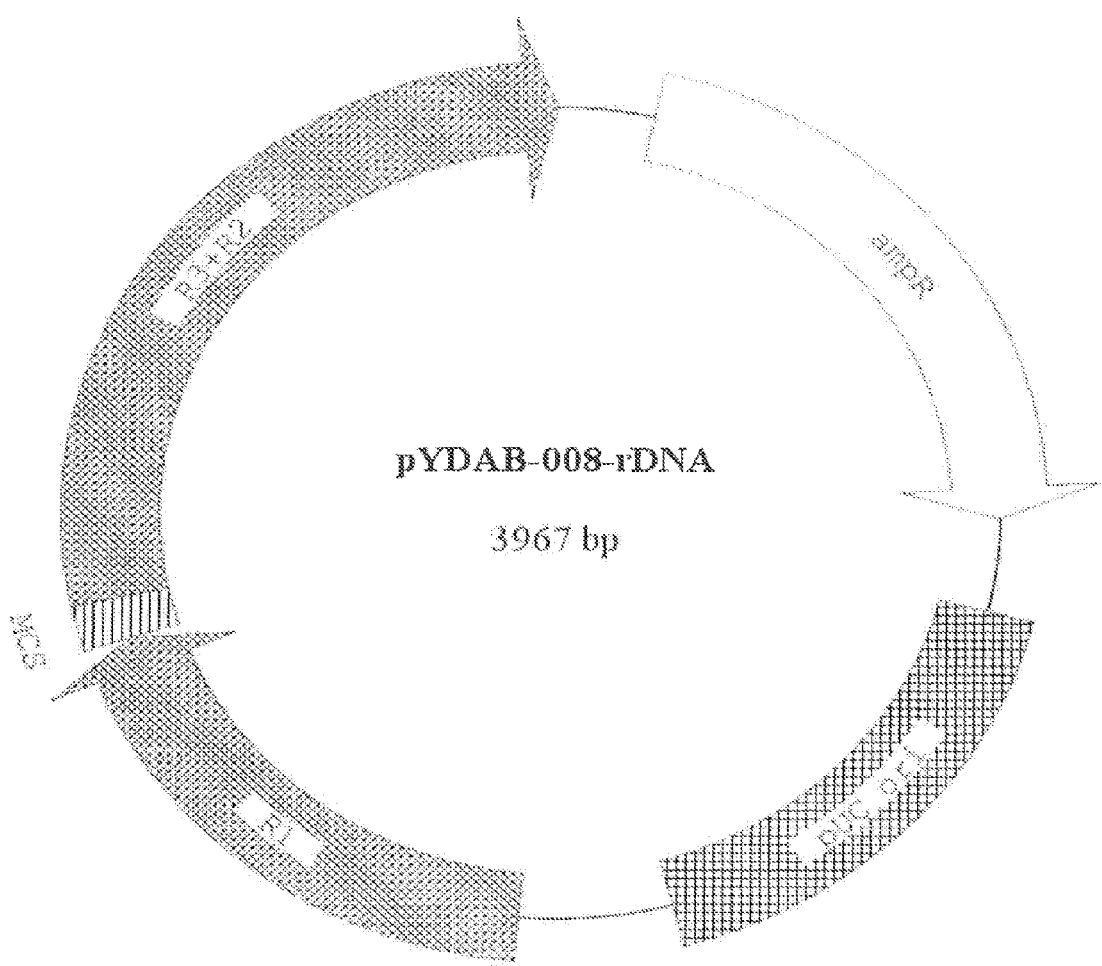
FIG. 6 is a map of vector YDAB008-rDNA for multiple XI integration into *S. cerevisiae* strain yBPB007 and yBPB008.

A vector named pYDAB008 rDNA (FIG. 6) for integration xylose isomerase into ribosomal DNA loci in *S. cerevisiae* genome was constructed using conventional cloning methods. This vector can confer high copy number integration of genes and resulting in high-level expression of proteins. The vector was derived from pBluescript II SK (+) (Agilent Technologies, Inc., Santa Clara, Calif.). The pUC origin of replication and bla gene encoding ampicillin resistance was amplified with specific primer sequences as a selectable marker for cloning. A 741 base-pair segment R1 region, 253 base-pair R3 region and a 874 base-pair R2 region were amplified from yeast genomic DNA by PCR amplifications. A multiple cloning site of SEQ ID NO:181 (:5'-GGCGCGCCTCTAGAAAGCTTACGCGTGAGCTC-CCTGCAGGGATATCGGTACCGCGGCCGC-3') was inserted between the R1 and R3/R2 regions by assembly using overlapping PCR. All primers used in above reactions are shown in Table 14. Overlapping PCR products were then ligated in one reaction and result in rDNA integration plasmid named pYDABOO8 rDNA (FIG. 6).

TABLE 14

Primers Used in pYDAB008 rDNA vector construction

| Primer | SEQ ID NO: | Sequence (Pac I restriction site is underlined) |
|---|---|---|
| Pac I-rDNA(R1)-R | 221 | CACCA<u>TTAATTAA</u>CCCGGGGCACCTGTCACTTTGGAA |
| rDNA (R1)-over-R | 222 | CGCGTAAGCTTTCTAGAGGCGCGCCAAGCTTTTACAC<br>TCTTGACCAGCGCA |

TABLE 14-continued

Primers Used in pYDAB008 rDNA vector construction

| Primer | SEQ ID NO: | Sequence (Pac I restriction site is underlined) |
|---|---|---|
| AB vector-MCS-R | 223 | CCGCTGGTGGGTACCGATATCCCTGCAGGGAGCTCAC GCGTAAGCTTTCTAGAGGCG |
| rDNA(R3)-over-R | 224 | CTGCAGGGATATCGGTACCCACCAGCGGCCGCAGGC CTTGGGTGCTTGCTGGCGAA |
| rDNA(R3)-over-R | 225 | ACCTCTGCATGCGAATTCTTAAGACAAATAAAATTTA TAGAGACTTGT |
| rDNA(R2)-over-R | 226 | GTCTTAAGAATTCGCATGCAGAGGTAGTTTCAAGGT |
| Pac I-rDNA(R2)-R | 227 | CACCA<u>TTAATTAA</u>TACGTATTTCTCGCCGAGAAAAAC TT | pYDABF 0015 (comprising a nucleic acid encoding a xylose isomerase of SEQ ID NO:78) and pYDABF-0026 (comprising a nucleic acid encoding a xylose isomerase of SEQ ID NO:96) (both described in Example 11) were digested with Asc I and Kpn I restriction enzymes (New England Biolabs Inc., MA, USA) and ligated to pYDAB008 rDNA integration vector described above (FIG. 6). The resulting plasmids were named pYDABF-0033 (SEQ ID NO:78) and pYDABF-0036 (SEQ ID NO:96).

The rDNA integration cassette was linearized by Pac I restriction enzyme digestion (New England Biolabs Inc., MA, USA) and purified with DNA column purification kit (Zymo Research, Irvine, Calif., USA). The integration cassette was transformed into modified haploid *S. cerevisiae* strain pBPB007 (MATa::ura3) and pBPB008 (MAT alpha::ura3) using the standard protocol described in previous examples. Transformants were plated on SC-xylose (SC complete +2% xylose) agar plates, about 2-3 days at about 30° C. Colonies that grew on SC-xylose agar plates were then checked by colony PCR analysis with primer sets shown in Table 15 (SEQ ID NOs:228, 229, 230 and 231) to confirm the presence of xylose isomerase in the genome.

TABLE 15

Primers Used in Integration Verification

| Primer | SEQ ID NO: | Sequence |
|---|---|---|
| N16PCR_F | 228 | CCCCATCGACAACTACGAGCTCACT |
| N16PCR_R | 229 | CAACTTGCCGTCCTCGAAGTCCTTG |
| N05PCR_F | 230 | CGAGCCTGAGAAGGTCGTGATGGGA |
| N05PCR_R | 231 | TACGTCGAAGTCGGGGTTGGTAGAA |

Confirmed haploid strains were BD31328 (MATa), BD31336 (MATalpha), BD31526 (MATa) and BD31527 (MATalpha). Diploid strains BD31378 (expressing a xylose isomerase of SEQ ID NO:96) and BD31365 (expressing a xylose isomerase of SEQ ID NO:78) were generated by conventional plate mating on YPXylose (YP+2% xylose) agar plates, about 2 days at about 30° C. Colony PCR with specific primers checking mating types were performed (shown in Table 14) and a single colony, which has both MATa and MATalpha were picked as diploid strains BD 31378 (SEQ ID NO:96) and BD31365 (SEQ ID NO:78).

A linear fragment encoding the URA3 sequence (SEQ ID NO:237; TTAATTAAGTTAATTACCTTTTTTGCGAGGCATATTTATGGTGAAGAATAAGTT TTGACCATCAAAGAAGGTTAATGTGGCTGTGGTTTCAGGGTCCATAAAGCTTTTCAATTCATCATTTTTTTTATTCTTTTTTTGATTCCGGTTTTCCTGAAATTTT TTTGATTCGGTAATCTCCGAACAGAAGGAAGAACGAAGGAAGGAGCACAGACTTAGATTGGTATATATACGCATATGTAGTGTTGAAGAAACATGAAATTGCCCA GTATTCTTAACCCAACTGCACAGAACAAAAACCTGCAGGAAACGAAGATAAATCATGTCGAAAGCTACATATAAGGAACGTGCTGCTACTCATCCTAGTCCTGTT GCTGCCAAGCTATTTAATATCATGCACGAAAAGCAAACAAACTTGTGTGCTTCATTGGATGTTCGTACCACCAAGGAATTACTGGAGTTAGTTGAAGCATTAGGTC CCAAAATTTGTTTACTAAAAACACATGTGGATATCTTGACTGATTTTTCCATGGAGGGCACAGTTAAGCCGCTAAAGGCATTATCCGCCAAGTACAATTTTTTACTC TTCGAAGACAGAAAATTTGCTGACATTGGTAATACAGTCAAATTGCAGTACTCTGCGGGTGTATACAGAATAGCAGAATGGGCAGACATTACGAATGCACACGGT GTGGTGGGCCCAGGTATTGTTAGCGGTTTGAAGCAGGCGGCAGAAGAAGTAACAAAGGAACCTAGAGGCCTTTGATGTTAGCAGAATTGTCATGCAAGGGCTCC CTAGCTACTGGAGAATATACTAAGGGTACTGTTGACATTGCGAAGAGCGACAAAGATTTTGTTATCGGCTTTATTGCTCAAAGAGACATGGGTGGAAGAGATGAA GGTTACGATTGGTTGATTATGACACCCGGTGTGGGTTTAGATGACAAGGGAGACGCATTGGGTCAACAGTATAGAACCGTGGATGATGTGGTCTCTACAGGATCTG ACATTATTATTGTTGGAAGAGGACTATTTGCAAAGGGAAGGGATGCTAAGGTAGAGGGTGAACGTTACAGAAAAGCAGGCTGGGAAGCATATTTGAAGAAGATGCG GCCAGCAAAACTAAAAAACTGTATTATAAGTAAATGCATGTATACTAAACTCACAAATTAGAGCTTCAATTTAATTATATCAGTTATTACCCGGGAATCTCGGTCGT AATGATTTTTATAATGACGAAAAAAAAAAATTGGAAAGAAAAAGCTTCATG GCCTTTATAAAAAGGAACCATCCAATACCTCGCCAGAACCAAGTAACAGTATT TTACGGTTAATTAA) was transformed into BD 31378 (SEQ ID NO:96) and BD31365 (SEQ ID NO:78) by a conventional transformation protocol, and transformants were plated on SCXylose-URA (Synthetic Complete, Uracil dropout) for selection. Colonies were checked by PCR with primers shown in Table 16, SEQ ID NO:235, SEQ ID NO:236). Confirmed strains are BD31446 (SEQ ID NO:78) and BD31448 (SEQ ID NO:96).

TABLE 16

Primers Used in Mating Type Verification

| Primer | SEQ ID NO: | Sequence |
|---|---|---|
| 1-mating type-R | 232 | AGTCACATCAAGATCGTTTAT |
| 2-mating type alpha-F | 233 | GCACGGAATATGGGACTACTT |
| 3-mating type a-F | 234 | ACTCCACTTCAAGTAAGAGTT |
| Ura fix-F | 235 | GAACAAAAACCTGCAGGAAACGAAGAT |
| Ura fix-R | 236 | GCTCTAATTTGTGAGTTTAGTATACATGCAT |

Table 17 below shows the genotypes of the resulting yeast strains:

TABLE 17

Strain Construction

| Name | Parent Strain | Description |
|---|---|---|
| pBPB007 | yBPA130 | MATa, ura3, adh2:: TAL1-XKS1, pho13:: TKL1-XKS1, gre3:: RPE1-RKI1 and YLR388.5:: GAL2 |
| pEPB008 | yBPA136 | MATalpha, ura3, adh2:: TAL1-XKS1, pho13:: TKL1-XKS1, gre3:: RPE1-RKI1 and YLR388.5:: GAL2 |
| BD31328 | pBPB007 | MATa, ura3, adh2:: TAL1-XKS1, pho13:: TKL1-XKS1, gre3:: RPE1-RKI1 and YLR388.5:: GAL2, rDNA:: XI (SEQ ID NO: 96) |
| BD31336 | pBPB008 | MATalpha, ura3, adh2:: TAL1-XKS1, pho13:: TKL1-XKS1, gre3:: RPE1-RKI1 and YLR388.5:: GAL2, rDNA:: XI (SEQ ID NO: 96) |
| BD31526 | pBPB007 | MATa, ura3, adh2:: TAL1-XKS1, pho13:: TKL1-XKS1, gre3:: RPE1-RKI1 and YLR388.5:: GAL2, rDNA:: XI (SEQ ID NO: 78) |
| BD31527 | pBPB008 | MATalpha, ura3, adh2:: TAL1-XKS1, pho13:: TKL1-XKS1, gre3:: RPE1-RKI1 and YLR388.5:: GAL2, rDNA:: XI (SEQ ID NO: 78) |
| BD31378 | BD31328 BD31336 | MATa/alpha, ura3, adh2:: TAL1-XKS1, pho13:: TKL1-XKS1, gre3:: RPE1-RKI1 and YLR388.5:: GAL2, rDNA:: XI (SEQ ID NO: 96) |
| BD31365 | BD31526 BD31527 | MATa/alpha, ura3, adh2:: TAL1-XKS1, pho13:: TKL1-XKS1, gre3:: RPE1-RKI1 and YLR388.5:: GAL2, rDNA:: XI (SEQ ID NO: 78) |
| BD31448 | BD31378 | MATa/alpha, adh2:: TAL1-XKS1, pho13:: TKL1-XKS1, gre3:: RPE1-RKI1 and YLR388.5:: GAL2, rDNA:: XI (SEQ ID NO: 96) |
| BD31446 | BD31365 | MATa/alpha, adh2:: TAL1-XKS1, pho13:: TKL1-XKS1, gre3:: RPE1-RKI1 and YLR388.5:: GAL2, rDNA:: XI (SEQ ID NO: 78 |

EXAMPLE 13

Fermentation Performance of Yeast Strain Expressing Different Xylose-Isomerases

Fermentation performances of two different XI-expressing yeast strains were evaluated using the DasGip fermentation systems (Eppendorf, Inc.). DasGip fermenters allowed close control over agitation, pH, and temperature ensuring consistency of the environment during fermentation. DasGip fermenters were used to test performance of the yeast strains expressing the XI genes on hydrolysate (Hz) (neutralized with magnesium bases) as a primary carbon source. Prior to the start of fermentation strains were subjected to propagation testing consisting of two steps as described below.

SEED 1: About 1 ml of strain glycerol stock was inoculated into about 100 ml of YP (Yeast extract, Peptone) medium containing about 2% glucose and about 1% xylose in the 250 ml bellco baffled flask (Bellco, Inc.). Strains were cultivated at about 30° C. with about 200 rpm agitation for at least 18 hours until at full saturation. Optical density was assessed by measuring light absorbance at wavelength of 600 nm.

SEED 2: About 20 ml of saturated SEED 1 (see preceding paragraph) was inoculated into 3 L Bioflo unit (New Brunswick, Inc.) containing about 2.1 L of basal medium at pH 6.0 (1% v/v inoculation). Cultivation was conducted at about 30° C. in a fed batch mode with constant air flow of about 2 L/min. Agitation ramp (rpm) was about 200-626 rpm over about 15 hours starting at about 5 hours of elapsed fermentation time (EFT). Feeding profile was about 0-4.8 ml/min over 20 hours. The basal medium contained (per 1 L): about 20% of neutralized hydrolysate (Hz); about 20 g/L sucrose (from cane juice); about 35 ml of nutrients mixture (Table 18), about 1 ml of vitamin mixture (Table 19); about 0.4 ml of antifoam 1410 (Dow Corning, Inc.) and water. Feed medium contained (per lL): about 20% neutralized hydrolysate (Hz), about 110 g/L sucrose (from cane juice), about 35 ml of nutrient mixture; about 1 ml of vitamin mixture, about 0.4 ml of antifoam 1410 (Dow Corning, Inc.) and water.

TABLE 18

Nutrients mixture

| Component | FW g/mol | Conc. |
|---|---|---|
| $KH_2PO_4$ $H_2O$ | 154.1 | 99.1 g/L |
| Urea | 60.06 | 65.6 g/L |
| $MgSO_4$—$7H_2O$ | 192.4 | 14.6 g/L |
| DI Water | NA | To 1.0 L |

TABLE 19

Vitamin mixture (1000x)

| Components | mM |
|---|---|
| $ZnSO_4$ | 100 |
| $H_3BO_3$ | 24 |
| KI | 1.8 |
| $MnSO_4$ | 20 |
| $CuSO_4$ | 10 |
| $Na_2MoO_4$ | 1.5 |
| $CoCl_2$ | 1.5 |
| $FeCl_3$ | 1.23 |

Figure 7A:
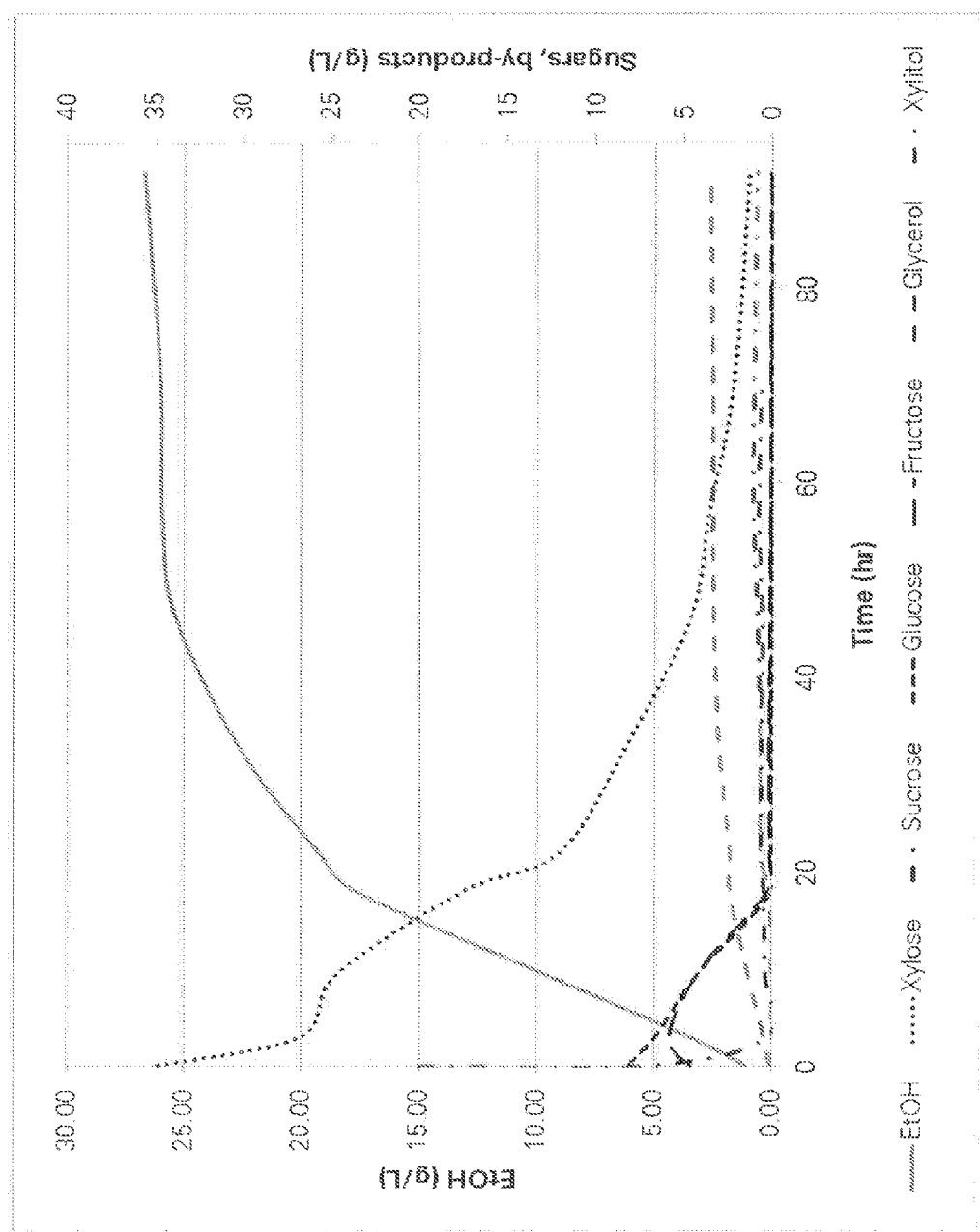
FIGS. 7A-7B show monosaccharide (including xylose) utilization and ethanol production by strains of industrial *S. cerevisiae* with multiple copies of XI clones integrated into ribosomal DNA loci.
Figure 7B:
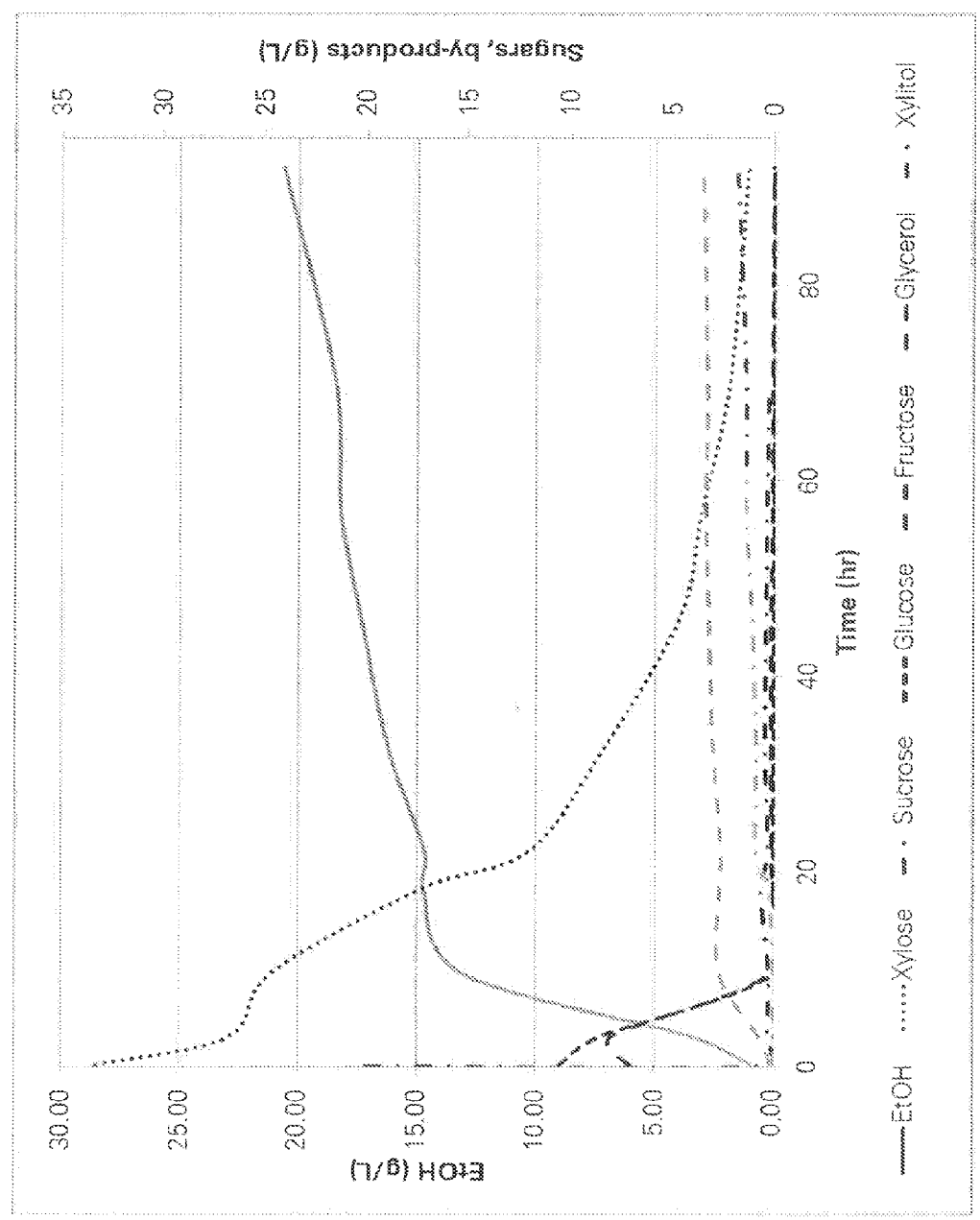
Figure 8:
FIG. 8 illustrate production of ethanol from glycolytic and pentose phosphate ("PPP") pathways. Not all steps are shown. For example, glyceraldehyde-3-phosphate is converted to pyruvate via a series of glycolytic steps: (1) glyceraldehyde-3-phosphate to 3-phospho-D-glycerol-phosphate catalyzed by glyceraldehyde-3-phosphate dehydrogenase (TDH1-3); (2) 3-phospho-D-glycerol-phosphate to 3-phosphoglycerate catalyzed by 3-phosphoglycerate kinase (PGK1); (3) 3-phosphoglycerate to 2-phosphoglycerate catalyzed by phosphoglycerate mutase (GPM1); (4) 2-phosphoglycerate to phosphoenolpyruvate catalyzed by enolase (ENO1; ENO2); and (5) phosphoenolpyruvate to pyruvate calatyzed by pyruvate kinase (PYK2; CDC19). Other abbreviations: DHAP=dihydroxy-acetone-phosphate; GPD=Glycerol-3-phosphate dehydrogenase; RHR2/HOR2=DL-glycerol-3-phosphatase; XI=xylose isomerase; GRE=xylose reductase/aldose reductase; XYL=xylitol dehydrogenase; XKS=xylulokinase; PDC=pyruvate decarboxylase; ADH=alcohol dehydrogenase; ALD=aldehyde dehydrogenase; HXK=hexokinase; PGI=phosphoglucose isomerase; PFK=phosphofructokinase; FBA=aldolase; TPI=triosephosphate isomerase; ZWF=glucose-6 phosphate dehydrogenase; SOL=6-phosphogluconolactonase; GND=6-phosphogluconate dehydrogenase; RPE=D-ribulose-5-Phosphate 3-epimerase; RKI=ribose-5-phosphate ketol-isomerase; TKL=transketolase; TAL=transaldolase. Heavy dashed arrows indicate reactions and corresponding enzymes that can be reduced or eliminated to increase xylose utilization; particularly in the production of ethanol, and heavy solid arrows indicate reactions and corresponding enzymes that can be increased to increase xylose utilization, particularly in the production of ethanol. The enzymes shown in FIG. 8 are encoded by *S. cerevisiae* genes. The *S. cerevisiae* genes are used for exemplification purposes. Analogous enzymes and modifications in other organisms are within the scope of the present disclosure.

DasGip Fermentation: Strains were tested in small scale fermentation using the DasGip system in the industrially relevant medium containing detoxified hydrolysate and sucrose. Strains were propagated as described above; DasGip inoculation was performed using the following protocol:

Cell dry weight of SEED 2 was assessed based on the final optical density. Cell dry weight and optical density (600 nm) correlation was used to estimate the volume of the SEED 2 culture needed for fermentation. Targeted inoculation level was about 7% v/v; about 1.5 g/L cell dry weight. Appropriate volume of SEED 2 culture was harvested by centrifugation (about 5000 rpm for 10 min) to pellet the cells and resuspended in about 17.5 ml of PBS. Resuspended cell solution was used to inoculate a 500 ml DasGip unit containing about 250 ml of detoxified hydrolysate and nutrient solution (about 3.5 ml/100 ml of medium). Fermentation was performed at about 32° C. at pH 6.3 with about 200 rpm. The duration of fermentation was about 92 hours with regular sampling. Sampling was conducted by a 25 ml steriological pipette through the port in the head plate of the DasGip unit. About 3 ml of culture were taken out, harvested by centrifugation (about 5000 rpm for 10 min) to pellet the cells and the supernatant was submitted for analysis. Standard analytical techniques such as high-pressure liquid chromatography (HPLC) were used to determine concentration of sugars and ethanol in the medium. Fermentation performances for yeast strains BD31378 (expressing a xylose isomerase of SEQ ID NO:96) and BD31365 (expressing a xylose isomerase of SEQ ID NO:78) are presented in FIG. 7A and FIG. 7B, respectively.

While various specific embodiments have been illustrated and described, it will be appreciated that various changes can be made without departing from the spirit and scope of the invention(s).

What is claimed is:

1. A vector comprising a nucleic acid which encodes a polypeptide comprising a xylose isomerase signature sequence, wherein the xylose isomerase signature sequence is selected from the group consisting of SEQ ID NO: 212, SEQ ID NO: 213 and SEQ ID NO: 214 or a combination thereof, wherein for SEQ ID NO:212:
Amino acid residue 3 is Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, or Valine,
Amino acid residue 6 is Arginine or Lysine;
Amino acid residue 7 is any 2 of Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, or Valine;
Amino acid residue 9 is Tryptophan, Tyrosine or Phenylalanine;
Amino acid residue 10 is Aspartic Acid, Asparagine or Glycine;
Amino acid residue 11 is any 2 or 3 of Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, or Valine;
Amino acid residue 12 is Aspartic Acid, Asparagine, Glutamic Acid, Glycine or Threonine; and
Amino acid residue 13 is Alanine or Threonine;
wherein for SEQ ID NO:213:
Amino acid residue 3 is Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, or Valine;
Amino acid residue 6 is Arginine or Lysine;
Amino acid residue 7 is any 2 of Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, or Valine;
Amino acid residue 9 is Tryptophan, Tyrosine or Phenylalanine;
Amino acid residue 10 is Aspartic Acid, Asparagine or Glycine;
Amino acid residue 11 is any 3 of Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, or Valine;
Amino acid residue 12 is Alanine, Arginine, Asparagine, Aspartic acid, Glutamic acid, Glutamine, Glycine, Histidine, Isoleucine, Leucine, Lysine, Methionine, Phenylalanine, Proline, Serine, Threonine, Tryptophan, Tyrosine, or Valine; and
Amino acid residue 13 is Alanine, Arginine, Asparagine, Aspartic acid, Cysteine, Glutamic acid, Glutamine, Glycine, Histidine, Isoleucine, Leucine, Lysine, Methionine, Phenylalanine, Serine, Threonine, Tryptophan, Tyrosine, or Valine; and
wherein for SEQ ID NO:214:
Amino acid residue 1 is Phenylalanine or Tryptophan;
Amino acid residue 4 is Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, or Valine;

Amino acid residue 6 is Leucine, Valine or Isoleucine;

Amino acid residue 7 is Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, or Valine;

Amino acid residue 8 is Aspartic Acid or Glutamic Acid;

Amino acid residue 11 is Alanine, Arginine, Asparagine, Aspartic acid, Cysteine, Glutamic acid, Glutamine, Glycine, Histidine, Isoleucine, Leucine, Lysine, Methionine, Phenylalanine, Serine, Threonine, Tryptophan, Tyrosine, or Valine;

Amino acid residue 12 is Threonine, Serine or Asparagine;

Amino acid residue 13 is Isoleucine or Valine; and

Amino acid residue 14 is Glutamic acid or Alanine.

2. The vector of claim 1, further comprising on origin of replication and/or a promoter operably linked to the nucleic acid.

3. The vector of claim 2, wherein the promoter is operable in yeast and/or filamentous fungi.

4. A host cell transformed with the vector of claim 1.

5. The host cell of claim 4, wherein the cell is selected from the group consisting of a prokaryotic cell, a bacterial cell and a eukaryotic cell.

6. A recombinant cell which expresses the polypeptide comprising a xylose isomerase signature sequence, wherein the xylose isomerase signature sequence is selected from the group consisting of SEQ ID NO: 212, SEQ ID NO: 213 and SEQ ID NO: 214 or a combination thereof, wherein for SEQ ID NO:212:

Amino acid residue 3 is Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, or Valine, Amino acid residue 6 is Arginine or Lysine;

Amino acid residue 7 is any 2 of Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, or Valine;

Amino acid residue 9 is Tryptophan, Tyrosine or Phenylalanine;

Amino acid residue 10 is Aspartic Acid, Asparagine or Glycine;

Amino acid residue 11 is any 2 or 3 of Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, or Valine;

Amino acid residue 12 is Aspartic Acid, Asparagine, Glutamic Acid, Glycine or Threonine; and Amino acid residue 13 is Alanine or Threonine;

wherein for SEQ ID NO:213:

Amino acid residue 3 is Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, or Valine;

Amino acid residue 6 is Arginine or Lysine;

Amino acid residue 7 is any 2 of Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, or Valine;

Amino acid residue 9 is Tryptophan, Tyrosine or Phenylalanine;

Amino acid residue 10 is Aspartic Acid, Asparagine or Glycine;

Amino acid residue 11 is any 3 of Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, or Valine;

Amino acid residue 12 is Alanine, Arginine, Asparagine, Aspartic acid, Glutamic acid, Glutamine, Glycine, Histidine, Isoleucine, Leucine, Lysine, Methionine, Phenylalanine, Proline, Serine, Threonine, Tryptophan, Tyrosine, or Valine; and Amino acid residue 13 is Alanine, Arginine, Asparagine, Aspartic acid, Cysteine, Glutamic acid, Glutamine, Glycine, Histidine, Isoleucine, Leucine, Lysine, Methionine, Phenylalanine, Serine, Threonine, Tryptophan, Tyrosine, or Valine; and wherein for SEQ ID NO:214:

Amino acid residue 1 is Phenylalanine or Tryptophan;

Amino acid residue 4 is Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, or Valine;

Amino acid residue 6 is Leucine, Valine or Isoleucine;

Amino acid residue 7 is Alanine, Arginine, Asparagine, Aspartic acid, Cysteine, Glutamic acid, Glutamine, Glycine, Histidine, Isoleucine, Leucine, Lysine, Methionine, Phenylalanine, Proline, Serine, Threonine, Tryptophan, Tyrosine, or Valine;

Amino acid residue 8 is Aspartic Acid or Glutamic Acid;

Amino acid residue 11 is Alanine, Arginine, Asparagine, Aspartic acid, Cysteine, Glutamic acid, Glutamine, Glycine, Histidine, Isoleucine, Leucine, Lysine, Methionine, Phenylalanine, Serine, Threonine, Tryptophan, Tyrosine, or Valine;

Amino acid residue 12 is Threonine, Serine or Asparagine;

Amino acid residue 13 is Isoleucine or Valine; and

Amino acid residue 14 is Glutamic acid or Alanine.

7. The recombinant cell of claim 6, wherein the cell is a eukaryotic, a yeast cell or a filamentous fungi cell.

8. The recombinant cell of claim 7, wherein the yeast cell is *Saccharomyces, Kluyveromyces, Candida, Pichia, Schizosaccharomyces, Hansenula, Klockera, Schwanniomyces, Issatchenkia* or *Yarrowia*.

9. The recombinant cell of claim 8, wherein the yeast cell is of the species *S. cerevisiae, S. bulderi, S. barnetti, S. exiguus, S. uvarum, S. diastaticus, K. lactis, K. marxianus* or *K. fragili*, or *Issatchenkia orientalis*.

10. The recombinant cell of claim 7, wherein the filamentous fungal cell is of the genus *Aspergillus, Penicillium, Rhizopus, Chrysosporium, Myceliophthora, Trichoderma, Humicola, Acremonium* or *Fusarium*.

11. The recombinant cell of claim 10, wherein the filamentous fungal cell is of the species *Aspergillus niger, Aspergillus oryzae, Trichoderma reesei, Penicillium chrysogenum, Myceliophthora thermophila*, or *Rhizopus oryzae*.

12. A method for producing a fermentation product, comprising culturing the recombinant cell of claim 6 in medium containing xylose under conditions in which the fermentation product is expressed.

13. The method of claim 12, wherein the xylose in the medium is provided by lignocellulosic hydrolysate.

14. The method of claim 12, wherein the fermentation product is selected from the group consisting of: ethanol, butanol, diesel, lactic acid, 3-hydroxy-propionic acid, acrylic acid, acetic acid, succinic acid, citric acid, malic acid, fumaric acid, itaconic acid, an amino acid, 1,3-propane-diol, ethylene, glycerol, a β-lactam antibiotic, a cephalosporin and a combination thereof.

15. The method of claim 12, wherein the recombinant cell comprises a genetic modification that results in decreased alcohol dehydrogenase activity.

16. The method of claim 12, wherein the recombinant cell expresses one or more enzymes that confers on the cell the ability to produce said fermentation product.

\* \* \* \* \*

SEQUENCE LISTING

```
<160> NUMBER OF SEQ ID NOS: 237

<210> SEQ ID NO 1
<211> LENGTH: 1314
<212> TYPE: DNA
<213> ORGANISM: Unknown
<220> FEATURE:
<223> OTHER INFORMATION: Obtained from environmental sample

<400> SEQUENCE: 1
atggcagtta aagaatattt cccggagata ggcaagatcg cctttgaagg aaaggagtcc      60
aagaaccctg tggcattcca ctactacaat ccagagcagg tagtagccgg aaagaaaatg     120
aaagattggt tcaagttcgc tatggcatgg tggcacaccc tctgcgctga aggtggcgac     180
cagttcggtc ctggtaccaa gaaattccct tggaacacag gtgcaactgc actcgaaaga     240
gcaaagaaca aaatggacgc aggtttcgag atcatgagca agctcggtat cgagtatttc     300
tgcttccacg atgttgacct tatcgacgag gctgacactg ttgaagagta cgaggctaac     360
atgaaggcta tcacagctta cgcaaaggag aaaatggccg ctactggcat caaactcctc     420
tggggaacag ccaatgtatt cggcaacaag agatatatga acggcgcttc taccaaccct     480
gacttcaacg tggctgcacg cgctatgctc cagatcaaga acgctatcga cgcaactatc     540
gctctcggtg gtgactgcta tgtattctgg ggcggccgtg agggttacat gagccttctc     600
aacaccgata tgaagagaga gaaagagcac atggctacca tgcttaccat ggcacgcgac     660
tatgctcgtt ctaagggctt caagggtacc ttccttatcg agcctaagcc aatggagccg     720
atgaagcacc agtacgatgt cgatactgag actgtcgtag gtttcctccg cgcccatggt     780
cttgacaagg acttcaaggt aaacatcgag gttaaccacg ctactctcgc aggccacacc     840
ttcgagcacg agctccagtg cgccgttgac gcaggcatgc tcggaagcat cgacgccaac     900
cgtggtgact accagaacgg ctgggatacc gaccagttcc ctatcgacct ctatgagctc     960
gtacaggcta tgatggttat catcaagggc ggcggtctcg tcggcggtac caacttcgac    1020
gccaagaccc gtcgtaactc aacagacctc gaggatatct tcatcgctca tgtatccggc    1080
atggatgtca tggcacgcgc tctcctcatc gctgctgacc ttctcgagaa atctcctatt    1140
cctgcaatgg tcaaggagcg ttacgcttcc tacgactcag gcatgggcaa ggacttcgag    1200
aacggcaagc ttactctcga gcaggttgtc gatttcgcaa gaaagaacgg cgagcctaag    1260
agcaccagcg gaaagcagga gctctacgag tctatcgtca atctctacat ctaa          1314
```

```
<210> SEQ ID NO 2
<211> LENGTH: 437
<212> TYPE: PRT
<213> ORGANISM: Unknown
<220> FEATURE:
<223> OTHER INFORMATION: Obtained from environmental sample

<400> SEQUENCE: 2

Met Ala Val Lys Glu Tyr Phe Pro Glu Ile Gly Lys Ile Ala Phe Glu
1               5                   10                  15

Gly Lys Glu Ser Lys Asn Pro Met Ala Phe His Tyr Tyr Asn Pro Glu
            20                  25                  30

Gln Val Val Ala Gly Lys Lys Met Lys Asp Trp Phe Lys Phe Ala Met
        35                  40                  45

Ala Trp Trp His Thr Leu Cys Ala Glu Gly Gly Asp Gln Phe Gly Pro
    50                  55                  60

Gly Thr Lys Lys Phe Pro Trp Asn Thr Gly Ala Thr Ala Leu Glu Arg
65                  70                  75                  80

Ala Lys Asn Lys Met Asp Ala Gly Phe Glu Ile Met Ser Lys Leu Gly
                85                  90                  95

Ile Glu Tyr Phe Cys Phe His Asp Val Asp Leu Ile Asp Glu Ala Asp
            100                 105                 110

Thr Val Glu Glu Tyr Glu Ala Asn Met Lys Ala Ile Thr Ala Tyr Ala
        115                 120                 125

Lys Glu Lys Met Ala Ala Thr Gly Ile Lys Leu Leu Trp Gly Thr Ala
    130                 135                 140

Asn Val Phe Gly Asn Lys Arg Tyr Met Asn Gly Ala Ser Thr Asn Pro
145                 150                 155                 160

Asp Phe Asn Val Ala Ala Arg Ala Met Leu Gln Ile Lys Asn Ala Ile
                165                 170                 175

Asp Ala Thr Ile Ala Leu Gly Gly Asp Cys Tyr Val Phe Trp Gly Gly
            180                 185                 190

Arg Glu Gly Tyr Met Ser Leu Leu Asn Thr Asp Met Lys Arg Glu Lys
        195                 200                 205

Glu His Met Ala Thr Met Leu Thr Met Ala Arg Asp Tyr Ala Arg Ser
    210                 215                 220

Lys Gly Phe Lys Gly Thr Phe Leu Ile Glu Pro Lys Pro Met Glu Pro
225                 230                 235                 240

Met Lys His Gln Tyr Asp Val Asp Thr Glu Thr Val Val Gly Phe Leu
                245                 250                 255

Arg Ala His Gly Leu Asp Lys Asp Phe Lys Val Asn Ile Glu Val Asn
            260                 265                 270

His Ala Thr Leu Ala Gly His Thr Phe Glu His Glu Leu Gln Cys Ala
        275                 280                 285

Val Asp Ala Gly Met Leu Gly Ser Ile Asp Ala Asn Arg Gly Asp Tyr
    290                 295                 300

Gln Asn Gly Trp Asp Thr Asp Gln Phe Pro Ile Asp Leu Tyr Glu Leu
305                 310                 315                 320

Val Gln Ala Met Met Val Ile Ile Lys Gly Gly Gly Leu Val Gly Gly
                325                 330                 335

Thr Asn Phe Asp Ala Lys Thr Arg Arg Asn Ser Thr Asp Leu Glu Asp
            340                 345                 350

Ile Phe Ile Ala His Val Ser Gly Met Asp Val Met Ala Arg Ala Leu
        355                 360                 365

Leu Ile Ala Ala Asp Leu Leu Glu Lys Ser Pro Ile Pro Ala Met Val
```

|     | 370 |     |     | 375 |     |     | 380 |     |     |     |     |
|-----|-----|-----|-----|-----|-----|-----|-----|-----|-----|-----|-----|
| Lys | Glu | Arg | Tyr | Ala | Ser | Tyr | Asp | Ser | Gly | Met | Gly | Lys | Asp | Phe | Glu |
| 385 |     |     |     | 390 |     |     |     | 395 |     |     |     |     |     |     | 400 |

Asn Gly Lys Leu Thr Leu Glu Gln Val Val Asp Phe Ala Arg Lys Asn
                405                 410                 415

Gly Glu Pro Lys Ser Thr Ser Gly Lys Gln Glu Leu Tyr Glu Ser Ile
            420                 425                 430

Val Asn Leu Tyr Ile
        435

<210> SEQ ID NO 3
<211> LENGTH: 1314
<212> TYPE: DNA
<213> ORGANISM: Unknown
<220> FEATURE:
<223> OTHER INFORMATION: Obtained from environmental sample

<400> SEQUENCE: 3

```
atggcaaaca aagagtactt cccggagatc gggaaaatca aattcgaagg caaggattcc      60
aagaacccgc ttgcattcca ttattacaat cctgagcagg tcgtctgcgg caagccgatg     120
aaggactggt caagttcgc tatggcatgg tggcacaccc tctgcgcaga gggtagcgac      180
cagttcggcg gacccaccaa gtcattccct tggaacaaag cttcggatcc catcgcaaag     240
gccaagcaga agtcgacgc cggtttcgag atcatgcaga agctcggtat cggatactat      300
tgcttccacg atgtagacct catcgacgag cccgccacca tcgaggagta tgaggccgat     360
ctcaaggaga tcgtcgctta cctcaaggag aagcaggccc agaccggcat caagctcctt     420
tggggcaccg ccaacgtctt cggtcacaag cggtacatga acggcgcctc caccaaccct     480
gatttcgacg tcgcagcccg cgccatggtc cagatcaaga acgccatgga cgccaccatc     540
gagctcggcg gcgagtgcta tgtcttctgg ggcggccgcg agggctacat gagcctcctc     600
aacaccgaca tgaagcgtga gaagcagcat atggccacca tgctcggcat ggcccgcgac     660
tatgcacgcg gcaagggctt caagggcacc ttcctcatcg agcccaagcc catggagccg     720
accaagcacc agtatgacgt cgacaccgag accgtcatcg gtttcctccg tgccaacggt     780
cttgacaagg acttcaaggt caacatcgag gtcaatcacg ccaccctcgc cggccacacc     840
ttcgagcatg agctccagtg cgccgccgat gccggtctcc tcggatccat cgacgccaac     900
cgcggcgact atcagaacgg ctgggatacc gaccagttcc cgatcgacct ctatgagctc     960
acccaggcca tgatggtcat cctcaagaat ggcggcctcg tcggcggtac caacttcgac    1020
gccaagaccc gtcgcaactc caccgacctg gacgacatca tcatcgccca cgtcagcggt    1080
atggacatca tggcacgcgc actcctcgtc gctgccgacg tcctcaccaa gtccgagctt    1140
cccaagatgc tcaaggagcg ttacgcttcc ttcgactccg gcaagggcaa ggagttcgaa    1200
gagggcaagc tcactctcga gcaggtcgta gagtacgcca agaccaaggg cgagcccaag    1260
gccaccagcg gcaagcagga gctctacgag accatcgtca acatgtacat ctaa          1314
```

<210> SEQ ID NO 4
<211> LENGTH: 437
<212> TYPE: PRT
<213> ORGANISM: Unknown
<220> FEATURE:
<223> OTHER INFORMATION: Obtained from environmental sample

<400> SEQUENCE: 4

Met Ala Asn Lys Glu Tyr Phe Pro Glu Ile Gly Lys Ile Lys Phe Glu

```
1               5                   10                  15
Gly Lys Asp Ser Lys Asn Pro Leu Ala Phe His Tyr Tyr Asn Pro Glu
            20                  25                  30
Gln Val Val Cys Gly Lys Pro Met Lys Asp Trp Leu Lys Phe Ala Met
            35                  40                  45
Ala Trp Trp His Thr Leu Cys Ala Glu Gly Ser Asp Gln Phe Gly Gly
            50                  55                  60
Pro Thr Lys Ser Phe Pro Trp Asn Lys Ala Ser Asp Pro Ile Ala Lys
65                  70                  75                  80
Ala Lys Gln Lys Val Asp Ala Gly Phe Glu Ile Met Gln Lys Leu Gly
                85                  90                  95
Ile Gly Tyr Tyr Cys Phe His Asp Val Asp Leu Ile Asp Glu Pro Ala
                100                 105                 110
Thr Ile Glu Glu Tyr Glu Ala Asp Leu Lys Glu Ile Val Ala Tyr Leu
                115                 120                 125
Lys Glu Lys Gln Ala Gln Thr Gly Ile Lys Leu Leu Trp Gly Thr Ala
            130                 135                 140
Asn Val Phe Gly His Lys Arg Tyr Met Asn Gly Ala Ser Thr Asn Pro
145                 150                 155                 160
Asp Phe Asp Val Ala Ala Arg Ala Met Val Gln Ile Lys Asn Ala Met
                165                 170                 175
Asp Ala Thr Ile Glu Leu Gly Gly Glu Cys Tyr Val Phe Trp Gly Gly
                180                 185                 190
Arg Glu Gly Tyr Met Ser Leu Leu Asn Thr Asp Met Lys Arg Glu Lys
            195                 200                 205
Gln His Met Ala Thr Met Leu Gly Met Ala Arg Asp Tyr Ala Arg Gly
            210                 215                 220
Lys Gly Phe Lys Gly Thr Phe Leu Ile Glu Pro Lys Pro Met Glu Pro
225                 230                 235                 240
Thr Lys His Gln Tyr Asp Val Asp Thr Glu Thr Val Ile Gly Phe Leu
                245                 250                 255
Arg Ala Asn Gly Leu Asp Lys Asp Phe Lys Val Asn Ile Glu Val Asn
                260                 265                 270
His Ala Thr Leu Ala Gly His Thr Phe Glu His Glu Leu Gln Cys Ala
            275                 280                 285
Ala Asp Ala Gly Leu Leu Gly Ser Ile Asp Ala Asn Arg Gly Asp Tyr
            290                 295                 300
Gln Asn Gly Trp Asp Thr Asp Gln Phe Pro Ile Asp Leu Tyr Glu Leu
305                 310                 315                 320
Thr Gln Ala Met Met Val Ile Leu Lys Asn Gly Gly Leu Val Gly Gly
                325                 330                 335
Thr Asn Phe Asp Ala Lys Thr Arg Arg Asn Ser Thr Asp Leu Asp Asp
                340                 345                 350
Ile Ile Ile Ala His Val Ser Gly Met Asp Ile Met Ala Arg Ala Leu
            355                 360                 365
Leu Val Ala Ala Asp Val Leu Thr Lys Ser Glu Leu Pro Lys Met Leu
            370                 375                 380
Lys Glu Arg Tyr Ala Ser Phe Asp Ser Gly Lys Gly Lys Glu Phe Glu
385                 390                 395                 400
Glu Gly Lys Leu Thr Leu Glu Gln Val Val Glu Tyr Ala Lys Thr Lys
                405                 410                 415
Gly Glu Pro Lys Ala Thr Ser Gly Lys Gln Glu Leu Tyr Glu Thr Ile
                420                 425                 430
```

Val Asn Met Tyr Ile
        435

<210> SEQ ID NO 5
<211> LENGTH: 1329
<212> TYPE: DNA
<213> ORGANISM: Unknown
<220> FEATURE:
<223> OTHER INFORMATION: Obtained from environmental sample

<400> SEQUENCE: 5

| | | | | | |
|---|---|---|---|---|---|
| atgaattttt | ataaaggcga | aaaagaattc | ttccccggaa | taggaaagat | tcagtttgaa | 60 |
| ggacgcgagt | caaagaaccc | gatggcgttt | cattattatg | acgaaaacaa | ggtggtgatg | 120 |
| ggtaaaacac | tgaaggatca | tcttcgtttt | gcaatggctt | actggcatac | gctttgtgcc | 180 |
| gaaggggcg | accagtttgg | cggtggtacg | aaaacattcc | cctggaatgc | tgctgccgac | 240 |
| ccgatcagcc | gtgccaaata | taagatggat | gcagcgttcg | agtttatgac | aaaatgcagc | 300 |
| atcccttatt | actgtttcca | tgatgtggac | gtggtggaca | agctcccac | gctggctcag | 360 |
| tttgaaaaag | accttcatac | gatggtaggc | catgccaaag | gcttcagca | ggcaaccgga | 420 |
| aaaaaactgt | tatggtctac | tgccaacgtg | ttcagcaaca | aacgctatat | gaacggggct | 480 |
| gccactaatc | ctgacttctc | ggccgtggct | tgtgccggta | cgcagatcaa | gaatgcgatc | 540 |
| gatgcctgta | tcgcgctgga | cggtgaaaac | tatgtgttct | ggggcggacg | tgaaggatat | 600 |
| atgggcttgc | tcaataccga | tatgaaacgc | gaaaagacc | atctggccat | gatgctgacg | 660 |
| atggcacgcg | actatggccg | caagaacggt | ttcaaaggta | cttttcctgat | cgagccgaaa | 720 |
| ccgatggaac | cgaccaagca | tcaatatgat | gtcgactcgg | aaactgtaat | cggcttccta | 780 |
| cgtcattatg | gcctggataa | agacttcgcc | ctgaatatcg | aagtaaatca | tgcaaccctg | 840 |
| gccggacata | cgttcgagca | cgaattgcag | gctgctgtcg | atgccggtat | gctgtgcagt | 900 |
| atcgatgcca | accgtggtga | ctaccagaat | ggctgggata | ccgaccaatt | cccgatggac | 960 |
| atctacgaac | tgactcaggc | ttggctggtc | attctgcaag | tggtggtct | gacaaccggc | 1020 |
| ggaacgaact | tcgatgccaa | gacccgccgc | aactcgaccg | acctggacga | tatcttcctg | 1080 |
| gctcatatag | gtggtatgga | tgcgtttgcc | cgtgccctga | tcacggctgc | tgccatcctt | 1140 |
| gaaaactccg | attacacgaa | gatgcgtgcc | gaacgttaca | ccagcttcga | tggtggcgaa | 1200 |
| ggcaaagcgt | ttgaagacgg | taaactttct | ctggaagacc | tgcgtacgat | cgctctccgc | 1260 |
| gacggagaac | cgaagatggt | cagcggcaaa | caggaattat | atgagatgat | tctcaattta | 1320 |
| tacatataa | | | | | | 1329 |

<210> SEQ ID NO 6
<211> LENGTH: 442
<212> TYPE: PRT
<213> ORGANISM: Unknown
<220> FEATURE:
<223> OTHER INFORMATION: Obtained from environmental sample

<400> SEQUENCE: 6

Met Asn Phe Tyr Lys Gly Glu Lys Glu Phe Phe Pro Gly Ile Gly Lys
1               5                   10                  15

Ile Gln Phe Glu Gly Arg Glu Ser Lys Asn Pro Met Ala Phe His Tyr
            20                  25                  30

Tyr Asp Glu Asn Lys Val Val Met Gly Lys Thr Leu Lys Asp His Leu
        35                  40                  45

```
Arg Phe Ala Met Ala Tyr Trp His Thr Leu Cys Ala Glu Gly Gly Asp
 50                  55                  60

Gln Phe Gly Gly Gly Thr Lys Thr Phe Pro Trp Asn Ala Ala Ala Asp
 65                  70                  75                  80

Pro Ile Ser Arg Ala Lys Tyr Lys Met Asp Ala Ala Phe Glu Phe Met
                 85                  90                  95

Thr Lys Cys Ser Ile Pro Tyr Tyr Cys Phe His Asp Val Asp Val Val
            100                 105                 110

Asp Glu Ala Pro Thr Leu Ala Gln Phe Glu Lys Asp Leu His Thr Met
        115                 120                 125

Val Gly His Ala Lys Gly Leu Gln Gln Ala Thr Gly Lys Lys Leu Leu
130                 135                 140

Trp Ser Thr Ala Asn Val Phe Ser Asn Lys Arg Tyr Met Asn Gly Ala
145                 150                 155                 160

Ala Thr Asn Pro Asp Phe Ser Ala Val Ala Cys Ala Gly Thr Gln Ile
                165                 170                 175

Lys Asn Ala Ile Asp Ala Cys Ile Ala Leu Asp Gly Glu Asn Tyr Val
            180                 185                 190

Phe Trp Gly Gly Arg Glu Gly Tyr Met Gly Leu Leu Asn Thr Asp Met
        195                 200                 205

Lys Arg Glu Lys Asp His Leu Ala Met Met Leu Thr Met Ala Arg Asp
210                 215                 220

Tyr Gly Arg Lys Asn Gly Phe Lys Gly Thr Phe Leu Ile Glu Pro Lys
225                 230                 235                 240

Pro Met Glu Pro Thr Lys His Gln Tyr Asp Val Asp Ser Glu Thr Val
                245                 250                 255

Ile Gly Phe Leu Arg His Tyr Gly Leu Asp Lys Asp Phe Ala Leu Asn
            260                 265                 270

Ile Glu Val Asn His Ala Thr Leu Ala Gly His Thr Phe Glu His Glu
        275                 280                 285

Leu Gln Ala Ala Val Asp Ala Gly Met Leu Cys Ser Ile Asp Ala Asn
290                 295                 300

Arg Gly Asp Tyr Gln Asn Gly Trp Asp Thr Asp Gln Phe Pro Met Asp
305                 310                 315                 320

Ile Tyr Glu Leu Thr Gln Ala Trp Leu Val Ile Leu Gln Gly Gly Gly
                325                 330                 335

Leu Thr Thr Gly Gly Thr Asn Phe Asp Ala Lys Thr Arg Arg Asn Ser
            340                 345                 350

Thr Asp Leu Asp Asp Ile Phe Leu Ala His Ile Gly Gly Met Asp Ala
        355                 360                 365

Phe Ala Arg Ala Leu Ile Thr Ala Ala Ile Leu Glu Asn Ser Asp
370                 375                 380

Tyr Thr Lys Met Arg Ala Glu Arg Tyr Thr Ser Phe Asp Gly Gly Glu
385                 390                 395                 400

Gly Lys Ala Phe Glu Asp Gly Lys Leu Ser Leu Glu Asp Leu Arg Thr
                405                 410                 415

Ile Ala Leu Arg Asp Gly Glu Pro Lys Met Val Ser Gly Lys Gln Glu
            420                 425                 430

Leu Tyr Glu Met Ile Leu Asn Leu Tyr Ile
        435                 440

<210> SEQ ID NO 7
<211> LENGTH: 1329
<212> TYPE: DNA
```

<213> ORGANISM: Unknown
<220> FEATURE:
<223> OTHER INFORMATION: Obtained from environmental sample

<400> SEQUENCE: 7

```
atgaattact ttaaaggtga gaaagagttc ttcccgggaa tcgggaaaat agagtttgaa      60
ggacgtgaat cgaagaatcc gatggctttt cattactatg acgagaacaa ggttgtcatg     120
gggaagacct tgaaggacca tctgcgtttt gcgatggctt attggcatac gctgtgtgcg     180
gaaggcgccg accagttcgg cggcgggacg aaggcatttc cctggaatac cggggcggat     240
cgtatttccc gtgccaagta taagatggat gctgcttttg agtttatgac gaaatgtaac     300
atcccgtact attgtttcca tgatgtggat gtggtggatg aagctccgac actggccgaa     360
tttgaaaaag acttgcatac gatggtcgaa tatgccaagc agcatcagga ggcaaccggg     420
aaaaaactgt tgtggtctac cgccaatgtg ttcagcaata acgttatat gaacgggct      480
gccacaaatc cgtatttccc tgctgtcgct tgtgcgggta cgcagatcaa gaatgctatc     540
gacgcttgta ttgccctggg cggcgaaaac tatgtgttct ggggcggtcg tgaagggtat     600
atgagcttgt tgaacaccaa tatgaaacgc gaaaaggaac atctcgccat gatgttgacg     660
atggctcgcg attatgcgcg taagaacggc ttcaaaggta ctttcctggt agagcctaaa     720
ccgatggaac cgaccaaaca tcagtatgat gtggacacag aaactgttat cggcttcctg     780
cgtcattacg gccttgacaa ggactttgcc atcaacatcg aagtgaatca tgctacattg     840
gctggacata cattcgaaca tgagcttcag gcggctgccg atgccggtat gctgtgcagc     900
atcgacgcca accgcggcga ttaccagaat ggttgggaca cggatcagtt cccggtcgac     960
atctacgaac tgacacaggc gtggctggtt atcctcgaag cgggtggcct gactaccggt    1020
ggtacgaact cgacgccaa gacgcgccgc aactcgactg acctggacga tatcttcctg    1080
gcacacatcg gtggtatgga ttcgtttgcc cgtgctttga tggcggctgc cgatatattg    1140
gaacactccg attacaaaaa gatgcgtgcc gaacgttatg ccagcttcga tcaaggcgac    1200
ggcaagaagt tcgaagatgg taaactcctt ctcgaggacc tccgcaccat cgctcttgcc    1260
tccggcgaac cgaagcaaat cagcgggaaa caggaattgt atgaaatgat tatcaaccag    1320
tacatttaa                                                             1329
```

<210> SEQ ID NO 8
<211> LENGTH: 442
<212> TYPE: PRT
<213> ORGANISM: Unknown
<220> FEATURE:
<223> OTHER INFORMATION: Obtained from environmental sample

<400> SEQUENCE: 8

```
Met Asn Tyr Phe Lys Gly Glu Lys Glu Phe Phe Pro Gly Ile Gly Lys
1               5                   10                  15

Ile Glu Phe Glu Gly Arg Glu Ser Lys Asn Pro Met Ala Phe His Tyr
            20                  25                  30

Tyr Asp Glu Asn Lys Val Val Met Gly Lys Thr Leu Lys Asp His Leu
        35                  40                  45

Arg Phe Ala Met Ala Tyr Trp His Thr Leu Cys Ala Glu Gly Ala Asp
    50                  55                  60

Gln Phe Gly Gly Gly Thr Lys Ala Phe Pro Trp Asn Thr Gly Ala Asp
65                  70                  75                  80

Arg Ile Ser Arg Ala Lys Tyr Lys Met Asp Ala Ala Phe Glu Phe Met
                85                  90                  95
```

Thr Lys Cys Asn Ile Pro Tyr Tyr Cys Phe His Asp Val Asp Val
            100                 105                 110

Asp Glu Ala Pro Thr Leu Ala Glu Phe Glu Lys Asp Leu His Thr Met
        115                 120                 125

Val Glu Tyr Ala Lys Gln His Gln Glu Ala Thr Gly Lys Lys Leu Leu
130                 135                 140

Trp Ser Thr Ala Asn Val Phe Ser Asn Lys Arg Tyr Met Asn Gly Ala
145                 150                 155                 160

Ala Thr Asn Pro Tyr Phe Pro Ala Val Ala Cys Ala Gly Thr Gln Ile
                165                 170                 175

Lys Asn Ala Ile Asp Ala Cys Ile Ala Leu Gly Gly Glu Asn Tyr Val
            180                 185                 190

Phe Trp Gly Gly Arg Glu Gly Tyr Met Ser Leu Leu Asn Thr Asn Met
        195                 200                 205

Lys Arg Glu Lys Glu His Leu Ala Met Met Leu Thr Met Ala Arg Asp
210                 215                 220

Tyr Ala Arg Lys Asn Gly Phe Lys Gly Thr Phe Leu Val Glu Pro Lys
225                 230                 235                 240

Pro Met Glu Pro Thr Lys His Gln Tyr Asp Val Asp Thr Glu Thr Val
                245                 250                 255

Ile Gly Phe Leu Arg His Tyr Gly Leu Asp Lys Asp Phe Ala Ile Asn
            260                 265                 270

Ile Glu Val Asn His Ala Thr Leu Ala Gly His Thr Phe Glu His Glu
        275                 280                 285

Leu Gln Ala Ala Ala Asp Ala Gly Met Leu Cys Ser Ile Asp Ala Asn
290                 295                 300

Arg Gly Asp Tyr Gln Asn Gly Trp Asp Thr Asp Gln Phe Pro Val Asp
305                 310                 315                 320

Ile Tyr Glu Leu Thr Gln Ala Trp Leu Val Ile Leu Glu Ala Gly Gly
                325                 330                 335

Leu Thr Thr Gly Gly Thr Asn Phe Asp Ala Lys Thr Arg Arg Asn Ser
            340                 345                 350

Thr Asp Leu Asp Asp Ile Phe Leu Ala His Ile Gly Gly Met Asp Ser
        355                 360                 365

Phe Ala Arg Ala Leu Met Ala Ala Asp Ile Leu Glu His Ser Asp
370                 375                 380

Tyr Lys Lys Met Arg Ala Glu Arg Tyr Ala Ser Phe Asp Gln Gly Asp
385                 390                 395                 400

Gly Lys Lys Phe Glu Asp Gly Lys Leu Leu Leu Glu Asp Leu Arg Thr
                405                 410                 415

Ile Ala Leu Ala Ser Gly Glu Pro Lys Gln Ile Ser Gly Lys Gln Glu
            420                 425                 430

Leu Tyr Glu Met Ile Ile Asn Gln Tyr Ile
        435                 440

<210> SEQ ID NO 9
<211> LENGTH: 1329
<212> TYPE: DNA
<213> ORGANISM: Unknown
<220> FEATURE:
<223> OTHER INFORMATION: Obtained from environmental sample

<400> SEQUENCE: 9
atgaattatt ttaaaggtga aaaagagttt ttccctggaa tcgggaaaat agagtttgaa    60

-continued

```
ggacgtgagt cgaagaatcc gatggctttt cattattatg atgaaaacaa ggtcgtaatg    120
ggcaagacct tgaaagatca cctccgcttt gcaatggctt actggcatac gttgtgcgcg    180
gaaggcgcag accagtttgg cggtggcaca aaatcattcc cctggaatac cgcagcggat    240
cgtatttccc gcgctaaata taaaatggat gctgctttcg agtttatgac caagtgcagt    300
atcccgtact attgtttcca tgatgtggac gtggtggacg aagctccggc actggccgaa    360
tttgaaaagg acctgcatac gatggtggga ttcgccaaac aacaccagga agcaaccgga    420
aagaaactgt tgtggtctac agccaatgta ttcgggcata acgttatat gaacggagcg    480 gctaccaatc cttatttccc ggctgtcgct tgtgccggta cgcagatcaa gaatgcaatc    540
gacgcctgta tcgagctggg tggagagaac tatgtattct ggggcggacg cgaaggctac    600
atgagcctgc tgaacaccaa tatgaaacgt gaaaaggatc atttggccat gatgctgaca    660
atggcacgcg attatgcccg caagaatggt ttcaagggta ctttcctggt ggaatctaag    720
ccgatggaac cgaccaaaca tcagtatgac gcagatacgg aaaccgtgat cggcttcctg    780
cgccactatg gcctcgacaa ggatttcgct atcaacattg aagtgaacca tgctacattg    840
gccggccata cattcgaaca tgaacttcag gctgctgccg atgccggtat gctgtgcagc    900
atcgatgcaa atagaggcga ctatcagaat ggttgggata cggatcagtt ccccgtagac    960
atttacgaac tgacacaggc ctggctggtt atcctggaag cgggcggact gacaaccgga   1020
ggtacgaact tcgatgcgaa gacccgtcgt aactcgactg acctcgacga tatcttcctg   1080
gcccatatcg gcggtatgga ttcgtttgca cgtgccttga tggcagctgc cgatatcctg   1140
gaacattctg attacaagaa gatgcgtgcc gaacgttacg ccagcttcga ccagggcgac   1200
ggcaagaagt tcgaagacgg caaactcctt ctcgaagacc tgcgcacaat tgcccttgcc   1260
ggcgacgaac cgaagcagat cagcggcaag caggagttgt atgagatgat tatcaatcag   1320
tatatttaa                                                           1329
```

<210> SEQ ID NO 10
<211> LENGTH: 442
<212> TYPE: PRT
<213> ORGANISM: Unknown
<220> FEATURE:
<223> OTHER INFORMATION: Obtained from environmental sample

<400> SEQUENCE: 10

```
Met Asn Tyr Phe Lys Gly Glu Lys Glu Phe Pro Gly Ile Gly Lys
1               5                   10                  15

Ile Glu Phe Glu Gly Arg Glu Ser Lys Asn Pro Met Ala Phe His Tyr
            20                  25                  30

Tyr Asp Glu Asn Lys Val Val Met Gly Lys Thr Leu Lys Asp His Leu
        35                  40                  45

Arg Phe Ala Met Ala Tyr Trp His Thr Leu Cys Ala Glu Gly Ala Asp
    50                  55                  60

Gln Phe Gly Gly Gly Thr Lys Ser Phe Pro Trp Asn Thr Ala Ala Asp
65                  70                  75                  80

Arg Ile Ser Arg Ala Lys Tyr Lys Met Asp Ala Ala Phe Glu Phe Met
                85                  90                  95

Thr Lys Cys Ser Ile Pro Tyr Tyr Cys Phe His Asp Val Asp Val Val
            100                 105                 110

Asp Glu Ala Pro Ala Leu Ala Glu Phe Glu Lys Asp Leu His Thr Met
        115                 120                 125

Val Gly Phe Ala Lys Gln His Gln Glu Ala Thr Gly Lys Lys Leu Leu
```

```
            130                 135                 140
Trp Ser Thr Ala Asn Val Phe Gly His Lys Arg Tyr Met Asn Gly Ala
145                 150                 155                 160

Ala Thr Asn Pro Tyr Phe Pro Ala Val Ala Cys Ala Gly Thr Gln Ile
                165                 170                 175

Lys Asn Ala Ile Asp Ala Cys Ile Glu Leu Gly Gly Glu Asn Tyr Val
                180                 185                 190

Phe Trp Gly Gly Arg Glu Gly Tyr Met Ser Leu Leu Asn Thr Asn Met
            195                 200                 205

Lys Arg Glu Lys Asp His Leu Ala Met Met Leu Thr Met Ala Arg Asp
210                 215                 220

Tyr Ala Arg Lys Asn Gly Phe Lys Gly Thr Phe Leu Val Glu Ser Lys
225                 230                 235                 240

Pro Met Glu Pro Thr Lys His Gln Tyr Asp Ala Asp Thr Glu Thr Val
                245                 250                 255

Ile Gly Phe Leu Arg His Tyr Gly Leu Asp Lys Asp Phe Ala Ile Asn
                260                 265                 270

Ile Glu Val Asn His Ala Thr Leu Ala Gly His Thr Phe Glu His Glu
            275                 280                 285

Leu Gln Ala Ala Ala Asp Ala Gly Met Leu Cys Ser Ile Asp Ala Asn
290                 295                 300

Arg Gly Asp Tyr Gln Asn Gly Trp Asp Thr Asp Gln Phe Pro Val Asp
305                 310                 315                 320

Ile Tyr Glu Leu Thr Gln Ala Trp Leu Val Ile Leu Glu Ala Gly Gly
                325                 330                 335

Leu Thr Thr Gly Gly Thr Asn Phe Asp Ala Lys Thr Arg Arg Asn Ser
            340                 345                 350

Thr Asp Leu Asp Asp Ile Phe Leu Ala His Ile Gly Gly Met Asp Ser
            355                 360                 365

Phe Ala Arg Ala Leu Met Ala Ala Asp Ile Leu Glu His Ser Asp
            370                 375                 380

Tyr Lys Lys Met Arg Ala Glu Arg Tyr Ala Ser Phe Asp Gln Gly Asp
385                 390                 395                 400

Gly Lys Lys Phe Glu Asp Gly Lys Leu Leu Leu Glu Asp Leu Arg Thr
                405                 410                 415

Ile Ala Leu Ala Gly Asp Glu Pro Lys Gln Ile Ser Gly Lys Gln Glu
                420                 425                 430

Leu Tyr Glu Met Ile Ile Asn Gln Tyr Ile
            435                 440
```

<210> SEQ ID NO 11
<211> LENGTH: 1308
<212> TYPE: DNA
<213> ORGANISM: Unknown
<220> FEATURE:
<223> OTHER INFORMATION: Obtained from environmental sample

<400> SEQUENCE: 11

```
atgaaacagt atttcccgaa catctccgcc atcaagtttg agggcgtcga gagcaagaat     60
cccctggctt accgctacta cgaccgcgac cgcgtcgtca tgggtaagaa gatgagcgaa    120
tggtttaagt tcgctatgtg ctggtggcac accctctgcg ccgagggctc cgatcagttc    180
ggtcccggca caaagacctt cccctggaac gccgccgccg accccgtgca ggctgccaag    240
gacaaggccg acgctggctt cgagatcatg cagaaactcg gcatcgagta ctactgcttc    300
```

```
cacgacgttg acctcgtggc cgaggctccc gacgtggaga cctacgagaa gaacctcaag    360
gagatcgtgg cttatctcaa gcagaaacag gctgagacgg gcatcaagct gctctgggc    420 actgccaacg tcttcggaca caagcgctac atgaacggag cctccacgaa ccccgacttc    480
gatgtcgtgg cacgcgctat cgtgcagatc aagaacgcca tcgatgctac catcgagctg    540
ggcggcacca actacgtctt ctggggcggt cgcgaaggct acatgagcct gctcaacacc    600
gatatgaagc gcgagaagga gcacatggct acgatgttga cgatggcacg cgactatgcc    660
cgttctaagg gattcaaggg cacgttcctc atcgaaccca aaccatgga acccacgaag    720 catcagtacg atgcggacac cgagacggtc atcggattcc tccgtgctca tggtctcgac    780
aaggatttca aggtcaacat cgaggtcaac cacgccacgc tggccggaca cacgttcgag    840
catgagctgg cctgcgccgt agacgccgat atgctcggca gcatcgatgc caatcgcggc    900
gactatcaga acggatggga caccgaccag ttccccatcg accactacga actcacgcag    960
gctatgctgc agatcatccg caacggaggt ttcaaggacg gtggcaccaa tttttgacgct   1020 aagacgcgcc gcaacagcac cgacctcgag gatatcttca tcgctcacgt agcagccatg   1080
gacgccatgg cccacgccct gttgtcggct gccgatatca tcgagaagtc gcccatctgc   1140
acgatggtca aggagcgtta cgccagcttc gatgccggcg aaggcaagcg cttcgaagaa   1200
ggcaagatga ccctcgagga agcctacgag tatggcaaga aggtcgggga gcccaagcag   1260
accagcggaa agcaggagct ctacgaagcc attgtcaata tgtattga                1308
```

<210> SEQ ID NO 12
<211> LENGTH: 435
<212> TYPE: PRT
<213> ORGANISM: Unknown
<220> FEATURE:
<223> OTHER INFORMATION: Obtained from environmental sample

<400> SEQUENCE: 12

```
Met Lys Gln Tyr Phe Pro Asn Ile Ser Ala Ile Lys Phe Glu Gly Val
1               5                  10                  15

Glu Ser Lys Asn Pro Leu Ala Tyr Arg Tyr Tyr Asp Arg Asp Arg Val
            20                  25                  30

Val Met Gly Lys Lys Met Ser Glu Trp Phe Lys Phe Ala Met Cys Trp
        35                  40                  45

Trp His Thr Leu Cys Ala Glu Gly Ser Asp Gln Phe Gly Pro Gly Thr
    50                  55                  60

Lys Thr Phe Pro Trp Asn Ala Ala Ala Asp Pro Val Gln Ala Ala Lys
65                  70                  75                  80

Asp Lys Ala Asp Ala Gly Phe Glu Ile Met Gln Lys Leu Gly Ile Glu
                85                  90                  95

Tyr Tyr Cys Phe His Asp Val Asp Leu Val Ala Glu Ala Pro Asp Val
            100                 105                 110

Glu Thr Tyr Glu Lys Asn Leu Lys Glu Ile Val Ala Tyr Leu Lys Gln
        115                 120                 125

Lys Gln Ala Glu Thr Gly Ile Lys Leu Leu Trp Gly Thr Ala Asn Val
    130                 135                 140

Phe Gly His Lys Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Thr Ile Glu Leu Gly Gly Thr Asn Tyr Val Phe Trp Gly Gly Arg Glu
            180                 185                 190
```

Gly Tyr Met Ser Leu Leu Asn Thr Asp Met Lys Arg Glu Lys Glu His
            195                 200                 205

Met Ala Thr Met Leu Thr Met Ala Arg Asp Tyr Ala Arg Ser Lys Gly
    210                 215                 220

Phe Lys Gly Thr Phe Leu Ile Glu Pro Lys Pro Met Glu Pro Thr Lys
225                 230                 235                 240

His Gln Tyr Asp Ala Asp Thr Glu Thr Val Ile Gly Phe Leu Arg Ala
                245                 250                 255

His Gly Leu Asp Lys Asp Phe Lys Val Asn Ile Glu Val Asn His Ala
                260                 265                 270

Thr Leu Ala Gly His Thr Phe Glu His Glu Leu Ala Cys Ala Val Asp
            275                 280                 285

Ala Asp Met Leu Gly Ser Ile Asp Ala Asn Arg Gly Asp Tyr Gln Asn
        290                 295                 300

Gly Trp Asp Thr Asp Gln Phe Pro Ile Asp His Tyr Glu Leu Thr Gln
305                 310                 315                 320

Ala Met Leu Gln Ile Ile Arg Asn Gly Gly Phe Lys Asp Gly Gly Thr
                325                 330                 335

Asn Phe Asp Ala Lys Thr Arg Arg Asn Ser Thr Asp Leu Glu Asp Ile
            340                 345                 350

Phe Ile Ala His Val Ala Ala Met Asp Ala Met Ala His Ala Leu Leu
        355                 360                 365

Ser Ala Ala Asp Ile Ile Glu Lys Ser Pro Ile Cys Thr Met Val Lys
    370                 375                 380

Glu Arg Tyr Ala Ser Phe Asp Ala Gly Glu Gly Lys Arg Phe Glu Glu
385                 390                 395                 400

Gly Lys Met Thr Leu Glu Glu Ala Tyr Glu Tyr Gly Lys Lys Val Gly
                405                 410                 415

Glu Pro Lys Gln Thr Ser Gly Lys Gln Glu Leu Tyr Glu Ala Ile Val
            420                 425                 430

Asn Met Tyr
        435

<210> SEQ ID NO 13
<211> LENGTH: 1317
<212> TYPE: DNA
<213> ORGANISM: Unknown
<220> FEATURE:
<223> OTHER INFORMATION: Obtained from environmental sample

<400> SEQUENCE: 13
atggcaacaa aagagtattt tcccggaata ggaaagatta aattcgaagg taaagagagt      60
atgaacccga tggcatatcg ttactacgat gctgagaagg taatcatggg taagaagatg     120
aaagattggt tgaagtttgc tatggcttgg tggcacactc tctgcgcaga aggtggtgac     180
caattcggtg gcggaacgaa acaattccct tggaatggtg actctgacgc tttgcaagca     240
gctaaaaata aattggatgc aggtttcgaa ttcatgcaga gatgggtat cgaatactat      300 tgcttccacg atgtagacct gatttctgaa ggtgcaagca tcgaagaata cgaagctaac     360
ttgaaagcta tcgtagctta tgcaaaagaa aaacaggctg aaactggtat caagctgttg     420
tggggtactg ctaacgtatt cggtcatgca cgttatatga acggtgctgc taccaatcct     480
gatttcgacg ttgtagcacg cgctgctgtt cagatcaaga acgctattga cgctactatc     540
gaactgggtg gttcaaacta tgtattctgg ggcggtcgcg aaggttacat gtctttgctg     600

-continued

```
aacactgacc agaaacgtga aaaagaacac cttgcaaaga tgttgactat cgctcgtgac    660
tatgcacgtg ctcgtggctt caaaggtact ttcctgattg agccgaaacc gatggaaccg    720
acaaaacatc agtatgatgt agatactgaa acagttatcg gcttcctgaa agctcacggt    780
ttggataagg atttcaaagt aaacatcgag gttaatcacg caactttggc tggccatact    840
ttcgaacacg aactggctgt agctgttgac aacggcatgt taggttctat cgacgctaac    900
cgtggtgact accagaacgg ttgggatact gaccaattcc ctatcgataa ctacgaactg    960
actcaagcta tgatgcagat catccgcaac ggtggtttgg gtaatggcgg tactaacttc   1020
gacgctaaga cccgtcgtaa ctctaccgac ctggaagata tcttcatcgc tcacattgca   1080
ggtatggatg ctatggcacg tgctctggaa agtgcagcta aattactgga agaatctcct   1140
tataagaaaa tgttggctga tcgttacgca tcattcgacg gtggcaaggg taaggaattc   1200
gaagaaggca aattgtcttt ggaagatgtt gtagcttatg cgaaagctaa cggcgaaccg   1260
aagcaaacca gcggcaagca agaattgtat gaagcaatcg tgaatatgta ttgctaa     1317
```

<210> SEQ ID NO 14
<211> LENGTH: 438
<212> TYPE: PRT
<213> ORGANISM: Unknown
<220> FEATURE:
<223> OTHER INFORMATION: Obtained from environmental sample

<400> SEQUENCE: 14

```
Met Ala Thr Lys Glu Tyr Phe Pro Gly Ile Gly Lys Ile Lys Phe Glu
1               5                   10                  15

Gly Lys Glu Ser Met Asn Pro Met Ala Tyr Arg Tyr Tyr Asp Ala Glu
            20                  25                  30

Lys Val Ile Met Gly Lys Lys Met Lys Asp Trp Leu Lys Phe Ala Met
        35                  40                  45

Ala Trp Trp His Thr Leu Cys Ala Glu Gly Gly Asp Gln Phe Gly Gly
    50                  55                  60

Gly Thr Lys Gln Phe Pro Trp Asn Gly Asp Ser Asp Ala Leu Gln Ala
65                  70                  75                  80

Ala Lys Asn Lys Leu Asp Ala Gly Phe Glu Phe Met Gln Lys Met Gly
                85                  90                  95

Ile Glu Tyr Tyr Cys Phe His Asp Val Asp Leu Ile Ser Glu Gly Ala
            100                 105                 110

Ser Ile Glu Glu Tyr Glu Ala Asn Leu Lys Ala Ile Val Ala Tyr Ala
        115                 120                 125

Lys Glu Lys Gln Ala Glu Thr Gly Ile Lys Leu Leu Trp Gly Thr Ala
    130                 135                 140

Asn Val Phe Gly His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Glu Leu Gly Gly Ser Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Lys Met Leu Thr Ile Ala Arg Asp Tyr Ala Arg Ala
    210                 215                 220

Arg Gly Phe Lys Gly Thr Phe Leu Ile Glu Pro Lys Pro Met Glu Pro
225                 230                 235                 240
```

```
Thr Lys His Gln Tyr Asp Val Asp Thr Glu Thr Val Ile Gly Phe Leu
            245                 250                 255
Lys Ala His Gly Leu Asp Lys Asp Phe Lys Val Asn Ile Glu Val Asn
        260                 265                 270
His Ala Thr Leu Ala Gly His Thr Phe Glu His Glu Leu Ala Val Ala
    275                 280                 285
Val Asp Asn Gly Met Leu Gly Ser Ile Asp Ala Asn Arg Gly Asp Tyr
290                 295                 300
Gln Asn Gly Trp Asp Thr Asp Gln Phe Pro Ile Asp Asn Tyr Glu Leu
305                 310                 315                 320
Thr Gln Ala Met Met Gln Ile Ile Arg Asn Gly Gly Leu Gly Asn Gly
            325                 330                 335
Gly Thr Asn Phe Asp Ala Lys Thr Arg Arg Asn Ser Thr Asp Leu Glu
        340                 345                 350
Asp Ile Phe Ile Ala His Ile Ala Gly Met Asp Ala Met Ala Arg Ala
    355                 360                 365
Leu Glu Ser Ala Ala Lys Leu Leu Glu Glu Ser Pro Tyr Lys Lys Met
370                 375                 380
Leu Ala Asp Arg Tyr Ala Ser Phe Asp Gly Gly Lys Gly Lys Glu Phe
385                 390                 395                 400
Glu Glu Gly Lys Leu Ser Leu Glu Asp Val Val Ala Tyr Ala Lys Ala
            405                 410                 415
Asn Gly Glu Pro Lys Gln Thr Ser Gly Lys Gln Glu Leu Tyr Glu Ala
        420                 425                 430
Ile Val Asn Met Tyr Cys
        435

<210> SEQ ID NO 15
<211> LENGTH: 1314
<212> TYPE: DNA
<213> ORGANISM: Unknown
<220> FEATURE:
<223> OTHER INFORMATION: Obtained from environmental sample

<400> SEQUENCE: 15
atggcaaaag agtattttcc tggcgtgaaa aaaatccagt tcgagggtaa ggacagtaag      60
aatccaatgg cttaccgtta ttatgatgca gagaaggtca tcatgggtaa gaagatgaag     120
gattggttga agttcgctat ggcttggtgg cacactttgt gcgctgaggg cgcagaccag     180
ttcggtggcg gtactaagac tttcccttgg aacgaaggtg caaacgcttt ggaagttgct     240
aagaataagg ctgatgctgg tttcgagatt atggagaagc ttggcatcga gtactactgt     300
ttccacgatg tagacctcgt tgaggaggct gcaactatcg aggagtatga ggctaacatg     360
aaggctatcg ttgcttatct taaggagaag caggctgcta ctggcaagaa gcttcttttgg    420 ggtactgcta acgtattcgg caacaagcgc tatatgaacg gtgcttctac aaaccctgac     480
ttcgacgttg ttgctcgcgc ttgtgttcag attaagaacg ctatcgacgc tactatcgaa     540
cttggtggta caaactacgt attctggggt ggccgcgagg gttatatgag ccttcttaac     600
acagatatga gcgtgagaa ggagcacatg gcaactatgc ttactaaggc tcgcgactac      660
gctcgttcaa agggctttac tggtacattc cttatcgagc aaagccaat ggaaccatca      720 aagcatcagt atgatgttga tactgagact gtttgtggtt tcttgagggc tcacggtctt    780
gacaaggact tcaaggtaaa catcgaggtt aaccacgcta ctttggctgg tcacacattc     840
gagcacgagt tggctgctgc tgttgataac ggtatgcttg ctctatcga cgctaaccgc      900
```

```
ggtgactacc agaacggttg ggatactgac cagttcccta tcgacaactt cgagcttatt    960
caggctatga tgcagattat ccgcaacggt ggtcttggca acggtggtac aaacttcgac   1020
gctaagactc gtcgtaactc aactgacctt gaggatatct tcatcgcaca catcgctggt   1080
atggatgcaa tggctcgcgc tcttgagaac gcagcagacc ttttggagaa ctctccaatc   1140
aagaagatgg ttgctgagcg ttacgcttca ttcgacagcg gcaagggtaa ggagttcgag   1200
gaaggcaagt tgagccttgg ggacatcgtt gcttatgcta agcagaacgg tgagcctaag   1260
cagacaagcg gtaagcagga gctttacgag gctatcgtaa acatgtactg ctaa         1314

<210> SEQ ID NO 16
<211> LENGTH: 437
<212> TYPE: PRT
<213> ORGANISM: Unknown
<220> FEATURE:
<223> OTHER INFORMATION: Obtained from environmental sample

<400> SEQUENCE: 16

Met Ala Lys Glu Tyr Phe Pro Gly Val Lys Lys Ile Gln Phe Glu Gly
1               5                   10                  15

Lys Asp Ser Lys Asn Pro Met Ala Tyr Arg Tyr Tyr Asp Ala Glu Lys
                20                  25                  30

Val Ile Met Gly Lys Lys Met Lys Asp Trp Leu Lys Phe Ala Met Ala
            35                  40                  45

Trp Trp His Thr Leu Cys Ala Glu Gly Ala Asp Gln Phe Gly Gly Gly
        50                  55                  60

Thr Lys Thr Phe Pro Trp Asn Glu Gly Ala Asn Ala Leu Glu Val Ala
65                  70                  75                  80

Lys Asn Lys Ala Asp Ala Gly Phe Glu Ile Met Glu Lys Leu Gly Ile
                85                  90                  95

Glu Tyr Tyr Cys Phe His Asp Val Asp Leu Val Glu Glu Ala Ala Thr
            100                 105                 110

Ile Glu Glu Tyr Glu Ala Asn Met Lys Ala Ile Val Ala Tyr Leu Lys
        115                 120                 125

Glu Lys Gln Ala Ala Thr Gly Lys Lys Leu Leu Trp Gly Thr Ala Asn
    130                 135                 140

Val Phe Gly Asn Lys Arg Tyr Met Asn Gly Ala Ser Thr Asn Pro Asp
145                 150                 155                 160

Phe Asp Val Val Ala Arg Ala Cys Val Gln Ile Lys Asn Ala Ile Asp
                165                 170                 175

Ala Thr Ile Glu Leu Gly Gly Thr Asn Tyr Val Phe Trp Gly Gly Arg
            180                 185                 190

Glu Gly Tyr Met Ser Leu Leu Asn Thr Asp Met Lys Arg Glu Lys Glu
        195                 200                 205

His Met Ala Thr Met Leu Thr Lys Ala Arg Asp Tyr Ala Arg Ser Lys
    210                 215                 220

Gly Phe Thr Gly Thr Phe Leu Ile Glu Pro Lys Pro Met Glu Pro Ser
225                 230                 235                 240

Lys His Gln Tyr Asp Val Asp Thr Glu Thr Val Cys Gly Phe Leu Arg
                245                 250                 255

Ala His Gly Leu Asp Lys Asp Phe Lys Val Asn Ile Glu Val Asn His
            260                 265                 270

Ala Thr Leu Ala Gly His Thr Phe Glu His Glu Leu Ala Ala Ala Val
        275                 280                 285

Asp Asn Gly Met Leu Gly Ser Ile Asp Ala Asn Arg Gly Asp Tyr Gln
```

```
         290                 295                 300
Asn Gly Trp Asp Thr Asp Gln Phe Pro Ile Asp Asn Phe Glu Leu Ile
305                 310                 315                 320

Gln Ala Met Met Gln Ile Ile Arg Asn Gly Leu Gly Asn Gly Gly
                325                 330                 335

Thr Asn Phe Asp Ala Lys Thr Arg Arg Asn Ser Thr Asp Leu Glu Asp
                340                 345                 350

Ile Phe Ile Ala His Ile Ala Gly Met Asp Ala Met Ala Arg Ala Leu
                355                 360                 365

Glu Asn Ala Ala Asp Leu Leu Glu Asn Ser Pro Ile Lys Lys Met Val
370                 375                 380

Ala Glu Arg Tyr Ala Ser Phe Asp Ser Gly Lys Gly Lys Glu Phe Glu
385                 390                 395                 400

Glu Gly Lys Leu Ser Leu Gly Asp Ile Val Ala Tyr Ala Lys Gln Asn
                405                 410                 415

Gly Glu Pro Lys Gln Thr Ser Gly Lys Gln Glu Leu Tyr Glu Ala Ile
                420                 425                 430

Val Asn Met Tyr Cys
        435

<210> SEQ ID NO 17
<211> LENGTH: 1317
<212> TYPE: DNA
<213> ORGANISM: Unknown
<220> FEATURE:
<223> OTHER INFORMATION: Obtained from environmental sample

<400> SEQUENCE: 17
atggcgacaa aagaatactt tcccggaata gggaaaatca agtttgaggg tgtgaatagc      60
tataatccgc tggcatacag atattacgat gccgagcgca tagtccttgg caagccgatg     120
aaggagtggc tcaagtttgc catggcatgg tggcacacac tctgcgcaga gggtggcgac     180
cagtttggcg gcggtacgaa gaattttccc tggaatggag atcccgatcc ggtacaggcc     240
gcaaaaaaca aagtagacgc cggcttcgaa ttcatgacca agatgggaat agagtatttc     300
tgtttccacg acgtggatct cgtcagcgag gcagcaacca tcgaggagta tgaggccaac     360
ctgaaggaag tggtgggcta catcaaggaa aagcaggccg agacggggat caaaaacctc     420
tggggcactg ccaacgtgtt cagccacgcg cgctacatga acgagccgc caccaacccc     480 gacttcgatg tagtggcccg cgcagccgtg cagatcaaga atgctatcga cgccacgata     540
gccttaggtg gcaccaacta cgtgttctgg ggtggccgtg aaggttacat gagcctgctc     600
aacaccgacc agaagcgcga gaaggagcat ctggcaatga tgctccgcat ggcccgcgac     660
tatgcgcgtg caaaaggctt caccggcacc ttccttatcg agcccaagcc gatggagccc     720
accaagcacc agtatgatgt agacaccgag actgtgatag gcttcctccg tgcccacggc     780
ctcgacaagg acttcaaggt caacatagag gtgaaccacg ccaccctggc cggccatacc     840
ttcgagcatg agctggcagt ggccgtggac aacggtatgc tcggcagcat cgacgccaac     900
cgcggtgact accagaacgg ctgggatacc gaccagttcc ccatcgacaa ctacgagctg     960
acccaggcca tgatgcagat aatacgcaac ggcggcttcg caacggcgg atgcaacttc    1020 gacgccaaga cacgccgcaa ctccaccgac ctggaggata tcttcatagc ccacatagca    1080
ggcatggacg ccatggcccg cgccctgctc agccagcag aagtgctgga gaaatcgccc    1140
tacaggaaga tgctcgccga gcgctacgca ccgtttgatg ccggccaggg aaaggcattt    1200
```

```
gaagagggcg caatgtcgct caccgacctt gtggagtatg ccaaggagca tggcgagccc    1260
acacagactt ccggcaagca ggaactctat gaggcaatcg tcaatatgta ttgctaa       1317
```

<210> SEQ ID NO 18
<211> LENGTH: 438
<212> TYPE: PRT
<213> ORGANISM: Unknown
<220> FEATURE:
<223> OTHER INFORMATION: Obtained from environmental sample

<400> SEQUENCE: 18

```
Met Ala Thr Lys Glu Tyr Phe Pro Gly Ile Gly Lys Ile Lys Phe Glu
1               5                   10                  15

Gly Val Asn Ser Tyr Asn Pro Leu Ala Tyr Arg Tyr Tyr Asp Ala Glu
            20                  25                  30

Arg Ile Val Leu Gly Lys Pro Met Lys Glu Trp Leu Lys Phe Ala Met
        35                  40                  45

Ala Trp Trp His Thr Leu Cys Ala Glu Gly Gly Asp Gln Phe Gly Gly
    50                  55                  60

Gly Thr Lys Asn Phe Pro Trp Asn Gly Asp Pro Asp Pro Val Gln Ala
65                  70                  75                  80

Ala Lys Asn Lys Val Asp Ala Gly Phe Glu Phe Met Thr Lys Met Gly
                85                  90                  95

Ile Glu Tyr Phe Cys Phe His Asp Val Asp Leu Val Ser Glu Ala Ala
            100                 105                 110

Thr Ile Glu Glu Tyr Glu Ala Asn Leu Lys Glu Val Val Gly Tyr Ile
        115                 120                 125

Lys Glu Lys Gln Ala Glu Thr Gly Ile Lys Asn Leu Trp Gly Thr Ala
    130                 135                 140

Asn Val Phe Ser His Ala Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Ala Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Met Met Leu Arg Met Ala Arg Asp Tyr Ala Arg Ala
    210                 215                 220

Lys Gly Phe Thr Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Arg Ala His Gly Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Tyr
    290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Phe Gly Asn Gly
                325                 330                 335

Gly Cys Asn Phe Asp Ala Lys Thr Arg Arg Asn Ser Thr Asp Leu Glu
            340                 345                 350
```

```
Asp Ile Phe Ile Ala His Ile Ala Gly Met Asp Ala Met Ala Arg Ala
        355                 360                 365

Leu Leu Ser Ala Ala Glu Val Leu Glu Lys Ser Pro Tyr Arg Lys Met
    370                 375                 380

Leu Ala Glu Arg Tyr Ala Pro Phe Asp Ala Gly Gln Gly Lys Ala Phe
385                 390                 395                 400

Glu Glu Gly Ala Met Ser Leu Thr Asp Leu Val Glu Tyr Ala Lys Glu
                405                 410                 415

His Gly Glu Pro Thr Gln Thr Ser Gly Lys Gln Glu Leu Tyr Glu Ala
            420                 425                 430

Ile Val Asn Met Tyr Cys
            435

<210> SEQ ID NO 19
<211> LENGTH: 1320
<212> TYPE: DNA
<213> ORGANISM: Unknown
<220> FEATURE:
<223> OTHER INFORMATION: Obtained from environmental sample

<400> SEQUENCE: 19
atggcaacaa aggaatattt tccccatata gggaagatcc agttcaaagg cacggaatcg      60
tacgatccga tgtcgtatcg ttactatgac gccgagcgcg tagttctggg caagcccatg     120
aaggaatggc tgaaattcgc catggcatgg tggcacacat tgtgcgccga gggcggcgac     180
cagttcggcg gcggaacgaa gaagttcccc tggaacgagg gcgaggacgc catgaccatc     240
gccaagcaga aggctgacgc cggcttcgag atcatgcaga agctcggcat cgagtatttc     300
tgcttccacg acatcgacct gatcggcgac ctgggcgacg catcgagga ctatgagaac      360 cgtatgcacg aaatcaccgc acacctgaag gagaagatgg ccgccacggg catcaagaac     420
ctgtggggca ctgccaacgt gttcggccac gcacgctata tgaacggcgc cgccaccaac     480
cccgacttcg acgttgtggc acgcgcatgt gtgcagatca agaacgccat cgacgccacc     540
atcgctctag gcggtacaaa ctatgtattc tggggcggcc gcgagggcta catgagcctg     600
ctgaacaccg accagaagcg cgagaaagag cacttggcta ccatgctgac catggcacgc     660
gactatgccc gcgccaatgg cttcaccgga acgttcctga tcgagcccaa acccatggag     720
cccagcaagc atcagtatga tgtggatacc gagaccgtaa tcggcttcct gaaggcccac     780
aacctggaca aggacttcaa ggtgaacatc gaggtgaacc atgccactct ggccggccac     840
acattcgagc atgagctggc agtagccgtg acaacggca tgctgggcag catcgacgcc      900
aaccgcggcg actatcagaa cggctgggac accgaccagt tccccatcga caactatgag     960
ctgacccagg ccatgatgca gataatccgc aacggtggcc tcggcaacgg cggtaccaac    1020
ttcgacgcca agacacgtcg caactccacc gacctggacg acatcttcat cgctcacatc    1080
gccggtatgg acgctatggc ccgcgctccg ctcagcgcag ccgacgtgct tgagaagtcg    1140
ccttacaaga agatgctggc cgaccgctac gcttcattcg acagcggcga gggcaagaag    1200
ttcgaggaag gcaagatgac tctggaggat gtcgtggcct acgccaagaa gaatcccgaa    1260
cccgctcaga ccagcggcaa gcaggaactc tacgaggcca tcatcaacat gtacgcctga    1320

<210> SEQ ID NO 20
<211> LENGTH: 439
<212> TYPE: PRT
<213> ORGANISM: Unknown
<220> FEATURE:
```

<223> OTHER INFORMATION: Obtained from environmental sample

<400> SEQUENCE: 20

| | | | | | | | | | | | | | | |
|---|---|---|---|---|---|---|---|---|---|---|---|---|---|---|
| Met | Ala | Thr | Lys | Glu | Tyr | Phe | Pro | His | Ile | Gly | Lys | Ile | Gln | Phe | Lys |
| 1 | | | | 5 | | | | | 10 | | | | | 15 | |
| Gly | Thr | Glu | Ser | Tyr | Asp | Pro | Met | Ser | Tyr | Arg | Tyr | Tyr | Asp | Ala | Glu |
| | | | 20 | | | | | 25 | | | | | 30 | | |
| Arg | Val | Val | Leu | Gly | Lys | Pro | Met | Lys | Glu | Trp | Leu | Lys | Phe | Ala | Met |
| | | 35 | | | | | 40 | | | | | 45 | | | |
| Ala | Trp | Trp | His | Thr | Leu | Cys | Ala | Glu | Gly | Gly | Asp | Gln | Phe | Gly | Gly |
| | 50 | | | | | 55 | | | | | 60 | | | | |
| Gly | Thr | Lys | Lys | Phe | Pro | Trp | Asn | Glu | Gly | Glu | Asp | Ala | Met | Thr | Ile |
| 65 | | | | | 70 | | | | | 75 | | | | | 80 |
| Ala | Lys | Gln | Lys | Ala | Asp | Ala | Gly | Phe | Glu | Ile | Met | Gln | Lys | Leu | Gly |
| | | | | 85 | | | | | 90 | | | | | 95 | |
| Ile | Glu | Tyr | Phe | Cys | Phe | His | Asp | Ile | Asp | Leu | Ile | Gly | Asp | Leu | Gly |
| | | | 100 | | | | | 105 | | | | | 110 | | |
| Asp | Asp | Ile | Glu | Asp | Tyr | Glu | Asn | Arg | Met | His | Glu | Ile | Thr | Ala | His |
| | | 115 | | | | | 120 | | | | | 125 | | | |
| Leu | Lys | Glu | Lys | Met | Ala | Ala | Thr | Gly | Ile | Lys | Asn | Leu | Trp | Gly | Thr |
| | 130 | | | | | 135 | | | | | 140 | | | | |
| Ala | Asn | Val | Phe | Gly | His | Ala | Arg | Tyr | Met | Asn | Gly | Ala | Ala | Thr | Asn |
| 145 | | | | | 150 | | | | | 155 | | | | | 160 |
| Pro | Asp | Phe | Asp | Val | Val | Ala | Arg | Ala | Cys | Val | Gln | Ile | Lys | Asn | Ala |
| | | | | 165 | | | | | 170 | | | | | 175 | |
| Ile | Asp | Ala | Thr | Ile | Ala | Leu | Gly | Gly | Thr | Asn | Tyr | Val | Phe | Trp | Gly |
| | | | 180 | | | | | 185 | | | | | 190 | | |
| Gly | Arg | Glu | Gly | Tyr | Met | Ser | Leu | Leu | Asn | Thr | Asp | Gln | Lys | Arg | Glu |
| | | 195 | | | | | 200 | | | | | 205 | | | |
| Lys | Glu | His | Leu | Ala | Thr | Met | Leu | Thr | Met | Ala | Arg | Asp | Tyr | Ala | Arg |
| | 210 | | | | | 215 | | | | | 220 | | | | |
| Ala | Asn | Gly | Phe | Thr | Gly | Thr | Phe | Leu | Ile | Glu | Pro | Lys | Pro | Met | Glu |
| 225 | | | | | 230 | | | | | 235 | | | | | 240 |
| Pro | Ser | Lys | His | Gln | Tyr | Asp | Val | Asp | Thr | Glu | Thr | Val | Ile | Gly | Phe |
| | | | | 245 | | | | | 250 | | | | | 255 | |
| Leu | Lys | Ala | His | Asn | Leu | Asp | Lys | Asp | Phe | Lys | Val | Asn | Ile | Glu | Val |
| | | | 260 | | | | | 265 | | | | | 270 | | |
| Asn | His | Ala | Thr | Leu | Ala | Gly | His | Thr | Phe | Glu | His | Glu | Leu | Ala | Val |
| | | 275 | | | | | 280 | | | | | 285 | | | |
| Ala | Val | Asp | Asn | Gly | Met | Leu | Gly | Ser | Ile | Asp | Ala | Asn | Arg | Gly | Asp |
| | 290 | | | | | 295 | | | | | 300 | | | | |
| Tyr | Gln | Asn | Gly | Trp | Asp | Thr | Asp | Gln | Phe | Pro | Ile | Asp | Asn | Tyr | Glu |
| 305 | | | | | 310 | | | | | 315 | | | | | 320 |
| Leu | Thr | Gln | Ala | Met | Met | Gln | Ile | Ile | Arg | Asn | Gly | Gly | Leu | Gly | Asn |
| | | | | 325 | | | | | 330 | | | | | 335 | |
| Gly | Gly | Thr | Asn | Phe | Asp | Ala | Lys | Thr | Arg | Arg | Asn | Ser | Thr | Asp | Leu |
| | | | 340 | | | | | 345 | | | | | 350 | | |
| Asp | Asp | Ile | Phe | Ile | Ala | His | Ile | Ala | Gly | Met | Asp | Ala | Met | Ala | Arg |
| | | 355 | | | | | 360 | | | | | 365 | | | |
| Ala | Pro | Leu | Ser | Ala | Ala | Asp | Val | Leu | Glu | Lys | Ser | Pro | Tyr | Lys | Lys |
| | 370 | | | | | 375 | | | | | 380 | | | | |
| Met | Leu | Ala | Asp | Arg | Tyr | Ala | Ser | Phe | Asp | Ser | Gly | Glu | Gly | Lys | Lys |
| 385 | | | | | 390 | | | | | 395 | | | | | 400 |

```
Phe Glu Glu Gly Lys Met Thr Leu Glu Asp Val Val Ala Tyr Ala Lys
            405                 410                 415

Lys Asn Pro Glu Pro Ala Gln Thr Ser Gly Lys Gln Glu Leu Tyr Glu
        420                 425                 430

Ala Ile Ile Asn Met Tyr Ala
        435
```

<210> SEQ ID NO 21
<211> LENGTH: 1320
<212> TYPE: DNA
<213> ORGANISM: Unknown
<220> FEATURE:
<223> OTHER INFORMATION: Obtained from environmental sample

<400> SEQUENCE: 21

```
atggcaacaa aagaattttt tcccgagatt ggtaaaatca agtttgaggg ccgcgaaagc      60
cgcaatcccc tcgcattccg ctactacggc cccgagaaag tcgttcttgg caagaagatg     120
aaagactggt tcaagtttgc gatggcttgg tggcacacac tgtgcgccca gggcaccgac     180
cagtttggtg gcgacaccaa gcagtttccg tggaacactg ccagtgaccc catgcaggcc     240
gccaaggata aggtggatgc cggatttgaa ttcatgacca agatgggcat tgagtacttc     300
tgcttccacg atgtggatct cgtcgccgag gccgccactg tcgaggagta tgaggctaac     360
ctcaagacca tcgtcgccta catcaaagag aaacaagccg agaccggcat caagaacctg     420
tggggcacag ccaacgtatt cggacacaaa cgctacatga acggtgccgc caccaacccc     480
gactttgatg tcgtggcacg cgccatcgtg caaatcaaga acgccatcga cgccaccatc     540
gagttgggcg gcacgagtta cgtctttggg ggcggccgcg agggccacat gagcctgctc     600
aacaccgacc agaagcgcga gaaggagcac cttgcacgca tgctgaccat ggcacgcgac     660
tatgcccgcg cacgtggttt caacggcacc ttcctcatcg agcccaagcc catggagccg     720
accaagcacc aatatgatgt ggacaccgag accgtcatcg gtttcctgcg tgcccatggt     780
ctggacaagg acttcaaggt caacatcgag gtgaaccacg ctacactggc cggacacacc     840
ttcgagcgcg aactggcagt ggccgtcgac aacggtctac tcggctcaat cgacgccaac     900
cgtggtgact atcagaatgg ttgggacacc gatcagttcc ccatcgacca ctatgagttg     960
gttcagggca tgttgcagat tatccgcaat ggtggtttca ccgacggtgg caccaacttc    1020
gatgccaaga cccgccgcaa ctcgaccgac ctcgaggaca tcttcatcgc ccacatcgcc    1080
gcgatggatg ccatggctca tgcgctggag agtgctgcct ccatcatcga ggagtcgccc    1140
tactgccaga tggtcaagga tcgctatgcc tcatttgact ccggcatcgg caaggacttt    1200
gaggacggca agttgacact ggaacaagcc tacgagtacg gtaagcaagt gggcgaaccc    1260
aagcagacca gtggcaagca agaactgtac gagtcaatca tcaatatgta ttccatttaa    1320
```

<210> SEQ ID NO 22
<211> LENGTH: 439
<212> TYPE: PRT
<213> ORGANISM: Unknown
<220> FEATURE:
<223> OTHER INFORMATION: Obtained from environmental sample

<400> SEQUENCE: 22

```
Met Ala Thr Lys Glu Phe Phe Pro Glu Ile Gly Lys Ile Lys Phe Glu
1               5                   10                  15

Gly Arg Glu Ser Arg Asn Pro Leu Ala Phe Arg Tyr Tyr Gly Pro Glu
            20                  25                  30
```

```
Lys Val Val Leu Gly Lys Lys Met Lys Asp Trp Phe Lys Phe Ala Met
            35                  40                  45
Ala Trp Trp His Thr Leu Cys Ala Gln Gly Thr Asp Gln Phe Gly Gly
 50                  55                  60
Asp Thr Lys Gln Phe Pro Trp Asn Thr Ala Ser Asp Pro Met Gln Ala
 65                  70                  75                  80
Ala Lys Asp Lys Val Asp Ala Gly Phe Glu Phe Met Thr Lys Met Gly
                 85                  90                  95
Ile Glu Tyr Phe Cys Phe His Asp Val Asp Leu Val Ala Glu Ala Ala
                100                 105                 110
Thr Val Glu Glu Tyr Glu Ala Asn Leu Lys Thr Ile Val Ala Tyr Ile
            115                 120                 125
Lys Glu Lys Gln Ala Glu Thr Gly Ile Lys Asn Leu Trp Gly Thr Ala
    130                 135                 140
Asn Val Phe Gly His Lys Arg Tyr Met Asn Gly Ala Ala Thr Asn Pro
145                 150                 155                 160
Asp Phe Asp Val Val Ala Arg Ala Ile Val Gln Ile Lys Asn Ala Ile
                165                 170                 175
Asp Ala Thr Ile Glu Leu Gly Gly Thr Ser Tyr Val Phe Trp Gly Gly
            180                 185                 190
Arg Glu Gly His Met Ser Leu Leu Asn Thr Asp Gln Lys Arg Glu Lys
    195                 200                 205
Glu His Leu Ala Arg Met Leu Thr Met Ala Arg Asp Tyr Ala Arg Ala
    210                 215                 220
Arg Gly Phe Asn Gly Thr Phe Leu Ile Glu Pro Lys Pro Met Glu Pro
225                 230                 235                 240
Thr Lys His Gln Tyr Asp Val Asp Thr Glu Thr Val Ile Gly Phe Leu
                245                 250                 255
Arg Ala His Gly Leu Asp Lys Asp Phe Lys Val Asn Ile Glu Val Asn
            260                 265                 270
His Ala Thr Leu Ala Gly His Thr Phe Glu Arg Glu Leu Ala Val Ala
    275                 280                 285
Val Asp Asn Gly Leu Leu Gly Ser Ile Asp Ala Asn Arg Gly Asp Tyr
    290                 295                 300
Gln Asn Gly Trp Asp Thr Asp Gln Phe Pro Ile Asp His Tyr Glu Leu
305                 310                 315                 320
Val Gln Gly Met Leu Gln Ile Ile Arg Asn Gly Gly Phe Thr Asp Gly
                325                 330                 335
Gly Thr Asn Phe Asp Ala Lys Thr Arg Arg Asn Ser Thr Asp Leu Glu
            340                 345                 350
Asp Ile Phe Ile Ala His Ile Ala Ala Met Asp Ala Met Ala His Ala
    355                 360                 365
Leu Glu Ser Ala Ala Ser Ile Ile Glu Glu Ser Pro Tyr Cys Gln Met
    370                 375                 380
Val Lys Asp Arg Tyr Ala Ser Phe Asp Ser Gly Ile Gly Lys Asp Phe
385                 390                 395                 400
Glu Asp Gly Lys Leu Thr Leu Glu Gln Ala Tyr Glu Tyr Gly Lys Gln
                405                 410                 415
Val Gly Glu Pro Lys Gln Thr Ser Gly Lys Gln Glu Leu Tyr Glu Ser
            420                 425                 430
Ile Ile Asn Met Tyr Ser Ile
            435
```

<210> SEQ ID NO 23
<211> LENGTH: 1317
<212> TYPE: DNA
<213> ORGANISM: Unknown
<220> FEATURE:
<223> OTHER INFORMATION: Obtained from environmental sample

<400> SEQUENCE: 23

```
atggcaacaa aagagtattt tcctggtata ggaaagatta aatttgaagg taaagagagt      60
aagaatccga tggcattccg ctattatgat gccaataaag taatcatggg caagaagatg     120
agcgagtggc tgaagtttgc catggcttgg tggcacacat tgtgcgccga aggtggtgac     180
cagtttggtg gtggaacaaa gactttcccg tggaacgatt cggacaacgc cgtagaagca     240
gccaaccata agtagatgc cggttttgaa tttatgcaga aatgggcat cgaatactat      300
tgcttccatg atgtagacct ctgcactgaa gctgctacca ttgaagaata tgaagccaat     360
ctgaaggaaa tagtagccta tccgaaacag aaacaggctg aaacaggtat caaacttctg     420
tggggtacgg caaatgtatt tggtcacaaa cgctatatga atggtgctgc taccaatccg     480
gattttgatg tagtggctcg tgctgctgta cagattaaga atgcgataga cgctacaatt     540
gaactcggtg gtagcaacta cgtgttctgg ggcggccgtg aaggttatat gagcttgctc     600
aatacagacc agaaacgtga gaaagagcat ttggcacaaa tgttgaccat ggctcgtgac     660
tatgctcgtg ccaaaggatt caagggtacc ttcctggttg aacccaaacc gatggaacca     720
actaaacacc agtatgatgt agatacggaa actgtaatcg gcttcctcaa ggctcataat     780
ttggataagg atttcaaggt aaatattgaa gtaaaccatg ctacattggc cggtcatact     840
tttgaacacg aattggctgt tgccgtagac aacgatatgc ttggctctat cgatgccaac     900
cgcggtgact atcagaacgg ttgggatact gaccagttcc ccattgacaa cttcgagctt     960
atccaagcca tgatgcagat tattcgcggt ggtggcttca agatggtgg tacaaacttc    1020
gacgctaaga ctcgtcgtaa ctctaccgac ctggaagata ttttcattgc acacatcgct    1080
ggtatggatg ctatggcacg tgctttggaa agtgcagcca agttgcttga ggaatctcct    1140
tataagaaaa tgttggctga ccgctatgca tcgttcgata gtggcaaagg taaggagttt    1200
gaagaaggca agctgacatt ggaagacgtt gtagtttatg ccaagcagaa tggcgagcct    1260
aaacagacca gcggtaagca ggaattgtat gaggcaattg taaatatgta tgcctga      1317
```

<210> SEQ ID NO 24
<211> LENGTH: 438
<212> TYPE: PRT
<213> ORGANISM: Unknown
<220> FEATURE:
<223> OTHER INFORMATION: Obtained from environmental sample

<400> SEQUENCE: 24

```
Met Ala Thr Lys Glu Tyr Phe Pro Gly Ile Gly Lys Ile Lys Phe Glu
1               5                   10                  15

Gly Lys Glu Ser Lys Asn Pro Met Ala Phe Arg Tyr Tyr Asp Ala Asn
            20                  25                  30

Lys Val Ile Met Gly Lys Lys Met Ser Glu Trp Leu Lys Phe Ala Met
        35                  40                  45

Ala Trp Trp His Thr Leu Cys Ala Glu Gly Gly Asp Gln Phe Gly Gly
    50                  55                  60

Gly Thr Lys Thr Phe Pro Trp Asn Asp Ser Asp Asn Ala Val Glu Ala
65                  70                  75                  80

Ala Asn His Lys Val Asp Ala Gly Phe Glu Phe Met Gln Lys Met Gly
```

```
                    85                  90                  95
Ile Glu Tyr Tyr Cys Phe His Asp Val Asp Leu Cys Thr Glu Ala Ala
            100                 105                 110

Thr Ile Glu Glu Tyr Glu Ala Asn Leu Lys Glu Ile Val Ala Tyr Pro
        115                 120                 125

Lys Gln Lys Gln Ala Glu Thr Gly Ile Lys Leu Leu Trp Gly Thr Ala
130                 135                 140

Asn Val Phe Gly His Lys Arg Tyr Met Asn Gly Ala Ala Thr Asn Pro
145                 150                 155                 160

Asp Phe Asp Val Val Ala Arg Ala Ala Val Gln Ile Lys Asn Ala Ile
                165                 170                 175

Asp Ala Thr Ile Glu Leu Gly Gly Ser Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Gln Met Leu Thr Met Ala Arg Asp Tyr Ala Arg Ala
    210                 215                 220

Lys Gly Phe Lys Gly Thr Phe Leu Val Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Asn Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Asp Met Leu Gly Ser Ile Asp Ala Asn Arg Gly Asp Tyr
    290                 295                 300

Gln Asn Gly Trp Asp Thr Asp Gln Phe Pro Ile Asp Asn Phe Glu Leu
305                 310                 315                 320

Ile Gln Ala Met Met Gln Ile Ile Arg Gly Gly Gly Phe Lys Asp Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Gly Met Asp Ala Met Ala Arg Ala
        355                 360                 365

Leu Glu Ser Ala Ala Lys Leu Leu Glu Glu Ser Pro Tyr Lys Lys Met
    370                 375                 380

Leu Ala Asp Arg Tyr Ala Ser Phe Asp Ser Gly Lys Gly Lys Glu Phe
385                 390                 395                 400

Glu Glu Gly Lys Leu Thr Leu Glu Asp Val Val Tyr Ala Lys Gln
                405                 410                 415

Asn Gly Glu Pro Lys Gln Thr Ser Gly Lys Gln Glu Leu Tyr Glu Ala
            420                 425                 430

Ile Val Asn Met Tyr Ala
            435

<210> SEQ ID NO 25
<211> LENGTH: 1317
<212> TYPE: DNA
<213> ORGANISM: Unknown
<220> FEATURE:
<223> OTHER INFORMATION: Obtained from environmental sample

<400> SEQUENCE: 25
atggcaacaa aagagtattt tcctggaata ggaaagatta aatttgaagg aaaagagagt    60
```

-continued

```
aagaacccga tggcattccg ttgctacgat gcagaaaaag ttatcatggg taagagaatg    120
aaagattggt tgaagtttgc aatggcgtgg tggcatacac tttgtgcaga aggcggtgac    180
caattcggtg gcggtacaaa gagtttcccc cggaacgact atactgataa aattcaggct    240
gctaaaaaca gatggatgc cggttttgag tttatgcaga gatggggat cgaatactat      300 tgttttcacg atgtagacct ctgcacggaa gctgatacca ttgaagaata cgaagctaat    360
ttgaaagaaa tcgtagttta cgcaaagcaa aagcaggtag aaacaggtat caaattattg    420
tggggtactg ccaatgtatt cggtcatgaa cgctatatga atggtgcggc taccaaccca    480
gattttgatg ttgtagcccg tgctgctgtt cagattaaga atgcaattga tgctaccatt    540
gaactaggtg gcttaaacta tgtgttctgg ggtggacgcg aaggttatat gtctttgctg    600
aacactgatc agaaacgtga gaaagaacat cttgcacaaa tgctgaccat tgcccgtgac    660
tatgcccgtg cccgtggctt caaaggtaca ttcttggttg aaccgaaacc gatggaacca    720
accaaacatc aatatgacgt agatacgaaa acagttatcg gttttttgaa agctcatgct    780
ttggataaag actttaaagt aaatattgaa gtaaatcatg caacattagc cggtcataca    840
tttgaacacg aactggcagt ggctgtcgac aacggtatgc tgggttctat tgacgctaat    900
cgtggtgatt gtcaaaacgg ttgggataca gaccaatttc ccattgataa ctatgaactg    960
actcaagcca tgatgcagat tattcgtaac ggtggtttgg gcaatggtgg tacgaatttt   1020
gacgctaaaa ctcgccgtaa ttctactgat cttggagata tcttcattgc tcacatcgca   1080
ggtatggatg ctatggcacg tgcattggaa agtgcggcca agttgttgga gaatctcccc   1140
tataagaaga tgctggcaga acgttatgca tcctttgaca gcggtaaggg taagagtttt   1200
gaagagggta agttgacctt ggaggatctt gttgcttatg caaaagtcaa tggcgaaccg   1260
aaacaaatca gtggtaaaca agaattgtat gaggcaattg tgaatatgta ttgctaa     1317
```

<210> SEQ ID NO 26
<211> LENGTH: 438
<212> TYPE: PRT
<213> ORGANISM: Unknown
<220> FEATURE:
<223> OTHER INFORMATION: Obtained from environmental sample

<400> SEQUENCE: 26

```
Met Ala Thr Lys Glu Tyr Phe Pro Gly Ile Gly Lys Ile Lys Phe Glu
1               5                   10                  15

Gly Lys Glu Ser Lys Asn Pro Met Ala Phe Arg Cys Tyr Asp Ala Glu
            20                  25                  30

Lys Val Ile Met Gly Lys Arg Met Lys Asp Trp Leu Lys Phe Ala Met
        35                  40                  45

Ala Trp Trp His Thr Leu Cys Ala Glu Gly Gly Asp Gln Phe Gly Gly
    50                  55                  60

Gly Thr Lys Ser Phe Pro Arg Asn Asp Tyr Thr Asp Lys Ile Gln Ala
65                  70                  75                  80

Ala Lys Asn Lys Met Asp Ala Gly Phe Glu Phe Met Gln Lys Met Gly
                85                  90                  95

Ile Glu Tyr Tyr Cys Phe His Asp Val Asp Leu Cys Thr Glu Ala Asp
            100                 105                 110

Thr Ile Glu Glu Tyr Glu Ala Asn Leu Lys Glu Ile Val Val Tyr Ala
        115                 120                 125

Lys Gln Lys Gln Val Glu Thr Gly Ile Lys Leu Leu Trp Gly Thr Ala
    130                 135                 140
```

Asn Val Phe Gly His Glu Arg Tyr Met Asn Gly Ala Ala Thr Asn Pro
145                 150                 155                 160

Asp Phe Asp Val Val Ala Arg Ala Ala Val Gln Ile Lys Asn Ala Ile
            165                 170                 175

Asp Ala Thr Ile Glu Leu Gly Gly Leu Asn Tyr Val Phe Trp Gly Gly
        180                 185                 190

Arg Glu Gly Tyr Met Ser Leu Leu Asn Thr Asp Gln Lys Arg Glu Lys
    195                 200                 205

Glu His Leu Ala Gln Met Leu Thr Ile Ala Arg Asp Tyr Ala Arg Ala
210                 215                 220

Arg Gly Phe Lys Gly Thr Phe Leu Val Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Ala Leu Asp Lys Asp Phe Lys Val Asn Ile Glu Val Asn
            260                 265                 270

His Ala Thr Leu Ala Gly His Thr Phe Glu His Glu Leu Ala Val Ala
        275                 280                 285

Val Asp Asn Gly Met Leu Gly Ser Ile Asp Ala Asn Arg Gly Asp Cys
    290                 295                 300

Gln Asn Gly Trp Asp Thr Asp Gln Phe Pro Ile Asp Asn Tyr Glu Leu
305                 310                 315                 320

Thr Gln Ala Met Met Gln Ile Ile Arg Asn Gly Gly Leu Gly Asn Gly
                325                 330                 335

Gly Thr Asn Phe Asp Ala Lys Thr Arg Arg Asn Ser Thr Asp Leu Gly
            340                 345                 350

Asp Ile Phe Ile Ala His Ile Ala Gly Met Asp Ala Met Ala Arg Ala
        355                 360                 365

Leu Glu Ser Ala Ala Lys Leu Leu Glu Glu Ser Pro Tyr Lys Lys Met
    370                 375                 380

Leu Ala Glu Arg Tyr Ala Ser Phe Asp Ser Gly Lys Gly Lys Glu Phe
385                 390                 395                 400

Glu Glu Gly Lys Leu Thr Leu Glu Asp Leu Val Ala Tyr Ala Lys Val
                405                 410                 415

Asn Gly Glu Pro Lys Gln Ile Ser Gly Lys Gln Glu Leu Tyr Glu Ala
            420                 425                 430

Ile Val Asn Met Tyr Cys
        435

<210> SEQ ID NO 27
<211> LENGTH: 1317
<212> TYPE: DNA
<213> ORGANISM: Unknown
<220> FEATURE:
<223> OTHER INFORMATION: Obtained from environmental sample

<400> SEQUENCE: 27
atggcaacaa aagagtattt tcccggaata ggaaagatta aattcgaagg taaagagagc      60
aagaacccga tggcattccg ttattacgat gccgataaag taatcatggg taagaaaatg     120
agcgaatggc tgaagttcgc catggcatgg tggcacactc tttgcgcaga aggtggtgac     180
cagttcggtg gcggaacaaa gaaattcccc tggaacggtg aggctgacaa ggttcaggct     240
gccaagaaca aaatggacgc cggctttgaa ttcatgcaga aatgggtat cgaatactac      300 tgcttccacg atgtagacct ctgcgaagaa gccgagacca ttgaagaata cgaagccaac     360

```
ttgaaggaaa tcgtagcgta tgccaagcag aaacaagcag aaaccggcat caagctgttg    420
tggggtactg ccaacgtatt cggccatgcc cgctacatga atggtgcagc caccaacccc    480
gatttcgatg ttgtggcacg tgcagccgtc caaatcaaaa gcgccatcga cgctactatc    540 gagctggag  gttcgaacta tgtgttctgg ggcggtcgcg aaggctacat gtcattgctg    600
aatacagacc agaagcgtga gaaagagcac ctcgcacaga tgttgaccat cgcccgcgac    660
tatgcccgtg cccgtggctt caaaggtacc ttcctgattg aaccgaaacc gatggaacct    720
acaaaacacc agtatgatgt agacaccgaa accgttatcg gcttcttgaa ggcccacaat    780
ctggacaaag atttcaaggt aaacatcgaa gtgaaccacg ctactttggc gggccacacc    840
ttcgagcacg aactcgcagt agccgtagac aacggtatgc tcggctccat cgatgccaac    900
cgtggtgact accagaacgg ctgggataca gaccagttcc ccattgacaa cttcgaactg    960
acccaggcaa tgatgcaaat catccgtaac ggcggctttg gcaatggcgg tacaaacttc   1020
gatgccaaga cccgtcgtaa ctccaccgac ctggaagaca tcttcattgc ccacatcgcc   1080
ggtatggacg tgatggcacg tgcactggaa agtgcagcca aattgcttga agagtctcct   1140
tacaagaaga tgcttgccga ccgctatgct tccttcgaca gtggtaaagg caaggaattc   1200
gaagacggca agctgacact ggaggatttg gcagcttacg caaaagccaa cggtgagccg   1260
aaacagacca gcggcaagca gggattgtat gaggcaatcg taaatatgta ctgctga      1317
```

<210> SEQ ID NO 28
<211> LENGTH: 438
<212> TYPE: PRT
<213> ORGANISM: Unknown
<220> FEATURE:
<223> OTHER INFORMATION: Obtained from environmental sample

<400> SEQUENCE: 28

```
Met Ala Thr Lys Glu Tyr Phe Pro Gly Ile Gly Lys Ile Lys Phe Glu
1               5                   10                  15

Gly Lys Glu Ser Lys Asn Pro Met Ala Phe Arg Tyr Tyr Asp Ala Asp
                20                  25                  30

Lys Val Ile Met Gly Lys Met Ser Glu Trp Leu Lys Phe Ala Met
            35                  40                  45

Ala Trp Trp His Thr Leu Cys Ala Glu Gly Gly Asp Gln Phe Gly Gly
        50                  55                  60

Gly Thr Lys Lys Phe Pro Trp Asn Gly Glu Ala Asp Lys Val Gln Ala
65                  70                  75                  80

Ala Lys Asn Lys Met Asp Ala Gly Phe Glu Phe Met Gln Lys Met Gly
                85                  90                  95

Ile Glu Tyr Tyr Cys Phe His Asp Val Asp Leu Cys Glu Glu Ala Glu
            100                 105                 110

Thr Ile Glu Glu Tyr Glu Ala Asn Leu Lys Glu Ile Val Ala Tyr Ala
        115                 120                 125

Lys Gln Lys Gln Ala Glu Thr Gly Ile Lys Leu Leu Trp Gly Thr Ala
    130                 135                 140

Asn Val Phe Gly His Ala Arg Tyr Met Asn Gly Ala Ala Thr Asn Pro
145                 150                 155                 160

Asp Phe Asp Val Val Ala Arg Ala Val Gln Ile Lys Ser Ala Ile
                165                 170                 175

Asp Ala Thr Ile Glu Leu Gly Gly Ser Asn Tyr Val Phe Trp Gly Gly
            180                 185                 190
```

Arg Glu Gly Tyr Met Ser Leu Leu Asn Thr Asp Gln Lys Arg Glu Lys
        195                 200                 205

Glu His Leu Ala Gln Met Leu Thr Ile Ala Arg Asp Tyr Ala Arg Ala
    210                 215                 220

Arg Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
            245                 250                 255

Lys Ala His Asn Leu Asp Lys Asp Phe Lys Val Asn Ile Glu Val Asn
                260                 265                 270

His Ala Thr Leu Ala Gly His Thr Phe Glu His Glu Leu Ala Val Ala
            275                 280                 285

Val Asp Asn Gly Met Leu Gly Ser Ile Asp Ala Asn Arg Gly Asp Tyr
290                 295                 300

Gln Asn Gly Trp Asp Thr Asp Gln Phe Pro Ile Asp Asn Phe Glu Leu
305                 310                 315                 320

Thr Gln Ala Met Met Gln Ile Ile Arg Asn Gly Gly Phe Gly Asn Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Gly Met Asp Val Met Ala Arg Ala
        355                 360                 365

Leu Glu Ser Ala Ala Lys Leu Leu Glu Ser Pro Tyr Lys Lys Met
    370                 375                 380

Leu Ala Asp Arg Tyr Ala Ser Phe Asp Ser Gly Lys Gly Lys Glu Phe
385                 390                 395                 400

Glu Asp Gly Lys Leu Thr Leu Glu Asp Leu Ala Ala Tyr Ala Lys Ala
            405                 410                 415

Asn Gly Glu Pro Lys Gln Thr Ser Gly Lys Gln Gly Leu Tyr Glu Ala
                420                 425                 430

Ile Val Asn Met Tyr Cys
            435

```
<210> SEQ ID NO 29
<211> LENGTH: 1314
<212> TYPE: DNA
<213> ORGANISM: Unknown
<220> FEATURE:
<223> OTHER INFORMATION: Obtained from environmental sample

<400> SEQUENCE: 29
atgacaaaag agtattttcc aaccattggt aaaattcagt ttgaaggtaa agagagtaag      60
aatccattag catatcgtta ttacgatgct aacaaagtaa taatgggtaa aaagatgagc     120
gaatggctca agtttgcaat ggcatggtgg cacactttgt gtgctgaggg tagcgaccag     180
tttggtcctg gcaccaagtc attcccatgg aacgcatcaa ccgaccgtat gcaggctgca     240
aaagataagg ctgacgcagg cttcgaaatc atgcaaaaac tgggcatcga atactactgt     300
ttccatgatg ttgacctcat cgacccagca gacgatattc aacatacga aaagaatctc     360 aaggaaatcg ttgcatacct caagcaaaaa caggccgaga caggtatcaa attgctatgg     420
ggtacagcta acgtatttgg ccacaagcgt tatatgaacg gtgcatctac caatcctgac     480
tttgacgttg ttgcacgagc tatcgtgcaa atcaagaatg ctatcgatgc aacaatcgaa     540
ctgggcggca cgaactacgt attctggggt ggtcgcgaag gttacatgtc actgctcaac     600
accgaccaaa agcgcgagaa agagcacatg gctaccatgt taggaatggc acgtgactat     660
```

```
gcacgttcta aaggctttac tggtactctc cttatcgagc caaagcctat ggaaccaact    720
aagcatcaat acgacgtcga tacagaaact gttattggtt tcctcaaagc tcacggatta    780
gacaaggact tcaaggtaaa tatcgaagtg aaccacgcta cattggctgg ccataccttc    840
gaacatgaat tagcatgtgc tgttgatgca ggtatgcttg gttccatcga tgctaaccgt    900
ggtgatatgc agaatggctg ggatacagat cagttcccta tcaacaatta cgagctcgtt    960
caggccatga tgcagattat ccgcaatggt ggtttcggta cggtggtac aaacttcgac    1020 gctaagacac gtcgtaattc aaccgatttg aagacatca tcattgctca cgtttcagct    1080
atggatgcta tggcacgtgc tcttgaatgt gctgcagaca ttcttcaaaa ctcacctatt    1140
ccacagatgg tggccaaccg ttatgcaagt tttgacaagg gtataggtaa agatttcgaa    1200
gacggcaagc tcaccctcga gcaagtatac gaatatggta agaccgtcgg cgaaccagct    1260
attacaagcg gcaaacagga gctctacgaa gctatcgtta atatgtattg ctga         1314
```

<210> SEQ ID NO 30
<211> LENGTH: 437
<212> TYPE: PRT
<213> ORGANISM: Unknown
<220> FEATURE:
<223> OTHER INFORMATION: Obtained from environmental sample

<400> SEQUENCE: 30

```
Met Thr Lys Glu Tyr Phe Pro Thr Ile Gly Lys Ile Gln Phe Glu Gly
1               5                   10                  15

Lys Glu Ser Lys Asn Pro Leu Ala Tyr Arg Tyr Tyr Asp Ala Asn Lys
            20                  25                  30

Val Ile Met Gly Lys Lys Met Ser Glu Trp Leu Lys Phe Ala Met Ala
        35                  40                  45

Trp Trp His Thr Leu Cys Ala Glu Gly Ser Asp Gln Phe Gly Pro Gly
    50                  55                  60

Thr Lys Ser Phe Pro Trp Asn Ala Ser Thr Asp Arg Met Gln Ala Ala
65                  70                  75                  80

Lys Asp Lys Ala Asp Ala Gly Phe Glu Ile Met Gln Lys Leu Gly Ile
                85                  90                  95

Glu Tyr Tyr Cys Phe His Asp Val Asp Leu Ile Asp Pro Ala Asp Asp
            100                 105                 110

Ile Pro Thr Tyr Glu Lys Asn Leu Lys Glu Ile Val Ala Tyr Leu Lys
        115                 120                 125

Gln Lys Gln Ala Glu Thr Gly Ile Lys Leu Leu Trp Gly Thr Ala Asn
    130                 135                 140

Val Phe Gly His Lys Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Thr Ile Glu Leu Gly Gly Thr Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Gly Met Ala Arg Asp Tyr Ala Arg Ser Lys
    210                 215                 220

Gly Phe Thr Gly Thr Leu Leu Ile Glu Pro Lys Pro Met Glu Pro Thr
225                 230                 235                 240

Lys His Gln Tyr Asp Val Asp Thr Glu Thr Val Ile Gly Phe Leu Lys
```

```
            245                 250                 255
Ala His Gly Leu Asp Lys Asp Phe Lys Val Asn Ile Glu Val Asn His
            260                 265                 270

Ala Thr Leu Ala Gly His Thr Phe Glu His Glu Leu Ala Cys Ala Val
            275                 280             285

Asp Ala Gly Met Leu Gly Ser Ile Asp Ala Asn Arg Gly Asp Met Gln
            290                 295                 300

Asn Gly Trp Asp Thr Asp Gln Phe Pro Ile Asn Asn Tyr Glu Leu Val
305                 310                 315                 320

Gln Ala Met Met Gln Ile Ile Arg Asn Gly Gly Phe Gly Asn Gly Gly
                    325                 330                 335

Thr Asn Phe Asp Ala Lys Thr Arg Arg Asn Ser Thr Asp Leu Glu Asp
                340                 345                 350

Ile Ile Ile Ala His Val Ser Ala Met Asp Ala Met Ala Arg Ala Leu
                355                 360                 365

Glu Cys Ala Ala Asp Ile Leu Gln Asn Ser Pro Ile Pro Gln Met Val
            370                 375                 380

Ala Asn Arg Tyr Ala Ser Phe Asp Lys Gly Ile Gly Lys Asp Phe Glu
385                 390                 395                 400

Asp Gly Lys Leu Thr Leu Glu Gln Val Tyr Glu Tyr Gly Lys Thr Val
                    405                 410                 415

Gly Glu Pro Ala Ile Thr Ser Gly Lys Gln Glu Leu Tyr Glu Ala Ile
                420                 425                 430

Val Asn Met Tyr Cys
            435

<210> SEQ ID NO 31
<211> LENGTH: 1317
<212> TYPE: DNA
<213> ORGANISM: Unknown
<220> FEATURE:
<223> OTHER INFORMATION: Obtained from environmental sample

<400> SEQUENCE: 31
atggctaaca aagaattttt ccccggtatt ggtaaaatca aattcgaagg taaagagagc    60
aagaacccca tggcatatcg ttactacgat gctgagaagg tagtccttgg caagaatatg   120
aaagactggt tcaagtttgc gatggcttgg tggcacacat tgtgcgccga gggtagcgac   180
cagtttggtc ccggcactaa gtctttcccc tggaacaccg cagagtgccc catgcaggca   240
gctaaggaca aggttgacgc tggcttcgag ttcatgacca agatgggtat tgaatacttc   300
tgcttccacg atgtagacct cgttgccgag gccgacactg ttgaggagta cgaggctcgc   360
atgaaggaaa tcgttgctta catcaaggag aaggtggccg agactggcat caagaacctg   420
tggggtacag ctaacgtatt tggcaacaag cgctacatga acggtgctgc tactaacccc   480
gactttgacg ttgtggctcg cgctatcgtt caaatcaaga acgctatcga cgctactatc   540
gagctcggtg gtacgtcata cgtattctgg ggcggccgcg agggttacat gagcctcttg   600
aacaccgacc agaagcgtga gaaagagcac ctggctacta tgctcactat ggcacgcgac   660
tacgctcgcg ctaagggttt caagggtaca ttcctcatcg agcccaagcc catggagccc   720
acaaagcacc agtacgatgt tgacactgag actgtaatcg gcttccttaa ggcacacaac   780
cttgacaagg acttcaaggt taacattgag gttaaccacg caactctcgc tggtcacaca   840
tttgagcacg agctcgcttg tgctgttgac gctggcatgc ttggcagcat cgacgctaac   900
cgcggtgact accagaacgg ctgggatact gaccaattcc ccatcgacaa cttcgacctc   960
```

-continued

```
actcaagcta tgctcgagat catccgcaac gatggtttca aggatggtgg tacaaacttc    1020
gacgctaaga ctcgccgcaa cagcaccgac ctcgaggata tcttcatcgc acacatcgct    1080
gctatggacg ctatggcacg tgctctcgag agcgctgctg cagtactcga ggagtcagct    1140
ctgccccaaa tgaagaagga ccgctatgca tcgttcgacg ctggcatggg taaggacttc    1200
gaggacggca agctcaccct ggagcaagtt tacgagtatg gtaagaaggt gggcgagccc    1260
aagcagacta gcggcaagca agagctgtat gaggctatcc tcaacatgta cgtataa      1317
```

<210> SEQ ID NO 32
<211> LENGTH: 438
<212> TYPE: PRT
<213> ORGANISM: Unknown
<220> FEATURE:
<223> OTHER INFORMATION: Obtained from environmental sample

<400> SEQUENCE: 32

```
Met Ala Asn Lys Glu Phe Phe Pro Gly Ile Gly Lys Ile Lys Phe Glu
1               5                   10                  15

Gly Lys Glu Ser Lys Asn Pro Met Ala Tyr Arg Tyr Tyr Asp Ala Glu
            20                  25                  30

Lys Val Val Leu Gly Lys Asn Met Lys Asp Trp Phe Lys Phe Ala Met
        35                  40                  45

Ala Trp Trp His Thr Leu Cys Ala Glu Gly Ser Asp Gln Phe Gly Pro
    50                  55                  60

Gly Thr Lys Ser Phe Pro Trp Asn Thr Ala Glu Cys Pro Met Gln Ala
65                  70                  75                  80

Ala Lys Asp Lys Val Asp Ala Gly Phe Glu Phe Met Thr Lys Met Gly
                85                  90                  95

Ile Glu Tyr Phe Cys Phe His Asp Val Asp Leu Val Ala Glu Ala Asp
            100                 105                 110

Thr Val Glu Glu Tyr Glu Ala Arg Met Lys Glu Ile Val Ala Tyr Ile
        115                 120                 125

Lys Glu Lys Val Ala Glu Thr Gly Ile Lys Asn Leu Trp Gly Thr Ala
    130                 135                 140

Asn Val Phe Gly Asn Lys Arg Tyr Met Asn Gly Ala Ala Thr Asn Pro
145                 150                 155                 160

Asp Phe Asp Val Val Ala Arg Ala Ile Val Gln Ile Lys Asn Ala Ile
                165                 170                 175

Asp Ala Thr Ile Glu Leu Gly Gly Thr Ser Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Leu Ala Thr Met Thr Met Ala Arg Asp Tyr Ala Arg Ala
    210                 215                 220

Lys Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Asn Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Tyr
    290                 295                 300
```

```
Gln Asn Gly Trp Asp Thr Asp Gln Phe Pro Ile Asp Asn Phe Asp Leu
305                 310                 315                 320

Thr Gln Ala Met Leu Glu Ile Ile Arg Asn Asp Gly Phe Lys Asp Gly
                325                 330                 335

Gly Thr Asn Phe Asp Ala Lys Thr Arg Arg Asn Ser Thr Asp Leu Glu
            340                 345                 350

Asp Ile Phe Ile Ala His Ile Ala Ala Met Asp Ala Met Ala Arg Ala
        355                 360                 365

Leu Glu Ser Ala Ala Ala Val Leu Glu Glu Ser Ala Leu Pro Gln Met
370                 375                 380

Lys Lys Asp Arg Tyr Ala Ser Phe Asp Ala Gly Met Gly Lys Asp Phe
385                 390                 395                 400

Glu Asp Gly Lys Leu Thr Leu Glu Gln Val Tyr Glu Tyr Gly Lys Lys
                405                 410                 415

Val Gly Glu Pro Lys Gln Thr Ser Gly Lys Gln Glu Leu Tyr Glu Ala
            420                 425                 430

Ile Leu Asn Met Tyr Val
        435
```

<210> SEQ ID NO 33
<211> LENGTH: 1317
<212> TYPE: DNA
<213> ORGANISM: Unknown
<220> FEATURE:
<223> OTHER INFORMATION: Obtained from environmental sample

<400> SEQUENCE: 33

| | | |
|---|---|---|
| atggctaaca aagaattttt cccaggtatt ggtaaaatca aattcgaagg caaagaaagc | 60 |
| aagaacccca tggcatatcg tcactacgat gccgagaagg tagtccttgg taagaagatg | 120 |
| aaggactggt tcaagtttgc gatggcttgg tggcacactc tgtgcgccga gggtagcgac | 180 |
| cagttcggcc ccgtgaccaa gtctttcccc tggaaccagg ccgagtgccc catgcaggct | 240 |
| gctaaggaca aggttgacgc cggcttcgag ttcatgacca agatgggtat cgaatacttc | 300 |
| tgtttccacg atgtagacct cgttgccgag gccgacaccg ttgaggagta cgaagctcgc | 360 |
| atgaaggaaa tcgtggctta catcaaggag aagatggccg agaccggcat caagaacctg | 420 |
| tggggtacag ccaacgtatt cggcaacaag cgctacatga acgtgctgc caccaacccc | 480 |
| gactttgacg ttgtggctcg cgcaatcgtt cagatcaaga acgccatcga cgctactatc | 540 |
| gagctcggcg gtacctctta cgtgttctgg ggcggccgcg agggttacat gactctcttg | 600 |
| aacaccgacc agaagcgcga aaggagcac ctggctacca tgctcaccat ggctcgcgac | 660 |
| tatgctcgcg ctaagggctt caagggtaca ttccttatcg agcccaagcc catggagccc | 720 |
| accaagcacc agtatgacgt ggataccgag accgttatcg gcttcctcaa ggctcacggc | 780 |
| ctggacaagg acttcaaggt gaacatcgag gttaaccatg caactctcgc cggccacaca | 840 |
| ttcgagcacg aactcgcttg cgctgttgac gctggcatgc tgggcagcat cgacgctaac | 900 |
| cgcggcgact accagaacgg ctgggatacc gaccagttcc ccatcgacaa cttcgacctc | 960 |
| actcaggcta tgctcgagat catccgcaac ggtggtttca aggacggtgg tacaaacttc | 1020 |
| gacgctaaga cccgtcgcaa cagcaccgat cttgaggaca tcttcatcgc tcacatcgct | 1080 |
| gctatgacg caatggcacg cgcgctcgag agcgctgccg ctgtgctcga gcagagcccc | 1140 |
| cttccccaga tgaagaaaga ccgctacgca tcgttcgatg ccggcatggg caaggacttc | 1200 |
| gaggacggca agctcactct ggagcaggtt tacgagtatg gtaagaaggt aggcgagccc | 1260 | aagcagacca gcggcaagca ggaactgtac gaggctatcc tcaacatgta tgtataa      1317

<210> SEQ ID NO 34
<211> LENGTH: 438
<212> TYPE: PRT
<213> ORGANISM: Unknown
<220> FEATURE:
<223> OTHER INFORMATION: Obtained from environmental sample

<400> SEQUENCE: 34

Met Ala Asn Lys Glu Phe Phe Pro Gly Ile Gly Lys Ile Lys Phe Glu
1               5                   10                  15

Gly Lys Glu Ser Lys Asn Pro Met Ala Tyr Arg His Tyr Asp Ala Glu
            20                  25                  30

Lys Val Val Leu Gly Lys Lys Met Lys Asp Trp Phe Lys Phe Ala Met
        35                  40                  45

Ala Trp Trp His Thr Leu Cys Ala Glu Gly Ser Asp Gln Phe Gly Pro
    50                  55                  60

Val Thr Lys Ser Phe Pro Trp Asn Gln Ala Glu Cys Pro Met Gln Ala
65                  70                  75                  80

Ala Lys Asp Lys Val Asp Ala Gly Phe Glu Phe Met Thr Lys Met Gly
                85                  90                  95

Ile Glu Tyr Phe Cys Phe His Asp Val Asp Leu Val Ala Glu Ala Asp
            100                 105                 110

Thr Val Glu Glu Tyr Glu Ala Arg Met Lys Glu Ile Val Ala Tyr Ile
        115                 120                 125

Lys Glu Lys Met Ala Glu Thr Gly Ile Lys Asn Leu Trp Gly Thr Ala
    130                 135                 140

Asn Val Phe Gly Asn Lys Arg Tyr Met Asn Gly Ala Ala Thr Asn Pro
145                 150                 155                 160

Asp Phe Asp Val Val Ala Arg Ala Ile Val Gln Ile Lys Asn Ala Ile
                165                 170                 175

Asp Ala Thr Ile Glu Leu Gly Gly Thr Ser Tyr Val Phe Trp Gly Gly
            180                 185                 190

Arg Glu Gly Tyr Met Thr Leu Leu Asn Thr Asp Gln Lys Arg Glu Lys
        195                 200                 205

Glu His Leu Ala Thr Met Leu Thr Met Ala Arg Asp Tyr Ala Arg Ala
    210                 215                 220

Lys Gly Phe Lys Gly Thr Phe Leu Ile Glu Pro Lys Pro Met Glu Pro
225                 230                 235                 240

Thr Lys His Gln Tyr Asp Val Asp Thr Glu Thr Val Ile Gly Phe Leu
                245                 250                 255

Lys Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Tyr
    290                 295                 300

Gln Asn Gly Trp Asp Thr Asp Gln Phe Pro Ile Asp Asn Phe Asp Leu
305                 310                 315                 320

Thr Gln Ala Met Leu Glu Ile Ile Arg Asn Gly Gly Phe Lys Asp Gly
                325                 330                 335

Gly Thr Asn Phe Asp Ala Lys Thr Arg Arg Asn Ser Thr Asp Leu Glu
            340                 345                 350

```
Asp Ile Phe Ile Ala His Ile Ala Ala Met Asp Ala Met Ala Arg Ala
            355                 360                 365

Leu Glu Ser Ala Ala Ala Val Leu Glu Gln Ser Pro Leu Pro Gln Met
    370                 375                 380

Lys Lys Asp Arg Tyr Ala Ser Phe Asp Ala Gly Met Gly Lys Asp Phe
385                 390                 395                 400

Glu Asp Gly Lys Leu Thr Leu Glu Gln Val Tyr Glu Tyr Gly Lys Lys
                405                 410                 415

Val Gly Glu Pro Lys Gln Thr Ser Gly Lys Gln Glu Leu Tyr Glu Ala
            420                 425                 430

Ile Leu Asn Met Tyr Val
            435

<210> SEQ ID NO 35
<211> LENGTH: 1320
<212> TYPE: DNA
<213> ORGANISM: Unknown
<220> FEATURE:
<223> OTHER INFORMATION: Obtained from environmental sample

<400> SEQUENCE: 35
atgaaagaat attttcctat gacaaaaaaa gttgaatatg agggcgcagc atctaaaaat      60
ccatttgcgt ttaaatacta tgatgccgaa agaattatag caggcaagcc tatgaaagaa     120
catcttaaat ttgctatgag ttggtggcat acactttgtg cgggcggtgc agacccattt     180
ggcacaacaa ctatggacag aacatacggc ggacttaccg acccaatgga aattgcaaag     240 gcaaagtag atgcaggctt tgagtttatg caaaaactcg gtatagagta ttttgtttt       300 cacgatgcgg atattgcacc ggaaggaagc agttttgttg aaacaaagaa aaacttttgg     360
gaaatagtag attatataca gcaaagatg aatgaaacag gcataaagtt gctttggggt      420
actgcaaact gctttaatgc tccacgttat atgcacggtg caggaacatc atgcaatgcg     480
cacagttttg catatgcagc cgcacagata aaaaatgcaa ttgaagctac cgttaaactg     540
ggtggaaaag gctatgtttt ctggggcgga agagagggtt atgaaacact tctcaatacg     600
gatatggcac ttgaacttga caatatgca agactatgc atatggcagt tgattatggc       660
agaagcattg gttttgacgg tgattttat atcgaaccaa agccaaagga accaacaaaa      720
catcaatatg actttgactc ggcaactgtt ttgggatttt tgagaaagta cggtttagat      780
aaggatttta aacttaatat agaggcaaat catgcgacac ttgcaggtca tacatttgaa      840
catgaattga ctgtagcgcg tataaacggt gcatttggca gcatagatgc aaatagcggc      900
gatcccaatc ttgctgggga taccgaccaa ttcccaacag atgtttattc ggcaaccctt      960
tgtatgcttg aagtgataag agcaggcggc tttacaaacg gaggtcttaa ttttgatgca     1020
aaggtcagaa gaggctcatt tacgtttgat gacattgttt atgcatatat cagcggtatg     1080
gacacttttg cgctgggttt tataaaggca tatgaaataa ttgaggacgg cagaatagat     1140
gaatttgtaa agaaagata cgcaagctat aatacaggca taggcaaaga tattatagat      1200
ggaaaggcaa gccttgaaag tttggaagaa tatattcttt caaatgataa tgttgtaatg     1260
caaagcggca gacaggaata tcttgaaaca gttttgaata tattttgtt taaagcataa      1320

<210> SEQ ID NO 36
<211> LENGTH: 439
<212> TYPE: PRT
<213> ORGANISM: Unknown
<220> FEATURE:
<223> OTHER INFORMATION: Obtained from environmental sample
```

<400> SEQUENCE: 36

| | | | | | | | | | | | | | | |
|---|---|---|---|---|---|---|---|---|---|---|---|---|---|---|
|Met|Lys|Glu|Tyr|Phe|Pro|Met|Thr|Lys|Lys|Val|Glu|Tyr|Glu|Gly|Ala|
|1| | | |5| | | | |10| | | | |15| |

Ala Ser Lys Asn Pro Phe Ala Phe Lys Tyr Tyr Asp Ala Glu Arg Ile
             20                  25                  30

Ile Ala Gly Lys Pro Met Lys Glu His Leu Lys Phe Ala Met Ser Trp
         35                  40                  45

Trp His Thr Leu Cys Ala Gly Ala Asp Pro Phe Gly Thr Thr Thr
         50                  55                  60

Met Asp Arg Thr Tyr Gly Gly Leu Thr Asp Pro Met Glu Ile Ala Lys
65                  70                  75                  80

Ala Lys Val Asp Ala Gly Phe Glu Phe Met Gln Lys Leu Gly Ile Glu
                 85                  90                  95

Tyr Phe Cys Phe His Asp Ala Asp Ile Ala Pro Glu Gly Ser Ser Phe
             100                 105                 110

Val Glu Thr Lys Asn Phe Trp Glu Ile Val Asp Tyr Ile Gln Gln
         115                 120                 125

Lys Met Asn Glu Thr Gly Ile Lys Leu Leu Trp Gly Thr Ala Asn Cys
130                 135                 140

Phe Asn Ala Pro Arg Tyr Met His Gly Ala Gly Thr Ser Cys Asn Ala
145                 150                 155                 160

His Ser Phe Ala Tyr Ala Ala Ala Gln Ile Lys Asn Ala Ile Glu Ala
                 165                 170                 175

Thr Val Lys Leu Gly Gly Lys Gly Tyr Val Phe Trp Gly Gly Arg Glu
             180                 185                 190

Gly Tyr Glu Thr Leu Leu Asn Thr Asp Met Ala Leu Glu Leu Asp Asn
         195                 200                 205

Met Ala Arg Leu Met His Met Ala Val Asp Tyr Gly Arg Ser Ile Gly
210                 215                 220

Phe Asp Gly Asp Phe Tyr Ile Glu Pro Lys Pro Lys Glu Pro Thr Lys
225                 230                 235                 240

His Gln Tyr Asp Phe Asp Ser Ala Thr Val Leu Gly Phe Leu Arg Lys
                 245                 250                 255

Tyr Gly Leu Asp Lys Asp Phe Lys Leu Asn Ile Glu Ala Asn His Ala
             260                 265                 270

Thr Leu Ala Gly His Thr Phe Glu His Glu Leu Thr Val Ala Arg Ile
         275                 280                 285

Asn Gly Ala Phe Gly Ser Ile Asp Ala Asn Ser Gly Asp Pro Asn Leu
290                 295                 300

Gly Trp Asp Thr Asp Gln Phe Pro Thr Asp Val Tyr Ser Ala Thr Leu
305                 310                 315                 320

Cys Met Leu Glu Val Ile Arg Ala Gly Gly Phe Thr Asn Gly Gly Leu
                 325                 330                 335

Asn Phe Asp Ala Lys Val Arg Arg Gly Ser Phe Thr Phe Asp Asp Ile
             340                 345                 350

Val Tyr Ala Tyr Ile Ser Gly Met Asp Thr Phe Ala Leu Gly Phe Ile
         355                 360                 365

Lys Ala Tyr Glu Ile Ile Glu Asp Gly Arg Ile Asp Glu Phe Val Lys
             370                 375                 380

Glu Arg Tyr Ala Ser Tyr Asn Thr Gly Ile Gly Lys Asp Ile Ile Asp
385                 390                 395                 400

Gly Lys Ala Ser Leu Glu Ser Leu Glu Glu Tyr Ile Leu Ser Asn Asp

```
            405                 410                 415
Asn Val Val Met Gln Ser Gly Arg Gln Glu Tyr Leu Glu Thr Val Leu
        420                 425                 430

Asn Asn Ile Leu Phe Lys Ala
        435

<210> SEQ ID NO 37
<211> LENGTH: 1323
<212> TYPE: DNA
<213> ORGANISM: Unknown
<220> FEATURE:
<223> OTHER INFORMATION: Obtained from environmental sample

<400> SEQUENCE: 37
atgaaagaaa ttttcccaaa tattcctgag attaaattcg aaggaaaaga cagcaaaaat      60
ccttttgctt tccattacta aacccagac caaatcatct taggcaaacc aatgaaagaa     120
cacctcccat tcgctatggc ttggtggcac aatcttggtg caacaggtgt tgatatgttt     180
ggcgctggcc cagctgataa gagtttcggt gctaaagttg gcacaatgga acacgctaag     240
gccaaagtcg atgccggttt cgaattcatg aagaaactcg gtatcagata tttctgcttc     300
catgatgttg acttagttcc agaatgtgca gatatcaaag atacaaacaa agaattagat     360
gaaatcagtg actacatctt agaaaagatg aaaggcacag atattaagtg tttatggggc     420
accgccaata tgttctctaa cccacgcttc tgcaatggtg cgggttccac aaacagtgcg     480
gatgtcttcg ctttcgccgc tgctcaagtt aagaaagcct agatatcac cgttaaatta     540
ggtggtaggg gttacgtctt ctggggtggt cgtgaaggtt acgaaacatt actcaataca     600
gacgttaaat tcgaacaaga aaacattgct cgtttaatga gatggctgt tgaatatggc     660
cgttccatcg gtttcaaagg cgatttctat atcgaaccaa aaccaaaaga accaatgaaa     720
caccaatatg acttcgacgc cgctacagct attggcttct taagagccca cggcttagac     780
aaagacttca agttgaacat cgaagctaac cacgctacat tagcgggtca tacattccaa     840
cacgatttaa gaatctccgc cattaatggt atgttaggtt ctatcgatgc taaccaaggc     900
gatatgctct aggttgggga tacagacgaa ttcccatttg atgtctacag tgcgacacaa     960
tgtatgtacg aagtcttaaa gaatggtggt cttacaggtg gtttcaactt tgactccaaa    1020
acacgtcgtc catcctacac aatggaagat atgttcttag cctatatctt aggtatggat    1080
acattcgctt taggtttaat caaagctgct caaatcatcg aagatggccg tattgatcaa    1140
ttcatcgaaa agaatattc ttccttccgt gaaacgaaa tcggtcaaaa gatcttaaac    1200
aacaagacaa gcttaaaaga attatccgat tacgcttgca agatgggtgc tccagaactt    1260
ccaggtagtg gtcgtcaaga aatgctcgaa gccatcgtta cgatgtctt attcggcaag    1320
taa                                                                 1323

<210> SEQ ID NO 38
<211> LENGTH: 440
<212> TYPE: PRT
<213> ORGANISM: Unknown
<220> FEATURE:
<223> OTHER INFORMATION: Obtained from environmental sample

<400> SEQUENCE: 38

Met Lys Glu Ile Phe Pro Asn Ile Pro Glu Ile Lys Phe Glu Gly Lys
1               5                   10                  15

Asp Ser Lys Asn Pro Phe Ala Phe His Tyr Tyr Asn Pro Asp Gln Ile
            20                  25                  30
```

Ile Leu Gly Lys Pro Met Lys Glu His Leu Pro Phe Ala Met Ala Trp
        35                  40                  45

Trp His Asn Leu Gly Ala Thr Gly Val Asp Met Phe Gly Ala Gly Pro
    50                  55                  60

Ala Asp Lys Ser Phe Gly Ala Lys Val Gly Thr Met Glu His Ala Lys
65                  70                  75                  80

Ala Lys Val Asp Ala Gly Phe Glu Phe Met Lys Lys Leu Gly Ile Arg
                85                  90                  95

Tyr Phe Cys Phe His Asp Val Asp Leu Val Pro Glu Cys Ala Asp Ile
            100                 105                 110

Lys Asp Thr Asn Lys Glu Leu Asp Glu Ile Ser Asp Tyr Ile Leu Glu
            115                 120                 125

Lys Met Lys Gly Thr Asp Ile Lys Cys Leu Trp Gly Thr Ala Asn Met
        130                 135                 140

Phe Ser Asn Pro Arg Phe Cys Asn Gly Ala Gly Ser Thr Asn Ser Ala
145                 150                 155                 160

Asp Val Phe Ala Phe Ala Ala Gln Val Lys Lys Ala Leu Asp Ile
                165                 170                 175

Thr Val Lys Leu Gly Gly Arg Gly Tyr Val Phe Trp Gly Gly Arg Glu
            180                 185                 190

Gly Tyr Glu Thr Leu Leu Asn Thr Asp Val Lys Phe Glu Gln Glu Asn
            195                 200                 205

Ile Ala Arg Leu Met Lys Met Ala Val Glu Tyr Gly Arg Ser Ile Gly
        210                 215                 220

Phe Lys Gly Asp Phe Tyr Ile Glu Pro Lys Pro Lys Glu Pro Met Lys
225                 230                 235                 240

His Gln Tyr Asp Phe Asp Ala Ala Thr Ala Ile Gly Phe Leu Arg Ala
                245                 250                 255

His Gly Leu Asp Lys Asp Phe Lys Leu Asn Ile Glu Ala Asn His Ala
            260                 265                 270

Thr Leu Ala Gly His Thr Phe Gln His Asp Leu Arg Ile Ser Ala Ile
        275                 280                 285

Asn Gly Met Leu Gly Ser Ile Asp Ala Asn Gln Gly Asp Met Leu Leu
        290                 295                 300

Gly Trp Asp Thr Asp Glu Phe Pro Phe Asp Val Tyr Ser Ala Thr Gln
305                 310                 315                 320

Cys Met Tyr Glu Val Leu Lys Asn Gly Gly Leu Thr Gly Gly Phe Asn
                325                 330                 335

Phe Asp Ser Lys Thr Arg Arg Pro Ser Tyr Thr Met Glu Asp Met Phe
            340                 345                 350

Leu Ala Tyr Ile Leu Gly Met Asp Thr Phe Ala Leu Gly Leu Ile Lys
        355                 360                 365

Ala Ala Gln Ile Ile Glu Asp Gly Arg Ile Asp Gln Phe Ile Glu Lys
        370                 375                 380

Lys Tyr Ser Ser Phe Arg Glu Thr Glu Ile Gly Gln Lys Ile Leu Asn
385                 390                 395                 400

Asn Lys Thr Ser Leu Lys Glu Leu Ser Asp Tyr Ala Cys Lys Met Gly
                405                 410                 415

Ala Pro Glu Leu Pro Gly Ser Gly Arg Gln Glu Met Leu Glu Ala Ile
            420                 425                 430

Val Asn Asp Val Leu Phe Gly Lys
        435                 440

-continued

<210> SEQ ID NO 39
<211> LENGTH: 1323
<212> TYPE: DNA
<213> ORGANISM: Unknown
<220> FEATURE:
<223> OTHER INFORMATION: Obtained from environmental sample

<400> SEQUENCE: 39

```
atgaaagaaa ttttcccaaa tattcctgag attaaattcg aaggaaaaga cagcaaaaat      60
cctttttgctt tccattacta caacccagac caaatcatct taggtaaacc aatgaaagaa     120
cacctcccat tcgctatggc ttggtggcac aatcttggtg caacaggtgt tgatatgttt     180
ggcgctggcc cagctgataa gagtttcggt gctaaagttg gcacaatgga acacgctaag     240
gccaaagtcg atgccggttt cgaattcatg aagaaacttg gtatcagata tttctgcttc     300
catgatgttg acttagttcc agaatgtgca gatatcaaag atacaaacaa agaattagat     360
gaaatcagtg actacatctt agaaaagatg aaaggcacag atatcaagtg tttatggggc     420
accgccaata tgttctctaa cccacgtttc tgcaatggtg cgggttccac aaacagtgcg     480
gatgtcttcg ctttcgccgc tgctcaagtt aagaaagcct agatatcac cgttaaatta     540
ggtggtaggg gttacgtctt ctggggtggt cgtgaaggtt acgaaacatt actcaataca     600
gacgttaaat tcgaacaaga aaacattgct cgtttaatga agatggctgt tgaatatggc     660
cgttccatcg gttcaaagg cgatttctat atcgaaccaa aaccaaaga accaatgaaa     720
caccaatatg acttcgacgc cgctacagct attggcttct taagagccca cggcttagac     780
aaagacttca agttgaacat cgaagctaac cacgctacat tagcgggtca tacattccaa     840
cacgatttaa gaatctccgc cattaatggt atgttaggtt ctatcgatgc taaccaaggc     900
gatatgctct taggttggga tacagacgaa ttcccatttg atgtctacag tgcgacacaa     960
tgtatgtacg aagtcttaaa gaatggtggt cttacaggtg gtttcaactt tgactccaaa    1020
acacgtcgtc catcctacac aatggaagat atgttcttag cctatatctt aggtatggat    1080
acattcgctt taggtttaat caaagctgct caaatcatcg aagatggccg tattgatcaa    1140
ttcatcgaaa agaaatattc ttccttccgt gaaacagaaa tcggtcaaaa gatcttaaac    1200
aacaagacaa gcttaaaaga attatccgat tacgcttgca agatgggtgc tccagaactt    1260
ccaggtagtg gtcgtcaaga aatgctcgaa gccatcgtta acgatgtctt attcggcaag    1320
taa                                                                  1323
```

<210> SEQ ID NO 40
<211> LENGTH: 440
<212> TYPE: PRT
<213> ORGANISM: Unknown
<220> FEATURE:
<223> OTHER INFORMATION: Obtained from environmental sample

<400> SEQUENCE: 40

Met Lys Glu Ile Phe Pro Asn Ile Pro Glu Ile Lys Phe Glu Gly Lys
1               5                   10                  15

Asp Ser Lys Asn Pro Phe Ala Phe His Tyr Tyr Asn Pro Asp Gln Ile
            20                  25                  30

Ile Leu Gly Lys Pro Met Lys Glu His Leu Pro Phe Ala Met Ala Trp
        35                  40                  45

Trp His Asn Leu Gly Ala Thr Gly Val Asp Met Phe Gly Ala Gly Pro
    50                  55                  60

Ala Asp Lys Ser Phe Gly Ala Lys Val Gly Thr Met Glu His Ala Lys

```
                65                  70                  75                  80
Ala Lys Val Asp Ala Gly Phe Glu Phe Met Lys Lys Leu Gly Ile Arg
                        85                  90                  95

Tyr Phe Cys Phe His Asp Val Asp Leu Val Pro Glu Cys Ala Asp Ile
                100                 105                 110

Lys Asp Thr Asn Lys Glu Leu Asp Glu Ile Ser Asp Tyr Ile Leu Glu
                115                 120                 125

Lys Met Lys Gly Thr Asp Ile Lys Cys Leu Trp Gly Thr Ala Asn Met
        130                 135                 140

Phe Ser Asn Pro Arg Phe Cys Asn Gly Ala Gly Ser Thr Asn Ser Ala
145                 150                 155                 160

Asp Val Phe Ala Phe Ala Ala Gln Val Lys Lys Ala Leu Asp Ile
                165                 170                 175

Thr Val Lys Leu Gly Gly Arg Gly Tyr Val Phe Trp Gly Gly Arg Glu
                180                 185                 190

Gly Tyr Glu Thr Leu Leu Asn Thr Asp Val Lys Phe Glu Gln Glu Asn
                195                 200                 205

Ile Ala Arg Leu Met Lys Met Ala Val Glu Tyr Gly Arg Ser Ile Gly
        210                 215                 220

Phe Lys Gly Asp Phe Tyr Ile Glu Pro Lys Pro Lys Glu Pro Met Lys
225                 230                 235                 240

His Gln Tyr Asp Phe Asp Ala Ala Thr Ala Ile Gly Phe Leu Arg Ala
                245                 250                 255

His Gly Leu Asp Lys Asp Phe Lys Leu Asn Ile Glu Ala Asn His Ala
                260                 265                 270

Thr Leu Ala Gly His Thr Phe Gln His Asp Leu Arg Ile Ser Ala Ile
        275                 280                 285

Asn Gly Met Leu Gly Ser Ile Asp Ala Asn Gln Gly Asp Met Leu Leu
        290                 295                 300

Gly Trp Asp Thr Asp Glu Phe Pro Phe Asp Val Tyr Ser Ala Thr Gln
305                 310                 315                 320

Cys Met Tyr Glu Val Leu Lys Asn Gly Gly Leu Thr Gly Gly Phe Asn
                325                 330                 335

Phe Asp Ser Lys Thr Arg Arg Pro Ser Tyr Thr Met Glu Asp Met Phe
                340                 345                 350

Leu Ala Tyr Ile Leu Gly Met Asp Thr Phe Ala Leu Gly Leu Ile Lys
        355                 360                 365

Ala Ala Gln Ile Ile Glu Asp Gly Arg Ile Asp Gln Phe Ile Glu Lys
        370                 375                 380

Lys Tyr Ser Ser Phe Arg Glu Thr Glu Ile Gly Gln Lys Ile Leu Asn
385                 390                 395                 400

Asn Lys Thr Ser Leu Lys Glu Leu Ser Asp Tyr Ala Cys Lys Met Gly
                405                 410                 415

Ala Pro Glu Leu Pro Gly Ser Gly Arg Gln Glu Met Leu Glu Ala Ile
                420                 425                 430

Val Asn Asp Val Leu Phe Gly Lys
        435                 440

<210> SEQ ID NO 41
<211> LENGTH: 1326
<212> TYPE: DNA
<213> ORGANISM: Unknown
<220> FEATURE:
<223> OTHER INFORMATION: Obtained from environmental sample
```

<400> SEQUENCE: 41

```
atggaatatt tcccttccgt caaatcggtc caatacaagg gaccaacctc aactgaacca    60
ttcgctttca agtactacga tgccaaccgt gtcgttcttg gaaaaccaat gaaagaatgg   120
atgccattcg ctatggcttg gtggcacaac ctcggcgctg ccggtaccga catgttcggc   180
ggcaacacca tggacaagtc ctggggagtc gataaagaaa agacccaat gggctatgcc    240
aaagccaaag ttgatgccgg cttcgaattc atgcagaaga tgggcatcga atactactgc   300
ttccacgatg tcgacctcgt cccagagtgc gacgacatca ccgttatgta ccagagactc   360
gatgagatcg tgattaccct tctcaagaaa cagaaggaaa ccggtatcaa gcttctttgg   420
tcaaccgcca atgccttcgg acaccgccgt ttcatgaacg gtgctggttc cagcaactcc   480
gccgaagtct attgcttcgc cgccgcccag atcaagaaag ctcttgagct ctgcgtcaaa   540
ctcggtggca aaggctatgt cttctggggt ggacgtgaag gctacgaaac ccttctcaac   600
accgacatga agttcgaaca agagaacatc gccaacctta tgagatgcgc ccgtgactac   660
ggccgcaaga tcggtttcaa aggcgacttc tacatcgaac caaaaccaaa agagccaaca   720
aagcatcagt atgacttcga cgccgctacc gccatcggat cctccgtca gtacggtctc    780
gacaaagact tcaagatgaa catcgaagcc aaccacgcta ccttagctgg ccacaccttc   840
gaacacgaac tccgcgtctc cgccatgaac ggcatgctcg gttccatcga cgccaacgaa   900
ggcgatatgc tcctcggatg ggatgtcgac cgtttcccag ccaacgtcta tagcgccacc   960
ttcgccatgc tcgaagtcat caaagccggt ggacttaccg gtggcttcaa cttcgacgcc  1020
aagacccgcc gcgcttccaa cacctatgaa gatatgttca aggctttcgt ccttggtatg  1080
gataccttcg ctttaggtct tctcaatgcc gaagccatca tcaaagacgg ccgcatcgac  1140
aagttcgtcg aggatagata tgccagcttc aagaccggca tcggtgctaa ggtccgcgat  1200
cactccgcta cccttgagga tttagctgcc cacgcccttg agaccaaggt tgcccagat   1260
ccaggcagcg gcgacgagga agaactccag gaaatcctca accagttaat gttcggtaag  1320
aaataa                                                              1326
```

<210> SEQ ID NO 42
<211> LENGTH: 441
<212> TYPE: PRT
<213> ORGANISM: Unknown
<220> FEATURE:
<223> OTHER INFORMATION: Obtained from environmental sample

<400> SEQUENCE: 42

```
Met Glu Tyr Phe Pro Phe Val Lys Ser Val Gln Tyr Lys Gly Pro Thr
1               5                   10                  15

Ser Thr Glu Pro Phe Ala Phe Lys Tyr Tyr Asp Ala Asn Arg Val Val
            20                  25                  30

Leu Gly Lys Pro Met Lys Glu Trp Met Pro Phe Ala Met Ala Trp Trp
        35                  40                  45

His Asn Leu Gly Ala Ala Gly Thr Asp Met Phe Gly Gly Asn Thr Met
    50                  55                  60

Asp Lys Ser Trp Gly Val Asp Lys Glu Lys Asp Pro Met Gly Tyr Ala
65                  70                  75                  80

Lys Ala Lys Val Asp Ala Gly Phe Glu Phe Met Gln Lys Met Gly Ile
                85                  90                  95

Glu Tyr Tyr Cys Phe His Asp Val Asp Leu Val Pro Glu Cys Asp Asp
            100                 105                 110
```

```
Ile Thr Val Met Tyr Gln Arg Leu Asp Glu Ile Gly Asp Tyr Leu Leu
            115                 120                 125

Lys Lys Gln Lys Glu Thr Gly Ile Lys Leu Leu Trp Ser Thr Ala Asn
    130                 135                 140

Ala Phe Gly His Arg Arg Phe Met Asn Gly Ala Gly Ser Ser Asn Ser
145                 150                 155                 160

Ala Glu Val Tyr Cys Phe Ala Ala Gln Ile Lys Lys Ala Leu Glu
                165                 170                 175

Leu Cys Val Lys Leu Gly Gly Lys Gly Tyr Val Phe Trp Gly Gly Arg
            180                 185                 190

Glu Gly Tyr Glu Thr Leu Leu Asn Thr Asp Met Lys Phe Glu Gln Glu
        195                 200                 205

Asn Ile Ala Asn Leu Met Arg Cys Ala Arg Asp Tyr Gly Arg Lys Ile
    210                 215                 220

Gly Phe Lys Gly Asp Phe Tyr Ile Glu Pro Lys Pro Lys Glu Pro Thr
225                 230                 235                 240

Lys His Gln Tyr Asp Phe Asp Ala Ala Thr Ala Ile Gly Phe Leu Arg
                245                 250                 255

Gln Tyr Gly Leu Asp Lys Asp Phe Lys Met Asn Ile Glu Ala Asn His
            260                 265                 270

Ala Thr Leu Ala Gly His Thr Phe Glu His Glu Leu Arg Val Ser Ala
        275                 280                 285

Met Asn Gly Met Leu Gly Ser Ile Asp Ala Asn Glu Gly Asp Met Leu
    290                 295                 300

Leu Gly Trp Asp Val Asp Arg Phe Pro Ala Asn Val Tyr Ser Ala Thr
305                 310                 315                 320

Phe Ala Met Leu Glu Val Ile Lys Ala Gly Gly Leu Thr Gly Gly Phe
                325                 330                 335

Asn Phe Asp Ala Lys Thr Arg Arg Ala Ser Asn Thr Tyr Glu Asp Met
            340                 345                 350

Phe Lys Ala Phe Val Leu Gly Met Asp Thr Phe Ala Leu Gly Leu Leu
        355                 360                 365

Asn Ala Glu Ala Ile Ile Lys Asp Gly Arg Ile Asp Lys Phe Val Glu
    370                 375                 380

Asp Arg Tyr Ala Ser Phe Lys Thr Gly Ile Gly Ala Lys Val Arg Asp
385                 390                 395                 400

His Ser Ala Thr Leu Glu Asp Leu Ala His Ala Leu Glu Thr Lys
                405                 410                 415

Val Cys Pro Asp Pro Gly Ser Gly Asp Glu Glu Glu Leu Gln Glu Ile
            420                 425                 430

Leu Asn Gln Leu Met Phe Gly Lys Lys
        435                 440
```

<210> SEQ ID NO 43
<211> LENGTH: 1323
<212> TYPE: DNA
<213> ORGANISM: Unknown
<220> FEATURE:
<223> OTHER INFORMATION: Obtained from environmental sample

<400> SEQUENCE: 43
atgagcgaat tttttaagaa tattccagag attaaattcg aaggaaaaga tagtaaaaat        60
ccatgggcat tcaagtatta caatcctgaa ttgaccatta tgggtaaaaa aatgtctgaa       120
catcttcctt ttgcaatggc ctggtggcat aaccttggcg caaatggagt tgatatgttc       180

-continued

```
ggttcgggaa ccgccgataa atctttcggt caggctccgg gaactatgga gcacgcaaag    240
gctaaggtag atgcaggtat cgagtttatg aagaaactcg gaatcaagta ctactgctgg    300
catgatgtag accttgttcc tgaagatcca acgatatca acgtaacaaa caagcgcctt    360
gatgagattt cagattatat ccttgaaaaa acaaagggaa ctgacatcaa gtgtctctgg    420
ggaactgcta acatgttcag taatccccgc tttatgaacg gggcaggctc aacaaactct    480
gctgacgttt actgctttgc agctgcccag gttaaaaagg ctcttgagat taccgtaaag    540
cttggtggcc gcggttatgt attctggggt ggacgcgaag ttatgaaac tcttcttaat     600 acagatgtaa agcttgaaca ggaaaatatt gcaaaccta tgcacatggc agttgattat     660
ggccgttcaa tcggtttcaa gggagacttc tacatcgagc ctaagccaaa ggagccgatg    720
agtcatcagt atgattttga tgccgcaact gcaatcggct tcctccgcca gtatggcctc    780
gacaaagact ttaagatgaa cattgaggct aaccacgctt ctcttgcaaa tcatacctc    840 cagcatgagc tttatatcag ccgcattaac ggaatgcttg gttctgtaga tgctaaccag    900
ggaaatccaa ttctcggctg ggatacagat aacttccctt ggaatgtcta cgacgcaact    960
cttgcaatgt acgaagtact caaggctggt ggacttacag gtggcttcaa ctttgactca   1020
aagaaccgcc gcccatcaaa tacatttgaa gatatgttcc acgcttacat catgggaatg   1080 gacactttg ctcttggtct tattaaggct gcagaaatta ttgaagacgg aagaatcgat    1140
ggcttcatta agaaaagta ttcaagctac gaaagtggaa ttggtaagaa gatccgcgac    1200
aagcagacaa cttttggaaga gcttgctgcc cgtgccgcag aaatgaaaaa gccatctgat   1260
ccaggttcag gccgcgagga atatctggaa ggagttgtta acaatatcct ctttcgcgga   1320
taa                                                                  1323
```

<210> SEQ ID NO 44
<211> LENGTH: 440
<212> TYPE: PRT
<213> ORGANISM: Unknown
<220> FEATURE:
<223> OTHER INFORMATION: Obtained from environmental sample

<400> SEQUENCE: 44

```
Met Ser Glu Phe Phe Lys Asn Ile Pro Glu Ile Lys Phe Glu Gly Lys
1               5                   10                  15

Asp Ser Lys Asn Pro Trp Ala Phe Lys Tyr Tyr Asn Pro Glu Leu Thr
            20                  25                  30

Ile Met Gly Lys Lys Met Ser Glu His Leu Pro Phe Ala Met Ala Trp
        35                  40                  45

Trp His Asn Leu Gly Ala Asn Gly Val Asp Met Phe Gly Ser Gly Thr
    50                  55                  60

Ala Asp Lys Ser Phe Gly Gln Ala Pro Gly Thr Met Glu His Ala Lys
65                  70                  75                  80

Ala Lys Val Asp Ala Gly Ile Glu Phe Met Lys Lys Leu Gly Ile Lys
                85                  90                  95

Tyr Tyr Cys Trp His Asp Val Asp Leu Val Pro Glu Asp Pro Asn Asp
            100                 105                 110

Ile Asn Val Thr Asn Lys Arg Leu Asp Glu Ile Ser Asp Tyr Ile Leu
        115                 120                 125

Glu Lys Thr Lys Gly Thr Asp Ile Lys Cys Leu Trp Gly Thr Ala Asn
    130                 135                 140

Met Phe Ser Asn Pro Arg Phe Met Asn Gly Ala Gly Ser Thr Asn Ser
145                 150                 155                 160
```

```
Ala Asp Val Tyr Cys Phe Ala Ala Gln Val Lys Ala Leu Glu
            165                 170                 175

Ile Thr Val Lys Leu Gly Gly Arg Gly Tyr Val Phe Trp Gly Gly Arg
            180                 185                 190

Glu Gly Tyr Glu Thr Leu Leu Asn Thr Asp Val Lys Leu Glu Gln Glu
            195                 200                 205

Asn Ile Ala Asn Leu Met His Met Ala Val Asp Tyr Gly Arg Ser Ile
            210                 215                 220

Gly Phe Lys Gly Asp Phe Tyr Ile Glu Pro Lys Pro Lys Glu Pro Met
225                 230                 235                 240

Ser His Gln Tyr Asp Phe Asp Ala Ala Thr Ala Ile Gly Phe Leu Arg
            245                 250                 255

Gln Tyr Gly Leu Asp Lys Asp Phe Lys Met Asn Ile Glu Ala Asn His
            260                 265                 270

Ala Ser Leu Ala Asn His Thr Phe Gln His Glu Leu Tyr Ile Ser Arg
            275                 280                 285

Ile Asn Gly Met Leu Gly Ser Val Asp Ala Asn Gln Gly Asn Pro Ile
            290                 295                 300

Leu Gly Trp Asp Thr Asp Asn Phe Pro Trp Asn Val Tyr Asp Ala Thr
305                 310                 315                 320

Leu Ala Met Tyr Glu Val Leu Lys Ala Gly Gly Leu Thr Gly Phe
            325                 330                 335

Asn Phe Asp Ser Lys Asn Arg Arg Pro Ser Asn Thr Phe Glu Asp Met
            340                 345                 350

Phe His Ala Tyr Ile Met Gly Met Asp Thr Phe Ala Leu Gly Leu Ile
            355                 360                 365

Lys Ala Ala Glu Ile Ile Glu Asp Gly Arg Ile Asp Gly Phe Ile Lys
            370                 375                 380

Glu Lys Tyr Ser Ser Tyr Glu Ser Gly Ile Gly Lys Lys Ile Arg Asp
385                 390                 395                 400

Lys Gln Thr Thr Leu Glu Glu Leu Ala Ala Arg Ala Ala Glu Met Lys
            405                 410                 415

Lys Pro Ser Asp Pro Gly Ser Gly Arg Glu Glu Tyr Leu Glu Gly Val
            420                 425                 430

Val Asn Asn Ile Leu Phe Arg Gly
            435                 440

<210> SEQ ID NO 45
<211> LENGTH: 1323
<212> TYPE: DNA
<213> ORGANISM: Unknown
<220> FEATURE:
<223> OTHER INFORMATION: Obtained from environmental sample

<400> SEQUENCE: 45
atgagcgagt tttttaagaa tattcctcaa ataaaatacg aaggaaaaga tagcaaaaat      60
ccctgggcat tcaagtatta caatcctgaa ttgacaatca tgggtaaaaa gatgagcgaa     120
catcttccat tcgcaatggc atggtggcat aaccttggcg caaacggcgt tgatatgttt     180
ggtcagggaa cagcagacaa gtctttcgga cagattcctg aactatgga gcatgcaaag      240 gctaaggttg atgctggtat agagtttatg aagaagctcg gaatcaaata ttactgctgg     300
cacgatgttg accttgttcc tgaggatcca acgatatca acgtaactaa caaacgtctg      360
gacgaaattt cagattacat ccttgaaaag acaaaaggaa cagacattaa gtgtctctgg     420
```

```
ggaactgcaa acatgttcgg taaccctcgc tttatgaacg gtgcaggctc tacaaactct    480
gctgacgttt actgttttgc tgccgctcag gtaaaaaagg ctcttgagat tactgtaaag    540
cttggtggcc gaggttatgt tttctggggt ggccgcgaag gttacgaaac tcttctcaat    600
acagacgtaa aacttgaaca ggaaaatatc gcaaacctca tgcatatggc tgttgattat    660
ggccgctcaa tcggtttcaa gggagacttc tacatcgagc ctaagccaaa ggagccaatg    720
agccatcagt atgattttga tgctgcaaca gcaatcggct tcctccgcca gtatggcctc    780
gacaaagatt ttaagatgaa catcgaagct aaccatgcct cacttgcaaa tcacaccttc    840
cagcacgagc tttgtatcag ccgcataaac ggaatgcttg gttctgtaga tgcaaatcag    900
ggaaatccaa ttcttggctg ggatacagat aacttcccat ggaatgttta cgatgcaact    960
ctggcaatgt acgaagttct caaggctggc ggtctaacag gtggcttcaa ctttgactca   1020
aagaaccgtc gcccatcaaa tacttttgaa gatatgttcc acgcttatat catgggtatg   1080
gatacttttg cccttggcct tattaaggct gcagaaatta ttgaagacgg cagaattgac   1140
ggcttcatca agaaaagta ttcaagcttt gaaagtggaa ttggtaagaa gattcgtgac   1200
aagcagacaa gtttggaaga gcttgcagct cgtgccgctg aaatgaaaaa gccatctgat   1260
ccaggttcag gccgcgagga ataccttgaa ggagttgtta caacatcct ctttcgcgga   1320 taa                                                                  1323
```

<210> SEQ ID NO 46
<211> LENGTH: 440
<212> TYPE: PRT
<213> ORGANISM: Unknown
<220> FEATURE:
<223> OTHER INFORMATION: Obtained from environmental sample

<400> SEQUENCE: 46

```
Met Ser Glu Phe Phe Lys Asn Ile Pro Gln Ile Lys Tyr Glu Gly Lys
 1               5                  10                  15

Asp Ser Lys Asn Pro Trp Ala Phe Lys Tyr Tyr Asn Pro Glu Leu Thr
            20                  25                  30

Ile Met Gly Lys Lys Met Ser Glu His Leu Pro Phe Ala Met Ala Trp
        35                  40                  45

Trp His Asn Leu Gly Ala Asn Gly Val Asp Met Phe Gly Gln Gly Thr
    50                  55                  60

Ala Asp Lys Ser Phe Gly Gln Ile Pro Gly Thr Met Glu His Ala Lys
65                  70                  75                  80

Ala Lys Val Asp Ala Gly Ile Glu Phe Met Lys Lys Leu Gly Ile Lys
                85                  90                  95

Tyr Tyr Cys Trp His Asp Val Asp Leu Val Pro Glu Asp Pro Asn Asp
            100                 105                 110

Ile Asn Val Thr Asn Lys Arg Leu Asp Glu Ile Ser Asp Tyr Ile Leu
        115                 120                 125

Glu Lys Thr Lys Gly Thr Asp Ile Lys Cys Leu Trp Gly Thr Ala Asn
    130                 135                 140

Met Phe Gly Asn Pro Arg Phe Met Asn Gly Ala Gly Ser Thr Asn Ser
145                 150                 155                 160

Ala Asp Val Tyr Cys Phe Ala Ala Ala Gln Val Lys Lys Ala Leu Glu
                165                 170                 175

Ile Thr Val Lys Leu Gly Gly Arg Gly Tyr Val Phe Trp Gly Gly Arg
            180                 185                 190

Glu Gly Tyr Glu Thr Leu Leu Asn Thr Asp Val Lys Leu Glu Gln Glu
```

```
                195                 200                 205
Asn Ile Ala Asn Leu Met His Met Ala Val Asp Tyr Gly Arg Ser Ile
        210                 215                 220

Gly Phe Lys Gly Asp Phe Tyr Ile Glu Pro Lys Pro Lys Glu Pro Met
225                 230                 235                 240

Ser His Gln Tyr Asp Phe Asp Ala Ala Thr Ala Ile Gly Phe Leu Arg
                245                 250                 255

Gln Tyr Gly Leu Asp Lys Asp Phe Lys Met Asn Ile Glu Ala Asn His
        260                 265                 270

Ala Ser Leu Ala Asn His Thr Phe Gln His Glu Leu Cys Ile Ser Arg
    275                 280                 285

Ile Asn Gly Met Leu Gly Ser Val Asp Ala Asn Gln Gly Asn Pro Ile
        290                 295                 300

Leu Gly Trp Asp Thr Asp Asn Phe Pro Trp Asn Val Tyr Asp Ala Thr
305                 310                 315                 320

Leu Ala Met Tyr Glu Val Leu Lys Ala Gly Gly Leu Thr Gly Gly Phe
                325                 330                 335

Asn Phe Asp Ser Lys Asn Arg Arg Pro Ser Asn Thr Phe Glu Asp Met
        340                 345                 350

Phe His Ala Tyr Ile Met Gly Met Asp Thr Phe Ala Leu Gly Leu Ile
    355                 360                 365

Lys Ala Ala Glu Ile Ile Glu Asp Gly Arg Ile Asp Gly Phe Ile Lys
    370                 375                 380

Glu Lys Tyr Ser Ser Phe Glu Ser Gly Ile Gly Lys Lys Ile Arg Asp
385                 390                 395                 400

Lys Gln Thr Ser Leu Glu Glu Leu Ala Ala Arg Ala Ala Glu Met Lys
                405                 410                 415

Lys Pro Ser Asp Pro Gly Ser Gly Arg Glu Glu Tyr Leu Glu Gly Val
        420                 425                 430

Val Asn Asn Ile Leu Phe Arg Gly
    435                 440

<210> SEQ ID NO 47
<211> LENGTH: 1311
<212> TYPE: DNA
<213> ORGANISM: Unknown
<220> FEATURE:
<223> OTHER INFORMATION: Obtained from environmental sample

<400> SEQUENCE: 47
atgatatttg aaatattcc cgcaattcct tatgagggtc cgaagagcac aaatccgctg      60
gcgtttaaat tctatgatcc ggacaagatc gttatgggaa agcccatgaa ggagcatctg     120 cccttttgcaa tggcctggtg gcacaacctt ggcgcggccg aaccgatat gttcgggcgc     180 gataccgccg acaaatcctt cggtgcggta aaaggcacaa tggagcatgc caaagcgaaa     240
gtcgatgccg gctttgagtt catgcagaag ctggggatcc gctatttctg cttccatgat     300
gtggatcttg ttccggaggc ggatgatata aaggagacca accgccgtct ggacgagatc     360
agcgattaca tccttgaaaa gatgaagggc accgatatca gtgcctttg ggcacggcc      420 aatatgttct caaatccgcg ctttatgaac ggcgcaggct cctccaattc tgccgatgta     480
ttcgcttttg cggcagcaca ggccaagaag gccttggatc tgaccgtcaa actcggcggg     540
cgcggctatg tcttctgggg cggacgtgag ggctatgaga cacttctcaa taccgacatg     600
aagttcgagc aggagaatat cgcgaagctc atgcatatgg ctgtcgatta cggccgcagc     660
```

-continued

```
ataggcttta ccggtgattt ctatatcgag cccaaaccga aagagccgat gaaacaccag    720
tatgatttcg atgcagccac tgcgataggc ttcctccgcc agtacggact cgataaggac    780
ttcaagctca acatcgaggc aaaccacgcc acactggcag gtcacacttt ccagcacgat    840
ctgcgtgttt ccgcaataaa cggaatgctg ggcagcattg acgccaacca gggcgatatg    900
ctcctcggct gggataccga cgagttccg ttcaatgtat atgatgcgac catgtgcatg    960
tatgaggtgc tcaagtcaga cgggctcacc ggcggcttta acttcgactc caaatcacgc   1020
cgcccgagct atacggtcga ggatatgttt acaagctata tcctcggcat ggacactttt   1080
gccctcggcc ttctgaaagc ggccgagctt atcgaagacg gaaggcttga cgccttcgtc   1140
aaagaacgct attcaagcta tgagagcggc atcggcgcaa agatccgcag cggagaaacc   1200
gatttgaagg aattggcgga atatgcggac tccctcggag cccccgaact tccgggcagc   1260
ggaaaacagg aacagctcga gagcatagta aatcagatac ttttcggata a            1311
```

<210> SEQ ID NO 48
<211> LENGTH: 436
<212> TYPE: PRT
<213> ORGANISM: Unknown
<220> FEATURE:
<223> OTHER INFORMATION: Obtained from environmental sample

<400> SEQUENCE: 48

```
Met Ile Phe Glu Asn Ile Pro Ala Ile Pro Tyr Glu Gly Pro Lys Ser
 1               5                  10                  15

Thr Asn Pro Leu Ala Phe Lys Phe Tyr Asp Pro Asp Lys Ile Val Met
             20                  25                  30

Gly Lys Pro Met Lys Glu His Leu Pro Phe Ala Met Ala Trp Trp His
         35                  40                  45

Asn Leu Gly Ala Ala Gly Thr Asp Met Phe Gly Arg Asp Thr Ala Asp
     50                  55                  60

Lys Ser Phe Gly Ala Val Lys Gly Thr Met Glu His Ala Lys Ala Lys
 65                  70                  75                  80

Val Asp Ala Gly Phe Glu Phe Met Gln Lys Leu Gly Ile Arg Tyr Phe
                 85                  90                  95

Cys Phe His Asp Val Asp Leu Val Pro Glu Ala Asp Ile Lys Glu
            100                 105                 110

Thr Asn Arg Arg Leu Asp Glu Ile Ser Asp Tyr Ile Leu Glu Lys Met
        115                 120                 125

Lys Gly Thr Asp Ile Lys Cys Leu Trp Gly Thr Ala Asn Met Phe Ser
    130                 135                 140

Asn Pro Arg Phe Met Asn Gly Ala Gly Ser Ser Asn Ser Ala Asp Val
145                 150                 155                 160

Phe Ala Phe Ala Ala Gln Ala Lys Lys Ala Leu Asp Leu Thr Val
                165                 170                 175

Lys Leu Gly Gly Arg Gly Tyr Val Phe Trp Gly Gly Arg Glu Gly Tyr
            180                 185                 190

Glu Thr Leu Leu Asn Thr Asp Met Lys Phe Glu Gln Glu Asn Ile Ala
        195                 200                 205

Lys Leu Met His Met Ala Val Asp Tyr Gly Arg Ser Ile Gly Phe Thr
    210                 215                 220

Gly Asp Phe Tyr Ile Glu Pro Lys Pro Lys Glu Pro Met Lys His Gln
225                 230                 235                 240

Tyr Asp Phe Asp Ala Ala Thr Ala Ile Gly Phe Leu Arg Gln Tyr Gly
                245                 250                 255
```

```
Leu Asp Lys Asp Phe Lys Leu Asn Ile Glu Ala Asn His Ala Thr Leu
            260                 265                 270

Ala Gly His Thr Phe Gln His Asp Leu Arg Val Ser Ala Ile Asn Gly
        275                 280                 285

Met Leu Gly Ser Ile Asp Ala Asn Gln Gly Asp Met Leu Leu Gly Trp
    290                 295                 300

Asp Thr Asp Glu Phe Pro Phe Asn Val Tyr Asp Ala Thr Met Cys Met
305                 310                 315                 320

Tyr Glu Val Leu Lys Ser Asp Gly Leu Thr Gly Gly Phe Asn Phe Asp
                325                 330                 335

Ser Lys Ser Arg Arg Pro Ser Tyr Thr Val Glu Asp Met Phe Thr Ser
            340                 345                 350

Tyr Ile Leu Gly Met Asp Thr Phe Ala Leu Gly Leu Leu Lys Ala Ala
        355                 360                 365

Glu Leu Ile Glu Asp Gly Arg Leu Asp Ala Phe Val Lys Glu Arg Tyr
    370                 375                 380

Ser Ser Tyr Glu Ser Gly Ile Gly Ala Lys Ile Arg Ser Gly Glu Thr
385                 390                 395                 400

Asp Leu Lys Glu Leu Ala Glu Tyr Ala Asp Ser Leu Gly Ala Pro Glu
                405                 410                 415

Leu Pro Gly Ser Gly Lys Gln Glu Gln Leu Glu Ser Ile Val Asn Gln
            420                 425                 430

Ile Leu Phe Gly
        435

<210> SEQ ID NO 49
<211> LENGTH: 1317
<212> TYPE: DNA
<213> ORGANISM: Unknown
<220> FEATURE:
<223> OTHER INFORMATION: Obtained from environmental sample

<400> SEQUENCE: 49
atgagcgagt tttttgccag cattcccaaa attcccttg  aaggcaagga cagcgccaat      60
cccctggcgt tcaaatacta cgacgccgac aggatgatac tgggcaagcc catgaaggag     120
caccttccct tcgccatggc ctggtggcac aacctgtgcg ccgcgggcac cgatatgttt     180
ggccgggaca ccgccgacaa gtccttcggc caggtcaagg gcaccatgga cacgccaag      240 gccaaggtgg acgcgggctt tgagttcatg aagaagctgg gcatccgcta cttctgcttc     300
cacgacgtgg acatcgtgcc cgaagccgac gacatcaagg aaaccaaccg ccgtctggac     360
gagatctccg actatatcct ggagaaaatg aaaggcaccg acatccagtg cctgtggggc     420
accgccaaca tgttcggcaa ccccgctat  atgaacggcg cgggcagctc caactccgcc     480
gacgtatact gcttcgccgc ggcccagatc aaaaaggccc tggacatcac cgtgaagctg     540
ggcggcaagg gctacgtgtt ctgggcgcgg cgcgagggct acgagaccct gctgaacacc     600
gatatgaagt tcgagcagga gaacatcgcc cgcctgatgc acatggccgt ggactacggc     660
cgcagcatcg gcttcaccgg cgatttctac atcgagccca gcccaaggga gcccatgaag     720
caccagtacg acttcgacgc cgccaccgcc ataggctttt gcgccagta cggcctggac     780 aaggatttca agctgaacat cgagtccaac cacgccaccc tggcgggcca taccttccag     840
cacgacctgc gcgtttccgc catcaacggc atgctgggct ccatcgacgc caaccagggc     900
gactacctgc tgggctggga taccgacgag ttcccctaca gcgtatacga gaccaccatg     960
```

-continued

```
tgcatgtacg aggtgctcaa ggccggaggt ctcaccggcg gcttcaattt cgacgccaag    1020
aaccgccgtc ccagctacac ccccgaggat atgttccacg cctacatcct tgggatggac    1080
agcttcgccc tgggcctgat caaggccgcc gagctcatcg aggacggtcg cctggacgcc    1140
ttcgtccggg accgctacca gagctgggag accggcatcg gcgataagat ccgcaagggc    1200
gagaccacac tggccgagct ggccgagtac gccgcccgga tgggcgcgcc cgcgctgccc    1260
ggcagcggcc gccaggaata cctggagggc gtggtcaaca atatcctgtt caaataa      1317
```

<210> SEQ ID NO 50
<211> LENGTH: 438
<212> TYPE: PRT
<213> ORGANISM: Unknown
<220> FEATURE:
<223> OTHER INFORMATION: Obtained from environmental sample

<400> SEQUENCE: 50

```
Met Ser Glu Phe Phe Ala Ser Ile Pro Lys Ile Pro Phe Glu Gly Lys
1               5                   10                  15

Asp Ser Ala Asn Pro Leu Ala Phe Lys Tyr Tyr Asp Ala Asp Arg Met
            20                  25                  30

Ile Leu Gly Lys Pro Met Lys Glu His Leu Pro Phe Ala Met Ala Trp
        35                  40                  45

Trp His Asn Leu Cys Ala Ala Gly Thr Asp Met Phe Gly Arg Asp Thr
    50                  55                  60

Ala Asp Lys Ser Phe Gly Gln Val Lys Gly Thr Met Glu His Ala Lys
65                  70                  75                  80

Ala Lys Val Asp Ala Gly Phe Glu Phe Met Lys Lys Leu Gly Ile Arg
                85                  90                  95

Tyr Phe Cys Phe His Asp Val Asp Ile Val Pro Glu Ala Asp Asp Ile
            100                 105                 110

Lys Glu Thr Asn Arg Arg Leu Asp Glu Ile Ser Asp Tyr Ile Leu Glu
        115                 120                 125

Lys Met Lys Gly Thr Asp Ile Gln Cys Leu Trp Gly Thr Ala Asn Met
    130                 135                 140

Phe Gly Asn Pro Arg Tyr Met Asn Gly Ala Gly Ser Ser Asn Ser Ala
145                 150                 155                 160

Asp Val Tyr Cys Phe Ala Ala Ala Gln Ile Lys Lys Ala Leu Asp Ile
                165                 170                 175

Thr Val Lys Leu Gly Gly Lys Gly Tyr Val Phe Trp Gly Gly Arg Glu
            180                 185                 190

Gly Tyr Glu Thr Leu Leu Asn Thr Asp Met Lys Phe Glu Gln Glu Asn
        195                 200                 205

Ile Ala Arg Leu Met His Met Ala Val Asp Tyr Gly Arg Ser Ile Gly
    210                 215                 220

Phe Thr Gly Asp Phe Tyr Ile Glu Pro Lys Pro Lys Glu Pro Met Lys
225                 230                 235                 240

His Gln Tyr Asp Phe Asp Ala Ala Thr Ala Ile Gly Phe Leu Arg Gln
                245                 250                 255

Tyr Gly Leu Asp Lys Asp Phe Lys Leu Asn Ile Glu Ser Asn His Ala
            260                 265                 270

Thr Leu Ala Gly His Thr Phe Gln His Asp Leu Arg Val Ser Ala Ile
        275                 280                 285

Asn Gly Met Leu Gly Ser Ile Asp Ala Asn Gln Gly Asp Tyr Leu Leu
    290                 295                 300
```

```
Gly Trp Asp Thr Asp Glu Phe Pro Tyr Ser Val Tyr Glu Thr Thr Met
305                 310                 315                 320

Cys Met Tyr Glu Val Leu Lys Ala Gly Leu Thr Gly Gly Phe Asn
                325                 330                 335

Phe Asp Ala Lys Asn Arg Arg Pro Ser Tyr Thr Pro Glu Asp Met Phe
            340                 345                 350

His Ala Tyr Ile Leu Gly Met Asp Ser Phe Ala Leu Gly Leu Ile Lys
            355                 360                 365

Ala Ala Glu Leu Ile Glu Asp Gly Arg Leu Asp Ala Phe Val Arg Asp
        370                 375                 380

Arg Tyr Gln Ser Trp Glu Thr Gly Ile Gly Asp Lys Ile Arg Lys Gly
385                 390                 395                 400

Glu Thr Thr Leu Ala Glu Leu Ala Glu Tyr Ala Ala Arg Met Gly Ala
                405                 410                 415

Pro Ala Leu Pro Gly Ser Gly Arg Gln Glu Tyr Leu Glu Gly Val Val
            420                 425                 430

Asn Asn Ile Leu Phe Lys
            435

<210> SEQ ID NO 51
<211> LENGTH: 1320
<212> TYPE: DNA
<213> ORGANISM: Unknown
<220> FEATURE:
<223> OTHER INFORMATION: Obtained from environmental sample

<400> SEQUENCE: 51
atgaagacct atttcaaaaa atccccgtg atccctacg agggaccgaa gtcccagaat      60
ccgctgtcgt tcaaattcta tgacgcggac cgcatcgttc tcggcaagcc catgaaggag     120 catctgcccct tcgccatggc ctggtggcac aatctgggtg ctgccggaac ggacatgttc    180
ggccgcgata ccgccgacaa gtccttcgga gcggagaagg gcaccatgga gcatgccaag    240
gccaaggtgg acgctggctt cgagtttatg aagaaggtgg gcatccggta tttctgcttc   300
catgacgtgg atctggtccc ggaagcggac gacatcaagg agaccaaccg ccgtctcgat   360
gagatcagcg actacatcct caagaagatg aagggcacgg atatcaagtg cctctggggc   420
accgccaaca tgttcggcaa tccccggttc atgaacggcg cgggcagctc caacagcgcg   480
gacgtgttct gctttgccgc ggcccaggtg aagaaggcct tggacatcac cgtcaagctg   540
ggcggccggg gctatgtgtt ctggggcggc cgtgagggt atgagtccct gctgaacacg    600
gacgtgaagt tgagcagga gaacatcgcc aagctcatgc accttgccgt ggactacggc    660
cgcagcatcg gcttcaccgg cgatttctac atcgagccca gcccaagga gcccatgaag    720 caccagtacg acttcgatgc cgccaccgcc atcggcttcc tcaggcagta cggcctcgat   780
aaggacttca agatgaacat tgaagccaac cacgcgaccc tggccggcca caccttccag    840
cacgacctca ggatcagcgc catcaacggg atgctgggct ccatcgacgc caaccagggc   900
gacctcctgc tgggatggga caccgacgaa ttccccttca cgtctatga ggccaccatg    960 tgcatgtacg aggtcctcaa ggccggcggc ctcaccggcg gcttcaactt cgactcaaag   1020
aaccgccgtc cctcctacac catggaggat atgttccacg cctacatcct gggcatggac   1080
accttcgccc tgggtcttct caaggccgcg gagctcatcg aggacggtcg gatcgacaaa   1140
ttcgtggagg agcgctacgc cagctacaag accggcatcg gcgccaagat ccgttccggc    1200
gagaccacgc ttcaggagct ggccgcctat gccgacaagt ggggcgcgcc tgcccttccc    1260
```

```
ggcagcggcc gtcaggagta cctggagagc atcgtcaacc aggtgctctt cgggatgtga      1320
```

<210> SEQ ID NO 52
<211> LENGTH: 439
<212> TYPE: PRT
<213> ORGANISM: Unknown
<220> FEATURE:
<223> OTHER INFORMATION: Obtained from environmental sample

<400> SEQUENCE: 52

Met Lys Thr Tyr Phe Lys Lys Ile Pro Val Ile Pro Tyr Glu Gly Pro
1               5                   10                  15

Lys Ser Gln Asn Pro Leu Ser Phe Lys Phe Tyr Asp Ala Asp Arg Ile
            20                  25                  30

Val Leu Gly Lys Pro Met Lys Glu His Leu Pro Phe Ala Met Ala Trp
        35                  40                  45

Trp His Asn Leu Gly Ala Ala Gly Thr Asp Met Phe Gly Arg Asp Thr
    50                  55                  60

Ala Asp Lys Ser Phe Gly Ala Glu Lys Gly Thr Met Glu His Ala Lys
65                  70                  75                  80

Ala Lys Val Asp Ala Gly Phe Glu Phe Met Lys Lys Val Gly Ile Arg
                85                  90                  95

Tyr Phe Cys Phe His Asp Val Asp Leu Val Pro Glu Ala Asp Asp Ile
            100                 105                 110

Lys Glu Thr Asn Arg Arg Leu Asp Glu Ile Ser Asp Tyr Ile Leu Lys
        115                 120                 125

Lys Met Lys Gly Thr Asp Ile Lys Cys Leu Trp Gly Thr Ala Asn Met
130                 135                 140

Phe Gly Asn Pro Arg Phe Met Asn Gly Ala Gly Ser Ser Asn Ser Ala
145                 150                 155                 160

Asp Val Phe Cys Phe Ala Ala Ala Gln Val Lys Lys Ala Leu Asp Ile
                165                 170                 175

Thr Val Lys Leu Gly Gly Arg Gly Tyr Val Phe Trp Gly Gly Arg Glu
            180                 185                 190

Gly Tyr Glu Ser Leu Leu Asn Thr Asp Val Lys Phe Glu Gln Glu Asn
        195                 200                 205

Ile Ala Lys Leu Met His Leu Ala Val Asp Tyr Gly Arg Ser Ile Gly
    210                 215                 220

Phe Thr Gly Asp Phe Tyr Ile Glu Pro Lys Pro Lys Glu Pro Met Lys
225                 230                 235                 240

His Gln Tyr Asp Phe Asp Ala Ala Thr Ala Ile Gly Phe Leu Arg Gln
                245                 250                 255

Tyr Gly Leu Asp Lys Asp Phe Lys Met Asn Ile Glu Ala Asn His Ala
            260                 265                 270

Thr Leu Ala Gly His Thr Phe Gln His Asp Leu Arg Ile Ser Ala Ile
        275                 280                 285

Asn Gly Met Leu Gly Ser Ile Asp Ala Asn Gln Gly Asp Leu Leu Leu
    290                 295                 300

Gly Trp Asp Thr Asp Glu Phe Pro Phe Asn Val Tyr Glu Ala Thr Met
305                 310                 315                 320

Cys Met Tyr Glu Val Leu Lys Ala Gly Gly Leu Thr Gly Gly Phe Asn
                325                 330                 335

Phe Asp Ser Lys Asn Arg Arg Pro Ser Tyr Thr Met Glu Asp Met Phe
            340                 345                 350

His Ala Tyr Ile Leu Gly Met Asp Thr Phe Ala Leu Gly Leu Leu Lys 355                 360                 365
Ala Ala Glu Leu Ile Glu Asp Gly Arg Ile Asp Lys Phe Val Glu Glu
        370                 375                 380

Arg Tyr Ala Ser Tyr Lys Thr Gly Ile Gly Ala Lys Ile Arg Ser Gly
385                 390                 395                 400

Glu Thr Thr Leu Gln Glu Leu Ala Ala Tyr Ala Asp Lys Leu Gly Ala
                405                 410                 415

Pro Ala Leu Pro Gly Ser Gly Arg Gln Glu Tyr Leu Glu Ser Ile Val
            420                 425                 430

Asn Gln Val Leu Phe Gly Met
        435

<210> SEQ ID NO 53
<211> LENGTH: 1314
<212> TYPE: DNA
<213> ORGANISM: Unknown
<220> FEATURE:
<223> OTHER INFORMATION: Obtained from environmental sample

<400> SEQUENCE: 53
atggctaaag agtattttcc agagattggc aaaatcaagt ttgaaggcaa ggacagcaaa      60
aacccaatgg ctttccacta ctatgacccc gagaaggtga tcatgggcaa gcctatgaaa     120
gactggctcc gcttcgctat ggcatggtgg cacaccctct cgcagaagg tggcgaccag      180
ttcggtggcg gcactaagaa gttcccttgg aacaacggcg ctgacgctgt agaaatcgca     240
aaacagaagg ctgacgcagg tttcgaaatc atgcagaagc tcggcatccc atatttctgc     300
ttccacgacg tggacctcgt gtctgagggc gcatctgtag aagagtatga ggctaaccte     360
aaggctatca cagactacct cgctgtgaag atgaaggaaa caggcatcaa gctcctgtgg     420
tctactgcca acgtattcgg caacggccgc tacatgaacg gtgcttctac caaccctgac     480
ttcgacgtcg ttgctcgcgc tatcgtgcag attaagaacg ctatcgacgc tggtatcaag     540
ctcggcgctg agaactacgt gttctgggge ggacgcgaag gctacatgag cctcctcaac     600
accgaccaga gcgtgagaa ggagcacatg ccactatgc tcactatggc tcgcgactac      660
gctcgcgcta agggcttcaa gggcacattc ctcatcgagc ctaagccaat ggagccttct     720
aagcaccagt atgacgttga cactgagact gtcatcggct tcctcaaggc acacaacctc    780
gacaaggact tcaaggtgaa catcgaggtg aaccacgcaa ctctcgctgg ccacaccttc    840
gagcacgagc tcgcagtggc agtggacaac aacatgctcg gctctatcga cgctaaccgt    900
ggtgactacc agaatggctg ggatactgac cagttcccaa tcgaccagta cgaactcgtt    960
caggcttgga tggaaatcat ccgtggcggc ggtctcggca ctggcggcac gaacttcgac   1020
gctaagactc gtcgtaactc taccgacctc gaagacatct tcatcgcaca catcgcaggc   1080
atggacgcta tggcacgcgc actcgaatca gctgctaagc tcctcgaaga gtctccatac   1140
aaggcaatga aggcagctcg ctacgcttca ttcgacaacg gtatcggtaa ggacttcgaa   1200
gatggcaagc tcactctcga gcaggcttac gaatacggta agaaggttgg tgagcctaag   1260
cagacttctg caagcagga gctctacgaa gccatcgttg caatgtacgc ttaa          1314

<210> SEQ ID NO 54
<211> LENGTH: 437
<212> TYPE: PRT
<213> ORGANISM: Unknown
<220> FEATURE:
<223> OTHER INFORMATION: Obtained from environmental sample

<400> SEQUENCE: 54

Met Ala Lys Glu Tyr Phe Pro Glu Ile Gly Lys Ile Lys Phe Glu Gly
1               5                   10                  15

Lys Asp Ser Lys Asn Pro Met Ala Phe His Tyr Tyr Asp Pro Glu Lys
            20                  25                  30

Val Ile Met Gly Lys Pro Met Lys Asp Trp Leu Arg Phe Ala Met Ala
        35                  40                  45

Trp Trp His Thr Leu Cys Ala Glu Gly Gly Asp Gln Phe Gly Gly Gly
    50                  55                  60

Thr Lys Lys Phe Pro Trp Asn Asn Gly Ala Asp Ala Val Glu Ile Ala
65                  70                  75                  80

Lys Gln Lys Ala Asp Ala Gly Phe Glu Ile Met Gln Lys Leu Gly Ile
                85                  90                  95

Pro Tyr Phe Cys Phe His Asp Val Asp Leu Val Ser Glu Gly Ala Ser
            100                 105                 110

Val Glu Glu Tyr Glu Ala Asn Leu Lys Ala Ile Thr Asp Tyr Leu Ala
        115                 120                 125

Val Lys Met Lys Glu Thr Gly Ile Lys Leu Leu Trp Ser Thr Ala Asn
130                 135                 140

Val Phe Gly Asn Gly Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Lys Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ala Lys
210                 215                 220

Gly Phe Lys Gly Thr Phe Leu Ile Glu Pro Lys Pro Met Glu Pro Ser
225                 230                 235                 240

Lys His Gln Tyr Asp Val Asp Thr Glu Thr Val Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Val Ala Val
        275                 280                 285

Asp Asn Asn Met Leu Gly Ser Ile Asp Ala Asn Arg Gly Asp Tyr Gln
290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Leu Gly Thr Gly Gly Gly
                325                 330                 335

Thr Asn Phe Asp Ala Lys Thr Arg Arg Asn Ser Thr Asp Leu Glu Asp
            340                 345                 350

Ile Phe Ile Ala His Ile Ala Gly Met Asp Ala Met Ala Arg Ala Leu
        355                 360                 365

Glu Ser Ala Ala Lys Leu Leu Glu Glu Ser Pro Tyr Lys Ala Met Lys
370                 375                 380

Ala Ala Arg Tyr Ala Ser Phe Asp Asn Gly Ile Gly Lys Asp Phe Glu
385                 390                 395                 400

Asp Gly Lys Leu Thr Leu Glu Gln Ala Tyr Glu Tyr Gly Lys Lys Val
                405                 410                 415

Gly Glu Pro Lys Gln Thr Ser Gly Lys Gln Glu Leu Tyr Glu Ala Ile
            420                 425                 430

Val Ala Met Tyr Ala
        435

<210> SEQ ID NO 55
<211> LENGTH: 1314
<212> TYPE: DNA
<213> ORGANISM: Unknown
<220> FEATURE:
<223> OTHER INFORMATION: Obtained from environmental sample

<400> SEQUENCE: 55

```
atggctaaag aattttccc agagattggt aaaatcaagt tcgaaggcaa ggattcaaag      60
aatccaatgg ctttccatta ctatgatgca gagaaggtaa tcatgggcaa acccatgaag    120
gactggctcc gtttcgctat ggcatggtgg cacacactct gtgcagaggg cggcgaccag    180
ttcggtggcg gtacgaagaa gttcccttgg aacgagggtg ctaatgctgt cgagattgct    240
aagcagaagg ctgacgctgg tttcgaaatc atgcagaagc ttggcattcc ttacttctgc    300
ttccacgatg ttgacctcgt ttctgaaggc gcatctgttg aggagtatga ggccaacctc    360
aaggctatca ctgactatct cgcggtgaag atgaaggaga ctggcattaa gctcctgtgg    420
tctactgcca acgtgttcgg caatggccgt tacatgaatg gtgcttccac caaccctgac    480
ttcgacgttg ttgctcgcgc catcgttcag attaagaacg ctatcgatgc aggtatcaag    540
ctcggtgctg agaactatgt gttctggggc ggtcgtgaag gttacatgag cctcctgaac    600
acagaccaga gcgtgagaa ggagcacatg gctactatgc tcactatggc tcgcgactac    660
gctcgcagca agggcttcaa gggtactttc ctcatcgagc ctaagccaat ggagccatct    720
aagcaccagt acgacgttga cacagagact gttatcggct tcctgaaggc acacaacctt    780
gacaaggact tcaaggtgaa catcgaggtg aaccacgcaa cactcgctgg tcacaccttc    840
gagcacgagc tcgctgtggc tgtcgacaac aatatgcttg gttctatcga tgctaaccgc    900
ggtgactacc agaatggttg ggatacggac cagttcccaa ttgaccagta cgagctcgtt    960
caggcttgga tggagatcat ccgtggtggc ggtctcggca caggtggtac aaacttcgac   1020
gctaagactc gtcgtaactc taccgacctc gaggacattt tcattgctca catcgctggt   1080
atggacgcta tggctcgcgc tcttgagtca gcagctaagc tccttgagga gtctccatac   1140
aagaagatga aggctgcccg ttatgcttct ttcgacagcg gcatgggtaa ggactttgag   1200
aacggcaagc tcacactcga acaggtttat gagtatggta agaaggtagg tgagcccaag   1260
cagacttctg gcaagcagga gctcttcgag gcaatcgtgg ccatgtacgc ataa         1314
```

<210> SEQ ID NO 56
<211> LENGTH: 437
<212> TYPE: PRT
<213> ORGANISM: Unknown
<220> FEATURE:
<223> OTHER INFORMATION: Obtained from environmental sample

<400> SEQUENCE: 56

Met Ala Lys Glu Phe Phe Pro Glu Ile Gly Lys Ile Lys Phe Glu Gly
1               5                   10                  15

Lys Asp Ser Lys Asn Pro Met Ala Phe His Tyr Tyr Asp Ala Glu Lys
            20                  25                  30

Val Ile Met Gly Lys Pro Met Lys Asp Trp Leu Arg Phe Ala Met Ala
        35                  40                  45

Trp Trp His Thr Leu Cys Ala Glu Gly Gly Asp Gln Phe Gly Gly Gly
50                  55                  60

Thr Lys Lys Phe Pro Trp Asn Glu Gly Ala Asn Ala Val Glu Ile Ala
65                  70                  75                  80

Lys Gln Lys Ala Asp Ala Gly Phe Glu Ile Met Gln Lys Leu Gly Ile
                85                  90                  95

Pro Tyr Phe Cys Phe His Asp Val Asp Leu Val Ser Glu Gly Ala Ser
            100                 105                 110

Val Glu Glu Tyr Glu Ala Asn Leu Lys Ala Ile Thr Asp Tyr Leu Ala
        115                 120                 125

Val Lys Met Lys Glu Thr Gly Ile Lys Leu Leu Trp Ser Thr Ala Asn
130                 135                 140

Val Phe Gly Asn Gly Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Lys Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
210                 215                 220

Gly Phe Lys Gly Thr Phe Leu Ile Glu Pro Lys Pro Met Glu Pro Ser
225                 230                 235                 240

Lys His Gln Tyr Asp Val Asp Thr Glu Thr Val Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Val Ala Val
        275                 280                 285

Asp Asn Asn Met Leu Gly Ser Ile Asp Ala Asn Arg Gly Asp Tyr Gln
290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Leu Gly Thr Gly Gly
                325                 330                 335

Thr Asn Phe Asp Ala Lys Thr Arg Arg Asn Ser Thr Asp Leu Glu Asp
            340                 345                 350

Ile Phe Ile Ala His Ile Ala Gly Met Asp Ala Met Ala Arg Ala Leu
        355                 360                 365

Glu Ser Ala Ala Lys Leu Leu Glu Glu Ser Pro Tyr Lys Lys Met Lys
370                 375                 380

Ala Ala Arg Tyr Ala Ser Phe Asp Ser Gly Met Gly Lys Asp Phe Glu
385                 390                 395                 400

Asn Gly Lys Leu Thr Leu Glu Gln Val Tyr Glu Tyr Gly Lys Lys Val
                405                 410                 415

Gly Glu Pro Lys Gln Thr Ser Gly Lys Gln Glu Leu Phe Glu Ala Ile
            420                 425                 430

Val Ala Met Tyr Ala
        435

<210> SEQ ID NO 57
<211> LENGTH: 1314

<212> TYPE: DNA
<213> ORGANISM: Unknown
<220> FEATURE:
<223> OTHER INFORMATION: Obtained from environmental sample

<400> SEQUENCE: 57

| | | | | | |
|---|---|---|---|---|---|
| atggctaaag | agtattttcc | agagattggt | aaaatcaagt | tgaaggcaa | ggattccaag | 60 |
| aatccaatgg | cattccacta | ttatgatgca | gagaaagtga | ttatgggtaa | gcctatgaag | 120 |
| gagtggctcc | gctttgcaat | ggcatggtgg | cacacactct | gtgcagaggg | tggcgaccag | 180 |
| tttggtggtg | gcactaagaa | attcccatgg | aacgagggca | ctgacgctgt | gacgattgct | 240 |
| aagcagaagg | ctgatgcagg | tttcgaaatc | atgcagaaac | tcggtttccc | atattttgc | 300 |
| ttccacgaca | ttgacctcgt | tccgaaggc | aacagcattg | aagagtatga | ggctaacctc | 360 |
| caggcaatca | ctgattatct | gaaagtgaag | atggaagaga | caggcatcaa | actcttgtgg | 420 |
| tcaactgcca | acgtattcgg | caatggtcgc | tacatgaatg | gtgcttccac | aaacccagac | 480 |
| tttgacgtgg | tggctcgtgc | catcgttcag | attaagaacg | caattgacgc | tggtatcaaa | 540 |
| ctcggtgctg | agaactatgt | attctggggc | ggtcgcgaag | gctacatgag | ccttctgaac | 600 |
| actgaccaga | agcgtgagaa | ggagcacatg | gcaaccatgc | tcactatggc | tcgcgactac | 660 |
| gctcgcagca | agggtttcaa | gggcactttc | ctcattgagc | caaagccaat | ggagccatct | 720 |
| aagcaccagt | atgacgttga | cacggagact | gtcatcggct | tcctcaaggc | acacaacctc | 780 |
| gacaaggatt | tcaaggtgaa | catcgaagtg | aaccacgcta | cacttgcagg | tcatactttc | 840 |
| gagcacgaac | ttgctgtggc | tgttgacaat | ggcatgctcg | gttctatcga | cgctaaccgt | 900 |
| ggtgactatc | agaacggttg | ggacactgac | cagttcccaa | tcgaccagta | cgaactcgtt | 960 |
| caggcttgga | tggaaatcat | ccgtggtggt | ggtctcggca | caggtggtac | taacttcgat | 1020 |
| gctaagactc | gtcgtaactc | aactgacctc | gaggacatct | tcatcgcaca | catctctggt | 1080 |
| atggatgcaa | tggcacgtgc | tctcgaatcg | gcggctaaac | ttcttgagga | gtctccatac | 1140 |
| tgcgctatga | agaaggctcg | ttacgcttcc | ttcgacagcg | gcatcggtaa | ggacttcgag | 1200 |
| gacggcaaac | tcacgctcga | gcaggcttac | gagtacggca | agaaagtcgg | cgaacccaag | 1260 |
| cagacttctg | gcaagcagga | actctacgag | gcaatcgttg | ccatgtacgc | ataa | 1314 |

<210> SEQ ID NO 58
<211> LENGTH: 437
<212> TYPE: PRT
<213> ORGANISM: Unknown
<220> FEATURE:
<223> OTHER INFORMATION: Obtained from environmental sample

<400> SEQUENCE: 58

Met Ala Lys Glu Tyr Phe Pro Glu Ile Gly Lys Ile Lys Phe Glu Gly
1               5                   10                  15

Lys Asp Ser Lys Asn Pro Met Ala Phe His Tyr Tyr Asp Ala Glu Lys
            20                  25                  30

Val Ile Met Gly Lys Pro Met Lys Glu Trp Leu Arg Phe Ala Met Ala
        35                  40                  45

Trp Trp His Thr Leu Cys Ala Glu Gly Gly Asp Gln Phe Gly Gly Gly
    50                  55                  60

Thr Lys Lys Phe Pro Trp Asn Glu Gly Thr Asp Ala Val Thr Ile Ala
65                  70                  75                  80

Lys Gln Lys Ala Asp Ala Gly Phe Glu Ile Met Gln Lys Leu Gly Phe
                85                  90                  95

Pro Tyr Phe Cys Phe His Asp Ile Asp Leu Val Ser Glu Gly Asn Ser
            100                 105                 110

Ile Glu Glu Tyr Glu Ala Asn Leu Gln Ala Ile Thr Asp Tyr Leu Lys
        115                 120                 125

Val Lys Met Glu Glu Thr Gly Ile Lys Leu Leu Trp Ser Thr Ala Asn
    130                 135                 140

Val Phe Gly Asn Gly Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Lys Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Met Ala Thr Met Leu Thr Met Ala Arg Asp Tyr Ala Arg Ser Lys
    210                 215                 220

Gly Phe Lys Gly Thr Phe Leu Ile Glu Pro Lys Pro Met Glu Pro Ser
225                 230                 235                 240

Lys His Gln Tyr Asp Val Asp Thr Glu Thr Val Ile Gly Phe Leu Lys
                245                 250                 255

Ala His Asn Leu Asp Lys Asp Phe Lys Val Asn Ile Glu Val Asn His
            260                 265                 270

Ala Thr Leu Ala Gly His Thr Phe Glu His Glu Leu Ala Val Ala Val
        275                 280                 285

Asp Asn Gly Met Leu Gly Ser Ile Asp Ala Asn Arg Gly Asp Tyr Gln
    290                 295                 300

Asn Gly Trp Asp Thr Asp Gln Phe Pro Ile Asp Gln Tyr Glu Leu Val
305                 310                 315                 320

Gln Ala Trp Met Glu Ile Ile Arg Gly Gly Leu Gly Thr Gly Gly
                325                 330                 335

Thr Asn Phe Asp Ala Lys Thr Arg Arg Asn Ser Thr Asp Leu Glu Asp
            340                 345                 350

Ile Phe Ile Ala His Ile Ser Gly Met Asp Ala Met Ala Arg Ala Leu
        355                 360                 365

Glu Ser Ala Ala Lys Leu Leu Glu Glu Ser Pro Tyr Cys Ala Met Lys
    370                 375                 380

Lys Ala Arg Tyr Ala Ser Phe Asp Ser Gly Ile Gly Lys Asp Phe Glu
385                 390                 395                 400

Asp Gly Lys Leu Thr Leu Glu Gln Ala Tyr Glu Tyr Gly Lys Lys Val
                405                 410                 415

Gly Glu Pro Lys Gln Thr Ser Gly Lys Gln Glu Leu Tyr Glu Ala Ile
            420                 425                 430

Val Ala Met Tyr Ala
        435

<210> SEQ ID NO 59
<211> LENGTH: 1317
<212> TYPE: DNA
<213> ORGANISM: Unknown
<220> FEATURE:
<223> OTHER INFORMATION: Obtained from environmental sample

<400> SEQUENCE: 59
atggcaaaag agtatttccc tacgatcggt aagatcgttt atgaaggacc ggagtccaag    60
aaccctatgg catttcatta ctatgacgca gagcgcgtag tagctggtaa aaaaatgaaa   120

-continued

```
gattggatgc gtttcgctat ggcatggtgg cacaccctct gtgcagaagg tgcagaccag    180
ttcggtggag gcaccaaaca cttcccgtgg agtgaaggtc ccgatgccgt aaccatcgcc    240
aagcagaaag cagacgcagg ttttgagatc atgcagaaac tcggcttccc gtatttctgt    300
ttccatgacg tggatctggt cagcgaaggc agcagcgtag aagagtacga ggcgaacctc    360
gcagccatca ccgattatct caagcagaaa atggacgagt cgggtatcaa actcctttgg    420
tccactgcta acgtattcgg tcacgcccgt tacatgaacg gtgccagcac caatcctgac    480
tttgatgtcg ttgcccgtgc gattgtgcag atcaagaatg ctatcgacgc aggtatcaaa    540
ctcggcgcag agaactacgt cttctggggc ggtcgtgaag gttatatgag cctgctcaat    600
accgaccaga aacgcgagaa agagcatacg gcaatgatgc tgcgtatggc gcgtgactat    660
gcccgcagca aggtttcaa aggtaccttc ctcatcgaac ccaaacccat ggagccgtcc    720
aagcaccagt atgacgtaga taccgagacg gtgataggtt cctcaaagc acacggtttg    780 gagaaagact ttaaggtaaa catcgaagtg aaccacgcta ccctcgccgg tcacactttc    840
gagcacgaac tggcagtagc cgtagataac ggcatgctcg gttcgatcga tgccaaccgc    900
ggtgactatc agaacggatg ggataccgac cagttcccca tcgataactt cgaactgacc    960
caagcatgga tgcagatcgt acgtaacggt ggtctcggca caggcggaac gaacttcgac   1020
tccaagaccc gtcgtaactc caccgatctc gaggatatct tcatcgctca catcagtggt   1080
atggacgctt gtgcccgtgc cctattgaat gccgtagaga tcatggagaa atcaccgatc   1140
cctgctatgc tcaaagagcg ttacgcttcc ttcgatagcg gtctgggtaa agatttcgag   1200
gacggcaaac tgacccttga gcaagtctat gagtacggta agaaagtagg cgaacccaaa   1260
caaaccagcg gcaaacaaga actctatgag gctatcgttg ccctctacgc taaataa     1317
```

<210> SEQ ID NO 60
<211> LENGTH: 438
<212> TYPE: PRT
<213> ORGANISM: Unknown
<220> FEATURE:
<223> OTHER INFORMATION: Obtained from environmental sample

<400> SEQUENCE: 60

```
Met Ala Lys Glu Tyr Phe Pro Thr Ile Gly Lys Ile Val Tyr Glu Gly
1               5                   10                  15

Pro Glu Ser Lys Asn Pro Met Ala Phe His Tyr Tyr Asp Ala Glu Arg
            20                  25                  30

Val Val Ala Gly Lys Lys Met Lys Asp Trp Met Arg Phe Ala Met Ala
        35                  40                  45

Trp Trp His Thr Leu Cys Ala Glu Gly Ala Asp Gln Phe Gly Gly Gly
    50                  55                  60

Thr Lys His Phe Pro Trp Ser Glu Gly Pro Asp Ala Val Thr Ile Ala
65                  70                  75                  80

Lys Gln Lys Ala Asp Ala Gly Phe Glu Ile Met Gln Lys Leu Gly Phe
                85                  90                  95

Pro Tyr Phe Cys Phe His Asp Val Asp Leu Val Ser Glu Gly Ser Ser
            100                 105                 110

Val Glu Glu Tyr Glu Ala Asn Leu Ala Ala Ile Thr Asp Tyr Leu Lys
        115                 120                 125

Gln Lys Met Asp Glu Ser Gly Ile Lys Leu Leu Trp Ser Thr Ala Asn
    130                 135                 140

Val Phe Gly His Ala Arg Tyr Met Asn Gly Ala Ser Thr Asn Pro Asp
```

```
        145                 150                 155                 160
    Phe Asp Val Val Ala Arg Ala Ile Val Gln Ile Lys Asn Ala Ile Asp
                    165                 170                 175
    Ala Gly Ile Lys Leu Gly Ala Glu Asn Tyr Val Phe Trp Gly Gly Arg
                    180                 185                 190
    Glu Gly Tyr Met Ser Leu Leu Asn Thr Asp Gln Lys Arg Glu Lys Glu
                    195                 200                 205
    His Thr Ala Met Met Leu Arg Met Ala Arg Asp Tyr Ala Arg Ser Lys
                    210                 215                 220
    Gly Phe Lys Gly Thr Phe Leu Ile Glu Pro Lys Pro Met Glu Pro Ser
    225                 230                 235                 240
    Lys His Gln Tyr Asp Val Asp Thr Glu Thr Val Ile Gly Phe Leu Lys
                    245                 250                 255
    Ala His Gly Leu Glu Lys Asp Phe Lys Val Asn Ile Glu Val Asn His
                    260                 265                 270
    Ala Thr Leu Ala Gly His Thr Phe Glu His Glu Leu Ala Val Ala Val
                    275                 280                 285
    Asp Asn Gly Met Leu Gly Ser Ile Asp Ala Asn Arg Gly Asp Tyr Gln
                    290                 295                 300
    Asn Gly Trp Asp Thr Asp Gln Phe Pro Ile Asp Asn Phe Glu Leu Thr
    305                 310                 315                 320
    Gln Ala Trp Met Gln Ile Val Arg Asn Gly Gly Leu Gly Thr Gly Gly
                    325                 330                 335
    Thr Asn Phe Asp Ser Lys Thr Arg Arg Asn Ser Thr Asp Leu Glu Asp
                    340                 345                 350
    Ile Phe Ile Ala His Ile Ser Gly Met Asp Ala Cys Ala Arg Ala Leu
                    355                 360                 365
    Leu Asn Ala Val Glu Ile Met Glu Lys Ser Pro Ile Pro Ala Met Leu
                    370                 375                 380
    Lys Glu Arg Tyr Ala Ser Phe Asp Ser Gly Leu Gly Lys Asp Phe Glu
    385                 390                 395                 400
    Asp Gly Lys Leu Thr Leu Glu Gln Val Tyr Glu Tyr Gly Lys Lys Val
                    405                 410                 415
    Gly Glu Pro Lys Gln Thr Ser Gly Lys Gln Glu Leu Tyr Glu Ala Ile
                    420                 425                 430
    Val Ala Leu Tyr Ala Lys
                    435

<210> SEQ ID NO 61
<211> LENGTH: 1314
<212> TYPE: DNA
<213> ORGANISM: Unknown
<220> FEATURE:
<223> OTHER INFORMATION: Obtained from environmental sample

<400> SEQUENCE: 61
atgaaagagt atttccctga gatcggtaag atccaatttg aaggcccgga gtccaagaac        60
ccgatggcat tcactacta tgacgcagag cgcgtcgtag ccggtaaaac aatgaaagag       120
tggatgcgtt tcgctatggc ttggtggcac accctctgtg cggaaggcgg cgaccagttc       180
ggaggcggaa cgaagaagtt ccctggaac gaaggcgcta acgctttgga gatcgccaag       240
cacaaagccg atgcgggatt tgagatcatg cagaaactcg gcatccctta tttctgtttc       300
catgacgtgg atctcatcgc cgagggcggt tcggtagaag agtacgaagc caacctcgct       360
gccatcaccg attacctcaa acagaaaatg gacgagactg gcatcaaact gctgtggtcc       420
```

```
acggcgaacg tcttcagcaa ccccgttat atgaacggcg ccagcacgaa ccccgatttc    480
gatgtagtag cgcgtgccat cgtccagatc aagaacgcta tcgacgccgg tatcaaactc    540
ggagcagaga actatgtctt ctggggtggt cgcgagggct atatgagcct cctcaacact    600
gaccagcgcc gagagaaaga gcatatggct accatgctcc gtatggcgcg tgactacgcg    660
cgtgccaaag gattcaaggg caccttcctc atcgaaccca aaccatgtga gccgtccaaa    720
catcagtatg atgtcgatac cgagaccgtc atcggtttcc tcaaagcgca tggactcgac    780
aaggatttca aagtcaatat cgaggtcaac cacgccaccc tcgcaggcca cgttcgaa       840 cacgaactgg cttgcgctgt agatgccggc atgctcggtt cgattgacgc caaccgcggt    900
gacgcccaga acggatggga caccgaccag ttccctattg ataacttcga actcacacag    960
gctttcatgc agatcgtccg caacggcggt ttcggaacag gcggtacgaa cttcgacgcc   1020
aagacacgcc gtaactccac cgacttggag gacatcttca tcgcccatat cagcggcatg   1080
gacgcttgcg cacgtgcgtt actcaatgct gtcgaaatcc tcgagaagag cccgattccg   1140
gcgatgctca agagcgttta tgcttccttt gacggcggca tcggaaagga cttcgaggag   1200
ggaaaactga ctttcgagca ggtctatgag tacggcaaga agtcggcga  acccaaacag   1260 accagcggca acaggagct ctacgaaacc atcgtcgccc tctatgccaa atag           1314
```

<210> SEQ ID NO 62
<211> LENGTH: 437
<212> TYPE: PRT
<213> ORGANISM: Unknown
<220> FEATURE:
<223> OTHER INFORMATION: Obtained from environmental sample

<400> SEQUENCE: 62

```
Met Lys Glu Tyr Phe Pro Glu Ile Gly Lys Ile Gln Phe Glu Gly Pro
1               5                   10                  15

Glu Ser Lys Asn Pro Met Ala Phe His Tyr Tyr Asp Ala Glu Arg Val
            20                  25                  30

Val Ala Gly Lys Thr Met Lys Glu Trp Met Arg Phe Ala Met Ala Trp
        35                  40                  45

Trp His Thr Leu Cys Ala Glu Gly Gly Asp Gln Phe Gly Gly Gly Thr
    50                  55                  60

Lys Lys Phe Pro Trp Asn Glu Gly Ala Asn Ala Leu Glu Ile Ala Lys
65                  70                  75                  80

His Lys Ala Asp Ala Gly Phe Glu Ile Met Gln Lys Leu Gly Ile Pro
                85                  90                  95

Tyr Phe Cys Phe His Asp Val Asp Leu Ile Ala Glu Gly Gly Ser Val
            100                 105                 110

Glu Glu Tyr Glu Ala Asn Leu Ala Ala Ile Thr Asp Tyr Leu Lys Gln
        115                 120                 125

Lys Met Asp Glu Thr Gly Ile Lys Leu Leu Trp Ser Thr Ala Asn Val
    130                 135                 140

Phe Ser Asn Pro Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Gly Ile Lys Leu Gly Ala Glu Asn Tyr Val Phe Trp Gly Gly Arg Glu
            180                 185                 190

Gly Tyr Met Ser Leu Leu Asn Thr Asp Gln Arg Arg Glu Lys Glu His
        195                 200                 205
```

```
Met Ala Thr Met Leu Arg Met Ala Arg Asp Tyr Ala Arg Ala Lys Gly
        210                 215                 220
Phe Lys Gly Thr Phe Leu Ile Glu Pro Lys Pro Cys Glu Pro Ser Lys
225                 230                 235                 240
His Gln Tyr Asp Val Asp Thr Glu Thr Val Ile Gly Phe Leu Lys Ala
                245                 250                 255
His Gly Leu Asp Lys Asp Phe Lys Val Asn Ile Glu Val Asn His Ala
            260                 265                 270
Thr Leu Ala Gly His Thr Phe Glu His Glu Leu Ala Cys Ala Val Asp
        275                 280                 285
Ala Gly Met Leu Gly Ser Ile Asp Ala Asn Arg Gly Asp Ala Gln Asn
    290                 295                 300
Gly Trp Asp Thr Asp Gln Phe Pro Ile Asp Asn Phe Glu Leu Thr Gln
305                 310                 315                 320
Ala Phe Met Gln Ile Val Arg Asn Gly Gly Phe Gly Thr Gly Gly Thr
                325                 330                 335
Asn Phe Asp Ala Lys Thr Arg Arg Asn Ser Thr Asp Leu Glu Asp Ile
            340                 345                 350
Phe Ile Ala His Ile Ser Gly Met Asp Ala Cys Ala Arg Ala Leu Leu
        355                 360                 365
Asn Ala Val Glu Ile Leu Glu Lys Ser Pro Ile Pro Ala Met Leu Lys
    370                 375                 380
Glu Arg Tyr Ala Ser Phe Asp Gly Gly Ile Gly Lys Asp Phe Glu Glu
385                 390                 395                 400
Gly Lys Leu Thr Phe Glu Gln Val Tyr Glu Tyr Gly Lys Lys Val Gly
                405                 410                 415
Glu Pro Lys Gln Thr Ser Gly Lys Gln Glu Leu Tyr Glu Thr Ile Val
            420                 425                 430
Ala Leu Tyr Ala Lys
        435

<210> SEQ ID NO 63
<211> LENGTH: 1317
<212> TYPE: DNA
<213> ORGANISM: Unknown
<220> FEATURE:
<223> OTHER INFORMATION: Obtained from environmental sample

<400> SEQUENCE: 63
atggcaaaag agtatttccc tacgatcggt aagatcgttt atgaaggacc ggaatccaag      60
aaccctatgg catttcatta ctatgacgca gagcgcgtag tagctggtaa aaaaatgaaa     120
gattggatgc gtttcgctat ggcatggtgg cacaccctct gtgcagaagg tgcagaccag     180
ttcggtggag gcaccaaaca cttcccgtgg aatgaaggtc ccgatgccgt aaccatcgcc     240
aagcagaaag cagacgcagg ttttgagatc atgcagaaac tcggcttccc gtatttctgt     300
ttccatgacg tggatctggt cggcgaaggc agcagcgtag aagagtacga ggcgaacctc     360
gcagccatca ccgattatct caagcagaaa atggacgagt cgggtatcaa actccttttgg    420 tccactgcta acgtattcgg tcacgcccgt tacatgaacg tgccagcac caatcctgac      480 tttgatgtcg ttgcccgtgc gattgtgcag atcaagaatg ctatcgacgc aggtatcaaa     540
ctcggcgcag agaactacgt cttctggggc ggtcgtgaag ttatatgag cctgctcaac      600 accgaccaga aacgcgagaa agagcatacg gcaatgatgc tgcgtatggc gcgtgactat     660
gcccgcagca aaggtttcaa aggtaccttc ctcatcgaac ccaaacccat ggagccgtcc     720
```

```
aagcaccagt atgacgtaga taccgagacg gtgataggtt tcctcaaagc acacggtttg    780
gagaaagact ttaaggtaaa catcgaagtg aaccacgcta ccctcgccgg tcacactttc    840
gagcacgaac tggcagtagc cgtagataac ggcatgctcg gttcgatcga tgccaaccgc    900
ggtgactatc agaacggatg ggataccgac cagttcccca tcgataactt cgaactgacc    960
caagcatgga tgcagatcgt acgtaacggt ggtctcggca caggcggaac gaacttcgac   1020
tccaagaccc gtcgtaactc caccgatctc gaggatatct tcatcgctca catcagtggt   1080
atggacgctt gtgcccgtgc cctattgaat gccgtagaga tcatggagaa atcaccgatc   1140
cctgctatgc tcaaagagcg ttacgcttcc ttcgatagcg gtctgggtaa agatttcgag   1200
gacggcaaac tgacccttga gcaagtctat gagtacggta agaaagtagg cgaacccaaa   1260
caaaccagcg gcaaacaaga actctatgag gctatcgttg ccctctacgc taaataa     1317
```

<210> SEQ ID NO 64
<211> LENGTH: 438
<212> TYPE: PRT
<213> ORGANISM: Unknown
<220> FEATURE:
<223> OTHER INFORMATION: Obtained from environmental sample

<400> SEQUENCE: 64

```
Met Ala Lys Glu Tyr Phe Pro Thr Ile Gly Lys Ile Val Tyr Glu Gly
1               5                   10                  15

Pro Glu Ser Lys Asn Pro Met Ala Phe His Tyr Tyr Asp Ala Glu Arg
            20                  25                  30

Val Val Ala Gly Lys Lys Met Lys Asp Trp Met Arg Phe Ala Met Ala
        35                  40                  45

Trp Trp His Thr Leu Cys Ala Glu Gly Ala Asp Gln Phe Gly Gly Gly
    50                  55                  60

Thr Lys His Phe Pro Trp Asn Glu Gly Pro Ala Val Thr Ile Ala
65                  70                  75                  80

Lys Gln Lys Ala Asp Ala Gly Phe Glu Ile Met Gln Lys Leu Gly Phe
                85                  90                  95

Pro Tyr Phe Cys Phe His Asp Val Asp Leu Val Gly Glu Gly Ser Ser
            100                 105                 110

Val Glu Glu Tyr Glu Ala Asn Leu Ala Ala Ile Thr Asp Tyr Leu Lys
        115                 120                 125

Gln Lys Met Asp Glu Ser Gly Ile Lys Leu Leu Trp Ser Thr Ala Asn
    130                 135                 140

Val Phe Gly His Ala Arg Tyr Met Asn Gly Ala Ser Thr Asn Pro Asp
145                 150                 155                 160

Phe Asp Val Val Ala Arg Ala Ile Val Gln Ile Lys Asn Ala Ile Asp
                165                 170                 175

Ala Gly Ile Lys Leu Gly Ala Glu Asn Tyr Val Phe Trp Gly Gly Arg
            180                 185                 190

Glu Gly Tyr Met Ser Leu Leu Asn Thr Asp Gln Lys Arg Glu Lys Glu
        195                 200                 205

His Thr Ala Met Met Leu Arg Met Ala Arg Asp Tyr Ala Arg Ser Lys
    210                 215                 220

Gly Phe Lys Gly Thr Phe Leu Ile Glu Pro Lys Pro Met Glu Pro Ser
225                 230                 235                 240

Lys His Gln Tyr Asp Val Asp Thr Glu Thr Val Ile Gly Phe Leu Lys
                245                 250                 255
```

```
Ala His Gly Leu Glu Lys Asp Phe Lys Val Asn Ile Glu Val Asn His
            260                 265                 270

Ala Thr Leu Ala Gly His Thr Phe Glu His Glu Leu Ala Val Ala Val
        275                 280                 285

Asp Asn Gly Met Leu Gly Ser Ile Asp Ala Asn Arg Gly Asp Tyr Gln
    290                 295                 300

Asn Gly Trp Asp Thr Asp Gln Phe Pro Ile Asp Asn Phe Glu Leu Thr
305                 310                 315                 320

Gln Ala Trp Met Gln Ile Val Arg Asn Gly Leu Gly Thr Gly Gly
                325                 330                 335

Thr Asn Phe Asp Ser Lys Thr Arg Arg Asn Ser Thr Asp Leu Glu Asp
            340                 345                 350

Ile Phe Ile Ala His Ile Ser Gly Met Asp Ala Cys Ala Arg Ala Leu
        355                 360                 365

Leu Asn Ala Val Glu Ile Met Glu Lys Ser Pro Ile Pro Ala Met Leu
    370                 375                 380

Lys Glu Arg Tyr Ala Ser Phe Asp Ser Gly Leu Gly Lys Asp Phe Glu
385                 390                 395                 400

Asp Gly Lys Leu Thr Leu Glu Gln Val Tyr Glu Tyr Gly Lys Lys Val
            405                 410                 415

Gly Glu Pro Lys Gln Thr Ser Gly Lys Gln Glu Leu Tyr Glu Ala Ile
        420                 425                 430

Val Ala Leu Tyr Ala Lys
        435

<210> SEQ ID NO 65
<211> LENGTH: 1314
<212> TYPE: DNA
<213> ORGANISM: Unknown
<220> FEATURE:
<223> OTHER INFORMATION: Obtained from environmental sample

<400> SEQUENCE: 65
atgaaagagt atttccctga ggtcggtaag atccaatttg aaggcccgga gtctaagaac      60
ccgatggcat tcactacta tgacgcagag cgcgtcgtag ccggtaaaac aatgaaagag      120
tggatgcgtt cgctatggc ttggtggcac accctctgtg cagaaggcgg cgaccagttc      180
ggaggcggaa cgaagcattt cccgtggaat gaaggcgcta acgctttgga gatcgccaaa      240
cacaaagccg atgcgggatt cgagatcatg cagaaactcg gcatcccta tttctgtttc      300 catgacgtgg atctcatcgc cgagggcggt tcggtagaag agtacgaaac caacctcgct      360
gctatcaccg actacctcaa gcagaaaatg gacgagaccg gcatcaaact gctgtggtcc      420
acggcgaacg tgttcagcaa ccccgttat atgaacggcg cgagcacgaa ccccgatttc      480
gatgtagtag cgcgtgccat cgtgcagatc aagaatgcca tcgacgccgg catcaaactg      540
ggcgcagaga actatgtctt ctggggcggt cgcgagggct acatgagcct gctcaacacc      600
gaccagcgcc gcgagaaaga gcatatggct actatgctcc gtatggcgcg tgactacgcg      660
cgtgccaaag gattcaaggg cacctttctc atcgaaccca aacgtgtga gccgtccaaa      720 catcagtatg atgtcgatac cgagaccgtc atcggttttcc tcaaagcgca tggactcgac      780
aaggatttca aggttaatat cgaggtcaac cacgccaccc tcgcaggcca cgttcgaa       840 cacgaactgg cttgcgctgt agatgccggc atgctcggtt cgattgacgc caaccgcggt      900
gacgcccaga acgatgggga caccgaccag ttccctattg ataacttcga actcacacag      960
gctttcatgc agatcgtccg caacggcggt ttcggaacag gcggtacgaa cttcgacgcc     1020
```

```
aagacacgcc gtaactccac cgacttggag gacatcttca tcgcccatat cagcggcatg    1080
gacgcttgcg cacgtgcgtt gctcaacgcc atcgaaatcc tcgagaagag cccgatcccg    1140
gctatgctca agaccgttta tgcctccttt gatggcggca tcggaaagga ctttgaggag    1200
ggcaaactga ctttcgagca ggtctatgag tacggcaaga aggtcggaga acccaaacag    1260
accagcggca acaggagct ctacgaaacc atcgtcgccc tctatgccaa atag          1314
```

```
<210> SEQ ID NO 66
<211> LENGTH: 437
<212> TYPE: PRT
<213> ORGANISM: Unknown
<220> FEATURE:
<223> OTHER INFORMATION: Obtained from environmental sample

<400> SEQUENCE: 66

Met Lys Glu Tyr Phe Pro Glu Val Gly Lys Ile Gln Phe Glu Gly Pro
1               5                   10                  15

Glu Ser Lys Asn Pro Met Ala Phe His Tyr Tyr Asp Ala Glu Arg Val
            20                  25                  30

Val Ala Gly Lys Thr Met Lys Glu Trp Met Arg Phe Ala Met Ala Trp
        35                  40                  45

Trp His Thr Leu Cys Ala Glu Gly Gly Asp Gln Phe Gly Gly Gly Thr
    50                  55                  60

Lys His Phe Pro Trp Asn Glu Gly Ala Asn Ala Leu Glu Ile Ala Lys
65                  70                  75                  80

His Lys Ala Asp Ala Gly Phe Glu Ile Met Gln Lys Leu Gly Ile Pro
                85                  90                  95

Tyr Phe Cys Phe His Asp Val Asp Leu Ile Ala Glu Gly Gly Ser Val
            100                 105                 110

Glu Glu Tyr Glu Thr Asn Leu Ala Ala Ile Thr Asp Tyr Leu Lys Gln
        115                 120                 125

Lys Met Asp Glu Thr Gly Ile Lys Leu Leu Trp Ser Thr Ala Asn Val
    130                 135                 140

Phe Ser Asn Pro Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Gly Ile Lys Leu Gly Ala Glu Asn Tyr Val Phe Trp Gly Gly Arg Glu
            180                 185                 190

Gly Tyr Met Ser Leu Leu Asn Thr Asp Gln Arg Arg Glu Lys Glu His
        195                 200                 205

Met Ala Thr Met Leu Arg Met Ala Arg Asp Tyr Ala Arg Ala Lys Gly
    210                 215                 220

Phe Lys Gly Thr Phe Leu Ile Glu Pro Lys Pro Cys Glu Pro Ser Lys
225                 230                 235                 240

His Gln Tyr Asp Val Asp Thr Glu Thr Val Ile Gly Phe Leu Lys Ala
                245                 250                 255

His Gly Leu Asp Lys Asp Phe Lys Val Asn Ile Glu Val Asn His Ala
            260                 265                 270

Thr Leu Ala Gly His Thr Phe Glu His Glu Leu Ala Cys Ala Val Asp
        275                 280                 285

Ala Gly Met Leu Gly Ser Ile Asp Ala Asn Arg Gly Asp Ala Gln Asn
    290                 295                 300

Gly Trp Asp Thr Asp Gln Phe Pro Ile Asp Asn Phe Glu Leu Thr Gln
```

```
            305                 310                 315                 320
Ala Phe Met Gln Ile Val Arg Asn Gly Gly Phe Gly Thr Gly Thr
                325                 330                 335
Asn Phe Asp Ala Lys Thr Arg Arg Asn Ser Thr Asp Leu Glu Asp Ile
                340                 345                 350
Phe Ile Ala His Ile Ser Gly Met Asp Ala Cys Ala Arg Ala Leu Leu
                355                 360                 365
Asn Ala Ile Glu Ile Leu Glu Lys Ser Pro Ile Pro Ala Met Leu Lys
            370                 375                 380
Asp Arg Tyr Ala Ser Phe Asp Gly Gly Ile Gly Lys Asp Phe Glu Glu
            385                 390                 395                 400
Gly Lys Leu Thr Phe Glu Gln Val Tyr Glu Tyr Gly Lys Lys Val Gly
                        405                 410                 415
Glu Pro Lys Gln Thr Ser Gly Lys Gln Glu Leu Tyr Glu Thr Ile Val
            420                 425                 430
Ala Leu Tyr Ala Lys
            435

<210> SEQ ID NO 67
<211> LENGTH: 1314
<212> TYPE: DNA
<213> ORGANISM: Unknown
<220> FEATURE:
<223> OTHER INFORMATION: Obtained from environmental sample

<400> SEQUENCE: 67
```

| | | | | | |
|---|---|---|---|---|---|
| atgaaagagt | atttccctga | gatcggtaag | atccaatttg | aaggcccgga | gtccaagaac       60 |
| ccgatggcgt | tcactacta  | tgacgctgag | cgcgtcgtag | ccggtaaaac | aatgaaagag      120 |
| tggatgcgtt | tcgctatggc | ttggtggcac | accctctgtg | cggaaggcgg | cgaccagttc      180 |
| ggaggaggaa | cgaagaaatt | cccctggaac | gaaggggcaa | acgctttgga | gatcgccaag      240 |
| cacaaagccg | atgcgggatt | cgagatcatg | cagaaactcg | gcatccctta | tttctgtttc      300 |
| catgacgtgg | atctcatcgc | cgagggcgaa | tcggtagaag | agtacgaagc | caacctcgct      360 |
| gccatcaccg | attacctcaa | acagaaaatg | gacgagaccg | gcatcaaact | gctgtggtcc      420 |
| acggcgaacg | tgttcagcaa | ccccgttat  | atgaacggcg | ccagcacgaa | ccccgatttc      480 |
| gatgtagtgg | cacgcgctat | cgtacaaatc | aagaacgcta | tcgacgccgg | tatcaaactc      540 |
| ggagcagaga | actatgtctt | ctggggcggt | cgcgagggct | atatgtcgct | cctcaacacc      600 |
| gaccagcgcc | gagagaaaga | gcatatggct | actatgctcc | gtatggcgcg | tgactacgcg      660 |
| cgttccaaag | gattcaaggg | caccttcctc | atcgaaccca | aaccgtgtga | gccgtccaaa      720 |
| catcagtacg | atgtggacac | agagaccgtc | atcggttttc | cttaaagcgca | tggactcgac      780 |
| aaggatttca | aagtcaatat | cgaggtcaac | cacgccaccc | tcgcaggcca | cacgttcgaa      840 |
| cacgaactgg | cttgcgctgt | agatgccggc | atgctcggtt | cgattgacgc | caaccgcggt      900 |
| gacgcccaga | acgatgggga | caccgaccaa | ttccctattg | ataacttcga | actcactcag      960 |
| gctttcatgc | agatcgtccg | caacggcggt | ttcggaacag | gcggtacgaa | cttcgacgcc     1020 |
| aagacacgcc | gtaactccac | cgacttggag | gacatcttca | tcgcccatat | cagcggcatg     1080 |
| gacgcttgcg | ctcgtgcgtt | gctcaatgct | gtcgaaatcc | tcgagaagag | cccgatcccg     1140 |
| gctatgctca | agagcgtta  | tgcttccttt | gacggcggca | tcggaaagga | ctttgaggag     1200 |
| ggcaaactga | ctttcgagca | ggtctatgag | tacggcaaga | aggtcggaga | acccaaacag     1260 |
| accagcggca | acaggagct  | ctacgaaacc | atcgtcgccc | tctatgccaa | atga           1314 |

<210> SEQ ID NO 68
<211> LENGTH: 437
<212> TYPE: PRT
<213> ORGANISM: Unknown
<220> FEATURE:
<223> OTHER INFORMATION: Obtained from environmental sample

<400> SEQUENCE: 68

| Met | Lys | Glu | Tyr | Phe | Pro | Glu | Ile | Gly | Lys | Ile | Gln | Phe | Glu | Gly | Pro |
|---|---|---|---|---|---|---|---|---|---|---|---|---|---|---|---|
| 1 | | | | 5 | | | | | 10 | | | | | 15 | |

Glu Ser Lys Asn Pro Met Ala Phe His Tyr Tyr Asp Ala Glu Arg Val
            20              25              30

Val Ala Gly Lys Thr Met Lys Glu Trp Met Arg Phe Ala Met Ala Trp
        35              40              45

Trp His Thr Leu Cys Ala Glu Gly Gly Asp Gln Phe Gly Gly Gly Thr
     50               55              60

Lys Lys Phe Pro Trp Asn Glu Gly Ala Asn Ala Leu Glu Ile Ala Lys
65              70              75            80

His Lys Ala Asp Ala Gly Phe Glu Ile Met Gln Lys Leu Gly Ile Pro
            85              90              95

Tyr Phe Cys Phe His Asp Val Asp Leu Ile Ala Glu Gly Glu Ser Val
        100              105            110

Glu Glu Tyr Glu Ala Asn Leu Ala Ala Ile Thr Asp Tyr Leu Lys Gln
        115              120            125

Lys Met Asp Glu Thr Gly Ile Lys Leu Leu Trp Ser Thr Ala Asn Val
    130              135            140

Phe Ser Asn Pro Arg Tyr Met Asn Gly Ala Ser Thr Asn Pro Asp Phe
145              150              155            160

Asp Val Val Ala Arg Ala Ile Val Gln Ile Lys Asn Ala Ile Asp Ala
            165            170            175

Gly Ile Lys Leu Gly Ala Glu Asn Tyr Val Phe Trp Gly Gly Arg Glu
        180              185            190

Gly Tyr Met Ser Leu Leu Asn Thr Asp Gln Arg Arg Glu Lys Glu His
        195              200            205

Met Ala Thr Met Leu Arg Met Ala Arg Asp Tyr Ala Arg Ser Lys Gly
    210              215            220

Phe Lys Gly Thr Phe Leu Ile Glu Pro Lys Pro Cys Glu Pro Ser Lys
225              230              235            240

His Gln Tyr Asp Val Asp Thr Glu Thr Val Ile Gly Phe Leu Lys Ala
            245            250            255

His Gly Leu Asp Lys Asp Phe Lys Val Asn Ile Glu Val Asn His Ala
        260              265            270

Thr Leu Ala Gly His Thr Phe Glu His Glu Leu Ala Cys Ala Val Asp
     275               280            285

Ala Gly Met Leu Gly Ser Ile Asp Ala Asn Arg Gly Asp Ala Gln Asn
    290              295            300

Gly Trp Asp Thr Asp Gln Phe Pro Ile Asp Asn Phe Glu Leu Thr Gln
305              310              315            320

Ala Phe Met Gln Ile Val Arg Asn Gly Gly Phe Gly Thr Gly Gly Thr
            325            330            335

Asn Phe Asp Ala Lys Thr Arg Arg Asn Ser Thr Asp Leu Glu Asp Ile
        340              345            350

Phe Ile Ala His Ile Ser Gly Met Asp Ala Cys Ala Arg Ala Leu Leu
     355               360            365

Asn Ala Val Glu Ile Leu Glu Lys Ser Pro Ile Pro Ala Met Leu Lys
         370                 375                 380

Glu Arg Tyr Ala Ser Phe Asp Gly Gly Ile Gly Lys Asp Phe Glu Glu
385                 390                 395                 400

Gly Lys Leu Thr Phe Glu Gln Val Tyr Glu Tyr Gly Lys Lys Val Gly
             405                 410                 415

Glu Pro Lys Gln Thr Ser Gly Lys Gln Glu Leu Tyr Glu Thr Ile Val
             420                 425                 430

Ala Leu Tyr Ala Lys
         435

<210> SEQ ID NO 69
<211> LENGTH: 1314
<212> TYPE: DNA
<213> ORGANISM: Unknown
<220> FEATURE:
<223> OTHER INFORMATION: Obtained from environmental sample

<400> SEQUENCE: 69

```
atgaaagagt atttccctga gatcggtaag atccaatttg aaggcccgga gtccaagaac      60
ccgatggcgt tcactacta tgacgcagag cgcgtagtag ccggtaaaac aatgaaagaa     120
tggatgcgtt cgccatggc atggtggcac accctctgtg cagaaggcgg cgaccagttc     180
ggaggaggaa cgaagcattt cccgtggaat gaaggcgcta acgctttgga gatcgccaaa     240
cacaaagccg atgcgggatt cgagatcatg cagaaactcg catcccta tttctgtttc      300
catgacgtgg atctcatcgc cgagggcgat cggtggagg agtacgaagc taaccccgct     360
gccatcaccg attacctcaa acagaaaatg gacgagaccg gcatcaaact gctgtggtcc     420
acggcgaacg tcttcagcaa ccccgttac atgaacggtg cgagcacgaa cccggatttc     480
gatgtagtgg cacgcgctat cgtacaaatc aagaacgcta tcgacgccgg tatcaaactc     540
ggagcagaga actatgtctt ctggggcggt cgcgagggct atatgtcgct cctcaacacc     600
gaccagcgtc gcgagaaaga gcatatggct actatgctcc gtatggcgcg tgactacgcg     660
cgtgccaaag gattcaaggg caccttcctc atcgaaccca aaccatgtga gccgtccaaa     720
catcagtacg atgtggacac agagactgtc atcggtttcc tcaaagcgca tggactcgac     780
aaggatttca agtcaacat cgaggtcaac cacgccaccc tcgcaggtca cacgttcgaa     840
cacgaactgg cttgcgctgt agatgccggc atgctcggtt cgattgacgc caaccgcggt     900
gacgcccaga acggatggga cactgaccag ttccctattg ataacttcga actcacacag     960
gctttcatgc agatcgtccg caacggcggt ttcggaacag gcggtacgaa cttcgacgcc    1020
aagcacgcc gtaactccac cgacttggag gacatcttca tcgcccatat cagcggcatg    1080
gacgcttgtg tccgtgcgtt gctcaacgcc atcgaaatcc tcgagaagag cccgatcccg    1140
gctatgctca aagagcgtta cgcttccttt gacggcggca tcggaaagga ctttgaggat    1200
ggtaaactga ctttcgagca ggtctatgag tacggcaaga aggtcggaga acccaaacag    1260
accagcggca acaggagct ctacgaaacc atcgtcgccc tctatgccaa gtaa           1314
```

<210> SEQ ID NO 70
<211> LENGTH: 437
<212> TYPE: PRT
<213> ORGANISM: Unknown
<220> FEATURE:
<223> OTHER INFORMATION: Obtained from environmental sample

<400> SEQUENCE: 70

-continued

```
Met Lys Glu Tyr Phe Pro Glu Ile Gly Lys Ile Gln Phe Glu Gly Pro
1               5                   10                  15

Glu Ser Lys Asn Pro Met Ala Phe His Tyr Tyr Asp Ala Glu Arg Val
            20                  25                  30

Val Ala Gly Lys Thr Met Lys Glu Trp Met Arg Phe Ala Met Ala Trp
            35                  40                  45

Trp His Thr Leu Cys Ala Glu Gly Asp Gln Phe Gly Gly Gly Thr
50                  55                  60

Lys His Phe Pro Trp Asn Gly Ala Asn Ala Leu Glu Ile Ala Lys
65                  70                  75                  80

His Lys Ala Asp Ala Gly Phe Glu Ile Met Gln Lys Leu Gly Ile Pro
                85                  90                  95

Tyr Phe Cys Phe His Asp Val Asp Leu Ile Ala Glu Gly Asp Ser Val
                100                 105                 110

Glu Glu Tyr Glu Ala Asn Pro Ala Ala Ile Thr Asp Tyr Leu Lys Gln
            115                 120                 125

Lys Met Asp Glu Thr Gly Ile Lys Leu Leu Trp Ser Thr Ala Asn Val
130                 135                 140

Phe Ser Asn Pro Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Gly Ile Lys Leu Gly Ala Glu Asn Tyr Val Phe Trp Gly Gly Arg Glu
                180                 185                 190

Gly Tyr Met Ser Leu Leu Asn Thr Asp Gln Arg Arg Glu Lys Glu His
            195                 200                 205

Met Ala Thr Met Leu Arg Met Ala Arg Asp Tyr Ala Arg Ala Lys Gly
            210                 215                 220

Phe Lys Gly Thr Phe Leu Ile Glu Pro Lys Pro Cys Glu Pro Ser Lys
225                 230                 235                 240

His Gln Tyr Asp Val Asp Thr Glu Thr Val Ile Gly Phe Leu Lys Ala
                245                 250                 255

His Gly Leu Asp Lys Asp Phe Lys Val Asn Ile Glu Val Asn His Ala
                260                 265                 270

Thr Leu Ala Gly His Thr Phe Glu His Glu Leu Ala Cys Ala Val Asp
            275                 280                 285

Ala Gly Met Leu Gly Ser Ile Asp Ala Asn Arg Gly Asp Ala Gln Asn
            290                 295                 300

Gly Trp Asp Thr Asp Gln Phe Pro Ile Asp Asn Phe Glu Leu Thr Gln
305                 310                 315                 320

Ala Phe Met Gln Ile Val Arg Asn Gly Gly Phe Gly Thr Gly Gly Thr
                325                 330                 335

Asn Phe Asp Ala Lys Thr Arg Arg Asn Ser Thr Asp Leu Glu Asp Ile
                340                 345                 350

Phe Ile Ala His Ile Ser Gly Met Asp Ala Cys Val Arg Ala Leu Leu
                355                 360                 365

Asn Ala Ile Glu Ile Leu Glu Lys Ser Pro Ile Pro Ala Met Leu Lys
            370                 375                 380

Glu Arg Tyr Ala Ser Phe Asp Gly Ile Gly Lys Asp Phe Glu Asp
385                 390                 395                 400

Gly Lys Leu Thr Phe Glu Gln Val Tyr Glu Tyr Gly Lys Lys Val Gly
                405                 410                 415
```

```
Glu Pro Lys Gln Thr Ser Gly Lys Gln Glu Leu Tyr Glu Thr Ile Val
            420                 425                 430

Ala Leu Tyr Ala Lys
        435
```

<210> SEQ ID NO 71
<211> LENGTH: 1314
<212> TYPE: DNA
<213> ORGANISM: Unknown
<220> FEATURE:
<223> OTHER INFORMATION: Obtained from environmental sample

<400> SEQUENCE: 71

```
atgaaagagt atttccctga gatcggaaag atccaattcg aaggcccgga gtccaagaat      60
cctatggcat ttcactacta tgacgcagag cgtgtagtag ccggtaaaac aatgaaagag     120
tggatgcgtt tcgctttggc atggtggcac acgctctgcg cagaaggcgg cgaccagttc     180
ggaggcggca cgaagcattt cccttggaat gaaggtgcaa acgctttgga gatcgccaag     240
cacaaagccg atgcaggctt cgagatcatg cagaaactcg gcatccccta tttctgtttc     300
catgacgtgg atctgatcgc cgagggcggt tcggtagaag agtatgaagc taatttaacg     360
gctatcaccg attacctcaa acagaaaatg gacgagaccg gcatcaaact gctgtggtcc     420
actgcgaacg tgttcggtaa cgcacgttat atgaacggcg cgagcacgaa ccccgatttc     480
gatgtagtgg cacgcgctat cgtgcagatc aagaacgcta tcgacgccgg catcaaactg     540
ggcgcagaga actacgtctt ctggggcggt cgcgagggat atatgtcgct cctgaacacc     600
gaccagaagc gtgagaaaga gcatatggct accatgctcc gtatggcgcg tgactacgcg     660
cgttccaaag gattcaaagg tacgttcctc atcgagccca accgtgtgaa gccgtccaaa     720
catcagtacg acgtggacac tgagaccgtc atcggtttcc tcaaagccca tggtctcggc     780
aaggatttca agtgaacat cgaggtgaat cacgccaccc tcgcaggggca cgttcgaa      840
cacgaactgg cttgcgccgt agatgccggc atgctcggtt cgatcgacgc caaccgcggt     900
gacgcacaaa acggatggga caccgaccag ttccctattg ataatttcga actcacccag     960
gcattcatgc agatcgtccg caacggcggt ttcggaacag gcggtacgaa cttcgacgcc    1020
aagacacgcc gtaattccac cgacttggag gacatcttca tcgcccatat cagcggcatg    1080
gacgcttgtg cccgtgcgtt gctcaatgct gtcgaaatcc ttgaaaagag cccgatcccg    1140
gcgatgctca aagagcgtta cgcctccttt gacagcggta tgggtaagga ctttgaggag    1200
ggcaagctga ccttcgagca ggtctatgag tacggcaaac aggtcggcga acccaaacag    1260
accagcggca agcaggagct ctacgaaacc atcgtcgccc tctatgccaa atag          1314
```

<210> SEQ ID NO 72
<211> LENGTH: 437
<212> TYPE: PRT
<213> ORGANISM: Unknown
<220> FEATURE:
<223> OTHER INFORMATION: Obtained from environmental sample

<400> SEQUENCE: 72

```
Met Lys Glu Tyr Phe Pro Glu Ile Gly Lys Ile Gln Phe Glu Gly Pro
1               5                   10                  15

Glu Ser Lys Asn Pro Met Ala Phe His Tyr Tyr Asp Ala Glu Arg Val
            20                  25                  30

Val Ala Gly Lys Thr Met Lys Glu Trp Met Arg Phe Ala Leu Ala Trp
        35                  40                  45
```

Trp His Thr Leu Cys Ala Glu Gly Gly Asp Gln Phe Gly Gly Gly Thr
 50                  55                  60

Lys His Phe Pro Trp Asn Glu Gly Ala Asn Ala Leu Glu Ile Ala Lys
 65                  70                  75                  80

His Lys Ala Asp Ala Gly Phe Glu Ile Met Gln Lys Leu Gly Ile Pro
                 85                  90                  95

Tyr Phe Cys Phe His Asp Val Asp Leu Ile Ala Glu Gly Gly Ser Val
                100                 105                 110

Glu Glu Tyr Glu Ala Asn Leu Thr Ala Ile Thr Asp Tyr Leu Lys Gln
            115                 120                 125

Lys Met Asp Glu Thr Gly Ile Lys Leu Leu Trp Ser Thr Ala Asn Val
130                 135                 140

Phe Gly Asn Ala Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Gly Ile Lys Leu Gly Ala Glu Asn Tyr Val Phe Trp Gly Gly Arg Glu
            180                 185                 190

Gly Tyr Met Ser Leu Leu Asn Thr Asp Gln Lys Arg Glu Lys Glu His
            195                 200                 205

Met Ala Thr Met Leu Arg Met Ala Arg Asp Tyr Ala Arg Ser Lys Gly
210                 215                 220

Phe Lys Gly Thr Phe Leu Ile Glu Pro Lys Pro Cys Glu Pro Ser Lys
225                 230                 235                 240

His Gln Tyr Asp Val Asp Thr Glu Thr Val Ile Gly Phe Leu Lys Ala
                245                 250                 255

His Gly Leu Gly Lys Asp Phe Lys Val Asn Ile Glu Val Asn His Ala
            260                 265                 270

Thr Leu Ala Gly His Thr Phe Glu His Glu Leu Ala Cys Ala Val Asp
            275                 280                 285

Ala Gly Met Leu Gly Ser Ile Asp Ala Asn Arg Gly Asp Ala Gln Asn
290                 295                 300

Gly Trp Asp Thr Asp Gln Phe Pro Ile Asp Asn Phe Glu Leu Thr Gln
305                 310                 315                 320

Ala Phe Met Gln Ile Val Arg Asn Gly Gly Phe Gly Thr Gly Gly Thr
                325                 330                 335

Asn Phe Asp Ala Lys Thr Arg Arg Asn Ser Thr Asp Leu Glu Asp Ile
            340                 345                 350

Phe Ile Ala His Ile Ser Gly Met Asp Ala Cys Ala Arg Ala Leu Leu
            355                 360                 365

Asn Ala Val Glu Ile Leu Glu Lys Ser Pro Ile Pro Ala Met Leu Lys
370                 375                 380

Glu Arg Tyr Ala Ser Phe Asp Ser Gly Met Gly Lys Asp Phe Glu Glu
385                 390                 395                 400

Gly Lys Leu Thr Phe Glu Gln Val Tyr Glu Tyr Gly Lys Gln Val Gly
                405                 410                 415

Glu Pro Lys Gln Thr Ser Gly Lys Gln Glu Leu Tyr Glu Thr Ile Val
            420                 425                 430

Ala Leu Tyr Ala Lys
            435

<210> SEQ ID NO 73
<211> LENGTH: 1314
<212> TYPE: DNA

<213> ORGANISM: Unknown
<220> FEATURE:
<223> OTHER INFORMATION: Obtained from environmental sample

<400> SEQUENCE: 73

```
atgaaagagt attttccaca aatcggcaag atcccatttg agggaccaga gtcaaagaac      60
ccaatggcat tccactacta tgacgcagag cgcgtagttg ccggtaagac aatgaaggaa     120
tggatgcgtt tcgctatggc ctggtggcac actctctgtg ctgagggtag cgatcagttc     180
ggccctggta caaagaagtt cccttggaac gagggcgaga cagcccttga gcgcgctaag     240
cacaaggcag atgctggctt cgaggttatg cagaagctcg gcatcccata tttctgcttc     300
cacgatgtag accttatcga cgagggtgct aacgtggctg agtatgaggc aaacctcgct     360
gctatcactg actacctgaa ggagaagatg gaggagactg gcgtaaagct cctctggtct     420
acagccaacg tgttcggtaa cgctcgctat atgaacggtg cttctacaaa tcctgacttc     480
gacgttgtgg ctcgtgccat cgtacagatt aagaacgcta tcgacgctgg tatcaagctt     540
ggtgctgaga actacgtgtt ctgggcggc cgcgagggct acatgagcct tctgaacact     600
gaccagaagc gcgagaagga gcacatggca actatgctcg gcatggctcg cgactatgcc     660
cgcgctaagg gattcaccgg taccttcctc attgagccaa agccaatgga gccaacaaag     720
catcagtatg atgttgacac agagaccgtt atcggtttcc tcaaggctca cggtctggac     780
aaggacttca aggtgaacat cgaggtgaac cacgctactc tcgccggtca caccttcgag     840
cacgagctcg cttgcgctgt tgacgctggt atgctcggtt ctatcgacgc taaccgcggt     900
gacgctcaga acgatggga taccgaccag ttcccaatcg acaacttcga gctgacacag     960
gcttggatgc agattgttcg caatggcggt cttggcacag gtggtaccaa cttcgacgca    1020
aagacccgtc gtaactctac cgacctcgag gacatcttca tcgctcacat tccggtatg    1080
gacgcttgtg cacgcgctct cctcaacgca gtagagatac tcgagaactc tccaatccca    1140
acaatgctga aggaccgcta tgcaagcttc gactcaggta tgggtaagga cttcgaggac    1200
ggcaagctca cacttgagca ggtttatgag tatggtaaga aggtcgacga gccaaagcag    1260
acctctggta agcaggaact ctatgagacc atcgttgctc tctatgcaaa ataa          1314
```

<210> SEQ ID NO 74
<211> LENGTH: 437
<212> TYPE: PRT
<213> ORGANISM: Unknown
<220> FEATURE:
<223> OTHER INFORMATION: Obtained from environmental sample

<400> SEQUENCE: 74

```
Met Lys Glu Tyr Phe Pro Gln Ile Gly Lys Ile Pro Phe Glu Gly Pro
1               5                   10                  15

Glu Ser Lys Asn Pro Met Ala Phe His Tyr Tyr Asp Ala Glu Arg Val
            20                  25                  30

Val Ala Gly Lys Thr Met Lys Glu Trp Met Arg Phe Ala Met Ala Trp
        35                  40                  45

Trp His Thr Leu Cys Ala Glu Gly Ser Asp Gln Phe Gly Pro Gly Thr
    50                  55                  60

Lys Lys Phe Pro Trp Asn Glu Gly Glu Thr Ala Leu Glu Arg Ala Lys
65                  70                  75                  80

His Lys Ala Asp Ala Gly Phe Glu Val Met Gln Lys Leu Gly Ile Pro
                85                  90                  95

Tyr Phe Cys Phe His Asp Val Asp Leu Ile Asp Glu Gly Ala Asn Val
```

```
            100                 105                 110
Ala Glu Tyr Glu Ala Asn Leu Ala Ala Ile Thr Asp Tyr Leu Lys Glu
            115                 120                 125

Lys Met Glu Glu Thr Gly Val Lys Leu Leu Trp Ser Thr Ala Asn Val
130                 135                 140

Phe Gly Asn Ala Arg Tyr Met Asn Gly Ala Ser Thr Asn Pro Asp Phe
145                 150                 155                 160

Asp Val Val Ala Arg Ala Ile Val Gln Ile Lys Asn Ala Ile Asp Ala
                165                 170                 175

Gly Ile Lys Leu Gly Ala Glu Asn Tyr Val Phe Trp Gly Gly Arg Glu
                180                 185                 190

Gly Tyr Met Ser Leu Leu Asn Thr Asp Gln Lys Arg Glu Lys Glu His
                195                 200                 205

Met Ala Thr Met Leu Gly Met Ala Arg Asp Tyr Ala Arg Ala Lys Gly
            210                 215                 220

Phe Thr Gly Thr Phe Leu Ile Glu Pro Lys Pro Met Glu Pro Thr Lys
225                 230                 235                 240

His Gln Tyr Asp Val Asp Thr Glu Thr Val Ile Gly Phe Leu Lys Ala
                245                 250                 255

His Gly Leu Asp Lys Asp Phe Lys Val Asn Ile Glu Val Asn His Ala
                260                 265                 270

Thr Leu Ala Gly His Thr Phe Glu His Glu Leu Ala Cys Ala Val Asp
            275                 280                 285

Ala Gly Met Leu Gly Ser Ile Asp Ala Asn Arg Gly Asp Ala Gln Asn
            290                 295                 300

Gly Trp Asp Thr Asp Gln Phe Pro Ile Asp Asn Phe Glu Leu Thr Gln
305                 310                 315                 320

Ala Trp Met Gln Ile Val Arg Asn Gly Gly Leu Gly Thr Gly Gly Thr
                325                 330                 335

Asn Phe Asp Ala Lys Thr Arg Arg Asn Ser Thr Asp Leu Glu Asp Ile
                340                 345                 350

Phe Ile Ala His Ile Ser Gly Met Asp Ala Cys Ala Arg Ala Leu Leu
            355                 360                 365

Asn Ala Val Glu Ile Leu Glu Asn Ser Pro Ile Pro Thr Met Leu Lys
370                 375                 380

Asp Arg Tyr Ala Ser Phe Asp Ser Gly Met Gly Lys Asp Phe Glu Asp
385                 390                 395                 400

Gly Lys Leu Thr Leu Glu Gln Val Tyr Glu Tyr Gly Lys Lys Val Asp
                405                 410                 415

Glu Pro Lys Gln Thr Ser Gly Lys Gln Glu Leu Tyr Glu Thr Ile Val
                420                 425                 430

Ala Leu Tyr Ala Lys
                435

<210> SEQ ID NO 75
<211> LENGTH: 1320
<212> TYPE: DNA
<213> ORGANISM: Unknown
<220> FEATURE:
<223> OTHER INFORMATION: Obtained from environmental sample

<400> SEQUENCE: 75
atggctaaag aatacttccc ctccatcggc aaaatccctt ttgaaggagg cgacagcaaa      60
aatcccctcg ctttccatta ttatgacgcc ggacgcgtgg ttatgggcaa gcccatgaag     120
```

-continued

```
gaatggctta aattcgccat ggcctggtgg cacacgctgg gccaggcctc cggagacccc    180
ttcggcggcc agacccgcag ctacgaatgg gacaagggcg aatgcccta ctgccgcgcc    240 aaagccaagg ccgacgccgg ttttgaaatc atgcaaaagc tgggtatcga atacttctgc    300
ttccacgatg tggaccttat cgaggattgc gatgacattg ccgaatacga agcccgcatg    360
aaggacatca cggactacct gctggaaaag atgaaggaga ccggcatcaa gaacctctgg    420
ggcaccgcca atgtcttcgg ccacaagcgc tacatgaacg gcgccggcac caatccgcag    480
ttcgatgtgg tggcccgtgc cgccgtccag atcaagaacg ccctggacgc caccatcaag    540
ctgggcggct ccaactatgt gttctggggc ggccgcgaag ctattacac cctcctcaac    600 acccagatgc agcgggaaaa agaccacctg gccaagttgc tgacggccgc ccgcgactat    660
gcccgcgcca agggcttcaa gggcaccttc ctcattgagc ccaaacccat ggaacccacc    720
aagcaccagt acgacgtgga tacggagacg gtcatcggct tcctccgtgc caacggcctg    780
gacaaggact tcaaggtgaa catcgaggtg aaccacgcca ccctggccgg ccacaccttc    840
gagcatgagc tcaccgtggc ccgcgagaac ggtttcctgg gctccatcgg tgccaaccgc    900
ggcgacgccc agaacggctg ggacacggac cagttccctg tggacccgta cgatcttacc    960
caggccatga tgcaggtgct gctgaacggc ggcttcggca acggcggcac caacttcgac   1020
gccaaactcc gccgctcctc caccgaccct gaggacatct tcatcgccca tatttccgcc   1080
atggatgcca tggcccacgc tttgcttaac gcagctgccg tgctggaaga gagcccctg   1140 tgccagatgg tcaaggagcg ttatgccagc ttcgacggcg gcctcggcaa acagttcgag   1200
gaaggcaagg ctaccctgga agacctgtac gaatacgcca aggtccaggg tgaacccgtt   1260
gtcgcctccg gcaagcagga gctttacgag actctcctga acctgtatgc cgtcaagtaa   1320
```

<210> SEQ ID NO 76
<211> LENGTH: 439
<212> TYPE: PRT
<213> ORGANISM: Unknown
<220> FEATURE:
<223> OTHER INFORMATION: Obtained from environmental sample

<400> SEQUENCE: 76

```
Met Ala Lys Glu Tyr Phe Pro Ser Ile Gly Lys Ile Pro Phe Glu Gly
1               5                   10                  15

Gly Asp Ser Lys Asn Pro Leu Ala Phe His Tyr Tyr Asp Ala Gly Arg
                20                  25                  30

Val Val Met Gly Lys Pro Met Lys Glu Trp Leu Lys Phe Ala Met Ala
            35                  40                  45

Trp Trp His Thr Leu Gly Gln Ala Ser Gly Asp Pro Phe Gly Gly Gln
        50                  55                  60

Thr Arg Ser Tyr Glu Trp Asp Lys Gly Glu Cys Pro Tyr Cys Arg Ala
65                  70                  75                  80

Lys Ala Lys Ala Asp Ala Gly Phe Glu Ile Met Gln Lys Leu Gly Ile
                85                  90                  95

Glu Tyr Phe Cys Phe His Asp Val Asp Leu Ile Glu Asp Cys Asp Asp
            100                 105                 110

Ile Ala Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
    130                 135                 140

Val Phe Gly His Lys Arg Tyr Met Asn Gly Ala Gly Thr Asn Pro Gln
145                 150                 155                 160
```

```
Phe Asp Val Val Ala Arg Ala Ala Val Gln Ile Lys Asn Ala Leu Asp
                165                 170                 175
Ala Thr Ile Lys Leu Gly Gly Ser Asn Tyr Val Phe Trp Gly Gly Arg
            180                 185                 190
Glu Gly Tyr Tyr Thr Leu Leu Asn Thr Gln Met Gln Arg Glu Lys Asp
        195                 200                 205
His Leu Ala Lys Leu Leu Thr Ala Ala Arg Asp Tyr Ala Arg Ala Lys
    210                 215                 220
Gly Phe Lys Gly Thr Phe Leu Ile Glu Pro Lys Pro Met Glu Pro Thr
225                 230                 235                 240
Lys His Gln Tyr Asp Val Asp Thr Glu Thr Val Ile Gly Phe Leu Arg
                245                 250                 255
Ala Asn Gly Leu Asp Lys Asp Phe Lys Val Asn Ile Glu Val Asn His
            260                 265                 270
Ala Thr Leu Ala Gly His Thr Phe Glu His Glu Leu Thr Val Ala Arg
        275                 280                 285
Glu Asn Gly Phe Leu Gly Ser Ile Gly Ala Asn Arg Gly Asp Ala Gln
    290                 295                 300
Asn Gly Trp Asp Thr Asp Gln Phe Pro Val Asp Pro Tyr Asp Leu Thr
305                 310                 315                 320
Gln Ala Met Met Gln Val Leu Leu Asn Gly Phe Gly Asn Gly Gly
                325                 330                 335
Thr Asn Phe Asp Ala Lys Leu Arg Arg Ser Ser Thr Asp Pro Glu Asp
            340                 345                 350
Ile Phe Ile Ala His Ile Ser Ala Met Asp Ala Met Ala His Ala Leu
        355                 360                 365
Leu Asn Ala Ala Ala Val Leu Glu Glu Ser Pro Leu Cys Gln Met Val
    370                 375                 380
Lys Glu Arg Tyr Ala Ser Phe Asp Gly Gly Leu Gly Lys Gln Phe Glu
385                 390                 395                 400
Glu Gly Lys Ala Thr Leu Glu Asp Leu Tyr Glu Tyr Ala Lys Val Gln
                405                 410                 415
Gly Glu Pro Val Val Ala Ser Gly Lys Gln Glu Leu Tyr Glu Thr Leu
            420                 425                 430
Leu Asn Leu Tyr Ala Val Lys
        435

<210> SEQ ID NO 77
<211> LENGTH: 1320
<212> TYPE: DNA
<213> ORGANISM: Unknown
<220> FEATURE:
<223> OTHER INFORMATION: Obtained from environmental sample

<400> SEQUENCE: 77
atggcaaaag agtattttcc gtttaccggt aagattcctt tcgaaggaaa ggacagtaag     60
aatgtaatgg ctttccacta ctacgagcct gagaaggtcg tgatgggaaa gaagatgaag    120
gactggctga agttcgctat ggcttggtgg catacactgg gtggcgcttc tgctgaccag    180
tttggtggtc agactcgttc atacgagtgg gacaaggctg tgacgctgt tcagcgcgct     240 aaggataaga tggacgctgg cttcgagatc atggacaagc tgggcatcga gtacttctgc    300
ttccacgatg ttgacctcgt tgaagagggt gacaccatcg aggagtatga ggctcgcatg    360
aaggccatca ccgactacgc tcaggagaag atgaagcagt tccccaacat caagctgctc    420
```

```
tggggtaccg caaacgtatt cggtaacaag cgctatgcta acggtgcttc taccaaccccc    480
gacttcgacg tagtggctcg cgccatcgtt cagatcaaga acgctattga tgctaccatc    540
aagctgggtg gtaccaacta tgtgttctgg ggtggtcgtg agggctatat gagtctgctg    600
aacaccgacc agaagcgtga gaaggagcac atggctacta tgctgaccat ggctcgcgac    660
tatgctcgcg ccaagggatt caagggtaca ttcctcattg agccgaagcc catggagccc    720
agcaagcacc agtatgatgt ggatacagag accgttatcg gcttcctgaa ggcacacaac    780
ctggacaagg acttcaaggt gaacatcgag gtgaaccacg ctacactcgc tggtcatacc    840
ttcgagcacg agctggcttg cgctgttgac gctggtatgc ttggttctat cgacgctaac    900
cgtggtgatg ctcagaacgg ttgggatacc gaccagttcc ccatcgacaa ctacgagctg    960
acacaggcta tgctcgagat catccgcaat ggtggtctgg gcaatggtgg taccaacttc   1020
gatgctaaga tccgtcgtaa cagcaccgac ctcgaggatc tcttcatcgc tcacatcagt   1080
ggtatggatg ctatggcacg cgctctgatg aacgctgctg acatccttga gaactctgag   1140
ctgcccgcaa tgaagaaggc tcgctacgca agcttcgacc agggtgttgg taaggacttc   1200
gaagatggca agctgaccct tgagcaggtt tacgagtatg gtaagaaggt gggtgagccc   1260
aagcagactt ctggtaagca ggagaagtac gagaccatcg ttgctctcta tgcaaaataa   1320
```

<210> SEQ ID NO 78
<211> LENGTH: 439
<212> TYPE: PRT
<213> ORGANISM: Unknown
<220> FEATURE:
<223> OTHER INFORMATION: Obtained from environmental sample

<400> SEQUENCE: 78

```
Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Gly Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Leu Val Glu Gly Asp Thr
            100                 105                 110

Ile Glu Glu Tyr Glu Ala Arg Met Lys Ala Ile Thr Asp Tyr Ala Gln
        115                 120                 125

Glu Lys Met Lys Gln Phe Pro Asn Ile Lys Leu Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205
```

Glu His Met Ala Thr Met Leu Thr Met Ala Arg Asp Tyr Ala Arg Ala
210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
            245                 250                 255

Lys Ala His Asn Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Ala
290                 295                 300

Gln Asn Gly Trp Asp Thr Asp Gln Phe Pro Ile Asp Asn Tyr Glu Leu
305                 310                 315                 320

Thr Gln Ala Met Leu Glu Ile Ile Arg Asn Gly Leu Gly Leu Asn Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Met Asn Ala Ala Asp Ile Leu Glu Asn Ser Glu Leu Pro Ala Met
370                 375                 380

Lys Lys Ala Arg Tyr Ala Ser Phe Asp Gln Gly Val Gly Lys Asp Phe
385                 390                 395                 400

Glu Asp Gly Lys Leu Thr Leu Glu Gln Val Tyr Glu Tyr Gly Lys Lys
                405                 410                 415

Val Gly Glu Pro Lys Gln Thr Ser Gly Lys Gln Glu Lys Tyr Glu Thr
            420                 425                 430

Ile Val Ala Leu Tyr Ala Lys
            435

<210> SEQ ID NO 79
<211> LENGTH: 1320
<212> TYPE: DNA
<213> ORGANISM: Unknown
<220> FEATURE:
<223> OTHER INFORMATION: Obtained from environmental sample

<400> SEQUENCE: 79
atggcaaaag agtatttttcc gtttaccggt aagattcctt tcgaaggaaa agagagcaag    60
aacgtaatgg ctttccatta ctatgagcct gaaaaggtgg tcatgggcaa gaaaatgaag   120
gattggctga aattcgccat ggcttggtgg cacaccctcg gtggagccag cgccgaccag   180
ttcggtggac agaccccgcag ctatgagtgg acaaggccg aggatgccgt acagcgtgct   240
aaggacaaga tggacgccgg cttcgagatc atggacaaac tgggcatcga gtatttctgc   300
ttccacgatg tcgacctcgt cgacgagggt gctaccgttg aggagtatga ggctcgcatg   360
aaagccatca ccgactatgc ccaggtcaag atgaaggaat atcccaacat caaactgctc   420
tggggcaccg ccaacgtgtt cggcaacaag cgttatgcca acggcgcttc caccaacccc   480
gacttcgacg tggtggcacg cgctatcgtt cagatcaaga atgccatcga cgctaccatc   540
aagctcggcg gtcagaacta cgtgttctgg ggcggacgcg agggctacat gagcctgctc   600
aataccgatc agaaacgtga gaaggaacac atggccacca tgctcaccat ggcgcgcgac   660
tatgctcgca gcaagggatt caagggcacc ttcctcatcg aacccaaacc catggagcct   720

-continued

| | | | | |
|---|---|---|---|---|
| tccaagcacc | agtatgatgt | cgacaccgag | acggtcatcg | gcttcctccg cgcccacaac | 780 |
| ctcgacaagg | acttcaaggt | gaacatcgag | gtcaaccacg | ccacgctcgc cggccacacc | 840 |
| ttcgagcacg | aactggcttg | cgccgtcgac | gccggcatgc | tcggcagcat cgacgccaac | 900 |
| cgcggcgacg | cacagaacgg | ctgggatacc | gaccagttcc | ccatcgacaa ctacgaactg | 960 |
| acacaggcca | tgctggagat | catccgcaat | ggcggcctcg | gcaatggtgg taccaacttc | 1020 |
| gacgccaaga | tccgtcgtaa | cagcaccgac | ctcgaagatc | tcttcatcgc tcacatcagc | 1080 |
| ggtatggatg | ccatggctcg | cgcgctgctc | aacgccgccg | ccatcctcga ggagagcgaa | 1140 |
| ctgcccgcca | tgaagaaggc | ccgctacgct | tccttcgacg | aaggtatcgg caaggacttc | 1200 |
| gaagacggca | aactcaccct | cgagcaggtt | tacgagtacg | gcaagaaggt aggcgagccc | 1260 |
| aagcagacct | ccggcaagca | agagaagtac | gagaccatcg | tggctctcta cagcaaataa | 1320 |

<210> SEQ ID NO 80
<211> LENGTH: 439
<212> TYPE: PRT
<213> ORGANISM: Unknown
<220> FEATURE:
<223> OTHER INFORMATION: Obtained from environmental sample

<400> SEQUENCE: 80

Met Ala Lys Glu Tyr Phe Pro Phe Thr Gly Lys Ile Pro Phe Glu Gly
1               5                   10                  15

Lys Glu Ser Lys Asn Val Met Ala Phe His Tyr Tyr Glu Pro Glu Lys
                20                  25                  30

Val Val Met Gly Lys Lys Met Lys Asp Trp Leu Lys Phe Ala Met Ala
            35                  40                  45

Trp Trp His Thr Leu Gly Gly Ala Ser Ala Asp Gln Phe Gly Gly Gln
        50                  55                  60

Thr Arg Ser Tyr Glu Trp Asp Lys Ala Glu Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Asp Glu Gly Ala Thr
            100                 105                 110

Val Glu Glu Tyr Glu Ala Arg Met Lys Ala Ile Thr Asp Tyr Ala Gln
        115                 120                 125

Val Lys Met Lys Glu Tyr Pro Asn Ile Lys Leu Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Gln Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Thr Met Ala Arg Asp Tyr Ala Arg Ser
    210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Arg Ala His Asn Leu Asp Lys Asp Phe Lys Val Asn Ile Glu Val Asn

```
            260                 265                 270
His Ala Thr Leu Ala Gly His Thr Phe Glu His Glu Leu Ala Cys Ala
            275                 280                 285

Val Asp Ala Gly Met Leu Gly Ser Ile Asp Ala Asn Arg Gly Asp Ala
            290                 295                 300

Gln Asn Gly Trp Asp Thr Asp Gln Phe Pro Ile Asp Asn Tyr Glu Leu
305                 310                 315                 320

Thr Gln Ala Met Leu Glu Ile Ile Arg Asn Gly Gly Leu Gly Asn Gly
                    325                 330                 335

Gly Thr Asn Phe Asp Ala Lys Ile Arg Arg Asn Ser Thr Asp Leu Glu
                340                 345                 350

Asp Leu Phe Ile Ala His Ile Ser Gly Met Asp Ala Met Ala Arg Ala
                    355                 360                 365

Leu Leu Asn Ala Ala Ala Ile Leu Glu Glu Ser Glu Leu Pro Ala Met
                370                 375                 380

Lys Lys Ala Arg Tyr Ala Ser Phe Asp Glu Gly Ile Gly Lys Asp Phe
385                 390                 395                 400

Glu Asp Gly Lys Leu Thr Leu Glu Gln Val Tyr Glu Tyr Gly Lys Lys
                    405                 410                 415

Val Gly Glu Pro Lys Gln Thr Ser Gly Lys Gln Glu Lys Tyr Glu Thr
                420                 425                 430

Ile Val Ala Leu Tyr Ser Lys
            435

<210> SEQ ID NO 81
<211> LENGTH: 1314
<212> TYPE: DNA
<213> ORGANISM: Unknown
<220> FEATURE:
<223> OTHER INFORMATION: Obtained from environmental sample

<400> SEQUENCE: 81
atgaaagagt atttcccgca aattggaaag attcccttcg agggaccaga gagcaagagt      60
ccattggcgt tccattatta tgagccggat cgcatggtgc tcggaaagag gatggaggat     120
tggctgaaat tcgccatggc atggtggcac acccttggcc aggccagcgg cgaccagttc     180
ggcggacaga cacgtgagta cgagtgggat aaggctggag atccgataca aagggcaaag     240
gataagatgg acgccggatt cgagatcatg gagaaattgg gtatcaagta cttctgcttc     300
catgatgtgg atctcgtcga ggaagctccc accatcgccg aatatgagga gcgtatgagg     360
atcatcaccg actatgcgct cgagaagatg aaagccactg gcatcaaact cctttggggt     420
acagccaatg ttttcggaca taagagatat atgaatgggg ccgccaccaa cccggagttc     480
ggtgttgtcg ccagggctgc tgtccagatc aagaacgcga tcgacgccac catcaagctg     540
ggaggaacaa actatgtgtt ctggggtggc cgcgagggct acatgagcct gctcaacacc     600
cagatgcaga gggagaagga ccatctcgcc aatatgctca aggctgctcg tgactatgct     660
cgcgccaagg gattcaaggg cacattcctc atcgagccga agccgatgga acctactaag     720
catcagtacg atgtcgacac tgagaccgtg atcggcttcc tccgcgcaaa cggtcttgac     780
aaggatttca aggtcaacat cgaggtcaat cacgccactc ttgcgggtca cactttcgag     840
catgagctcg ccgtggctgt cgacaatggt ctccttggct caatcgatgc gaacagggga     900
gattatcaga acgttggga caccgaccag ttccctgttg atctctttga tttgacccag     960
gccatgctcc agatcatccg taacggaggc ctcggtaatg gtggatccaa cttcgacgcc    1020
```

```
aagcttcgcc gtaactccac tgatcctgag gatatattca ttgcccatat ttgcggtatg      1080
gacgctatgg ccagggctct ccttgccgcc gccgcgatcg tggaggagtc tcctatcccg      1140
gctatggtca agagcgtta cgcatccttc gacgaaggtg agggcaagag attcgaggat      1200
ggtaagatga gtctggagga acttgttgat tacgcgaaga ctcacggaga gcccgcccag      1260
aagagtggca acaggagct ctacgaaacc cttgtcaaca tgtacatcaa ataa            1314
```

<210> SEQ ID NO 82
<211> LENGTH: 437
<212> TYPE: PRT
<213> ORGANISM: Unknown
<220> FEATURE:
<223> OTHER INFORMATION: Obtained from environmental sample

<400> SEQUENCE: 82

```
Met Lys Glu Tyr Phe Pro Gln Ile Gly Lys Ile Pro Phe Glu Gly Pro
1               5                   10                  15

Glu Ser Lys Ser Pro Leu Ala Phe His Tyr Tyr Glu Pro Asp Arg Met
            20                  25                  30

Val Leu Gly Lys Arg Met Glu Asp Trp Leu Lys Phe Ala Met Ala Trp
        35                  40                  45

Trp His Thr Leu Gly Gln Ala Ser Gly Asp Gln Phe Gly Gly Gln Thr
    50                  55                  60

Arg Glu Tyr Glu Trp Asp Lys Ala Gly Asp Pro Ile Gln Arg Ala Lys
65                  70                  75                  80

Asp Lys Met Asp Ala Gly Phe Glu Ile Met Glu Lys Leu Gly Ile Lys
                85                  90                  95

Tyr Phe Cys Phe His Asp Val Asp Leu Val Glu Glu Ala Pro Thr Ile
            100                 105                 110

Ala Glu Tyr Glu Glu Arg Met Arg Ile Ile Thr Asp Tyr Ala Leu Glu
        115                 120                 125

Lys Met Lys Ala Thr Gly Ile Lys Leu Leu Trp Gly Thr Ala Asn Val
    130                 135                 140

Phe Gly His Lys Arg Tyr Met Asn Gly Ala Ala Thr Asn Pro Glu Phe
145                 150                 155                 160

Gly Val Val Ala Arg Ala Ala Val Gln Ile Lys Asn Ala Ile Asp Ala
                165                 170                 175

Thr Ile Lys Leu Gly Gly Thr Asn Tyr Val Phe Trp Gly Gly Arg Glu
            180                 185                 190

Gly Tyr Met Ser Leu Leu Asn Thr Gln Met Gln Arg Glu Lys Asp His
        195                 200                 205

Leu Ala Asn Met Leu Lys Ala Ala Arg Asp Tyr Ala Arg Ala Lys Gly
    210                 215                 220

Phe Lys Gly Thr Phe Leu Ile Glu Pro Lys Pro Met Glu Pro Thr Lys
225                 230                 235                 240

His Gln Tyr Asp Val Asp Thr Glu Thr Val Ile Gly Phe Leu Arg Ala
                245                 250                 255

Asn Gly Leu Asp Lys Asp Phe Lys Val Asn Ile Glu Val Asn His Ala
            260                 265                 270

Thr Leu Ala Gly His Thr Phe Glu His Glu Leu Ala Val Ala Val Asp
        275                 280                 285

Asn Gly Leu Leu Gly Ser Ile Asp Ala Asn Arg Gly Asp Tyr Gln Asn
    290                 295                 300

Gly Trp Asp Thr Asp Gln Phe Pro Val Asp Leu Phe Asp Leu Thr Gln
305                 310                 315                 320
```

```
Ala Met Leu Gln Ile Ile Arg Asn Gly Gly Leu Gly Asn Gly Gly Ser
            325                 330                 335

Asn Phe Asp Ala Lys Leu Arg Arg Asn Ser Thr Asp Pro Glu Asp Ile
        340                 345                 350

Phe Ile Ala His Ile Cys Gly Met Asp Ala Met Ala Arg Ala Leu Leu
    355                 360                 365

Ala Ala Ala Ala Ile Val Glu Glu Ser Pro Ile Pro Ala Met Val Lys
370                 375                 380

Glu Arg Tyr Ala Ser Phe Asp Glu Gly Glu Gly Lys Arg Phe Glu Asp
385                 390                 395                 400

Gly Lys Met Ser Leu Glu Glu Leu Val Asp Tyr Ala Lys Thr His Gly
                405                 410                 415

Glu Pro Ala Gln Lys Ser Gly Lys Gln Glu Leu Tyr Glu Thr Leu Val
            420                 425                 430

Asn Met Tyr Ile Lys
            435

<210> SEQ ID NO 83
<211> LENGTH: 1320
<212> TYPE: DNA
<213> ORGANISM: Unknown
<220> FEATURE:
<223> OTHER INFORMATION: Obtained from environmental sample

<400> SEQUENCE: 83
atggcaaaag agtattttcc gtttaccggt aagattcctt tcgagggaaa ggacagtaag      60
aatgtaatgg cgttccacta ctacgagccc gagcgcgtgg taatgggcaa gaagatgaag     120
gagtggctga agtttgccat ggcctggtgg cacacgctgg gtggagccag tgccgaccag     180
tttggcggac agacccgcag ctacgagtgg gacaaggctg aagacgccgt gcagcgtgcc     240
aaggacaaga tggatgccgg cttcgagatc atggacaagc tgggcatcga gtatttctgc     300
ttccatgatg tcgatctcgt tgacgagggt gccactgtcg aggagtatga ggctcgcatg     360
caggccatca ccgactatgc gcaggagaag atgaagcagt atcctgccat caagctgctg     420
tggggtacgg ccaatgtctt tggcaacaag cgttatgcca acggtgcctc taccaatccc     480
gacttcgatg tggtggcccg cgccatcgtg cagattaaga atgccattga tgccaccatc     540
aagctgggcg gcagcaacta tgtgttctgg ggcggtcgcg agggctacat gtcgctgctc     600
aacaccgacc agaagcgtga gaaggaacac atggcccgga tgctgaccat ggcccgcgac     660
tatgcccgct cgaagggctt caagggcaac ttcctgattg agcccaagcc catggagccg     720
tcgaagcatc agtacgacgt ggacaccgag acggttatcg gattcctccg cgcacatggc     780
cttgacaagg acttcaaggt gaacatcgag gtgaaccatg ccacgctggc cggtcatacc     840
ttcgagcacg aactggcttg cgccgtagat gccggcatgc tgggcagcat tgatgccaac     900
cgcggcgacg cacagaacgg atgggacacc gaccagttcc ccatcgacaa ctatgagttg     960
acacaggcca tgatggagat tatccgcaat ggcggtctgg gtcttggcgg taccaatttc    1020
gatgccaaga ttcgccgtaa ctccaccgac ctggaagacc tcttcatcgc ccacatcagt    1080
ggcatggacg ccatggctcg tgcgctcctt aatgctgccg acattctgga gaacagcgaa    1140
ctgcccgcca tgaagaaagc gcgctacgcc tcgttcgaca gtggcatggg caaggacttc    1200
gaggacggca aactgaccct tgagcaggtt tacgaatacg caaaaaagt cggcgaacct    1260 aagcagacct ccggcaagca ggagaagtac gagaccatcg tggctctcta tgccaagtaa    1320
```

-continued

```
<210> SEQ ID NO 84
<211> LENGTH: 439
<212> TYPE: PRT
<213> ORGANISM: Unknown
<220> FEATURE:
<223> OTHER INFORMATION: Obtained from environmental sample

<400> SEQUENCE: 84

Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Tyr Glu Pro Glu Arg
            20                  25                  30

Val Val Met Gly Lys Lys Met Lys Glu Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Glu Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Asp Glu Gly Ala Thr
            100                 105                 110

Val Glu Glu Tyr Glu Ala Arg Met Gln Ala Ile Thr Asp Tyr Ala Gln
        115                 120                 125

Glu Lys Met Lys Gln Tyr Pro Ala Ile Lys Leu Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Ser Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Arg Met Leu Thr Met Ala Arg Asp Tyr Ala Arg Ser
    210                 215                 220

Lys Gly Phe Lys Gly Asn Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Arg Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Ala
    290                 295                 300

Gln Asn Gly Trp Asp Thr Asp Gln Phe Pro Ile Asp Asn Tyr Glu Leu
305                 310                 315                 320

Thr Gln Ala Met Met Glu Ile Ile Arg Asn Gly Gly Leu Gly Leu Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365
```

```
Leu Leu Asn Ala Ala Asp Ile Leu Glu Asn Ser Glu Leu Pro Ala Met
    370                 375                 380

Lys Lys Ala Arg Tyr Ala Ser Phe Asp Ser Gly Met Gly Lys Asp Phe
385                 390                 395                 400

Glu Asp Gly Lys Leu Thr Leu Glu Gln Val Tyr Glu Tyr Gly Lys Lys
                405                 410                 415

Val Gly Glu Pro Lys Gln Thr Ser Gly Lys Gln Glu Lys Tyr Glu Thr
            420                 425                 430

Ile Val Ala Leu Tyr Ala Lys
            435

<210> SEQ ID NO 85
<211> LENGTH: 1320
<212> TYPE: DNA
<213> ORGANISM: Unknown
<220> FEATURE:
<223> OTHER INFORMATION: Obtained from environmental sample

<400> SEQUENCE: 85
atggcaaaag agtattttcc gtttacaggt aaaattcctt tcgaaggaaa ggacagtaag      60
aacgtaatgg ctttccacta ctacgagccc gaaaaggtcg tgatgggaaa gaaaatgaaa     120
gactggctga agttcgccat ggcctggtgg cacacactgg gtggcgccag cgccgaccag     180
tttggcggcc agacacgcag ctatgagtgg gacaaggctg ccgatgccgt gcagcgcgca     240
aaggacaaga tggacgccgg cttcgaaatc atggacaagc tgggcatcga gtatttctgc     300
ttccacgacg tggacctcgt tgaggaggga gccaccatcg aggagtatga ggcccgcatg     360
aaggctatca ccgactatgc ccaggagaag atgaaacagt atcccagcat caagctgctc     420
tggggcaccg ccaatgtgtt tggcaacaag cgctacgcca acggcgccag caccaacccc     480
gacttcgacg tcgtggcccg tgccatcgtg cagatcaaga acgccatcga tgccaccatc     540
aagctgggcg gcaccaacta cgtgttctgg ggcggacgcg agggctacat gagcctgctc     600
aacaccgacc agaagcgcga gaaggagcac atggccacca tgctcaccat ggcccgcgac     660
tacgcccgcg caaagggatt caagggcacc ttcctcatcg agcccaagcc catggagccg     720
tcgaagcacc agtacgacgt ggacaccgag accgtcatcg gtttcctgaa ggcccacggt     780
ctggacaagg acttcaaggt gaacatcgag gtgaaccacg ccacgctggc cggccacacc     840
ttcgagcatg agctggcctg cgccgtcgac gccggtatgc tgggcagcat cgatgccaac     900
cgcggcgacg cccagaacgg ctgggacacc gaccagttcc ccatcgacaa cttcgagctc     960
acccaggcca tgatggaaat tatccgcaac ggcggcctcg gcaacggcgg caccaacttc    1020
gacgctaaga tccgccgcaa ctccaccgac ctcgaggacc tcttcatcgc ccacatcagc    1080
ggcatggacg ccatggcccg cgcactgatg aacgctgccg acattatgga gaacagcgag    1140
ctgcccgcca tgaagaaggc acgctacgcc agcttcgacg ccggcatcgg caaggacttt    1200
gaggatggca gctctcgct ggagcaggtc tacgagtatg gcaagaaggt ggaagagccc    1260
aagcagacca gcggcaagca ggagaagtac gagaccatcg tcgccctcta tgccaagtaa    1320

<210> SEQ ID NO 86
<211> LENGTH: 439
<212> TYPE: PRT
<213> ORGANISM: Unknown
<220> FEATURE:
<223> OTHER INFORMATION: Obtained from environmental sample

<400> SEQUENCE: 86
```

-continued

```
Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Ala Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Gly Ala Thr
            100                 105                 110

Ile Glu Glu Tyr Glu Ala Arg Met Lys Ala Ile Thr Asp Tyr Ala Gln
        115                 120                 125

Glu Lys Met Lys Gln Tyr Pro Ser Ile Lys Leu Leu Trp Gly Thr Ala
    130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Thr Met Ala Arg Asp Tyr Ala Arg Ala
    210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Lys Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Ala
    290                 295                 300

Gln Asn Gly Trp Asp Thr Asp Gln Phe Pro Ile Asp Asn Phe Glu Leu
305                 310                 315                 320

Thr Gln Ala Met Met Glu Ile Ile Arg Asn Gly Gly Leu Gly Asn Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Met Asn Ala Ala Asp Ile Met Glu Asn Ser Glu Leu Pro Ala Met
    370                 375                 380

Lys Lys Ala Arg Tyr Ala Ser Phe Asp Ala Gly Ile Gly Lys Asp Phe
385                 390                 395                 400

Glu Asp Gly Lys Leu Ser Leu Glu Gln Val Tyr Glu Tyr Gly Lys Lys
                405                 410                 415

Val Glu Glu Pro Lys Gln Thr Ser Gly Lys Gln Glu Lys Tyr Glu Thr
```

Ile Val Ala Leu Tyr Ala Lys
      435

<210> SEQ ID NO 87
<211> LENGTH: 1320
<212> TYPE: DNA
<213> ORGANISM: Unknown
<220> FEATURE:
<223> OTHER INFORMATION: Obtained from environmental sample

<400> SEQUENCE: 87

| | |
|---|---|
| atggcaaaag agtatttcgc ctttacaggc aagattcctt tcgagggaaa agacagtaag | 60 |
| aacgtgatgg ctttccacta ctacgagccg agcgtgtgg tgatgggcaa aagatgaag | 120 |
| gagtggctga agttcgccat ggcctggtgg cacacactgg gtggcgcatc ggccgaccag | 180 |
| ttcggaggcc agacacgcag ctacgagtgg acaaggccg ccgacgccgt gcagcgcgcc | 240 |
| aaggacaaga tggacgccgg cttcgagatt atggacaagc tgggcatcga gtacttctgc | 300 |
| ttccacgatg tagacctcgt tgaggagggt gagaccatag ccgagtacga gcgccgcatg | 360 |
| aaggaaatca ccgactacgc acaggagaag atgaagcagt tccccaacat caagctgctc | 420 |
| tggggcacag ccaacgtgtt cggcaacaag cgctacgcca acggcgcatc gaccaacccc | 480 |
| gacttcgacg ttgtggcacg cgccatcgtg cagatcaaga acgccatcga cgccaccatc | 540 |
| aagctcggcg gctccaacta tgtgttctgg ggcggacgcg agggctatat gagcctgctc | 600 |
| aacaccgacc agaagcgcga gaaggagcac atggccacca tgctcaccat ggcccgcgac | 660 |
| tatgcacgcg ccaagggatt caagggcaca ttcctcatcg agccgaagcc catggagccc | 720 |
| tcgaagcacc agtacgacgt agacacagag accgtcatcg gcttcctccg tgcacacggg | 780 |
| ctggacaagg acttcaaggt gaacatcgag gtaaaccacg ccacactggc cggccacacc | 840 |
| ttcgagcacg agctggcttg cgccgtcgac gctggcatgc tgggcagcat cgacgccaac | 900 |
| cgtggcgacg cacagaacgg atgggacacc gaccagttcc ccatcgacaa cttcgagctc | 960 |
| acacaggcca tgatggaaat catccgcaat ggcggactgg gcaatggcgg caccaacttc | 1020 |
| gacgccaaga tccgtcgtaa cagcaccgac ctcgaagacc tcttcatcgc ccacatcagc | 1080 |
| ggcatggacg ccatggcacg cgcactgctc aacgctgccg acatcctgga gcacagcgag | 1140 |
| ctgcccaaga tgaagaagga cgctacgcc agcttcgacg caggcatcgg caaggacttc | 1200 |
| gaagacggca agctcacact cgagcaggtc tacgagtacg caagaaggt cgaagagccc | 1260 |
| cgtcagacca gcggcaagca ggagaagtac gagaccatcg tcgccctcta tgccaagtaa | 1320 |

<210> SEQ ID NO 88
<211> LENGTH: 439
<212> TYPE: PRT
<213> ORGANISM: Unknown
<220> FEATURE:
<223> OTHER INFORMATION: Obtained from environmental sample

<400> SEQUENCE: 88

Met Ala Lys Glu Tyr Phe Ala Phe Thr Gly Lys Ile Pro Phe Glu Gly
1               5                   10                  15

Lys Asp Ser Lys Asn Val Met Ala Phe His Tyr Tyr Glu Pro Glu Arg
            20                  25                  30

Val Val Met Gly Lys Lys Met Lys Glu Trp Leu Lys Phe Ala Met Ala
        35                  40                  45

Trp Trp His Thr Leu Gly Gly Ala Ser Ala Asp Gln Phe Gly Gly Gln

```
            50                  55                  60
Thr Arg Ser Tyr Glu Trp Asp Lys Ala Ala Asp Ala Val Gln Arg Ala
 65                  70                  75                  80

Lys Asp Lys Met Asp Ala Gly Phe Glu Ile Met Asp Lys Leu Gly Ile
                 85                  90                  95

Glu Tyr Phe Cys Phe His Asp Val Asp Leu Val Glu Glu Gly Glu Thr
                100                 105                 110

Ile Ala Glu Tyr Glu Arg Arg Met Lys Glu Ile Thr Asp Tyr Ala Gln
                115                 120                 125

Glu Lys Met Lys Gln Phe Pro Asn Ile Lys Leu Leu Trp Gly Thr Ala
130                 135                 140

Asn Val Phe Gly Asn Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Ser Asn Tyr Val Phe Trp Gly Gly
                180                 185                 190

Arg Glu Gly Tyr Met Ser Leu Leu Asn Thr Asp Gln Lys Arg Glu Lys
                195                 200                 205

Glu His Met Ala Thr Met Leu Thr Met Ala Arg Asp Tyr Ala Arg Ala
                210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Arg Ala His Gly Leu Asp Lys Asp Phe Lys Val Asn Ile Glu Val Asn
                260                 265                 270

His Ala Thr Leu Ala Gly His Thr Phe Glu His Glu Leu Ala Cys Ala
                275                 280                 285

Val Asp Ala Gly Met Leu Gly Ser Ile Asp Ala Asn Arg Gly Asp Ala
                290                 295                 300

Gln Asn Gly Trp Asp Thr Asp Gln Phe Pro Ile Asp Asn Phe Glu Leu
305                 310                 315                 320

Thr Gln Ala Met Met Glu Ile Ile Arg Asn Gly Gly Leu Gly Asn Gly
                325                 330                 335

Gly Thr Asn Phe Asp Ala Lys Ile Arg Arg Asn Ser Thr Asp Leu Glu
                340                 345                 350

Asp Leu Phe Ile Ala His Ile Ser Gly Met Asp Ala Met Ala Arg Ala
                355                 360                 365

Leu Leu Asn Ala Ala Asp Ile Leu Glu His Ser Glu Leu Pro Lys Met
370                 375                 380

Lys Lys Glu Arg Tyr Ala Ser Phe Asp Ala Gly Ile Gly Lys Asp Phe
385                 390                 395                 400

Glu Asp Gly Lys Leu Thr Leu Glu Gln Val Tyr Glu Tyr Gly Lys Lys
                405                 410                 415

Val Glu Glu Pro Arg Gln Thr Ser Gly Lys Gln Glu Lys Tyr Glu Thr
                420                 425                 430

Ile Val Ala Leu Tyr Ala Lys
                435

<210> SEQ ID NO 89
<211> LENGTH: 1320
<212> TYPE: DNA
<213> ORGANISM: Unknown
```

<220> FEATURE:
<223> OTHER INFORMATION: Obtained from environmental sample

<400> SEQUENCE: 89

```
atggcaaaag agtattttcc gtttactggt aagattcctt tcgagggaaa ggatagtaag       60
aatgtaatgg ctttccacta ttacgagccc gagaaagtcg tgatgggaaa gaagatgaag      120
gactggctga agttcgcaat ggcttggtgg catacactgg gtggtgcatc tgcagaccag      180
ttcggtggag agacccgcag ctacgagtgg agcaaggctg ctgatcccgt tcagcgcgcc      240
aaggacaaga tggacgccgg ctttgagatt atggataagc tgggcatcga gtacttctgt      300
ttccacgata tagacctcgt tcaggaggca gataccattg cagaatatga ggagcgcatg      360
aaggcaatta ccgactatgc tctggagaag atgaagcagt tccccaacat caagttgctc      420
tggggtaccg ctaacgtatt tagcaacaag cgctatatga acggtgcttc taccaatccc      480
gacttcgacg tggtggcccg tgccatcgtt cagatcaaga acgctattga tgcaaccatc      540
aaactcggtg gtaccaacta tgtattctgg ggtggtcgtg agggttacat gagcctattg      600
aataccgacc agaagcgtga aaaggagcac atggcaatga tgctcggtat ggctcgcgac      660
tatgcccgca gcaagggatt caagggtacg ttcctcatcg agccgaagcc gatggagccc      720
tctaagcatc agtatgatgt cgatacggag actgtgattg gtttcctgaa ggcacacggt      780
ctggacaagg acttcaaggt gaacatcgag gtgaaccacg ctacactggc tggtcatacc      840
ttcgagcatg agctggcttg cgctgttgac gcaggtatgc tgggctctat cgacgctaac      900
cgcggtgatg cccagaacgg ctgggatacc gaccagttcc ccatcgacaa ctacgagctg      960
acacaggcta tgatggaaat catccgcaac ggtggtctgg gcaatggtgg taccaacttc     1020
gacgctaaga tccgccgtaa ctctaccgac ctcgaggatc tgttcatcgc tcatatcagt     1080
ggtatggatg ctatggcccg tgctttgttg aatgctgccg acattctgga gaactctgaa     1140
ctgcccgcta tgaagaaggc ccgctacgcc agcttcgaca acggtatcgg taaggacttc     1200
gaggatggca agctgacctt cgagcaggtt tacgaatatg gtaagaaagt tgaagagccg     1260
aagcagacct ctggcaagca ggagaaatac gagaccatcg ttgctctgta tgctaaataa     1320
```

<210> SEQ ID NO 90
<211> LENGTH: 439
<212> TYPE: PRT
<213> ORGANISM: Unknown
<220> FEATURE:
<223> OTHER INFORMATION: Obtained from environmental sample

<400> SEQUENCE: 90

Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Glu
    50                  55                  60

Thr Arg Ser Tyr Glu Trp Ser Lys Ala Ala Asp Pro Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Ile Asp Leu Val Gln Glu Ala Asp Thr
            100                 105                 110

Ile Ala Glu Tyr Glu Glu Arg Met Lys Ala Ile Thr Asp Tyr Ala Leu
            115                 120                 125

Glu Lys Met Lys Gln Phe Pro Asn Ile Lys Leu Leu Trp Gly Thr Ala
130                 135                 140

Asn Val Phe Ser Asn Lys Arg Tyr Met Asn Gly Ala Ser Thr Asn Pro
145                 150                 155                 160

Asp Phe Asp Val Val Ala Arg Ala Ile Val Gln Ile Lys Asn Ala Ile
            165                 170                 175

Asp Ala Thr Ile Lys Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
            195                 200                 205

Glu His Met Ala Met Met Leu Gly Met Ala Arg Asp Tyr Ala Arg Ser
            210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
            245                 250                 255

Lys Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
            275                 280                 285

Val Asp Ala Gly Met Leu Gly Ser Ile Asp Ala Asn Arg Gly Asp Ala
            290                 295                 300

Gln Asn Gly Trp Asp Thr Asp Gln Phe Pro Ile Asp Asn Tyr Glu Leu
305                 310                 315                 320

Thr Gln Ala Met Met Glu Ile Ile Arg Asn Gly Gly Leu Gly Asn Gly
            325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
            355                 360                 365

Leu Leu Asn Ala Ala Asp Ile Leu Glu Asn Ser Glu Leu Pro Ala Met
            370                 375                 380

Lys Lys Ala Arg Tyr Ala Ser Phe Asp Asn Gly Ile Gly Lys Asp Phe
385                 390                 395                 400

Glu Asp Gly Lys Leu Thr Phe Glu Gln Val Tyr Glu Tyr Gly Lys Lys
            405                 410                 415

Val Glu Glu Pro Lys Gln Thr Ser Gly Lys Gln Glu Lys Tyr Glu Thr
            420                 425                 430

Ile Val Ala Leu Tyr Ala Lys
            435

<210> SEQ ID NO 91
<211> LENGTH: 1320
<212> TYPE: DNA
<213> ORGANISM: Unknown
<220> FEATURE:
<223> OTHER INFORMATION: Obtained from environmental sample

<400> SEQUENCE: 91
atggcaaaag agtattttcc gtttaccggt aaaattcctt tcgagggaaa ggacagtaag      60
aatgtaatgg ctttccacta ctacgagcct gagcgcgtag tgatgggaaa gaagatgaag     120
gattggttgc gatttgcaat ggcttggtgg cacacactgg gtggcgcttc tgccgaccag     180

```
tttggtggtc agacccgcag ttacgaatgg gacaaggctg ctgatgctgt tcagcgtgct      240
aaggacaaga tggatgccgg cttcgagatt atggataagc tgggaatcga gttcttctgc      300
tggcacgata tcgacctcgt tgaagagggt gagaccattg aagagtatga gcgccgcatg      360
aaggctatca ccgactatgc tcttgagaag atgcagcagt atcccaacat caagaacctc      420
tggggaacag ccaatgtgtt tggcaacaag cgttatgcca acggtgccag cacaaaccca      480
gactttgacg tcgttgctcg tgctatcgta cagattaaga atgctatcga cgctactatc      540
aagttgggtg gtcagaatta tgtgttctgg ggtggccgtg agggctacat gagcctgctc      600
aatactgacc agaagcgtga gaaggagcac atggctacaa tgctgaccat ggcacgcgac      660
tatgcccgca gcaagggatt caagggtaac ttcctcattg agcccaagcc catggagccg      720
tcaaagcacc agtatgatgt tgacaccgag accgtatgcg tttcctgcg tgcccacaac      780
cttgacaagg atttcaaggt aaatatcgag gttaaccatg ctactctggc tggtcatact      840
ttcgagcaca aactggcatg cgctgttgac gctggtatgc ttggttctat cgatgctaac      900
cgtggtgatg cccagaatgg ctgggatacc gaccagttcc ccatcaacaa ctatgaactc      960
actcaggcta tgcttgagat catccgtaat ggtggtctgg gtcttggcgg cacaaacttc     1020
gatgccaaga ttcgtcgtaa ctcaacagat cttgaggatc tcttcatcgc tcacatcagt     1080
ggtatggatg ccatggcccg tgctctgctg aatgctgctg ctattctgga ggagagcgag     1140
ctgcctaaga tgaagaagga gcgttatgct tctttcgatg ccggtatcgg taaggacttc     1200
gaggatggca agcttaccct tgagcaggct tacgagtatg gtaagaaggt tgaggagccc     1260
aagcagactt caggcaagca ggagaagtac gagaccatcg ttgctctgta tgcaaaataa     1320
```

<210> SEQ ID NO 92
<211> LENGTH: 439
<212> TYPE: PRT
<213> ORGANISM: Unknown
<220> FEATURE:
<223> OTHER INFORMATION: Obtained from environmental sample

<400> SEQUENCE: 92

```
Met Ala Lys Glu Tyr Phe Pro Phe Thr Gly Lys Ile Pro Phe Glu Gly
1               5                   10                  15

Lys Asp Ser Lys Asn Val Met Ala Phe His Tyr Glu Pro Glu Arg
            20                  25                  30

Val Val Met Gly Lys Lys Met Lys Asp Trp Leu Arg Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Ala Asp Ala Val Gln Arg Ala
65                  70                  75                  80

Lys Asp Lys Met Asp Ala Gly Phe Glu Ile Met Asp Lys Leu Gly Ile
                85                  90                  95

Glu Phe Phe Cys Trp His Asp Ile Asp Leu Val Glu Glu Gly Glu Thr
            100                 105                 110

Ile Glu Glu Tyr Glu Arg Arg Met Lys Ala Ile Thr Asp Tyr Ala Leu
        115                 120                 125

Glu Lys Met Gln Gln Tyr Pro Asn Ile Lys Asn Leu Trp Gly Thr Ala
    130                 135                 140

Asn Val Phe Gly Asn Lys Arg Tyr Ala Asn Gly Ala Ser Thr Asn Pro
145                 150                 155                 160
```

Asp Phe Asp Val Val Ala Arg Ala Ile Val Gln Ile Lys Asn Ala Ile
                165                 170                 175

Asp Ala Thr Ile Lys Leu Gly Gly Gln Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Thr Met Ala Arg Asp Tyr Ala Arg Ser
    210                 215                 220

Lys Gly Phe Lys Gly Asn Phe Leu Ile Glu Pro Lys Pro Met Glu Pro
225                 230                 235                 240

Ser Lys His Gln Tyr Asp Val Asp Thr Glu Thr Val Cys Gly Phe Leu
                245                 250                 255

Arg Ala His Asn Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Ala Gly Met Leu Gly Ser Ile Asp Ala Asn Arg Gly Asp Ala
    290                 295                 300

Gln Asn Gly Trp Asp Thr Asp Gln Phe Pro Ile Asn Asn Tyr Glu Leu
305                 310                 315                 320

Thr Gln Ala Met Leu Glu Ile Ile Arg Asn Gly Gly Leu Gly Leu Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Leu Asn Ala Ala Ala Ile Leu Glu Glu Ser Glu Leu Pro Lys Met
370                 375                 380

Lys Lys Glu Arg Tyr Ala Ser Phe Asp Ala Gly Ile Gly Lys Asp Phe
385                 390                 395                 400

Glu Asp Gly Lys Leu Thr Leu Glu Gln Ala Tyr Glu Tyr Gly Lys Lys
                405                 410                 415

Val Glu Glu Pro Lys Gln Thr Ser Gly Lys Gln Glu Lys Tyr Glu Thr
            420                 425                 430

Ile Val Ala Leu Tyr Ala Lys
        435

<210> SEQ ID NO 93
<211> LENGTH: 1317
<212> TYPE: DNA
<213> ORGANISM: Unknown
<220> FEATURE:
<223> OTHER INFORMATION: Obtained from environmental sample

<400> SEQUENCE: 93
atgaaacagt attttcccca gattggaaag atacccttcg agggtgtaga gagcaagaat      60
gtgatggctt ccactatta tgagccagaa agagtagtca tgggcaagcc tatgaaagaa     120
tggctgcgct tcgctatggc gtggtggcac acgctgggggc aggcgagcgg cgacccttc    180 ggcggacaga cccgcagcta cgagtgggac cgtgcggccg acgcgctaca gcgcgccaag     240
gacaagatgg atgcgggctt cgagctgatg gagaagcttg cattgagta cttctgcttc     300 cacgacgtgg acctcgtaga agagggcgcc acggtggagg aatacgagcg gcggatggct     360
gccatcaccg actacgcggt agagaagatg cgcgagcatc ccgagataca ctgcctgtgg     420
ggcacggcca atgtcttcgg ccacaagcgc tacatgaacg gagccgccac caaccccgac    480

-continued

```
ttcgacgtgg tggcgcgtgc ggtggtgcag ataaagaaca gcatcgacgc cacgatcaag    540
ctgggcggcg agaactatgt gttctggggc ggacgcgagg gatatatgag cctgctcaac    600
accgaccagc gccgcgagaa ggagcacctg gccatgatgc ttgcgaaggc ccgcgactat    660
ggccgcgccc acggcttcaa gggcaccttc ctgatagagc ccaagccgat ggagcccatg    720
aagcaccagt acgacgtgga caccgagacg gtgataggtt tcctgcgtgc ccacggactg    780
gacaaggact tcaaggtgaa catcgaggtg aaccacgcca cgttggcggg ccacacgttc    840
gagcacgagc tggcctgtgc cgtcgatgcc ggcatgctgg gcagcatcga cgccaaccgt    900
ggcgacgcgc agaacggatg ggatacggac cagttcccca tagactgcta cgagctcacg    960
caggcgtgga tggagatcat tcgtggcggc ggcttcacca ccggcggcac caacttcgac   1020
gctaagctgc gccgcaactc gaccgacccc gaggatatct tcatagctca catcagcggc   1080
atggatgcta tggcccgcgc cctgctctgc gccgccgaca tcttggagca cagcgagctg   1140
ccggagatga agcggaagcg ctatgcctcg ttcgacagcg gcatgggcaa ggagttcgaa   1200
gagggcaatc tcagcttcga gcaaatctat gcctacggca agcaggcggg cgaaccggcc   1260
acgaccagcg gcaagcagga gaaatacgaa gccattgttt cactttatac ccgatga      1317
```

<210> SEQ ID NO 94
<211> LENGTH: 438
<212> TYPE: PRT
<213> ORGANISM: Unknown
<220> FEATURE:
<223> OTHER INFORMATION: Obtained from environmental sample

<400> SEQUENCE: 94

```
Met Lys Gln Tyr Phe Pro Gln Ile Gly Lys Ile Pro Phe Glu Gly Val
1               5                   10                  15

Glu Ser Lys Asn Val Met Ala Phe His Tyr Tyr Glu Pro Glu Arg Val
            20                  25                  30

Val Met Gly Lys Pro Met Lys Glu Trp Leu Arg Phe Ala Met Ala Trp
        35                  40                  45

Trp His Thr Leu Gly Gln Ala Ser Gly Asp Pro Phe Gly Gly Gln Thr
    50                  55                  60

Arg Ser Tyr Glu Trp Asp Arg Ala Ala Asp Ala Leu Gln Arg Ala Lys
65                  70                  75                  80

Asp Lys Met Asp Ala Gly Phe Glu Leu Met Glu Lys Leu Gly Ile Glu
                85                  90                  95

Tyr Phe Cys Phe His Asp Val Asp Leu Val Glu Glu Gly Ala Thr Val
            100                 105                 110

Glu Glu Tyr Glu Arg Arg Met Ala Ala Ile Thr Asp Tyr Ala Val Glu
        115                 120                 125

Lys Met Arg Glu His Pro Glu Ile His Cys Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Val Ala Arg Ala Val Val Gln Ile Lys Asn Ser Ile Asp
                165                 170                 175

Ala Thr Ile Lys Leu Gly Gly Glu Asn Tyr Val Phe Trp Gly Gly Arg
            180                 185                 190

Glu Gly Tyr Met Ser Leu Leu Asn Thr Asp Gln Arg Arg Glu Lys Glu
        195                 200                 205

His Leu Ala Met Met Leu Ala Lys Ala Arg Asp Tyr Gly Arg Ala His
```

```
                     210                 215                 220
Gly Phe Lys Gly Thr Phe Leu Ile Glu Pro Lys Pro Met Glu Pro Met
225                 230                 235                 240

Lys His Gln Tyr Asp Val Asp Thr Glu Thr Val Ile Gly Phe Leu Arg
                245                 250                 255

Ala His Gly Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp Ala Gly Met Leu Gly Ser Ile Asp Ala Asn Arg Gly Asp Ala Gln
    290                 295                 300

Asn Gly Trp Asp Thr Asp Gln Phe Pro Ile Asp Cys Tyr Glu Leu Thr
305                 310                 315                 320

Gln Ala Trp Met Glu Ile Ile Arg Gly Gly Phe Thr Thr Gly Gly
                325                 330                 335

Thr Asn Phe Asp Ala Lys Leu Arg Arg Asn Ser Thr Asp Pro Glu Asp
                340                 345                 350

Ile Phe Ile Ala His Ile Ser Gly Met Asp Ala Met Ala Arg Ala Leu
            355                 360                 365

Leu Cys Ala Ala Asp Ile Leu Glu His Ser Glu Leu Pro Glu Met Lys
        370                 375                 380

Arg Lys Arg Tyr Ala Ser Phe Asp Ser Gly Met Gly Lys Glu Phe Glu
385                 390                 395                 400

Glu Gly Asn Leu Ser Phe Glu Gln Ile Tyr Ala Tyr Gly Lys Gln Ala
                405                 410                 415

Gly Glu Pro Ala Thr Thr Ser Gly Lys Gln Glu Lys Tyr Glu Ala Ile
            420                 425                 430

Val Ser Leu Tyr Thr Arg
        435

<210> SEQ ID NO 95
<211> LENGTH: 1320
<212> TYPE: DNA
<213> ORGANISM: Unknown
<220> FEATURE:
<223> OTHER INFORMATION: Obtained from environmental sample

<400> SEQUENCE: 95
atggcaaaag agtattttcc gtttatcggt aaggttcctt tcgaaggaac agagagcaag     60
aacgtgatgg cattccacta ctatgagccc gaaaaggtgg tcatgggtaa gaaaatgaag    120
gactggctga agttcgctat ggcttggtgg cacacactgg gtggtgccag cgccgaccag    180
tttggtggtc agactcgcag ctacgagtgg gacaaggctg ctgatgccgt tcagcgcgcc    240
aaggacaaga tggatgctgg cttcgagatc atggataagc tcggcattga gtacttctgc    300
ttccatgacg tagacctcgt tgaggagggt gaaaccgtcg ctgagtatga ggctcgcatg    360
aaggtcatca ccgactatgc cctggagaag atgcagcagt ccccaacat caaactgctc    420 tggggtactg ctaacgtgtt cggccacaag cgctatgcca acggtgccag caccaatccc    480
gacttcgacg tcgtggcccg tgctatcgtt cagatcaaga atgccatcga tgctaccatt    540
aagctcggcg gtacgaacta tgtgttctgg ggtggtcgtg agggctacat gagccttctc    600
aacaccgacc agaagcgcga gaaggagcac atgcaacga tgctgaccat ggctcgcgac    660
tatgcccgcg ccaagggatt caagggcacg ttcctcatcg agccgaagcc catggagccc    720
tcgaagcatc agtacgacgt cgacaccgag accgtcatcg gcttcctccg tgcccacggt    780
```

-continued

```
ctggataagg acttcaaggt gaacatcgag gtgaaccacg ccacgctggc cggtcatacc      840
ttcgagcacg aactggcttg cgccgttgat gccggcatgc tcggctctat cgatgccaac      900
cgcggcgacg ctcagaacgg ctgggacacc gaccagttcc ccatcgacaa ctacgagctc      960
actcaggcca tgatggaaat catccgtaat ggcggtctgg caacggcgg cacgaacttc      1020 gatgccaaga tccgtcgtaa cagcaccgac ctcgaggacc tcttcatcgc tcacatcagc     1080
ggcatggatg ccatggcacg cgctctgatg aacgctgctg ccatcctcga agagagcgag      1140
ctgcccgcca tgaagaaggc ccgctatgct tcgttcgacg agggtatcgg caaggacttc      1200
gaggacggca agttgtcact tgagcaggtc tacgaatatg gtaagaaggt tgaggagccc      1260
aagcagacct cgggcaagca ggagaagtac gagaccatcg tggccctcta tgccaagtaa     1320
```

<210> SEQ ID NO 96
<211> LENGTH: 439
<212> TYPE: PRT
<213> ORGANISM: Unknown
<220> FEATURE:
<223> OTHER INFORMATION: Obtained from environmental sample

<400> SEQUENCE: 96

```
Met Ala Lys Glu Tyr Phe Pro Phe Ile Gly Lys Val Pro Phe Glu Gly
1               5                   10                  15

Thr Glu Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gly Ala Ser Ala Asp Gln Phe Gly Gly Gln
    50                  55                  60

Thr Arg Ser Tyr Glu Trp Asp Lys Ala Ala Asp Ala Val Gln Arg Ala
65                  70                  75                  80

Lys Asp Lys Met Asp Ala Gly Phe Glu Ile Met Asp Lys Leu Gly Ile
                85                  90                  95

Glu Tyr Phe Cys Phe His Asp Val Asp Leu Val Glu Glu Gly Glu Thr
            100                 105                 110

Val Ala Glu Tyr Glu Ala Arg Met Lys Val Ile Thr Asp Tyr Ala Leu
        115                 120                 125

Glu Lys Met Gln Gln Phe Pro Asn Ile Lys Leu Leu Trp Gly Thr Ala
    130                 135                 140

Asn Val Phe Gly His Lys Arg Tyr Ala Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Thr Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Thr Met Ala Arg Asp Tyr Ala Arg Ala
    210                 215                 220

Lys Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Ile Gly Phe Leu
                245                 250                 255

Arg Ala His Gly Leu Asp Lys Asp Phe Lys Val Asn Ile Glu Val Asn
            260                 265                 270
```

```
His Ala Thr Leu Ala Gly His Thr Phe Glu His Glu Leu Ala Cys Ala
            275                 280                 285

Val Asp Ala Gly Met Leu Gly Ser Ile Asp Ala Asn Arg Gly Asp Ala
        290                 295                 300

Gln Asn Gly Trp Asp Thr Asp Gln Phe Pro Ile Asp Asn Tyr Glu Leu
305                 310                 315                 320

Thr Gln Ala Met Met Glu Ile Ile Arg Asn Gly Leu Gly Asn Gly
            325                 330                 335

Gly Thr Asn Phe Asp Ala Lys Ile Arg Arg Asn Ser Thr Asp Leu Glu
        340                 345                 350

Asp Leu Phe Ile Ala His Ile Ser Gly Met Asp Ala Met Ala Arg Ala
            355                 360                 365

Leu Met Asn Ala Ala Ile Leu Glu Glu Ser Glu Leu Pro Ala Met
        370                 375                 380

Lys Lys Ala Arg Tyr Ala Ser Phe Asp Glu Gly Ile Gly Lys Asp Phe
385                 390                 395                 400

Glu Asp Gly Lys Leu Ser Leu Glu Gln Val Tyr Glu Tyr Gly Lys Lys
            405                 410                 415

Val Glu Glu Pro Lys Gln Thr Ser Gly Lys Gln Glu Lys Tyr Glu Thr
        420                 425                 430

Ile Val Ala Leu Tyr Ala Lys
        435

<210> SEQ ID NO 97
<211> LENGTH: 1320
<212> TYPE: DNA
<213> ORGANISM: Unknown
<220> FEATURE:
<223> OTHER INFORMATION: Obtained from environmental sample

<400> SEQUENCE: 97
atggcaaaag agtattttcc gtttgttggt aagattcctt tcgagggaaa ggatagtaag      60
aatgtaatgg ctttccacta ttacgaacca gagaaggtcg tgatgggaaa gaagatgaag     120
gactggctga agttcgccat ggcatggtgg cacacactgg acaggccag tgccgacccg      180 tttggaggtc agacccgcag ctacgagtgg acaaggctg acgatgctgt gcagcgcgca      240
aaggacaaga tggatgccgg atttgagatc atggacaagc tgggcatcga gtacttctgc     300
ttccacgatg tagacctcgt tgaggaggga gcaactgttg aggagtacga ggctcgcatg     360
aaggccatca ccgactatgc attggagaag atgaaagagt atcccaacat caagaacctc     420
tggggtacag ccaatgtatt cagcaacaag cgctatatga acggtgccag caccaacccc     480
gacttcgacg ttgttgcacg tgccatcgta cagataaaga acgccattga cgctaccatc     540
aagctcggcg gtcagaacta cgtgttctgg ggcggacgtg agggatacat gagcctgctc     600
aacaccgacc agaagcgcga gaaggagcac atggcaacca tgctgaccat ggctcgcgac     660
tacgctcgca gaacggtttt caagggcaca ttcctcatcg agcctaagcc catggaaccc     720
tcaaagcacc agtacgacgt agacacagag accgtatgcg gtttcctccg cgcccatggt     780
cttgacaagg atttcaaggt gaacattgag gtgaaccacg ctaccctcgc cggccacacc     840
tttgagcatg aactggcttg cgccgtcgac aacggcatgc tcggcagcat cgatgccaac     900
cgcggcgacg ttcagaacgg ctgggacacc gaccagttcc ccatcgacaa ctacgagctg     960
actcaggcca tgctcgaaat catccgcaac ggtggtctgg caacggcgg taccaacttc    1020 gacgccaaga tccgtcgtaa ctctaccgac ctcgaggatc tgttcatcgc ccacatcagc    1080
```

```
ggtatggacg ccatggcacg tgcactgctc aatgcagcag ccatactgga ggagagcgag   1140
ctgcctgcca tgaagaagga gcgttacgcc agcttcgaca gcggcatcgg caaggacttc   1200
gaggacggca agctcacact tgagcaggcc tatgagtatg gtaagaaggt tgaggagcca   1260
aagcagacct ctggcaagca ggagaagtat gagactatag tagccctcta cgctaagtag   1320
```

<210> SEQ ID NO 98
<211> LENGTH: 439
<212> TYPE: PRT
<213> ORGANISM: Unknown
<220> FEATURE:
<223> OTHER INFORMATION: Obtained from environmental sample

<400> SEQUENCE: 98

```
Met Ala Lys Glu Tyr Phe Pro Phe Val Gly Lys Ile Pro Phe Glu Gly
1               5                   10                  15

Lys Asp Ser Lys Asn Val Met Ala Phe His Tyr Tyr Glu Pro Glu Lys
            20                  25                  30

Val Val Met Gly Lys Lys Met Lys Asp Trp Leu Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Ala Asp Ala Val Gln Arg Ala
65              70                  75                  80

Lys Asp Lys Met Asp Ala Gly Phe Glu Ile Met Asp Lys Leu Gly Ile
            85                  90                  95

Glu Tyr Phe Cys Phe His Asp Val Asp Leu Val Glu Gly Ala Thr
            100                 105                 110

Val Glu Glu Tyr Glu Ala Arg Met Lys Ala Ile Thr Asp Tyr Ala Leu
        115                 120                 125

Glu Lys Met Lys Glu Tyr Pro Asn Ile Lys Asn Leu Trp Gly Thr Ala
    130                 135                 140

Asn Val Phe Ser Asn Lys Arg Tyr Met Asn Gly Ala Ser Thr Asn Pro
145                 150                 155                 160

Asp Phe Asp Val Val Ala Arg Ala Ile Val Gln Ile Lys Asn Ala Ile
                165                 170                 175

Asp Ala Thr Ile Lys Leu Gly Gly Gln Asn Tyr Val Phe Trp Gly Gly
            180                 185                 190

Arg Glu Gly Tyr Met Ser Leu Leu Asn Thr Asp Gln Lys Arg Glu Lys
        195                 200                 205

Glu His Met Ala Thr Met Leu Thr Met Ala Arg Asp Tyr Ala Arg Lys
    210                 215                 220

Asn Gly Phe Lys Gly Thr Phe Leu Ile Glu Pro Lys Pro Met Glu Pro
225                 230                 235                 240

Ser Lys His Gln Tyr Asp Val Asp Thr Glu Thr Val Cys Gly Phe Leu
                245                 250                 255

Arg Ala His Gly Leu Asp Lys Asp Phe Lys Val Asn Ile Glu Val Asn
            260                 265                 270

His Ala Thr Leu Ala Gly His Thr Phe Glu His Glu Leu Ala Cys Ala
        275                 280                 285

Val Asp Asn Gly Met Leu Gly Ser Ile Asp Ala Asn Arg Gly Asp Val
    290                 295                 300

Gln Asn Gly Trp Asp Thr Asp Gln Phe Pro Ile Asp Asn Tyr Glu Leu
305                 310                 315                 320
```

```
Thr Gln Ala Met Leu Glu Ile Ile Arg Asn Gly Gly Leu Gly Asn Gly
                325                 330                 335

Gly Thr Asn Phe Asp Ala Lys Ile Arg Arg Asn Ser Thr Asp Leu Glu
            340                 345                 350

Asp Leu Phe Ile Ala His Ile Ser Gly Met Asp Ala Met Ala Arg Ala
        355                 360                 365

Leu Leu Asn Ala Ala Ala Ile Leu Glu Glu Ser Glu Leu Pro Ala Met
    370                 375                 380

Lys Lys Glu Arg Tyr Ala Ser Phe Asp Ser Gly Ile Gly Lys Asp Phe
385                 390                 395                 400

Glu Asp Gly Lys Leu Thr Leu Glu Gln Ala Tyr Glu Tyr Gly Lys Lys
                405                 410                 415

Val Glu Glu Pro Lys Gln Thr Ser Gly Lys Gln Glu Lys Tyr Glu Thr
            420                 425                 430

Ile Val Ala Leu Tyr Ala Lys
        435

<210> SEQ ID NO 99
<211> LENGTH: 1317
<212> TYPE: DNA
<213> ORGANISM: Unknown
<220> FEATURE:
<223> OTHER INFORMATION: Obtained from environmental sample

<400> SEQUENCE: 99
atgactaaag agtatttccc taccattggc aagattccct ttgagggacc tgaaagcaag      60
aacccgcttg cattccatta ctatgagccc gaccgcctgg tcatgggcaa gaagatgaaa     120
gactggctgc gtttcgccat ggcctggtgg cacaccctgg ccaggcctc cggcgaccag      180 ttcggcggcc agacccgcca ctatgcctgg gatgatccgg attgcccgta tgcacgtgcc     240
aaagccaagg ccgacgccgg tttcgaaatc atgcagaaac tgggcattga attcttctgc     300
ttccacgaca tcgacctggt cgaggatgcc gatgaaatcg ccgagtacga ggcccggatg     360
aaggacatca ccgactatct gctcgtcaag atgaaagaga ccggcatcaa gaacctttgg     420
ggaacggcca acgtatttgg ccacaagcgc tacatgaacg cgccgccac caaccccgat      480 tcgacgtgc tggcccgtgc cgccgtccag atcaagaacg ccatcgacgc caccatcaag     540
ttgggcggtc agaactatgt gttctggggc ggccgtgaag ctaccagac cctgctcaat      600 acccagatgc agcgcgagaa ggaacacatg gcccgtatgt tggcactggc ccgcgactat     660
ggccgtgcac acggtttcaa gggcacgttc ctcatcgagc ccaaaccgat ggagccgacc     720
aagcaccagt acgatcagga tacggaaacc gtcatcggct cctgcgccg ccatggcctc      780 gacaaggact tcaaggtcaa catcgaggtg aaccatgcta ccctggcggg ccacaccttc     840
gagcacgagc tggcttgcgc cgtcgaccac ggcatgctgg cagcatcga cgccaaccgg      900 ggtgatgccc agaacggctg gacaccgac cagttcccga tcgataacta tgagctgacg      960
ctggccatgc tccagatcat ccgcaacggc ggcctggcac ccggcggctc gaacttcgat    1020
gcgaagctgc gtcgcaactc caccgatccg gaagatatct tcatcgcgca catcagcgcc    1080
atggatgcca tggcccgcgc cctggtcaat gctgtcgcca ttctcgagga tcgcccatc     1140 ccggccatgg tcagggaacg ttacgcctcg ttcgacagcg gaaagggcag ggaatatgag    1200
gaaggcaggc tgtctctcga agacatcgtg gcctatgcca agcccacgg cgaaccgaaa    1260 cagatttccg gcaagcagga actctacgaa accatcgtgg ctctctattg caagtag       1317
```

```
<210> SEQ ID NO 100
<211> LENGTH: 438
<212> TYPE: PRT
<213> ORGANISM: Unknown
<220> FEATURE:
<223> OTHER INFORMATION: Obtained from environmental sample

<400> SEQUENCE: 100

Met Thr Lys Glu Tyr Phe Pro Thr Ile Gly Lys Ile Pro Phe Glu Gly
1               5                   10                  15

Pro Glu Ser Lys Asn Pro Leu Ala Phe His Tyr Glu Pro Asp Arg
            20                  25                  30

Leu Val Met Gly Lys Lys Met Lys Asp Trp Leu Arg Phe Ala Met Ala
        35                  40                  45

Trp Trp His Thr Leu Gly Gln Ala Ser Gly Asp Gln Phe Gly Gly Gln
50                  55                  60

Thr Arg His Tyr Ala Trp Asp Asp Pro Asp Cys Pro Tyr Ala Arg Ala
65                  70                  75                  80

Lys Ala Lys Ala Asp Ala Gly Phe Glu Ile Met Gln Lys Leu Gly Ile
                85                  90                  95

Glu Phe Phe Cys Phe His Asp Ile Asp Leu Val Glu Asp Ala Asp Glu
            100                 105                 110

Ile Ala Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
130                 135                 140

Val Phe Gly His Lys Arg Tyr Met Asn Gly Ala Ala Thr Asn Pro Asp
145                 150                 155                 160

Phe Asp Val Leu Ala Arg Ala Ala Val Gln Ile Lys Asn Ala Ile Asp
                165                 170                 175

Ala Thr Ile Lys Leu Gly Gly Gln Asn Tyr Val Phe Trp Gly Gly Arg
            180                 185                 190

Glu Gly Tyr Gln Thr Leu Leu Asn Thr Gln Met Gln Arg Glu Lys Glu
        195                 200                 205

His Met Gly Arg Met Leu Ala Leu Ala Arg Asp Tyr Gly Arg Ala His
210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Arg His Gly Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp His Gly Met Leu Gly Ser Ile Asp Ala Asn Arg Gly Asp Ala Gln
290                 295                 300

Asn Gly Trp Asp Thr Asp Gln Phe Pro Ile Asp Asn Tyr Glu Leu Thr
305                 310                 315                 320

Leu Ala Met Leu Gln Ile Ile Arg Asn Gly Gly Leu Ala Pro Gly Gly
                325                 330                 335

Ser Asn Phe Asp Ala Lys Leu Arg Arg Asn Ser Thr Pro Glu Asp
            340                 345                 350

Ile Phe Ile Ala His Ile Ser Ala Met Asp Ala Met Ala Arg Ala Leu
        355                 360                 365

Val Asn Ala Val Ala Ile Leu Glu Glu Ser Pro Ile Pro Ala Met Val
```

```
                370            375             380
Arg Glu Arg Tyr Ala Ser Phe Asp Ser Gly Lys Gly Arg Glu Tyr Glu
385                 390                 395                 400

Glu Gly Arg Leu Ser Leu Glu Asp Ile Val Ala Tyr Ala Lys Ala His
                405                 410                 415

Gly Glu Pro Lys Gln Ile Ser Gly Lys Gln Leu Tyr Glu Thr Ile
            420                 425                 430

Val Ala Leu Tyr Cys Lys
        435
```

<210> SEQ ID NO 101
<211> LENGTH: 1317
<212> TYPE: DNA
<213> ORGANISM: Unknown
<220> FEATURE:
<223> OTHER INFORMATION: Obtained from environmental sample

<400> SEQUENCE: 101

| | | | | | |
|---|---|---|---|---|---|
| atggcaaaag | agtatttccc | gcagatcgga | aagatcggct | tgagggtcc | tgcaagcaag | 60 |
| aacccgctgg | cattccatta | ttatgacgcc | gagcgcgtgg | tgatgggtaa | acccatgaaa | 120 |
| gactggttta | aattcgccct | cgcgtggtgg | cacagcctcg | gccaggcctc | cggcgacccg | 180 |
| ttcggcggcc | agacccgctc | ctacgagtgg | gacaagggcg | aatgcccta | ctgccgcgcc | 240 |
| cgcgccaagg | cggacgccgg | cttcgagatc | atgcaaaagc | tcggcatcgg | ctatttctgc | 300 |
| ttccacgacg | tcgacctcat | cgaagacacg | gacgacatcg | ccgaatatga | ggcccgcctc | 360 |
| aaggacatca | cggactacct | gctcgaaagg | atgcaggaaa | ccggcatcaa | gaacctctgg | 420 |
| ggcacggcca | atgtcttcgg | tcacaagcgc | tacatgaacg | gcgccggcac | caatccgcag | 480 |
| ttcgacatcg | tcgcccgcgc | tgccgtccag | atcaagaacg | ccctcgacgc | caccatcaag | 540 |
| ctcggtggct | cgaactacgt | cttctggggc | ggccgcgaag | gttattacac | gctgctcaac | 600 |
| acccagatgc | agcgcgagaa | agaccacctc | gccaagctcc | tcaccgccgc | ccgcgactat | 660 |
| gcccgcgcca | agggcttcca | gggcaccttc | ctgatcgagc | ccaagccgat | ggagccgacc | 720 |
| aagcaccagt | acgatgtcga | cacggagact | gtaatcggat | tcctccgcgc | caacggactg | 780 |
| gacaaggact | tcaaggtcaa | catcgaggtc | aaccacgcca | ccctcgccgg | ccataccttc | 840 |
| gagcatgagc | tgaccgtcgc | ccgcgagaac | ggattcctcg | gcagcatcga | cgccaaccgc | 900 |
| ggtgacgccc | agaacggctg | ggacaccgac | cagttccccg | tggacgccta | cgacctcacc | 960 |
| caggccatga | tgcaggtgct | cctgaacggc | ggtttcggca | acggcggcac | caatttcgac | 1020 |
| gccaagctcc | gtcgcagctc | caccgatccc | gaggacatct | tcatcgccca | catcagcgcg | 1080 |
| atggacgcca | tggcccacgc | cctgctgaac | gccgcggcca | ttctcgagga | gagcccgctg | 1140 |
| cccgcgatgg | tcaaggagcg | ttacgcctcc | ttcgacagcg | gtctcggcaa | gcagttcgag | 1200 |
| gagggaaagg | ccacgctgga | ggacctctac | gactacgcca | aggcccatgg | cgagcccgtc | 1260 |
| gccgcctccg | gcaagcagga | actgtgtgaa | acttacctga | atctgtatgc | aaagtaa | 1317 |

<210> SEQ ID NO 102
<211> LENGTH: 438
<212> TYPE: PRT
<213> ORGANISM: Unknown
<220> FEATURE:
<223> OTHER INFORMATION: Obtained from environmental sample

<400> SEQUENCE: 102

Met Ala Lys Glu Tyr Phe Pro Gln Ile Gly Lys Ile Gly Phe Glu Gly

```
1               5                   10                  15
    Pro Ala Ser Lys Asn Pro Leu Ala Phe His Tyr Tyr Asp Ala Glu Arg
                20                  25                  30

Val Val Met Gly Lys Pro Met Lys Asp Trp Phe Lys Phe Ala Leu Ala
                35                  40                  45

Trp Trp His Ser Leu Gly Gln Ala Ser Gly Asp Pro Phe Gly Gly Gln
                50                  55                  60

Thr Arg Ser Tyr Glu Trp Asp Lys Gly Glu Cys Pro Tyr Cys Arg Ala
    65                  70                  75                  80

Arg Ala Lys Ala Asp Ala Gly Phe Glu Ile Met Gln Lys Leu Gly Ile
                    85                  90                  95

Gly Tyr Phe Cys Phe His Asp Val Asp Leu Ile Glu Asp Thr Asp Asp
                    100                 105                 110

Ile Ala Glu Tyr Glu Ala Arg Leu Lys Asp Ile Thr Asp Tyr Leu Leu
                    115                 120                 125

Glu Arg Met Gln Glu Thr Gly Ile Lys Asn Leu Trp Gly Thr Ala Asn
                130                 135                 140

Val Phe Gly His Lys Arg Tyr Met Asn Gly Ala Gly Thr Asn Pro Gln
    145                 150                 155                 160

Phe Asp Ile Val Ala Arg Ala Ala Val Gln Ile Lys Asn Ala Leu Asp
                    165                 170                 175

Ala Thr Ile Lys Leu Gly Gly Ser Asn Tyr Val Phe Trp Gly Gly Arg
                    180                 185                 190

Glu Gly Tyr Tyr Thr Leu Leu Asn Thr Gln Met Gln Arg Glu Lys Asp
                    195                 200                 205

His Leu Ala Lys Leu Leu Thr Ala Ala Arg Asp Tyr Ala Arg Ala Lys
                210                 215                 220

Gly Phe Gln Gly Thr Phe Leu Ile Glu Pro Lys Pro Met Glu Pro Thr
    225                 230                 235                 240

Lys His Gln Tyr Asp Val Asp Thr Glu Thr Val Ile Gly Phe Leu Arg
                    245                 250                 255

Ala Asn Gly Leu Asp Lys Asp Phe Lys Val Asn Ile Glu Val Asn His
                    260                 265                 270

Ala Thr Leu Ala Gly His Thr Phe Glu His Glu Leu Thr Val Ala Arg
                    275                 280                 285

Glu Asn Gly Phe Leu Gly Ser Ile Asp Ala Asn Arg Gly Asp Ala Gln
                290                 295                 300

Asn Gly Trp Asp Thr Asp Gln Phe Pro Val Asp Ala Tyr Asp Leu Thr
    305                 310                 315                 320

Gln Ala Met Met Gln Val Leu Leu Asn Gly Gly Phe Gly Asn Gly Gly
                    325                 330                 335

Thr Asn Phe Asp Ala Lys Leu Arg Arg Ser Ser Thr Asp Pro Glu Asp
                    340                 345                 350

Ile Phe Ile Ala His Ile Ser Ala Met Asp Ala Met Ala His Ala Leu
                    355                 360                 365

Leu Asn Ala Ala Ala Ile Leu Glu Glu Ser Pro Leu Pro Ala Met Val
                370                 375                 380

Lys Glu Arg Tyr Ala Ser Phe Asp Ser Gly Leu Gly Lys Gln Phe Glu
    385                 390                 395                 400

Glu Gly Lys Ala Thr Leu Glu Asp Leu Tyr Asp Tyr Ala Lys Ala His
                    405                 410                 415

Gly Glu Pro Val Ala Ala Ser Gly Lys Gln Glu Leu Cys Glu Thr Tyr
                    420                 425                 430
```

-continued

Leu Asn Leu Tyr Ala Lys
        435

<210> SEQ ID NO 103
<211> LENGTH: 1317
<212> TYPE: DNA
<213> ORGANISM: Unknown
<220> FEATURE:
<223> OTHER INFORMATION: Obtained from environmental sample

<400> SEQUENCE: 103

```
atgacaaaag agtatttccc taccatcggc aagatcccct tgagggacc cgagagcaaa        60
aaccccctcg cttttcatta ctatgagccc gaccgcctgg tcatgggcaa gaagatgaaa      120
gactggctgc gtttcgccat ggcctggtgg cacaccctgg ccaggcctc cggcgaccag       180
tttggcggcc agacccgcca ctatgcctgg gatgatccgg attgcccgta tgcacgtgcc      240
aaagccaagg ccgacgccgg tttcgaaatc atgcagaaac tgggcattga attcttctgc      300
ttccacgaca tcgacctgat cgaggatacc gatgacatcg tcgagtatga ggcccggatg      360
aaggacatca ccgactatct gctggtcaag atgaaagaga ccggcatcaa gaatctctgg      420
ggaacggcca acgtattcgg gcacaagcgc tatatgaacg cgctgccac caaccccgat       480
ttcgacgtgc tggcccgtgc cgccgtccag atcaagaacg ccatcgacgc caccatcaag     540
ctgggcggcc agaattatgt gttctggggc gggcgtgaag gctaccagag cctgctcaat     600
acccagatgc agcgcgaaaa ggaacacatg ggccgtatgt tggcactagc ccgcgactat     660
ggccgtgcac acggtttcaa gggcacgttc ctcatcgagc ccaaaccgat ggagccgacc     720
aagcaccagt acgatcagga tacggagacc gtcatcggtt ttctgcgccg ccatggcctc     780
gacaaggact tcaaggtcaa catcgaggtg aaccatgcta ccctggcggg ccacaccttc     840
gagcacgagc tggcctgcgc cgtcgaccac ggcatgctgg gcagtattga cgccaaccgc     900
ggtgacgccc agaacggctg ggacaccgac cagttcccga tcgataacta tgagctgacg     960
ctggccatgc tccagatcat ccgcaacggc ggcctggcac ccggcggctc gaacttcgat    1020
gcgaagctgc gtcgcaactc caccgatccg gaagatatct tcatcgcgca catcagcgcc    1080
atggatgcca tggcccgcgc cctggtcaac gctgtcgcca ttcttgagga atcgcccatt    1140
ccggacatgg tcaaggagcg ctacgcttcg ttcgacagcg gaaaaggcag ggagtacgaa    1200
gagggggaaac tttccttcga ggacctcgtg gcctatgcca agcccacgg cgaaccgaaa    1260
cagatttccg gcaagcagga actctacgaa accatcgtgg ctctctattg caagtag       1317
```

<210> SEQ ID NO 104
<211> LENGTH: 438
<212> TYPE: PRT
<213> ORGANISM: Unknown
<220> FEATURE:
<223> OTHER INFORMATION: Obtained from environmental sample

<400> SEQUENCE: 104

Met Thr Lys Glu Tyr Phe Pro Thr Ile Gly Lys Ile Pro Phe Glu Gly
1               5                   10                  15

Pro Glu Ser Lys Asn Pro Leu Ala Phe His Tyr Tyr Glu Pro Asp Arg
            20                  25                  30

Leu Val Met Gly Lys Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Arg His Tyr Ala Trp Asp Asp Pro Asp Cys Pro Tyr Ala Arg Ala
65                  70                  75                  80

Lys Ala Lys Ala Asp Ala Gly Phe Glu Ile Met Gln Lys Leu Gly Ile
            85                  90                  95

Glu Phe Phe Cys Phe His Asp Ile Asp Leu Ile Glu Asp Thr Asp Asp
        100                 105                 110

Ile Val Glu Tyr Glu Ala Arg Met Lys Asp Ile Thr Asp Tyr Leu Leu
    115                 120                 125

Val Lys Met Lys Glu Thr Gly Ile Lys Asn Leu Trp Gly Thr Ala Asn
130                 135                 140

Val Phe Gly His Lys Arg Tyr Met Asn Gly Ala Ala Thr Asn Pro Asp
145                 150                 155                 160

Phe Asp Val Leu Ala Arg Ala Val Gln Ile Lys Asn Ala Ile Asp
                165                 170                 175

Ala Thr Ile Lys Leu Gly Gly Gln Asn Tyr Val Phe Trp Gly Gly Arg
            180                 185                 190

Glu Gly Tyr Gln Ser Leu Leu Asn Thr Gln Met Gln Arg Glu Lys Glu
        195                 200                 205

His Met Gly Arg Met Leu Ala Leu Ala Arg Asp Tyr Gly Arg Ala His
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Arg His Gly Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp His Gly Met Leu Gly Ser Ile Asp Ala Asn Arg Gly Asp Ala Gln
    290                 295                 300

Asn Gly Trp Asp Thr Asp Gln Phe Pro Ile Asp Asn Tyr Glu Leu Thr
305                 310                 315                 320

Leu Ala Met Leu Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Val Asn Ala Val Ala Ile Leu Glu Glu Ser Pro Ile Pro Asp Met Val
    370                 375                 380

Lys Glu Arg Tyr Ala Ser Phe Asp Ser Gly Lys Gly Arg Glu Tyr Glu
385                 390                 395                 400

Glu Gly Lys Leu Ser Phe Glu Asp Leu Val Ala Tyr Ala Lys Ala His
                405                 410                 415

Gly Glu Pro Lys Gln Ile Ser Gly Lys Gln Glu Leu Tyr Glu Thr Ile
            420                 425                 430

Val Ala Leu Tyr Cys Lys
            435

<210> SEQ ID NO 105
<211> LENGTH: 1317
<212> TYPE: DNA
<213> ORGANISM: Unknown
<220> FEATURE:

<223> OTHER INFORMATION: Obtained from environmental sample

<400> SEQUENCE: 105

```
atgacaaaag agtatttccc taccatcggc aagatcccct tgagggacc  cgagagcaaa      60
aaccccctcg cttttcatta ctatgagccc gaccgcctgg tcatgggcaa gaagatgaaa     120
gactggctgc gtttcgccat ggcctggtgg cacaccctgg gccaggcctc cggcgaccag     180
tttggcggcc agaccgcca  ctatgcctgg gatgatccgg attgcccgta tgcacgtgcc     240
aaagccaagg ccgacgccgg tttcgaaatc atgcagaaac tgggcattga attcttctgc     300
ttccacgaca tcgacctgat cgaggatacc gatgacatcg tcgagtatga ggcccggatg     360
aaggacatca ccgactatct gctggtcaag atgaaagaga ccggcatcaa gaatctctgg     420
ggaacggcca acgtattcgg gcacaagcgc tatatgaacg cgctgccac  caaccccgat     480
ttcgacgtgc tggcccgtgc cgccgcccag atcaagaacg ccatcgacgc caccatcaag     540
ctgggcggcc agaattatgt gttctggggc gggcgtgaag gctaccagag cctgctcaat     600
acccagatgc agcgcgaaaa ggaacacatg gccgtatgt  tggcactagc ccgcgactat     660
ggccgtgcac acggtttcaa gggcacgctc ctcatcgagc ccaaaccgat ggagccgacc     720
aagcaccagt acgatcagga tacgagaccc gtcatcggtt ttctgcgccg ccatggcctc     780
gacaaggact tcaaggtcaa catcgaggtg aaccatgcta ccctggcggg ccacaccttc     840
gagcacgagc tggcctgcgc cgtcgaccac ggcatgctgg gcagtattga cgccaaccgc     900
ggtgacgccc aggacggctg gacaccgac  cagttcccga tcgataacta tgagctgacg     960
ctggccatgt ccagatcat  ccgcaacggc ggcctggcac ccggcggctc gaacttcgat    1020
gcgaagctgc gtcgcaactc caccgatccg gaagatatct tcatcgcgca catcagcgcc    1080
atggatgcca tggcccgcgc cctggtcaac gctgtcgcca ttcttgagga atcgcccatt    1140
ccggacatgg tcaaggagcg ctacgcttcg ttcgacagcg gaaaaggcag ggagtacgaa    1200
gaggggaaac tttccttcga ggacctcgtg gcctatgcca agcccacgg  cgaaccgaaa    1260
cagatttccg gcaagcagga actctacgaa accatcgtgg ctctctattg caagtag       1317
```

<210> SEQ ID NO 106
<211> LENGTH: 438
<212> TYPE: PRT
<213> ORGANISM: Unknown
<220> FEATURE:
<223> OTHER INFORMATION: Obtained from environmental sample

<400> SEQUENCE: 106

```
Met Thr Lys Glu Tyr Phe Pro Thr Ile Gly Lys Ile Pro Phe Glu Gly
 1               5                  10                  15

Pro Glu Ser Lys Asn Pro Leu Ala Phe His Tyr Tyr Glu Pro Asp Arg
            20                  25                  30

Leu Val Met Gly Lys Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Arg His Tyr Ala Trp Asp Asp Pro Asp Cys Pro Tyr Ala Arg Ala
65                  70                  75                  80

Lys Ala Lys Ala Asp Ala Gly Phe Glu Ile Met Gln Lys Leu Gly Ile
                85                  90                  95

Glu Phe Phe Cys Phe His Asp Ile Asp Leu Ile Glu Asp Thr Asp Asp
            100                 105                 110
```

Ile Val Glu Tyr Glu Ala Arg Met Lys Asp Ile Thr Asp Tyr Leu Leu
115                 120                 125

Val Lys Met Lys Glu Thr Gly Ile Lys Asn Leu Trp Gly Thr Ala Asn
130                 135                 140

Val Phe Gly His Lys Arg Tyr Met Asn Gly Ala Ala Thr Asn Pro Asp
145                 150                 155                 160

Phe Asp Val Leu Ala Arg Ala Ala Gln Ile Lys Asn Ala Ile Asp
            165                 170                 175

Ala Thr Ile Lys Leu Gly Gly Gln Asn Tyr Val Phe Trp Gly Gly Arg
            180                 185                 190

Glu Gly Tyr Gln Ser Leu Leu Asn Thr Gln Met Gln Arg Glu Lys Glu
            195                 200                 205

His Met Gly Arg Met Leu Ala Leu Ala Arg Asp Tyr Gly Arg Ala His
210                 215                 220

Gly Phe Lys Gly Thr Leu Leu Ile Glu Pro Lys Pro Met Glu Pro Thr
225                 230                 235                 240

Lys His Gln Tyr Asp Gln Asp Thr Glu Thr Val Ile Gly Phe Leu Arg
            245                 250                 255

Arg His Gly Leu Asp Lys Asp Phe Lys Val Asn Ile Glu Val Asn His
            260                 265                 270

Ala Thr Leu Ala Gly His Thr Phe Glu His Glu Leu Ala Cys Ala Val
            275                 280                 285

Asp His Gly Met Leu Gly Ser Ile Asp Ala Asn Arg Gly Asp Ala Gln
290                 295                 300

Asp Gly Trp Asp Thr Asp Gln Phe Pro Ile Asp Asn Tyr Glu Leu Thr
305                 310                 315                 320

Leu Ala Met Leu Gln Ile Ile Arg Asn Gly Gly Leu Ala Pro Gly Gly
            325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
            355                 360                 365

Val Asn Ala Val Ala Ile Leu Glu Glu Ser Pro Ile Pro Asp Met Val
370                 375                 380

Lys Glu Arg Tyr Ala Ser Phe Asp Ser Gly Lys Gly Arg Glu Tyr Glu
385                 390                 395                 400

Glu Gly Lys Leu Ser Phe Glu Asp Leu Val Ala Tyr Ala Lys Ala His
            405                 410                 415

Gly Glu Pro Lys Gln Ile Ser Gly Lys Gln Glu Leu Tyr Glu Thr Ile
            420                 425                 430

Val Ala Leu Tyr Cys Lys
        435

<210> SEQ ID NO 107
<211> LENGTH: 1317
<212> TYPE: DNA
<213> ORGANISM: Unknown
<220> FEATURE:
<223> OTHER INFORMATION: Obtained from environmental sample

<400> SEQUENCE: 107
atgacaaaag agtatttccc taccatcggc aagatcccct tgagggacc cgagagcaaa         60 aaccccctcg cttttcatta ctatgagccc daccgcctgg tcatgggcaa gaagatgaaa       120
gactggctgc gtttcgccat ggcctggtgg cacaccctgg gccaggcctc cggcgaccag       180

```
tttggcggcc agacccgcca ctatgcctgg gatgatccgg attgcccgta tgcacgtgcc    240
aaagccaagg ccgacgccgg tttcgaaatc atgcagaaac tgggcattga attcttctgc    300
ttccacgaca tcgacctgat cgaggatacc gatgacatcg tcgagtatga ggcccggatg    360
aaggacatca ccgactatct gctggtcaag atgaaagaga ccggcatcaa gaatctctgg    420
ggaacggcca acgtattcgg gcacaagcgc tatatgaacg gcgctgccac caaccccgat    480
ttcgacgtgc tggcccgtgc cgccgtccag atcaagaacg ccatcgacgc caccatcaag    540
ctgggcggcc agaattatgt gttctggggc gggcgtgaag gctaccagag cctgctcaat    600
acccagatgc agcgcgaaaa ggaacacatg ggccgtatgt tggcactagc ccgcgactat    660
ggccgtgcac acggtttcaa gggcacgttc ctcatcgagc ccaaaccgat ggagccgacc    720
aagcaccagt acgatcagga tacggagacc gtcatcggtt ttctgcgccg ccatggcctc    780
gacaaggact tcaaggtcaa catcgaggtg aaccatgcta ccctggcggg ccacaccttc    840
gagcacgagc tggcctgcgc cgtcgaccac ggcatgctgg gcagtattga cgccaaccgc    900
ggtgacgccc agaacggctg ggacaccgac cagttcccga tcgataacta tgagctgacg    960
ctggccatgc tccagatcat ccgcaacggc ggcctggcac ccggcggctc gaacttcgat   1020
gcgaagctgc gtcgcaactc caccgatccg gaagatgtct tcatcgcgca catcagcgcc   1080
atggatgcca tggcccgcgc cctggtcaac gctgtcgcca ttcttgagga atcgcccatt   1140
ccggacatgg tcaaggagcg ctacgcttcg ttcgacagcg gaaaaggcag ggagtacgaa   1200
gaggggaaac tttccttcga ggacctcgtg gcctatgcca agcccacgg cgaaccgaaa    1260 cagatttccg gcaagcagga actctacgaa accatcgtgg ctctctattg caagtag     1317
```

<210> SEQ ID NO 108
<211> LENGTH: 438
<212> TYPE: PRT
<213> ORGANISM: Unknown
<220> FEATURE:
<223> OTHER INFORMATION: Obtained from environmental sample

<400> SEQUENCE: 108

```
Met Thr Lys Glu Tyr Phe Pro Thr Ile Gly Lys Ile Pro Phe Glu Gly
1               5                   10                  15

Pro Glu Ser Lys Asn Pro Leu Ala Phe His Tyr Tyr Glu Pro Asp Arg
            20                  25                  30

Leu Val Met Gly Lys Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Arg His Tyr Ala Trp Asp Asp Pro Asp Cys Pro Tyr Ala Arg Ala
65                  70                  75                  80

Lys Ala Lys Ala Asp Ala Gly Phe Glu Ile Met Gln Lys Leu Gly Ile
                85                  90                  95

Glu Phe Phe Cys Phe His Asp Ile Asp Leu Ile Glu Asp Thr Asp Asp
            100                 105                 110

Ile Val Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Leu Ala Arg Ala Ala Val Gln Ile Lys Asn Ala Ile Asp
```

```
              165                 170                 175
Ala Thr Ile Lys Leu Gly Gly Gln Asn Tyr Val Phe Trp Gly Gly Arg
        180                 185                 190

Glu Gly Tyr Gln Ser Leu Leu Asn Thr Gln Met Gln Arg Glu Lys Glu
        195                 200                 205

His Met Gly Arg Met Leu Ala Leu Ala Arg Asp Tyr Gly Arg Ala His
        210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Arg His Gly Leu Asp Lys Asp Phe Lys Val Asn Ile Glu Val Asn His
                260                 265                 270

Ala Thr Leu Ala Gly His Thr Phe Glu His Glu Leu Ala Cys Ala Val
                275                 280                 285

Asp His Gly Met Leu Gly Ser Ile Asp Ala Asn Arg Gly Asp Ala Gln
                290                 295                 300

Asn Gly Trp Asp Thr Asp Gln Phe Pro Ile Asp Asn Tyr Glu Leu Thr
305                 310                 315                 320

Leu Ala Met Leu Gln Ile Ile Arg Asn Gly Leu Ala Pro Gly Gly
                325                 330                 335

Ser Asn Phe Asp Ala Lys Leu Arg Arg Asn Ser Thr Asp Pro Glu Asp
                340                 345                 350

Val Phe Ile Ala His Ile Ser Ala Met Asp Ala Met Ala Arg Ala Leu
                355                 360                 365

Val Asn Ala Val Ala Ile Leu Glu Glu Ser Pro Ile Pro Asp Met Val
                370                 375                 380

Lys Glu Arg Tyr Ala Ser Phe Asp Ser Gly Lys Gly Arg Glu Tyr Glu
385                 390                 395                 400

Glu Gly Lys Leu Ser Phe Glu Asp Leu Val Ala Tyr Ala Lys Ala His
                405                 410                 415

Gly Glu Pro Lys Gln Ile Ser Gly Lys Gln Glu Leu Tyr Glu Thr Ile
                420                 425                 430

Val Ala Leu Tyr Cys Lys
                435

<210> SEQ ID NO 109
<211> LENGTH: 1317
<212> TYPE: DNA
<213> ORGANISM: Unknown
<220> FEATURE:
<223> OTHER INFORMATION: Obtained from environmental sample

<400> SEQUENCE: 109
atggcaaaag agtatttccc gacaatcgga aagatcccct tcgagggcgt tgagagcaag      60 aatcccttg ctttccatta ttatgacgcc gagcgcgtgg tcatgggcaa gcccatgaag     120
gactggttca agttcgcgat ggcctggtgg cacaccctgg gccaggcttc cgcggacccg     180
ttcggcggcc agacccgctc ctacgagtgg gacaagggcg agtgccccta ctgccgcgcc     240
cgcgccaagg ctgacgccgg cttcgagatc atgcagaagc tcggaatcgg ctactattgc     300
ttccacgaca tcgacctggt ggaggacacc gaggacatcg ccgaatacga ggcccgcatg     360
aaggacatca ccgactacct cgtcgagaag cagaaggaga ccggcatcaa gaacctctgg     420
ggcaccgcga acgtgttcgg caacaagcgc tacatgaacg cgccgccac gaacccgcag     480
```

```
ttcgacatcg tcgcccgcgc ggccctgcag atcaagaacg cgatcgatgc caccatcaag    540
ctcggcggca ccggctacgt gttctggggc ggccgggaag ctactacac cctgctgaac     600 acccagatgc agcgcgagaa ggaccacctc gccaagatgc tcaccgccgc ccgcgactac    660
gcccgcgcca acggcttcaa gggcaccttc ctcatcgagc ccaagccgat ggagcccacc    720
aagcaccaat acgacgtgga cacggagacc gtgatcggct tcctccgcgc caatggcctg    780
gacaaggact tcaaggtgaa catcgaggtg aaccacgcca ccctcgccgg ccacaccttc    840
gagcacgagc tcaccgtggc cgttgacaac ggcttcctcg gcagcatcga cgccaaccgc    900
ggcgacgccc agaacggctg ggataccgac cagttcccgg tggatccgta cgatctcacc    960
caggcgatga tccagatcat ccgcaacggc ggcttcaagg acggcggcac caacttcgac   1020
gccaggctcc gccgctcttc caccgacccg gaggacatct tcatcgccca catcagcgcg   1080
atggacgcca tggcccacgc cctgctgaac gccgccgccg tcatcgagga gagcccgctc   1140
tgcgagatgg tcgccaagcg ttacgcttcc ttcgacagcg gcctcggcaa aaagttcgag   1200
gaaggcaagg ccaccctcga ggaactctac gagtatgcca aggcgaacgg tgaggtcaag   1260
gccgaatccg gcaagcagga gctctacgag acccttctga acctctacgc gaaatag      1317
```

<210> SEQ ID NO 110
<211> LENGTH: 438
<212> TYPE: PRT
<213> ORGANISM: Unknown
<220> FEATURE:
<223> OTHER INFORMATION: Obtained from environmental sample

<400> SEQUENCE: 110

```
Met Ala Lys Glu Tyr Phe Pro Thr Ile Gly Lys Ile Pro Phe Glu Gly
1               5                   10                  15

Val Glu Ser Lys Asn Pro Leu Ala Phe His Tyr Tyr Asp Ala Glu Arg
            20                  25                  30

Val Val Met Gly Lys Pro Met Lys Asp Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Arg Ala Lys Ala Asp Ala Gly Phe Glu Ile Met Gln Lys Leu Gly Ile
                85                  90                  95

Gly Tyr Tyr Cys Phe His Asp Ile Asp Leu Val Glu Asp Thr Glu Asp
            100                 105                 110

Ile Ala Glu Tyr Glu Ala Arg Met Lys Asp Ile Thr Asp Tyr Leu Val
        115                 120                 125

Glu Lys Gln Lys Glu Thr Gly Ile Lys Asn Leu Trp Gly Thr Ala Asn
    130                 135                 140

Val Phe Gly Asn Lys Arg Tyr Met Asn Gly Ala Ala Thr Asn Pro Gln
145                 150                 155                 160

Phe Asp Ile Val Ala Arg Ala Ala Leu Gln Ile Lys Asn Ala Ile Asp
                165                 170                 175

Ala Thr Ile Lys Leu Gly Gly Thr Gly Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Met Leu Thr Ala Ala Arg Asp Tyr Ala Arg Ala Asn
    210                 215                 220
```

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
            245                 250                 255

Ala Asn Gly Leu Asp Lys Asp Phe Lys Val Asn Ile Glu Val Asn His
        260                 265                 270

Ala Thr Leu Ala Gly His Thr Phe Glu His Glu Leu Thr Val Ala Val
    275                 280                 285

Asp Asn Gly Phe Leu Gly Ser Ile Asp Ala Asn Arg Gly Asp Ala Gln
290                 295                 300

Asn Gly Trp Asp Thr Asp Gln Phe Pro Val Asp Pro Tyr Asp Leu Thr
305                 310                 315                 320

Gln Ala Met Ile Gln Ile Ile Arg Asn Gly Gly Phe Lys Asp Gly Gly
            325                 330                 335

Thr Asn Phe Asp Ala Arg Leu Arg Arg Ser Ser Thr Asp Pro Glu Asp
        340                 345                 350

Ile Phe Ile Ala His Ile Ser Ala Met Asp Ala Met Ala His Ala Leu
    355                 360                 365

Leu Asn Ala Ala Ala Val Ile Glu Glu Ser Pro Leu Cys Glu Met Val
370                 375                 380

Ala Lys Arg Tyr Ala Ser Phe Asp Ser Gly Leu Gly Lys Lys Phe Glu
385                 390                 395                 400

Glu Gly Lys Ala Thr Leu Glu Glu Leu Tyr Glu Tyr Ala Lys Ala Asn
            405                 410                 415

Gly Glu Val Lys Ala Glu Ser Gly Lys Gln Glu Leu Tyr Glu Thr Leu
        420                 425                 430

Leu Asn Leu Tyr Ala Lys
        435

<210> SEQ ID NO 111
<211> LENGTH: 1317
<212> TYPE: DNA
<213> ORGANISM: Unknown
<220> FEATURE:
<223> OTHER INFORMATION: Obtained from environmental sample

<400> SEQUENCE: 111
atggcacaag cgtatttcc taccatcggg aaaatcccct tcgagggacc cgaaagcaag      60
aatcccctgg cattccatta ttatgagccc gaccgcctgg tcctgggcaa gaagatgaag    120
gactggctgc gtttcgccat ggcctggtgg cacacgctgg ccaggcttc cggcgaccag     180 ttcggcggcc agacccgcca ctacgcctgg gacgagcccg ccacgcccct ggaacgggcc    240
aaggccaagg cggatgccgg tttcgagatc atgcagaaac tgggcatcga attcttctgc    300
ttccacgatg tggacctcat cgaagagggc gccacgatcg aggaatacga gcagcggatg    360
cagcagatca cggattatct gctggtcaag atgaaagaga ccggcatccg caacctctgg    420
ggtacggcca acgtgttcgg cacgagcgc tacatgaacg cgcggccac gaaccccgat      480 ttcgatgtcg tggcccgcgc ggccgtgcag atcaagacgg ccatcgacgc caccatcaag    540
ttgggcggcg agaactatgt gttctgggc ggccgggaag ctatatgag cctgctcaat      600 acgcagatgc accgcgagaa gctgcatctg gcaagatgc tcgccgcggc ccgcgactac    660
ggacgcgccc acgcttcaa ggggaccttc ctcatcgaac ccaagccgat ggaacccacc    720
aagcatcagt atgaccagga tacggagacg gtcatcggtt cctgcgccg ctacggcctg     780

```
gacgaagact tcaaggtgaa catcgaggtc aaccacgcta cgctggccgg ccataccttc    840
gaacacgaac tggccacggc ggtcgatgcc ggcctgctgg gcagcatcga cgccaaccgc    900
ggcgacgccc agaacggctg ggataccgac cagttcccga tcgacaacta cgaactgacc    960
ctggcgatgc tgcaggtcat ccgcaacggc ggtctggccc cgggcggctc gaatttcgat   1020
gccaagctcc gccggaactc caccgatccg gaagacatct tcattgccca catcagcgcg   1080
atggatgcga tggcgcgggc cctgctcaat gcggccgccc tctgcgagac gtccccgatt   1140
ccggcgatgg tcaaggcgcg ttacgcttcg ttcgacagcg cgccggcaa ggatttcgaa    1200 gagggaagga tgacgctgga agacctcgtg gcctatgcca ggaccacgg cgagccgaag    1260 cggacctcgg gcaagcagga actctatgag accctcgtgg cgctttattg caaatag      1317
```

<210> SEQ ID NO 112
<211> LENGTH: 438
<212> TYPE: PRT
<213> ORGANISM: Unknown
<220> FEATURE:
<223> OTHER INFORMATION: Obtained from environmental sample

<400> SEQUENCE: 112

```
Met Ala Gln Ala Tyr Phe Pro Thr Ile Gly Lys Ile Pro Phe Glu Gly
1               5                   10                  15

Pro Glu Ser Lys Asn Pro Leu Ala Phe His Tyr Tyr Glu Pro Asp Arg
            20                  25                  30

Leu Val Leu Gly Lys Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Arg His Tyr Ala Trp Asp Glu Pro Ala Thr Pro Leu Glu Arg Ala
65                  70                  75                  80

Lys Ala Lys Ala Asp Ala Gly Phe Glu Ile Met Gln Lys Leu Gly Ile
                85                  90                  95

Glu Phe Phe Cys Phe His Asp Val Asp Leu Ile Glu Glu Gly Ala Thr
            100                 105                 110

Ile Glu Glu Tyr Glu Gln Arg Met Gln Gln Ile Thr Asp Tyr Leu Leu
        115                 120                 125

Val Lys Met Lys Glu Thr Gly Ile Arg Asn Leu Trp Gly Thr Ala Asn
    130                 135                 140

Val Phe Gly His Glu Arg Tyr Met Asn Gly Ala Ala Thr Asn Pro Asp
145                 150                 155                 160

Phe Asp Val Val Ala Arg Ala Ala Val Gln Ile Lys Thr Ala Ile Asp
                165                 170                 175

Ala Thr Ile Lys Leu Gly Gly Glu Asn Tyr Val Phe Trp Gly Gly Arg
            180                 185                 190

Glu Gly Tyr Met Ser Leu Leu Asn Thr Gln Met His Arg Glu Lys Leu
        195                 200                 205

His Leu Gly Lys Met Leu Ala Ala Ala Arg Asp Tyr Gly Arg Ala His
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Arg Tyr Gly Leu Asp Glu Asp Phe Lys Val Asn Ile Glu Val Asn His
            260                 265                 270
```

```
Ala Thr Leu Ala Gly His Thr Phe Glu His Glu Leu Ala Thr Ala Val
            275                 280                 285

Asp Ala Gly Leu Leu Gly Ser Ile Asp Ala Asn Arg Gly Asp Ala Gln
        290                 295                 300

Asn Gly Trp Asp Thr Asp Gln Phe Pro Ile Asp Asn Tyr Glu Leu Thr
305                 310                 315                 320

Leu Ala Met Leu Gln Val Ile Arg Asn Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Arg Ala Leu
        355                 360                 365

Leu Asn Ala Ala Ala Leu Cys Glu Thr Ser Pro Ile Pro Ala Met Val
        370                 375                 380

Lys Ala Arg Tyr Ala Ser Phe Asp Ser Gly Ala Gly Lys Asp Phe Glu
385                 390                 395                 400

Glu Gly Arg Met Thr Leu Glu Asp Leu Val Ala Tyr Ala Arg Thr His
                405                 410                 415

Gly Glu Pro Lys Arg Thr Ser Gly Lys Gln Glu Leu Tyr Glu Thr Leu
            420                 425                 430

Val Ala Leu Tyr Cys Lys
        435

<210> SEQ ID NO 113
<211> LENGTH: 1317
<212> TYPE: DNA
<213> ORGANISM: Unknown
<220> FEATURE:
<223> OTHER INFORMATION: Obtained from environmental sample

<400> SEQUENCE: 113
atgaccaacg agtatttcc cggaatcggt gtgattccgt ttgaaggaca ggaaagcaag     60
aatcccctgg ctttccatta ttatgacgcc aaccgcgtag tgatgggcaa acccatgaag    120
gaatggttca aatttgccat ggcctggtgg catacgctgg ggcaggcatc ggccgatccc    180
ttcggcggac agaccgctc ctacgcatgg gacaagggcg agtgccctta ctgccgtgcc    240
cgccagaagg ccgacgccgg cttgaactg atgcagaagc tgggaatcgg ctatttctgc    300
ttccacgatg tgaatatcat cgaggactgc gaggacattg ccgagtatga ggcccgtatg    360
aaggacatca cggactatct gctggtgaag atgaaggaaa cgggcatcaa gaatctgtgg    420
ggcacggcca acgtcttcgg ccacaagcgc tatatgaacg cgccgccac caacccgcaa    480 ttcgacgtgg tagcccgcgc tgcggtccag atcaagaacg ccctggacgc caccatcaag    540
ctgggcggca gcaattatgt gttctggggc ggccggaag ctactacac cctttttgaac    600 acgcagatgc agcgggagaa ggaccacctg gcccagatgc tcaaggcggc ccgcgactat    660
gcccgcggca aggattcaa gggcacgttc ctcattgagc caagcccat ggagcccacc    720 aagcaccagt acgacgtaga tacggagacc gtgattggtt tcctgcgcgc caacgggctg    780
gacaaggact tcaaggtgaa tatcgaagtg aaccacgcca ccctggccgg ccataccttc    840
gagcacgagc tcaccgtggc ccgcgaaaac ggcttcctgg cagcatcga cgccaaccgc    900 ggagacgccc agaacggctg ggatacagac cagttccccg tggacgcctt tgacctcacc    960
caggccatga tgcaggtcct gctcaacggg ggattcggca acggcggcac caacttcgac   1020
gccaaactgc gccgttcctc cacggatccc gaggacatct tcatcgccca catcagcgcc   1080
```

```
atggacgcca tggcccacgc cctcctgaac gccgccgcca tcctggaaga gagcccatg    1140 ccgggcatgg tgaaggagcg ctacgcttcc ttcgacaatg ccttggcaa gaagttcgag    1200 gaaggaaagg ccacgctgga agagctgtac gactatgcca agaagaacgg cgagcctgtg    1260
gccgcttccg gaaagcagga actgtacgaa acgctgctga acctgtacgc caagtaa     1317
```

<210> SEQ ID NO 114
<211> LENGTH: 438
<212> TYPE: PRT
<213> ORGANISM: Unknown
<220> FEATURE:
<223> OTHER INFORMATION: Obtained from environmental sample

<400> SEQUENCE: 114

```
Met Thr Asn Glu Tyr Phe Pro Gly Ile Gly Val Ile Pro Phe Glu Gly
1               5                   10                  15

Gln Glu Ser Lys Asn Pro Leu Ala Phe His Tyr Tyr Asp Ala Asn Arg
            20                  25                  30

Val Val Met Gly Lys Pro Met Lys Glu Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Ala Trp Asp Lys Gly Glu Cys Pro Tyr Cys Arg Ala
65                  70                  75                  80

Arg Gln Lys Ala Asp Ala Gly Phe Glu Leu Met Gln Lys Leu Gly Ile
                85                  90                  95

Gly Tyr Phe Cys Phe His Asp Val Asn Ile Ile Glu Asp Cys Glu Asp
            100                 105                 110

Ile Ala Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Val Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Gln Met Leu Lys Ala Ala Arg Asp Tyr Ala Arg Gly Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Val Asp Ala Phe Asp Leu Thr
305                 310                 315                 320

Gln Ala Met Met Gln Val Leu Leu Asn Gly Gly Phe Gly Asn Gly Gly
```

|  |  |  | 325 |  |  |  | 330 |  |  |  | 335 |  |
|---|---|---|---|---|---|---|---|---|---|---|---|---|

Thr Asn Phe Asp Ala Lys Leu Arg Arg Ser Ser Thr Asp Pro Glu Asp
                340                 345                 350

Ile Phe Ile Ala His Ile Ser Ala Met Asp Ala Met Ala His Ala Leu
            355                 360                 365

Leu Asn Ala Ala Ala Ile Leu Glu Glu Ser Pro Met Pro Gly Met Val
        370                 375                 380

Lys Glu Arg Tyr Ala Ser Phe Asp Asn Gly Leu Gly Lys Lys Phe Glu
385                 390                 395                 400

Glu Gly Lys Ala Thr Leu Glu Glu Leu Tyr Asp Tyr Ala Lys Lys Asn
                405                 410                 415

Gly Glu Pro Val Ala Ala Ser Gly Lys Gln Glu Leu Tyr Glu Thr Leu
            420                 425                 430

Leu Asn Leu Tyr Ala Lys
            435

<210> SEQ ID NO 115
<211> LENGTH: 1317
<212> TYPE: DNA
<213> ORGANISM: Unknown
<220> FEATURE:
<223> OTHER INFORMATION: Obtained from environmental sample

<400> SEQUENCE: 115

| atggcaaaag agtatttccc gactatcggc aagattccct tcgagggcgt cgaatccaag | 60 |
|---|---|
| aacccgatgg cattccacta ttatgacgcg aaacgcgtcg tgatgggcaa gcccatgaag | 120 |
| gactggctca agttcgcgat ggcctggtgg cacaccctgg acaggcttc cggcgacccg | 180 |
| ttcggcggcc agacccgttc ctacgagtgg gacaagggcg agtgcccta ctgccgcgcc | 240 |
| aaggccaagg ccgacgccgg tttcgagatc atgcagaaac tgggcatcga gtactactgc | 300 |
| ttccatgaca tcgacctggt ggaggacacc gaggacatcg ccgagtacga ggcccgcatg | 360 |
| aaggacatca ccgactacct cgtcgagaag cagaaggaga ccggtatcaa gaacctctgg | 420 |
| ggcacggcca acgtgttcgg caacaagcgc tacatgaacg cgccgccac gaacccgcag | 480 |
| ttcgacgtcg tcgcccgcgc cgccgtccag atcaagaacg ccatcgacgc caccatcaaa | 540 |
| ctcggcggca cctcttacgt gttctgggc ggccgtgaag ctactacac cctcctgaac | 600 |
| acccagatgc agcgcgagaa ggaccacctc gccaagatgc tcaccgccgc cgcgactac | 660 |
| gcccgcgccc acggcttcaa gggcaccttc ctcatcgagc ccaagcccat ggagcccacc | 720 |
| aagcaccagt acgacgtgga cacggagacc gtgatcggct tcctccgcgc caacggcctg | 780 |
| gacaaggact tcaaggtcaa tatcgaagtg aaccacgcca ccctcgccgg ccacaccttc | 840 |
| gagcatgagc tcaccgtggc ggtcgataac ggcttcctcg gctccatcga cgccaaccgt | 900 |
| ggcgacgccc agaacggctg ggataccgac cagttcccgg tggatccgta cgacctcacc | 960 |
| caggccatga tgcagatcat ccgcaacggc ggcttcaagg acggcggcac caacttcgac | 1020 |
| gccaaactcc gccgctcctc caccgacccg gaggacatct tcatcgccca catcagcgcg | 1080 |
| atggacgcca tggcccacgc gctcctgaac gccgccgccg tcatcgagga gagcccgctc | 1140 |
| tgcaagatgg tcgaggagcg ctacgcttcc ttcgacagcg gtctcggcaa gcagttcgag | 1200 |
| gaaggcaagg ccacccttga ggacctctac gagtatgcca agaagaacgg cgagcccgtc | 1260 |
| gtcgcttccg gcaagcagga gctctacgag acccttctga acctctacgc gaagtag | 1317 |

<210> SEQ ID NO 116

```
<211> LENGTH: 438
<212> TYPE: PRT
<213> ORGANISM: Unknown
<220> FEATURE:
<223> OTHER INFORMATION: Obtained from environmental sample

<400> SEQUENCE: 116
```

| | | | | | | | | | | | | | | |
|---|---|---|---|---|---|---|---|---|---|---|---|---|---|---|
| Met | Ala | Lys | Glu | Tyr | Phe | Pro | Thr | Ile | Gly | Lys | Ile | Pro | Phe | Glu | Gly |
| 1 | | | | 5 | | | | | 10 | | | | | 15 | |
| Val | Glu | Ser | Lys | Asn | Pro | Met | Ala | Phe | His | Tyr | Tyr | Asp | Ala | Lys | Arg |
| | | | 20 | | | | | 25 | | | | | 30 | | |
| Val | Val | Met | Gly | Lys | Pro | Met | Lys | Asp | Trp | Leu | Lys | Phe | Ala | Met | Ala |
| | | | 35 | | | | | 40 | | | | | 45 | | |
| Trp | Trp | His | Thr | Leu | Gly | Gln | Ala | Ser | Gly | Asp | Pro | Phe | Gly | Gly | Gln |
| 50 | | | | | 55 | | | | | 60 | | | | | |
| Thr | Arg | Ser | Tyr | Glu | Trp | Asp | Lys | Gly | Glu | Cys | Pro | Tyr | Cys | Arg | Ala |
| 65 | | | | | 70 | | | | | 75 | | | | | 80 |
| Lys | Ala | Lys | Ala | Asp | Ala | Gly | Phe | Glu | Ile | Met | Gln | Lys | Leu | Gly | Ile |
| | | | | 85 | | | | | 90 | | | | | 95 | |
| Glu | Tyr | Tyr | Cys | Phe | His | Asp | Ile | Asp | Leu | Val | Glu | Asp | Thr | Glu | Asp |
| | | | 100 | | | | | 105 | | | | | 110 | | |
| Ile | Ala | Glu | Tyr | Glu | Ala | Arg | Met | Lys | Asp | Ile | Thr | Asp | Tyr | Leu | Val |
| | | | 115 | | | | | 120 | | | | | 125 | | |
| Glu | Lys | Gln | Lys | Glu | Thr | Gly | Ile | Lys | Asn | Leu | Trp | Gly | Thr | Ala | Asn |
| 130 | | | | | 135 | | | | | 140 | | | | | |
| Val | Phe | Gly | Asn | Lys | Arg | Tyr | Met | Asn | Gly | Ala | Ala | Thr | Asn | Pro | Gln |
| 145 | | | | | 150 | | | | | 155 | | | | | 160 |
| Phe | Asp | Val | Val | Ala | Arg | Ala | Ala | Val | Gln | Ile | Lys | Asn | Ala | Ile | Asp |
| | | | | 165 | | | | | 170 | | | | | 175 | |
| Ala | Thr | Ile | Lys | Leu | Gly | Gly | Thr | Ser | Tyr | Val | Phe | Trp | Gly | Gly | Arg |
| | | | 180 | | | | | 185 | | | | | 190 | | |
| Glu | Gly | Tyr | Tyr | Thr | Leu | Leu | Asn | Thr | Gln | Met | Gln | Arg | Glu | Lys | Asp |
| | | | 195 | | | | | 200 | | | | | 205 | | |
| His | Leu | Ala | Lys | Met | Leu | Thr | Ala | Ala | Arg | Asp | Tyr | Ala | Arg | Ala | His |
| 210 | | | | | 215 | | | | | 220 | | | | | |
| Gly | Phe | Lys | Gly | Thr | Phe | Leu | Ile | Glu | Pro | Lys | Pro | Met | Glu | Pro | Thr |
| 225 | | | | | 230 | | | | | 235 | | | | | 240 |
| Lys | His | Gln | Tyr | Asp | Val | Asp | Thr | Glu | Thr | Val | Ile | Gly | Phe | Leu | Arg |
| | | | | 245 | | | | | 250 | | | | | 255 | |
| Ala | Asn | Gly | Leu | Asp | Lys | Asp | Phe | Lys | Val | Asn | Ile | Glu | Val | Asn | His |
| | | | 260 | | | | | 265 | | | | | 270 | | |
| Ala | Thr | Leu | Ala | Gly | His | Thr | Phe | Glu | His | Glu | Leu | Thr | Val | Ala | Val |
| | | | 275 | | | | | 280 | | | | | 285 | | |
| Asp | Asn | Gly | Phe | Leu | Gly | Ser | Ile | Asp | Ala | Asn | Arg | Gly | Asp | Ala | Gln |
| 290 | | | | | 295 | | | | | 300 | | | | | |
| Asn | Gly | Trp | Asp | Thr | Asp | Gln | Phe | Pro | Val | Asp | Pro | Tyr | Asp | Leu | Thr |
| 305 | | | | | 310 | | | | | 315 | | | | | 320 |
| Gln | Ala | Met | Met | Gln | Ile | Ile | Arg | Asn | Gly | Gly | Phe | Lys | Asp | Gly | Gly |
| | | | | 325 | | | | | 330 | | | | | 335 | |
| Thr | Asn | Phe | Asp | Ala | Lys | Leu | Arg | Arg | Ser | Ser | Thr | Asp | Pro | Glu | Asp |
| | | | 340 | | | | | 345 | | | | | 350 | | |
| Ile | Phe | Ile | Ala | His | Ile | Ser | Ala | Met | Asp | Ala | Met | Ala | His | Ala | Leu |
| | | | 355 | | | | | 360 | | | | | 365 | | |
| Leu | Asn | Ala | Ala | Ala | Val | Ile | Glu | Glu | Ser | Pro | Leu | Cys | Lys | Met | Val |
| 370 | | | | | 375 | | | | | 380 | | | | | |

Glu Arg Tyr Ala Ser Phe Asp Ser Gly Leu Gly Lys Gln Phe Glu
385                 390                 395                 400

Glu Gly Lys Ala Thr Leu Glu Asp Leu Tyr Glu Tyr Ala Lys Lys Asn
                405                 410                 415

Gly Glu Pro Val Val Ala Ser Gly Lys Gln Glu Leu Tyr Glu Thr Leu
            420                 425                 430

Leu Asn Leu Tyr Ala Lys
        435

<210> SEQ ID NO 117
<211> LENGTH: 1317
<212> TYPE: DNA
<213> ORGANISM: Unknown
<220> FEATURE:
<223> OTHER INFORMATION: Obtained from environmental sample

<400> SEQUENCE: 117

```
atgtcaactg agtatttccc tacaatcggc aagattccct tcgagggacc cgagagcaag      60
aaccccatgg ccttccacta ctatgaaccc gaaaagttgg tgatgggcaa gaagatgaag     120
gactggctgc gtttcgcaat ggcctggtgg cacacccttg agccgcatc cggcgaccag      180
ttcggcggac agacccgcag ttacgcctgg gacaagggcg actgcccta cagccgcgcc      240
cgcgccaagg tcgacgccgg cttcgagatc atgcagaagc tcggcataga gttcttctgc    300
ttccatgaca tcgacctggt cgaggatacc gacgacatcg ccgagtatga agcccggatg    360
aaagacatca cggactatct gctggaaaag atggaggcta ccggcatcaa gaacctctgg    420
ggcacggcca atgtcttcgg tcacaagcgt tatatgaacg gtgcagccac aaaccccgat    480
ttcgcagtgg tcgcaagggc ggccgtgcag atcaagaacg ccatcgacgc caccatcaag    540
ctgggtggtg agaactatgt gttctggggt ggacgcgagg gttatatgag cctgctcaac    600
acccagatgc agagggagaa ggaacaccct gccaagatgc tcaccgccgc acgtgactat    660
gcacgcgcca aggtttcaa gggcacgttc ctcatcgaac ccaagccgat ggaacccacc     720
aagcaccagt atgaccagga taccgagacc gttatcggat ccctccgcag ccacggcctg    780
gacaaggact tcaaggtcaa catcgaggtg aaccacgcca cctgcgggg ccataccttc     840
gagcacgaac tggccaccgc cgtcgacaac ggcatgctcg gcagcatcga cgccaaccgc    900
ggagacgccc agaacggctg ggacaccgac cagttcccga tcgacaactt cgagctcacg    960
cttgccatga tgcagataat ccgcaacggc ggcctggcac cgggcggttc gaacttcgac   1020
gcaaagctgc cgccgcaattc caccgatccc gaggacatct tcatcgccca catcagcgcg   1080
atggacgcca tggcccgcgc cctcgtcaac gccgccgcca tcctcggcga gtcgcccgtt   1140
ccggctatgg tcaaggaccg ctatgcttcg ttcgactgcg gcaagggcaa ggacttcgaa   1200
gacggcaaac tgactctcga agacatcgtc gcctacgcca gggagaatgg cgagccgaaa   1260
cagatttccg gcaagcagga actctacgaa actatcgtcg ctctttactg caagtaa      1317
```

<210> SEQ ID NO 118
<211> LENGTH: 438
<212> TYPE: PRT
<213> ORGANISM: Unknown
<220> FEATURE:
<223> OTHER INFORMATION: Obtained from environmental sample

<400> SEQUENCE: 118

Met Ser Thr Glu Tyr Phe Pro Thr Ile Gly Lys Ile Pro Phe Glu Gly
1               5                   10                  15

```
Pro Glu Ser Lys Asn Pro Met Ala Phe His Tyr Tyr Glu Pro Glu Lys
             20                  25                  30

Leu Val Met Gly Lys Lys Met Lys Asp Trp Leu Arg Phe Ala Met Ala
         35                  40                  45

Trp Trp His Thr Leu Gly Ala Ala Ser Gly Asp Gln Phe Gly Gly Gln
     50                  55                  60

Thr Arg Ser Tyr Ala Trp Asp Lys Gly Asp Cys Pro Tyr Ser Arg Ala
 65                  70                  75                  80

Arg Ala Lys Val Asp Ala Gly Phe Glu Ile Met Gln Lys Leu Gly Ile
                 85                  90                  95

Glu Phe Phe Cys Phe His Asp Ile Asp Leu Val Glu Asp Thr Asp Asp
            100                 105                 110

Ile Ala Glu Tyr Glu Ala Arg Met Lys Asp Ile Thr Asp Tyr Leu Leu
        115                 120                 125

Glu Lys Met Glu Ala Thr Gly Ile Lys Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Ala Val Val Ala Arg Ala Ala Val Gln Ile Lys Asn Ala Ile Asp
                165                 170                 175

Ala Thr Ile Lys Leu Gly Gly Glu Asn Tyr Val Phe Trp Gly Gly Arg
            180                 185                 190

Glu Gly Tyr Met Ser Leu Leu Asn Thr Gln Met Gln Arg Glu Lys Glu
        195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Ser His Gly Leu Asp Lys Asp Phe Lys Val Asn Ile Glu Val Asn His
            260                 265                 270

Ala Thr Leu Ala Gly His Thr Phe Glu His Glu Leu Ala Thr Ala Val
        275                 280                 285

Asp Asn Gly Met Leu Gly Ser Ile Asp Ala Asn Arg Gly Asp Ala Gln
    290                 295                 300

Asn Gly Trp Asp Thr Asp Gln Phe Pro Ile Asp Asn Phe Glu Leu Thr
305                 310                 315                 320

Leu Ala Met Met Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Val Asn Ala Ala Ala Ile Leu Gly Glu Ser Pro Val Pro Ala Met Val
    370                 375                 380

Lys Asp Arg Tyr Ala Ser Phe Asp Cys Gly Lys Gly Lys Asp Phe Glu
385                 390                 395                 400

Asp Gly Lys Leu Thr Leu Glu Asp Ile Val Ala Tyr Ala Arg Glu Asn
                405                 410                 415

Gly Glu Pro Lys Gln Ile Ser Gly Lys Gln Glu Leu Tyr Glu Thr Ile
            420                 425                 430
```

Val Ala Leu Tyr Cys Lys
        435

<210> SEQ ID NO 119
<211> LENGTH: 1314
<212> TYPE: DNA
<213> ORGANISM: Unknown
<220> FEATURE:
<223> OTHER INFORMATION: Obtained from environmental sample

<400> SEQUENCE: 119

| | | | | | |
|---|---|---|---|---|---|
| atgtcatatt | ttcctactat | cggtaacatc | cccttttgagg | gtgtagagag | caagaatccc | 60 |
| cttgccttcc | attattatga | cgcttcccgc | gtagttatgg | gcaagcccat | gaaggagtgg | 120 |
| ctcaagtttg | ccatggcctg | gtggcacacg | ctgggtcagg | catcggccga | ccctttcggc | 180 |
| ggacaaaccc | gcagctatgc | ctgggacaaa | ggcgagtgcc | cctactgccg | tgcccgtgcc | 240 |
| aaggccgacg | ccggcttcga | gctcatgcag | aaactgggca | tcgagtattt | ctgctcccac | 300 |
| gacattgacc | tcatcgagga | ctgcgacgac | attgcagagt | acgaggcccg | tctgaaggac | 360 |
| attacggact | acctcctgga | gaagatgaag | aagaccggta | tcaagaacct | gtggggtacg | 420 |
| gccaatgtgt | tcggtaacaa | gcgttacatg | aacggtgctg | ctaccaaccc | tcagtttgac | 480 |
| gttgtggccc | gcgctgccgt | ccagatcaag | aacgccattg | acgctaccat | caagctgggc | 540 |
| ggttccaact | atgtgttctg | gggtggccgt | gagggttact | acacgcttct | gaacacccag | 600 |
| atgcagcgtg | agaagaatca | cctggctgcc | atgctcaagg | ctgcccgcga | ctatgcccgc | 660 |
| gccaacggtt | tcaagggcac | cttcctcatt | gagcccaagc | ccatggagcc | caccaagcac | 720 |
| cagtacgacg | tagacacgga | gaccgtgatt | ggattcctcc | gcgccaacgg | tctggagaag | 780 |
| gacttcaagg | tgaacattga | ggtgaaccac | gctactcttg | ccggtcacac | cttcgagcac | 840 |
| gagctcaccg | tggcccgtga | gaacggcttc | ctgggttcca | ttgacgccaa | ccgcggagat | 900 |
| gcccagaacg | gctgggacac | cgaccagttc | ccggtagatg | cctttgacct | cacccaggcc | 960 |
| atgatgcaga | ttctcctcaa | cggaggctcc | ggcaatggcg | gtaccaactt | tgacgccaag | 1020 |
| ctgcgccgtt | cctccaccga | ccccgaggac | atcttcatcg | cgcacatcag | cgccatggat | 1080 |
| gccatggctc | acgccctgct | caatgcagct | gccgtgctgg | aggagagccc | gctttgcaag | 1140 |
| atggtcaagg | agcgttacgc | ttccttcgac | agcggtcttg | gcaagcagtt | cgaggaagga | 1200 |
| aaggctacgc | tggaagatct | gtatgcctat | gccgtcaaga | acggtgagcc | cgtggtggct | 1260 |
| tccggcaagc | aggaactgta | cgaaaccttc | ctgaacctct | atgcaaaatg | gtaa | 1314 |

<210> SEQ ID NO 120
<211> LENGTH: 437
<212> TYPE: PRT
<213> ORGANISM: Unknown
<220> FEATURE:
<223> OTHER INFORMATION: Obtained from environmental sample

<400> SEQUENCE: 120

Met Ser Tyr Phe Pro Thr Ile Gly Asn Ile Pro Phe Glu Gly Val Glu
1               5                   10                  15

Ser Lys Asn Pro Leu Ala Phe His Tyr Tyr Asp Ala Ser Arg Val Val
            20                  25                  30

Met Gly Lys Pro Met Lys Glu Trp Leu Lys Phe Ala Met Ala Trp Trp
        35                  40                  45

His Thr Leu Gly Gln Ala Ser Ala Asp Pro Phe Gly Gly Gln Thr Arg
    50                  55                  60

```
Ser Tyr Ala Trp Asp Lys Gly Glu Cys Pro Tyr Cys Arg Ala Arg Ala
 65                  70                  75                  80

Lys Ala Asp Ala Gly Phe Glu Leu Met Gln Lys Leu Gly Ile Glu Tyr
                 85                  90                  95

Phe Cys Ser His Asp Ile Asp Leu Ile Glu Asp Cys Asp Asp Ile Ala
            100                 105                 110

Glu Tyr Glu Ala Arg Leu Lys Asp Ile Thr Asp Tyr Leu Leu Glu Lys
        115                 120                 125

Met Lys Lys Thr Gly Ile Lys Asn Leu Trp Gly Thr Ala Asn Val Phe
130                 135                 140

Gly Asn Lys Arg Tyr Met Asn Gly Ala Ala Thr Asn Pro Gln Phe Asp
145                 150                 155                 160

Val Val Ala Arg Ala Ala Val Gln Ile Lys Asn Ala Ile Asp Ala Thr
                165                 170                 175

Ile Lys Leu Gly Gly Ser Asn Tyr Val Phe Trp Gly Gly Arg Glu Gly
            180                 185                 190

Tyr Tyr Thr Leu Leu Asn Thr Gln Met Gln Arg Glu Lys Asn His Leu
        195                 200                 205

Ala Ala Met Leu Lys Ala Ala Arg Asp Tyr Ala Arg Ala Asn Gly Phe
210                 215                 220

Lys Gly Thr Phe Leu Ile Glu Pro Lys Pro Met Glu Pro Thr Lys His
225                 230                 235                 240

Gln Tyr Asp Val Asp Thr Glu Thr Val Ile Gly Phe Leu Arg Ala Asn
                245                 250                 255

Gly Leu Glu Lys Asp Phe Lys Val Asn Ile Glu Val Asn His Ala Thr
            260                 265                 270

Leu Ala Gly His Thr Phe Glu His Glu Leu Thr Val Ala Arg Glu Asn
        275                 280                 285

Gly Phe Leu Gly Ser Ile Asp Ala Asn Arg Gly Asp Ala Gln Asn Gly
290                 295                 300

Trp Asp Thr Asp Gln Phe Pro Val Asp Ala Phe Asp Leu Thr Gln Ala
305                 310                 315                 320

Met Met Gln Ile Leu Leu Asn Gly Gly Ser Gly Asn Gly Gly Thr Asn
                325                 330                 335

Phe Asp Ala Lys Leu Arg Arg Ser Ser Thr Asp Pro Glu Asp Ile Phe
            340                 345                 350

Ile Ala His Ile Ser Ala Met Asp Ala Met Ala His Ala Leu Leu Asn
        355                 360                 365

Ala Ala Ala Val Leu Glu Glu Ser Pro Leu Cys Lys Met Val Lys Glu
370                 375                 380

Arg Tyr Ala Ser Phe Asp Ser Gly Leu Gly Lys Gln Phe Glu Glu Gly
385                 390                 395                 400

Lys Ala Thr Leu Glu Asp Leu Tyr Ala Tyr Ala Val Lys Asn Gly Glu
                405                 410                 415

Pro Val Val Ala Ser Gly Lys Gln Glu Leu Tyr Glu Thr Phe Leu Asn
            420                 425                 430

Leu Tyr Ala Lys Trp
        435

<210> SEQ ID NO 121
<211> LENGTH: 1317
<212> TYPE: DNA
<213> ORGANISM: Unknown
<220> FEATURE:
<223> OTHER INFORMATION: Obtained from environmental sample
```

<400> SEQUENCE: 121

```
atgtcaactg agtatttccc tacaatcggc aagattccct tcgagggacc cgagagcaag      60
aaccccatgg ccttccacta ctatgaaccc gaaaagttgg tgatgggcaa gaagatgaag     120
gactggctgc gtttcgcaat ggcctggtgg cacacccttg gagccgcatc cggcgaccag     180
ttcggcggac agaccgcag ttacgcctgg acaagggcg actgcccctta cagccgcgcc     240
cgcgccaagg tcgacgccgg cttcgagatc atgcagaagc tcggcataga gttcttctgc     300
ttccatgaca tcgacctggt cgaggatacc gacgacatcg ccgagtatga agcccggatg     360
aaagacatca cggactatct gctggaaaag atggaggtta ccggcatcaa gaacctctgg     420
ggcacggcca atgtcttcgg tcacaagcgt tatatgaacg atgcagccac aaaccccgat     480
ttcgcagtgg tcgcaagggc ggccgtgcag atcaagaacg ccatcgacgc caccatcaag     540
ctgggtggtg agaactatgt gttctggggt ggacgcgagg gttatatgag cctgctcaac     600
acccagatgc agagggagaa ggaacacctt gccaagatgc tcaccgccgc acgtgactat     660
gcacgcgcca aggtttcaa gggcacgttc ctcatcgaac ccgagccgat ggaacccacc     720
aagcaccagt atgaccagga taccgagacc gttatcggat cctccgcag ccacggcctg     780
gacaaggact tcaaggtcaa catcgaggtg aaccacgcca ccctggcggg ccataccttc     840
gagcacgaac tggccaccgc cgtcgacaac ggcatgctcg gcagcatcga cgccaaccgc     900
ggagacgccc agaacggctg ggacaccgac cagttcccga tcgacaactt cgagctcacg     960
cttgccatga tgcagataat ccgcaacggc ggcctggcac cgggcggttc gaacttcgac    1020
gcaaagctgc ccgcaattc caccgatccc gaggacatca tcatcgccca catcagcgcg    1080
atggacgcca tggcccgcgc cctcgtcaac gccgccgcca tcctcggcga gtcgcccgtt    1140
ccggctatgg tcaaggaccg ctatgcttcg ttcgactgcg gcaagggcaa ggacttcgaa    1200
gacggcaaac tgactctcga agacatcgtc gcctacgcca gggagaatgg cgagccgaaa    1260
cagatttccg gcaagcagga actctacgaa actatcgtcg ctctttactg caagtaa      1317
```

<210> SEQ ID NO 122
<211> LENGTH: 438
<212> TYPE: PRT
<213> ORGANISM: Unknown
<220> FEATURE:
<223> OTHER INFORMATION: Obtained from environmental sample

<400> SEQUENCE: 122

```
Met Ser Thr Glu Tyr Phe Pro Thr Ile Gly Lys Ile Pro Phe Glu Gly
1               5                   10                  15

Pro Glu Ser Lys Asn Pro Met Ala Phe His Tyr Tyr Glu Pro Glu Lys
            20                  25                  30

Leu Val Met Gly Lys Lys Met Lys Asp Trp Leu Arg Phe Ala Met Ala
        35                  40                  45

Trp Trp His Thr Leu Gly Ala Ala Ser Gly Asp Gln Phe Gly Gly Gln
    50                  55                  60

Thr Arg Ser Tyr Ala Trp Asp Lys Gly Asp Cys Pro Tyr Ser Arg Ala
65                  70                  75                  80

Arg Ala Lys Val Asp Ala Gly Phe Glu Ile Met Gln Lys Leu Gly Ile
                85                  90                  95

Glu Phe Phe Cys Phe His Asp Ile Asp Leu Val Glu Asp Thr Asp Asp
            100                 105                 110

Ile Ala Glu Tyr Glu Ala Arg Met Lys Asp Ile Thr Asp Tyr Leu Leu
```

```
                  115                 120                 125
Glu Lys Met Glu Val Thr Gly Ile Lys Asn Leu Trp Gly Thr Ala Asn
    130                 135                 140

Val Phe Gly His Lys Arg Tyr Met Asn Asp Ala Ala Thr Asn Pro Asp
145                 150                 155                 160

Phe Ala Val Val Ala Arg Ala Ala Val Gln Ile Lys Asn Ala Ile Asp
                165                 170                 175

Ala Thr Ile Lys Leu Gly Gly Glu Asn Tyr Val Phe Trp Gly Gly Arg
            180                 185                 190

Glu Gly Tyr Met Ser Leu Leu Asn Thr Gln Met Gln Arg Glu Lys Glu
        195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Pro Met Glu Pro Thr
225                 230                 235                 240

Lys His Gln Tyr Asp Gln Asp Thr Glu Thr Val Ile Gly Phe Leu Arg
                245                 250                 255

Ser His Gly Leu Asp Lys Asp Phe Lys Val Asn Ile Glu Val Asn His
            260                 265                 270

Ala Thr Leu Ala Gly His Thr Phe Glu His Glu Leu Ala Thr Ala Val
        275                 280                 285

Asp Asn Gly Met Leu Gly Ser Ile Asp Ala Asn Arg Gly Asp Ala Gln
    290                 295                 300

Asn Gly Trp Asp Thr Asp Gln Phe Pro Ile Asp Asn Phe Glu Leu Thr
305                 310                 315                 320

Leu Ala Met Met Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Ile Ile Ala His Ile Ser Ala Met Asp Ala Met Ala Arg Ala Leu
        355                 360                 365

Val Asn Ala Ala Ala Ile Leu Gly Glu Ser Pro Val Pro Ala Met Val
    370                 375                 380

Lys Asp Arg Tyr Ala Ser Phe Asp Cys Gly Lys Gly Lys Asp Phe Glu
385                 390                 395                 400

Asp Gly Lys Leu Thr Leu Glu Asp Ile Val Ala Tyr Ala Arg Glu Asn
                405                 410                 415

Gly Glu Pro Lys Gln Ile Ser Gly Lys Gln Glu Leu Tyr Glu Thr Ile
            420                 425                 430

Val Ala Leu Tyr Cys Lys
        435

<210> SEQ ID NO 123
<211> LENGTH: 1317
<212> TYPE: DNA
<213> ORGANISM: Unknown
<220> FEATURE:
<223> OTHER INFORMATION: Obtained from environmental sample

<400> SEQUENCE: 123
atgaccaacg agtattttcc cggaatcggt gtgattccgt ttgaaggaca ggaaagcaag     60
aatcccctgg ctttccatta ttatgacgcc aaccgcgtag tgatgggcaa acccatgaag    120
gaatggttca aatttgccat ggcctggtgg catacgctgg gcaggcatc ggccgatccc     180 ttcggcggac agaccgctc ctacgcatgg gacaagggcg agtgcccctta ctgccgtgcc    240
```

-continued

```
cgccagaagg ccgacgccgg ctttgaactg atgcagaagc tgggaatcgg ctatttctgc    300
ttccacgatg tggatatcat cgaggactgc gaggacattg ccgagtatga ggcccgtatg    360
aaggacatca cggactatct gctggtgaag atgaaggaaa cgggcatcaa gaatctgtgg    420
ggcacggcca acgtcttcgg ccacaagcgc tatatgaacg gcgccgccac caacccgcaa    480
ttcgacgtgg tagcccgcgc tgcggtccag atcaagaacg ccctggacgc caccatcaag    540
ctgggcggca gcaattatgt gttctggggc ggccggaagg ctactacac ccttttgaac     600 acgcagatgc agcgggagaa ggaccacctg cccagatgc tcaaggcggc ccgcgactat     660
gcccgcggca aggattcaa gggcacgttc ctcattgagc ccaagcccat ggagcccacc     720
aagcaccagt acgacgtaga tacggagacc gtgattggtt tcctgcgcgc caacgggctg    780
gacaaggact tcaaggtgaa tatcgaagtg aaccacgcca ccctggccgg ccataccttc    840
gagcacgagc tcaccgtggc ccgcgaaaac ggcttcctgg gcagcatcga cgccaaccgc    900
ggagacgccc agaacggctg ggatacagac cagttccccg tggacgcctt tgacctcacc    960
caggccatga tgcaggtcct gctcaacggc ggattcggca acggcggcac caacttcgac   1020
gccaaactgc ccgttcctc cacggatccc gaggacatct tcatcgccca catcagcgcc    1080
atggacgcca tggcccacgc cctcctgaac gccgccgcca tcctggaaga gagccccatg   1140
ccgggcatgg tgaaggagcg ctacgcttcc ttcgacaatg gccttggcaa gaagttcgag   1200
gaaggaaagg ccacgctgga agagctgtac gactatgcca agaagaacgg cgagcctgtg   1260
gccgcttccg gaaagcagga actgtacgaa acgctgctga acctgtacgc caagtaa      1317
```

<210> SEQ ID NO 124
<211> LENGTH: 438
<212> TYPE: PRT
<213> ORGANISM: Unknown
<220> FEATURE:
<223> OTHER INFORMATION: Obtained from environmental sample

<400> SEQUENCE: 124

```
Met Thr Asn Glu Tyr Phe Pro Gly Ile Gly Val Ile Pro Phe Glu Gly
1               5                   10                  15

Gln Glu Ser Lys Asn Pro Leu Ala Phe His Tyr Tyr Asp Ala Asn Arg
            20                  25                  30

Val Val Met Gly Lys Pro Met Lys Glu Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Ala Trp Asp Lys Gly Glu Cys Pro Tyr Cys Arg Ala
65                  70                  75                  80

Arg Gln Lys Ala Asp Ala Gly Phe Glu Leu Met Gln Lys Leu Gly Ile
                85                  90                  95

Gly Tyr Phe Cys Phe His Asp Val Asp Ile Ile Glu Asp Cys Glu Asp
            100                 105                 110

Ile Ala Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Val Val Ala Arg Ala Ala Val Gln Ile Lys Asn Ala Leu Asp
                165                 170                 175
```

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Gln Met Leu Lys Ala Ala Arg Asp Tyr Ala Arg Gly Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
            245                 250                 255

Ala Asn Gly Leu Asp Lys Asp Phe Lys Val Asn Ile Glu Val Asn His
        260                 265                 270

Ala Thr Leu Ala Gly His Thr Phe Glu His Glu Leu Thr Val Ala Arg
    275                 280                 285

Glu Asn Gly Phe Leu Gly Ser Ile Asp Ala Asn Arg Gly Asp Ala Gln
290                 295                 300

Asn Gly Trp Asp Thr Asp Gln Phe Pro Val Asp Ala Phe Asp Leu Thr
305                 310                 315                 320

Gln Ala Met Met Gln Val Leu Asn Gly Gly Phe Gly Asn Gly Gly
            325                 330                 335

Thr Asn Phe Asp Ala Lys Leu Arg Arg Ser Ser Thr Asp Pro Glu Asp
        340                 345                 350

Ile Phe Ile Ala His Ile Ser Ala Met Asp Ala Met Ala His Ala Leu
    355                 360                 365

Leu Asn Ala Ala Ala Ile Leu Glu Glu Ser Pro Met Pro Gly Met Val
    370                 375                 380

Lys Glu Arg Tyr Ala Ser Phe Asp Asn Gly Leu Gly Lys Lys Phe Glu
385                 390                 395                 400

Glu Gly Lys Ala Thr Leu Glu Glu Leu Tyr Asp Tyr Ala Lys Lys Asn
            405                 410                 415

Gly Glu Pro Val Ala Ala Ser Gly Lys Gln Glu Leu Tyr Glu Thr Leu
        420                 425                 430

Leu Asn Leu Tyr Ala Lys
        435

<210> SEQ ID NO 125
<211> LENGTH: 1317
<212> TYPE: DNA
<213> ORGANISM: Unknown
<220> FEATURE:
<223> OTHER INFORMATION: Obtained from environmental sample

<400> SEQUENCE: 125
atggcaaaag agtatttccc gcagatcgga aagatcggct tgagggtct tgagagcaag      60 aacccgatgg cattccatta ttatgacgcc gagcgtgtcg tgctcggaaa gaagatgaag    120
gactggctga agttcgcgat ggcctggtgg catacgctcg acaggcttc cggcgaccca     180 ttcggcggcc agactcgcag ctatgagtgg gacaagggcg agtgcccta ctgccgtgcc     240 cgcgccaagg ccgacgccgg cttcgagctc atgcagaagc tcggcatcga gtacttctgc    300
ttccacgaca tcgacctcat cgaggactgc gacgacatcg acgagtacga ggcccggatg    360
aaggacatca ccgactacct gctggagaag atgaaggaga ccggaatcaa gaatctctgg    420
ggaacggcca acgtcttcgg tcacaagcgc tacatgaacg cgccgctac caatccgcag     480 tttgaaatcg tcgccgcgc tgccgtccag atcaagaacg cgctcgacgc caccatcaag    540

```
ctcggcggct ccaactacgt cttctggggc ggccgcgagg gctattacac gctgctgaat      600
acccagatgc agcgcgagaa ggaccatctc gccaggctcc ttaccgccgc ccgcgactat      660
gcgcgcgcca aggggttcaa ggggaccttc cccatcgagc cgaagccgat ggagccgacc      720
aagcaccagt atgacgtcga cacggagacc gtcatcggtt tcctccgcca gaatggcctc      780
gacaaggact tcaaggtcaa tatcgaggtg aaccacgcca ccctcgccgg ccataccttc      840
gagcacgagc tgaccgcggc ccgggagaac ggcttcctcg gcagcatcga cgccaaccgc      900
ggcgacgccc agaacggctg ggacaccgac cagttcccgg tggacgcctt cgatctcacg      960
cgggccatga tgcagatcct gctcaatggc ggtttcggca acggcggcac caacttcgac     1020
gccaagctgc gccgcagctc caccgatccc gaggacatct tcatcgccca catcagcgcg     1080
atggacgcca tggcccacgc cctgctgaat gcggccgcca tcctcgagga aagcccgctg     1140
ccggccctgg tcaagcagcg ctatgcgtcc ttcgacagcg gtctcggcaa gcagttcgag     1200
gagggtaagg ccacgctcga ggacctgtac gcatacgcga aggagcacgg cgagcccgtc     1260
gcggcctccg gcaagcagga gctctgcgag acctatctca acctctacgc gaaataa        1317
```

<210> SEQ ID NO 126
<211> LENGTH: 438
<212> TYPE: PRT
<213> ORGANISM: Unknown
<220> FEATURE:
<223> OTHER INFORMATION: Obtained from environmental sample

<400> SEQUENCE: 126

```
Met Ala Lys Glu Tyr Phe Pro Gln Ile Gly Lys Ile Gly Phe Glu Gly
  1               5                  10                  15

Leu Glu Ser Lys Asn Pro Met Ala Phe His Tyr Tyr Asp Ala Glu Arg
             20                  25                  30

Val Val Leu Gly Lys Lys Met Lys Asp Trp Leu Lys Phe Ala Met Ala
         35                  40                  45

Trp Trp His Thr Leu Gly Gln Ala Ser Gly Asp Pro Phe Gly Gly Gln
     50                  55                  60

Thr Arg Ser Tyr Glu Trp Asp Lys Gly Glu Cys Pro Tyr Cys Arg Ala
 65                  70                  75                  80

Arg Ala Lys Ala Asp Ala Gly Phe Glu Leu Met Gln Lys Leu Gly Ile
                 85                  90                  95

Glu Tyr Phe Cys Phe His Asp Ile Asp Leu Ile Glu Asp Cys Asp Asp
            100                 105                 110

Ile Asp Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Glu Ile Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Arg Leu Leu Thr Ala Ala Arg Asp Tyr Ala Arg Ala Lys
    210                 215                 220
```

```
Gly Phe Lys Gly Thr Phe Pro Ile Glu Pro Lys Pro Met Glu Pro Thr
225                 230                 235                 240

Lys His Gln Tyr Asp Val Asp Thr Glu Thr Val Ile Gly Phe Leu Arg
            245                 250                 255

Gln Asn Gly Leu Asp Lys Asp Phe Lys Val Asn Ile Glu Val Asn His
        260                 265                 270

Ala Thr Leu Ala Gly His Thr Phe Glu His Glu Leu Thr Ala Ala Arg
    275                 280                 285

Glu Asn Gly Phe Leu Gly Ser Ile Asp Ala Asn Arg Gly Asp Ala Gln
290                 295                 300

Asn Gly Trp Asp Thr Asp Gln Phe Pro Val Asp Ala Phe Asp Leu Thr
305                 310                 315                 320

Arg Ala Met Met Gln Ile Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Leu Pro Ala Leu Val
370                 375                 380

Lys Gln Arg Tyr Ala Ser Phe Asp Ser Gly Leu Gly Lys Gln Phe Glu
385                 390                 395                 400

Glu Gly Lys Ala Thr Leu Glu Asp Leu Tyr Ala Tyr Ala Lys Glu His
                405                 410                 415

Gly Glu Pro Val Ala Ala Ser Gly Lys Gln Glu Leu Cys Glu Thr Tyr
            420                 425                 430

Leu Asn Leu Tyr Ala Lys
            435

<210> SEQ ID NO 127
<211> LENGTH: 1317
<212> TYPE: DNA
<213> ORGANISM: Unknown
<220> FEATURE:
<223> OTHER INFORMATION: Obtained from environmental sample

<400> SEQUENCE: 127
atgagtaaag agtattttcc tgggattggc aaaatcccgt atgagggagc cgagagcaag      60
aatgtgatgg cattccacta ttatgatccc gaacgcgtgg tcatgggcaa gaaaatgaaa     120
gactggttca agttcgctat tgcctggtgg catacgctgg gcaggccag tgctgaccag     180 tttggcggac agaccgtttt ctatgaatgg acaaagccg aggacccctt gcagcgtgcc     240
aaggacaaga tggatgccgg tttgaaatc atgcagaagc tgggcatcga gtatttctgt     300
ttccatgatg tggacctcat cgaggaggcc gataccatcg aggaatatga agcccgcatg     360
caggcgatta ccgactacgc gctggagaag atgaaggcaa cgggtatcaa gttgctgtgg     420
ggcactgcca acgtgttcgg ccacaagcgt tacatgaacg cgccgccac caatcccgac     480 ttcaatgtcg tggcacgtgc agccgtgcag atcaagaacg ccctcgatgc taccatcaag     540
ttgggcggaa cgagctacgt cttctggggc ggtcgtgaag ctatcagag cctgctcaac     600 acccagatgc agcgcgagaa gaaccacctg gccaagatgc tcacggcagc ccgtgactat     660
gcccgtgcta agggcttcaa gggcaccttc ctgattgagc caagccgat ggaacccacc     720 aagcaccagt atgaccagga caccgagacc gttatcggct tcttgcgtgc caatggcctt     780
gacaaggact ttaaggtcaa cattgaggtc aaccatgcca cgctggctgg ccacaccttt     840
```

```
gcacatgagt tggcagtggc tgtggataac ggtatgctgg gcagcatcga tgctaaccgt      900
ggtgaccacc agaacggctg ggatacagac cagttcccca tcaacagtta tgaactcacc      960
aatgctatgc tgcagatcat gcacggcggc ggtttcaagg acggcggtac caactttgac     1020
gccaagctgc gccgcaacag taccgacccc gaggacatct ttaccgctca catcagtggt     1080
atggacgctc tggcccgtgc cctgttgagt gctgccgata tccttgagaa gagcgagttg     1140
cctgaaatgc tcaaggaacg ctatgccagc tttgacgcgg gtgaaggcaa gcgctttgag     1200
gatggccaga tgactcttga ggaactggtt gcctatgcca agtcccatgg cgagcctgct     1260
accatcagtg gcaagcagga aaaatatgaa gccatcgtgg ctttgcacgt caagtaa       1317
```

<210> SEQ ID NO 128
<211> LENGTH: 438
<212> TYPE: PRT
<213> ORGANISM: Unknown
<220> FEATURE:
<223> OTHER INFORMATION: Obtained from environmental sample

<400> SEQUENCE: 128

```
Met Ser Lys Glu Tyr Phe Pro Gly Ile Gly Lys Ile Pro Tyr Glu Gly
1               5                   10                  15

Ala Glu Ser Lys Asn Val Met Ala Phe His Tyr Tyr Asp Pro Glu Arg
            20                  25                  30

Val Val Met Gly Lys Lys Met Lys Asp Trp Phe Lys Phe Ala Ile Ala
        35                  40                  45

Trp Trp His Thr Leu Gly Gln Ala Ser Ala Asp Gln Phe Gly Gly Gln
    50                  55                  60

Thr Arg Phe Tyr Glu Trp Asp Lys Ala Glu Asp Pro Leu Gln Arg Ala
65                  70                  75                  80

Lys Asp Lys Met Asp Ala Gly Phe Glu Ile Met Gln Lys Leu Gly Ile
                85                  90                  95

Glu Tyr Phe Cys Phe His Asp Val Asp Leu Ile Glu Glu Ala Asp Thr
            100                 105                 110

Ile Glu Glu Tyr Glu Ala Arg Met Gln Ala Ile Thr Asp Tyr Ala Leu
        115                 120                 125

Glu Lys Met Lys Ala Thr Gly Ile Lys Leu Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asn Val Val Ala Arg Ala Ala Val Gln Ile Lys Asn Ala Leu Asp
                165                 170                 175

Ala Thr Ile Lys Leu Gly Gly Thr Ser Tyr Val Phe Trp Gly Gly Arg
            180                 185                 190

Glu Gly Tyr Gln Ser Leu Leu Asn Thr Gln Met Gln Arg Glu Lys Asn
        195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Ala His Glu Leu Ala Val Ala Val
```

```
                275                 280                 285
Asp Asn Gly Met Leu Gly Ser Ile Asp Ala Asn Arg Gly Asp His Gln
    290                 295                 300

Asn Gly Trp Asp Thr Asp Gln Phe Pro Ile Asn Ser Tyr Glu Leu Thr
305                 310                 315                 320

Asn Ala Met Leu Gln Ile Met His Gly Gly Phe Lys Asp Gly Gly
                325                 330                 335

Thr Asn Phe Asp Ala Lys Leu Arg Arg Asn Ser Thr Asp Pro Glu Asp
            340                 345                 350

Ile Phe Thr Ala His Ile Ser Gly Met Asp Ala Leu Ala Arg Ala Leu
        355                 360                 365

Leu Ser Ala Ala Asp Ile Leu Glu Lys Ser Glu Leu Pro Glu Met Leu
    370                 375                 380

Lys Glu Arg Tyr Ala Ser Phe Asp Ala Gly Glu Gly Lys Arg Phe Glu
385                 390                 395                 400

Asp Gly Gln Met Thr Leu Glu Glu Leu Val Ala Tyr Ala Lys Ser His
                405                 410                 415

Gly Glu Pro Ala Thr Ile Ser Gly Lys Gln Glu Lys Tyr Glu Ala Ile
            420                 425                 430

Val Ala Leu His Val Lys
        435

<210> SEQ ID NO 129
<211> LENGTH: 1329
<212> TYPE: DNA
<213> ORGANISM: Unknown
<220> FEATURE:
<223> OTHER INFORMATION: Obtained from environmental sample

<400> SEQUENCE: 129
atgagtaaag agtattatcc tgagattggc aaaatcccgt ttgagggtcc cgagagcaag      60
aatgtgatgg cgttccatta ctatgaaccc gaacgcgtcg tcatgggtaa gaagatgaaa     120
gactggctca agtttgccat gtgctggtgg cacagcctgg gtcaggccag tgccgaccag     180
ttcggcggac agacacgttt ctacgagtgg gacaaggccg ataccccct gcagcgtgcc      240
aaggacaaaa tggatgccgg atttgaaatc atgcagaagt gggcatcga gtacttctgc     300
ttccacgatg tggacctcat cgaggaggcc gataccatcg aggaatacga ggcccgcatg    360
aaggccatta ccgactatgc gctggagaag atgcaggcca ccggcatcaa gttgctgtgg    420
ggcactgcca atgtgttcgg ccacaagcgc tacatgaacg cgccgccac caatcccgat    480
ttcaatgtcg tggcacgtgc cgccgtccaa atcaagaatg ccatcgatgc caccatcaag    540
ctgggcggca cgagttacgt cttctggggt ggtcgtgagg ctatcagag tctgctcaac     600
acgcagatgc agcgcgagaa ggaccatctg gcccgcatgc tggcggcagc ccgcgactat    660
ggccgtgccc atggcttcaa gggcactttc ctgatcgagc ccaaacccat ggagcccacc    720
aagcaccagt atgatgtgga caccgagacc gtgctcggct tcctgcgtgc ccacggcctg    780
gacaaggact tcaaggttaa catcgaggtc aatcatgcta cgctggcggg acacactttc    840
agccacgaac tggctgtggc cgtggacaac ggtatgctgg cagcatcga cgccaaccgc    900
ggcgattatc agaatggctg ggacaccgac cagttcccca tcgacagctt cgagctcacc    960
caggccatgc tgcagatcat gcggcggcgg ggcttcaagg acggaggtac caacttcgat  1020
gccaagctgc gtcgcaacag taccgaccct gaggacatct tcatcgccca catcagcggt  1080
atggatgcca tggcacgcgg cctgttgagc gctgccgcta tcctcgagga tggcgagttg  1140
```

-continued

```
cccgcgatgc tcaaggcacg ttatgccagc tttgaccagg gcgagggtaa gcgctttgag    1200
gacggcgaga tgacgctcga gcagctggtg gattatgcaa aggattatgc caaatcgcac    1260
ggcgagcctg atgtcatcag cggcaagcag gagaagtttg aaaccatcgt ggcccttta c    1320 gccaagtaa                                                            1329
```

<210> SEQ ID NO 130
<211> LENGTH: 442
<212> TYPE: PRT
<213> ORGANISM: Unknown
<220> FEATURE:
<223> OTHER INFORMATION: Obtained from environmental sample

<400> SEQUENCE: 130

```
Met Ser Lys Glu Tyr Tyr Pro Glu Ile Gly Lys Ile Pro Phe Glu Gly
1               5                   10                  15

Pro Glu Ser Lys Asn Val Met Ala Phe His Tyr Tyr Glu Pro Glu Arg
            20                  25                  30

Val Val Met Gly Lys Lys Met Lys Asp Trp Leu Lys Phe Ala Met Cys
        35                  40                  45

Trp Trp His Ser Leu Gly Gln Ala Ser Ala Asp Gln Phe Gly Gly Gln
    50                  55                  60

Thr Arg Phe Tyr Glu Trp Asp Lys Ala Asp Thr Pro Leu Gln Arg Ala
65                  70                  75                  80

Lys Asp Lys Met Asp Ala Gly Phe Glu Ile Met Gln Lys Leu Gly Ile
                85                  90                  95

Glu Tyr Phe Cys Phe His Asp Val Asp Leu Ile Glu Glu Ala Asp Thr
            100                 105                 110

Ile Glu Glu Tyr Glu Ala Arg Met Lys Ala Ile Thr Asp Tyr Ala Leu
        115                 120                 125

Glu Lys Met Gln Ala Thr Gly Ile Lys Leu Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asn Val Val Ala Arg Ala Ala Val Gln Ile Lys Asn Ala Ile Asp
                165                 170                 175

Ala Thr Ile Lys Leu Gly Gly Thr Ser Tyr Val Phe Trp Gly Gly Arg
            180                 185                 190

Glu Gly Tyr Gln Ser Leu Leu Asn Thr Gln Met Gln Arg Glu Lys Asp
        195                 200                 205

His Leu Ala Arg Met Leu Ala Ala Arg Asp Tyr Gly Arg Ala His
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Leu Gly Phe Leu Arg
                245                 250                 255

Ala His Gly Leu Asp Lys Asp Phe Lys Val Asn Ile Glu Val Asn His
            260                 265                 270

Ala Thr Leu Ala Gly His Thr Phe Ser His Glu Leu Ala Val Ala Val
        275                 280                 285

Asp Asn Gly Met Leu Gly Ser Ile Asp Ala Asn Arg Gly Asp Tyr Gln
    290                 295                 300

Asn Gly Trp Asp Thr Asp Gln Phe Pro Ile Asp Ser Phe Glu Leu Thr
305                 310                 315                 320
```

```
Gln Ala Met Leu Gln Ile Met Arg Gly Gly Phe Lys Asp Gly Gly
                325                 330                 335

Thr Asn Phe Asp Ala Lys Leu Arg Arg Asn Ser Thr Pro Glu Asp
            340                 345                 350

Ile Phe Ile Ala His Ile Ser Gly Met Asp Ala Met Ala Arg Gly Leu
        355                 360                 365

Leu Ser Ala Ala Ala Ile Leu Glu Asp Gly Glu Leu Pro Ala Met Leu
    370                 375                 380

Lys Ala Arg Tyr Ala Ser Phe Asp Gln Gly Glu Gly Lys Arg Phe Glu
385                 390                 395                 400

Asp Gly Glu Met Thr Leu Glu Gln Leu Val Asp Tyr Ala Lys Asp Tyr
                405                 410                 415

Ala Lys Ser His Gly Glu Pro Asp Val Ile Ser Gly Lys Gln Glu Lys
            420                 425                 430

Phe Glu Thr Ile Val Ala Leu Tyr Ala Lys
                435                 440

<210> SEQ ID NO 131
<211> LENGTH: 1317
<212> TYPE: DNA
<213> ORGANISM: Unknown
<220> FEATURE:
<223> OTHER INFORMATION: Obtained from environmental sample

<400> SEQUENCE: 131
atgaccaacg agtattttcc cggaatcggt gtgattccgt ttgaaggaca ggaaagcaag      60
aatcccctgg ctttccatta ttatgacgcc aaccgcgtag tgatgggcaa acccatgaag     120
gaatggttca aatttgccat ggcctggtgg catacgctgg ggcaggcatc ggccgatccc     180
ttcggcggac agaccgcctc ctacgcatgg acaagggcg agtgcccctta ctgccgtgcc     240
cgccagaagg ccgacgccgg ctttgaactg atgcagaagc tgggaatcgg ctatttctgc     300
ttccacgatg tggatatcat cgaggactgc gaggacattg ccgagtatga ggcccgtatg     360
aaggacatca cggactatct gctggtgaag atgaaggaaa cgggcatcaa gaatctgtgg     420
ggcacggcca acgtcttcgg ccacaagcgc tatatgaacg cgccgccac caacccgcaa     480
ttcgacgtgg tagcccgcgc ctgcggtcca gatcaagaacg ccctggacgc caccatcaag     540
ctgggcggca gcaattatgt gttctggggc ggccggaag ctactacac ccttttgaac     600
acgcagatgc agcgggagaa ggaccacctg cccagatgc tcaaggcggc ccgcgactat     660
gccccgcggca agggattcaa gggcacgttc ctcattgagc ccaagcccat ggagcccacc     720
aagcaccagt acgacgtaga tacggagacc gtgattggtt tcctgcgcgc caacgggccg     780
gacaaggact tcaaggtgaa tatcgaagtg aaccacgcca ccctggccgg ccataccttc     840
gagcacgagc tcaccgtggc ccgcgaaaac ggcttcctgg gcagcatcga cgccaaccgc     900
ggagacgccc agaacggctg ggatacagac cagttccccg tggacgcctt tgacctcacc     960
caggccatga tgcaggtcct gctcaacggc ggattcggca acggcggcac caacttcgac    1020
gccaaactgc gccgttcctc cacggatccc gaggacatct tcatcgccca tcagcgcc     1080
atggacgcca tggcccacgc cctcctgaac gccgccgcca tcctggaaga gagccccatg    1140
ccgggcatgg tgaaggagcg ctacgcttcc ttcgacaatg gccttggcaa gaagttcgag    1200
gaaggaaagg ccacgctgga agagctgtac gactatgcca agaagaacgg cgagcctgtg    1260
gccgcttccg aaagcagga actgtacgaa acgctgctga acctgtacgc caagtaa        1317
```

```
<210> SEQ ID NO 132
<211> LENGTH: 438
<212> TYPE: PRT
<213> ORGANISM: Unknown
<220> FEATURE:
<223> OTHER INFORMATION: Obtained from environmental sample

<400> SEQUENCE: 132
```

| | | | | | | | | | | | | | | | |
|---|---|---|---|---|---|---|---|---|---|---|---|---|---|---|---|
| Met | Thr | Asn | Glu | Tyr | Phe | Pro | Gly | Ile | Gly | Val | Ile | Pro | Phe | Glu | Gly |
| 1 | | | | 5 | | | | | 10 | | | | | 15 | |
| Gln | Glu | Ser | Lys | Asn | Pro | Leu | Ala | Phe | His | Tyr | Asp | Ala | Asn | Arg | |
| | | | 20 | | | | | 25 | | | | | 30 | | |
| Val | Val | Met | Gly | Lys | Pro | Met | Lys | Glu | Trp | Phe | Lys | Phe | Ala | Met | Ala |
| | | | 35 | | | | | 40 | | | | | 45 | | |
| Trp | Trp | His | Thr | Leu | Gly | Gln | Ala | Ser | Ala | Asp | Pro | Phe | Gly | Gly | Gln |
| 50 | | | | | 55 | | | | | 60 | | | | | |
| Thr | Arg | Ser | Tyr | Ala | Trp | Asp | Lys | Gly | Glu | Cys | Pro | Tyr | Cys | Arg | Ala |
| 65 | | | | | 70 | | | | | 75 | | | | | 80 |
| Arg | Gln | Lys | Ala | Asp | Ala | Gly | Phe | Glu | Leu | Met | Gln | Lys | Leu | Gly | Ile |
| | | | | 85 | | | | | 90 | | | | | 95 | |
| Gly | Tyr | Phe | Cys | Phe | His | Asp | Val | Asp | Ile | Ile | Glu | Asp | Cys | Glu | Asp |
| | | | 100 | | | | | 105 | | | | | 110 | | |
| Ile | Ala | Glu | Tyr | Glu | Ala | Arg | Met | Lys | Asp | Ile | Thr | Asp | Tyr | Leu | Leu |
| | | | 115 | | | | | 120 | | | | | 125 | | |
| Val | Lys | Met | Lys | Glu | Thr | Gly | Ile | Lys | Asn | Leu | Trp | Gly | Thr | Ala | Asn |
| | | 130 | | | | | 135 | | | | | 140 | | | |
| Val | Phe | Gly | His | Lys | Arg | Tyr | Met | Asn | Gly | Ala | Ala | Thr | Asn | Pro | Gln |
| 145 | | | | | 150 | | | | | 155 | | | | | 160 |
| Phe | Asp | Val | Val | Ala | Arg | Ala | Ala | Val | Gln | Ile | Lys | Asn | Ala | Leu | Asp |
| | | | | 165 | | | | | 170 | | | | | 175 | |
| Ala | Thr | Ile | Lys | Leu | Gly | Gly | Ser | Asn | Tyr | Val | Phe | Trp | Gly | Gly | Arg |
| | | | 180 | | | | | 185 | | | | | 190 | | |
| Glu | Gly | Tyr | Tyr | Thr | Leu | Leu | Asn | Thr | Gln | Met | Gln | Arg | Glu | Lys | Asp |
| | | | 195 | | | | | 200 | | | | | 205 | | |
| His | Leu | Ala | Gln | Met | Leu | Lys | Ala | Ala | Arg | Asp | Tyr | Ala | Arg | Gly | Lys |
| | | 210 | | | | | 215 | | | | | 220 | | | |
| Gly | Phe | Lys | Gly | Thr | Phe | Leu | Ile | Glu | Pro | Lys | Pro | Met | Glu | Pro | Thr |
| 225 | | | | | 230 | | | | | 235 | | | | | 240 |
| Lys | His | Gln | Tyr | Asp | Val | Asp | Thr | Glu | Thr | Val | Ile | Gly | Phe | Leu | Arg |
| | | | | 245 | | | | | 250 | | | | | 255 | |
| Ala | Asn | Gly | Pro | Asp | Lys | Asp | Phe | Lys | Val | Asn | Ile | Glu | Val | Asn | His |
| | | | 260 | | | | | 265 | | | | | 270 | | |
| Ala | Thr | Leu | Ala | Gly | His | Thr | Phe | Glu | His | Glu | Leu | Thr | Val | Ala | Arg |
| | | | 275 | | | | | 280 | | | | | 285 | | |
| Glu | Asn | Gly | Phe | Leu | Gly | Ser | Ile | Asp | Ala | Asn | Arg | Gly | Asp | Ala | Gln |
| | | 290 | | | | | 295 | | | | | 300 | | | |
| Asn | Gly | Trp | Asp | Thr | Asp | Gln | Phe | Pro | Val | Asp | Ala | Phe | Asp | Leu | Thr |
| 305 | | | | | 310 | | | | | 315 | | | | | 320 |
| Gln | Ala | Met | Met | Gln | Val | Leu | Leu | Asn | Gly | Gly | Phe | Gly | Asn | Gly | Gly |
| | | | | 325 | | | | | 330 | | | | | 335 | |
| Thr | Asn | Phe | Asp | Ala | Lys | Leu | Arg | Arg | Ser | Ser | Thr | Pro | Glu | Asp | |
| | | | 340 | | | | | 345 | | | | | 350 | | |
| Ile | Phe | Ile | Ala | His | Ile | Ser | Ala | Met | Asp | Ala | Met | Ala | His | Ala | Leu |
| | | | 355 | | | | | 360 | | | | | 365 | | |
| Leu | Asn | Ala | Ala | Ala | Ile | Leu | Glu | Glu | Ser | Pro | Met | Pro | Gly | Met | Val |

```
                370             375             380
Lys Glu Arg Tyr Ala Ser Phe Asp Asn Gly Leu Gly Lys Lys Phe Glu
385                 390                 395                 400

Glu Gly Lys Ala Thr Leu Glu Leu Tyr Asp Tyr Ala Lys Lys Asn
                405                 410                 415

Gly Glu Pro Val Ala Ala Ser Gly Lys Gln Glu Leu Tyr Glu Thr Leu
            420                 425                 430

Leu Asn Leu Tyr Ala Lys
        435

<210> SEQ ID NO 133
<211> LENGTH: 1317
<212> TYPE: DNA
<213> ORGANISM: Unknown
<220> FEATURE:
<223> OTHER INFORMATION: Obtained from environmental sample

<400> SEQUENCE: 133
atgactaaag agtatttccc ttccgtcggc aagattgcct tgaaggaccc cgaaagcaag      60
aaccctatgg ccttccatta ttatgacgcc aatcgcgtgg taatgggaaa gccgatgaaa    120
gaatggctta aatttgccat ggcctggtgg cacaccctgg ccaggcctc tgcagacccc     180 ttcggcggtc agacccgctc ctacgagtgg gacaagggcg agtgcccta ctgccgcgcc     240 aaggccaagg ccgatgccgg ctttgaactg atgcagaaac tgggcatcga gtatttctgc    300
ttccacgata tagacctggt ggaagactgc gatgatatcg ccgaatacga ggcccgcatg    360
aaggacatca cggactatct cctggagaag atgaaggaaa ccggcatcaa gaacctctgg    420
ggaaccgcca acgtgttcgg ccacaagcgc tatatgaacg gcgccgccac caaccctcag    480
ttcgacatcg tggcccgtgc cgctgtccag atcaagaacg ccctggatgc caccatcaag    540
ctgggcggct ccaactatgt gttctggggc ggccgtgagg gctactatac cctcctgaac    600
acccagatgc agagagagaa ggaccacctg gccaagatgc tcaccgccgc ccgcgactat    660
gcccgtgcca agggcttcaa gggcaccttc ctcatcgaac ccaagccgat ggagcccacc    720
aagcaccagt acgacgtaga tacggagacc gtgatcggct cctccgcgc caacggcctg    780 gacaaggact tcaaggtgaa tattgaggtg aaccacgcca ccctggccgg ccacaccttc    840
gagcacgagc tcaccgtggc ccgcgagaac ggcttcctgg gcagcatcga cgccaaccgc    900
ggagacgccc agaacggctg ggatacggac cagttcccgg tggatgcctt cgacctcacc    960
caggctatga tgcagatcct tctgaacgga ggcttcggca acggcggtac caacttcgac   1020
gccaaactgc gccgctcctc cacggacccc gaggacatct tcatcgccca catcagcgct   1080
atggatgcca tggcccacgc cctgctgaat gcagccgcca tcctggagga agccccgctt   1140
ccgaagatgc tgaaagagcg ttatgccagc tttgacggcg gtctgggcaa gaagttcgaa   1200
gaaggcaagg cctctctgga agaactctac gagtatgcca gagcaacgg agagcccgtg   1260 gccgcttccg gcaagcagga gctctgcgaa acgtacctga acctctacgc taagtaa      1317

<210> SEQ ID NO 134
<211> LENGTH: 438
<212> TYPE: PRT
<213> ORGANISM: Unknown
<220> FEATURE:
<223> OTHER INFORMATION: Obtained from environmental sample

<400> SEQUENCE: 134

Met Thr Lys Glu Tyr Phe Pro Ser Val Gly Lys Ile Ala Phe Glu Gly
```

```
1               5                   10                  15
    Pro Glu Ser Lys Asn Pro Met Ala Phe His Tyr Tyr Asp Ala Asn Arg
                20                  25                  30
    Val Val Met Gly Lys Pro Met Lys Glu Trp Leu Lys Phe Ala Met Ala
                35                  40                  45
    Trp Trp His Thr Leu Gly Gln Ala Ser Ala Asp Pro Phe Gly Gly Gln
                50                  55                  60
    Thr Arg Ser Tyr Glu Trp Asp Lys Gly Glu Cys Pro Tyr Cys Arg Ala
65                  70                  75                  80
    Lys Ala Lys Ala Asp Ala Gly Phe Glu Leu Met Gln Lys Leu Gly Ile
                85                  90                  95
    Glu Tyr Phe Cys Phe His Asp Ile Asp Leu Val Glu Asp Cys Asp Asp
                100                 105                 110
    Ile Ala Glu Tyr Glu Ala Arg Met Lys Asp Ile Thr Asp Tyr Leu Leu
                115                 120                 125
    Glu Lys Met Lys Glu Thr Gly Ile Lys Asn Leu Trp Gly Thr Ala Asn
                130                 135                 140
    Val Phe Gly His Lys Arg Tyr Met Asn Gly Ala Ala Thr Asn Pro Gln
145                 150                 155                 160
    Phe Asp Ile Val Ala Arg Ala Ala Val Gln Ile Lys Asn Ala Leu Asp
                165                 170                 175
    Ala Thr Ile Lys Leu Gly Gly Ser Asn Tyr Val Phe Trp Gly Gly Arg
                180                 185                 190
    Glu Gly Tyr Tyr Thr Leu Leu Asn Thr Gln Met Gln Arg Glu Lys Asp
                195                 200                 205
    His Leu Ala Lys Met Leu Thr Ala Ala Arg Asp Tyr Ala Arg Ala Lys
                210                 215                 220
    Gly Phe Lys Gly Thr Phe Leu Ile Glu Pro Lys Pro Met Glu Pro Thr
225                 230                 235                 240
    Lys His Gln Tyr Asp Val Asp Thr Glu Thr Val Ile Gly Phe Leu Arg
                245                 250                 255
    Ala Asn Gly Leu Asp Lys Asp Phe Lys Val Asn Ile Glu Val Asn His
                260                 265                 270
    Ala Thr Leu Ala Gly His Thr Phe Glu His Glu Leu Thr Val Ala Arg
                275                 280                 285
    Glu Asn Gly Phe Leu Gly Ser Ile Asp Ala Asn Arg Gly Asp Ala Gln
                290                 295                 300
    Asn Gly Trp Asp Thr Asp Gln Phe Pro Val Asp Ala Phe Asp Leu Thr
305                 310                 315                 320
    Gln Ala Met Met Gln Ile Leu Leu Asn Gly Gly Phe Gly Asn Gly Gly
                325                 330                 335
    Thr Asn Phe Asp Ala Lys Leu Arg Arg Ser Ser Thr Asp Pro Glu Asp
                340                 345                 350
    Ile Phe Ile Ala His Ile Ser Ala Met Asp Ala Met Ala His Ala Leu
                355                 360                 365
    Leu Asn Ala Ala Ala Ile Leu Glu Glu Ser Pro Leu Pro Lys Met Leu
                370                 375                 380
    Lys Glu Arg Tyr Ala Ser Phe Asp Gly Leu Gly Lys Lys Phe Glu
                385                 390                 395                 400
    Glu Gly Lys Ala Ser Leu Glu Glu Leu Tyr Glu Tyr Ala Lys Ser Asn
                405                 410                 415
    Gly Glu Pro Val Ala Ala Ser Gly Lys Gln Glu Leu Cys Glu Thr Tyr
                420                 425                 430
```

Leu Asn Leu Tyr Ala Lys
        435

<210> SEQ ID NO 135
<211> LENGTH: 1320
<212> TYPE: DNA
<213> ORGANISM: Unknown
<220> FEATURE:
<223> OTHER INFORMATION: Obtained from environmental sample

<400> SEQUENCE: 135

```
atggctaaag aatacttccc ctccatcggc aaaatcccctt ttgaaggagc cgacagcaaa      60
aatcccctcg ctttccatta ttatgacgcc ggacgcgtgg ttatgggcaa gcccatgaag     120
gaatggctta aattcgccat ggcctggtgg cacacgctgg gccaggcctc cggagacccc     180
ttcggcggcc agacccgcag ctacgaatgg acaagggcg aatgccccta ctgccgcgcc      240
aaggccaagg ccgacgccgg ttttgaaatc atgcaaaagc tgggcatcga atacttctgc     300
ttccacgatg tggaccttat cgaggattgc gatgacattg ccgaatacga agcccgcatg     360
aaggacatca cggactacct gctggaaaag atgaaggaga ccggcatcaa gaacctctgg     420
ggcaccgcca atgtcttcgg ccacaagcgc tacatgaacg cgccggcac caatccgcag      480
ttcgatgtgg tggcccgtgc cgccgtccag atcaagaacg ccctggacgc caccatcaag     540
ctgggcggct ccaactatgt gttctggggc ggccgcgaag ctattacac cctcctcaac      600
acacagatgc agcgggaaaa agaccacctg gccaagttgc tgacggccgc ccgcgactat     660
gcccgcgcca agggcttcaa gggcaccttc ctcattgagc ccaaacccat ggaacccacc     720
aagcaccagt acgacgtgga tacggagacg gtcatcggct tcctccgtgc caacggcctg     780
gacaaggact tcaaggtgaa catcgaggtg aaccacgcca ccctggccgg ccacaccttc     840
gagcatgagc tcaccgtggc ccgcgagaac ggtttcctgg gctccatcga tgccaaccgc     900
ggcgacgccc agaacggctg ggacacggac cagttccctg tggacccgta cgatcttacc     960
caggccatga tgcaggtgct gctgaacggc ggcttcggca acggcggcac caacttcgac    1020
gccaaactcc gccgctcctc caccgaccct gaggacatct tcatcgccca tatttccgcc    1080
atggatgcca tggcccacgc tttgcttaac gcagctgccg tgctggaaga gagccccctg    1140
tgccagatgg tcaaggagcg ttatgccagc ttcgacgatg gcctcggcaa acagttcgag    1200
gaaggcaagg ctaccctgga agacctgtac gaatacgcca aggcccaggg tgaacccgtt    1260
gtcgcctccg gcaagcagga gctttacgag actctcctga acctgtatgc cgtcaagtaa    1320
```

<210> SEQ ID NO 136
<211> LENGTH: 439
<212> TYPE: PRT
<213> ORGANISM: Unknown
<220> FEATURE:
<223> OTHER INFORMATION: Obtained from environmental sample

<400> SEQUENCE: 136

Met Ala Lys Glu Tyr Phe Pro Ser Ile Gly Lys Ile Pro Phe Glu Gly
1               5                   10                  15

Ala Asp Ser Lys Asn Pro Leu Ala Phe His Tyr Tyr Asp Ala Gly Arg
            20                  25                  30

Val Val Met Gly Lys Pro Met Lys Glu Trp Leu Lys Phe Ala Met Ala
        35                  40                  45

Trp Trp His Thr Leu Gly Gln Ala Ser Gly Asp Pro Phe Gly Gly Gln
    50                  55                  60

Thr Arg Ser Tyr Glu Trp Asp Lys Gly Glu Cys Pro Tyr Cys Arg Ala
 65                  70                  75                  80

Lys Ala Lys Ala Asp Ala Gly Phe Glu Ile Met Gln Lys Leu Gly Ile
             85                  90                  95

Glu Tyr Phe Cys Phe His Asp Val Asp Leu Ile Glu Asp Cys Asp Asp
            100                 105                 110

Ile Ala Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
130                 135                 140

Val Phe Gly His Lys Arg Tyr Met Asn Gly Ala Gly Thr Asn Pro Gln
145                 150                 155                 160

Phe Asp Val Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Leu Leu Thr Ala Ala Arg Asp Tyr Ala Arg Ala Lys
210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
290                 295                 300

Asn Gly Trp Asp Thr Asp Gln Phe Pro Val Asp Pro Tyr Asp Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Leu Glu Glu Ser Pro Leu Cys Gln Met Val
370                 375                 380

Lys Glu Arg Tyr Ala Ser Phe Asp Asp Gly Leu Gly Lys Gln Phe Glu
385                 390                 395                 400

Glu Gly Lys Ala Thr Leu Glu Asp Leu Tyr Glu Tyr Ala Lys Ala Gln
                405                 410                 415

Gly Glu Pro Val Val Ala Ser Gly Lys Gln Glu Leu Tyr Glu Thr Leu
            420                 425                 430

Leu Asn Leu Tyr Ala Val Lys
            435

<210> SEQ ID NO 137
<211> LENGTH: 1317
<212> TYPE: DNA
<213> ORGANISM: Unknown
<220> FEATURE:

<223> OTHER INFORMATION: Obtained from environmental sample

<400> SEQUENCE: 137

```
atgaccaaag aatatttccc taccgtcggg aagatcccct tcgagggccc cgaaagcaag      60
aaccctatgg cgttccatta ctatgacccc aaccgtctgg tgatgggcaa gaagatgaaa     120
gactggctgc gtttcgccat ggcctggtgg cacaccctcg gccaggcgtc gggcgaccag     180
ttcggcggcc agacccgcag ttatgcgtgg gacgagggag aatgcccgta cgagcgcgcc     240
cgtgccaagg ctgacgccgg cttcgagatc atgcagaaac tcggtatcga gttcttctgc     300
ttccacgaca tcgacctgat cgaggatacc gacgacatcg ccgagtatga ggcccgcctg     360
aaagacatca cggactatct gctcgagaag atgaaagcca ctggcatcaa aaatctctgg     420
ggaacggcca acgtgttcgg ccacaagcgt tgcatgaacg cgccgccac caacccggac      480
ttcgccgtgc tggcccgcgc tgccgtccag atcaagaacg ccatcgacgc caccatcaag     540
ctgggcggcg agaactatgt gttctggggt ggccgcgaag gctacacgag cctgctcaac     600
acccagatgc agcgtgagaa agagcacctg gccgcctgc tgtccctggc cgcgactat       660
ggccgcgccc acggcttcaa gggtaccttc ctgatcgagc ccaagccgat gggaccgacg     720
aaacaccagt acgaccagga tacgaaaact gtcatcggtt cctgcgccg ccacggtcta      780
gacaaggact tcaaggtcaa tatcgaggtg aaccatgcca cgctggcggg ccacaccttc     840
gaacacgaac tggcctgcgc cgtggatcac ggtatgctgg cagcatcga cgccaaccgc      900
ggtgacgcac agaacggctg ggataccgac cagttcccga tcgacaactt cgagctgacc     960
ctttccatgc tccagatcat ccgcaacggt ggcctggcac ccggcggctc gaatttcgat    1020
gccaagctgc gccgcaactc caccgatccc gaagacattt tcatcgcgca catcagcgcc    1080
atggacgcca tggcccgcgc attggtcaat gcggccgcca tcctggagga gagcgctatt    1140
ccgaagatgg tcaaggagcg ttacgcttcg ttcgacagcg gcaaaggcaa ggaatacgag    1200
gaaggcaagc tgacgctcga agacatcgtg gcctatgcca aggcgaacgg agaaccgaag    1260
cagatttccg gcaaacagga actctacgag acgcttgtcg cactctatag caaataa      1317
```

<210> SEQ ID NO 138
<211> LENGTH: 438
<212> TYPE: PRT
<213> ORGANISM: Unknown
<220> FEATURE:
<223> OTHER INFORMATION: Obtained from environmental sample

<400> SEQUENCE: 138

```
Met Thr Lys Glu Tyr Phe Pro Thr Val Gly Lys Ile Pro Phe Glu Gly
1               5                   10                  15

Pro Glu Ser Lys Asn Pro Met Ala Phe His Tyr Tyr Asp Pro Asn Arg
            20                  25                  30

Leu Val Met Gly Lys Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Arg Ser Tyr Ala Trp Asp Glu Gly Glu Cys Pro Tyr Glu Arg Ala
65                  70                  75                  80

Arg Ala Lys Ala Asp Ala Gly Phe Glu Ile Met Gln Lys Leu Gly Ile
                85                  90                  95

Glu Phe Phe Cys Phe His Asp Ile Asp Leu Ile Glu Asp Thr Asp Asp
            100                 105                 110
```

```
Ile Ala Glu Tyr Glu Ala Arg Leu Lys Asp Ile Thr Asp Tyr Leu Leu
            115                 120                 125

Glu Lys Met Lys Ala Thr Gly Ile Lys Asn Leu Trp Gly Thr Ala Asn
130                 135                 140

Val Phe Gly His Lys Arg Cys Met Asn Gly Ala Ala Thr Asn Pro Asp
145                 150                 155                 160

Phe Ala Val Leu Ala Arg Ala Ala Val Gln Ile Lys Asn Ala Ile Asp
                165                 170                 175

Ala Thr Ile Lys Leu Gly Gly Glu Asn Tyr Val Phe Trp Gly Gly Arg
            180                 185                 190

Glu Gly Tyr Thr Ser Leu Leu Asn Thr Gln Met Gln Arg Glu Lys Glu
        195                 200                 205

His Leu Gly Arg Leu Leu Ser Leu Ala Arg Asp Tyr Gly Arg Ala His
    210                 215                 220

Gly Phe Lys Gly Thr Phe Leu Ile Glu Pro Lys Pro Met Gly Pro Thr
225                 230                 235                 240

Lys His Gln Tyr Asp Gln Asp Thr Glu Thr Val Ile Gly Phe Leu Arg
                245                 250                 255

Arg His Gly Leu Asp Lys Asp Phe Lys Val Asn Ile Glu Val Asn His
            260                 265                 270

Ala Thr Leu Ala Gly His Thr Phe Glu His Glu Leu Ala Cys Ala Val
        275                 280                 285

Asp His Gly Met Leu Gly Ser Ile Asp Ala Asn Arg Gly Asp Ala Gln
    290                 295                 300

Asn Gly Trp Asp Thr Asp Gln Phe Pro Ile Asp Asn Phe Glu Leu Thr
305                 310                 315                 320

Leu Ser Met Leu Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Val Asn Ala Ala Ala Ile Leu Glu Glu Ser Ala Ile Pro Lys Met Val
    370                 375                 380

Lys Glu Arg Tyr Ala Ser Phe Asp Ser Gly Lys Gly Lys Glu Tyr Glu
385                 390                 395                 400

Glu Gly Lys Leu Thr Leu Glu Asp Ile Val Ala Tyr Ala Lys Ala Asn
                405                 410                 415

Gly Glu Pro Lys Gln Ile Ser Gly Lys Gln Glu Leu Tyr Glu Thr Leu
            420                 425                 430

Val Ala Leu Tyr Ser Lys
        435

<210> SEQ ID NO 139
<211> LENGTH: 1317
<212> TYPE: DNA
<213> ORGANISM: Unknown
<220> FEATURE:
<223> OTHER INFORMATION: Obtained from environmental sample

<400> SEQUENCE: 139
atgaccaaag ggtatttccc taccatcggc aggattccct tcgagggaac tgaaagcaag      60
aatcccctcg cattccatta ctatgagccc gaccggctcg tactgggcaa gaaaatgaaa     120
gactggctgc gtttcgcgat ggcctggtgg cacaccctgg gccaggcgtc cggcgaccag     180
```

```
ttcggcggcc agacccgcag ctatgcctgg acaaggccg  agtgccccta tgagcgcgcc      240
aaggccaaag ccgacgccgg cttcgagatc atgcagaaac tcggcatcga gttcttctgt      300
ttccacgaca ttgacctcgt tgaggatacc gacgacatcg ccgagtatga ggcccggatg      360
aaggacatta ccgactatct cctggtcaag atgaaggaga ccggaatcaa gaacctctgg      420
ggtacggcca atgtcttcgg ccacaagcgc tatatgaacg gcgccgccac caatcccgac      480
ttcgacgtgg tggcccgcgc cgccgtccag atcaagaacg ccctcgatgc caccatcaag      540
ctgggcggtg aaaactatgt gttctggggc ggccgcgaag gctatatgag cctgctcaac      600
acgcagatgc agcgtgagaa ggagcacctg ggccggatgc tggtcgccgc ccgcgactac      660
gcccgcgccc acggcttcaa gggtaccttc ctcatcgagc ccaaaccgat ggaaccgacc      720
aagcaccagt acgaccagga tacgaaaacc gtgatcggct ccttcgccg  ccacggcctg      780 gacaaggatt tcaaggtgaa catcgaagtg aaccacgcca cgctggccgg ccacaccttc      840
gagcacgaac tggccaccgc cgtcgactgc ggcctgctgg gcagcatcga cgccaatcgc      900
ggcgacgctc agaacggctg ggataccgac cagttcccga tcgacaactt cgaactcacg      960
ctggccatgc tgcagattat ccgcaacggc ggtctggcac ccgcggctc  gaacttcgac     1020 gccaaactgc gccgtaactc caccgatccg gaagatatct tcatcgccca catcagtgcg     1080
atggacgcga tggcccgtgc gctggtcaac gccgccgcaa tctgggaaga gtctcccatc     1140
ccgcagatga agaaagaacg ctacgcgtcg ttcgacagcg gcaagggcaa ggaattcgaa     1200
gagggcaagc tctgcctcga agacctcgtg gcctatgcca aggcgaacgg agaaccgaaa     1260
cagatctccg gcaggcagga actatatgag accatcgtcg cccttattg  caaatag       1317
```

<210> SEQ ID NO 140
<211> LENGTH: 438
<212> TYPE: PRT
<213> ORGANISM: Unknown
<220> FEATURE:
<223> OTHER INFORMATION: Obtained from environmental sample

<400> SEQUENCE: 140

```
Met Thr Lys Gly Tyr Phe Pro Thr Ile Gly Arg Ile Pro Phe Glu Gly
1               5                   10                  15

Thr Glu Ser Lys Asn Pro Leu Ala Phe His Tyr Tyr Glu Pro Asp Arg
            20                  25                  30

Leu Val Leu Gly Lys Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Arg Ser Tyr Ala Trp Asp Lys Ala Glu Cys Pro Tyr Glu Arg Ala
65                  70                  75                  80

Lys Ala Lys Ala Asp Ala Gly Phe Glu Ile Met Gln Lys Leu Gly Ile
                85                  90                  95

Glu Phe Phe Cys Phe His Asp Ile Asp Leu Val Glu Asp Thr Asp Asp
            100                 105                 110

Ile Ala Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Val Ala Arg Ala Ala Val Gln Ile Lys Asn Ala Leu Asp
```

```
            165                 170                 175
Ala Thr Ile Lys Leu Gly Gly Glu Asn Tyr Val Phe Trp Gly Gly Arg
        180                 185                 190

Glu Gly Tyr Met Ser Leu Leu Asn Thr Gln Met Gln Arg Glu Lys Glu
        195                 200                 205

His Leu Gly Arg Met Leu Val Ala Ala Arg Asp Tyr Ala Arg Ala His
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Arg His Gly Leu Asp Lys Asp Phe Lys Val Asn Ile Glu Val Asn His
            260                 265                 270

Ala Thr Leu Ala Gly His Thr Phe Glu His Glu Leu Ala Thr Ala Val
        275                 280                 285

Asp Cys Gly Leu Leu Gly Ser Ile Asp Ala Asn Arg Gly Asp Ala Gln
    290                 295                 300

Asn Gly Trp Asp Thr Asp Gln Phe Pro Ile Asp Asn Phe Glu Leu Thr
305                 310                 315                 320

Leu Ala Met Leu Gln Ile Ile Arg Asn Gly Gly Leu Ala Pro Gly Gly
                325                 330                 335

Ser Asn Phe Asp Ala Lys Leu Arg Asn Ser Thr Asp Pro Glu Asp
            340                 345                 350

Ile Phe Ile Ala His Ile Ser Ala Met Asp Ala Met Ala Arg Ala Leu
        355                 360                 365

Val Asn Ala Ala Ala Ile Trp Glu Glu Ser Pro Ile Pro Gln Met Lys
    370                 375                 380

Lys Glu Arg Tyr Ala Ser Phe Asp Ser Gly Lys Gly Lys Glu Phe Glu
385                 390                 395                 400

Glu Gly Lys Leu Cys Leu Glu Asp Leu Val Ala Tyr Ala Lys Ala Asn
                405                 410                 415

Gly Glu Pro Lys Gln Ile Ser Gly Arg Gln Glu Leu Tyr Glu Thr Ile
            420                 425                 430

Val Ala Leu Tyr Cys Lys
        435

<210> SEQ ID NO 141
<211> LENGTH: 1317
<212> TYPE: DNA
<213> ORGANISM: Unknown
<220> FEATURE:
<223> OTHER INFORMATION: Obtained from environmental sample

<400> SEQUENCE: 141
atgaccaacg agtattttcc cggaatcggt gtgattccgt ttgaaggaca ggaaagcaag    60
aatcccatgg ctttccatta ttatgacgcc aaccgcgtag tgatgggcaa acccatgaag   120
gaatggttca aatttgccat ggcctggtgg catacgctgg ggcaggcatc ggccgatccc   180
ttcggcggac agacccgctc ctacgcatgg gacaagggcg agtgcccctta ctgccgtgcc   240 cgccagaagg ccgacgccgg ctttgaactg atgcagaagc tgggtatcgg ctatttctgc   300
ttccacgatg tggatatcat cgaggactgc gaagacattg ccgagtatga ggcccgtatg   360
aaggacatca cggactatct gctggtgaag atgaaggaaa cgggcatcaa gaacctgtgg   420
ggcacggcca acgtcttcgg ccacaagcgc tatatgaacg gcgctgccac caacccgcag   480
```

-continued

```
ttcgacgtgg tggcccgcgc tgcggtccag atcaagaacg ccctggacgc caccatcaag    540
ctgggcggca gcaattacgt gttctggggc ggccgcgaag ctattatac cctttggaac     600 acgcagatgc ggcgggagaa ggaccacctg gcccagatgc tcaaggcagc ccgtgactat    660
gcccgcggca aggattcaa gggcacgttc tcattgagc ccaagcccat ggagcccacc     720
aagcaccagt acgacgtaga tacggagacc gtgattggct tcctgcgcgc aaacggactg    780
gacaaggact tcaaggtgaa tatcgaagtg aaccacgcca ccctggccgg ccacaccttc    840
gagcacgaac tcaccgtggc ccgcgaaaac ggcttcctgg gcagcatcga cgccaaccgc    900
ggagacgccc agaacggttg ggatacagac cagttcccca tagatgcctt tgacctcacc    960
caggccatga tgcaggtcct gctcaacggc ggattcggca acggcggcac caacttcgac   1020
gccaaactgc gccgttcctc cacggatccc gaggacatct tcatcgccca catcggcgcc   1080
atggacgcca tggcccacgc cctcctgaac gccgccgcca tcctggaaga gagccccatg   1140
ccgggcatgg tgaaggagcg ctacgcttcc ttcgacaatg ccttggcaa gaagttcgag    1200 gaaggaaagg ccacgctgga agagctgtac gactatgcca agaagaacgg cgagcctgtg   1260
gccgcttccg gcaagcagga actgtacgaa acgctgctga acctgtacgc caagtaa      1317
```

<210> SEQ ID NO 142
<211> LENGTH: 438
<212> TYPE: PRT
<213> ORGANISM: Unknown
<220> FEATURE:
<223> OTHER INFORMATION: Obtained from environmental sample

<400> SEQUENCE: 142

```
Met Thr Asn Glu Tyr Phe Pro Gly Ile Gly Val Ile Pro Phe Glu Gly
1               5                   10                  15

Gln Glu Ser Lys Asn Pro Met Ala Phe His Tyr Asp Ala Asn Arg
            20                  25                  30

Val Val Met Gly Lys Pro Met Lys Glu Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Ala Trp Asp Lys Gly Glu Cys Pro Tyr Cys Arg Ala
65                  70                  75                  80

Arg Gln Lys Ala Asp Ala Gly Phe Glu Leu Met Gln Lys Leu Gly Ile
                85                  90                  95

Gly Tyr Phe Cys Phe His Asp Val Asp Ile Ile Glu Asp Cys Glu Asp
            100                 105                 110

Ile Ala Glu Tyr Glu Ala Arg Met Lys Asp Ile Thr Asp Tyr Leu Leu
        115                 120                 125

Val Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Val Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Gly Arg
            180                 185                 190

Glu Gly Tyr Tyr Thr Leu Trp Asn Thr Gln Met Arg Arg Glu Lys Asp
        195                 200                 205

His Leu Ala Gln Met Leu Lys Ala Ala Arg Asp Tyr Ala Arg Gly Lys
    210                 215                 220
```

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
            245                 250                 255

Ala Asn Gly Leu Asp Lys Asp Phe Lys Val Asn Ile Glu Val Asn His
        260                 265                 270

Ala Thr Leu Ala Gly His Thr Phe Glu His Glu Leu Thr Val Ala Arg
    275                 280                 285

Glu Asn Gly Phe Leu Gly Ser Ile Asp Ala Asn Arg Gly Asp Ala Gln
290                 295                 300

Asn Gly Trp Asp Thr Asp Gln Phe Pro Ile Asp Ala Phe Asp Leu Thr
305                 310                 315                 320

Gln Ala Met Met Gln Val Leu Leu Asn Gly Gly Phe Gly Asn Gly Gly
            325                 330                 335

Thr Asn Phe Asp Ala Lys Leu Arg Arg Ser Ser Thr Asp Pro Glu Asp
        340                 345                 350

Ile Phe Ile Ala His Ile Gly Ala Met Asp Ala Met Ala His Ala Leu
    355                 360                 365

Leu Asn Ala Ala Ala Ile Leu Glu Glu Ser Pro Met Pro Gly Met Val
370                 375                 380

Lys Glu Arg Tyr Ala Ser Phe Asp Asn Gly Leu Gly Lys Lys Phe Glu
385                 390                 395                 400

Glu Gly Lys Ala Thr Leu Glu Glu Leu Tyr Asp Tyr Ala Lys Lys Asn
            405                 410                 415

Gly Glu Pro Val Ala Ala Ser Gly Lys Gln Glu Leu Tyr Glu Thr Leu
        420                 425                 430

Leu Asn Leu Tyr Ala Lys
        435

<210> SEQ ID NO 143
<211> LENGTH: 1314
<212> TYPE: DNA
<213> ORGANISM: Unknown
<220> FEATURE:
<223> OTHER INFORMATION: Obtained from environmental sample

<400> SEQUENCE: 143
atgaaagaat acttccctac catcggaaaa atccctttcg agggccctca gagcaagaat      60
ccgctcgcat tccattacta tgacgccaac cgcgttgtcg ccggcaaacc catgaaggac     120
tggctcaagt tcgccatggc ttggtggcac accctgggcg cagcatcggc agacccttc      180 ggcggccaga cccgcagcta cgagtgggac aaagccgagt gcccttactg ccgtgcccgt     240
gaaaaggccg acgccggctt cgagatcatg cagaaacttg aatcgagta cttctgcttc      300 catgacatcg accttgtgga agactgcgag gacattgccg agtacgaggc ccgcatgaag     360
gacatcacgg actacctcct ggagaagatg aaggccaccg gcatcaagaa cctgtgggc      420 accgccaacg tctttggcaa caagcgctac atgaacggcg cagccaccaa ccctcagttc     480
gacatcgttg cccgtgcagc tgtccagatc aagaacgcca tcgacgcaac aatcaagctg     540
ggcggtaccg gttacgtatt ctggggcggc gcgagggct actacaccct cctgaacacc      600
cagatgcagc gcgagaagga ccaccttgcc aagatgctca ccgcagcccg cgactacgcc     660
cgcgccaagg gattcaaggg cacattcctc atcgagccca agcccatgga gcccaccaag     720
caccagtacg atgttgacac ggaaaccgtc atcggcttcc tccgcgccaa cggcctggac     780

```
aaggacttca aggtgaacat cgaggtgaac cacgccaccc tggccggcca caccttcgag    840
cacgagctca ccgtggccgt ggacaacggc ttcctgggca gcatcgacgc aaaccgcggc    900
gacgcccaga acggctggga cactgaccag ttccctgtgg atccttacga cctcacccag    960
gcaatgatgc agattatccg caacggcggc ttcaaggacg gcggcaccaa cttcgacgcc   1020
aaactccgcc gcagctccac ggaccccgag gacatcttca tcgcccacat cagcgcaatg   1080
gatgcaatgg cacacgccct catcaacgct gctgcagtgc ttgaggaaag ccctctgtgc   1140
gagatggttg caaagcgcta cgccagcttt gacagcggtc ttggcaagaa gttcgaggaa   1200
ggcaaagcca ctctcgagga gatctacgag tatgccaaga aggccccggc acccgtcgcc   1260
gcctccggca agcaggagct ctacgagaca ctgctcaatc tgtacgctaa ataa         1314
```

<210> SEQ ID NO 144
<211> LENGTH: 437
<212> TYPE: PRT
<213> ORGANISM: Unknown
<220> FEATURE:
<223> OTHER INFORMATION: Obtained from environmental sample

<400> SEQUENCE: 144

```
Met Lys Glu Tyr Phe Pro Thr Ile Gly Lys Ile Pro Phe Glu Gly Pro
1               5                   10                  15

Gln Ser Lys Asn Pro Leu Ala Phe His Tyr Tyr Asp Ala Asn Arg Val
            20                  25                  30

Val Ala Gly Lys Pro Met Lys Asp Trp Leu Lys Phe Ala Met Ala Trp
        35                  40                  45

Trp His Thr Leu Gly Ala Ala Ser Ala Asp Pro Phe Gly Gly Gln Thr
    50                  55                  60

Arg Ser Tyr Glu Trp Asp Lys Ala Glu Cys Pro Tyr Cys Arg Ala Arg
65                  70                  75                  80

Glu Lys Ala Asp Ala Gly Phe Glu Ile Met Gln Lys Leu Gly Ile Glu
                85                  90                  95

Tyr Phe Cys Phe His Asp Ile Asp Leu Val Glu Asp Cys Glu Asp Ile
            100                 105                 110

Ala Glu Tyr Glu Ala Arg Met Lys Asp Ile Thr Asp Tyr Leu Leu Glu
        115                 120                 125

Lys Met Lys Ala Thr Gly Ile Lys Asn Leu Trp Gly Thr Ala Asn Val
    130                 135                 140

Phe Gly Asn Lys Arg Tyr Met Asn Gly Ala Ala Thr Asn Pro Gln Phe
145                 150                 155                 160

Asp Ile Val Ala Arg Ala Ala Val Gln Ile Lys Asn Ala Ile Asp Ala
                165                 170                 175

Thr Ile Lys Leu Gly Gly Thr Gly Tyr Val Phe Trp Gly Gly Arg Glu
            180                 185                 190

Gly Tyr Tyr Thr Leu Leu Asn Thr Gln Met Gln Arg Glu Lys Asp His
        195                 200                 205

Leu Ala Lys Met Leu Thr Ala Ala Arg Asp Tyr Ala Arg Ala Lys Gly
    210                 215                 220

Phe Lys Gly Thr Phe Leu Ile Glu Pro Lys Pro Met Glu Pro Thr Lys
225                 230                 235                 240

His Gln Tyr Asp Val Asp Thr Glu Thr Val Ile Gly Phe Leu Arg Ala
                245                 250                 255

Asn Gly Leu Asp Lys Asp Phe Lys Val Asn Ile Glu Val Asn His Ala
            260                 265                 270
```

```
Thr Leu Ala Gly His Thr Phe Glu His Glu Leu Thr Val Ala Val Asp
            275                 280                 285

Asn Gly Phe Leu Gly Ser Ile Asp Ala Asn Arg Gly Asp Ala Gln Asn
        290                 295                 300

Gly Trp Asp Thr Asp Gln Phe Pro Val Asp Pro Tyr Asp Leu Thr Gln
305                 310                 315                 320

Ala Met Met Gln Ile Ile Arg Asn Gly Gly Phe Lys Asp Gly Gly Thr
                325                 330                 335

Asn Phe Asp Ala Lys Leu Arg Arg Ser Ser Thr Asp Pro Glu Asp Ile
            340                 345                 350

Phe Ile Ala His Ile Ser Ala Met Asp Ala Met Ala His Ala Leu Ile
        355                 360                 365

Asn Ala Ala Ala Val Leu Glu Glu Ser Pro Leu Cys Glu Met Val Ala
370                 375                 380

Lys Arg Tyr Ala Ser Phe Asp Ser Gly Leu Gly Lys Lys Phe Glu Glu
385                 390                 395                 400

Gly Lys Ala Thr Leu Glu Glu Ile Tyr Glu Tyr Ala Lys Lys Ala Pro
                405                 410                 415

Ala Pro Val Ala Ala Ser Gly Lys Gln Glu Leu Tyr Glu Thr Leu Leu
            420                 425                 430

Asn Leu Tyr Ala Lys
        435

<210> SEQ ID NO 145
<211> LENGTH: 1317
<212> TYPE: DNA
<213> ORGANISM: Unknown
<220> FEATURE:
<223> OTHER INFORMATION: Obtained from environmental sample

<400> SEQUENCE: 145
atgaccaaag agtatttccc tacaatcgga aagattccct tcgaaggccc ggagagcaag     60
aatccgctgg cattccatta ctatgaaccc gacagaatca tcctcggcag aagatgaag    120 gactggctgc gcttcgccgt ggcctggtgg cacaccctcg gccaggcgtc cggcgaccag    180
ttcggaggcc agaccgcaa ctatgcgtgg gacgagcccg aatgcccggt agagcgcgcg    240
aaagccaagg ccgacgccgg cttcgagctg atgcagaagc tgggcatcga gtatttctgc    300
ttccacgacg tagacctcat agaggaggcc gcaaccatcg aagaatatga ggagcgcatg    360
ggcatcataa ccgactacct gctcgggaag atgaaggaga caggtatcaa gaacctctgg    420
ggcaccgcca acgtgttcgg ccacaagcgt tacatgaacg gagccgccac caaccccgac    480
ttcgacgtgg tggcccgtgc ggccgtgcag atcaagaacg ccatcgacgc caccatcaag    540
ctgggcggcg agaattacgt attctggggc ggacgcgagg gctatgcaag cctgctcaac    600
actcagatgc agcgcgagaa agaccacctg ggacgcatgc tggctgcagc ccgcgactat    660
ggccgcgccc acggattcaa gggcactttc ctcatcgagc ccaaacccat ggagcctacc    720
aagcaccagt acgaccagga taccgagacc gttatcgcct tcctgcgcag gaacggcctc    780
gacaaggatt tcaaggtaaa catcgaggtg aaccacgcca ccctggcggg ccacaccttc    840
gagcacgaac tggcggtggc agtggacaac ggcctgcttg gcagcatcga cgccaaccgc    900
ggcgacgcgc agaacggatg ggacaccgac cagttcccca tcgacaactt cgagctcacc    960
caggccatgc tgcagataat ccgcaacggc ggactgggaa ccggcggatc gaacttcgac   1020
gccaagctgc gccgcaattc caccgaccct gaggatatct tcatcgccca catcagtgcg   1080
```

```
atggacgcca tggcacgcgc gctggcaaac gccgccgcaa tcatcgaaga gagcccatc   1140 cccgcaatgc tgaaggagcg ctacgcatcg ttcgacagcg gcaagggcaa ggagttcgag   1200
gacggcaaac tgagcctcga agaactggta gcctacgcca aggcgaacgg cgagccgaag   1260
cagatttccg gcaagcagga actctacgaa accatagtgg ccctctattg caagtaa     1317
```

<210> SEQ ID NO 146
<211> LENGTH: 438
<212> TYPE: PRT
<213> ORGANISM: Unknown
<220> FEATURE:
<223> OTHER INFORMATION: Obtained from environmental sample

<400> SEQUENCE: 146

```
Met Thr Lys Glu Tyr Phe Pro Thr Ile Gly Lys Ile Pro Phe Glu Gly
1               5                   10                  15

Pro Glu Ser Lys Asn Pro Leu Ala Phe His Tyr Tyr Glu Pro Asp Arg
            20                  25                  30

Ile Ile Leu Gly Arg Lys Met Lys Asp Trp Leu Arg Phe Ala Val Ala
        35                  40                  45

Trp Trp His Thr Leu Gly Gln Ala Ser Gly Asp Gln Phe Gly Gly Gln
    50                  55                  60

Thr Arg Asn Tyr Ala Trp Asp Glu Pro Glu Cys Pro Val Glu Arg Ala
65                  70                  75                  80

Lys Ala Lys Ala Asp Ala Gly Phe Glu Leu Met Gln Lys Leu Gly Ile
                85                  90                  95

Glu Tyr Phe Cys Phe His Asp Val Asp Leu Ile Glu Glu Ala Ala Thr
            100                 105                 110

Ile Glu Glu Tyr Glu Glu Arg Met Gly Ile Ile Thr Asp Tyr Leu Leu
        115                 120                 125

Gly Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Val Ala Arg Ala Ala Val Gln Ile Lys Asn Ala Ile Asp
                165                 170                 175

Ala Thr Ile Lys Leu Gly Gly Glu Asn Tyr Val Phe Trp Gly Gly Arg
            180                 185                 190

Glu Gly Tyr Ala Ser Leu Leu Asn Thr Gln Met Gln Arg Glu Lys Asp
        195                 200                 205

His Leu Gly Arg Met Leu Ala Ala Ala Arg Asp Tyr Gly Arg Ala His
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Ala Phe Leu Arg
                245                 250                 255

Arg Asn Gly Leu Asp Lys Asp Phe Lys Val Asn Ile Glu Val Asn His
            260                 265                 270

Ala Thr Leu Ala Gly His Thr Phe Glu His Glu Leu Ala Val Ala Val
        275                 280                 285

Asp Asn Gly Leu Leu Gly Ser Ile Asp Ala Asn Arg Gly Asp Ala Gln
    290                 295                 300

Asn Gly Trp Asp Thr Asp Gln Phe Pro Ile Asp Asn Phe Glu Leu Thr
305                 310                 315                 320

Gln Ala Met Leu Gln Ile Ile Arg Asn Gly Gly Leu Gly Thr Gly Gly
```

|  | 325 |  |  |  | 330 |  |  |  |  | 335 |  |  |
|---|---|---|---|---|---|---|---|---|---|---|---|---|

Ser Asn Phe Asp Ala Lys Leu Arg Arg Asn Ser Thr Asp Pro Glu Asp
    340                        345                        350

Ile Phe Ile Ala His Ile Ser Ala Met Asp Ala Met Ala Arg Ala Leu
    355                        360                        365

Ala Asn Ala Ala Ala Ile Ile Glu Glu Ser Pro Ile Pro Ala Met Leu
    370                        375                        380

Lys Glu Arg Tyr Ala Ser Phe Asp Ser Gly Lys Gly Lys Glu Phe Glu
385                        390                        395                     400

Asp Gly Lys Leu Ser Leu Glu Glu Leu Val Ala Tyr Ala Lys Ala Asn
                405                        410                        415

Gly Glu Pro Lys Gln Ile Ser Gly Lys Gln Glu Leu Tyr Glu Thr Ile
            420                        425                        430

Val Ala Leu Tyr Cys Lys
            435

<210> SEQ ID NO 147
<211> LENGTH: 1317
<212> TYPE: DNA
<213> ORGANISM: Unknown
<220> FEATURE:
<223> OTHER INFORMATION: Obtained from environmental sample

<400> SEQUENCE: 147

```
atggcacaag aatacttccc taccattggg aaaatcccct tcgagggcac tgagagcaag      60
aatcccttg ctttccatta ctatgagccg gagcgcattg tctgcggcaa acccatgaaa     120
gaatggctca agtttgccat ggcctggtgg cacacgctgg ggcaggcatc ggccgatccc     180
ttcggcggcc aaacccgcag ctatgcctgg gataagggcg aatgcccta ctgccgtgcc     240
cgcgccaagg cggacgccgg cttcgagatt atgcaaaagc tgggcatcga gtacttctgc     300
ttccacgata tcgacctggt agaagactgt gacgatattg cggaatacga agcccgcatg     360
aaggacatca cggactacct cctggagaag atgaaggaaa ccggtatcaa gaacctctgg     420
ggcaccgcca atgtgtttgg tcacaagcgc tacatgaacg cgccgccac caacccgcag     480
tttgacgtag tggcccgtgc cgctgttcag attaagaacg ccattgacgc caccatcaag     540
ttgggcggtg ccaattacgt gttctggggc ggccgcgagg ctattacag cctcctgaac     600
acccagatgc agcgggagaa ggaccacctg ccaagctgc tcacggcagc ccgcgactat     660
gcccgcgcca acggcttcaa gggaaccttc ctgattgagc ccaagcccat ggagcccacc     720
aagcaccagt acgacgtgga tacgagacg gtcattggct cctccgcgc caacggcctg     780
gacaaggact tcaaggtgaa tatcgaggtg aaccacgcca cgttggccgg ccacaccttt     840
gagcacgagc tcaccgtggc ccgcgagaac ggcttcctgg gcagcatcga cgccaaccgc     900
ggcgatgccc agaacggctg ggatacggac cagttcccgg tagacgctta tgagctcacc     960
caggccatga tgcaggtgct cctgaacgga ggcttcggca acggcggcac caacttcgac    1020
gccaagctgc gccgctcctc cacggaccc gaggacatct tcatcgccca tatcagtgcg    1080
atggatgcca tggcccacgc cctgctcaac gccgccgccg tgctggagga aagcccctg    1140
tgccagatgg tgaaggagcg ctacgccagc tttgacagcg gtccgggcaa gcagttcgag    1200
gaaggaaagg ccaccctgga ggacctgtac aactacgcca aagccaccgg tgaacccgtg    1260
gttgcctccg gcaagcagga actttacgag accctcctga acctctatgc aaagtag      1317
```

<210> SEQ ID NO 148

```
<211> LENGTH: 438
<212> TYPE: PRT
<213> ORGANISM: Unknown
<220> FEATURE:
<223> OTHER INFORMATION: Obtained from environmental sample

<400> SEQUENCE: 148
```

| | | | | | | | | | | | | | | |
|---|---|---|---|---|---|---|---|---|---|---|---|---|---|---|
| Met | Ala | Gln | Glu | Tyr | Phe | Pro | Thr | Ile | Gly | Lys | Ile | Pro | Phe | Gly |
| 1 | | | | 5 | | | | | 10 | | | | | 15 |
| Thr | Glu | Ser | Lys | Asn | Pro | Leu | Ala | Phe | His | Tyr | Tyr | Glu | Pro | Glu | Arg |
| | | | 20 | | | | | 25 | | | | | 30 | | |
| Ile | Val | Cys | Gly | Lys | Pro | Met | Lys | Glu | Trp | Leu | Lys | Phe | Ala | Met | Ala |
| | | | 35 | | | | | 40 | | | | | 45 | | |
| Trp | Trp | His | Thr | Leu | Gly | Gln | Ala | Ser | Ala | Asp | Pro | Phe | Gly | Gly | Gln |
| 50 | | | | | 55 | | | | | 60 | | | | | |
| Thr | Arg | Ser | Tyr | Ala | Trp | Asp | Lys | Gly | Glu | Cys | Pro | Tyr | Cys | Arg | Ala |
| 65 | | | | | 70 | | | | | 75 | | | | | 80 |
| Arg | Ala | Lys | Ala | Asp | Ala | Gly | Phe | Glu | Ile | Met | Gln | Lys | Leu | Gly | Ile |
| | | | | 85 | | | | | 90 | | | | | 95 | |
| Glu | Tyr | Phe | Cys | Phe | His | Asp | Ile | Asp | Leu | Val | Glu | Asp | Cys | Asp | Asp |
| | | | 100 | | | | | 105 | | | | | 110 | | |
| Ile | Ala | Glu | Tyr | Glu | Ala | Arg | Met | Lys | Asp | Ile | Thr | Asp | Tyr | Leu | Leu |
| | | | 115 | | | | | 120 | | | | | 125 | | |
| Glu | Lys | Met | Lys | Glu | Thr | Gly | Ile | Lys | Asn | Leu | Trp | Gly | Thr | Ala | Asn |
| | 130 | | | | | 135 | | | | | 140 | | | | |
| Val | Phe | Gly | His | Lys | Arg | Tyr | Met | Asn | Gly | Ala | Ala | Thr | Asn | Pro | Gln |
| 145 | | | | | 150 | | | | | 155 | | | | | 160 |
| Phe | Asp | Val | Val | Ala | Arg | Ala | Ala | Val | Gln | Ile | Lys | Asn | Ala | Ile | Asp |
| | | | | 165 | | | | | 170 | | | | | 175 | |
| Ala | Thr | Ile | Lys | Leu | Gly | Gly | Ala | Asn | Tyr | Val | Phe | Trp | Gly | Gly | Arg |
| | | | 180 | | | | | 185 | | | | | 190 | | |
| Glu | Gly | Tyr | Tyr | Ser | Leu | Leu | Asn | Thr | Gln | Met | Gln | Arg | Glu | Lys | Asp |
| | | | 195 | | | | | 200 | | | | | 205 | | |
| His | Leu | Ala | Lys | Leu | Leu | Thr | Ala | Ala | Arg | Asp | Tyr | Ala | Arg | Ala | Asn |
| | 210 | | | | | 215 | | | | | 220 | | | | |
| Gly | Phe | Lys | Gly | Thr | Phe | Leu | Ile | Glu | Pro | Lys | Pro | Met | Glu | Pro | Thr |
| 225 | | | | | 230 | | | | | 235 | | | | | 240 |
| Lys | His | Gln | Tyr | Asp | Val | Asp | Thr | Glu | Thr | Val | Ile | Gly | Phe | Leu | Arg |
| | | | | 245 | | | | | 250 | | | | | 255 | |
| Ala | Asn | Gly | Leu | Asp | Lys | Asp | Phe | Lys | Val | Asn | Ile | Glu | Val | Asn | His |
| | | | 260 | | | | | 265 | | | | | 270 | | |
| Ala | Thr | Leu | Ala | Gly | His | Thr | Phe | Glu | His | Glu | Leu | Thr | Val | Ala | Arg |
| | | | 275 | | | | | 280 | | | | | 285 | | |
| Glu | Asn | Gly | Phe | Leu | Gly | Ser | Ile | Asp | Ala | Asn | Arg | Gly | Asp | Ala | Gln |
| | 290 | | | | | 295 | | | | | 300 | | | | |
| Asn | Gly | Trp | Asp | Thr | Asp | Gln | Phe | Pro | Val | Asp | Ala | Tyr | Glu | Leu | Thr |
| 305 | | | | | 310 | | | | | 315 | | | | | 320 |
| Gln | Ala | Met | Met | Gln | Val | Leu | Leu | Asn | Gly | Gly | Phe | Gly | Asn | Gly | Gly |
| | | | | 325 | | | | | 330 | | | | | 335 | |
| Thr | Asn | Phe | Asp | Ala | Lys | Leu | Arg | Arg | Ser | Ser | Thr | Pro | Glu | Asp |
| | | | 340 | | | | | 345 | | | | | 350 | |
| Ile | Phe | Ile | Ala | His | Ile | Ser | Ala | Met | Asp | Ala | Met | Ala | His | Ala | Leu |
| | | | 355 | | | | | 360 | | | | | 365 | | |
| Leu | Asn | Ala | Ala | Ala | Val | Leu | Glu | Glu | Ser | Pro | Leu | Cys | Gln | Met | Val |
| | 370 | | | | | 375 | | | | | 380 | | | | |

Lys Glu Arg Tyr Ala Ser Phe Asp Ser Gly Pro Gly Lys Gln Phe Glu
385                 390                 395                 400

Glu Gly Lys Ala Thr Leu Glu Asp Leu Tyr Asn Tyr Ala Lys Ala Thr
                405                 410                 415

Gly Glu Pro Val Val Ala Ser Gly Lys Gln Glu Leu Tyr Glu Thr Leu
            420                 425                 430

Leu Asn Leu Tyr Ala Lys
        435

<210> SEQ ID NO 149
<211> LENGTH: 1317
<212> TYPE: DNA
<213> ORGANISM: Unknown
<220> FEATURE:
<223> OTHER INFORMATION: Obtained from environmental sample

<400> SEQUENCE: 149

| | |
|---|---|
| atggcacaag aatacttccc taccattggg aaaatcccct tcgagggcac tgagagcaag | 60 |
| aatccccttg ctttccatta ctatgagccg gagcgcattg tctgcggcaa acccatgaaa | 120 |
| gaatggctca agtttgccat ggcctggtgg cacacgctgg ggcaggcatc ggccgatccc | 180 |
| ttcggcggcc aaacccgcag ctatgcctgg gataagggcg aatgccccta ctgccgtgcc | 240 |
| cgtgccaagg cggacgccgg ttttgagatt atgcaaaagc tgggcatcga gtacttctgc | 300 |
| ttccacgata tcgacctggt agaagactgt gacgatattg cggaatacga agcccgcatg | 360 |
| aaggacatca cggactacct cctggagaag atgaaggaaa ccggcatcaa gaacctctgg | 420 |
| ggcaccgcca atgtgtttgg tcacaagcgc tacatgaacg cgccggcac caatccgcag | 480 |
| tttgacgtgg tggcccgtgc tgccgtgcaa atcaagaacg ccattgacgc caccatcaag | 540 |
| ttgggcggtg ccaattacgt gttctggggc ggccgcgagg gctattacag cctcctgaac | 600 |
| acccagatgc agcgggagaa ggaccacctg gccaagctgc tcacggcagc ccgcgactat | 660 |
| gcccgcgcca acggcttcaa gggaaccttc ctgattgagc ccaagcccat ggagcccacc | 720 |
| aagcaccagt acgacgtgga tacggagacg gtcattggct tcctccgcgc caacggcctg | 780 |
| gacaaggact tcaaggtgaa tatcgaggtg aaccacgcca cgctggccgg ccacaccttt | 840 |
| gagcacgaac tcaccgtggc ccgcgagaac ggcttcctgg gcagcatcga cgccaaccgc | 900 |
| ggcgatgccc agaacggctg ggatacggac cagttcccgg tagacgctta tgagctcacc | 960 |
| caggccatga tgcaggtgct cctgaacgga ggcttcggca acggcggcac caacttcgac | 1020 |
| gccaagctgc gccgctcctc cacggacctg gaggacatct tcatcgccca tatcagtgcg | 1080 |
| atggatgcca tggcccacgc cctgctcaac gccgccgccg tgctggagga agcccccctg | 1140 |
| tgccagatgg tgaaggagcg ctacgccagc tttgacagcg gtccgggcaa gcagttcgag | 1200 |
| gaaggaaagg ccaccctgga ggacctgtac aactacgcca agccaacgg tgaacccgtg | 1260 |
| gttgcctccg gcaagcagga actttacgag accctcctga acctctatgc aaagtag | 1317 |

<210> SEQ ID NO 150
<211> LENGTH: 438
<212> TYPE: PRT
<213> ORGANISM: Unknown
<220> FEATURE:
<223> OTHER INFORMATION: Obtained from environmental sample

<400> SEQUENCE: 150

Met Ala Gln Glu Tyr Phe Pro Thr Ile Gly Lys Ile Pro Phe Glu Gly
1               5                   10                  15

```
Thr Glu Ser Lys Asn Pro Leu Ala Phe His Tyr Tyr Glu Pro Glu Arg
         20                  25                  30

Ile Val Cys Gly Lys Pro Met Lys Glu Trp Leu Lys Phe Ala Met Ala
             35                  40                  45

Trp Trp His Thr Leu Gly Gln Ala Ser Ala Asp Pro Phe Gly Gly Gln
 50                  55                  60

Thr Arg Ser Tyr Ala Trp Asp Lys Gly Glu Cys Pro Tyr Cys Arg Ala
 65                  70                  75                  80

Arg Ala Lys Ala Asp Ala Gly Phe Glu Ile Met Gln Lys Leu Gly Ile
                 85                  90                  95

Glu Tyr Phe Cys Phe His Asp Ile Asp Leu Val Glu Asp Cys Asp Asp
                100                 105                 110

Ile Ala Glu Tyr Glu Ala Arg Met Lys Asp Ile Thr Asp Tyr Leu Leu
                115                 120                 125

Glu Lys Met Lys Glu Thr Gly Ile Lys Asn Leu Trp Gly Thr Ala Asn
        130                 135                 140

Val Phe Gly His Lys Arg Tyr Met Asn Gly Ala Gly Thr Asn Pro Gln
145                 150                 155                 160

Phe Asp Val Val Ala Arg Ala Ala Val Gln Ile Lys Asn Ala Ile Asp
                165                 170                 175

Ala Thr Ile Lys Leu Gly Gly Ala Asn Tyr Val Phe Trp Gly Gly Arg
            180                 185                 190

Glu Gly Tyr Tyr Ser Leu Leu Asn Thr Gln Met Gln Arg Glu Lys Asp
            195                 200                 205

His Leu Ala Lys Leu Leu Thr Ala Ala Arg Asp Tyr Ala Arg Ala Asn
        210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
        290                 295                 300

Asn Gly Trp Asp Thr Asp Gln Phe Pro Val Asp Ala Tyr Glu Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Leu Glu Asp
                340                 345                 350

Ile Phe Ile Ala His Ile Ser Ala Met Asp Ala Met Ala His Ala Leu
            355                 360                 365

Leu Asn Ala Ala Ala Val Leu Glu Glu Ser Pro Leu Cys Gln Met Val
        370                 375                 380

Lys Glu Arg Tyr Ala Ser Phe Asp Ser Gly Pro Gly Lys Gln Phe Glu
385                 390                 395                 400

Glu Gly Lys Ala Thr Leu Glu Asp Leu Tyr Asn Tyr Ala Lys Ala Asn
                405                 410                 415

Gly Glu Pro Val Val Ala Ser Gly Lys Gln Glu Leu Tyr Glu Thr Leu
                420                 425                 430
```

Leu Asn Leu Tyr Ala Lys
         435

<210> SEQ ID NO 151
<211> LENGTH: 1317
<212> TYPE: DNA
<213> ORGANISM: Unknown
<220> FEATURE:
<223> OTHER INFORMATION: Obtained from environmental sample

<400> SEQUENCE: 151

```
atggcaaaag aatatttccc taccatcggc aagattcctt ttgaaggaac cgacagcaag      60
agtcccctcg ccttccatta ctatgacgcc cagcgcgttg tgatgggcaa acccatgaag     120
gaatggctca agttcgccat ggcctggtgg cacaccctgg gccaggcatc ggccgacccc     180
ttcggcggtc agacccgcca ctatgcctgg gatgaaggcg aatgccccta ctgccgcgcc     240
aaagccaagg ccgacgccgg cttcgagatc atgcagaaac tgggcatcga gtacttctgc     300
ttccacgatg tggacctggt ggaagactgc gacgacatcg ccgagtacga agcccgcatg     360
aaggacatca cggactacct gctggagaag atgaaggaaa ccggcatcaa gaacctctgg     420
ggcacggcca atgtgttcgg ccacaagcgt tacatgaacg cgccgggac caacccgcag     480
tttgacattg tggcccgcgc tgccgtccag atcaaaaacg ccctggacgc caccatcaag     540
ctgggcggtt ccaactacgt gttctggggc agccgcaag gctactacac cctcctgaac     600
acccagatgc agcgggagaa agaccacctg gccaagctcc tgaccgccgc ccgcgactac     660
gcccgcgcca aaggcttcaa gggaaccttc ctcatcgagc ccaaacccat ggagcccacc     720
aagcaccagt acgacgtgga caccgagacc gtaatcggct tcctgcgtgc aacggcctg     780
gacaaggact tcaaggtgaa catcgaggtg aaccacgcca ccctggctgg ccacaccttc     840
gagcacgaac tcaccgtcgc ccgtgaaaac ggcttcctcg gatcgatcga cgccaaccgc     900
ggcgacgccc agaacggctg ggacaccgac cagttccccg tagacgccta tgacctcacc     960
caggccatga tgcaggtgct gctgaacggc ggtttcggca atggcggtac caacttcgac    1020
gccaagctcc gccgctcctc cacggatccg gaagacatct tcatcgccca catcagcgcc    1080
atggacgcca tggcccacgc cctgctgaac gccgccgccg tgctggaaga aagcccgctt    1140
cccgccatgg cgaaagagcg ctacgcctcc tttgacagcg gacttggcaa gaagttcgaa    1200
gagggaaagg ccaccctcga agagctgtac gactatgcca aggctaacga cgcccctgtc    1260
gccgcctccg gcaagcagga actttacgaa accttcttga acctctatgc aaaatag       1317
```

<210> SEQ ID NO 152
<211> LENGTH: 438
<212> TYPE: PRT
<213> ORGANISM: Unknown
<220> FEATURE:
<223> OTHER INFORMATION: Obtained from environmental sample

<400> SEQUENCE: 152

Met Ala Lys Glu Tyr Phe Pro Thr Ile Gly Lys Ile Pro Phe Glu Gly
1               5                   10                  15

Thr Asp Ser Lys Ser Pro Leu Ala Phe His Tyr Tyr Asp Ala Gln Arg
            20                  25                  30

Val Val Met Gly Lys Pro Met Lys Glu Trp Leu Lys Phe Ala Met Ala
        35                  40                  45

Trp Trp His Thr Leu Gly Gln Ala Ser Ala Asp Pro Phe Gly Gly Gln
    50                  55                  60

Thr Arg His Tyr Ala Trp Asp Glu Gly Glu Cys Pro Tyr Cys Arg Ala
 65                  70                  75                  80

Lys Ala Lys Ala Asp Ala Gly Phe Glu Ile Met Gln Lys Leu Gly Ile
                 85                  90                  95

Glu Tyr Phe Cys Phe His Asp Val Asp Leu Val Glu Asp Cys Asp Asp
            100                 105                 110

Ile Ala Glu Tyr Glu Ala Arg Met Lys Asp Ile Thr Asp Tyr Leu Leu
        115                 120                 125

Glu Lys Met Lys Glu Thr Gly Ile Lys Asn Leu Trp Gly Thr Ala Asn
130                 135                 140

Val Phe Gly His Lys Arg Tyr Met Asn Gly Ala Gly Thr Asn Pro Gln
145                 150                 155                 160

Phe Asp Ile Val Ala Arg Ala Ala Val Gln Ile Lys Asn Ala Leu Asp
                165                 170                 175

Ala Thr Ile Lys Leu Gly Gly Ser Asn Tyr Val Phe Trp Gly Ser Arg
            180                 185                 190

Glu Gly Tyr Tyr Thr Leu Leu Asn Thr Gln Met Gln Arg Glu Lys Asp
        195                 200                 205

His Leu Ala Lys Leu Leu Thr Ala Ala Arg Asp Tyr Ala Arg Ala Lys
210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
290                 295                 300

Asn Gly Trp Asp Thr Asp Gln Phe Pro Val Asp Ala Tyr Asp Leu Thr
305                 310                 315                 320

Gln Ala Met Met Gln Val Leu Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Leu Glu Glu Ser Pro Leu Pro Ala Met Ala
370                 375                 380

Lys Glu Arg Tyr Ala Ser Phe Asp Ser Gly Leu Gly Lys Lys Phe Glu
385                 390                 395                 400

Glu Gly Lys Ala Thr Leu Glu Glu Leu Tyr Asp Tyr Ala Lys Ala Asn
                405                 410                 415

Asp Ala Pro Val Ala Ala Ser Gly Lys Gln Glu Leu Tyr Glu Thr Phe
            420                 425                 430

Leu Asn Leu Tyr Ala Lys
        435

<210> SEQ ID NO 153
<211> LENGTH: 1317
<212> TYPE: DNA
<213> ORGANISM: Unknown
<220> FEATURE:
<223> OTHER INFORMATION: Obtained from environmental sample

<400> SEQUENCE: 153

```
atggcaaaac agtattttcc gcaaatcgga aagattaaat tcgaaggaac agagagcaag      60
aatccgcttg cgttccatta ttatgacgca acagggtag tcctcggaaa ggcaatggag      120
gagtggctca agttcgcaat ggcttggtgg catactctcg acaggcttc cggagaccag      180
ttcggcggcc agaccccgcag ctacgagtgg gatcttgcag ccaccccga gcagcgcgca     240
aaggacaagc tcgacgccgg cttcgaaata tggagaaac ttggaatcaa gtatttctgt     300
ttccacgatg ttgaccttat cgaagacagc gacgatattg cgacatatga ggctcgtctc    360
aaggacctta cagactacgc tgcagagcag atgaagctcc acgacatcaa gctcctctgg    420
ggtacagcga atgtattcgg caacaagcgc tacatgaacg gtgcggctac aaaccctgat    480
ttcgatgtag ttgcccgcgc agccgttcag attaagaacg ctatcgacgc gaccatcaag    540
ctcggtggta ccagctatgt attctggggc ggtcgtgagg atatcagag cctgctcaac    600
actcagatgc agcgtgagaa ggaccacctc gcaaccatgc ttacaatcgc tcgcgactat    660
gctcgcagca agggctttac cggaaccttc cttatcgagc ctaagccgat ggagcctaca    720
aaacaccagt acgacgtaga tacagagact gttgtcggct tcctcaaggc acacggcctg    780
gacaaggact tcaaggtaaa tatcgaggtt aaccacgcaa ctctcgcagg ccacaccttc    840
gagcacgaac tcaccgttgc tgtggataac ggaatgctcg gttctatcga cgctaaccgc    900
ggtgatgcac agaacggctg ggatacagac cagttccctg taagcgctga ggagcttacc    960
ctcgctatga tgcagattat ccgtaatggt ggccttggca acggaggatc caacttcgac   1020
gcaaagcttc gccgcaactc taccgatcct gaagacatct catcgcaca catctgcggt    1080
atggatgcaa tggcacacgc tctcctcaat gcagctgcaa ttatcgagga gtctcctatc   1140
cctacaatgg ttaaggagcg ttacgcttcc ttcgacagcg gtatgggtaa ggacttcgag   1200
gatggaaagc ttaccctcga ggatctctac agctacggcg tgaagaacgg agagccaaag   1260
cagaccagcg caaagcagga gctctatgag actctcatga atatctattg caagtaa      1317
```

<210> SEQ ID NO 154
<211> LENGTH: 438
<212> TYPE: PRT
<213> ORGANISM: Unknown
<220> FEATURE:
<223> OTHER INFORMATION: Obtained from environmental sample

<400> SEQUENCE: 154

```
Met Ala Lys Gln Tyr Phe Pro Gln Ile Gly Lys Ile Lys Phe Glu Gly
1               5                   10                  15

Thr Glu Ser Lys Asn Pro Leu Ala Phe His Tyr Tyr Asp Ala Asn Arg
            20                  25                  30

Val Val Leu Gly Lys Ala Met Glu Glu Trp Leu Lys Phe Ala Met Ala
        35                  40                  45

Trp Trp His Thr Leu Gly Gln Ala Ser Gly Asp Gln Phe Gly Gly Gln
    50                  55                  60

Thr Arg Ser Tyr Glu Trp Asp Leu Ala Ala Thr Pro Glu Gln Arg Ala
65                  70                  75                  80

Lys Asp Lys Leu Asp Ala Gly Phe Glu Ile Met Glu Lys Leu Gly Ile
                85                  90                  95

Lys Tyr Phe Cys Phe His Asp Val Asp Leu Ile Glu Asp Ser Asp Asp
            100                 105                 110

Ile Ala Thr Tyr Glu Ala Arg Leu Lys Asp Leu Thr Asp Tyr Ala Ala
```

```
            115                 120                 125
Glu Gln Met Lys Leu His Asp Ile Lys Leu Leu Trp Gly Thr Ala Asn
    130                 135                 140

Val Phe Gly Asn Lys Arg Tyr Met Asn Gly Ala Ala Thr Asn Pro Asp
145                 150                 155                 160

Phe Asp Val Val Ala Arg Ala Ala Val Gln Ile Lys Asn Ala Ile Asp
                165                 170                 175

Ala Thr Ile Lys Leu Gly Gly Thr Ser Tyr Val Phe Trp Gly Gly Arg
            180                 185                 190

Glu Gly Tyr Gln Ser Leu Leu Asn Thr Gln Met Gln Arg Glu Lys Asp
        195                 200                 205

His Leu Ala Thr Met Leu Thr Ile Ala Arg Asp Tyr Ala Arg Ser Lys
    210                 215                 220

Gly Phe Thr Gly Thr Phe Leu Ile Glu Pro Lys Pro Met Glu Pro Thr
225                 230                 235                 240

Lys His Gln Tyr Asp Val Asp Thr Glu Thr Val Val Gly Phe Leu Lys
                245                 250                 255

Ala His Gly Leu Asp Lys Asp Phe Lys Val Asn Ile Glu Val Asn His
            260                 265                 270

Ala Thr Leu Ala Gly His Thr Phe Glu His Glu Leu Thr Val Ala Val
        275                 280                 285

Asp Asn Gly Met Leu Gly Ser Ile Asp Ala Asn Arg Gly Asp Ala Gln
    290                 295                 300

Asn Gly Trp Asp Thr Asp Gln Phe Pro Val Ser Ala Glu Glu Leu Thr
305                 310                 315                 320

Leu Ala Met Met Gln Ile Ile Arg Asn Gly Gly Leu Gly Asn Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Cys Gly Met Asp Ala Met Ala His Ala Leu
        355                 360                 365

Leu Asn Ala Ala Ala Ile Ile Glu Glu Ser Pro Ile Pro Thr Met Val
    370                 375                 380

Lys Glu Arg Tyr Ala Ser Phe Asp Ser Gly Met Gly Lys Asp Phe Glu
385                 390                 395                 400

Asp Gly Lys Leu Thr Leu Glu Asp Leu Tyr Ser Tyr Gly Val Lys Asn
                405                 410                 415

Gly Glu Pro Lys Gln Thr Ser Ala Lys Gln Glu Leu Tyr Glu Thr Leu
            420                 425                 430

Met Asn Ile Tyr Cys Lys
        435

<210> SEQ ID NO 155
<211> LENGTH: 1317
<212> TYPE: DNA
<213> ORGANISM: Unknown
<220> FEATURE:
<223> OTHER INFORMATION: Obtained from environmental sample

<400> SEQUENCE: 155
atggcaaaag aatttttcc acaagtaggc aagattccat tgagggtcc tgaaagtact      60 aacgtactcg cattccacta ctatgatcca gaacgcgaag ttcttggtaa gaaaatgaaa   120
gattggctga agtatgctat ggcttggtgg cacacactcg gtcaggcaag tggcgaccaa   180
ttcggtggtc aaactcgttc gtatgaatgg gatgaagccg acgatgttct tcaacgcgca   240
```

-continued

```
aaggataaaa tggatgctgg ttttgaattg atgaccaaac ttggcattga atactactgc    300
ttccatgatg tcgaccttat tgaagaaggt gcaacaattg aagaatatga agctcgtatg    360
caagctatca ccgactacgc attagaaaaa caaaagaaa ccggcattaa gctcctttgg     420
ggtactgcta atgtgtttgg tcataagcgt tatatgaatg gtgcggcaac aaaccctgac    480
tttgatgtag tggctcgcgc tgctgtacaa atcaagaacg ctatcgatgc aactatcaag    540
cttggtggtc aaaactatgt attctggggt ggccgcgaag ttatatgag  tttgctcaac    600
actcaaatgc aacgcgaaaa agaccacttg gcaaagatgc ttaccgcagc tcgcgactat    660
gctcgtgcta agggcttcaa gggtacattc ctcgttgaac ctaagcctat ggaaccaact    720
aagcatcaat atgataccga tacagaaact gtgattggtt tcctccgtgc aaatggtctt    780
gaaaaagact tcaaggtgaa cattgaagtg aaccatgcta ctctcgctca gcacactttc    840
gaacacgaac tcgctgtggc tgtcgacaat ggcatgctcg gttctatcga cgctaaccgt    900
ggcgatgctc aaaatggctg ggataccgac caattcccaa tcgacaacta cgaactcacc    960
ctcgctatgc tccaaatcat tcgcaatggt ggtcttggca atggcggtag caacctcgac   1020
gctaagattc gtcgtaatag caccgacctt gaagacctct ttatcgctca catcagtggt   1080
atggatgcta tggctcgtgc acttctcaat gctgctgcaa tcgttgaaaa gagcgaaatt   1140
cctgctatgt tgaagcagcg ttatgcaagc tctgatgcag gtatgggtaa ggacttcgaa   1200
gaaggaaaac tcactctcga caactcgta gactatgcta aggctaacgg cgaacctgct    1260
acagtaagcg gcaagcaaga aaagtatgaa actctcgttg ctctctacgc taagtaa      1317
```

<210> SEQ ID NO 156
<211> LENGTH: 438
<212> TYPE: PRT
<213> ORGANISM: Unknown
<220> FEATURE:
<223> OTHER INFORMATION: Obtained from environmental sample

<400> SEQUENCE: 156

```
Met Ala Lys Glu Phe Phe Pro Gln Val Gly Lys Ile Pro Phe Glu Gly
1               5                  10                  15

Pro Glu Ser Thr Asn Val Leu Ala Phe His Tyr Tyr Asp Pro Glu Arg
            20                  25                  30

Glu Val Leu Gly Lys Lys Met Lys Asp Trp Leu Lys Tyr Ala Met Ala
        35                  40                  45

Trp Trp His Thr Leu Gly Gln Ala Ser Gly Asp Gln Phe Gly Gly Gln
    50                  55                  60

Thr Arg Ser Tyr Glu Trp Asp Glu Ala Asp Val Leu Gln Arg Ala
65                  70                  75                  80

Lys Asp Lys Met Asp Ala Gly Phe Glu Leu Met Thr Lys Leu Gly Ile
                85                  90                  95

Glu Tyr Tyr Cys Phe His Asp Val Asp Leu Ile Glu Glu Gly Ala Thr
            100                 105                 110

Ile Glu Glu Tyr Glu Ala Arg Met Gln Ala Ile Thr Asp Tyr Ala Leu
        115                 120                 125

Glu Lys Gln Lys Glu Thr Gly Ile Lys Leu Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Val Ala Arg Ala Ala Val Gln Ile Lys Asn Ala Ile Asp
                165                 170                 175
```

Ala Thr Ile Lys Leu Gly Gly Gln Asn Tyr Val Phe Trp Gly Gly Arg
            180                 185                 190

Glu Gly Tyr Met Ser Leu Leu Asn Thr Gln Met Gln Arg Glu Lys Asp
        195                 200                 205

His Leu Ala Lys Met Leu Thr Ala Ala Arg Asp Tyr Ala Arg Ala Lys
    210                 215                 220

Gly Phe Lys Gly Thr Phe Leu Val Glu Pro Lys Pro Met Glu Pro Thr
225                 230                 235                 240

Lys His Gln Tyr Asp Thr Asp Thr Glu Thr Val Ile Gly Phe Leu Arg
                245                 250                 255

Ala Asn Gly Leu Glu Lys Asp Phe Lys Val Asn Ile Glu Val Asn His
            260                 265                 270

Ala Thr Leu Ala Gln His Thr Phe Glu His Glu Leu Ala Val Ala Val
        275                 280                 285

Asp Asn Gly Met Leu Gly Ser Ile Asp Ala Asn Arg Gly Asp Ala Gln
    290                 295                 300

Asn Gly Trp Asp Thr Asp Gln Phe Pro Ile Asp Asn Tyr Glu Leu Thr
305                 310                 315                 320

Leu Ala Met Leu Gln Ile Ile Arg Asn Gly Gly Leu Gly Asn Gly Gly
                325                 330                 335

Ser Asn Leu Asp Ala Lys Ile Arg Arg Asn Ser Thr Asp Leu Glu Asp
            340                 345                 350

Leu Phe Ile Ala His Ile Ser Gly Met Asp Ala Met Ala Arg Ala Leu
        355                 360                 365

Leu Asn Ala Ala Ala Ile Val Glu Lys Ser Glu Ile Pro Ala Met Leu
    370                 375                 380

Lys Gln Arg Tyr Ala Ser Ser Asp Ala Gly Met Gly Lys Asp Phe Glu
385                 390                 395                 400

Glu Gly Lys Leu Thr Leu Glu Gln Leu Val Asp Tyr Ala Lys Ala Asn
                405                 410                 415

Gly Glu Pro Ala Thr Val Ser Gly Lys Gln Glu Lys Tyr Glu Thr Leu
            420                 425                 430

Val Ala Leu Tyr Ala Lys
        435

<210> SEQ ID NO 157
<211> LENGTH: 1317
<212> TYPE: DNA
<213> ORGANISM: Unknown
<220> FEATURE:
<223> OTHER INFORMATION: Obtained from environmental sample

<400> SEQUENCE: 157
atgactaaag agtatttccc gggaatcgga aagattccgt tgaaggaac caagagcaag      60 aaccccctgg ccttccatta ttataacgcc tcccaggtag cgatgggcaa gcccatgaag    120
gactggctca gtatgccat ggcctggtgg cacaccctgg ccaggcctc tgcagacccc      180 tttggcggcc agacccgctc ctacgaatgg acaagggcg agtgcccta ttgccgcgcc      240 aagcagaagg ccgatgccgg ctttgagctc atgcagaagc tgggcatcga gtactactgc    300
ttccacgacg tggacatcat cgaggactgc gaggacattg ccgagtacga ggcccgcatg    360
aaggacatca cggactacct gctggagaag cagaaagaga ccggcatcaa gaacctctgg    420
ggcaccgcca acgtgtttgg ccacaagcgc tacatgaacg cgccgccac caaccctcag    480 tttgacattg tggcccgtgc cgccgtccag atcaagaacg ccctggatgc caccatcaag    540

```
ctgggtggta ccaactacgt gttctggggt ggccgcgaag gctactacac gctgctcaac    600
acccagatgc agcgggagaa gaaccacctg gccaagatgc tcaccgccgc cgcgactac    660
gcccgcgcca agggcttcaa gggcaccttc ctcattgagc ccaaacccat ggagcccacc    720
aagcaccagt acgacgtgga caccgagacc gtgattggtt tcatccgcgc caacggcctg    780
gacaaggact tcaaggtaaa cattgaggta aaccacgcca ccctggccgg ccacaccttt    840
gagcacgagc tcaccgtggc ccgcgagaac ggcttcctgg gctccatcga cgccaaccgc    900
ggagatgccc agaacggctg ggatacggac cagttcccca tcgacgccct ggatctcacc    960
caggctatga tgcaggtcat cctcaacggt ggcttcggca tggcggcac caactttgac    1020
gccaagctcc gccgctcctc caccgatccc gaggacatct tcatcgccca tcagcgcc    1080
atggatgcca tggcacacgc cctcctgaac gcagccgcca tcctggaaga gagccccctg    1140
cccgccatgg tcaaggagcg ttacgcttcc ttcgacagcg gtctgggcaa gaagttcgaa    1200
gaaggcaagg cctccctgga agaactttac gaatatgcca agaagaatgg agagcccgtg    1260
gccgcttccg gcaaacagga gctctgcgaa acttacttga acctctatgc aaagtag      1317
```

<210> SEQ ID NO 158
<211> LENGTH: 438
<212> TYPE: PRT
<213> ORGANISM: Unknown
<220> FEATURE:
<223> OTHER INFORMATION: Obtained from environmental sample

<400> SEQUENCE: 158

```
Met Thr Lys Glu Tyr Phe Pro Gly Ile Gly Lys Ile Pro Phe Glu Gly
1               5                   10                  15

Thr Lys Ser Lys Asn Pro Leu Ala Phe His Tyr Tyr Asn Ala Ser Gln
            20                  25                  30

Val Ala Met Gly Lys Pro Met Lys Asp Trp Leu Lys Tyr Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Lys Gln Lys Ala Asp Ala Gly Phe Glu Leu Met Gln Lys Leu Gly Ile
                85                  90                  95

Glu Tyr Tyr Cys Phe His Asp Val Asp Ile Ile Glu Asp Cys Glu Asp
            100                 105                 110

Ile Ala Glu Tyr Glu Ala Arg Met Lys Asp Ile Thr Asp Tyr Leu Leu
        115                 120                 125

Glu Lys Gln Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Ile Val Ala Arg Ala Ala Val Gln Ile Lys Asn Ala Leu Asp
                165                 170                 175

Ala Thr Ile Lys Leu Gly Gly Thr Asn Tyr Val Phe Trp Gly Gly Arg
            180                 185                 190

Glu Gly Tyr Tyr Thr Leu Leu Asn Thr Gln Met Gln Arg Glu Lys Asn
        195                 200                 205

His Leu Ala Lys Met Leu Thr Ala Ala Arg Asp Tyr Ala Arg Ala Lys
    210                 215                 220
```

```
Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Ile Arg
            245                 250                 255

Ala Asn Gly Leu Asp Lys Asp Phe Lys Val Asn Ile Glu Val Asn His
        260                 265                 270

Ala Thr Leu Ala Gly His Thr Phe Glu His Glu Leu Thr Val Ala Arg
    275                 280                 285

Glu Asn Gly Phe Leu Gly Ser Ile Asp Ala Asn Arg Gly Asp Ala Gln
290                 295                 300

Asn Gly Trp Asp Thr Asp Gln Phe Pro Ile Asp Ala Leu Asp Leu Thr
305                 310                 315                 320

Gln Ala Met Met Gln Val Ile Leu Asn Gly Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Leu Pro Ala Met Val
370                 375                 380

Lys Glu Arg Tyr Ala Ser Phe Asp Ser Gly Leu Gly Lys Lys Phe Glu
385                 390                 395                 400

Glu Gly Lys Ala Ser Leu Glu Glu Leu Tyr Glu Tyr Ala Lys Lys Asn
                405                 410                 415

Gly Glu Pro Val Ala Ala Ser Gly Lys Gln Glu Leu Cys Glu Thr Tyr
            420                 425                 430

Leu Asn Leu Tyr Ala Lys
        435

<210> SEQ ID NO 159
<211> LENGTH: 1317
<212> TYPE: DNA
<213> ORGANISM: Unknown
<220> FEATURE:
<223> OTHER INFORMATION: Obtained from environmental sample

<400> SEQUENCE: 159
atgactaaag agtatttccc gggaatcgga aagattccgt tgaaggaac caagagcaag      60 aaccccctgg ccttccatta ttataacgcc tcccaggtag tgatgggcaa gcccatgaag     120
gactggctca gtatgccat ggcctggtgg cacaccctgg ccaggcctc tgcagacccc       180 tttggcggcc agaccgctc ctacgaatgg gacaagggcg agtgcccgta ctgccgcgcc      240
aagcagaagg ccgatgccgg ctttgagctc atgcagaagc tgggcatcga gtactactgc    300
ttccacgacg tggacatcat cgaggactgc gaggacattg ccgagtacga ggcccgcatg    360
aaggacatca cggactacct gctggagaag cagaaagaga ccggcatcaa gaacctctgg    420
ggcaccgcca acgtgtttgg ccacaagcgc tacatgaacg cgccgccac caaccctcag     480 tttgacattg tggcccgtgc cgccgtccag atcaagaacg ccctggatgc caccatcaaa    540
ctgggtggta ccaactacgt gttctggggt ggccgcaag ctactacac gctgctcaac      600 acccagatgc agcgggagaa gaaccacctg gccaagatgc tcaccgccgc cgcgactac    660 gcccgcgcca aggcttcaa gggcaccttc tcattgagc ccaaacccat ggagcccacc      720
aagcaccagt acgacgtgga caccgagacc gtgattggtt catccgcgc aacggcctg     780 gacaaggact tcaaggtaaa cattgaggta aaccacgcca ccctggccgg ccacaccttt    840
```

```
gagcacgagc tcaccgtggc ccgcgagaac ggcttcctgg gctccatcga cgccaaccgc    900
ggagatgccc agaacggctg ggatacggac cagttcccca tcgacgccct ggatctcacc    960
caggctatga tgcaggtcat cctcaacggt ggcttcggca atggcggcac caactttgac   1020
gccaagctcc gccgctcctc caccgatccc gaggacatct tcatcgccca catcagcgcc   1080
atggatgcca tggcacacgc cctcctgaac gcagccgcca tcctggaaga gagccccctg   1140
cccgccatgg tcaaggagcg ttacgcttcc ttcgacagcg gtctgggcaa gaagttcgaa   1200
gaaggcaagg cctccctgga agaactttac gaatatgcca agaagaatgg agagcccgtg   1260
gccgcttccg gcaaacagga gctctgcgaa acttacttga acctctatgc aaagtag      1317
```

<210> SEQ ID NO 160
<211> LENGTH: 438
<212> TYPE: PRT
<213> ORGANISM: Unknown
<220> FEATURE:
<223> OTHER INFORMATION: Obtained from environmental sample

<400> SEQUENCE: 160

```
Met Thr Lys Glu Tyr Phe Pro Gly Ile Gly Lys Ile Pro Phe Glu Gly
1               5                   10                  15

Thr Lys Ser Lys Asn Pro Leu Ala Phe His Tyr Tyr Asn Ala Ser Gln
            20                  25                  30

Val Val Met Gly Lys Pro Met Lys Asp Trp Leu Lys Tyr Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Lys Gln Lys Ala Asp Ala Gly Phe Glu Leu Met Gln Lys Leu Gly Ile
                85                  90                  95

Glu Tyr Tyr Cys Phe His Asp Val Asp Ile Ile Glu Asp Cys Glu Asp
            100                 105                 110

Ile Ala Glu Tyr Glu Ala Arg Met Lys Asp Ile Thr Asp Tyr Leu Leu
        115                 120                 125

Glu Lys Gln Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Ile Val Ala Arg Ala Ala Val Gln Ile Lys Asn Ala Leu Asp
                165                 170                 175

Ala Thr Ile Lys Leu Gly Gly Thr Asn Tyr Val Phe Trp Gly Gly Arg
            180                 185                 190

Glu Gly Tyr Tyr Thr Leu Leu Asn Thr Gln Met Gln Arg Glu Lys Asn
        195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Ile Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
```

```
                275                 280                 285
Glu Asn Gly Phe Leu Gly Ser Ile Asp Ala Asn Arg Gly Asp Ala Gln
    290                 295                 300

Asn Gly Trp Asp Thr Asp Gln Phe Pro Ile Ala Leu Asp Leu Thr
305                 310                 315                 320

Gln Ala Met Met Gln Val Ile Leu Asn Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
                355                 360                 365

Leu Asn Ala Ala Ala Ile Leu Glu Glu Ser Pro Leu Pro Ala Met Val
            370                 375                 380

Lys Glu Arg Tyr Ala Ser Phe Asp Ser Gly Leu Gly Lys Lys Phe Glu
385                 390                 395                 400

Glu Gly Lys Ala Ser Leu Glu Glu Leu Tyr Glu Tyr Ala Lys Lys Asn
                405                 410                 415

Gly Glu Pro Val Ala Ala Ser Gly Lys Gln Glu Leu Cys Glu Thr Tyr
            420                 425                 430

Leu Asn Leu Tyr Ala Lys
            435
```

<210> SEQ ID NO 161
<211> LENGTH: 1317
<212> TYPE: DNA
<213> ORGANISM: Unknown
<220> FEATURE:
<223> OTHER INFORMATION: Obtained from environmental sample

<400> SEQUENCE: 161

```
atggcaaaag agtatttccc gactatcggc aagattccct tcgagggcgt cgaatccaag      60
aacccgatgg cattccacta ctatgacgcg aaccgcgtcg tgatgggcaa gcccatgaag     120
gactggctca agttcgcgat ggcctggtgg cacaccctgg acaggcttc cggcgacccg      180
ttcggcggcc agacccgttc ctacgagtgg gacaagggcg agtgcccta ctgccgcgcc      240
aaggccaagg ccgacgccgg cttcgagatc atgcagaagc tcggtatcga gtactactgc     300
ttccatgaca tcgacctcgt ggaggacacc gaggacatcg ccgagtacga ggcccgcatg     360
aaggacatca ccgactacct cgtcgagaag cagaaggaaa ccggcatcaa gaacctctgg     420
ggcacggcca acgtgttcgg caacaagcgc tacatgaacg gcgccgccac gaacccgcag     480
ttcgacgtcg tcgcccgcgc cgccgtccag atcaagaacg ccatcgacgc caccatcaag     540
ctcggcggta ccggttacgt gttctggggc ggccgtgaag gctactacac cctcctgaac     600
acccagatgc agcgcgagaa ggaccactc gccaagatgc tcaccgccgc cgcgactac      660
gcccgcgccc acggcttcca gggcaccttc ctcatcgagc ccaagcccat ggagcccacc     720
aagcaccagt acgacgtgga cacggagacc gtgatcggct cctgcgcgc caacggtctg     780
gacaaggact tcaaggtcaa tatcgaggtg aaccacgcca ccctcgccgg ccacaccttc     840
gagcacgagc tcaccgtggc tgtcgataac ggcttcctcg ctccatcga cgccaaccgc     900
ggcgacgccc agaacggctg gacaccgac cagttccccg tggacccgta cgacctcacc     960
caggccatga tgcagatcat ccgcaacggc ggtttcaagg acggcggcac caacttcgac    1020
gccaagctcc gccgctcttc caccgacccg gaggacatct tcatcgccca catcagcgcg    1080
atggacgcca tggcccacgc cctgctgaac gccgccgccg tcatcgagga gagcccgctc    1140
```

```
tgcaagatgg tcgaggagcg ctacgcttcc ttcgacagcg gcctcggcaa gcagttcgag    1200
gaaggcaagg ccaccctcga ggacctctac gagtatgcca agaagaatgg cgagcccgtc    1260
gtcgcctccg gcaagcagga gctctacgag acgctgctga acctttacgc gaagtag       1317
```

<210> SEQ ID NO 162
<211> LENGTH: 438
<212> TYPE: PRT
<213> ORGANISM: Unknown
<220> FEATURE:
<223> OTHER INFORMATION: Obtained from environmental sample

<400> SEQUENCE: 162

```
Met Ala Lys Glu Tyr Phe Pro Thr Ile Gly Lys Ile Pro Phe Glu Gly
1               5                   10                  15

Val Glu Ser Lys Asn Pro Met Ala Phe His Tyr Asp Ala Asn Arg
            20                  25                  30

Val Val Met Gly Lys Pro Met Lys Asp Trp Leu Lys Phe Ala Met Ala
            35                  40                  45

Trp Trp His Thr Leu Gly Gln Ala Ser Gly Asp Pro Phe Gly Gly Gln
    50                  55                  60

Thr Arg Ser Tyr Glu Trp Asp Lys Gly Glu Cys Pro Tyr Cys Arg Ala
65              70                  75                  80

Lys Ala Lys Ala Asp Ala Gly Phe Glu Ile Met Gln Lys Leu Gly Ile
                85                  90                  95

Glu Tyr Tyr Cys Phe His Asp Ile Asp Leu Val Glu Asp Thr Glu Asp
            100                 105                 110

Ile Ala Glu Tyr Glu Ala Arg Met Lys Asp Ile Thr Asp Tyr Leu Val
            115                 120                 125

Glu Lys Gln Lys Glu Thr Gly Ile Lys Asn Leu Trp Gly Thr Ala Asn
    130                 135                 140

Val Phe Gly Asn Lys Arg Tyr Met Asn Gly Ala Ala Thr Asn Pro Gln
145             150                 155                 160

Phe Asp Val Val Ala Arg Ala Ala Val Gln Ile Lys Asn Ala Ile Asp
                165                 170                 175

Ala Thr Ile Lys Leu Gly Gly Thr Gly Tyr Val Phe Trp Gly Gly Arg
            180                 185                 190

Glu Gly Tyr Tyr Thr Leu Leu Asn Thr Gln Met Gln Arg Glu Lys Asp
            195                 200                 205

His Leu Ala Lys Met Leu Thr Ala Ala Arg Asp Tyr Ala Arg Ala His
    210                 215                 220

Gly Phe Gln Gly Thr Phe Leu Ile Glu Pro Lys Pro Met Glu Pro Thr
225             230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Val
            275                 280                 285

Asp Asn Gly Phe Leu Gly Ser Ile Asp Ala Asn Arg Gly Asp Ala Gln
    290                 295                 300

Asn Gly Trp Asp Thr Asp Gln Phe Pro Val Asp Pro Tyr Asp Leu Thr
305             310                 315                 320

Gln Ala Met Met Gln Ile Ile Arg Asn Gly Gly Phe Lys Asp Gly Gly
                325                 330                 335
```

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Ile Glu Ser Pro Leu Cys Lys Met Val
370                 375                 380

Glu Glu Arg Tyr Ala Ser Phe Asp Ser Gly Leu Gly Lys Gln Phe Glu
385                 390                 395                 400

Glu Gly Lys Ala Thr Leu Glu Asp Leu Tyr Glu Tyr Ala Lys Lys Asn
            405                 410                 415

Gly Glu Pro Val Val Ala Ser Gly Lys Gln Glu Leu Tyr Glu Thr Leu
            420                 425                 430

Leu Asn Leu Tyr Ala Lys
        435

<210> SEQ ID NO 163
<211> LENGTH: 1317
<212> TYPE: DNA
<213> ORGANISM: Unknown
<220> FEATURE:
<223> OTHER INFORMATION: Obtained from environmental sample

<400> SEQUENCE: 163

| | | | | | |
|---|---|---|---|---|---|
| atggcaaaag | agtatttccc | gacaatcggt | aagatcccct | tcgagggacc | cgagtccaag | 60 |
| aacccgatgg | cattccacta | ctatgacgcg | gagcgcgtgg | tgatgggcaa | gaagatgaag | 120 |
| gactggttca | agttcgcgat | ggcctggtgg | cacaccctgg | ccaggcttc | cgccgacccg | 180 |
| ttcggcggcc | agaccgctc | ctacgagtgg | gacaagggcg | aaggcccctg | ctcccgcgcc | 240 |
| cgcgccaagg | ctgacgccgg | tttcgagatc | atgcagaaac | tgggcatcgg | ctactactgc | 300 |
| ttccacgaca | tcgacctggt | ggaggacacc | gaggacatcg | ccgagtatga | agcccgcatg | 360 |
| aaggacatca | ccgactacct | cgtggagaag | cagaaggaga | ccggcatcaa | gaacctctgg | 420 |
| ggcacggcca | acgtattcgg | caacaagccc | tacatgaacg | cgccgccac | gaacccgcag | 480 |
| ttcgacatcg | ccgcccgcgc | ggccctgcag | accaagaacg | ccatcgatgc | caccatcaag | 540 |
| ctgggcggca | ccggttacgt | gttctggggc | ggccgtgaag | gctactacac | cctcctgaac | 600 |
| acccagatgc | agcgcgagaa | ggaccacctt | gccaagatgc | tcaccgcggc | tgccgactat | 660 |
| gcccgcgccc | acggcttcaa | gggcaccttc | ttcatcgagc | cgaaaccgat | ggagcccacc | 720 |
| aagcaccagt | acgacgtgga | cacggagacc | gtgatcggct | tcctccgcgc | caacggcctg | 780 |
| gacaaggact | tcaaggtgaa | catcgaagtg | aaccacgcca | ccctcgccgg | ccacaccttc | 840 |
| gagcacgggc | tcaccgtggc | cgttgacaac | ggcttcctcg | gcagcatcga | cgccaaccgc | 900 |
| ggagacgccc | agaacggctg | ggataccgac | cagttcccgg | tggatccgta | cgacctcacc | 960 |
| caggcgatga | tccagatcat | ccgcaatggc | ggcttcaagg | acggcggtac | caacttcgac | 1020 |
| gccaagctcc | gccgctcttc | caccgacccg | gaggacatct | tcatcgccca | catcagcgcg | 1080 |
| atggacgcca | tggcccacgc | cctgctgaac | gccgccgccg | tgctcgagga | gagcccgctc | 1140 |
| tgcgagatgg | ttgcaaagcg | ttacgcttcc | ttcgacagcg | gtctcggcaa | gaagttcgag | 1200 |
| gaaggcaacg | ccaccctcga | ggaactctac | gagtacgcca | aggcgaaggg | cgaggtcgtt | 1260 |
| gccgaatccg | gcaagcagga | actctacgag | accctgctga | acctctacgc | gaagtag | 1317 |

<210> SEQ ID NO 164
<211> LENGTH: 438

```
<212> TYPE: PRT
<213> ORGANISM: Unknown
<220> FEATURE:
<223> OTHER INFORMATION: Obtained from environmental sample

<400> SEQUENCE: 164
```

| | | | | | | | | | | | | | | |
|---|---|---|---|---|---|---|---|---|---|---|---|---|---|---|
| Met | Ala | Lys | Glu | Tyr | Phe | Pro | Thr | Ile | Gly | Lys | Ile | Pro | Phe | Glu | Gly |
| 1 | | | | 5 | | | | | 10 | | | | | 15 | |

Pro Glu Ser Lys Asn Pro Met Ala Phe His Tyr Tyr Asp Ala Glu Arg
            20                  25                  30

Val Val Met Gly Lys Lys Met Lys Asp Trp Phe Lys Phe Ala Met Ala
                35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Gly Pro Cys Ser Arg Ala
65                  70                  75                  80

Arg Ala Lys Ala Asp Ala Gly Phe Glu Ile Met Gln Lys Leu Gly Ile
                85                  90                  95

Gly Tyr Tyr Cys Phe His Asp Ile Asp Leu Val Glu Asp Thr Glu Asp
                100                 105                 110

Ile Ala Glu Tyr Glu Ala Arg Met Lys Asp Ile Thr Asp Tyr Leu Val
            115                 120                 125

Glu Lys Gln Lys Glu Thr Gly Ile Lys Asn Leu Trp Gly Thr Ala Asn
130                 135                 140

Val Phe Gly Asn Lys Pro Tyr Met Asn Gly Ala Ala Thr Asn Pro Gln
145                 150                 155                 160

Phe Asp Ile Ala Ala Arg Ala Ala Leu Gln Thr Lys Asn Ala Ile Asp
                165                 170                 175

Ala Thr Ile Lys Leu Gly Gly Thr Gly Tyr Val Phe Trp Gly Gly Arg
                180                 185                 190

Glu Gly Tyr Tyr Thr Leu Leu Asn Thr Gln Met Gln Arg Glu Lys Asp
            195                 200                 205

His Leu Ala Lys Met Leu Thr Ala Ala Arg Asp Tyr Ala Arg Ala His
210                 215                 220

Gly Phe Lys Gly Thr Phe Phe Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
                260                 265                 270

Ala Thr Leu Ala Gly His Thr Phe Glu His Gly Leu Thr Val Ala Val
            275                 280                 285

Asp Asn Gly Phe Leu Gly Ser Ile Asp Ala Asn Arg Gly Asp Ala Gln
290                 295                 300

Asn Gly Trp Asp Thr Asp Gln Phe Pro Val Asp Pro Tyr Asp Leu Thr
305                 310                 315                 320

Gln Ala Met Ile Gln Ile Ile Arg Asn Gly Gly Phe Lys Asp Gly Gly
                325                 330                 335

Thr Asn Phe Asp Ala Lys Leu Arg Arg Ser Ser Thr Asp Pro Glu Asp
                340                 345                 350

Ile Phe Ile Ala His Ile Ser Ala Met Asp Ala Met Ala His Ala Leu
            355                 360                 365

Leu Asn Ala Ala Ala Val Leu Glu Glu Ser Pro Leu Cys Glu Met Val
370                 375                 380

Ala Lys Arg Tyr Ala Ser Phe Asp Ser Gly Leu Gly Lys Lys Phe Glu
385                 390                 395                 400

Glu Gly Asn Ala Thr Leu Glu Glu Leu Tyr Glu Tyr Ala Lys Ala Lys
                405                 410                 415

Gly Glu Val Val Ala Glu Ser Gly Lys Gln Glu Leu Tyr Glu Thr Leu
            420                 425                 430

Leu Asn Leu Tyr Ala Lys
        435

<210> SEQ ID NO 165
<211> LENGTH: 1317
<212> TYPE: DNA
<213> ORGANISM: Unknown
<220> FEATURE:
<223> OTHER INFORMATION: Obtained from environmental sample

<400> SEQUENCE: 165

| | | | | | |
|---|---|---|---|---|---|
| atggcaaaag | agtatttccc | gacaatcgga | aagatcccct | tcgagggcgc | tgagagcaag | 60 |
| aatccccttg | ctttccacta | ttatgacgcc | gagcgtgtgg | tcatgggcaa | gcccatgaag | 120 |
| gactggttca | agttcgcgat | ggcctggtgg | cacaccctgg | ccaggcttc | cgccacccg | 180 |
| ttcggcggcc | agacccgctc | ctacgagtgg | gacaaggggga | agtgccccta | ctgccgcgcc | 240 |
| cgccagaagg | ctgacgccgg | tttcgagatc | atgcagaagc | tcggcatcgg | ctactactgc | 300 |
| ttccacgaca | tcgacctggt | cgaggacacc | gaggacatcg | ccgagtacga | ggcccgcatg | 360 |
| aaggacatca | ccgactacct | cgtcgagaag | cagaaggaga | ccggcatcaa | gaacctctgg | 420 |
| ggcacggcca | acgtgttcgg | caacaagcgc | tacatgaacg | cgccgccac | gaacccgcag | 480 |
| ttcgacatcg | tcgcccacgc | ggccctgcag | atcaagaacg | cgatcggcgc | caccatcaag | 540 |
| ctcggcggca | ccggttacgt | gttctggggc | ggccgtgaag | gttactacac | cctcctgaac | 600 |
| acccagatgc | agcgcgagaa | ggaccacctc | gccaagatgc | tcaccgccgc | ccgcgactac | 660 |
| gcccgcgcca | acgcttcaa | gggcaccttc | ctcatcgagc | cgaagccgat | ggagcccacc | 720 |
| aagcaccagt | atgacgtgga | cacggagacc | gtgatcggct | cctccgcgc | caacggcctg | 780 |
| gacaaggact | tcaaggtgaa | catcgaggtg | aaccacgcca | ccctcgccgg | ccacaccttc | 840 |
| gagcacgagc | tcaccgtggc | ggtcgacaac | ggcttcctcg | gcagcatcga | cgccaaccgc | 900 |
| ggtgacgccc | agaacggctg | ggataccgac | cagttcccgg | tggatccgta | cgatctcacc | 960 |
| caggcgatga | tccagatcat | ccgcaacggc | ggcttcaagg | atgcggcac | caacttcgac | 1020 |
| gccaagctcc | gccgctcttc | caccgacccg | gaggacatct | tcatcgccca | catcagcgcg | 1080 |
| atggacgcca | tggcccacgc | cctgctgaac | gccgccgccg | tcatcgagga | gagcccgctc | 1140 |
| tgcgagatgg | tcgccaagcg | ctacgcttcc | ttcgacagcg | gtctcggcaa | gaagttcgag | 1200 |
| gaaggcaacg | ccaccctcga | ggaactctac | gagtacgcca | aggcgaacgg | tgaggtcaag | 1260 |
| gccgaatccg | gcaagcagga | gctctacgag | acccttctga | acctctacgc | gaaatag | 1317 |

<210> SEQ ID NO 166
<211> LENGTH: 438
<212> TYPE: PRT
<213> ORGANISM: Unknown
<220> FEATURE:
<223> OTHER INFORMATION: Obtained from environmental sample

<400> SEQUENCE: 166

Met Ala Lys Glu Tyr Phe Pro Thr Ile Gly Lys Ile Pro Phe Glu Gly
1               5                   10                  15

```
Ala Glu Ser Lys Asn Pro Leu Ala Phe His Tyr Tyr Asp Ala Glu Arg
            20                  25                  30

Val Val Met Gly Lys Pro Met Lys Asp Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Arg Gln Lys Ala Asp Ala Gly Phe Glu Ile Met Gln Lys Leu Gly Ile
                85                  90                  95

Gly Tyr Tyr Cys Phe His Asp Ile Asp Leu Val Glu Asp Thr Glu Asp
            100                 105                 110

Ile Ala Glu Tyr Glu Ala Arg Met Lys Asp Ile Thr Asp Tyr Leu Val
        115                 120                 125

Glu Lys Gln Lys Glu Thr Gly Ile Lys Asn Leu Trp Gly Thr Ala Asn
    130                 135                 140

Val Phe Gly Asn Lys Arg Tyr Met Asn Gly Ala Ala Thr Asn Pro Gln
145                 150                 155                 160

Phe Asp Ile Val Ala His Ala Ala Leu Gln Ile Lys Asn Ala Ile Gly
                165                 170                 175

Ala Thr Ile Lys Leu Gly Gly Thr Gly Tyr Val Phe Trp Gly Gly Arg
            180                 185                 190

Glu Gly Tyr Tyr Thr Leu Leu Asn Thr Gln Met Gln Arg Glu Lys Asp
        195                 200                 205

His Leu Ala Lys Met Leu Thr Ala Ala Arg Asp Tyr Ala Arg Ala Asn
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Phe Leu Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Val
        275                 280                 285

Asp Asn Gly Phe Leu Gly Ser Ile Asp Ala Asn Arg Gly Asp Ala Gln
    290                 295                 300

Asn Gly Trp Asp Thr Asp Gln Phe Pro Val Asp Pro Tyr Asp Leu Thr
305                 310                 315                 320

Gln Ala Met Ile Gln Ile Arg Asn Gly Gly Phe Lys Asp Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Val Ile Glu Glu Ser Pro Leu Cys Glu Met Val
    370                 375                 380

Ala Lys Arg Tyr Ala Ser Phe Asp Ser Gly Leu Gly Lys Lys Phe Glu
385                 390                 395                 400

Glu Gly Asn Ala Thr Leu Glu Glu Leu Tyr Glu Tyr Ala Lys Ala Asn
                405                 410                 415

Gly Glu Val Lys Ala Glu Ser Gly Lys Gln Glu Leu Tyr Glu Thr Leu
            420                 425                 430

Leu Asn Leu Tyr Ala Lys
```

<210> SEQ ID NO 167
<211> LENGTH: 1317
<212> TYPE: DNA
<213> ORGANISM: Unknown
<220> FEATURE:
<223> OTHER INFORMATION: Obtained from environmental sample

<400> SEQUENCE: 167

```
atggcaaaag agtatttccc cactatcggg aagattcctt tcgaaggagt cgagagcaag      60
aaccccttg cattccatta ttatgacgca aaccgcatgg tcatgggcaa gcccatgaag     120
gactggttca agttcgccat ggcatggtgg cacaccctgg acaggcctc cgcagacccg     180
ttcggcggcc agacccgctc ctacgaatgg gacaagggcg aatgcccta ctgccgcgcc     240
agggcaaagg ccgatgccgg cttcgagatc atgcagaaac tgggtatcga gtatttctgc     300
ttccatgaca tcgacctggt agaggactgc gacgacatcg ccgagtacga ggcccgcatg     360
aaggacatca cggactatct cctggagaag atgaaggaaa ccggcatcaa gaacctctgg     420
ggcaccgcca acgtgttcgg caacaagcgt tacatgaacg gcgccggcac caatccgcag     480
ttcgacgtag tggcccgcgc tgccgtccag atcaagaacg ccatcgacgc caccatcaag     540
ctcggcggtt ccaactatgt gttctggggc ggccgtgaag atactacac cctgctgaac     600
acccagatgc agcgcgagaa ggaccactc ggcaaactgc tcaccgccgc ccgcgactat     660
gcccgcaaga acggcttcaa gggcaccttc ctcatcgagc ccaagccgat ggagcccacc     720
aagcaccagt acgacgtaga cacggagacc gtgatcggct tcctccgcgc caacggcctg     780
gagaaagact tcaaggtgaa catcgaggtg aaccacgcca ccctggccgg ccatacttc     840
gagcatgaac tcaccgtggc cgtggacaac ggcttcctgg atccatcga cgccaaccgc     900
ggcgacgccc agaacggctg ggatacggac cagttcccgg tagacccgta cgacctcacc     960
caggccatga tgcagatcat ccgcaacggc ggcctcggca acggcggtac caacttcgac    1020
gccaaactgc gccgttcctc caccgatcct gaggacatct tcatcgccca catcagcgcc    1080
atggacgcca tggcccacgc cctgctcaac gcagccgccg tgctggaaga agtccgctc    1140
tgtgagatgg tcaaggagcg ctacgcttcc ttcgacagcg gtctcggcaa gaagttcgaa    1200
gagggcaagg ctaccctgga gaaaatctac gagtatgcca agaagagcgg cgaacccgtg    1260
gtcgcttccg gcaagcagga gctctacgaa accctgctga acctctacgc caagtag       1317
```

<210> SEQ ID NO 168
<211> LENGTH: 438
<212> TYPE: PRT
<213> ORGANISM: Unknown
<220> FEATURE:
<223> OTHER INFORMATION: Obtained from environmental sample

<400> SEQUENCE: 168

Met Ala Lys Glu Tyr Phe Pro Thr Ile Gly Lys Ile Pro Phe Glu Gly
1               5                   10                  15

Val Glu Ser Lys Asn Pro Leu Ala Phe His Tyr Tyr Asp Ala Asn Arg
            20                  25                  30

Met Val Met Gly Lys Pro Met Lys Asp Trp Phe Lys Phe Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Cys Pro Tyr Cys Arg Ala

```
                65                  70                  75                  80
Arg Ala Lys Ala Asp Ala Gly Phe Glu Ile Met Gln Lys Leu Gly Ile
                85                  90                  95
Glu Tyr Phe Cys Phe His Asp Ile Asp Leu Val Glu Asp Cys Asp Asp
               100                 105                 110
Ile Ala Glu Tyr Glu Ala Arg Met Lys Asp Ile Thr Asp Tyr Leu Leu
               115                 120                 125
Glu Lys Met Lys Glu Thr Gly Ile Lys Asn Leu Trp Gly Thr Ala Asn
           130                 135                 140
Val Phe Gly Asn Lys Arg Tyr Met Asn Gly Ala Gly Thr Asn Pro Gln
145                 150                 155                 160
Phe Asp Val Val Ala Arg Ala Val Gln Ile Lys Asn Ala Ile Asp
               165                 170                 175
Ala Thr Ile Lys Leu Gly Gly Ser Asn Tyr Val Phe Trp Gly Gly Arg
               180                 185                 190
Glu Gly Tyr Tyr Thr Leu Leu Asn Thr Gln Met Gln Arg Glu Lys Asp
           195                 200                 205
His Leu Gly Lys Leu Leu Thr Ala Ala Arg Asp Tyr Ala Arg Lys Asn
       210                 215                 220
Gly Phe Lys Gly Thr Phe Leu Ile Glu Pro Lys Pro Met Glu Pro Thr
225                 230                 235                 240
Lys His Gln Tyr Asp Val Asp Thr Glu Thr Val Ile Gly Phe Leu Arg
               245                 250                 255
Ala Asn Gly Leu Glu Lys Asp Phe Lys Val Asn Ile Glu Val Asn His
               260                 265                 270
Ala Thr Leu Ala Gly His Thr Phe Glu His Glu Leu Thr Val Ala Val
           275                 280                 285
Asp Asn Gly Phe Leu Gly Ser Ile Asp Ala Asn Arg Gly Asp Ala Gln
       290                 295                 300
Asn Gly Trp Asp Thr Asp Gln Phe Pro Val Asp Pro Tyr Asp Leu Thr
305                 310                 315                 320
Gln Ala Met Met Gln Ile Ile Arg Asn Gly Gly Leu Gly Asn Gly Gly
               325                 330                 335
Thr Asn Phe Asp Ala Lys Leu Arg Arg Ser Ser Thr Asp Pro Glu Asp
           340                 345                 350
Ile Phe Ile Ala His Ile Ser Ala Met Asp Ala Met Ala His Ala Leu
       355                 360                 365
Leu Asn Ala Ala Ala Val Leu Glu Ser Pro Leu Cys Glu Met Val
370                 375                 380
Lys Glu Arg Tyr Ala Ser Phe Asp Ser Gly Leu Gly Lys Lys Phe Glu
385                 390                 395                 400
Glu Gly Lys Ala Thr Leu Glu Glu Ile Tyr Glu Tyr Ala Lys Lys Ser
               405                 410                 415
Gly Glu Pro Val Val Ala Ser Gly Lys Gln Glu Leu Tyr Glu Thr Leu
               420                 425                 430
Leu Asn Leu Tyr Ala Lys
        435

<210> SEQ ID NO 169
<211> LENGTH: 1317
<212> TYPE: DNA
<213> ORGANISM: Unknown
<220> FEATURE:
<223> OTHER INFORMATION: Obtained from environmental sample
```

<400> SEQUENCE: 169

```
atggctaaag aatacttccc ctccatcggc aaaatcccct ttgaaggagg cgacagcaaa        60
aatcccctcg ctttccatta ttatgacgcc ggacgcgtgg ttatgggcaa gcccatgaag       120
gaatggctta aattcgccat ggcctggtgg cacacgctgg gccaggcctc cggagacccc       180
ttcggcggcc agacccgcag ctacgaatgg gacaagggcg aatgccccta ctgccgcgcc       240
aaagccaagg ccgacgccgg ttttgaaatc atgcaaaagc tgggtatcga atacttctgc       300
ttccacgatg tggaccttat cgaggattgc gatgacattg ccgaatacga agcccgcatg       360
aaggacatca cggactacct gctggaaaag atgaaggaga ccggcatcaa gaacctctgg       420
ggcaccgcca atgtcttcgg ccacaagcgc tacatgaacg cgccgccac gaacccgcag        480
ttcgacgtgg tcgcccgcgc cgccgtccag atcaagaacg cgattgacgc caccatcaag       540
ctcggcggta ccagttatgt attctggggc ggccgcgagg gctactacac cctcctgaac       600
acccagatgc agcgtgagaa agaccacctg ccaagatgc tcaccgcagc ccgcgactac        660
gcccgcgcca agggcttcaa gggcaccttc ctcatcgagc ccaagccgat ggagcccacc       720
aagcaccagt acgacgttga cacggagacc gtgatcggct ccctgcgcgc caacggcctg       780
gacaaggact tcaaggtgaa catcgaggtg aaccacgcca ccctggccgg ccacaccttc       840
gagcacgaac tcaccgtggc tgttgacaac ggcttcctgg gctccatcga cgccaaccgc       900
ggcgacgccc agaacggctg ggatacggac cagttcccgg tagacccgta cgacctcacc       960
caggccatga tgcagattat ccgcaacggc ggcttcaagg acggcggcac caacttcgat      1020
gccaaactgc cgctcttc caccgatccg gaagacatct tcatcgccca catcagcgct       1080
atggatgcca tggcacacgc cctgctcaac gccgccgccg tgctggaaga gagcccgctg      1140
tgcaacatgt tcaaggagcg ttacgccggc ttcgacagcg gccttggcaa gaagttcgag      1200
gaagggaagg caacgctgga ggaaatctat gactatgcca agaagagcgg cgaacccgtc      1260
gtggcttccg gcaagcagga actctacgaa accatcctga acctctatgc caagtag         1317
```

<210> SEQ ID NO 170
<211> LENGTH: 438
<212> TYPE: PRT
<213> ORGANISM: Unknown
<220> FEATURE:
<223> OTHER INFORMATION: Obtained from environmental sample

<400> SEQUENCE: 170

```
Met Ala Lys Glu Tyr Phe Pro Ser Ile Gly Lys Ile Pro Phe Glu Gly
1               5                   10                  15

Gly Asp Ser Lys Asn Pro Leu Ala Phe His Tyr Tyr Asp Ala Gly Arg
            20                  25                  30

Val Val Met Gly Lys Pro Met Lys Glu Trp Leu Lys Phe Ala Met Ala
        35                  40                  45

Trp Trp His Thr Leu Gly Gln Ala Ser Gly Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Lys Ala Lys Ala Asp Ala Gly Phe Glu Ile Met Gln Lys Leu Gly Ile
                85                  90                  95

Glu Tyr Phe Cys Phe His Asp Val Asp Leu Ile Glu Asp Cys Asp Asp
            100                 105                 110

Ile Ala Glu Tyr Glu Ala Arg Met Lys Asp Ile Thr Asp Tyr Leu Leu
        115                 120                 125
```

Glu Lys Met Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Val Val Ala Arg Ala Val Gln Ile Lys Asn Ala Ile Asp
                165                 170                 175

Ala Thr Ile Lys Leu Gly Gly Thr Ser Tyr Val Phe Trp Gly Gly Arg
                180                 185                 190

Glu Gly Tyr Tyr Thr Leu Leu Asn Thr Gln Met Gln Arg Glu Lys Asp
                195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
225                 230                 235                 240

Lys His Gln Tyr Asp Val Asp Thr Glu Thr Val Ile Gly Ser Leu Arg
                245                 250                 255

Ala Asn Gly Leu Asp Lys Asp Phe Lys Val Asn Ile Glu Val Asn His
                260                 265                 270

Ala Thr Leu Ala Gly His Thr Phe Glu His Glu Leu Thr Val Ala Val
    275                 280                 285

Asp Asn Gly Phe Leu Gly Ser Ile Asp Ala Asn Arg Gly Asp Ala Gln
290                 295                 300

Asn Gly Trp Asp Thr Asp Gln Phe Pro Val Asp Pro Tyr Asp Leu Thr
305                 310                 315                 320

Gln Ala Met Met Gln Ile Ile Arg Asn Gly Gly Phe Lys Asp Gly Gly
                325                 330                 335

Thr Asn Phe Asp Ala Lys Leu Arg Arg Ser Ser Thr Asp Pro Glu Asp
                340                 345                 350

Ile Phe Ile Ala His Ile Ser Ala Met Asp Ala Met Ala His Ala Leu
                355                 360                 365

Leu Asn Ala Ala Ala Val Leu Glu Glu Ser Pro Leu Cys Asn Met Val
    370                 375                 380

Lys Glu Arg Tyr Ala Gly Phe Asp Ser Gly Leu Gly Lys Lys Phe Glu
385                 390                 395                 400

Glu Gly Lys Ala Thr Leu Glu Glu Ile Tyr Asp Tyr Ala Lys Lys Ser
                405                 410                 415

Gly Glu Pro Val Val Ala Ser Gly Lys Gln Glu Leu Tyr Glu Thr Ile
                420                 425                 430

Leu Asn Leu Tyr Ala Lys
        435

<210> SEQ ID NO 171
<211> LENGTH: 1317
<212> TYPE: DNA
<213> ORGANISM: Unknown
<220> FEATURE:
<223> OTHER INFORMATION: Obtained from environmental sample

<400> SEQUENCE: 171
atgtcaaaag agtatttccc tacaatcggc agggtcccct tcgagggacc tgagagcaag    60
aatccgctgg cgttccacta ttacgagccg accggctcg tcctgggcag gaaaatgaag    120
gactggctgc gcttcgcaat ggcctggtgg catacgctcg ggcaggcttc cggcgaccag    180
ttcggcggac agacctgcac atacgcctgg gatgaaggcg agtgtcccgt ctgccgggca    240

-continued

```
aaggccaagg ctgacgccgg ctttgaactg atgcagaaac tgggcatcgg gtatttctgc    300
ttccacgacg tggacctggt cgaggaggcc gacaccattg aagaatacga ggagcggatg    360
cggatcatca ccgactacct gctcgagaag atggaagaga ccggcatccg caatctctgg    420
ggaaccgcca atgtcttcgg cacacaagcg ctatatgaacg cgccgccac caatcccgac    480
ttcgacgtcg tggcccgtgc cgcggtccag atcaagaatg ccatcgatgc caccatcaaa    540
ctgggtggtg agaactatgt gttctggggt ggccgcgagg ctatacgag cctgctcaac    600
acgcagatgc accgggaaaa acaccacctc ggaaatatgc tcagggcagc ccgcgactat    660
ggccgtgccc acggtttcaa gggaacgttc ctgatcgagc ccaagccgat ggagccgacc    720
aagcatcagt acgaccagga tacgagacg gtcatcggtt cctgcgctg tcacggcctg    780
gacaaggatt tcaaggtgaa catcgaggtg aaccacgcca cgctcgccgg acacaccttc    840
gagcacgaac tggccactgc ggtcgatgcc ggcctgctgg gcagcatcga tgccaaccgc    900
ggcgacgccc agaacggctg ggataccgac cagttcccga tcgacaacta cgaactcacg    960
ctggcgatgc tgcagatcat ccgcaatggc ggactcgcac ccggcggatc gaacttcgat   1020
gccaagttgc gccgcaattc caccgatccg gaagacatct tcatcgccca catcagcgcg   1080
atggacgcga tggcccgtgc cctgctcaat gcggcggcca tctggaccga atcgccgatt   1140
caggatatgg tcagggaccg ctatgcttcc ttcgacagcg gaaagggcag ggagttcgag   1200
gaaggcagac tcagtctgga agacctcgtg gcctatgcga aggagcacgg tgagccgcgc   1260
cagatctccg gcaggcagga actttatgaa accatcgtag cgctttactg caggtaa    1317
```

<210> SEQ ID NO 172
<211> LENGTH: 438
<212> TYPE: PRT
<213> ORGANISM: Unknown
<220> FEATURE:
<223> OTHER INFORMATION: Obtained from environmental sample

<400> SEQUENCE: 172

```
Met Ser Lys Glu Tyr Phe Pro Thr Ile Gly Arg Val Pro Phe Glu Gly
1               5                   10                  15

Pro Glu Ser Lys Asn Pro Leu Ala Phe His Tyr Tyr Glu Pro Asp Arg
            20                  25                  30

Leu Val Leu Gly Arg Lys Met Lys Asp Trp Leu Arg Phe Ala Met Ala
        35                  40                  45

Trp Trp His Thr Leu Gly Gln Ala Ser Gly Asp Gln Phe Gly Gly Gln
    50                  55                  60

Thr Cys Thr Tyr Ala Trp Asp Glu Gly Glu Cys Pro Val Cys Arg Ala
65                  70                  75                  80

Lys Ala Lys Ala Asp Ala Gly Phe Glu Leu Met Gln Lys Leu Gly Ile
                85                  90                  95

Gly Tyr Phe Cys Phe His Asp Val Asp Leu Val Glu Glu Ala Asp Thr
            100                 105                 110

Ile Glu Glu Tyr Glu Glu Arg Met Arg Ile Ile Thr Asp Tyr Leu Leu
        115                 120                 125

Glu Lys Met Glu Glu Thr Gly Ile Arg Asn Leu Trp Gly Thr Ala Asn
    130                 135                 140

Val Phe Gly His Lys Arg Tyr Met Asn Gly Ala Ala Thr Asn Pro Asp
145                 150                 155                 160

Phe Asp Val Val Ala Arg Ala Ala Val Gln Ile Lys Asn Ala Ile Asp
                165                 170                 175
```

```
Ala Thr Ile Lys Leu Gly Gly Glu Asn Tyr Val Phe Trp Gly Gly Arg
            180                 185                 190

Glu Gly Tyr Thr Ser Leu Leu Asn Thr Gln Met His Arg Glu Lys His
        195                 200                 205

His Leu Gly Asn Met Leu Arg Ala Ala Arg Asp Tyr Gly Arg Ala His
    210                 215                 220

Gly Phe Lys Gly Thr Phe Leu Ile Glu Pro Lys Pro Met Glu Pro Thr
225                 230                 235                 240

Lys His Gln Tyr Asp Gln Asp Thr Glu Thr Val Ile Gly Phe Leu Arg
                245                 250                 255

Cys His Gly Leu Asp Lys Asp Phe Lys Val Asn Ile Glu Val Asn His
            260                 265                 270

Ala Thr Leu Ala Gly His Thr Phe Glu His Glu Leu Ala Thr Ala Val
        275                 280                 285

Asp Ala Gly Leu Leu Gly Ser Ile Asp Ala Asn Arg Gly Asp Ala Gln
    290                 295                 300

Asn Gly Trp Asp Thr Asp Gln Phe Pro Ile Asp Asn Tyr Glu Leu Thr
305                 310                 315                 320

Leu Ala Met Leu Gln Ile Ile Arg Asn Gly Gly Leu Ala Pro Gly Gly
                325                 330                 335

Ser Asn Phe Asp Ala Lys Leu Arg Arg Asn Ser Thr Asp Pro Glu Asp
            340                 345                 350

Ile Phe Ile Ala His Ile Ser Ala Met Asp Ala Met Ala Arg Ala Leu
        355                 360                 365

Leu Asn Ala Ala Ala Ile Trp Thr Glu Ser Pro Ile Gln Asp Met Val
    370                 375                 380

Arg Asp Arg Tyr Ala Ser Phe Asp Ser Gly Lys Gly Arg Glu Phe Glu
385                 390                 395                 400

Glu Gly Arg Leu Ser Leu Glu Asp Leu Val Ala Tyr Ala Lys Glu His
                405                 410                 415

Gly Glu Pro Arg Gln Ile Ser Gly Arg Gln Glu Leu Tyr Glu Thr Ile
            420                 425                 430

Val Ala Leu Tyr Cys Arg
        435

<210> SEQ ID NO 173
<211> LENGTH: 1317
<212> TYPE: DNA
<213> ORGANISM: Unknown
<220> FEATURE:
<223> OTHER INFORMATION: Obtained from environmental sample

<400> SEQUENCE: 173
atgactaaag agtatttccc gggaatcgga acgattccgt tgaaggaac caagagcaag      60 aaccccctgg ccttccatta ttataacgcc tcccaggtag tgatgggcaa gcccatgaag     120
gactggctca gtatgccat ggcctggtgg cacaccctgg ccaggcctc tgcagacccc      180 tttgcggcc agaccgctc ctacgaatgg acaagggcg agtgccgta ctgccgcgcc        240 aagcagaagg ccgatgccgg ctttgagctc atgcagaagc tgggcatcga gtactactgc    300
ttccacgacg tggacatcat cgaggactgc gaggacattg ccgagtacga ggcccgcatg    360
aaggacatca cggactacct gctggagaag cagaaagaga ccggcatcaa gaacctctgg    420
ggcaccgcca acgtgtttgg ccacaagcgc tacatgaacg cgccgccac caaccctcag    480 tttgacattg tggcccgtgc cgccgtccag atcaagaacg ccctggatgc cgccatcaaa    540
```

```
ctgggtggta ccaactacgt gttctggggt ggccgcgaag gctactacac gctgctcaac      600
acccagatgc agcgggagaa gaaccacctg gccaagatgc tcaccgccgc cgcgactac       660 gcccgcgcca agggcttcaa gggcaccttc ctcattgagc ccaaacccat ggagcccacc      720
aagcaccagt acgacgtgga caccgagacc gtgattggtt tcatccgcgc caacggcctg      780
gacaaggact tcaaggtaaa cattgaggta aaccacgcca ccctggccgg ccacaccttt      840
gagcacgagc tcaccgtggc ccgcgagaac ggcttcctgg gctccatcga cgccaaccgc      900
ggagatgccc agaacggctg ggatacggac cagttcccca tcgacgccct ggatctcacc      960
caggctatga tgcaggtcat cctcaacggt ggcttcggca atggcggcac caactttgac     1020
gccaagctcc gccgctcctc caccgatccc gaggacatct tcatcgccca catcagcgcc     1080
atggatgcca tggcacacgc cctcctgaac gcagccgcca tcctggaaga gagccccctg     1140
cccgccatgg tcaaggagcg ttacgcttcc ttcgacagcg gtctgggcaa gaagttcgaa     1200
gaaggcaagg cctccctgga agaactttac gaatatgcca agaagaatgg agagcccgtg     1260
gccgcttccg gcaaacagga gctctgcgaa acttacttga acctctatgc aaagtag         1317

<210> SEQ ID NO 174
<211> LENGTH: 438
<212> TYPE: PRT
<213> ORGANISM: Unknown
<220> FEATURE:
<223> OTHER INFORMATION: Obtained from environmental sample

<400> SEQUENCE: 174

Met Thr Lys Glu Tyr Phe Pro Gly Ile Gly Thr Ile Pro Phe Glu Gly
 1               5                  10                  15

Thr Lys Ser Lys Asn Pro Leu Ala Phe His Tyr Tyr Asn Ala Ser Gln
            20                  25                  30

Val Val Met Gly Lys Pro Met Lys Asp Trp Leu Lys Tyr Ala Met Ala
        35                  40                  45

Trp Trp His Thr Leu Gly Gln Ala Ser Ala Asp Pro Phe Gly Gly Gln
    50                  55                  60

Thr Arg Ser Tyr Glu Trp Asp Lys Gly Glu Cys Pro Tyr Cys Arg Ala
65                  70                  75                  80

Lys Gln Lys Ala Asp Ala Gly Phe Glu Leu Met Gln Lys Leu Gly Ile
                85                  90                  95

Glu Tyr Tyr Cys Phe His Asp Val Asp Ile Ile Glu Asp Cys Glu Asp
            100                 105                 110

Ile Ala Glu Tyr Glu Ala Arg Met Lys Asp Ile Thr Asp Tyr Leu Leu
        115                 120                 125

Glu Lys Gln Lys Glu Thr Gly Ile Lys Asn Leu Trp Gly Thr Ala Asn
    130                 135                 140

Val Phe Gly His Lys Arg Tyr Met Asn Gly Ala Ala Thr Asn Pro Gln
145                 150                 155                 160

Phe Asp Ile Val Ala Arg Ala Ala Val Gln Ile Lys Asn Ala Leu Asp
                165                 170                 175

Ala Ala Ile Lys Leu Gly Gly Thr Asn Tyr Val Phe Trp Gly Gly Arg
            180                 185                 190

Glu Gly Tyr Tyr Thr Leu Leu Asn Thr Gln Met Gln Arg Glu Lys Asn
        195                 200                 205

His Leu Ala Lys Met Leu Thr Ala Ala Arg Asp Tyr Ala Arg Ala Lys
    210                 215                 220

Gly Phe Lys Gly Thr Phe Leu Ile Glu Pro Lys Pro Met Glu Pro Thr
```

```
              225                 230                 235                 240
Lys His Gln Tyr Asp Val Asp Thr Glu Thr Val Ile Gly Phe Ile Arg
                245                 250                 255

Ala Asn Gly Leu Asp Lys Asp Phe Lys Val Asn Ile Glu Val Asn His
            260                 265                 270

Ala Thr Leu Ala Gly His Thr Phe Glu His Glu Leu Thr Val Ala Arg
        275                 280                 285

Glu Asn Gly Phe Leu Gly Ser Ile Asp Ala Asn Arg Gly Asp Ala Gln
    290                 295                 300

Asn Gly Trp Asp Thr Asp Gln Phe Pro Ile Asp Ala Leu Asp Leu Thr
305                 310                 315                 320

Gln Ala Met Met Gln Val Ile Leu Asn Gly Phe Gly Asn Gly Gly
                325                 330                 335

Thr Asn Phe Asp Ala Lys Leu Arg Arg Ser Ser Thr Asp Pro Glu Asp
            340                 345                 350

Ile Phe Ile Ala His Ile Ser Ala Met Asp Ala Met Ala His Ala Leu
        355                 360                 365

Leu Asn Ala Ala Ala Ile Leu Glu Glu Ser Pro Leu Pro Ala Met Val
    370                 375                 380

Lys Glu Arg Tyr Ala Ser Phe Asp Ser Gly Leu Gly Lys Lys Phe Glu
385                 390                 395                 400

Glu Gly Lys Ala Ser Leu Glu Glu Leu Tyr Glu Tyr Ala Lys Lys Asn
                405                 410                 415

Gly Glu Pro Val Ala Ala Ser Gly Lys Gln Glu Leu Cys Glu Thr Tyr
            420                 425                 430

Leu Asn Leu Tyr Ala Lys
        435

<210> SEQ ID NO 175
<211> LENGTH: 1308
<212> TYPE: DNA
<213> ORGANISM: Unknown
<220> FEATURE:
<223> OTHER INFORMATION: Obtained from environmental sample

<400> SEQUENCE: 175
gtgactgatt tcttcaaggg catcgcgccc gtcaagtttg agggccgca gagctccaat      60 ccgctggcct atcgccacta taacaaggac gaaatcgtcc tcggcaagcg gatggaagac     120
catatccgtc ccggcgttgc ctattggcac accttcgcct atgagggcgg cgatccgttt     180
ggcggccgca ccttcgatcg ccctggttc gacaagggta tggacggcgc ccgcctcaag     240
gccgacgtgg ccttcgaact gttcgacctg ctcgacgttc ctttcttctg tttccacgat     300
gctgatatcg ctcccgaagg cgcaacgctg gccgagagca accgcaatgt gcgcgagatt     360
ggcgagatct tcgctcgcaa gatggaaacc agccgcacca agctgctctg gggtacggca     420
aacctgttct ccaatcgccg ctacatggcc ggcgccgcca ccaacccgga cccggaaatc     480
ttcgcctatg ccgctgggca ggtgaagaac gtgctggaac tgacccacga actgggcggc     540
gccaactatg tgctgtgggg cggtcgcgag ggttatgaaa ccctgctcaa caccaagatc     600
ggccaggaaa tggaccagat gggccgtttt ctgtcgatgg tcgtcgagca tgccgaaaag     660
atcggcttca agggccagat cctgatcgag cccaagccgc aggagccgag caagcaccag     720
tatgacttcg acgttgcaac cgtttacggc ttcctcaaga gtatggtct cgaaaccaag     780 gtgaagtgca atatcgaggt cggccatgcc ttcctcgcca tcactccttc gagcatgaa     840
```

```
ctggctttgg ccgcatcgct gggcattctc ggctcggtcg acgccaatcg caacgatcta    900
cagtccggct gggataccga ccagttcccc aataatgtcc ccgaaaccgc actcgccttc    960
tatcagattc tcaaggcggg cggactgggc aatggcggct ggaacttcga cgcccgcgtg   1020
cgccgccagt cacttgatcc ggccgacctg ctgcacggcc atatcggcgg cctcgacgtg   1080
ctggcgcgcg gcctcaaggc cgccgcggcg ctgatcgagg acggcaccta tgacaaggtc   1140
gtcgacgccc gctatgccgg ctggaaccag ggcctgggca aggatatcct tggtggcaag   1200
ctgaaccttg ccgacctggc tgccaaggtc gacgccgaaa acctcaaccc gcagcctagg   1260
tccggccagc aggaatatct cgaaaacctg atcaaccggt tcgtttag                1308
```

<210> SEQ ID NO 176
<211> LENGTH: 435
<212> TYPE: PRT
<213> ORGANISM: Unknown
<220> FEATURE:
<223> OTHER INFORMATION: Obtained from environmental sample

<400> SEQUENCE: 176

```
Met Thr Asp Phe Phe Lys Gly Ile Ala Pro Val Lys Phe Glu Gly Pro
  1               5                  10                  15
Gln Ser Ser Asn Pro Leu Ala Tyr Arg His Tyr Asn Lys Asp Glu Ile
                 20                  25                  30
Val Leu Gly Lys Arg Met Glu Asp His Ile Arg Pro Gly Val Ala Tyr
             35                  40                  45
Trp His Thr Phe Ala Tyr Glu Gly Gly Asp Pro Phe Gly Gly Arg Thr
         50                  55                  60
Phe Asp Arg Pro Trp Phe Asp Lys Gly Met Asp Gly Ala Arg Leu Lys
 65                  70                  75                  80
Ala Asp Val Ala Phe Glu Leu Phe Asp Leu Leu Asp Val Pro Phe Phe
                 85                  90                  95
Cys Phe His Asp Ala Asp Ile Ala Pro Glu Gly Ala Thr Leu Ala Glu
            100                 105                 110
Ser Asn Arg Asn Val Arg Glu Ile Gly Glu Ile Phe Ala Arg Lys Met
        115                 120                 125
Glu Thr Ser Arg Thr Lys Leu Leu Trp Gly Thr Ala Asn Leu Phe Ser
    130                 135                 140
Asn Arg Arg Tyr Met Ala Gly Ala Ala Thr Asn Pro Asp Pro Glu Ile
145                 150                 155                 160
Phe Ala Tyr Ala Ala Gly Gln Val Lys Asn Val Leu Glu Leu Thr His
                165                 170                 175
Glu Leu Gly Gly Ala Asn Tyr Val Leu Trp Gly Gly Arg Glu Gly Tyr
            180                 185                 190
Glu Thr Leu Leu Asn Thr Lys Ile Gly Gln Glu Met Asp Gln Met Gly
        195                 200                 205
Arg Phe Leu Ser Met Val Val Glu His Ala Glu Lys Ile Gly Phe Lys
    210                 215                 220
Gly Gln Ile Leu Ile Glu Pro Lys Pro Gln Glu Pro Ser Lys His Gln
225                 230                 235                 240
Tyr Asp Phe Asp Val Ala Thr Val Tyr Gly Phe Leu Lys Lys Tyr Gly
                245                 250                 255
Leu Glu Thr Lys Val Lys Cys Asn Ile Glu Val Gly His Ala Phe Leu
            260                 265                 270
Ala Asn His Ser Phe Glu His Glu Leu Ala Leu Ala Ala Ser Leu Gly
        275                 280                 285
```

-continued

```
Ile Leu Gly Ser Val Asp Ala Asn Arg Asn Asp Leu Gln Ser Gly Trp
    290                 295                 300
Asp Thr Asp Gln Phe Pro Asn Asn Val Pro Glu Thr Ala Leu Ala Phe
305                 310                 315                 320
Tyr Gln Ile Leu Lys Ala Gly Leu Gly Asn Gly Trp Asn Phe
            325                 330                 335
Asp Ala Arg Val Arg Arg Gln Ser Leu Asp Pro Ala Asp Leu Leu His
                340                 345                 350
Gly His Ile Gly Gly Leu Asp Val Leu Ala Arg Gly Leu Lys Ala Ala
            355                 360                 365
Ala Ala Leu Ile Glu Asp Gly Thr Tyr Asp Lys Val Val Asp Ala Arg
    370                 375                 380
Tyr Ala Gly Trp Asn Gln Gly Leu Gly Lys Asp Ile Leu Gly Gly Lys
385                 390                 395                 400
Leu Asn Leu Ala Asp Leu Ala Ala Lys Val Asp Ala Glu Asn Leu Asn
                405                 410                 415
Pro Gln Pro Arg Ser Gly Gln Glu Tyr Leu Glu Asn Leu Ile Asn
            420                 425                 430
Arg Phe Val
        435

<210> SEQ ID NO 177
<211> LENGTH: 23
<212> TYPE: PRT
<213> ORGANISM: Unknown
<220> FEATURE:
<223> OTHER INFORMATION: Obtained from environmental sample

<400> SEQUENCE: 177

Gly Cys Ile Gly Cys Ile Cys Ala Arg Gly Ala Arg Gly Gly Asn Ala
1               5                   10                  15

Thr Tyr Gly Thr Val Thr Thr
            20

<210> SEQ ID NO 178
<211> LENGTH: 8
<212> TYPE: PRT
<213> ORGANISM: Unknown
<220> FEATURE:
<223> OTHER INFORMATION: Obtained from environmental sample

<400> SEQUENCE: 178

Ala Ala Gln Glu Gly Ile Val Phe
1               5

<210> SEQ ID NO 179
<211> LENGTH: 23
<212> TYPE: PRT
<213> ORGANISM: Unknown
<220> FEATURE:
<223> OTHER INFORMATION: Obtained from environmental sample

<400> SEQUENCE: 179

Gly Cys Asp Ala Thr Tyr Thr Cys Asn Gly Cys Arg Ala Thr Arg Thr
1               5                   10                  15

Ala Cys Ala Thr Ser Gly Gly
            20

<210> SEQ ID NO 180
<211> LENGTH: 8
```

```
<212> TYPE: PRT
<213> ORGANISM: Unknown
<220> FEATURE:
<223> OTHER INFORMATION: Obtained from environmental sample

<400> SEQUENCE: 180

Pro Met Tyr Ile Ala Glu Ile Ala
1               5

<210> SEQ ID NO 181
<211> LENGTH: 60
<212> TYPE: DNA
<213> ORGANISM: Unknown
<220> FEATURE:
<223> OTHER INFORMATION: Obtained from environmental sample

<400> SEQUENCE: 181
ggcgcgcctc tagaaagctt acgcgtgagc tccctgcagg gatatcggta ccgcggccgc    60

<210> SEQ ID NO 182
<211> LENGTH: 53
<212> TYPE: DNA
<213> ORGANISM: Unknown
<220> FEATURE:
<223> OTHER INFORMATION: Obtained from environmental sample

<400> SEQUENCE: 182
caccattaat taaagctttg taaatatgat gagagaataa tataaatcaa acg           53

<210> SEQ ID NO 183
<211> LENGTH: 57
<212> TYPE: DNA
<213> ORGANISM: Unknown
<220> FEATURE:
<223> OTHER INFORMATION: Obtained from environmental sample

<400> SEQUENCE: 183
ggcgcgcctc tagaaagctt aatcgacaag aacacttcta tttatatagg tatgaaa       57

<210> SEQ ID NO 184
<211> LENGTH: 57
<212> TYPE: DNA
<213> ORGANISM: Unknown
<220> FEATURE:
<223> OTHER INFORMATION: Obtained from environmental sample

<400> SEQUENCE: 184
gcagggatat cggtacccac cagcggccgc tgaagaaggt ttatttcgtt tcgctgt       57

<210> SEQ ID NO 185
<211> LENGTH: 38
<212> TYPE: DNA
<213> ORGANISM: Unknown
<220> FEATURE:
<223> OTHER INFORMATION: Obtained from environmental sample

<400> SEQUENCE: 185
caccattaat taacccaggt gagactggat gctccata                            38

<210> SEQ ID NO 186
<211> LENGTH: 60
<212> TYPE: DNA
<213> ORGANISM: Unknown
<220> FEATURE:
<223> OTHER INFORMATION: Obtained from environmental sample

<400> SEQUENCE: 186
```

```
gcctctagaa agcttacgcg tgagctccct gcagggatat cggtacccac cagcggccgc    60
```

<210> SEQ ID NO 187
<211> LENGTH: 60
<212> TYPE: DNA
<213> ORGANISM: Unknown
<220> FEATURE:
<223> OTHER INFORMATION: Obtained from environmental sample

<400> SEQUENCE: 187

```
cgctggtggg taccgatatc cctgcaggga gctcacgcgt aagctttcta gaggcgcgcc    60
```

<210> SEQ ID NO 188
<211> LENGTH: 200
<212> TYPE: DNA
<213> ORGANISM: Unknown
<220> FEATURE:
<223> OTHER INFORMATION: Obtained from environmental sample

<400> SEQUENCE: 188

```
tgcgtgtgcc gcgagtccac gtctactcgc gaaccgagtg caggcgggtc ttcggccagg    60
acggccgtgc gtgaccccgg ccgccagacg aaacggaccg cgctcgccag acgctaccca   120
gcccgttcat gccggccgcg agccgacctg tctcggtcgc ttcgacgcac gcgcggtcct   180
ttcgggtact cgcctaagac                                               200
```

<210> SEQ ID NO 189
<211> LENGTH: 39
<212> TYPE: DNA
<213> ORGANISM: Unknown
<220> FEATURE:
<223> OTHER INFORMATION: Obtained from environmental sample

<400> SEQUENCE: 189

```
caatagcggc cgcggtacct gcgtgtgccg cgagtccac                           39
```

<210> SEQ ID NO 190
<211> LENGTH: 34
<212> TYPE: DNA
<213> ORGANISM: Unknown
<220> FEATURE:
<223> OTHER INFORMATION: Obtained from environmental sample

<400> SEQUENCE: 190

```
tgttaggatc cgtcttaggc gagtacccga aagg                                34
```

<210> SEQ ID NO 191
<211> LENGTH: 37
<212> TYPE: DNA
<213> ORGANISM: Unknown
<220> FEATURE:
<223> OTHER INFORMATION: Obtained from environmental sample

<400> SEQUENCE: 191

```
caataggatc caggcatatt tatggtgaag aataagt                             37
```

<210> SEQ ID NO 192
<211> LENGTH: 35
<212> TYPE: DNA
<213> ORGANISM: Unknown
<220> FEATURE:
<223> OTHER INFORMATION: Obtained from environmental sample

<400> SEQUENCE: 192

```
tgttactcga gaaatcatta cgaccgagat tcccg                                    35

<210> SEQ ID NO 193
<211> LENGTH: 31
<212> TYPE: DNA
<213> ORGANISM: Unknown
<220> FEATURE:
<223> OTHER INFORMATION: Obtained from environmental sample

<400> SEQUENCE: 193
caatactcga gtgcgtgtgc cgcgagtcca c                                        31

<210> SEQ ID NO 194
<211> LENGTH: 36
<212> TYPE: DNA
<213> ORGANISM: Unknown
<220> FEATURE:
<223> OTHER INFORMATION: Obtained from environmental sample

<400> SEQUENCE: 194
tgttagcggc cgcgtcttag gcgagtaccc gaaagg                                   36

<210> SEQ ID NO 195
<211> LENGTH: 32
<212> TYPE: DNA
<213> ORGANISM: Unknown
<220> FEATURE:
<223> OTHER INFORMATION: Obtained from environmental sample

<400> SEQUENCE: 195
actagtggat ccctcgaggt cgacgtttaa ac                                       32

<210> SEQ ID NO 196
<211> LENGTH: 64
<212> TYPE: DNA
<213> ORGANISM: Unknown
<220> FEATURE:
<223> OTHER INFORMATION: Obtained from environmental sample

<400> SEQUENCE: 196
caccaggcgc gcctctagaa agcttacgcg tagtttatca ttatcaatac tgccatttca         60
aaga                                                                      64

<210> SEQ ID NO 197
<211> LENGTH: 57
<212> TYPE: DNA
<213> ORGANISM: Unknown
<220> FEATURE:
<223> OTHER INFORMATION: Obtained from environmental sample

<400> SEQUENCE: 197
aacgtcgacc tcgagggatc cactagttcg aaactaagtt cttggtgttt taaaact           57

<210> SEQ ID NO 198
<211> LENGTH: 58
<212> TYPE: DNA
<213> ORGANISM: Unknown
<220> FEATURE:
<223> OTHER INFORMATION: Obtained from environmental sample

<400> SEQUENCE: 198
gtggatccct cgaggtcgac gtttaaacat tgaattgaat tgaaatcgat agatcaat          58

<210> SEQ ID NO 199
<211> LENGTH: 69
```

```
<212> TYPE: DNA
<213> ORGANISM: Unknown
<220> FEATURE:
<223> OTHER INFORMATION: Obtained from environmental sample

<400> SEQUENCE: 199
caccagcggc cgcggtaccg atatccctgc agggagctcg aaatatcgaa tgggaaaaaa     60
aaactggat                                                            69

<210> SEQ ID NO 200
<211> LENGTH: 25
<212> TYPE: DNA
<213> ORGANISM: Unknown
<220> FEATURE:
<223> OTHER INFORMATION: Obtained from environmental sample

<400> SEQUENCE: 200
acagggataa caaagtttct ccagc                                          25

<210> SEQ ID NO 201
<211> LENGTH: 25
<212> TYPE: DNA
<213> ORGANISM: Unknown
<220> FEATURE:
<223> OTHER INFORMATION: Obtained from environmental sample

<400> SEQUENCE: 201
cataccaagt catgcgttac cagag                                          25

<210> SEQ ID NO 202
<211> LENGTH: 25
<212> TYPE: DNA
<213> ORGANISM: Unknown
<220> FEATURE:
<223> OTHER INFORMATION: Obtained from environmental sample

<400> SEQUENCE: 202
tttcccattc gatatttcga gctcc                                          25

<210> SEQ ID NO 203
<211> LENGTH: 25
<212> TYPE: DNA
<213> ORGANISM: Unknown
<220> FEATURE:
<223> OTHER INFORMATION: Obtained from environmental sample

<400> SEQUENCE: 203
cataccaagt catgcgttac cagag                                          25

<210> SEQ ID NO 204
<211> LENGTH: 7
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (1)..(1)
<223> OTHER INFORMATION: Can be either Leu or Ile
<220> FEATURE:
<221> NAME/KEY: MISC_FEATURE
<222> LOCATION: (6)..(6)
<223> OTHER INFORMATION: Can be any two amino acids

<400> SEQUENCE: 204

Xaa Glu Pro Lys Pro Xaa Pro
1               5
```

```
<210> SEQ ID NO 205
<211> LENGTH: 10
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (1)..(1)
<223> OTHER INFORMATION: Can be either Phe or Leu
<220> FEATURE:
<221> NAME/KEY: MISC_FEATURE
<222> LOCATION: (4)..(4)
<223> OTHER INFORMATION: Can be any amino acid but Lys
<220> FEATURE:
<221> NAME/KEY: MISC_FEATURE
<222> LOCATION: (6)..(6)
<223> OTHER INFORMATION: Can be either Leu, Ile, or Val
<220> FEATURE:
<221> NAME/KEY: MISC_FEATURE
<222> LOCATION: (7)..(7)
<223> OTHER INFORMATION: Can be any amino acid
<220> FEATURE:
<221> NAME/KEY: MISC_FEATURE
<222> LOCATION: (8)..(8)
<223> OTHER INFORMATION: Can be either Asp or Pro
<220> FEATURE:
<221> NAME/KEY: MISC_FEATURE
<222> LOCATION: (9)..(9)
<223> OTHER INFORMATION: Can be any amino acid
<220> FEATURE:
<221> NAME/KEY: MISC_FEATURE
<222> LOCATION: (10)..(10)
<223> OTHER INFORMATION: Can be either Asp, Gly, or Glu

<400> SEQUENCE: 205

Xaa His Asp Xaa Asp Xaa Xaa Xaa Xaa Xaa
1               5                   10

<210> SEQ ID NO 206
<211> LENGTH: 12
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (2)..(2)
<223> OTHER INFORMATION: Can be either Phe or Tyr
<220> FEATURE:
<221> NAME/KEY: MISC_FEATURE
<222> LOCATION: (3)..(3)
<223> OTHER INFORMATION: Can be either Ala, Ser, or Thr
<220> FEATURE:
<221> NAME/KEY: MISC_FEATURE
<222> LOCATION: (4)..(4)
<223> OTHER INFORMATION: Can be either Met, Leu, Val, or Ile
<220> FEATURE:
<221> NAME/KEY: MISC_FEATURE
<222> LOCATION: (5)..(5)
<223> OTHER INFORMATION: Can be either Ala or Ser
<220> FEATURE:
<221> NAME/KEY: MISC_FEATURE
<222> LOCATION: (6)..(6)
<223> OTHER INFORMATION: Can be either Trp, Tyr, Phe, or Leu
<220> FEATURE:
<221> NAME/KEY: MISC_FEATURE
<222> LOCATION: (8)..(8)
<223> OTHER INFORMATION: Can be either His or Thr
<220> FEATURE:
<221> NAME/KEY: MISC_FEATURE
<222> LOCATION: (10)..(10)
<223> OTHER INFORMATION: Can be either Leu, Phe, Met, or Gly

<400> SEQUENCE: 206
```

```
Pro Xaa Xaa Xaa Xaa Xaa Trp Xaa Asn Xaa Gly Ala
1               5                   10
```

<210> SEQ ID NO 207
<211> LENGTH: 11
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (2)..(2)
<223> OTHER INFORMATION: Can be either Phe or Tyr
<220> FEATURE:
<221> NAME/KEY: MISC_FEATURE
<222> LOCATION: (3)..(3)
<223> OTHER INFORMATION: Can be either Ala or Ser
<220> FEATURE:
<221> NAME/KEY: MISC_FEATURE
<222> LOCATION: (4)..(4)
<223> OTHER INFORMATION: Can be any two amino acids
<220> FEATURE:
<221> NAME/KEY: MISC_FEATURE
<222> LOCATION: (5)..(5)
<223> OTHER INFORMATION: Can be either Trp, Tyr, Phe, or Leu
<220> FEATURE:
<221> NAME/KEY: MISC_FEATURE
<222> LOCATION: (7)..(7)
<223> OTHER INFORMATION: Can be either His or Thr
<220> FEATURE:
<221> NAME/KEY: MISC_FEATURE
<222> LOCATION: (8)..(8)
<223> OTHER INFORMATION: Can be any amino acid but Thr or Val
<220> FEATURE:
<221> NAME/KEY: MISC_FEATURE
<222> LOCATION: (9)..(9)
<223> OTHER INFORMATION: Can be any amino acid

<400> SEQUENCE: 207

```
Pro Xaa Xaa Xaa Xaa Trp Xaa Xaa Xaa Gly Ala
1               5                   10
```

<210> SEQ ID NO 208
<211> LENGTH: 11
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (1)..(1)
<223> OTHER INFORMATION: Can be either Gly, Ser, or Asn
<220> FEATURE:
<221> NAME/KEY: MISC_FEATURE
<222> LOCATION: (2)..(2)
<223> OTHER INFORMATION: Can be either Ile, Val, or Ala
<220> FEATURE:
<221> NAME/KEY: MISC_FEATURE
<222> LOCATION: (4)..(4)
<223> OTHER INFORMATION: Can be either Tyr, Phe, His, or Gly
<220> FEATURE:
<221> NAME/KEY: MISC_FEATURE
<222> LOCATION: (5)..(5)
<223> OTHER INFORMATION: Can be either Phe, Tyr, Leu, Ile, or Val
<220> FEATURE:
<221> NAME/KEY: MISC_FEATURE
<222> LOCATION: (7)..(7)
<223> OTHER INFORMATION: Can be either Phe or Trp
<220> FEATURE:
<221> NAME/KEY: MISC_FEATURE
<222> LOCATION: (10)..(10)
<223> OTHER INFORMATION: Can be any amino acid

<400> SEQUENCE: 208

```
Xaa Xaa Arg Xaa Xaa Cys Xaa His Asp Xaa Asp
1               5                   10
```

<210> SEQ ID NO 209
<211> LENGTH: 11
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (2)..(2)
<223> OTHER INFORMATION: Can be either Ala, Ser, Thr, or Cys
<220> FEATURE:
<221> NAME/KEY: MISC_FEATURE
<222> LOCATION: (3)..(3)
<223> OTHER INFORMATION: Can be either Asn or Lys
<220> FEATURE:
<221> NAME/KEY: MISC_FEATURE
<222> LOCATION: (4)..(4)
<223> OTHER INFORMATION: Can be any amino acid but Leu
<220> FEATURE:
<221> NAME/KEY: MISC_FEATURE
<222> LOCATION: (6)..(6)
<223> OTHER INFORMATION: Can be any amino acid
<220> FEATURE:
<221> NAME/KEY: MISC_FEATURE
<222> LOCATION: (7)..(7)
<223> OTHER INFORMATION: Can be either Asn, Asp, or His
<220> FEATURE:
<221> NAME/KEY: MISC_FEATURE
<222> LOCATION: (8)..(8)
<223> OTHER INFORMATION: Can be either Pro, Arg, Lys, Ala, or Gly
<220> FEATURE:
<221> NAME/KEY: MISC_FEATURE
<222> LOCATION: (9)..(9)
<223> OTHER INFORMATION: Can be either Arg, Val, or Ala
<220> FEATURE:
<221> NAME/KEY: MISC_FEATURE
<222> LOCATION: (10)..(10)
<223> OTHER INFORMATION: Can be either Phe or Tyr

<400> SEQUENCE: 209

```
Thr Xaa Xaa Xaa Phe Xaa Xaa Xaa Xaa Xaa Cys
1               5                   10
```

<210> SEQ ID NO 210
<211> LENGTH: 13
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (1)..(1)
<223> OTHER INFORMATION: Can be either Trp, Phe, or Tyr
<220> FEATURE:
<221> NAME/KEY: MISC_FEATURE
<222> LOCATION: (3)..(3)
<223> OTHER INFORMATION: Can be either Thr, Gln, Val, or Ile
<220> FEATURE:
<221> NAME/KEY: MISC_FEATURE
<222> LOCATION: (5)..(5)
<223> OTHER INFORMATION: Can be any amino acid
<220> FEATURE:
<221> NAME/KEY: MISC_FEATURE
<222> LOCATION: (6)..(6)
<223> OTHER INFORMATION: Can be either Phe or Tyr
<220> FEATURE:
<221> NAME/KEY: MISC_FEATURE
<222> LOCATION: (7)..(7)
<223> OTHER INFORMATION: Can be either Pro or Phe
<220> FEATURE:
<221> NAME/KEY: MISC_FEATURE
<222> LOCATION: (8)..(8)
<223> OTHER INFORMATION: Can be any amino acid but Thr

```
<220> FEATURE:
<221> NAME/KEY: MISC_FEATURE
<222> LOCATION: (9)..(9)
<223> OTHER INFORMATION: Can be any combination of 2, 3 or 4 amino acids
<220> FEATURE:
<221> NAME/KEY: MISC_FEATURE
<222> LOCATION: (10)..(10)
<223> OTHER INFORMATION: Can be either Tyr, Phe, or His
<220> FEATURE:
<221> NAME/KEY: MISC_FEATURE
<222> LOCATION: (12)..(12)
<223> OTHER INFORMATION: Can be either Ala, Thr, or Leu

<400> SEQUENCE: 210

Xaa Asp Xaa Asp Xaa Xaa Xaa Xaa Xaa Xaa Ser Xaa Thr
1               5                   10

<210> SEQ ID NO 211
<211> LENGTH: 9
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (3)..(3)
<223> OTHER INFORMATION: Can be either Asn or His
<220> FEATURE:
<221> NAME/KEY: MISC_FEATURE
<222> LOCATION: (6)..(6)
<223> OTHER INFORMATION: Can be either Ser or Ala

<400> SEQUENCE: 211

Gly Phe Xaa Phe Asp Xaa Lys Thr Arg
1               5

<210> SEQ ID NO 212
<211> LENGTH: 13
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (3)..(3)
<223> OTHER INFORMATION: Can be any amino acid
<220> FEATURE:
<221> NAME/KEY: MISC_FEATURE
<222> LOCATION: (6)..(6)
<223> OTHER INFORMATION: Can be either Arg or Lys
<220> FEATURE:
<221> NAME/KEY: MISC_FEATURE
<222> LOCATION: (7)..(7)
<223> OTHER INFORMATION: Can be any 2 amino acids
<220> FEATURE:
<221> NAME/KEY: MISC_FEATURE
<222> LOCATION: (9)..(9)
<223> OTHER INFORMATION: Can be either Trp, Tyr, or Phe
<220> FEATURE:
<221> NAME/KEY: MISC_FEATURE
<222> LOCATION: (10)..(10)
<223> OTHER INFORMATION: Can be either Asp, Asn, or Gly
<220> FEATURE:
<221> NAME/KEY: MISC_FEATURE
<222> LOCATION: (11)..(11)
<223> OTHER INFORMATION: Can be any 2 or 3 amino acids
<220> FEATURE:
<221> NAME/KEY: MISC_FEATURE
<222> LOCATION: (12)..(12)
<223> OTHER INFORMATION: Can be either Asp, Asn, Glu, Gly, or Thr
<220> FEATURE:
<221> NAME/KEY: MISC_FEATURE
<222> LOCATION: (13)..(13)
<223> OTHER INFORMATION: Can be either Ala or Thr
```

<400> SEQUENCE: 212

Phe Gly Xaa Gln Thr Xaa Xaa Glu Xaa Xaa Xaa Xaa
1               5                   10

<210> SEQ ID NO 213
<211> LENGTH: 13
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (3)..(3)
<223> OTHER INFORMATION: Can be any amino acid
<220> FEATURE:
<221> NAME/KEY: MISC_FEATURE
<222> LOCATION: (6)..(6)
<223> OTHER INFORMATION: Can be either Arg or Lys
<220> FEATURE:
<221> NAME/KEY: MISC_FEATURE
<222> LOCATION: (7)..(7)
<223> OTHER INFORMATION: Can be any 2 amino acids
<220> FEATURE:
<221> NAME/KEY: MISC_FEATURE
<222> LOCATION: (9)..(9)
<223> OTHER INFORMATION: Can be either Trp, Tyr, or Phe
<220> FEATURE:
<221> NAME/KEY: MISC_FEATURE
<222> LOCATION: (10)..(10)
<223> OTHER INFORMATION: Can be either Asp, Asn, or Gly
<220> FEATURE:
<221> NAME/KEY: MISC_FEATURE
<222> LOCATION: (11)..(11)
<223> OTHER INFORMATION: Can be any 3 amino acids
<220> FEATURE:
<221> NAME/KEY: MISC_FEATURE
<222> LOCATION: (12)..(12)
<223> OTHER INFORMATION: Can be any amino acid but Cys
<220> FEATURE:
<221> NAME/KEY: MISC_FEATURE
<222> LOCATION: (13)..(13)
<223> OTHER INFORMATION: Can be any amino acid but Pro

<400> SEQUENCE: 213

Phe Gly Xaa Gln Thr Xaa Xaa Glu Xaa Xaa Xaa Xaa Xaa
1               5                   10

<210> SEQ ID NO 214
<211> LENGTH: 15
<212> TYPE: PRT
<213> ORGANISM: Artificial Sequence
<220> FEATURE:
<223> OTHER INFORMATION: Sequence Motif
<220> FEATURE:
<221> NAME/KEY: MISC_FEATURE
<222> LOCATION: (1)..(1)
<223> OTHER INFORMATION: Can be either Phe or Trp
<220> FEATURE:
<221> NAME/KEY: MISC_FEATURE
<222> LOCATION: (4)..(4)
<223> OTHER INFORMATION: Can be any amino acid
<220> FEATURE:
<221> NAME/KEY: MISC_FEATURE
<222> LOCATION: (6)..(6)
<223> OTHER INFORMATION: Can be either Leu, Val, or Ile
<220> FEATURE:
<221> NAME/KEY: MISC_FEATURE
<222> LOCATION: (7)..(7)
<223> OTHER INFORMATION: Can be any amino acid
<220> FEATURE:
<221> NAME/KEY: MISC_FEATURE
<222> LOCATION: (8)..(8)
<223> OTHER INFORMATION: Can be either Asp or Glu
<220> FEATURE:
<221> NAME/KEY: MISC_FEATURE

```
<222> LOCATION: (11)..(11)
<223> OTHER INFORMATION: Can be any amino acid but Pro
<220> FEATURE:
<221> NAME/KEY: MISC_FEATURE
<222> LOCATION: (12)..(12)
<223> OTHER INFORMATION: Can be either Thr, Ser, or Asp
<220> FEATURE:
<221> NAME/KEY: MISC_FEATURE
<222> LOCATION: (13)..(13)
<223> OTHER INFORMATION: Can be either Ile or Val
<220> FEATURE:
<221> NAME/KEY: MISC_FEATURE
<222> LOCATION: (14)..(14)
<223> OTHER INFORMATION: Can be either Glu or Ala

<400> SEQUENCE: 214

Xaa His Asp Xaa Asp Xaa Xaa Xaa Glu Gly Xaa Xaa Xaa Xaa Glu
1               5                   10                  15

<210> SEQ ID NO 215
<211> LENGTH: 1008
<212> TYPE: DNA
<213> ORGANISM: Saccharomyces cerevisiae

<400> SEQUENCE: 215
atgtctgaac cagctcaaaa gaaacaaaag gttgctaaca actctctaga acaattgaaa      60
gcctccggca ctgtcgttgt tgccgacact ggtgatttcg gctctattgc caagtttcaa     120
cctcaagact ccacaactaa cccatcattg atcttggctg ctgccaagca accaacttac     180
gccaagttga tcgatgttgc cgtggaatac ggtaagaagc atggtaagac caccgaagaa     240
caagtcgaaa atgctgtgga cagattgtta gtcgaattcg gtaaggagat cttaaagatt     300
gttccaggca gagtctccac cgaagttgat gctagattgt cttttgacac tcaagctacc     360
attgaaaagg ctagacatat cattaaattg tttgaacaag aaggtgtctc caaggaagaa     420
gtccttatta aaattgcttc cacttgggaa ggtattcaag ctgccaaaga attggaagaa     480
aaggacggta tccactgtaa tttgactcta ttattctcct tcgttcaagc agttgcctgt     540
gccgaggccc aagttacttt gatttcccca tttgttggta gaattctaga ctggtacaaa     600
tccagcactg gtaaagatta caggggtgaa gccgacccag tgttatttc cgtcaagaaa     660 atctacaact actacaagaa gtacggttac aagactattg ttatgggtgc ttcttttcaga    720 agcactgacg aaatcaaaaa cttggctggt gttgactatc taacaatttc tccagctta     780 ttggacaagt tgatgaacag tactgaacct ttcccaagag ttttggaccc tgtctccgct    840
aagaaggaag ccggcgacaa gatttcttac atcagcgacg aatctaaatt cagattcgac    900
ttgaatgaag acgctatggc cactgaaaaa ttgtccgaag gtatcagaaa attctctgcc    960
gatattgtta ctctattcga cttgattgaa agaaagtta ccgcttaa                 1008

<210> SEQ ID NO 216
<211> LENGTH: 1803
<212> TYPE: DNA
<213> ORGANISM: Saccharomyces cerevisiae

<400> SEQUENCE: 216
atgttgtgtt cagtaattca gagacagaca agagaggttt ccaacacaat gtctttagac      60
tcatactatc ttgggtttga tctttcgacc caacaactga atgtctcgc cattaaccag      120 gacctaaaaa ttgtccattc agaaacagtg gaatttgaaa aggatcttcc gcattatcac     180
acaaagaagg gtgtctatat acacggcgac actatcgaat gtcccgtagc catgtggtta     240
gaggctctag atctggttct ctcgaaatat cgcgaggcta aatttccatt gaacaaagtt     300
```

```
atggccgtct cagggtcctg ccagcagcac gggtctgtct actggtcctc ccaagccgaa    360
tctctgttag agcaattgaa taagaaaccg gaaaaagatt tattgcacta cgtgagctct    420
gtagcatttg caaggcaaac cgcccccaat tggcaagacc acagtactgc aaagcaatgt    480
caagagtttg aagagtgcat aggtgggcct gaaaaaatgg ctcaattaac agggtccaga    540
gcccatttta gatttactgg tcctcaaatt ctgaaaattg cacaattaga accagaagct    600
tacgaaaaaa caaagaccat ttctttagtg tctaattttt tgacttctat cttagtgggc    660
catcttgttg aattagagga ggcagatgcc tgtggtatga acctttatga tatacgtgaa    720
agaaaattca gtgatgagct actacatcta attgatagtc ttctaaggga taaaactatc    780
agacaaaaat taatgagagc acccatgaaa aatttgatag cgggtaccat ctgtaaatat    840
tttattgaga agtacggttt caatacaaac tgcaaggtct ctcccatgac tggggataat    900
ttagccacta tatgttcttt accctgcgg aagaatgacg ttctcgtttc cctaggaaca    960
agtactacag ttcttctggt caccgataag tatcacccct ctccgaacta tcatcttttc   1020
attcatccaa ctctgccaaa ccattatatg ggtatgattt gttattgtaa tggttctttg   1080
gcaagggaga ggataagaga cgagttaaac aaagaacggg aaaataatta tgagaagact   1140
aacgattgga ctcttttaa tcaagctgtg ctagatgact agaaagtag tgaaaatgaa   1200 ttaggtgtat atttcctct ggggagatc gttcctagcg taaagccat aaacaaagg   1260 gttatcttca atccaaaaac gggtatgatt gaaagagagg tggccaagtt caagacaag   1320 aggcacgatg ccaaaaatat tgtagaatca caggctttaa gttgcagggt aagaatatct   1380
cccctgcttt cggattcaaa cgcaagctca aacagagac tgaacgaaga tacaatcgtg   1440
aagtttgatt acgatgaatc tccgctgcgg gactacctaa ataaaaggcc agaaaggact   1500 tttttgtag gtgggcttc taaaaacgat gctattgtga agaagtttgc tcaagtcatt   1560
ggtgctacaa agggtaattt taggctagaa acaccaaact catgtgccct tggtggttgt   1620
tataaggcca tgtggtcatt gttatatgac tctaataaaa ttgcagttcc ttttgataaa   1680
tttctgaatg acaatttttcc atggcatgta atggaaagca tatccgatgt ggataatgaa   1740
aattgggatc gctataattc caagattgtc cccttaagcg aactggaaaa gactctcatc   1800
taa                                                                 1803
```

<210> SEQ ID NO 217
<211> LENGTH: 2043
<212> TYPE: DNA
<213> ORGANISM: Saccharomyces cerevisiae

<400> SEQUENCE: 217

```
atgactcaat tcactgacat tgataagcta gccgtctcca ccataagaat tttggctgtg     60
gacaccgtat ccaaggccaa ctcaggtcac ccaggtgctc cattgggtat ggcaccagct    120
gcacacgttc tatggagtca aatgcgcatg aacccaacca acccagactg atcaacaga    180 gatagatttg tcttgtctaa cggtcacgcg gtcgcttgt tgtattctat gctacatttg    240
actggttacg atctgtctat tgaagacttg aaacagttca gacagttggg ttccagaaca    300
ccaggtcatc ctgaatttga gttgccaggt gttgaagtta ctaccggtcc attaggtcaa    360
ggtatctcca acgctgttgg tatggccatg gctcaagcta acctggctgc cacttacaac    420
aagccgggct ttaccttgtc tgacaactac acctatgttt tcttgggtga cggttgtttg    480
caagaaggta tttcttcaga agcttcctcc ttggctggtc atttgaaatt gggtaacttg    540
```

```
attgccatct acgatgacaa caagatcact atcgatggtg ctaccagtat ctcattcgat    600
gaagatgttg ctaagagata cgaagcctac ggttgggaag ttttgtacgt agaaaatggt    660
aacgaagatc tagccggtat tgccaaggct attgctcaag ctaagttatc caaggacaaa    720
ccaactttga tcaaaatgac cacaaccatt ggttacggtt ccttgcatgc cggctctcac    780
tctgtgcacg gtgccccatt gaaagcagat gatgttaaac aactaaagag caaattcggt    840
ttcaacccag acaagtcctt tgttgttcca caagaagttt acgaccacta ccaaaagaca    900
attttaaagc caggtgtcga agccaacaac aagtggaaca agttgttcag cgaataccaa    960
aagaaattcc cagaattagg tgctgaattg gctagaagat gagcggcca actacccgca   1020
aattgggaat ctaagttgcc aacttacacc gccaaggact ctgccgtggc cactagaaaa   1080
ttatcagaaa ctgttcttga ggatgtttac aatcaattgc cagagttgat ggtggttct   1140
gccgatttaa caccttctaa cttgaccaga tggaaggaag cccttgactt ccaacctcct   1200
tcttccggtt caggtaacta ctctggtaga tacattaggt acggtattag agaacacgct   1260
atgggtgcca taatgaacgg tatttcagct ttcggtgcca actacaaacc atacggtggt   1320
actttcttga acttcgtttc ttatgctgct ggtgccgtta gattgtccgc tttgtctggc   1380
cacccagtta tttgggttgc tacacatgac tctatcggtg tcggtgaaga tggtccaaca   1440
catcaaccta ttgaaacttt agcacacttc agatccctac caaacattca agtttggaga   1500
ccagctgatg gtaacgaagt ttctgccgcc tacaagaact ctttagaatc caagcatact   1560
ccaagtatca ttgctttgtc cagacaaaac ttgccacaat ggaaggtag ctctattgaa   1620
agcgcttcta agggtggtta cgtactacaa gatgttgcta acccagatat tattttagtg   1680
gctactggtt ccgaagtgtc tttgagtgtt gaagctgcta gactttggc cgcaaagaac   1740
atcaaggctc gtgttgtttc tctaccagat ttcttcactt ttgacaaaca acccctagaa   1800
tacagactat cagtcttacc agacaacgtt ccaatcatgt ctgttgaagt tttggctacc   1860
acatgttggg gcaaatacgc tcatcaatcc ttcggtattg acagatttgg tgcctccggt   1920
aaggcaccag aagtcttcaa gttcttcggt ttcacccccag aaggtgttgc tgaaagagct   1980
caaaagacca ttgcattcta aagggtgac aagctaattt ctcctttgaa aaaagctttc   2040
taa                                                                  2043
```

<210> SEQ ID NO 218
<211> LENGTH: 717
<212> TYPE: DNA
<213> ORGANISM: Saccharomyces cerevisiae

<400> SEQUENCE: 218

```
atggtcaaac caattatagc tcccagtatc cttgcttctg acttcgccaa cttgggttgc     60
gaatgtcata aggtcatcaa cgccggcgca gattggttac atatcgatgt catggacggc    120
cattttgttc caaacattac tctgggccaa ccaattgtta cctccctacg tcgttctgtg    180
ccacgccctg gcgatgctag caacacagaa aagaagccca ctgcgttctt cgattgtcac    240
atgatggttg aaaatcctga aaaatgggtc gacgattttg ctaaatgtgg tgctgaccaa    300
tttacgttcc actacgaggc cacacaagac cctttgcatt tagttaagtt gattaagtct    360
aagggcatca agctgcatg cgccatcaaa cctggtactt ctgttgacgt tttatttgaa    420
ctagctcctc atttggatat ggctcttgtt atgactgtgg aacctgggtt tggaggccaa    480
aaattcatgg aagacatgat gccaaaagtg gaaactttga gagccaagtt cccccatttg    540
aatatccaag tcgatggtgg tttgggcaag agaccatcc cgaaagccgc caaagccggt    600
```

```
gccaacgtta ttgtcgctgg taccagtgtt ttcactgcag ctgacccgca cgatgttatc    660
tccttcatga aagaagaagt ctcgaaggaa ttgcgttcta gagatttgct agattag       717

<210> SEQ ID NO 219
<211> LENGTH: 777
<212> TYPE: DNA
<213> ORGANISM: Saccharomyces cerevisiae

<400> SEQUENCE: 219
atggctgccg gtgtcccaaa aattgatgcg ttagaatctt tgggcaatcc tttggaggat     60
gccaagagag ctgcagcata cagagcagtt gatgaaaatt taaaatttga tgatcacaaa    120
attattggaa ttggtagtgg tagcacagtg gtttatgttg ccgaaagaat tggacaatat    180
ttgcatgacc ctaaatttta tgaagtagcg tctaaattca tttgcattcc aacaggattc    240
caatcaagaa acttgatttt ggataacaag ttgcaattag ctccattga acagtatcct    300 cgcattgata tagcgtttga cggtgctgat gaagtggatg agaatttaca attaattaaa    360
ggtggtggtg cttgtctatt tcaagaaaaa ttggttagta ctagtgctaa aaccttcatt    420
gtcgttgctg attcaagaaa aaagtcacca aaacatttag gtaagaactg gaggcaaggt    480
gttcccattg aaattgtacc ttcctcatac gtgagggtca agaatgatct attagaacaa    540
ttgcatgctg aaaaagttga catcagacaa ggaggttctg ctaaagcagg tcctgttgta    600
actgacaata ataacttcat tatcgatgcg gatttcggtg aaatttccga tccaagaaaa    660
ttgcatagag aaatcaaact gttagtgggc gtggtggaaa caggtttatt catcgacaac    720
gcttcaaaag cctacttcgg taattctgac ggtagtgttg aagttaccga aaagtga       777

<210> SEQ ID NO 220
<211> LENGTH: 1725
<212> TYPE: DNA
<213> ORGANISM: Saccharomyces cerevisiae

<400> SEQUENCE: 220
atggcagttg aggagaacaa tatgcctgtt gtttcacagc aaccccaagc tggtgaagac     60
gtgatctctt cactcagtaa agattcccat ttaagcgcac aatctcaaaa gtattctaat    120
gatgaattga agccggtga gtcagggtct gaaggctccc aaagtgttcc tatagagata    180
cccaagaagc ccatgtctga atatgttacc gtttccttgc tttgtttgtg tgttgccttc    240
ggcggcttca tgtttggctg ggataccggt actatttctg ggtttgttgt ccaaacagac    300 ttttttgagaa ggtttggtat gaaacataag gatggtaccc actatttgtc aaacgtcaga    360
acaggtttaa tcgtcgccat tttcaatatt ggctgtgcct ttggtggtat tatactttcc    420
aaaggtggag atatgtatgg ccgtaaaaag gtctttcga ttgtcgtctc ggtttatata    480
gttggtatta tcattcaaat tgcctctatc aacaagtggt accaatattt cattggtaga    540
atcatatctg gttgggtgt cggcggcatc gccgtcttat gtcctatgtt gatctctgaa    600
attgctccaa agcacttgag aggcacacta gtttcttgtt atcagctgat gattactgca    660
ggtatctttt tgggctactg tactaattac ggtacaaaga gctattcgaa ctcagttcaa    720
tggagagttc cattagggct atgtttcgct tggtcattat ttatgattgg cgctttgacg    780
ttagttcctg aatccccacg ttatttatgt gaggtgaata aggtagaaga cgccaagcgt    840
tccattgcta agtctaacaa ggtgtcacca gaggatcctg ccgtccaggc agagttagat    900
ctgatcatgg ccggtataga agctgaaaaa ctggctggca atgcgtcctg ggggaatta    960
```

-continued

```
ttttccacca agaccaaagt atttcaacgt ttgttgatgg gtgtgtttgt tcaaatgttc    1020
caacaattaa ccggtaacaa ttattttttc tactacggta ccgttatttt caagtcagtt    1080
ggcctggatg attcctttga acatccatt gtcattggtg tagtcaactt tgcctccact     1140
ttctttagtt tgtggactgt cgaaaacttg gacatcgta aatgtttact tttgggcgct     1200
gccactatga tggcttgtat ggtcatctac gcctctgttg gtgttactag attatatcct    1260
cacggtaaaa gccagccatc ttctaaaggt gccggtaact gtatgattgt ctttacctgt    1320
ttttatattt tctgttatgc cacaacctgg gcgccagttg cctgggtcat cacagcagaa    1380
tcattcccac tgagagtcaa gtcgaaatgt atggcgttgg cctctgcttc caattgggta    1440
tgggggttct tgattgcatt tttcacccca ttcatcacat ctgccattaa cttctactac    1500
ggttatgtct tcatgggctg tttggttgcc atgttttttt atgtcttttt ctttgttcca    1560
gaaactaaag gcctatcgtt agaagaaatt caagaattat gggaagaagg tgttttacct    1620
tggaaatctg aaggctggat tccttcatcc agaagaggta ataattacga tttagaggat    1680
ttacaacatg acgacaaacc gtggtacaag gccatgctag aataa                   1725
```

<210> SEQ ID NO 221
<211> LENGTH: 37
<212> TYPE: DNA
<213> ORGANISM: Unknown
<220> FEATURE:
<223> OTHER INFORMATION: Obtained from environmental sample

<400> SEQUENCE: 221
caccattaat taacccgggg cacctgtcac tttggaa                              37

<210> SEQ ID NO 222
<211> LENGTH: 51
<212> TYPE: DNA
<213> ORGANISM: Unknown
<220> FEATURE:
<223> OTHER INFORMATION: Obtained from environmental sample

<400> SEQUENCE: 222
cgcgtaagct ttctagaggc gcgccaagct tttacactct tgaccagcgc a             51

<210> SEQ ID NO 223
<211> LENGTH: 57
<212> TYPE: DNA
<213> ORGANISM: Unknown
<220> FEATURE:
<223> OTHER INFORMATION: Obtained from environmental sample

<400> SEQUENCE: 223
ccgctggtgg gtaccgatat ccctgcaggg agctcacgcg taagctttct agaggcg       57

<210> SEQ ID NO 224
<211> LENGTH: 56
<212> TYPE: DNA
<213> ORGANISM: Unknown
<220> FEATURE:
<223> OTHER INFORMATION: Obtained from environmental sample

<400> SEQUENCE: 224
ctgcagggat atcggtaccc accagcggcc gcaggccttg ggtgcttgct ggcgaa        56

<210> SEQ ID NO 225
<211> LENGTH: 48
<212> TYPE: DNA
<213> ORGANISM: Unknown

```
<220> FEATURE:
<223> OTHER INFORMATION: Obtained from environmental sample

<400> SEQUENCE: 225
acctctgcat gcgaattctt aagacaaata aaatttatag agacttgt                    48

<210> SEQ ID NO 226
<211> LENGTH: 36
<212> TYPE: DNA
<213> ORGANISM: Unknown
<220> FEATURE:
<223> OTHER INFORMATION: Obtained from environmental sample

<400> SEQUENCE: 226
gtcttaagaa ttcgcatgca gaggtagttt caaggt                                 36

<210> SEQ ID NO 227
<211> LENGTH: 39
<212> TYPE: DNA
<213> ORGANISM: Unknown
<220> FEATURE:
<223> OTHER INFORMATION: Obtained from environmental sample

<400> SEQUENCE: 227
caccattaat taatacgtat ttctcgccga gaaaaactt                              39

<210> SEQ ID NO 228
<211> LENGTH: 25
<212> TYPE: DNA
<213> ORGANISM: Unknown
<220> FEATURE:
<223> OTHER INFORMATION: Obtained from environmental sample

<400> SEQUENCE: 228
ccccatcgac aactacgagc tcact                                             25

<210> SEQ ID NO 229
<211> LENGTH: 25
<212> TYPE: DNA
<213> ORGANISM: Unknown
<220> FEATURE:
<223> OTHER INFORMATION: Obtained from environmental sample

<400> SEQUENCE: 229
caacttgccg tcctcgaagt ccttg                                             25

<210> SEQ ID NO 230
<211> LENGTH: 25
<212> TYPE: DNA
<213> ORGANISM: Unknown
<220> FEATURE:
<223> OTHER INFORMATION: Obtained from environmental sample

<400> SEQUENCE: 230
cgagcctgag aaggtcgtga tggga                                             25

<210> SEQ ID NO 231
<211> LENGTH: 25
<212> TYPE: DNA
<213> ORGANISM: Unknown
<220> FEATURE:
<223> OTHER INFORMATION: Obtained from environmental sample

<400> SEQUENCE: 231
tacgtcgaag tcggggttgg tagaa                                             25
```

<210> SEQ ID NO 232
<211> LENGTH: 21
<212> TYPE: DNA
<213> ORGANISM: Unknown
<220> FEATURE:
<223> OTHER INFORMATION: Obtained from environmental sample

<400> SEQUENCE: 232
agtcacatca agatcgttta t                                         21

<210> SEQ ID NO 233
<211> LENGTH: 21
<212> TYPE: DNA
<213> ORGANISM: Unknown
<220> FEATURE:
<223> OTHER INFORMATION: Obtained from environmental sample

<400> SEQUENCE: 233
gcacggaata tgggactact t                                         21

<210> SEQ ID NO 234
<211> LENGTH: 21
<212> TYPE: DNA
<213> ORGANISM: Unknown
<220> FEATURE:
<223> OTHER INFORMATION: Obtained from environmental sample

<400> SEQUENCE: 234
actccacttc aagtaagagt t                                         21

<210> SEQ ID NO 235
<211> LENGTH: 27
<212> TYPE: DNA
<213> ORGANISM: Unknown
<220> FEATURE:
<223> OTHER INFORMATION: Obtained from environmental sample

<400> SEQUENCE: 235
gaacaaaaac ctgcaggaaa cgaagat                                   27

<210> SEQ ID NO 236
<211> LENGTH: 31
<212> TYPE: DNA
<213> ORGANISM: Unknown
<220> FEATURE:
<223> OTHER INFORMATION: Obtained from environmental sample

<400> SEQUENCE: 236
gctctaattt gtgagtttag tatacatgca t                              31

<210> SEQ ID NO 237
<211> LENGTH: 1338
<212> TYPE: DNA
<213> ORGANISM: Unknown
<220> FEATURE:
<223> OTHER INFORMATION: Obtained from environmental sample

<400> SEQUENCE: 237
ttaattaagt taattacctt ttttgcgagg catatttatg gtgaagaata agttttgacc      60
atcaaagaag gttaatgtgg ctgtggtttc agggtccata aagcttttca attcatcatt    120
ttttttttat tcttttttttt gattccggtt tccttgaaat ttttttgatt cggtaatctc    180
cgaacagaag gaagaacgaa ggaaggagca cagacttaga ttggtatata tacgcatatg    240
tagtgttgaa gaaacatgaa attgcccagt attcttaacc caactgcaca gaacaaaaac    300

-continued

```
ctgcaggaaa cgaagataaa tcatgtcgaa agctacatat aaggaacgtg ctgctactca    360
tcctagtcct gttgctgcca agctatttaa tatcatgcac gaaaagcaaa caaacttgtg    420
tgcttcattg gatgttcgta ccaccaagga attactggag ttagttgaag cattaggtcc    480
caaaatttgt ttactaaaaa cacatgtgga tatcttgact gattttccca tggagggcac    540
agttaagccg ctaaaggcat tatccgccaa gtacaatttt ttactcttcg aagacagaaa    600
atttgctgac attggtaata cagtcaaatt gcagtactct gcgggtgtat acagaatagc    660
agaatgggca gacattacga atgcacacgg tgtggtgggc ccaggtattg ttagcggttt    720
gaagcaggcg gcagaagaag taacaaagga acctagaggc cttttgatgt tagcagaatt    780
gtcatgcaag ggctccctag ctactggaga atatactaag ggtactgttg acattgcgaa    840
gagcgacaaa gattttgtta tcggctttat tgctcaaaga gacatgggtg aagagatga    900 aggttacgat tggttgatta tgacacccgg tgtgggttta gatgacaagg gagacgcatt    960
gggtcaacag tatagaaccg tggatgatgt ggtctctaca ggatctgaca ttattattgt   1020
tggaagagga ctatttgcaa agggaaggga tgctaaggta gagggtgaac gttacagaaa   1080
agcaggctgg gaagcatatt tgagaagatg cggccagcaa aactaaaaaa ctgtattata   1140
agtaaatgca tgtatactaa actcacaaat tagagcttca atttaattat atcagttatt   1200
acccgggaat ctcggtcgta atgattttta taatgacgaa aaaaaaaaaa ttggaaagaa   1260
aaagcttcat ggcctttata aaaaggaacc atccaatacc tcgccagaac caagtaacag   1320
tattttacgg ttaattaa                                                 1338
```